US012351566B2

(12) United States Patent (10) Patent No.: US 12,351,566 B2
Hall et al. (45) Date of Patent: Jul. 8, 2025

(54) MEK INHIBITORS AND THERAPEUTIC USES THEREOF

(71) Applicant: Immuneering Corporation, Cambridge, MA (US)

(72) Inventors: Brett Matthew Hall, San Diego, CA (US); Bart Lieven Decorte, Southampton, PA (US); Peter John King, San Diego, CA (US); Ruben Leenders, Cambridge, MA (US); Anita Wegert, Cambridge, MA (US); Kevin Fowler, Cambridge, MA (US); Sarah Kolitz, Cambridge, MA (US); Robin Doodeman, Cambridge, MA (US); Jarno Poelakker, Cambridge, MA (US); Rutger Henk Adriaan Folmer, Cambridge, MA (US)

(73) Assignee: Immuneering Corporation, Cambridge, MA (US)

( * ) Notice: Subject to any disclaimer, the term of this patent is extended or adjusted under 35 U.S.C. 154(b) by 584 days.

(21) Appl. No.: 17/791,755

(22) PCT Filed: Jan. 7, 2021

(86) PCT No.: PCT/US2021/012531
§ 371 (c)(1),
(2) Date: Jul. 8, 2022

(87) PCT Pub. No.: WO2021/142144
PCT Pub. Date: Jul. 15, 2021

(65) Prior Publication Data

US 2023/0119327 A1 Apr. 20, 2023

Related U.S. Application Data

(60) Provisional application No. 62/959,732, filed on Jan. 10, 2020.

(51) Int. Cl.
*C07D 311/06* (2006.01)
*A61P 35/00* (2006.01)
(Continued)

(52) U.S. Cl.
CPC ............ *C07D 311/06* (2013.01); *A61P 35/00* (2018.01); *C07D 405/12* (2013.01); *C07D 407/12* (2013.01); *C07D 409/12* (2013.01)

(58) Field of Classification Search
CPC .. C07D 311/06; C07D 405/12; C07D 407/12; C07D 409/12; C07D 311/16;
(Continued)

(56) References Cited

U.S. PATENT DOCUMENTS 8,278,465 B2 10/2012 Iikura et al.
8,569,378 B2 10/2013 Sakai et al.
(Continued)

FOREIGN PATENT DOCUMENTS

CN 102964326 3/2013
CN 103172606 6/2013
(Continued)

OTHER PUBLICATIONS

CAS Registry No. 1347726-71-9; STN Entry Date Dec. 2, 2011.
(Continued)

*Primary Examiner* — Clinton A Brooks
*Assistant Examiner* — Izabela Schmidt
(74) *Attorney, Agent, or Firm* — Knobbe, Martens, Olson & Bear, LLP

(57) ABSTRACT

The present disclosure provides compounds, compositions containing such compounds, and methods of designing, developing, producing and preparing compounds represented by general Formula (I), including pharmaceutically acceptable salts thereof or a synthetic intermediate thereof:
(Continued)

(I)

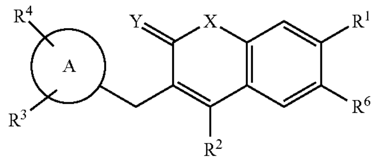

The compounds act as MEK inhibitors and are capable of displaying one or more beneficial therapeutic effects, including treating cancer.

21 Claims, 22 Drawing Sheets

(51) Int. Cl.

| | |
|---|---|
| ***C07D 405/12*** | (2006.01) |
| ***C07D 407/12*** | (2006.01) |
| ***C07D 409/12*** | (2006.01) |

(58) Field of Classification Search

CPC .. C07D 405/06; C07D 413/06; C07D 471/08; C07D 487/08; C07D 487/10; C07D 491/107; C07D 311/18; C07D 405/14; C07D 417/12; A61P 35/00; A61K 31/352; A61K 31/397; A61K 31/496; A61K 31/5377

See application file for complete search history.

(56) References Cited

U.S. PATENT DOCUMENTS

| | | | |
|---|---|---|---|
| 9,133,174 B2 | 9/2015 | Murakata et al. | |
| 9,265,765 B2 | 2/2016 | Stogniew et al. | |
| 9,376,437 B2 | 6/2016 | Stogniew et al. | |
| 9,611,258 B2 | 4/2017 | Ross et al. | |
| 10,548,897 B2 | 2/2020 | Dar et al. | |
| 10,668,055 B2 | 6/2020 | Saha et al. | |
| 2003/0216463 A1 | 11/2003 | Kanojia et al. | |
| 2004/0259915 A1 | 12/2004 | Kanojia et al. | |
| 2010/0004233 A1* | 1/2010 | Iikura | C07D 405/12 544/94 |
| 2011/0009398 A1* | 1/2011 | Sakai | A61P 29/00 514/369 |
| 2011/0092700 A1 | 4/2011 | Iikura et al. | |
| 2014/0038920 A1 | 2/2014 | Ballabio et al. | |
| 2016/0002212 A1* | 1/2016 | Ross | A61P 35/00 544/113 |
| 2016/0310476 A1 | 10/2016 | Saha et al. | |
| 2016/0355510 A1 | 12/2016 | Spinger et al. | |
| 2016/0367539 A1 | 12/2016 | Saha et al. | |
| 2017/0042881 A1 | 2/2017 | Fagin et al. | |
| 2017/0080045 A1 | 3/2017 | Ehrhardt et al. | |
| 2017/0112865 A1 | 4/2017 | Morrison et al. | |
| 2018/0312844 A1 | 11/2018 | Morrison et al. | |
| 2018/0369203 A1 | 12/2018 | Dai et al. | |
| 2019/0262342 A1 | 8/2019 | Janes et al. | |
| 2020/0190596 A1 | 6/2020 | Klijn et al. | |
| 2020/0323863 A1 | 10/2020 | Gutkind et al. | |
| 2020/0325543 A1 | 10/2020 | Flückiger-Mangual et al. | |
| 2020/0338074 A1 | 10/2020 | Hammerman et al. | |
| 2021/0275595 A1 | 9/2021 | Zambidis et al. | |
| 2021/0361578 A1 | 11/2021 | Salem et al. | |

FOREIGN PATENT DOCUMENTS

| | | |
|---|---|---|
| CN | 105287509 | 2/2016 |
| CN | 108658962 | 10/2018 |
| EA | 20523 B9 | 1/2015 |
| EP | 1 982 982 | 10/2008 |
| EP | 2 754 654 | 7/2014 |
| JP | 2004-509855 | 4/2004 |
| JP | 2012-092038 | 5/2012 |
| JP | 2018-150293 | 9/2018 |
| KR | 10-2010-0042623 | 4/2010 |
| WO | WO 06/78834 | 7/2006 |
| WO | WO 09/014100 | 1/2009 |
| WO | WO 12/174488 | 12/2012 |
| WO | WO 14/071109 | 5/2014 |
| WO | WO 14/107713 | 7/2014 |
| WO | WO 14/164942 | 10/2014 |
| WO | WO 15/89810 | 6/2015 |
| WO | WO 15/94998 | 6/2015 |
| WO | WO 15/120289 | 8/2015 |
| WO | WO 16/025648 | 2/2016 |
| WO | WO 16/098873 | 6/2016 |
| WO | WO 17/007495 | 1/2017 |
| WO | WO 17/026878 | 2/2017 |
| WO | WO 18/107146 | 6/2018 |
| WO | WO 18/213302 | 11/2018 |
| WO | WO 19/051084 | 3/2019 |
| WO | WO 19/096397 | 5/2019 |
| WO | WO 19/096449 | 5/2019 |
| WO | WO 19/123207 | 6/2019 |
| WO | WO 20/055760 | 3/2020 |
| WO | WO 20/097023 | 5/2020 |
| WO | WO 20/106304 | 5/2020 |
| WO | WO 20/123414 | 6/2020 |
| WO | WO 20/130125 | 6/2020 |
| WO | WO 20/188034 | 9/2020 |
| WO | WO 21/037956 | 3/2021 |
| WO | WO 21/047573 | 3/2021 |
| WO | WO 21/047783 | 3/2021 |
| WO | WO 21/047798 | 3/2021 |
| WO | WO 21/048339 | 3/2021 |
| WO | WO 21/069486 | 4/2021 |
| WO | WO 21/108672 | 6/2021 |
| WO | WO 21/149776 | 7/2021 |
| WO | WO 21/154929 | 8/2021 |
| WO | WO 21/178595 | 9/2021 |
| WO | WO 21/198440 | 10/2021 |
| WO | WO 21/222278 | 11/2021 |
| WO | WO 21/234097 | 11/2021 |
| WO | WO 22/015736 | 1/2022 |
| WO | WO 22/018875 | 1/2022 |
| WO | WO 22/019329 | 1/2022 |
| WO | WO 22/170060 | 8/2022 |
| WO | WO 23/009572 | 2/2023 |
| WO | WO 23/076991 | 5/2023 |
| WO | WO 23/081676 | 5/2023 |
| WO | WO 23/108110 | 6/2023 |
| WO | WO 23/133472 | 8/2023 |
| WO | WO 23/147297 | 8/2023 |
| WO | WO 23/173053 | 9/2023 |
| WO | WO 23/211812 | 11/2023 |
| WO | WO 23/235356 | 12/2023 |

OTHER PUBLICATIONS

CAS Registry No. 307547-08-6; STN Entry Date Dec. 8, 2000.

CAS Registry No. 312941-16-5; STN Entry Date Jan. 5, 2001.

Ganeshapillai et al., 2018, C-3- and C-4-Substituted Bicyclic Coumarin Sulfamates as Potent Steroid Sulfatase Inhibitors, Acs Omega, 3(9):10748-10772.

Han et al., 2005, Identification of coumarin derivatives as a novel class of allosteric MEK1 inhibitors, Bioorganic & Medicinal Chemistry Letters, 15(24):5467-5473.

Harada et al., 2010, Coumarins as novel 17b-hydroxysteroid dehydrogenase type 3 inhibitors for potential treatment of prostate cancer, Bioorganic & Medicinal Chemistry Letters, 20(1):272-275.

Johnson et al., Aug. 1, 2023, IMM-1-104 show promising activity in patient-aligned, RAS-mutated models of acute myeloid leukemia and multiple myeloma, Immuneering Corporation, 2 pp.

Kolitz et al., Apr. 14-19, 2023, Pan-RAS IMM-1-104 activity in humanized 3D tumor models is independent of specific amino acid substitution, AACR Annual Meeting 2023, Orlando, FL, 1 p.

(56) References Cited

OTHER PUBLICATIONS

Nair et al., Aug. 2017, Humanized 3d tumor modesl that are mutationally aligned with AACR GENIE pateitns predict IMM-1-104 activity in RAS-addicted tumors, Cancer Discov, 7(8):818-831, abstract.
Nair et al., Oct. 12, 2023, Predicting activity of IMM-1-104 as single agent and in combination for patients with RAS or RAF mutant tumors, AACR-NCI-EORTC International Conference on Molecular Targets and Cancer Therapeutics, Boston, Abstract A134 poster.
Noolvi et al., 2011, A QSAR Analysis of Coumarin Derivatives as TNF-α Inhibitor—A Rational Approach to Anticancer Drug Design, Letters in Drug Design & Descovery, 8(9):868-876.
Travesa et al., Oct. 12, 2023, Deep Cyclic Inhibition (DCI) of the MAPK pathway with IMM-6-415, alone and in combination with encorafenib, demonstrates anti-tumor activity and tolerability in RAF mutant tumors in vivo, AACR-NCI-EORTC International Conference on Molecular Targets and Cancer Therapeutics, Boston, Abstract A093 poster.
Zou et al., 2017, Identification of novel MEK1 inhibitors by pharmacophore and docking based virtual screening, Medicinal Chemistry Research, 26(4):701-713.
AACR Project GENIE Consortium, Aug. 2017, AACR project Genie: powering precision medicine through an international consortium, Cancer Discov, 7(8):818-831.
Adjei et al., May 1, 2008, Phase 1 pharmacokinetic and pharmacodynamic study of the oral, small-molecule mitogen-activated protein kinase kinase 1/2 inhibitor AZD6244 (ARRY-142886) in patients with advanced cancers, J. Clin Oncol., 26(13):2139-2146.
Aikin et al., 2020, MAPK activity dynamics regulate non-cell autonomous effects of oncogene expression, eLife, 9:e60541.
Ambrogio et al., Feb. 8, 2018, KRAS dimerization impacts MEK inhibitor sensitivity and oncogenic activity of mutant KRAS, Cell, 172:857-868.
Amitani et al., 2013, Control of food intake and muscle wasting in cachexia, The International Journal of Biochemistry & Cell Biology, 45:2179-2185.
Ancrile et al., 2007, Oncogenic Ras-induced secretion of IL6 is required for tumorigenesis, Genes & Development, 21:1714-1719.
Aoki et al., 2013, The sulfamide moiety affords higher inhibitory activity and oral bioavailability to a series of coumarin dual selective RAF/MEK inhibitors, Bioorganic & Medicinal Chemistry Letters: 23:6223-6227.
Aoki et al., 2014, Optimizing the physicochemical properties of RAF/MEK inhibitors by nitrogen scanning, ACS Med. Chem. Lett, 5:309-314.
Argiles et al., Jan. 2019, Inter-tissue communication in cancer cachexia, Nature Reviews Endocrinology, 15:9-20.
Argiles et al., Nov. 2014, Cancer cachexia: understanding the molecular basis, Nature Reviews Cancer, 14:754-672.
Array BioPharma Inc., Jun. 2018, Braftovi™ (encorafenib) capsules, for oral use, prescribing information, 19 pp.
Array BioPharma Inc., Jun. 2018, Mektovi® (binimetinib) tablets, for oral use, prescribing information, 19 pp.
Asada et al., Nov. 20, 2014, Rescuing dicer defects via inhibition of an anti-dicing nuclease, Cell Reports, 9:1471-1481.
Ascierto et al., Mar. 2013, MEK162 for patients with advanced melanoma harbouring NRAS or Val600 BRAF mutations; a non-randomized, open-label phase 2 study, The Lancet/Oncology, 14:249-256.
AstraZeneca Pharmaceuticals LP, Apr. 2020, Koselugo (selumetiib) capsules, for oral use, prescribing information, 28 pp.
Attaix et al., 2013, A dedication to Alfred L. Goldberg, The International Journal of Biochemistry & Cell Biology, 45:2120.
Au et al., Jan. 18, 2017, The MED-inhibitor selumetinib attenuates tumor growth and reduced IL-6 expression but does not protect against muscle wasting in Lewis lunch cancer cachexia, Frontiers in Physiology, 7(article 682):1-10.
Aulino et al., 2010, Molecular, cellular and physiological characterization of the cancer cachexia-inducing C26 colon carcinoma in mouse, BMC Cancer, 10:363.
Bambouskova et al., 2018, Electrophilic properties of itaconate and derivatives regulate I?B?/ATF3 inflammatory axis, Nature, https://doi.org/10.1038/s41586-018-0052-z, 16 pp.
Banerji et al., Mar. 1, 2010, The first-in-human study of the hydrogen sulfate (hyd-sulfate) capsule of the MEK1/2 inhibitor AXD6244 (ARRY-142886): a phase 1 open-label multicenter trial in patients with advanced cancer, Clinical Cancer Research, 16(5):1613-1623.
Baracos et al., 2013, Clinical outcomes related to muscle mass in humans with cancer and catabolic illnesses, The International Journal of Biochemistry & Cell Biology, 45:2302-2308.
Baracos et al., 2018, Cancer-associated cachexia, Nature Reviews/Disease Primers, 4(article No. 17105):1-18.
Basch et al., Jun. 2015, Patient-reported outcomes in cancer drug development and US regulatory review: perspectives from industry, the Food and Drug Administration, and the patient, JAMA Oncology, 1(3):375-379.
Bayliss et al., 2011, A humanized anti-IL-6 antibody (ALD518) in non-small cell lung cancer, Expert Opin. Biol. Ther., 11(12):1663-1668.
Bendell et al., 2017, A phase 1 dose-escalation and expansion study of binimetinib (MEK162), a potent and selective oral MEK1/2 inhibitor, British Journal of Cancer, 116:575-583.
Benien et al., 2014, 3D tumor models: history, advances and future perspectives, Future Oncology, 10(7):1311-1327.
Bhadury et al., 2013, Identification of tumorigenic and therapeutically actionable mutations in transplantable mouse tumor cells by exome sequencing, Oncogenesis, 2(e44):1-5.
Bindels et al., 2013, Muscle wasting: the gut microbiota as a new therapeutic target?, The International Journal of Biochemistry & Cell Biology, 45:2186-2190.
Bodine, 2013, Disuse-induced muscle wasting, The International Journal of Biochemistry & Cell Biology, 45:2200-2208.
Bohovych et al., Oct. 3, 2016, Sending out an SO: mitochondria as a signaling hub, Frontiers in Cell and Developmental Biology, 4(Article 109):1-15.
Brennan et al., Apr. 21, 2011, A Raf-induced allosteric transition of KSR stimulates phosphorylation of MEK, Nature, 472:366-369.
Brown, 2004, Drugs, hERG and sudden death, Cell Calcium, 35:543-547.
Buck et al., 2015, T cell metabolism drives immunity, J. Exp. Med, 212(9):1345-1360.
Bugaj et al., Aug. 31, 2018, Supplementary materials for Cancer mutations and targeted drugs can disrupt dynamic signal encoding by the Ras-Erk pathway, Science, 361:eaao3048, 18 pp.
Camporeale et al., 2014, STAT3 activities and energy metabolism: dangerous liaisons, Cancers, 6:1579-1596.
Canon et al., 2019, The clinical KRAS9G12C) inhibitor AMG 510 drives anti-tumour immunity, Nature, https://doi.org/10.1038/s41586-019-1694-1, 26 pp.
Casneuf et al., 2016, Interkeukin-6 is a potential therapeutic target in interleukin-6 dependent, estrogen receptor-?-positive breast cancer, Breast Cancer: Targets and Therapy, 8:13-27.
Catalanotti et al., Mar. 2009, A Mek1-Mek2 heterodimer determines the strength and duration of the Erk signal, Nature Structural & Molecular Biology, 16(3):294-303.
Caunt et al., Oct. 2015, MEK1 and MEK2 inhibitors and cancer therapy: the long and winding road, Nature Reviews Cancer, 15:577-592.
Chandel, 2014, Mitochondria as signaling organelles, BMC Biology, 12:34, 7 pp.
Chen et al., 2006, Synthesis of novel tetracyclic chromenes through carbanion chemistry of 4-methyl coumarins, Tetrahedron Letters: 47:5909-5913.
Cheng et al., 2004, Discovery and structure-activity relationship of coumarin derivatives as TNF-? inhibitors, Bioorganic & Medicinal Chemistry Letters, 14:2411-2415.

(56) References Cited

OTHER PUBLICATIONS

Chung et al., Nov. 1997, STAT3 serine phosphorylation by EKR-dependent and -independent pathways negatively modulates its tyrosine phosphorylation, Molecular and Cellular Biology, 17(11):6508-6516.
Ciciliot et al., 2013, Muscle type and fiber type specificity in muscle wasting, The International Journal of Biochemistry & Cell Biology, 45:2191-2199.
Coma et al., Jul. 1, 2021, Dual RAF/MEK inhibitor VS-6766 enhances antitumor efficacy of KRAS-G12C inhibitors through a vertical pathway inhibition strategy, Proceedings of the American Association for Cancer Res, 81(13_Suppl):Abstract nr 1263.
Corbett et al., Sep. 1975, Tumor induction relationships in development of transplantable cancers of the colon in mice for chemotherapy assays, with a note on carcinogen structure, Cancer Research 35:2434-2439.
Corcoran et al., Apr. 2011, Potential therapeutic strategies of overcome acquired resistance to BRAF or MEK inhibitors in BRAF mutant cancers, Oncotarget, 2(4):336-346.
DeBerardinis et al., May 27, 2016, Fundamentals of cancer metabolism, Sci. Adv., 2(5):e1600200, 19 pp.
Denton et al., Feb. 2011, Pharmacokinetics and pharmacodynamics of AZD6244 (ARRY-142886) in tumor-bearing nude mice, Cancer Chemother Pharmacol, 62(2):349-360.
Desideri et al., May 21, 2015, Alike but different: RAF paralogs and their signaling outputs, Cell, 161:967-970.
Dodson et al., 2011, Muscle wasting in cancer cachexia: clinical implications, diagnosis, and emerging treatment strategies, Annu. Rev. Med., 62:265-279.
Dougherty et al., Jan. 21, 2006, Regulation of Raf-1 by direct feedback phosphorylation, Molecular Cell, 15:215-224.
Dummer et al., Mar. 8, 2017, Binimetinib versus dacarbazine in patients with advanced NRAS-mutant melanoma (NEMO): a multicentre, open-label, randomized, phase 3 trial, http://dx.doi.org/10.1016/S1470-2045(17)30180-8, 11 pp.
Duncan et al., 2015, MEK inhibitors: a new class of chemotherapeutic agents with ocular toxicity, Eye, 29:1003-1012.
Dymond et al., Nov. 2016, Metabolism, excretion, and pharmacokinetics of selumetinib, an MEK1/2 inhibitor, in healthy adult male subjects, Clinical Therapeutics, 38(11): 2447-2458.
Emery et al., 2017, BRAF-inhibitor associated MEK mutations increase RAF-dependent and -independent enzymatic activity, Molecular Cancer Research, DOI: 10.1158/1541-7786.MCR-17-0211, 15 pp.
Emery et al., Dec. 1, 2009, MEK1 mutations confer resistance to MEK and B-RAF inhibition, PNAS, 106(48):20411-20416.
Eroglu et al., 2016, Combination therapy with BRAF and MEK inhibitors for melanoma: latest evidence and place in therapy, Therapeutic Advances in Medical Oncology, 8(1):48-56.
Favata et al., Jul. 17, 1998, Identification of a novel inhibitor of mitogen-activated protein kinase kinase, J. Biol. Chem., 273(29):18623-18632.
Fernandez-Medarde et al., 2011, Ras in cancer and developmental disease, Genes & Cancer, 2(3):344-358.
Finn et al., 2018, Phase 1b investigation of the MEK inhibitor binimetinib in patients with advanced or metastatic biliary tract cancer, Investigational New Drugs, 36:1037-1043.
Gajewski, Aug. 2015, The next hurdle in cancer immunotherapy: overcoming the non-T-cell-inflamed tumor microenvironment, Seminars in Oncology, 42(4):663-671.
Gale et al., Jun. 2, 2018, A longitudinal study of muscle strength and function in patients with cancer cachexia, Supportive Care in Cancer, https://doi.org/10.1007/s00520-018-4297-8, 7 pp.
Garbers et al., 2013, Interleukin-6 and inteleukin-11: same same but different, Biol. Chem. 394(9):1145-1161.
Garbers et al., 2018, Interleukin?6: designing specific therapeutics for a complex cytokine, Nature Reviews/Drug Discovery, doi:10.1038/nrd.2018.45, 18 pp.
Genentech, Inc., Aug. 2016, Zelboraf® (vemurafenib) tablet for oral use, prescribing information, 21 pp.
Genentech, Inc., Nov. 2015, Cotellic (cobimetinib) tablets, for oral use, prescribing information, 19 pp.
Gerosa et al., Nov. 18, 2020, Receptor-driven ERK pulses reconfigure MAPK signaling and enable persistence of drug-adapted BRAF-mutant melanoma cells, Cell Systems, 11:478-494.
Ghandi et al., May 23, 2019, Next-generation characterization of the cancer cell line encyclopedia, Nature, 569:503-508.
Gimple et al., Sep. 24, 2019, RAS: striking at the core of the oncogenic circuitry, Frontiers in Oncology, 9(Article 965), 16 pp.
GlaxoSmithKline, Jan. 2014, Tafinlar (dabrafenib) capsules, for oral use, prescribing information, 41 pp.
Gopalbhai et al., Mar. 7, 2003, Negative regulation of MAPKK by phosphorylation of a conserved serine residue equivalent to Ser212 of MEK1, The Journal of Biological Chemistry, 278(19):8118-8125.
Gordon et al., 2013, Regulation of muscle protein synthesis and the effects of catabolic states, Ther International Journal of Biochemistry & Cell Biology, 45:2147-2157.
Gough et al., Nov. 2013, The MEK-ERK pathway is necessary for serine phosphorylation of mitochondrial STAT3 and Ras-mediated transformation, PLOS One, 8(11):e83395, 9 pp.
Gough et al., Oct. 2, 2014, STAT3 supports experimental K-RasG12D-induced murine myeloproliferative neoplasms dependent on serine phosphorylation, Blood, 124(14):2252-2261.
Guo et al., Oct. 28, 2020, Intermittent schedules of the oral RAF-MEK inhibitor CH5126766/VS-6766 in patients with RAS/RAF-mutant solid tumours and multiple myeloma: a single-centre, open-label, phase 1 dose-escalation and basket dose expansion study, The Lancet/Oncology, https://doi.org/10.1016/S1470-2045(20)30464-2, 11 pp.
Hall et al., Nov. 2022, Cyclic disruption of the mitogen-activated protein kinase (MAPK) pathway by the dual MEK inhibitor, IMM-6-415, enhances PD-1 and CTLA-4 checkpoint blockade in RAS mutant tumors, poster presented as SITC, abstract No. 449, 1 p.
Han et al., 2013, Myostatin/activin pathway antagonism: molecular basis and therapeutic potential, The International Journal of Biochemistry & Cell Biology, 45:2333-2347.
Han et al., Mar. 1-2, 2021, Pre-clinical evaluation of a potent and orally bioavailable next-generation inhibitor targeting the family of mutants that drive oncogenic BRAF dimer formation, ESMO TAT, Poster 43P, 1 p.
Hartung et al., 2015, Modular assembly of allosteric MEK inhibitor structural elements unravels potency and feedback-modulation handles, ChemMedChem, 10:2004-2013.
Hartung et al., 2016, Optimization of allosteric MEK inhibitors. Part 2: taming the sulfamide group balances compound distribution properties, Bioorganic & Medicinal Chemistry Letters, 26:186-193.
Hatzivassiliou et al., 2013, Mechanism of MEK inhibition determines efficacy in mutant KRAS- versus BRAF-driven cancers, Nature, doi:10.1038/nature12441, 6 pp.
Heinzerling et al., 2019, Tolerability of BRAF/MEK inhibitor combinations: adverse event evaluation and management, ESMO Open, 4:e000491. doi:10.1136/esmoopen-2019-000491, 15 pp.
Hobbs et al., 2016, RAS isoforms and mutations in cancer at a glance, Journal of Cell Science, 129:1287-1292.
Hoeflich et al., Jul. 15, 2009, In vivo antitumor activity of MEK and phosphatidylinositol 3-kinase inhibitors in basal-like breast cancer models, Clin Cancer Res., 15(14):4649-4664.
Horstman et al., 2016, Is cancer cachexia attributed to impairments in basal or postprandial muscle protein metabolism?, Nutrients, 8:499, 6 pp.
Hudson et al., 2013, Calcineurin: a poorly understood regulator of muscle mass, The International Journal of Biochemistry & Cell Biology, 45:2173-2178.
Hyohdoh et al, Nov. 14, 2013, Fluorine scanning by non-selective fluorination: enhancing Raf/MEK inhibition while keeping physiochemical properties, 4(11):S1-S25.
Hyohdoh et al., 2013, Fluorine scanning by nonselective fluorination: enhancing Raf/MEK inhibition while keeping physicochemical properties, ACS Med. Chem. Lett, 4:1059-1063.
Infante et al., 2012, Safety, pharmacokinetic, pharmacodynamic, and efficacy data for the oral MEK inhibitor trametinib: a phase 1 dose-escalation trial, Lancet Oncol, 13:773-781.

(56) References Cited

OTHER PUBLICATIONS

Infantet et al., 2014, A randomised, double-blind, placebo-controlled trial of trametinib, an oral MEK inhibitor, in combination with gemcitabine for patients with untreated metastatic adenocarcinoma of the pancreas, European Journal of Cancer, http://dx.doi.org/10.1016/j.ejca.2014.04.024, 10 pp.
Ishii et al., Jul. 1, 2013, Enhanced inhibition of ERK signaling by a novel allosteric MEK inhibitor, CH5126766, that suppresses feedback reactivation of RAF activity, Cancer Res., 73(13):4050-4060.
Janes et al., Jan. 25, 2018, Targeting KRAS mutant cancers with a covalent G12C-specific inhibitor, Cell, 172:578-589.
Joassard et al., 2013, ?2-adrenergic agonists and the treatment of skeletal muscle wasting disorders, The International Journal of Biochemistry & Cell Biology, 45:2309-2321.
Johns et al., 2013, Muscle wasting in cancer, The International Journal of Biochemistry & Cell Biology, http://dx.doi.org/10.1016/j.biocel.2013.05.032, 15 pp.
Johns et al., 2017, New genetic signatures associated with cancer cachexia as define by low skeletal muscle index and weight loss, Journal of Cachexia, Sarcopenia and Muscle, 8:122-130.
Kanojia et al., 2004, A facile synthesis of an unsymmetric benzopyranobenzopyran ring system, Tetrahedron Letters, 45:5837-5839.
Kargul et al., Muscle atrophy: from molecular pathways to clinical therapy, The International Journal of Biochemistry & Cell Biology, 45:2119.
Kenney et al., 2021, Phase II study of selumetinib, an orally active inhibitor of MEK1 and MEK2 kinases, in KRASG12R-muitant pancreatic ductal adenocarcinoma, Investigational New Drugs, 39:821-828.
Khan et al., 2020, Structural basis for the action of the drug trametinib at KSR-bound MEK, Nature, https://doi.org/10.1038/s41586-020-2760-4, 35 pp.
Kim et al., Aug. 2021, Oncogenic KRAS recruits an expansive transcriptional network through mutant p53 to drive pancreatic cancer metastasis, Cancer Discovery, pp. 2095-2011.
Kir et al., Sep. 2016, Cachexia and brown fat: a burning issue in cancer, Trends in Cancer, 2(9):461-463.
Kwon et al., Jun. 2009, What is a meaningful change in physical performance? Findings from a clinical trial in older adults (the life-p study), J. Nutr Health Aging, 13(6):538-544.
Langen et al., 2013, Triggers and mechanisms of skeletal muscle wasting in chronic obstructive pulmonary disease, The International Journal of Biochemistry & Cell Biology, http://dx.doi.org/10.1016/j.biocel.2013.06.015, 12 pp.
Lapins et al., 2018, A confidence predictor for logD using conformal regression and a support-vector machine, Journal of Cheminformatics, 10:17, 10 pp.
Lavoie et al., Feb. 22, 2018, MEK drives BRAF activation through allosteric control of KSR proteins, Nature, 554:549-553 with additional material.
Lavoie et al., May 2015, Regulation of RAF protein kinases in ERK signaling, Nature Reviews/Molecular Cell Biology, 16:281-298.
Ledford, Apr. 16, 2015, The RAS renaissance: thirty years of pursuit have failed to yield a drug to take on one of the deadliest families of cancer-causing proteins. Now some researchers are taking another shot, Nature, 520:278-280.
Lee et al., Apr. 15, 2010, Preclinical development of ARRY-162, a potent and selective MEK 1/2 inhibitor, Abtract #2515, poster presentation, Cancer Res., 79(8_Supplement):2515.
Lee et al., Dec. 14, 2020, Dosing of BRAF and MEK inhibitors in melanoma: no point in taking a break, Cancer Cell, 38:779-781.
Leijen et al., Sep. 1, 2012, Phase 1 dose-escalation study of the safety, pharmacokinetics, and pharmacodynamics of the MEK inhibitor RO4987655 (CH4987655) in patients with advanced solid tumors, Clinical Cancer Research, 18(17):4794-4805.
Leonetti et al., 2004, Design, synthesis, and 3D QSAR of novel potent and selective aromatase inhibitors, J. Med. Chem., 47(27):6792-6803.
Leung et al., Jan. 2019, Hyperactivation of MAPK signaling is deleterious to RAS/RAF-mutant melanoma, Molecular Cancer Research, 17(1):199-211.
Li et al., 2007, Synthesis of tetracyclic heterocompounds as selective estrogen receptor modulators. Part 1. Process development for scale-up of 2,5,8-substituted 5,11-dihydrochromeno[4,3-c]chromene derivatives, Organic Process Research & Development, 11(3):414-421.
Lim et al., 2020, Development and progression of cancer cachexia: perspectives from bench to bedside, Sports Medicine and Health Science, 2:177-185.
Lim et al., Jun. 15, 2001, Regulation of Stat3 activation of MEK kinase 1, The Journal of Biological Chemistry, 276(24):21004-21011.
Lito et al., May 12, 2014, Disruption of CRAF-mediated MEK activation is required for effective MEK inhibition in KRAS mutant tumors, Cancer Cell, 25:697-710.
Liu et al., 2019, IMB0901 inhibits muscle atrophy induced by cancer cachexia through MSTN signaling pathway, Skeletal Muscle, 9:8, 14 pp.
Livingstone et al., 2014, BRAF, MEK and KIT inhibitors for melanoma: adverse events and their management, Chin Clin Oncol, 3(3):29, 18 pp.
Loumaye et al., Biomarkers of cancer cachexia, Clinical Biochemistry, 50:1281-1288.
Majmundar et al., Jan. 2012, O2 regulates skeletal muscle progenitor differentiation through phosphatidylinositol 3-kinase/AKT signaling, Molecular and Cellular Biology, 32(1):36-49.
Marg et al., 2014, Human satellite cells have regenerative capacity and are genetically manipulable, The Journal of Clinical Investigation, 124(10):4257-4265.
Marshall, Jan. 27, 1995, Specificity of receptor tyrosine kinase signaling: transient versus sustained extracellular signal-regulated kinase activation, Cell, 80:179-185.
Martinez-Garcia et al., Sep. 1, 2012, First-in-human, phase 1 dose-escalation study of the safety, pharmacokinetics, and pharmacodynamics of RO5126766, a first-in-class dual MEK/RAF inhibitor in patients with solid tumors, Clinical Cancer Research, 18(17):4806-4819.
Marzetti et al., 2013, Mitochondrial dysfunction and sarcopenia of aging: from signaling pathways to clinical trials, The International Journal of Biochemistry & Cell Biology, 45:2288-2301.
McDermott et al., Allosteric MEK1/2 inhibitors for the treatment of cancer: an overview, Journal of Drug Research and Development, 1(1): http://dx.doi.org/10.16966/2470-1009.101, 9 pp.
McKay et al., Jul. 7, 2009, Signaling dynamics of the KSR1 scaffold complex, PNAS, 106(27):11022-11027.
Meier et al., Mar. 28, 2017, Stress-induced dynamic regulation of mitochondrial STAT3 and its association with cyclophilin D reduce mitochondrial ROS production, 10:eaag2588, 15 pp.
Meirson et al., 2020, Safety of BRAF+MEK inhibitor combinations; sever adverse event evaluation, Cancers, 12:1650, 16 pp.
Michailovici et al., 2014, Nuclear to cytoplasmic shuttling of ERK promotes differentiation of muscle stem/progenitor cells, Stem Cells and Regeneration, 141:2611-2620.
Michalek et al., 2011, Cutting edge: distinct glycolytic and lipid oxidative metabolic programs are essential for effector and regulatory CD4+ T cell subsets, J Immunol, 186:3299-3303.
Moore et al., RAS-targeted therapies: is the undruggable drugged?, Nature Reviews/Drug Discovery, https://doi.org/10.1038/s41573-020-0068-6, 20 pp.
Mulligan et al., Jan. 2014, Mutation of NRAS but not KRAS significantly reduced myeloma sensitivity to single-agent bortezomib therapy, Blood, 123(5):632-639.
Murgia et al., 2015, Single muscle fiber proteomics reveals unexpected mitochondrial specialization, EMBO Reports, 16(3):387-395.
Murgia et al., Jun. 13, 2017, Single muscle fiber proteomics reveals fiber-type-specific features of human muscle aging, Cell Reports, 19:2396-2409.
Murton et al., Resistance exercise and the mechanisms of muscle mass regulation in humans: Acute effects on muscle protein turnover and the gaps in our understanding of chronic resistance

(56) References Cited

OTHER PUBLICATIONS exercise training adaptation, The International Journal of Biochemistry & Cell Biology, 45:2209-2214.
Nakamichi et al., 2015, Phase I and pharmacokinetics/pharmacodynamics study of the MEK inhibitor RO4987655 in Japanese patients with advanced solid tumors, Invest New Drugs, 33:641-651.
Narita et al., Apr. 2014, Novel ATP-Competitive MEK Inhibitor E6201 Is Effective against Vemurafenib- Resistant Melanoma Harboring the MEK1-C121S Mutation in a Preclinical Model, Molecular Cancer Therapeutics, 13(4):823-832.
Nollmann et al., 2020, Targeting mutant KRAS in pancreatic cancer: futile of promising?, Biomedicines, 8:281, 15 pp.
Novartis Pharmaceuticals Corporation, Jun. 2022, Mekinist® (trametinib) tablets, for oral use, prescribing information, 40 pp.
Nussinov et al., Nov. 15, 2019, Does Ras activate Raf and PI3K allosterically?, Frontiers in Oncology, 9(Article 1231):1-10.
Onion et al., Apr. 2016, 3-Dimensional Patient-Derived Lung Cancer Assays Reveal Resistance to Standards-of-Care Promoted by Stromal Cells but Sensitivity to Histone Deacetylase Inhibitors, Molecular Cancer Therapeutics, 15(4):753-763.
Pacetti et al., Association of AKT1 and SELP polymorphisms with cachexia and survival of patients with Pancreatic cancer, PowerPoint presentation, 14 pp.
Pardoll, Apr. 2012, The blockage of immune checkpoints in cancer immunotherapy, Nature Reviews, 12:252-264.
Patel et al., 2017, Population pharmacokinetics of selumetinib and its metabolite n-desmethyl-selumetinib in adult patients with advanced solid tumors and children with low-grade gliomas, CPT Pharmacometrics Syst. Pharmacol., 6:305-314.
Patel et al., 2020, Application and impact of human dose projection from discovery to early drug development, AAPS PharmSciTech, 21:44, 9 pp.
Patricelli et al., Jun. 24, 2011, In situ kinase profiling reveals functionally relevant properties of native kinases, Chem Biol., 18(6):699-710.
Perera et al., May 2006, Meaningful change and responsiveness in common physical performance measures in older adults, JAGS, 54(5):743-749.
Philpott et al., 2017, The NF1 somatic mutational landscape in sporadic human cancers, Human Genomics, 11:13, 19 pp.
Polge et al., 2013, Deciphering the ubiquitin proteome: Limits and advantages of high throughput global affinity purification-mass spectrometry approaches, The International Journal of Biochemistry & Cell Biology, 45:2136-3146.
Poli et al., Jun. 8, 2015, STAT3-mediated metabolic reprograming in cellular transformation and implications for drug resistance, Frontiers in Oncology, 5(Article 121):1-9.
Poon et al., 2017, The MEK inhibitor selumetinib complements CTLA-4 blockade by reprogramming the tumor immune microenvironment, Journal for Immuno Therapy of Cancer, 5:63.
Porporato et al., Mar. 2018, Mitochondrial metabolism and cancer, Cell Research, 28(3):265-280.
Prado et al., 2012, Skeletal muscle anabolism is a side effect of therapy with the MEK inhibitor: selumetinib in patients with cholangiocarcinoma, British Journal of Cancer, 106:1583-1586.
Pratilas et al., Mar. 17, 2009, V600EBRAF is associated with disabled feedback inhibition of RAF-MEK signaling and elevated transcriptional output of the pathway, PNAS, 106(11):4519-4524.
Prior et al., Jul. 15, 2020, The frequency of RAS mutations in cancer, Cancer Res., 84(14):2969-2974.
Proietti et al., 2020, Mechanisms of acquired BRAF inhibitor resistance in melanoma: a systematic review, Cancers, 12:2801, 28 pp.
Purvis et al., Feb. 28, 2013, Encoding and decoding cellular information through signaling dynamics, Cell, 152:945-956.
Qu et al., 2016, Fatty acid oxidation and carnitine palmitoyltransferase I: emerging therapeutic targets in cancer, Cell Death and Disease, 7:e2226, doi:10.1038/cddis.2016.132, 9 pp.
Rincon et al. 2018, A new perspective: mitochondrial STAT3 as a regulator for lymphocyte function, Int. J. Mol. Sci., 19:1656, 14 pp.
Ritz et al., Dec. 30, 2015, Dose-response analysis using R, PLOS One, 10(12):e0146021, 13 pp.
Rommel et al., Nov. 26, 1999, Differentiation Stage-Specific Inhibition of the Raf-MEK-ERK Pathway by Akt, Science, 286:1738-1741.
Rosen et al., A first-in-human phase I study to evaluate the MEK1/2 inhibitor, cobimetinib, administered daily in patients with advanced solid tumors, Invest New Drugs, DOI 10.1007/s10637-016-0374-3, 10 pp.
Roskoski, 2012, MED 1/2 dual-specificity protein kinases; structure and regulation, Biochemical and Biophysical Research Communications, 417:5-10.
Sala et al., May 2016, STAT3 signaling as a potential target to treat muscle-wasting diseases, Curr Opin Clin Nutr Metab Care. 19(3):171-176.
Sanchez et al., 2013, elF3f: A central regulator of the antagonism atrophy/hypertrophy in skeletal muscle, The International Journal of Biochemistry & Cell Biology, 45:2158-2162.
Sanchez-Vega et al., Apr. 5, 2018, Oncogenic signaling pathways in the cancer genome atlas, Cell, 173:321-337.
Sanclemente et al., Feb. 12, 2018, c-RAF ablation induces regression of advanced kras/trp53 mutant lung adenocarcinomas by a mechanism independent of MAPK signaling, Cancer Cell, 33:217-228.
Sandri, 2013, Protein breakdown in muscle wasting: Role of autophagy-lysosome and ubiquitin-proteasome, The International Journal of Biochemistry & Cell Biology, 45:2121-2129.
Sasser et al., Nov. 2007, Interleukin-6 is a potent growth factor for ER-?-positive human breast cancer, The FASEB Journal, 21:3763-3770.
Schakman et al., 2013, Glucocorticoid-induced skeletal muscle atrophy, The International Journal of Biochemistry & Cell Biology, http://dx.doi.org/10.1016/j.biocel.2013.05.036, 10 pp.
Shapiro ed., 2020, Next Generation Kinase Inhibitors: Moving Beyond the ATP Binding/Catalytic Sites, Springer Nature Switzerland, 224 pp.
Shen et al., Jan. 2004, Essential role of STAT3 in postnatal survival and growth revealed by mice lacking STAT3 serine 727 phosphorylation, Molecular and Cellular Biology, 24(1):407-419.
Shin et al., 2013, Wasting mechanisms in muscular dystrophy, The International Journal of Biochemistry & Cell Biology, 45:2266-2279.
Shin et al., 2020, Current insights into combination therapies with MAPK inhibitors and immune checkpoint blockade, Int. J. Mol. Sci 21(7):2531, 34 pp.
Shukla et al., 2014, Metabolic reprogramming induced by ketone bodies diminishes pancreatic cancer cachexia, Cancer & Metabolism, 2:18, 19 pp.
Smalley et al., Feb. 2018, ERK Inhibition: A new front in the War against MAPK Pathway-Driven Cancers? Cancer Discov. 8(2):140-142.
Smith et al., Apr. 12, 2018, Apalutamide treatment and metastasis-free survival in prostate cancer, The New England Journal of Medicine, 378(15):1408-1418.
Su et al., 2012, Protein tyrosine phosphatase Meg2 dephosphorylates signal transducer and activator of transcription 3 and suppresses tumor growth in breast cancer, Breast Cancer Research, 14:R38, 13 pp.
Subbiah et al., 2020, Clinical development of BRAF plus MEK inhibitor combinations, Trends in Cancer 6(9):797-810.
Sullivan et al., Feb. 2018, First-in-Class ERK1/2 Inhibitor Ulixertinib (BVD-523) in Patients with MAPK Mutant Advanced Solid Tumors: Results of a Phase I Dose-Escalation and Expansion Study, Cancer Discovery, OF1-OF12.
Szczepanek et al., Aug. 2012, Multi-tasking: nuclear transcription factors with novel roles in the mitochondria, Trends in Cell Biology, 22(8):429-437.
Talbert et al., Aug. 6, 2019, Modeling human cancer-induced cachexia, Cell Reports, 28:1612-1622.

(56) References Cited

OTHER PUBLICATIONS

Talbert et al., Feb. 2017, Dual inhibition of MEK and PI3K/Akt rescues cancer cachexia through both tumor extrinsic and intrinsic activities, Mol Cancer Ther, 16(2):344-356.
Tanaka et al., Apr. 15, 1990, Experimental cancer cachexia induced by transplantable colon 26 adenocarcinoma in mice, Cancer Research, 50:2290-2295.
Tang et al., 2014, The JAK-STAT Pathway Is Critical in Ventilator-Induced Diaphragm Dysfunction, Molecular Medicine, 20:579-589.
Tanoue et al., Feb. 2000, A conserved docking motif in MAP kinases common to substrates, activators and regulators, Nature Cell Biology, 2:110-116.
Terai et al., 2005, Ras binding opens c-Raf to expose the docking site for mitogen-activated protein kinase kinase, EMBO Reports, 6(3):251-255.
Timchenko, 2013, Molecular mechanisms of muscle atrophy in myotonic dystrophies, The International Journal of Biochemistry & Cell Biology, 45:2280-2287.
Tomkinson et al., 2017, Comparison of the Pharmacokinetics of the Phase II and Phase III Capsule Formulations of Selumetinib and the Effects of Food on Exposure: Results From Two Randomized Crossover Trials in Healthy Male Subjects, Clinical Therapeutics, 39(11):2260-2275.
Toutain et al., Plasma clearance, J. Vet. Pharmacol. Therap. 27:415-425.
Tran et al., Jul. 2021, The discovery and development of binimetinib for the treatment of melanoma, Expert Opin Drug Discov, 15(7):745-754.
Troiani et al., 2012, Intrinsic resistance to selumetinib, a selective inhibitor of MEK1/2, by cAMP-dependent protein kinase A activation in human lung and colorectal cancer cells, British Journal of Cancer, 106:1648-1659.
V. Pechmann, January 1884, Neue Bildungsweise der Cumarine, Synthese des Daphnetins. I., pp. 929-936.
Von Haehling et al., 2013, Muscle wasting in heart failure: an overview, The International Journal of Biochemistry & Cell Biology, 45:2257-2265.
Wang et al., 2013, Muscle wasting from kidney failure—A model for catabolic conditions, The International Journal of Biochemistry & Cell Biology, 45:2230-2238.
Weinberg et al., Jan. 24, 2019, Mitochondrial complex III is essential for suppressive function of regulatory T cells, Nature, 565:495-499.
Welsh et al., 2015, Management of BRAF and MEK inhibitor toxicities in patients with metastatic melanoma, Therapeutic Advances in Medical Oncology, 7(2):122-136.
Wheelwright et al., Dec. 2015, Patient-reported outcomes in cancer cachexia clinical trials, Supportive and Palliative Care, 9(4):325-332.
Wilson et al., Sep. 7, 2017, Tracing information flow from Erk to target gene induction reveals mechanisms of dynamic and combinatorial control, Molecular Cell, 67:1-13.
Wing, 2013, Deubiquitinases in skeletal muscle atrophy, The International Journal of Biochemistry & Cell Biology, http://dx.doi.org/10.1016/j.biocel.2013.05.002, 24 pp.
Winski et al., Nov. 17, 2010, 162. MEK162 (ARRY-162), a novel MEK 1/2 inhibitor, inhibits tumor growth regardless of KRas/Raf pathway mutations, Poster Session—Molecular-targeted therapies-preclinical, European Journal of Cancer Supplements, p. 56.
Witzel et al., Dec. 21, 2012, How scaffolds shape MAPK signaling: what we know and opportunities for systems approaches, Frontiers in Physiology, 3(Article 475):1-14.
Workeneh, et al., 2013, The regulation of muscle protein turnover in diabetes, The International Journal of Biochemistry & Cell Biology, 45:2239-2244.
Wu et al., Dec. 1, 2016, MEK1/2 inhibitors: molecular activity and resistance mechanisms, Semin Oncol., 42(6):849-862.
Xu et al., 2016, The role of IL-11 in immunity and cancer, Cancer Letters, http://dx.doi.org/doi: 10.1016/j.canlet.2016.01.004, 36 pp.
Xu et al., 2017, FoxO1: a novel insight into its molecular mechanisms in the regulation of skeletal muscle differentiation and fiber type specification, Oncotarget, 8(6):10662-10674.
Yang et al., 2016, Mitochondrial Stat3, the need for design thinking, Int. J. Bio. Sci., 12(5):532-544.
Yang et al., Nov. 2008, Sorafenib inhibits signal transducer and activator of transcription 3 signaling associated with growth arrest and apoptosis of medulloblastomas, Mol Cancer Ther., 7(11):3519-3526.
Yeh et al., Mar. 2, 2007, Biological characterization of ARRY-142886 (AZD6244), a potent, highly selective mitogen-activated protein kinase kinase 1/2 inhibitor, Clin Cancer Res, 13(5):1576-1583.
Yohe et al., Jul. 4, 2018, MEK inhibition induces MYOG and remodels super-enhancers in RAS-driven rhabdomyosarcoma, Sci. Transl. Med, 10:eaan4470, pp. 1-17.
Yoon et al., 2010, KRAS mutant lung cancer cells are differentially responsive to mek inhibitor due to AKT or STAT3 activation: implication for combinatorial approach, Molecular Carcinogenesis, 49:353-362.
Yoshida et al., 2013, Molecular mechanisms and signaling pathways of angiotensin II-induced muscle wasting: Potential therapeutic targets for cardiac cachexia, The International Journal of Biochemistry & Cell Biology, 45:2322-2332.
Zhan et al., 2019, MEK inhibitors activate Wnt signalling and induce stem cell plasticity in colorectal cancer, Nature Communications, https://doi.org/10.1038/s41467-019-09898-0, 17 pp.
Zhang et al., Feb. 1, 2016, The opposing function of STAT3 as an oncoprotein and tumor suppressor is dictated by the expression status of stat3b in esophageal squamous cell carcinoma, Clinical Cancer Research, 22(3):691-703.
Zhao et al., Jun. 19, 2017, Insights into the binding mode of MEK type-III inhibitors. A step towards discovering and designing allosteric kinase inhibitors across the human kinome, PLOS One, 12(6):e0179936.
Zhao et al., Nov. 10, 2021, Diverse alterations associated with resistance to KRAS(G12C) inhibition, Nature, https://doi.org/10.1038/s41586-021-04065-2, 23 pp.
Zhu et al., Aug. 23, 2016, STAT3 regulates self-renewal of adult muscle satellite cells during injury-induced muscle regeneration, Cell Reports, 16:1-14.
Zimmer et al., Aug. 15, 2014, Phase I Expansion and Pharmacodynamic Study of the Oral MEK Inhibitor RO4987655 (CH4987655) in Selected Patients with Advanced Cancer with RAS-RAF Mutations, Clinical Cancer Research, 20(16):4251-4261.
International Search Report and Written Opinion dated Jun. 11, 2021 in application No. PCT/US2021/012531.
Lipson et al., Nov. 15, 2011, Ipilimumab: an anti-CLTA-4 antibody fo metastatic melanoma, Clin Cancer Res., 17(22):6958-6962.
PubChem-CID-50922675, create date Mar. 21, 2011, Encorafenib, 45 pp.
Reita et al., 2022, Direct targeting KRAS mutation in non-small cell lung cancer: focus on resistance, Cancers, 14:1321.
Tomalik-Scharte et al., 2009, Plasma 4beta-Hydroxycholesterol: An Endogenous CYP3A Metric?, Clinical Pharmacology and Therapeutics, 86(2):147-153.
Ung et al., Dec. 8, 2019, Data-driven identification and optimization of new medicines to cancel cancer cachexia, 12th International Conference on Cachexia, Sarcopenia & Muscle Wasting, presentation, 12 pp.
Ung et al., Dec. 8-10, 2017, Cachexia mechanisms in cancer through the lens of transcriptomics, 10th International SCWD Conference, poster, 1 p.
Ung et al., Sep. 16, 2018, Data-driven identification and optimization of new medicines for cancer cachexia, presentation, 17 pp.
Verastem Oncology, May 24, 2024, Verastem Oncology Announces the Initiation of a Rolling Submission of NDA to FDA Seeking Accelerated Approval of Avutometinib and Defactinib Combination for the Treatment of Adult Patients with Recurrent KRAS Mutant Low-Grade Serous Ovarian Cancer, press release, https://investor.verastem.com/news-releases/news-release-details/verastem-oncology-announces-initiation-rolling-submission-nda, 7 pp.

(56) References Cited

OTHER PUBLICATIONS

Wu, May 24, 2024, Verastem's stock takes a hit after sharing updated filing plans in ovarian cancer, Endpoints News, https://endpts.com/verastems-stock-takes-a-hit-after-sharing-updated-fi ling-plans-in-ovarian-cancer/, 2 pp.
King et al., Apr. 9, 2024, Activity of IMM-1-104 alone or in combination with chemotherapy in RAS-altered pancreatic cancer models, conference poster presented at AACR 2024, San Diego, CA (Apr. 9, 2024), abstract #4195, 1 p.
Ahn et al., 2017, A modified regimen of biweekly gemcitabine and nab-paclitaxel in patients with metastatic pancreatic cancer is both tolerable and effective: a retrospective analysis, Ther Adv Med Oncol, 9(2):75-82.
Chung et al., Sep. 16, 2024, Preliminary Phase 1 Safety and Activity of IMM-1-104, an Orally Dosed Universal RAS Inhibitor That Drives Deep Cyclic Inhibition of the MAPK Pathway at MEK, in Patients with Advanced Unresectable or Metastatic Solid Tumors, poster presented at ESMO Annual Conference 2024, Barcelona, Spain, 1 p.
Immuneering, Apr. 9, 2024, IMM-1-104 is Synergistic with Chemotherapy in Pancreatic Cancer Models, press release, 2 pp.
Immuneering, Feb. 20, 2024, Immuneering Receives FDA Fast Track Designation for IMM-1-104 in Pancreatic Cancer, press release, 2 pp.
Immuneering, Jul. 31, 2024, Immuneering Granted FDA Fast Track Designation for IMM-1-104 in First-line Pancreatic Cancer, press release, 2 pp.
Immuneering, Mar. 11, 2024, Immuneering Doses First Patient in Phase 2a Clinical Trial of IMM-1-104 in RAS-mutant Solid Tumors, press release, 2 pp.
Immuneering, Mar. 24, 2024, Immuneering Announces Positive Topline Results from Phase 1 Portion of its Phase 1/2a Clinical Trial of IMM-1-104 in RAS-Mutant Solid Tumors, press release, 3 pp.
Immuneering, Mar. 27, 2024, Immuneering Announces First Patient Dosed in its Phase 1/2a Trial of IMM-6-415 to Treat Advanced Solid Tumors with RAF or RAS Mutations, press release, 2 pp.
Immuneering, Sep. 12, 2024, Immuneering Announces Positive Initial Phase 2a Data Including Complete and Partial Responses with IMM-1-104 in Combination with Chemotherapy in First-Line Pancreatic Cancer Patients, press release, 3 pp.
Von Hoff et al., Oct. 31, 2013, Increased Survival in Pancreatic Cancer with nab-Paclitaxel plus Gemcitabine, N Engl J Med, 369(18)1691-1703.
De Jong et al., Nov. 13, 2024, Phase 1 Interim Population PK/PD Modeling and Recommended Phase 2 Dose Exploration for IMM-1-104, a Novel Concept Oral Deep Cyclic Inhibitor of MEK, ACoP 2024 poster, 1 p.
De Jong et al., Nov. 13, 2024, Phase 1 Interim Population PK/PD Modeling and Recommended Phase 2 Dose Exploration for IMM-1-104, a Novel Concept Oral Deep Cyclic Inhibitor of MEK, ACoP 2024 presentation, 2 pp.
Immuneering, Jan. 7, 2025, Immuneering Announces Positive Data Update from Three Pancreatic Cancer Arms of Ongoing Phase 2a Trial of IMM-1-104; Plans to Expand Trial with Additional Arms, press release, 5 pp.
King et al., Dec. 2024, Potential anti-cachexia properties of novel dual-MEK inhibitor IMM-1-104, International Conference on Sarcopenia, Cachexia & Wasting Disorders, poster, 1 p.

* cited by examiner

MEK INHIBITORS AND THERAPEUTIC USES THEREOF

BACKGROUND

Field

The present invention relates to the fields of chemistry and medicine. More particularly, the present invention relates to MEK inhibitors, techniques for designing and synthesizing such MEK inhibitors, compositions comprising MEK inhibitors, and methods of treating disease comprising administering MEK inhibitors.

Description of the Related Technology

Cancer is among the most common causes of death in the United States. In the United States, cancer has accounted for approximately one of every four deaths. The 5-year relative survival rate for cancer patients diagnosed in 1996-2003 is approximately two-thirds, up from about one half in 1975-1977 (Cancer Facts & Figures, American Cancer Society: Atlanta, Ga. (2008)). The rate of new cancer cases decreased by an average 0.6% per year among men between 2000 and 2009, but stayed the same for women. From 2000 through 2009, death rates from all cancers combined decreased on average 1.8% per year among men and 1.4% per year among women. This improvement in survival reflects progress in diagnosing at an earlier stage as well as improvements in treatment, for which there remain a need. Discovering highly effective anticancer agents with low toxicity is a primary goal of cancer research.

Furthermore, cancer-related cachexia is a debilitating condition associated with loss of muscle mass, fatigue, weakness, and loss of appetite in cancer patients. Cachexia is also associated with severe clinical consequences including muscle weakness which can result in ambulation difficulties, and pulmonary complications. Cachexia is a significant contributing factor in the death of cancer patients.

Cachexia has been characterized, in part, by depletion of skeletal muscle mass that is not reversed by conventional nutritional support, leading to pronounced weight loss that severely impacts patient morbidity and mortality. Cachexia has been identified in more than 80% of patients with gastric, pancreatic, and esophageal cancer; approximately 70% of those with head and neck cancer; and approximately 60% of patients with lung, colorectal, and prostate cancer. See, Muscle (2012) 3, 245-51. Despite the impact of cachexia on mortality among cancer patients, effective therapies have not been developed to prevent or impede the progression of cachexia. For example, more than 85% of pancreatic cancer patients, including early stage patients, are estimated to lose an average of 14% of their pre-illness weight. See, BMC Cancer, 2010 Jul. 8; 10:363. Cachectic pancreatic cancer patients are often weak and fatigued, and have a lower tolerance to therapy and more adverse outcomes to surgery. Consequently, cachexia is the main driver for mortality in pancreas cancer. Unfortunately, the 5-year survival rate for pancreatic cancer has not exceeded 6% for the last four decades, which is the lowest survival rate among all malignancies.

Substantial efforts have been invested in designing a treatment for the cachectic syndrome, but unfortunately there is no single, fully satisfactory treatment for reversing weight loss associated with cancer cachexia. The development of different therapeutic strategies has focused on two targets: counteracting anorexia and neutralizing metabolic disturbances. However, providing complete nutritional requirements by way of total parenteral nutrition does not abrogate weight loss. Instead, many drugs have been proposed and used in clinical trials, while others are still under investigation using experimental animals in order to revert metabolic alterations. See, Toledo, et al. 2014 PloS One. In one study, Selumetinib, an MEK inhibitor, was found to promote muscle gain in patients with cholangiocarcinoma. See, British Journal of Cancer, (2012), 106, 1583-1586. In another study, binimetinib, an MEK inhibitor, was found to promote muscle gain in patients with BTC. See, Inv New Drugs (2018) 36, 1037-1043.

In addition to its potential role in cachexia, MEK is a critical signaling intermediate in the MAPK/ERK pathway, which is inappropriately activated across a broad spectrum of human tumors, including those derived from lung, pancreas, ovary, skin and colon. While several MEK inhibitors have achieved regulatory approval to date, these MEK inhibitors have yet to deliver against clinical efficacy expectations. Indentification of a new class of MEK inhibitors that maximize pathologic reversal of the MAPK/ERK pathway, while limiting drug-related toxicity would have a significant impact on cancer patient morbidity and mortality.

SUMMARY OF THE DISCLOSURE

The compounds disclosed in the present application have been discovered to exhibit surprising and unexpected biological effects. These compounds are MEK inhibitors that maximize pathologic reversal of the MAPK/ERK pathway, and are effective anti-cancer and anti-cancer cachexia agents suitable for use in anti-cancer and anti-cancer cachexia pharmaceutical formulations.

Some embodiments provide for a compound having the structure of Formula (I):

(I)

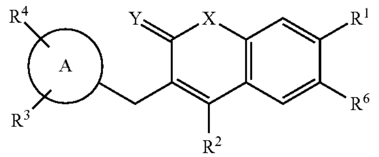

including pharmaceutically acceptable salts thereof, wherein:

Ring A is

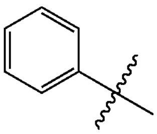, 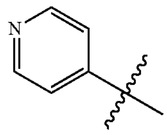,

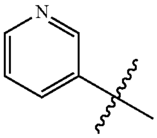, 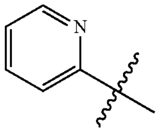, 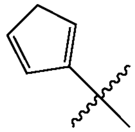,

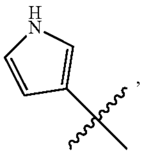, 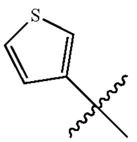, 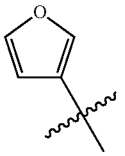,

-continued

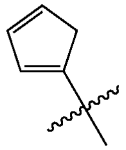, 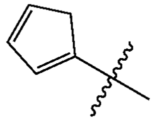, 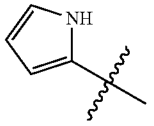,

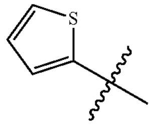, or 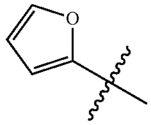;

$R^1$, $R^2$, $R^3$, $R^4$ and $R^6$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

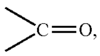, 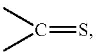, or 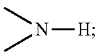;

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that R1 is not pyrimidyl.

In some embodiments of Formula (I), the Ring A is

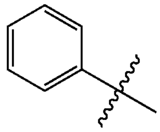, 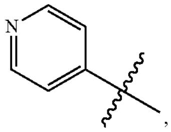, 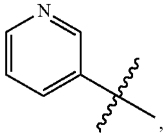, or

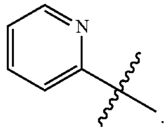.

In some embodiments, $R^2$ is $—CH_3$. In some embodiments, $R^2$ is L. In some embodiments, L is $—Z_1—Z_2$. In some embodiments, $Z_1$ is $—CH_2—$. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$. In some embodiments, $R^5$ is selected from H or $CH_3$. In some embodiments, L is $—Z_1—Z_2—Z_3$. In some embodiments, $Z_1$ is $—CH_2—$ and $Z_2$ is optionally substituted $C_3$ to $C_8$ heterocyclyl, and $Z_3$ is $—CH_2$-(optionally substituted aryl). In some embodiments, $Z_1$ is $—CH_2—$ and $Z_2$ is optionally substituted

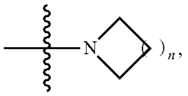, wherein n is 1, 2, 3 or 4. In some embodiments, $Z_1$ is $—CH_2—$ and $Z_2$ is optionally substituted

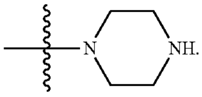.

Some embodiments provide a compound of Formula (Ia):

(Ia)

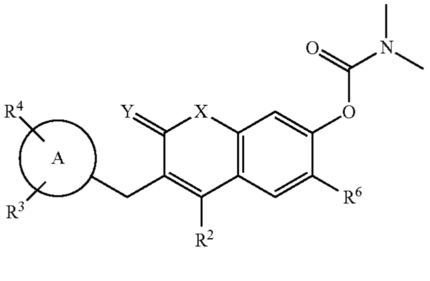

including pharmaceutically acceptable salts thereof, wherein:

Ring A is

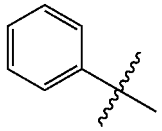, 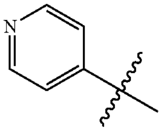,

-continued

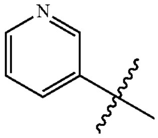, 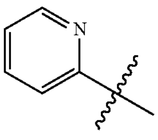, 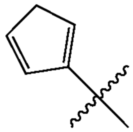, 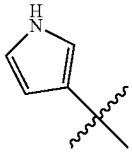, 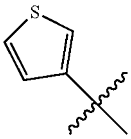, 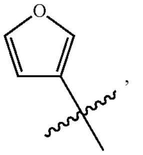, 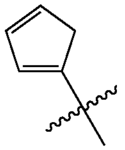, 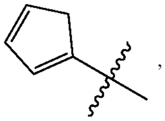, 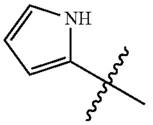, 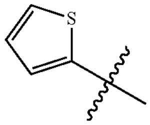, or 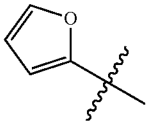;

$R^2$, $R^3$, $R^4$ and $R^6$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

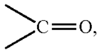, 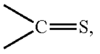, or 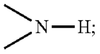;

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

In some embodiments of Formula (Ia), the Ring A is

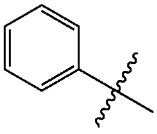, 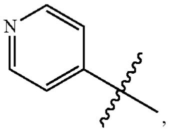, 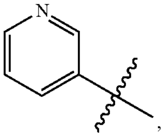, or 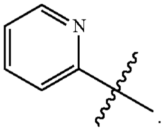.

In some embodiments, $R^2$ is $—CH_3$. In some embodiments, $R^2$ is L. In some embodiments, L is $—Z_1—Z_2$. In some embodiments, $Z_1$ is $—CH_2—$. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$. In some embodiments, $R^5$ is selected from H or $CH_3$. In some embodiments, L is $—Z_1—Z_2—Z_3$. In some embodiments, $Z_1$ is $—CH_2—$, $Z_2$ is optionally substituted $C_3$ to $C_8$ heterocyclyl, and $Z_3$ is $—CH_2$-(optionally substituted aryl). In some embodiments, $Z_1$ is $—CH_2—$ and $Z_2$ is optionally substituted

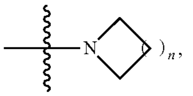

wherein n is 1, 2, 3 or 4. In some embodiments, $Z_1$ is $—CH_2—$ and $Z_2$ is optionally substituted

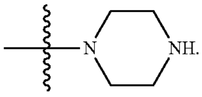 [SMILES: *N1CCNCC1]

Some embodiments provide a compound of Formula (Ib):

(Ib)

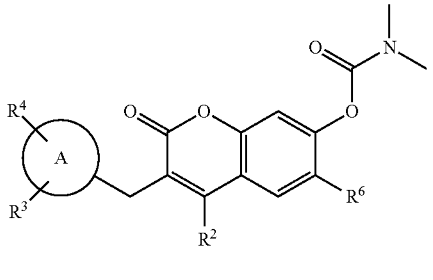

including pharmaceutically acceptable salts thereof, wherein:

Ring A is

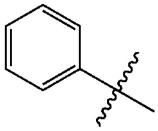, 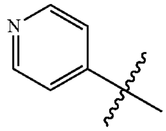, 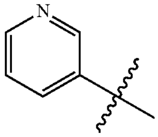, 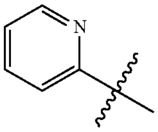, 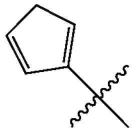, 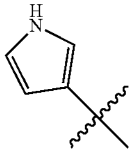, 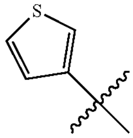, 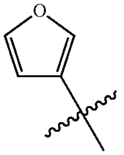, 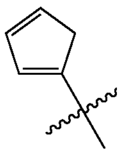, 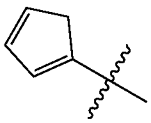, 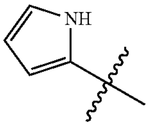, 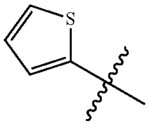, or 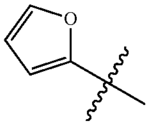;

$R^2$, $R^3$, $R^4$ and $R^6$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

L is $—Z_1—Z_2$ or $—Z_1—Z_2—Z_3$;

$Z_1$, $Z_2$, and $Z_3$ are independently $—CH_2$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and with the proviso that $R^1$ is not pyrimidyl.

In some embodiments of Formula (Ib), the Ring A is

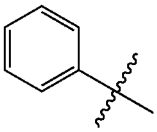, 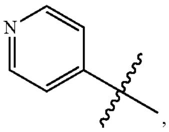, 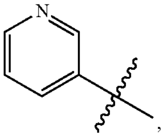, or 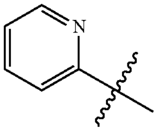.

In some embodiments, $R^2$ is $—CH_3$. In some embodiments, $R^2$ is L. In some embodiments, L is $—Z_1—Z_2$. In some embodiments, $Z_1$ is $—CH_2—$. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$. In some embodiments, $R^5$ is selected from H or $CH_3$. In some embodiments, L is $—Z_1—Z_2—Z_3$. In some embodiments, $Z_1$ is $—CH_2—$, $Z_2$ is optionally substituted $C_3$ to $C_8$ heterocyclyl, and $Z_3$ is $—CH_2$-(optionally substituted aryl).

Some embodiments provide a compound of Formula (Ic):

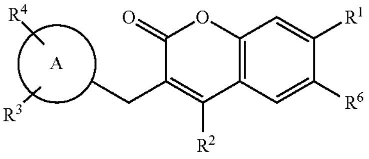

(Ic)

including pharmaceutically acceptable salts thereof, wherein:

Ring A is

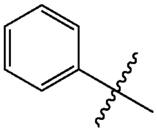, 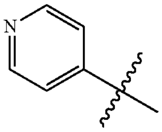, 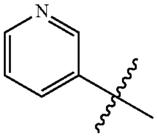, 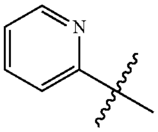, 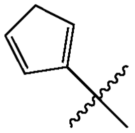,

-continued

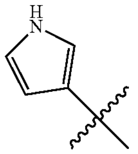, 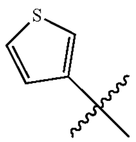, 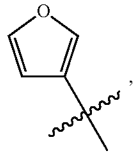, 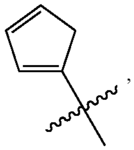, 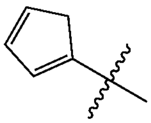, 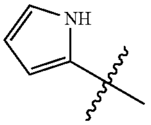, 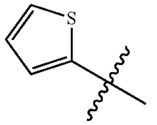, or 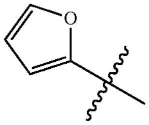;

$R^1$, $R^2$, $R^3$, $R^4$, and $R^6$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

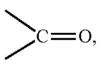, 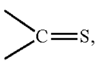, or 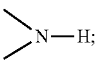;

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

In some embodiments of Formula (Ic), the Ring A is

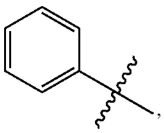, 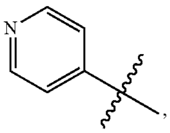, 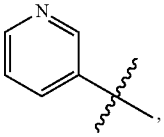, or 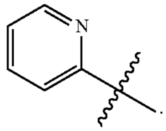.

In some embodiments, $R^2$ is $—CH_3$. In some embodiments, $R^2$ is L. In some embodiments, L is $—Z_1—Z_2$. In some embodiments, $Z_1$ is $—CH_2—$. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$. In some embodiments, $R^5$ is selected from H or $CH_3$. In some embodiments, L is $—Z_1—Z_2—Z_3$. In some embodiments, $Z_1$ is $—CH_2—$, $Z_2$ is optionally substituted $C_3$ to $C_8$ heterocyclyl, and $Z_3$ is $—CH_2$-(optionally substituted aryl). In some embodiments, $Z_1$ is $—CH_2—$ and $Z_2$ is optionally substituted

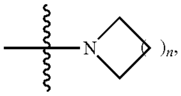

wherein n is an integer selected from 1, 2, 3 and 4. In some embodiments, $Z_1$ is $—CH_2—$ and $Z_2$ is optionally substituted

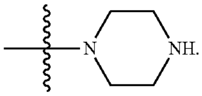 [SMILES: *N1CCNCC1]

A compound of Formula (I), having the structure depicted in Formula (Id):

(Id)

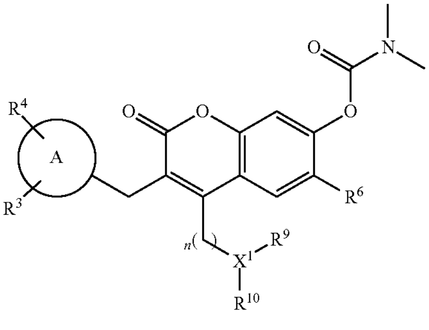

including pharmaceutically acceptable salts thereof, wherein:

Ring A is

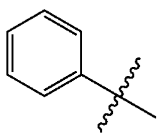 , 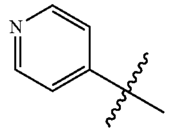 ,

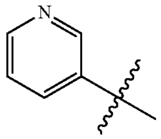 , 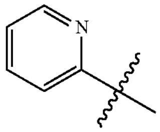 , 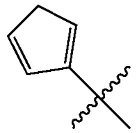 ,

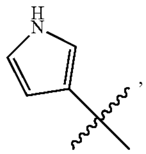 , 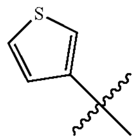 , 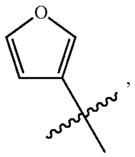 ,

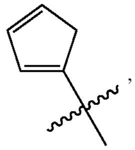 , 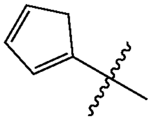 , 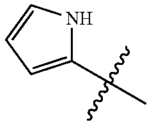 ,

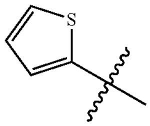 , or 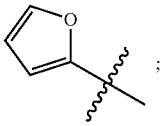 ;

$R^3$ and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, and L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

$R^9$ and $R^{10}$ are each independently selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

$X^1$ is selected from the group consisting of CH, B, N, or $PO_4$;

n is selected from 1, 2, 3, or 4;

each $R^5$ and $R^{5'}$ is independently selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_3$ to $C_{10}$ heteroaryl; and Y is $CH_2$, NH, or O, with the proviso that $R^1$ is not pyrimidyl.

In some embodiments, n is 1 or 2. In some embodiments, wherein $X^1$ is CH or N. In some embodiments, $R^9$ is selected from optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl. In some embodiments, $R^{10}$ is selected from optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

Some embodiments provide a compound of Formula (II):

(II)

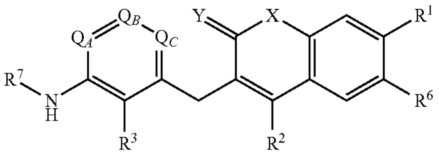

including pharmaceutically acceptable salts thereof, wherein:

$Q_A$, $Q_B$, $Q_C$ are independently C or N;

$R^1$, $R^2$, $R^3$, $R^6$, and $R^7$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

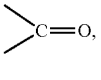, 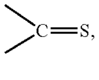, or 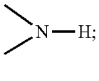;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^5$, —NH(CO)—, —(CO)NH—, —(CO)$NR^5R^5$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N, with the proviso that $R^1$ is not pyrimidyl.

In some embodiments of Formula (II), $R^2$ is —$CH_3$. In some embodiments, $R^2$ is L. In some embodiments, L is —$Z_1$—$Z_2$. In some embodiments, $Z_1$ is —$CH_2$—. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^5$, —$CH_2CH$, or —$CH_2CN$. In some embodiments, $R^5$ is selected from H or $CH_3$. In some embodiments, L is —$Z_1$—$Z_2$—$Z_3$. In some embodiments, $Z_1$ is —$CH_2$—, $Z_2$ is optionally substituted $C_3$ to $C_8$ heterocyclyl, and $Z_3$ is —$CH_2$-(optionally substituted aryl). In some embodiments, $Z_1$ is —$CH_2$— and $Z_2$ is optionally substituted

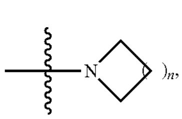

wherein n an integer selected from is 1, 2, 3, and 4. In some embodiments, $Z_1$ is —$CH_2$— and $Z_2$ is optionally substituted

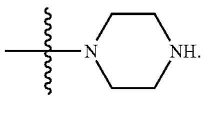 [SMILES: *N1CCNCC1]

Some embodiments provide a compound of Formula (IIa):

(IIa)

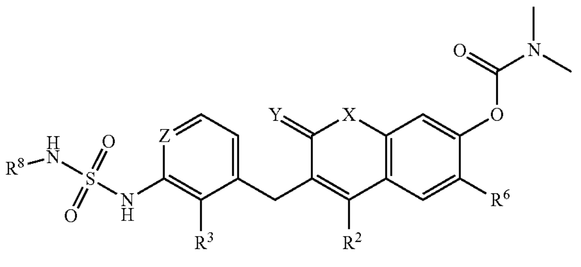

including pharmaceutically acceptable salts thereof, wherein:

$R^2$, $R^3$, $R^6$ and $R^8$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

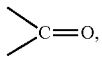 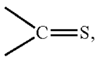 or 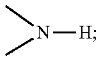

L is —$Z_1$—$Z_2$ or —$Z_1$—$Z_2$—$Z_3$;

$Z_1$, $Z_2$, and $Z_3$ are independently selected from halo, —$CH_2$, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each of $R^5$ and $R^{5'}$ is independently selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N.

In some embodiments of Formula (IIa), $R^2$ is —$CH_3$. In some embodiments, $R^2$ is L. In some embodiments, L is —$Z_1$—$Z_2$. In some embodiments, $Z_1$ is —$CH_2$—. In some embodiments, $Z_2$ is selected from optionally substituted $C_3$ to C8 cycloalkyl, optionally substituted $C_3$ to $C_8$ heterocyclyl, optionally substituted $C_3$ to $C_8$ heteroaryl, —$NR^5R^5$, —$CH_2CCH$, or —$CH_2CN$. In some embodiments, $R^5$ is selected from H or $CH_3$. In some embodiments, L is —$Z_1$—$Z_2$—$Z_3$. In some embodiments, $Z_1$ is —$CH_2$—, $Z_2$ is optionally substituted $C_3$ to $C_8$ heterocyclyl, and $Z_3$ is —$CH_2$-(optionally substituted aryl). In some embodiments, $Z_1$ is —$CH_2$— and $Z_2$ is optionally substituted

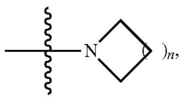

wherein n is selected from 1, 2, 3 and 4. In some embodiments, $Z_1$ is —$CH_2$— and $Z_2$ is optionally substituted

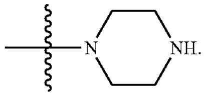 [SMILES: *N1CCNCC1]

Some embodiments provide a structure depicted in Formula (IIb):

(IIb)

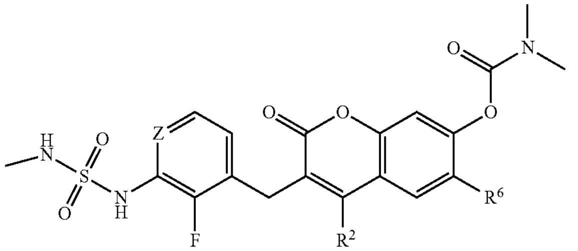

including pharmaceutically acceptable salts thereof, wherein:

$R^2$ is L;

$R^6$ is H, deuterium, halo, or optionally substituted $C_1$ to $C_6$ alkyl;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2$CCH, —$CH_2$CN, —$NR^5R^5$, —NH(CO)—, —(CO)NH—, —(CO)$NR^5R^5$—, —NH—$SO_2$—, —$SO_2$—NH—, —$R^5CH_2$—, —$R^5$O—, —$R^5$S—, $R^5$—S═O, —$R^5SO_2$—, $R^5$—C═O, —$R^5CO_2$—, —$R^5$NH—, —$R^5$NH(CO)—, —$R^5$(CO)NH—, —$R^5$NH—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Z is C or N.

In some embodiments of Formula (IIb), L is —$Z_1$—$Z_2$. In some embodiments, $Z_1$ is —$CH_2$—. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^5$, —$CH_2$CCH, or —$CH_2$CN. In some embodiments, $R^5$ is selected from H or $CH_3$. In some embodiments, L is —$Z_1$—$Z_2$—$Z_3$. In some embodiments, $Z_1$ is —$CH_2$—, $Z_2$ is optionally substituted $C_3$ to $C_8$ heterocyclyl, and $Z_3$ is —$CH_2$-(optionally substituted aryl). In some embodiments, $Z_1$ is —$CH_2$— and $Z_2$ is optionally substituted

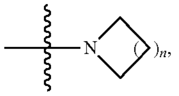

wherein n is 1, 2, 3 or 4. In some embodiments, $Z_1$ is —$CH_2$— and $Z_2$ is optionally substituted

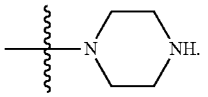

In some embodiments, a compound of Formula (II) is represented by the structure of Formula (IIc):

(IIc)

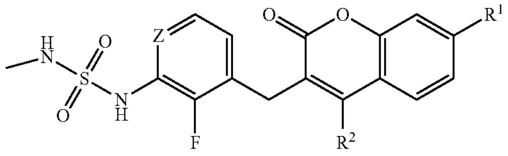

including pharmaceutically acceptable salts thereof, wherein:

$R^1$ and $R^2$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

L is —$Z_1$—$Z_2$ or —$Z_1$—$Z_2$—$Z_3$;

$Z_1$, $Z_2$, and $Z_3$ are independently —$CH_2$, —O—, —S—, S═O, —$SO_2$—, C═O, —$CO_2$—, —$NO_2$, —NH—, —$CH_2$CCH, —$CH_2$CN, —$NR^5R^{5'}$, —NH(CO)—, —(CO)NH—, —(CO)$NR^5R^{5'}$—, —NH—$SO_2$—, —$SO_2$—NH—, —$R^5CH_2$—, —$R^5$O—, —$R^5$S—, $R^5$—S═O, —$R^5SO_2$—, $R^5$—C═O, —$R^5CO_2$—, —$R^5$NH—, —$R^5$NH(CO)—, —$R^5$(CO)NH—, —$NHCH_2$CO—, —$R^5$NH—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)NH$R^5$—, —NH—$SO_2R^5$—, —$SO_2$—NH$R^5$—, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Z is C or N, with the proviso that $R^1$ is not pyrimidyl.

In some embodiments, $R^2$ is not —$CH_3$. In some embodiments, $R^2$ is L. In some embodiments, L is —$Z_1$—$Z_2$. In some embodiments, $Z_1$ is —$CH_2$—. In some embodiments, $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CCH$, or —$CH_2CN$. In some embodiments, $R^5$ and $R^{5'}$ are each selected from H or $CH_3$. In some embodiments, L is —$Z_1$—$Z_2$—$Z_3$. In some embodiments, $Z_1$ is —$CH_2$—, $Z_2$ is selected from N or an optionally substituted $C_3$ to $C_8$ heterocyclyl, and $Z_3$ is selected optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

In some embodiments, a compound of Formula (II) is represented by the structure of Formula (IId):

(IId)

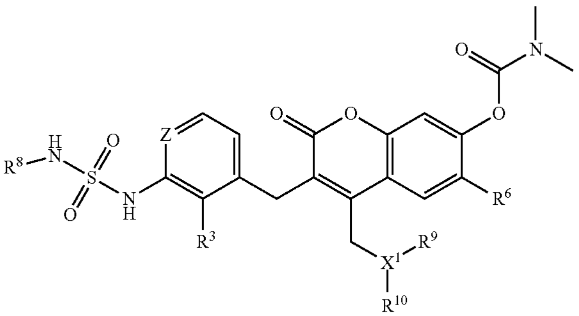

including pharmaceutically acceptable salts thereof, wherein:

$R^3$ is selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

$R^8$ selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_3$ to $C_{10}$ heteroaryl;

$R^9$ and $R^{10}$ are each independently selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl); and $X^1$ is selected from the group consisting of CH, B, N.

In some embodiments, $R^3$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

In some embodiments, $R^6$ is selected from H, deuterium, hydroxyl, halogen, cyano, nitro, optionally substituted amino, optionally optionally substituted $C_1$ to $C_6$ alkoxy, optionally substituted $C_1$ to $C_6$ alkyl.

In some embodiments, $R^8$ is selected from H, deuterium, hydroxyl, halogen, cyano, nitro, optionally substituted amino, optionally optionally substituted $C_1$ to $C_6$ alkoxy, optionally substituted $C_1$ to $C_6$ alkyl.

In some embodiments, $R^9$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

In some embodiments, $R^{10}$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

In some embodiments, a compound Formula (I), (Ia), (Ib), (Ic), (Id), (II), (IIa), (IIb), (IIc), or (IId) is selected from a compound of Table A. In some embodiments, a compound of Formula (I) or Formula (II) is selected from the group consisting of:

-continued
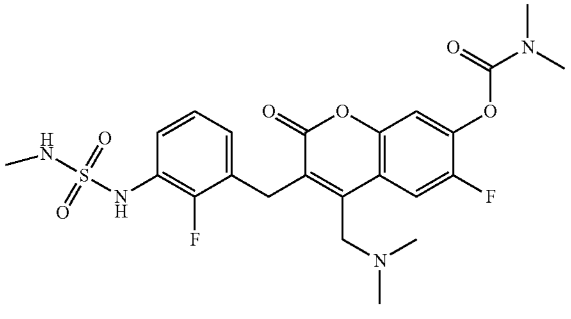
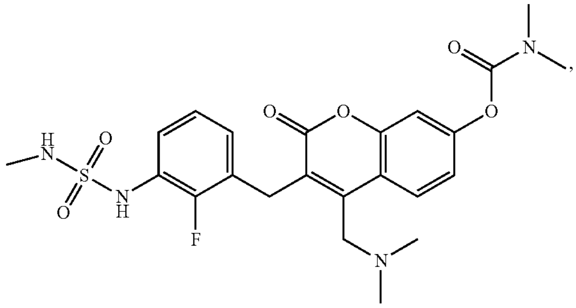
,
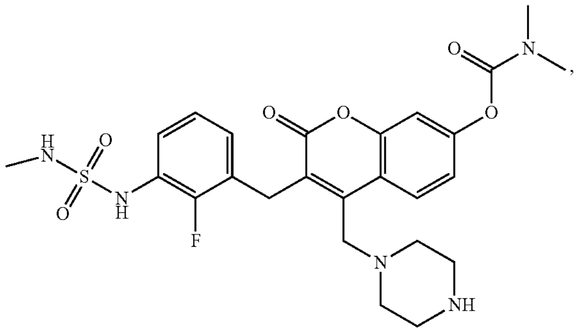
,
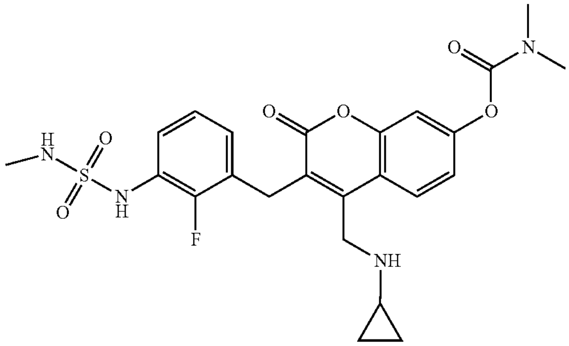
,
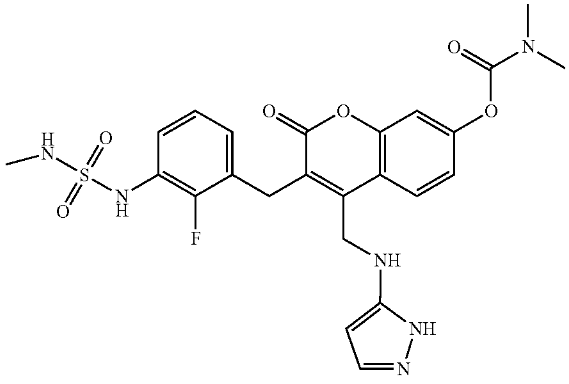
,
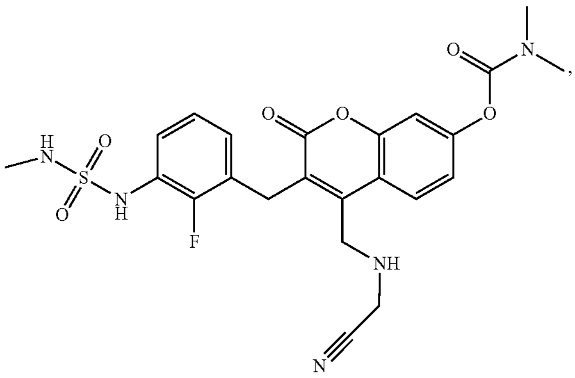
,
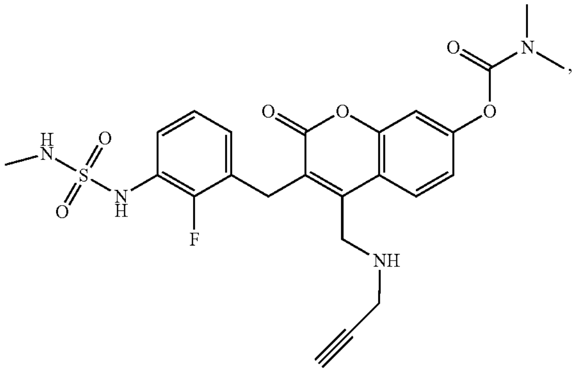
,
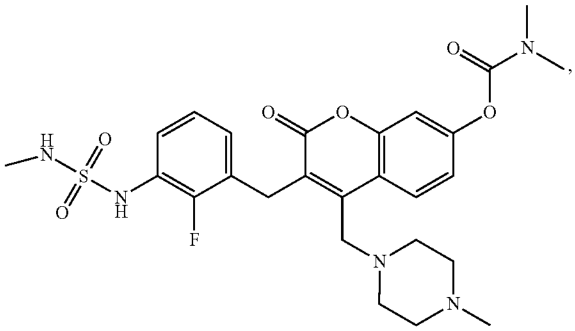
,
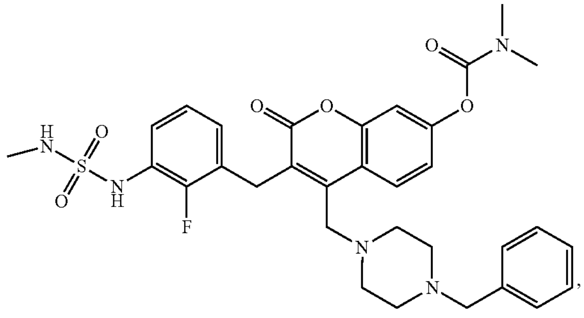
,
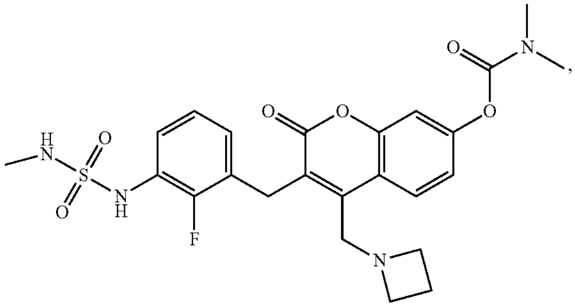
, -continued

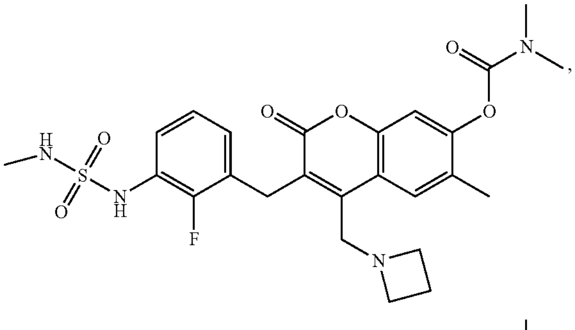

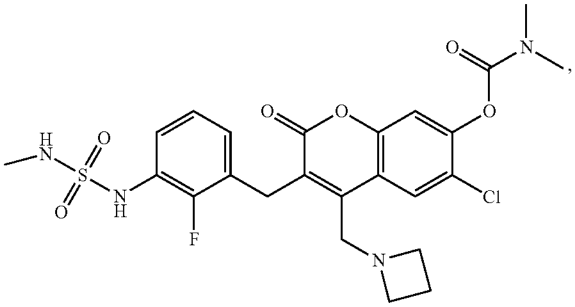

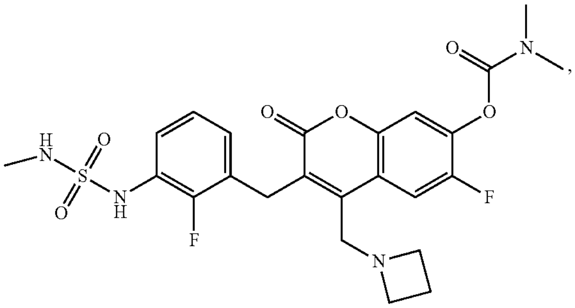

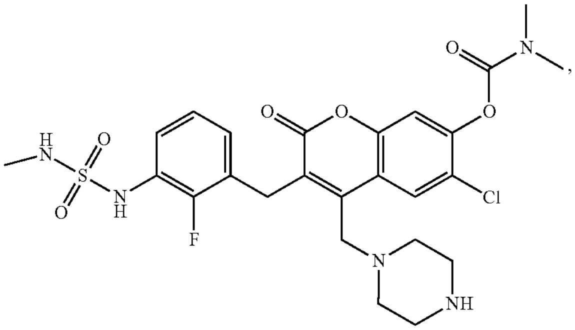

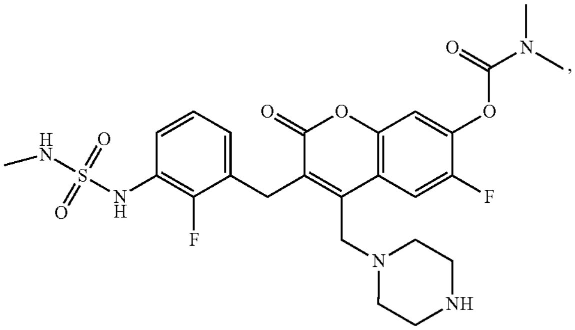

-continued

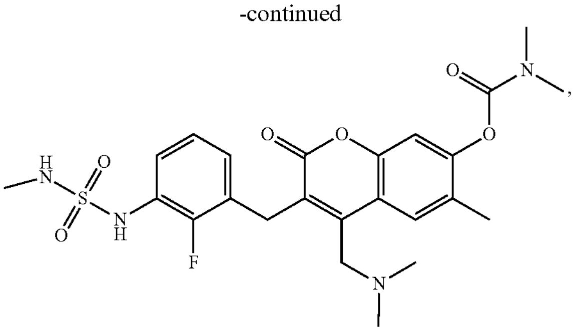

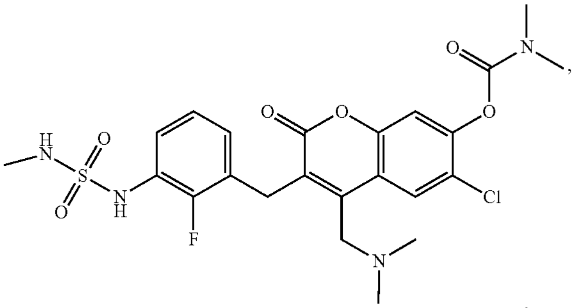

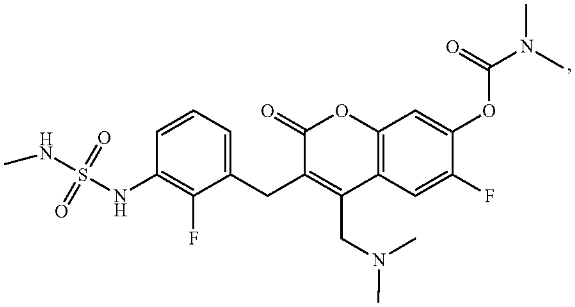

and pharmaceutically acceptable salts thereof.

In some embodiments, the pharmaceutically acceptable salt is an alkaline metal salt or an ammonium salt.

Some embodiments provide a pharmaceutical composition comprising a therapeutically effective amount of at least one compound having the structure of the Formula (I):

1.

(I)

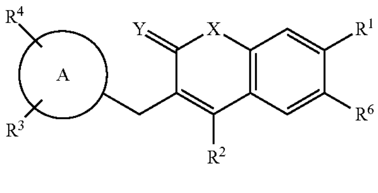

including pharmaceutically acceptable salts thereof, wherein:

Ring A is

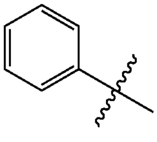
,
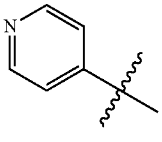
,

-continued

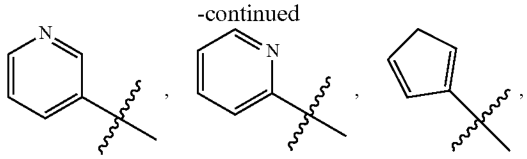

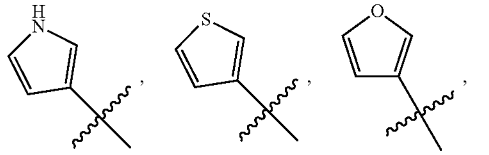

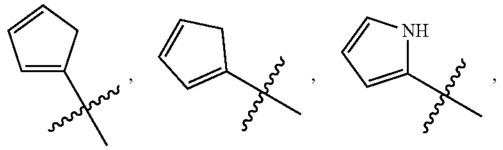

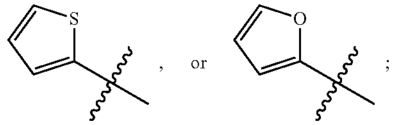

$R^1$, $R^2$, $R^3$, $R^4$, and $R^6$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

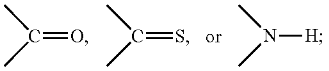

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

Some embodiments provide a pharmaceutical composition comprising a therapeutically effective amount of at least one compound having the structure of the Formula (II):

2.

(II)

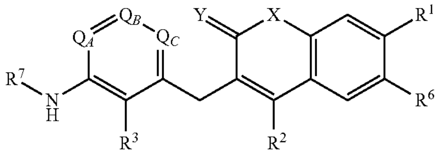

including pharmaceutically acceptable salts thereof, wherein:

$Q_A$, $Q_B$, $Q_C$ are independently C or N;

$R^1$, $R^2$, $R^3$, $R^6$, and $R^7$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

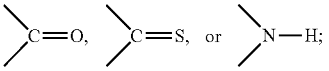

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N, with the proviso that $R^1$ is not pyrimidyl.

Some embodiments relate to a method of treating a mammal having a disease or disorder. In some embodiments, the method includes administering to the mammal a therapeutically effective amount of a compound as described herein. Some embodiments relate to a method of treating a mammal having a disease or disorder. In some embodiments, the method includes administering to the mammal a therapeutically effective amount of a pharmaceutical composition as described herein. In some embodiments, the mammal is a human. In some embodiments, the method further includes administering to the mammal an additional medicament. In some embodiments, the method includes administering to a subject suffering from said disease or disorder an effective amount of a compound of any one of the compounds as described herein or a pharmaceutically acceptable salt thereof.

Some embodiments relate to a method of treating a disease. In some embodiments, the method includes administering to a subject suffering from said disease an effective amount of a pharmaceutical composition as described herein. In some embodiments, the disease is cancer. In some embodiments, cancer is selected from the group consisting of brain cancer, breast cancer, lung cancer, non-small cell lung cancer, ovarian cancer, pancreatic cancer, stomach cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In some embodiments, the cancer is associated with a RAS mutation. In some embodiments, the RAS mutation is a KRAS mutation selected from the group consisting of G12C, G12S, G12R, G12F, G12L, G12N, G12A, G12D, G12V, G13C, G13S, G13D, G13V, G13P, S17G, P34S, A59E, A59G, A59T, Q61K, Q61L, Q61R, and Q61H. In some embodiments, the disease is cancer cachexia.

Some embodiments relate to a method of inhibiting proliferation of a cell. In some embodiments, the method includes contacting the cell with an effective amount of a compound as described herein or a pharmaceutical composition as described herein. In some embodiments, the cell has a RAS mutation.

Some embodiments relate to a method of inducing apoptosis in a cell. In some embodiments, the method includes contacting the cell with an effective amount of a compound as described herein or a pharmaceutical composition as described herein.

Some embodiments relate to a method of treating a subject with cancer resistant to treatment of a MEK protein kinase inhibitor. In some embodiments, the method includes contacting the cell with an effective amount of a compound as described herein or a pharmaceutical composition as described herein.

Some embodiments relate to a method of treating a subject with cancer resistant to treatment of a RAF protein kinase inhibitor. In some embodiments, the method includes contacting the cell with an effective amount of a compound as described herein or a pharmaceutical composition as described herein.

Some embodiments relate to a method of treating cancer cachexia in a mammal with cancer. In some embodiments, the method includes administering an effective amount of a compound as described herein or a pharmaceutical composition as described herein.

In some embodiments, the compound as described herein or a pharmaceutical composition as described herein may be administered in a single dose. In some embodiments, the compound as described herein or a pharmaceutical composition as described herein may be administered a single dose, once daily.

In some embodiments, the compound as described herein or a pharmaceutical composition as described herein may be administered in multiple doses, more than once per day. In some embodiments, the compound as described herein or a pharmaceutical composition as described herein may be administered twice a day. In some embodiments, the compound as described herein or a pharmaceutical composition as described herein may be administered three times a day. In some embodiments, the compound as described herein or a pharmaceutical composition as described herein may be administered as a dose between 0.1 mg and 2000 mg. In some embodiments, the compound as described herein or a pharmaceutical composition as described herein may be administered as a dose between from about 0.001 to about 1000 mg/kg body weight/day.

In some embodiments, a compound as described herein a drug profile of RAF resistant, BID dosing, balance metabolism, and active between about 3 and about 6 hours.

In some embodiments, the compound as described herein interacts with a first region comprising L115, L118, V127, and M143 of an MEK Kinase.

In some embodiments, the compound interacts with a second region comprising K97 of an MEK Kinase.

In some embodiments, a compound as described herein interacts with a third region comprising S212, 1215 and M219 of an MEK Kinase.

In some embodiments, a method of developing molecules based on evaluation and balance of two downstream molecular targets is described herein.

In some embodiments, the method may include administering a compound targeting pERK (T202/Y204) and pSTAT3(5727).

In some embodiments, a method for preventing re-activation of MEK by CRAF-bypass is described herein.

In some embodiments, the method may include administering an effective amount of any one of compounds or pharmaceutical composition as described herein.

In some embodiments, a method for designing a drug therapeutic window for dual RAF/MEK inhibitors is described herein.

In some embodiments, the method may include administering a therapeutic agent with a plasma half-life of less than 12 hours, QD or BID dosing, resistant to MEK reactivation by CRAF-bypass, and optimal metabolic balance between pERK and pSTAT3(S727) inhibition.

DETAILED DESCRIPTION

Figure 1:
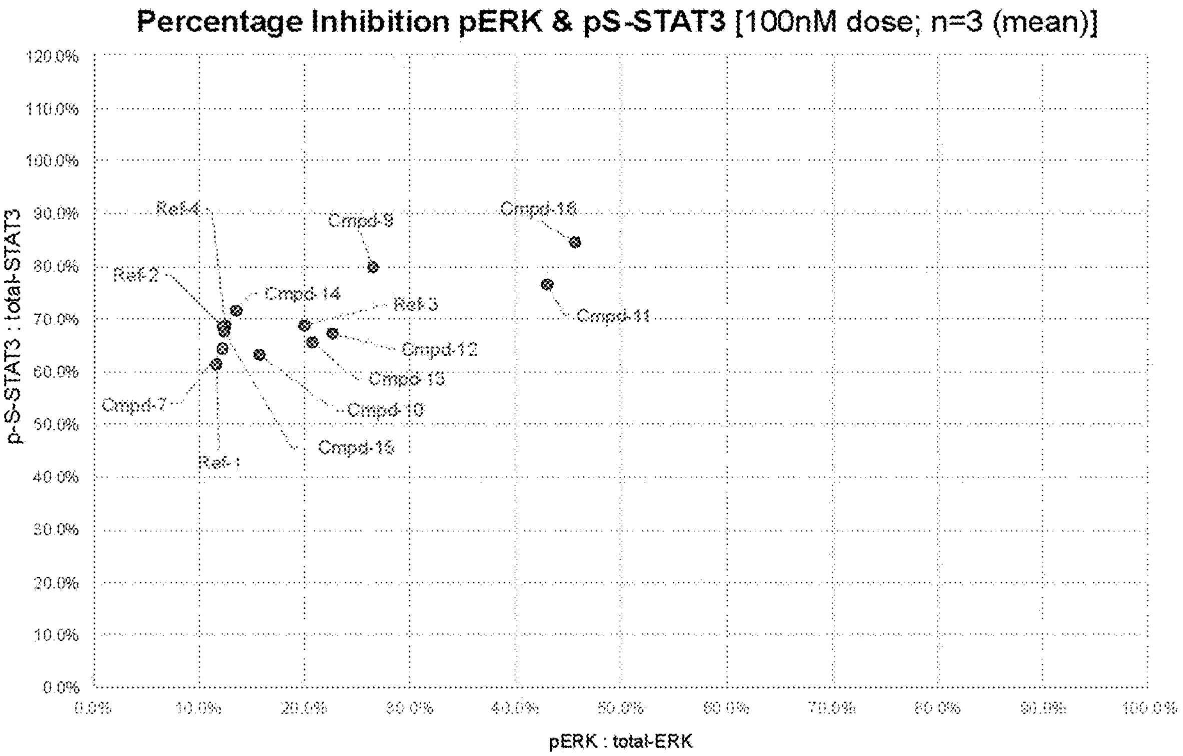
FIG. 1 illustrates pERK(T202/Y204):total-ERK vs pSTAT3(S727):total-STAT3 ratio in A549 KRAS mutant lung cancer for Reference-1, Reference-2, Compound (Cmpd)-7, Compound-10, Compound-9, Compound-11, Compound-12, Compound-13, Compound-14, Compound-15, and Compound-16.
Figure 2:
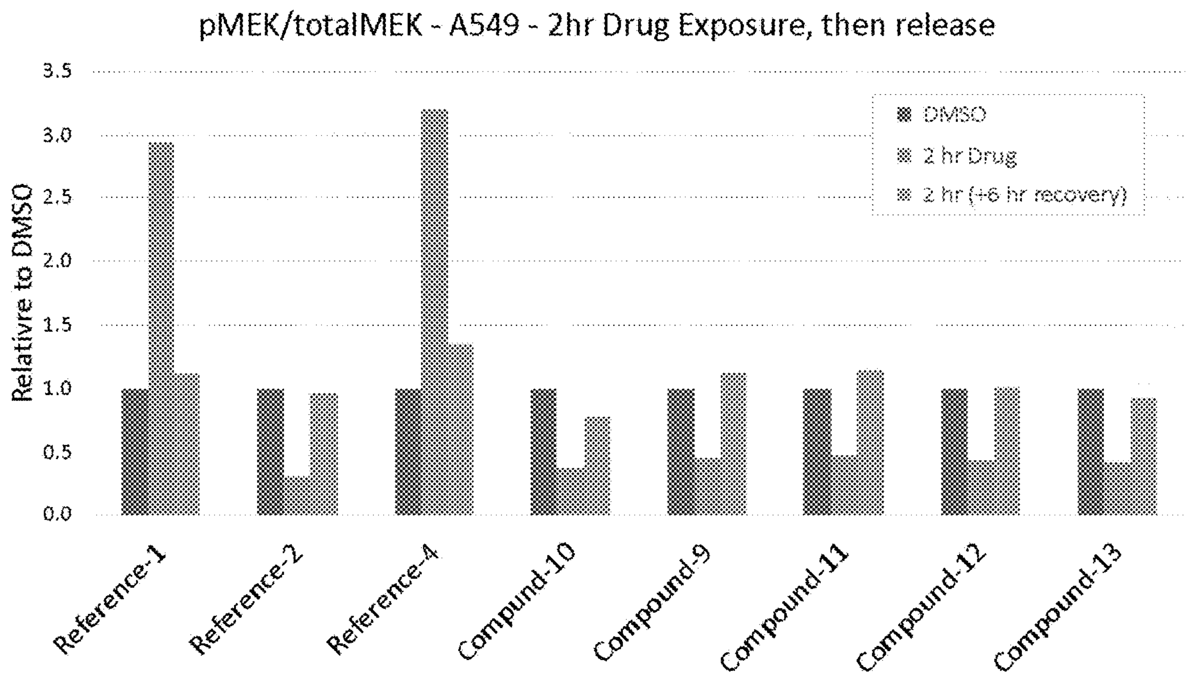
FIG. 2 illustrates CRAF-bypass through elevated pMEK: total-MEK ratios in A549 KRAS mutant lung cancer following treatment with select reference MEK inhibitors.

In some embodiments, MEK inhibitors are provided. Various embodiments of these compounds include compounds having the structure of Formula I as described herein or pharmaceutically acceptable salts thereof. In some embodiments, prodrugs, metabolites, stereoisomers, hydrates, solvates, polymorphs, and pharmaceutically acceptable salts of the compounds disclosed herein are provided.

In certain aspects, therapeutic methods or uses are providing herein for the treatment, prevention, or amelioration of a disease or condition in a subject, these methods comprising administering at least one compound disclosed herein to the subject. In some embodiments, therapeutic methods or uses are provided for the treatment, prevention or amelioration of cancer comprising administering of a compound having the structures of Formula (I), (Ia), (Ib), (Ic), (Id) (II), (IIa), (IIb), (IIc), or (IId) as described herein. In some embodiments, therapeutic methods or uses are provided for the treatment of cancer cachexia comprising administering a compound having the structures of Formula (I), (Ia), (Ib), (Ic), (Id) (II), (IIa), (IIb), (IIc), or (IId) as described herein.

Definitions

Unless expressly defined otherwise, technical and/or scientific terms used herein have the same meaning as is commonly understood by one of ordinary skill in the art. In the event that there are a plurality of definitions for a term herein, those in this section prevail unless stated otherwise. As used in the specification and the appended claims, the singular forms "a," "an," and "the" include plural referents unless the context clearly dictates otherwise. Unless otherwise indicated, conventional methods of mass spectroscopy, NMR, HPLC, protein chemistry, biochemistry, and pharmacology are employed. The use of either the conjunction "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

The term "prodrug," as used herein, refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

Metabolites of the compounds disclosed herein include active species that are produced upon introduction of the compounds into the biological milieu.

Compounds disclosed herein having at least one chiral center they may exist as a racemate or as each enantiomer, and may exist as enantiomeric-enriched mixtures of the enantimoers. It should be noted that all such isomers and mixtures thereof are included in the scope of the present invention. Furthermore, the crystalline forms for the compounds disclosed herein may exist as alternative polymorphs. Such polymorphs are included in one embodiment of the present invention. In addition, some of the compounds of the present invention may form solvates with water (i.e., hydrates) or common organic solvents. Such solvates are included in one embodiment of the present invention.

The term "pharmaceutically acceptable salt," as used herein, refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein can be used alone, in combination with other compounds disclosed herein, or in combination with one or more other agents active in the therapeutic areas described herein.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester," as used herein, refers to a chemical moiety with formula $-(R)_n-COOR'$, where R and R' are independently selected from the group consisting of alkyl, cycloalkyl, aryl, heteroaryl (bonded through a ring carbon) and heteroalicyclic (bonded through a ring carbon), and where n is 0 or 1.

The term "amide," as used herein, refers to a chemical moiety with formula $-(R)_n-C(O)NHR'$ or $-(R)_n-NHC(O)R'$, where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxyl, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3rd Ed., John Wiley & Sons, New York, NY, 1999, which is incorporated herein in its entirety.

The term "aromatic," as used herein, refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, "$C_a$ to $C_b$" in which "a" and "b" are integers refer to the number of carbon atoms in an alkyl, alkenyl or alkynyl group, or the number of carbon atoms in the ring of a cycloalkyl, aryl, heteroaryl or heterocyclyl group. That is, the alkyl, alkenyl, alkynyl, ring of the cycloalkyl, ring of the aryl, ring of the heteroaryl or ring of the heterocyclyl can contain from "a" to "b", inclusive, carbon atoms. Thus, for example, a "$C_1$ to $C_4$ alkyl" group or a "$C_1$-$C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. Likewise, for example, cycloalkyl group may contain from "a" to "b", inclusive, total atoms, such as a $C_3$-$C_8$ cycloalkyl group, 3 to 8 carbon atoms in the ring(s). If no "a" and "b" are designated with regard to an alkyl, cycloalkyl, or cycloalkenyl, the broadest range described in these definitions is to be assumed. Similarly, a "4 to 7 membered heterocyclyl" group refers to all heterocyclyl groups with 4 to 7 total ring atoms, for example, azetidine, oxetane, oxazoline, pyrrolidine, piperidine, piperazine, morpholine, and the like. As used herein, the term "$C_1$-$C_6$" includes $C_1$, $C_2$, $C_3$, $C_4$, $C_5$ and $C_6$, and a range defined by any of the two preceding numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl. As another example, 3 to 10 membered heterocyclyl includes 3, 4, 5, 6, 7, 8, 9, or 10 ring atoms, or a range defined by any of the two preceding numbers, such as 4 to 6 membered or 5 to 7 membered heterocyclyl.

As used herein, "alkyl" refers to a straight or branched hydrocarbon chain fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Wherever a substituent is described as being "optionally substituted" that substituent may be substituted with one of the above substituents.

As used herein, "alkenyl" refers to an alkyl group that contains in the straight or branched hydrocarbon chain one or more double bonds. An alkenyl group may be unsubstituted or substituted. When substituted, the substituent(s) may be selected from the same groups disclosed above with regard to alkyl group substitution. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to an alkyl group that contains in the straight or branched hydrocarbon chain one or more triple bonds. An alkynyl group may be unsubstituted or substituted. When substituted, the substituent(s) may be selected from the same groups disclosed above with regard to alkyl group substitution. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to a monocyclic or multicyclic aromatic ring system (a ring system with fully delocalized pi-electron system), one or two or more fused rings that contain(s) one or more heteroatoms, that is, an element other than carbon, including but not limited to, nitrogen, oxygen and sulfur. Examples of heteroaryl rings include, but are not limited to, furan, thiophene, phthalazine, pyrrole, oxazole, thiazole, imidazole, pyrazole, isoxazole, isothiazole, triazole, thiadiazole, pyridine, pyridazine, pyrimidine, pyrazine and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on a heteroaryl group may form a non-aromatic ring fused to the aryl group, including a cycloalkyl, cycloalkenyl, cycloalkynyl, and heterocyclyl.

As used herein, an "aralkyl" or "arylalkyl" refers to an aryl group connected, as a substituent, via an alkylene group. The alkylene and aryl group of an aralkyl may be substituted or unsubstituted. Examples include but are not limited to benzyl, substituted benzyl, 2-phenylethyl, 3-phenylpropyl, and naphtylalkyl. In some cases, the alkylene group is a lower alkylene group.

As used herein, a "heteroaralkyl" or "heteroarylalkyl" is heteroaryl group connected, as a substituent, via an alkylene group. The alkylene and heteroaryl group of heteroaralkyl may be substituted or unsubstituted. Examples include but are not limited to 2-thienylmethyl, 3-thienylmethyl, furylmethyl, thienylethyl, pyrrolylalkyl, pyridylalkyl, isoxazollylalkyl, and imidazolylalkyl, and their substituted as well as benzo-fused analogs. In some cases, the alkylene group is a lower alkylene group.

As used herein, a "alkylene" refers to a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" refers to a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

As used herein, "alkylidene" refers to a divalent group, such as $=CR'R''$, which is attached to one carbon of another group, forming a double bond, alkylidene groups include, but are not limited to, methylidene ($=CH_2$) and ethylidene ($=CHCH_3$). As used herein, "arylalkylidene" refers to an alkylidene group in which either R' and R'' is an aryl group. An alkylidene group may be substituted or unsubstituted.

As used herein, "alkoxy" refers to the formula —OR wherein R is an alkyl is defined as above, e.g. methoxy, ethoxy, n-propoxy, 1-methylethoxy (isopropoxy), n-butoxy, iso-butoxy, sec-butoxy, tert-butoxy, amoxy, tert-amoxy and the like. An alkoxy may be substituted or unsubstituted.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like. An alkylthio may be substituted or unsubstituted.

As used herein, "aryloxy" and "arylthio" refers to RO— and RS—, respectively, in which R is an aryl, such as but not limited to phenyl. Both an aryloxyl and arylthio may be substituted or unsubstituted.

As used herein, "acyl" refers to —C(═O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups may range from $C_3$ to $C_{10}$, in other embodiments it may range from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. When substituted, substituents on a cycloalkyl group may form an aromatic ring fused to the cycloalkyl group, including an aryl and a heteroaryl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). When composed of two or more rings, the rings may be connected together in a fused, bridged or spiro-connected fashion. A cycloalkenyl group may be unsubstituted or substituted. When substituted, the substituent(s) may be an alkyl or selected from the groups disclosed above with regard to alkyl group substitution unless otherwise indicated. When substituted, substituents on a cycloalkenyl group may form an aromatic ring fused to the cycloalkenyl group, including an aryl and a heteroaryl.

As used herein, "cycloalkynyl" refers to a cycloalkyl group that contains one or more triple bonds in the ring. When composed of two or more rings, the rings may be joined together in a fused, bridged or spiro-connected fashion. A cycloalkynyl group may be unsubstituted or substituted. When substituted, the substituent(s) may be an alkyl or selected from the groups disclosed above with regard to alkyl group substitution unless otherwise indicated. When substituted, substituents on a cycloalkynyl group may form an aromatic ring fused to the cycloalkynyl group, including an aryl and a heteroaryl.

As used herein, "heteroalicyclic" or "heteroalicyclyl" refers to a stable 3- to 18 membered ring which consists of carbon atoms and from one to five heteroatoms selected from the group consisting of nitrogen, oxygen and sulfur. The "heteroalicyclic" or "heteroalicyclyl" may be monocyclic, bicyclic, tricyclic, or tetracyclic ring system, which may be joined together in a fused, bridged or spiro-connected fashion; and the nitrogen, carbon and sulfur atoms in the "heteroalicyclic" or "heteroalicyclyl" may be optionally oxidized; the nitrogen may be optionally quaternized; and the rings may also contain one or more double bonds provided that they do not form a fully delocalized pi-electron system throughout all the rings. Heteroalicyclyl groups may be unsubstituted or substituted. When substituted, the substituent(s) may be one or more groups independently selected from the group consisting of alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, haloalkyl, haloalkoxy, trihalomethanesulfonyl, trihalomethanesulfonamido, and amino, including mono- and di-substituted amino groups, and the protected derivatives thereof. Examples of such "heteroalicyclic" or "heteroalicyclyl" include but are not limited to, azepinyl, acridinyl, carbazolyl, cinnolinyl, dioxolanyl, imidazolinyl, morpholinyl, oxiranyl, piperidinyl N-oxide, piperidinyl, piperazinyl, pyrrolidinyl, 4-piperidonyl, pyrazolidinyl, 2-oxopyrrolidinyl, thiamorpholinyl, thiamorpholinyl sulfoxide, and thiamorpholinyl sulfone. When substituted, substituents on a heteroalicyclyl group may form an aromatic ring fused to the heteroalicyclyl group, including an aryl and a heteroaryl.

As used herein, the term "(cycloalkenyl)alkyl" refers to a cycloalkenyl group connected, as a substituent, via an alkylene group. The alkylene and cycloalkenyl of a (cycloalkenyl)alkyl may be substituted or unsubstituted. In some cases, the alkylene group is a lower alkylene group.

As used herein, the term "(cycloalkynyl)alkyl" to a cycloalkynyl group connected, as a substituent, via an alkylene group. The alkylene and cycloalkynyl of a (cycloalkynyl)alkyl may be substituted or unsubstituted. In some cases, the alkylene group is a lower alkylene group.

As used herein, the term "O-carboxy" refers to a "RC(═O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

As used herein, the term "C-carboxy" refers to a "—C(═O)R" group in which R can be the same as defined with respect to O-carboxy. A C-carboxy may be substituted or unsubstituted.

As used herein, the term "trihalomethanesulfonyl" refers to an "$X_3CSO_2$—" group wherein X is a halogen.

As used herein, the term "cyano" refers to a "—CN" group.

As used herein, the term "cyanato" refers to an "—OCN" group.

As used herein, the term "isocyanato" refers to a "—NCO" group.

As used herein, the term "thiocyanato" refers to a "—SCN" group.

As used herein, the term "isothiocyanato" refers to an "—NCS" group.

As used herein, the term "sulfinyl" refers to a "—S(═O)—R" group in which R can be the same as defined with respect to O-carboxy. A sulfinyl may be substituted or unsubstituted.

As used herein, the term "sulfonyl" refers to an "—$SO_2R$" group in which R can be the same as defined with respect to O-carboxy. A sulfonyl may be substituted or unsubstituted.

As used herein, the term "S-sulfonamido" refers to a "—$SO_2NR_AR_B$" group in which $R_A$ and $R_B$ can be the same as defined with respect to O-carboxy. An S-sulfonamido may be substituted or unsubstituted.

As used herein, the term "N-sulfonamido" refers to a "—$SO_2N(R_A)(R_B)$" group in which R, $R_A$, and $R_B$ can be the same as defined with respect to O-carboxy. A sulfonyl may be substituted or unsubstituted.

As used herein, the term "trihalomethanesulfonamido" refers to an "$X_3CSO_2N(R)$—" group with X as halogen and R can be the same as defined with respect to O-carboxy. A trihalomethanesulfonamido may be substituted or unsubstituted.

As used herein, the term "O-carbamyl" refers to a "—OC(=O)$NR_AR_B$" group in which $R_A$ and $R_B$ can be the same as defined with respect to O-carboxy. An O-carbamyl may be substituted or unsubstituted.

As used herein, the term "N-carbamyl" refers to an "ROC(=O)$NR_A$—" group in which R and $R_A$ can be the same as defined with respect to O-carboxy. An N-carbamyl may be substituted or unsubstituted.

As used herein, the term "O-thiocarbamyl" refers to a "—OC(=S)—$NR_AR_B$" group in which $R_A$ and $R_B$ can be the same as defined with respect to O-carboxy. An O-thiocarbamyl may be substituted or unsubstituted.

As used herein, the term "N-thiocarbamyl" refers to an "ROC(=S)$NR_A$—" group in which R and $R_A$ can be the same as defined with respect to O-carboxy. An N-thiocarbamyl may be substituted or unsubstituted.

As used herein, the term "C-amido" refers to a "—C(=O)$NR_AR_B$" group in which $R_A$ and $R_B$ can be the same as defined with respect to O-carboxy. A C-amido may be substituted or unsubstituted.

As used herein, the term "N-amido" refers to a "RC(=O)$NR_A$—" group in which R and $R_A$ can be the same as defined with respect to O-carboxy. An N-amido may be substituted or unsubstituted.

As used herein, the term "amino" refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, the term "aminoalkyl" refers to an amino group connected via an alkylene group.

As used herein, the term "ester" refers to a "—C(=O)OR" group in which R can be the same as defined with respect to O-carboxy. An ester may be substituted or unsubstituted.

As used herein, the term "lower aminoalkyl" refers to an amino group connected via a lower alkylene group. A lower aminoalkyl may be substituted or unsubstituted.

As used herein, the term "lower alkoxyalkyl" refers to an alkoxy group connected via a lower alkylene group. A lower alkoxyalkyl may be substituted or unsubstituted.

As used herein, the term "acetyl" refers to a —C(=O)$CH_3$, group.

As used herein, the term "trihalomethanesulfonyl" refers to a $X_3CS(=O)_2$— group where X is a halogen.

As used herein, the term "O-carbamyl" refers to a —OC(=O)—NR, in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carbamyl can be substituted or unsubstituted.

As used herein, the term "N-carbamyl" refers to a ROC(=O)NH— group, in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An N-carbamyl can be substituted or unsubstituted.

As used herein, the term "O-thiocarbamyl" refers to a —OC(=S)—NR, in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-thiocarbamyl can be substituted or unsubstituted.

As used herein, the term "N-thiocarbamyl" refers to an ROC(=S)NH— group, in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An N-thiocarbamyl can be substituted or unsubstituted.

As used herein, the term "perhaloalkyl" refers to an alkyl group where all of the hydrogen atoms are replaced by halogen atoms.

As used herein, the term "halogen" or "halo," refer to any one of the radio-stable atoms of column 7 of the Periodic Table of the Elements, e.g., fluorine, chlorine, bromine, or iodine, with fluorine and chlorine being preferred.

As used herein, the term "carbocyclyl" refers to a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, the term "(cycloalkyl)alkyl" refers to a cycloalkyl group connected, as a substituent, via an alkylene group. The alkylene and cycloalkyl of a (cycloalkyl)alkyl may be substituted or unsubstituted. Examples include but are not limited cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, the term "cycloalkyl" refers to a fully saturated carbocyclyl ring or ring system. Examples include cyclopropyl, cyclobutyl, cyclopentyl, and cyclohexyl.

As used herein, the term "cycloalkenyl" means a carbocyclyl ring or ring system having at least one double bond, wherein no ring in the ring system is aromatic. An example is cyclohexenyl.

As used herein, the term "heterocyclyl" refers to three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

As used herein, "heterocyclyl" refers to a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, the term "(heterocyclyl)alkyl" refers to a heterocyclyl group connected, as a substituent, via an alkylene group. Examples include, but are not limited to, imidazolinylmethyl and indolinylethyl.

The terms "purified," "substantially purified," and "isolated" as used herein, refer to compounds disclosed herein being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

Substituted groups are based upon or derived from the unsubstituted parent group in which there has been an exchange of one or more hydrogen atoms for another atom or group. Unless otherwise indicated, when a group is deemed to be "substituted," the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., $-CF_3$), halo($C_1$-$C_6$)alkoxy (e.g., $-OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, a substituted group is substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $-CH_2-$, $-CH_2CH_2-$, $-CH_2CH(CH_3)CH_2-$, and the like. Other radical naming conventions clearly indicate that the radical is a di-radical such as "alkylene" or "alkenylene."

Unless otherwise indicated, when a substituent is deemed to be "optionally substituted," it is meant that the substituent" is a group that may be substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "agent" or "test agent," as used herein, includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog," as used herein, refers to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal," as used herein, is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection," as used herein, refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient," as used herein, includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

The term "subject," as used herein, refers to a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "effective amount" or a "therapeutically effective amount." as used herein, refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

The term "treat," "treatment," or "treating," as used herein, refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

The term "about," as used herein, refers to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Compounds

Some embodiments provide a compound of Formula (I):

(I)

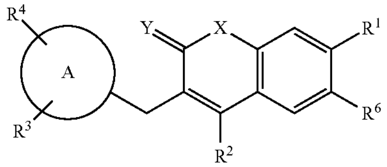

In some embodiments, Formula (I) is a pharmaceutically acceptable salt as described herein.

In some embodiments, Formula (I) is represented by Formula (Ia), Formula (Ib), Formula (Ic), or Formula (Id):

(Ia)

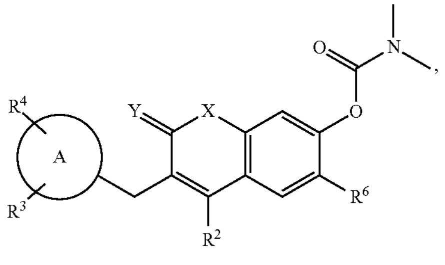

(Ib)

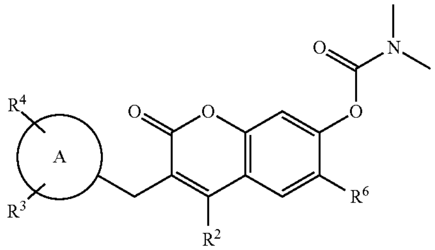

-continued (Ic)

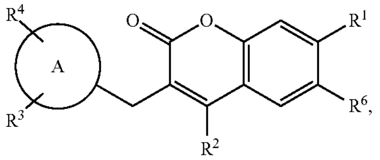

(Id)

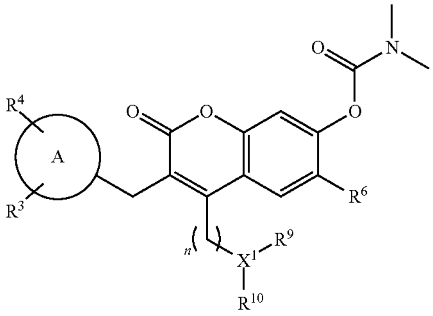

In some embodiments, Formula (Ia), Formula (Ib), Formula (Ic), or Formula (Id) are a pharmaceutically acceptable salt as described herein.

In some embodiments, Ring A is

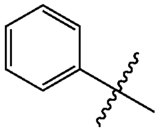, 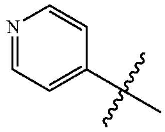, 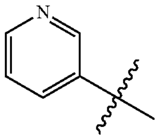, 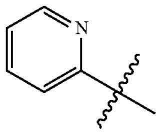, 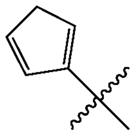, 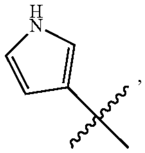, 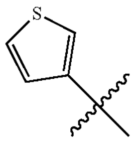, 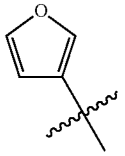, 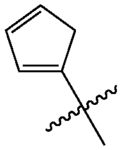, 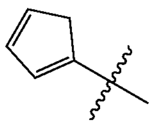, 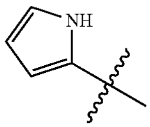, 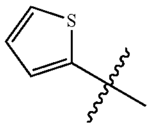, or 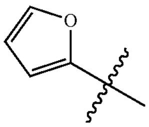.

In some embodiments of the compounds of Formula (I) or (Ic), $R^1$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, O-aryl, O-heteroaryl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments, $R^1$ is not O-pyrimidinyl. In some embodiments, $R^1$ is not an ether-linked pyrimidyl.

In some embodiments of the compounds of Formula (I), (Ia), or (Ib), $R^2$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L. In some further embodiments, $R^2$ is L. In some further embodiments, $R^2$ is $—CH_3$.

In some embodiments of the compounds Formula (I), (Ia), (Ib), (Ic) or (Id), $R^3$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments of the compounds of Formula (I), (Ia), (Ib), (Ic), or (Id), $R^4$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments of the compounds of Formula (I), (Ia), (Ib), or (Ic), $R^5$ may be selected from H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^5$ is H, deuterium, halo, or an optionally substituted $C_1$ to $C_6$ alkyl.

In some embodiments of the compounds of Formula (I), (Ia), (Ib), or (Ic), $R^{5'}$ may be selected from H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^{5'}$ is H, deuterium, halo, or an optionally substituted $C_1$ to $C_6$ alkyl.

In some embodiments of the compounds of Formula (I), (Ia), (Ib), or (Ic), $R^6$ may be selected from H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^6$ is H, deuterium, halo, or an optionally substituted $C_1$ to $C_6$ alkyl.

In some embodiments of the compounds of Formula (I) or (Ia), X may be selected from $C(R^5)_2$, $CH(R^5)$, $CH_2$, —O—,

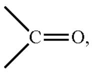, 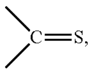, or 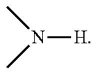.

In some further embodiments, X is $CH_2$ or —O—. In some further embodiments, X is —O—.

In some embodiments of the compounds of Formula (I), (Ia), (Ib), or (Ic), L may be selected from —$Z_1$—$Z_2$. In some embodiments of the compounds of Formula (I), (Ia), (Ib), or (Ic), L may be selected from —$Z_1$—$Z_2$—$Z_3$.

In some embodiments of the compounds of Formula (I), (Ia), (Ib), or (Ic), $Z_1$ may be selected from —$CH_2$, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$NHCH_2CO$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_1$ is —$CH_2$—.

In some embodiments of the compounds of Formula (I), (Ia), (Ib), or (Ic), $Z_2$ may be selected from hydrogen, deuterium, halo, —$CH_2$, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^5$—, —$NHCH_2CO$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, —$NR^5R^5$, —$CH_2CH$, or —$CH_2CN$. In some further embodiments, $Z_2$ is optionally substituted $C_3$ to $C_8$ heterocyclyl. In some embodiments, $Z_2$ is —$CH_2$— and $Z_2$ is —$NR^5R^{5'}$. In some embodiments, $Z_2$ is an optionally substituted $C_3$ to $C_8$ heterocyclyl.

In some embodiments of the compounds of Formula (I), (Ia), (Ib), or (Ic), $Z_3$ may be selected from hydrogen, deuterium, halo, —COH, —$CO_2H$, —$NO_2$, —$CH_2CCH$, —$CH_2CN$, —$NR^5R^{5'}$, —(CO)$NH_2$, —(CO)$NR^5R^{5'}$, —$SO_2$—$NH_2$, —$R^5CH_3$, —$R^5$—COH, —$R^5CO_2H$, —$R^5NH_2$, —$R^5NH(COH)$, —$R^5(CO)NH_2$, —$R^5NH$—$SO_2H$, —$R^5SO_2$—$NH_2$, —$CH_2R^5$, —$OR^5$, —$SO_2R^5$—, —$CO_2R^5$, —$NHR^5$, —NH(CO)$R^5$, —(CO)$NHR^5$, —NH—$SO_2R^5$, —$SO_2$—$NHR^5$, optionally substituted amino, optionally substituted $C_1$ to $C_4$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl).

In some embodiments of the compounds of Formula (Id), n is 1, 2, 3, or 4. In some embodiments, n is 1, 2 or 3. In some embodiments, n is 1 or 2. In some embodiments, n is 2 or 3. In some embodiments, n is 1. In some embodiments, n is 2. In some embodiments, n is 3. In some embodiments, n is 4.

In some embodiments of the compounds of Formula (Id), $X^1$ may be selected from —CH, B, N, or $PO_4$. In some embodiments, $X^1$ is —$CO_2$—, N, or —$SO_2$—. In some embodiments, $X^1$ is N.

In some embodiments of the compounds of Formula (Id), $R^9$ may be selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CH$, or —$CH_2CN$.

In some embodiments of the compounds of Formula (Id), $R^{10}$ may be selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CH$, or —$CH_2CN$.

In some embodiments, the optionally substituted $C_3$ to $C_8$ heterocyclyl is

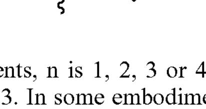

In some embodiments, n is 1, 2, 3 or 4. In some embodiments, n is 1, 2 or 3. In some embodiments, n is 1 or 2. In some embodiments, n is 1. In some embodiments, n is 2. In some embodiments, n is 3. In some embodiments, the optionally substituted $C_3$ to $C_8$ heterocyclyl is

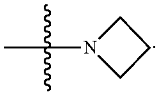 [SMILES: *N1CCC1]

In some embodiments, the optionally substituted $C_3$ to $C_8$ heterocyclyl is

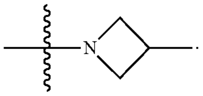 [SMILES: *N1CC(C)C1]

In some embodiments, the optionally substituted $C_3$ to $C_8$ heterocyclyl is

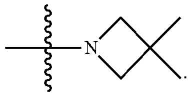 [SMILES: *N1CC(C)(C)C1]

In some embodiments, the optionally substituted $C_3$ to $C_8$ heterocyclyl is

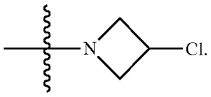 [SMILES: *N1CC(Cl)C1]

In some embodiments, $Z_2$ is

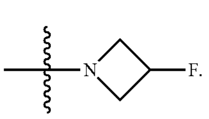 [SMILES: *N1CC(F)C1]

In some embodiments, the optionally substituted $C_3$ to $C_8$ heterocyclyl is

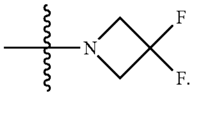

In some embodiments, $Z_1$ is —$CH_2$— and $Z_2$ is an optionally substituted $C_3$ to $C_8$ heterocyclyl, and $Z_3$ is an optionally substituted aryl. In some embodiments, $Z_1$ is —$CH_2$— and $Z_2$ is an optionally substituted $C_3$ to $C_8$ heterocyclyl, and $Z_3$ is hydrogen. In some embodiments, $Z_1$ is —$CH_2$— and $Z_2$ is an optionally substituted $C_3$ to $C_8$ heterocyclyl, and $Z_3$ is an optionally substituted alkyl. In some embodiments, $Z_1$ is —$CH_2$— and $Z_2$ is an optionally substituted $C_3$ to $C_8$ heterocyclyl, and $Z_3$ is —$CH_2$-(optionally substituted aryl). In some embodiments, $Z_1$ is —$CH_2$— and $Z_2$ is

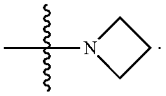

In some embodiments of the compounds of Formula (I), or (Ia), Y is $CH_2$, NH or O.

In some embodiments, Formula (I) is a compound of a disclosed formula, for example Formula (I), Formula (Ia), Formula (Ib), Formula (Ic), Formula (Id), Formula (II), Formula (IIa), Formula (IIb), Formula (IIc), or Formula (IId) but excluding the compounds:

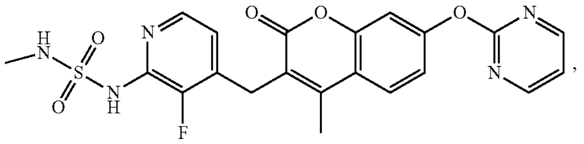

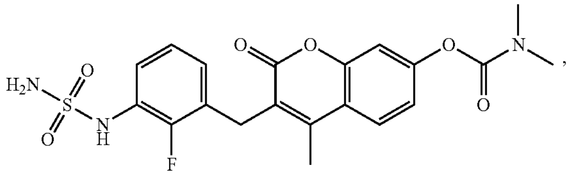

and

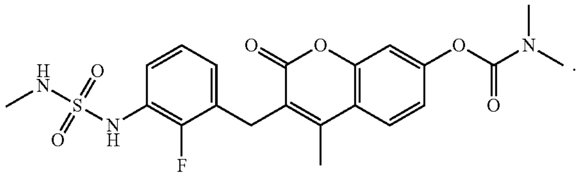

In some embodiments, Formula (I) is a compound of a disclosed formula, for example Formula (I), Formula (Ia), Formula (Ib), Formula (Ic), Formula (Id), Formula (II), Formula (IIa), Formula (IIb), Formula (IIc), or Formula (IId) but excluding $R^2$ as $C_1$ to $C_6$ alkyl. In some embodiments, Formula (I) is a compound of a disclosed formula, for example Formula (I), Formula (Ia), Formula (Ib), Formula (Ic), Formula (Id), Formula (II), Formula (IIa), Formula (IIb), Formula (IIc), or Formula (IId) but excluding $R^2$ as methyl. In some embodiments, Formula (I) is a compound of a disclosed formula, for example Formula (I), Formula (Ia), Formula (Ib), Formula (Ic), Formula (Id), Formula (II), Formula (IIa), Formula (IIb), Formula (IIc), or Formula (IId) but excluding $R^2$ as ethyl.

Some embodiments provide a compound of Formula (II):

(II)

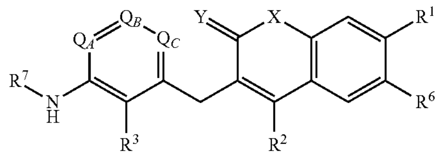

In some embodiments, Formula (II) is a pharmaceutically acceptable salt as described herein.

In some embodiments, Formula (II) is represented by Formula (IIa), Formula (IIb), Formula (IIc):

(IIa)

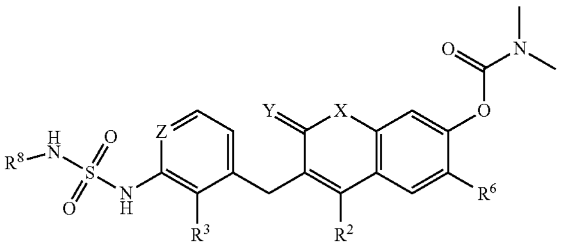

(IIb)

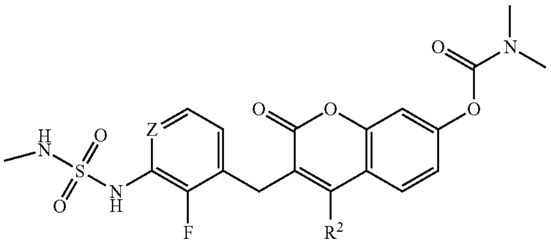

(IIc)

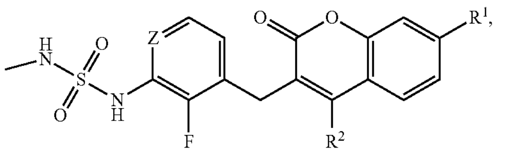

(IId)

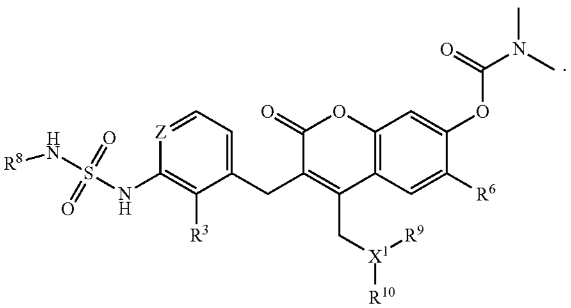

In some embodiments, Formula (IIa), Formula (IIb), Formula (IIc), Formula (IId) may be a pharmaceutically acceptable salt as described herein.

In some embodiments of Formula (II), $Q_A$, $Q_B$, $Q_C$ are independently C or N.

In some embodiments of the compounds of Formula (II) or (IIc), $R^1$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, O-aryl, O-heteroaryl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments, $R^1$ is not O-pyrimidinyl. In some embodiments, $R^1$ is not an ether-linked pyrimidyl.

In some embodiments of the compounds of Formula (II), (IIa), or (IIb), $R^2$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L. In some further embodiments, $R^2$ is L. In some further embodiments, $R^2$ is $—CH_3$.

In some embodiments of the compounds Formula (II), (IIa), or (IId), $R^3$ is H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments of the compounds of Formula (II) or (IIa), $R^4$ may be selected from H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L.

In some embodiments of the compounds of Formula (II), (IIa), (IIb), or (IIc), $R^5$ is H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^5$ is H, deuterium, halo, or an optionally substituted $C_1$ to $C_6$ alkyl.

In some embodiments of the compounds of Formula (II), (IIa), (IIb), or (IIc), $R^{5'}$ is H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^5$ is H, deuterium, halo, or an optionally substituted $C_1$ to $C_6$ alkyl.

In some embodiments of the compounds of Formula (II), (IIa), (IIb), (IIc), or (IId), $R^6$ is H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl. In some embodiments, $R^6$ is H, deuterium, halo, or an optionally substituted $C_1$ to $C_6$ alkyl.

In some embodiments of the compounds of Formula (II) or (IIa), X is $C(R^5)_2$, $CH(R^5)$, $CH_2$, —O—,

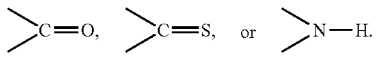

In some further embodiments, X is $CH_2$ or —O—. In some further embodiments, X is —O—.

In some embodiments of the compounds of Formula (II), (IIa), (IIb), or (IIc), L is $—Z_1—Z_2$. In some embodiments of the compounds of Formula (II), (IIa) or (IIb) $—Z_1—Z_2—Z_3$.

In some embodiments of the compounds of Formula (II), (IIa), (IIb), or (IIc), $Z_1$ is $—CH_2—$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl). In some further embodiments, $Z_1$ is $—CH_2—$.

In some embodiments of the compounds of Formula (II), (IIa), (IIb), or (IIc), $Z_2$ is halo, $—CH_2$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$. In some further embodiments, $Z_2$ is optionally substituted $C_3$ to $C_8$ heterocyclyl. In some embodiments, $Z_1$ is $—CH_2—$ and $Z_2$ is $—NR^5R^5$. In some embodiments, $Z_2$ an optionally an optionally substituted $C_3$ to $C_7$ heterocyclyl.

In some embodiments of the compounds of Formula (II), (IIa), (IIb), or (IIc), $Z_3$ is hydrogen, halo, —COH, $—CO_2H$, $—NO_2$, $—CH_2CCH$, $—CH_2CN$, $—NR^5R^5$, $—(CO)NH_2$, $—(CO)NR^5R^5$, $—SO_2—NH_2$, $—R^5CH_3$, $—R^5—COH$, $—R^5CO_2H$, $—R^5NH_2$, $—R^5NH(COH)$, $—R^5(CO)NH_2$, $—R^5NH—SO_2H$, $—R^5SO_2—NH_2$, $—CH_2R^5$, $—OR^5$, $—SO_2R^5—$, $—CO_2R^5$, $—NHR^5$, $—NH(CO)R^5$, $—(CO)NHR^5$, $—NH—SO_2R^5$, $—SO_2—NHR^5$, optionally substituted amino, optionally substituted $C_1$ to $C_4$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl).

In some embodiments, $Z_1$ is $—CH_2—$ and $Z_2$ is an optionally substituted $C_3$ to $C_8$ heterocyclyl, and $Z_3$ is an optionally substituted aryl. In some embodiments, $Z_1$ is $—CH_2—$ and $Z_2$ is an optionally substituted $C_3$ to $C_8$ heterocyclyl, and $Z_3$ is hydrogen. In some embodiments, $Z_1$ is $—CH_2—$ and $Z_2$ is an optionally substituted $C_3$ to $C_8$ heterocyclyl, and $Z_3$ is an optionally substituted alkyl. In some embodiments, $Z_1$ is $—CH_2—$ and $Z_2$ is an optionally substituted $C_3$ to $C_8$ heterocyclyl, and $Z_3$ is $—CH_2$-(optionally substituted aryl). In some embodiments, the optionally substituted $C_3$ to $C_8$ heterocyclyl is

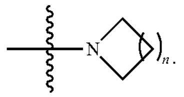

In some embodiments, n is 1, 2, 3 or 4. In some embodiments, n is 1, 2 or 3. In some embodiments, n is 1 or 2. In some embodiments, n is 1. In some embodiments, n is 2. In some embodiments, n is 3. In some embodiments, the optionally substituted $C_3$ to $C_8$ heterocyclyl is

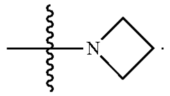

In some embodiments, the optionally substituted $C_3$ to $C_8$ heterocyclyl is optionally substituted

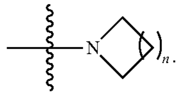

In some embodiments, the optionally substituted $C_3$ to $C_8$ heterocyclyl is optionally substituted

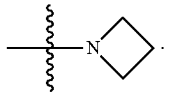 [SMILES: *N1CCC1]

In some embodiments, the optionally substituted $C_3$ to $C_8$ heterocyclyl is

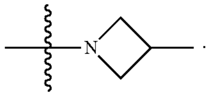 [SMILES: *N1CC(C)C1]

In some embodiments, the optionally substituted $C_3$ to $C_8$ heterocyclyl is

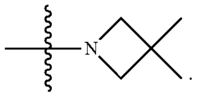 [SMILES: *N1CC(C)(C)C1]

In some embodiments, the optionally substituted $C_3$ to $C_8$ heterocyclyl is

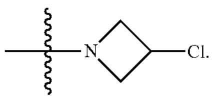 [SMILES: *N1CC(Cl)C1]

In some embodiments, $Z_2$ is

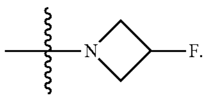 [SMILES: *N1CC(F)C1]

In some embodiments, the optionally substituted $C_3$ to $C_8$ heterocyclyl is

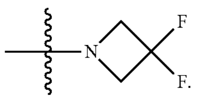 [SMILES: *N1CC(F)(F)C1]

In some embodiments of the compounds of Formula (II), $R^7$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_3$ to $C_{10}$ heteroaryl, or L. In some further embodiments, $R^7$ is selected from halo, H or $CH_3$.

In some embodiments of the compounds of Formula (IIa), $R^8$ selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_3$ to $C_{10}$ heteroaryl. In some further embodiments, $R^8$ is selected from halo, H, deuterium, or $CH_3$.

In some embodiments of the compounds of Formula (Id), $X^1$ may be selected from —CH, —$CO_2$—, N, or —$SO_2$—. In some embodiments, $X^1$ is —$CO_2$—, N, or —$SO_2$—. In some embodiments, $X^1$ is N.

In some embodiments of the compounds of Formula (Id), $R^9$ may be selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CH$, or —$CH_2CN$.

In some embodiments of the compounds of Formula (Id), $R^{10}$ may be selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl). In some further embodiments, $Z_2$ is $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CH$, or —$CH_2CN$.

In some embodiments of the compounds of Formula (II), or (IIa), Y is $CH_2$, NH or O.

In some embodiments of the compounds of Formula (II), or (IIa), X is $CH_2$ or O.

In some embodiments of the compounds of Formula (II), (IIa), or (IId), Z is C or N.

In some embodiments, Formula (II) excludes

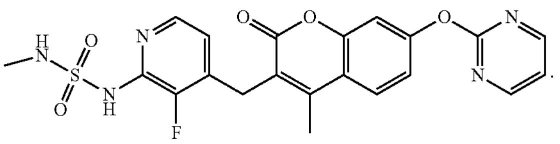 [SMILES: CNS(=O)(=O)Nc1nccc(Cc2c(C)c3ccc(Oc4ncccn4)cc3oc2=O)c1F]

In some embodiments, Formula (II), (IIa), (IIb), or (IIc) excludes $R^2$ as $CH_3$.

In some embodiments of the compounds of Formula (I), (Ia), (Ib), (Ic), (II), (IIa), (IIb), or (IIc) are selected from Compounds of Table A, and pharmaceutically acceptable salts thereof.

Table A. Exemplary Compounds of Formula (I), (Ia), (Ib), (Ic), (Id), (II), (IIa), (IIb), (IIc), or (IId):
TABLE A
| No. | Structure |
|---|---|
| 7 | 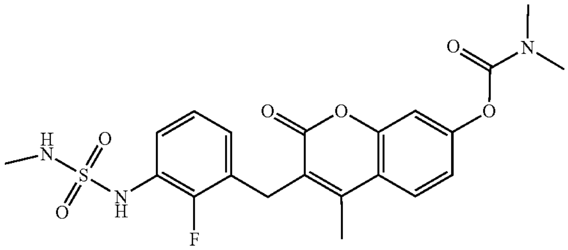 |
| 9 | 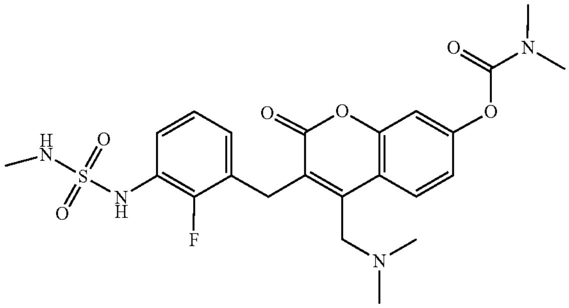 |
| 10 | 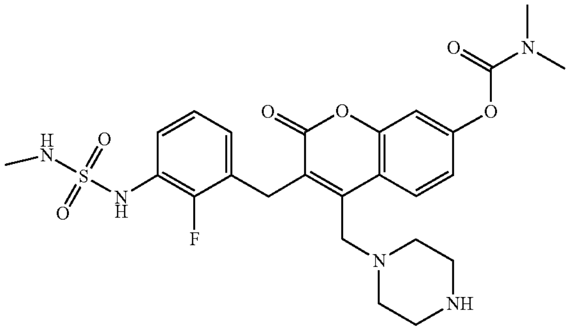 |
| 11 | 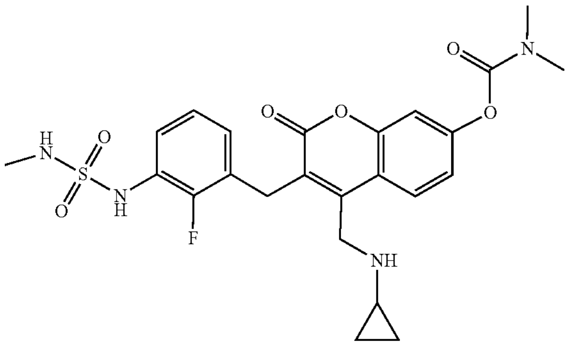 |

TABLE A-continued
| No. | Structure |
| --- | --- |
| 12 | 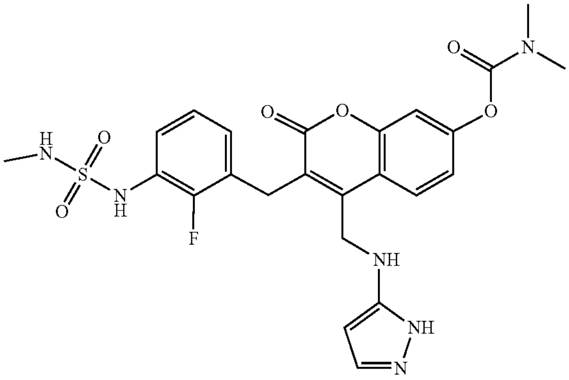 |
| 13 | 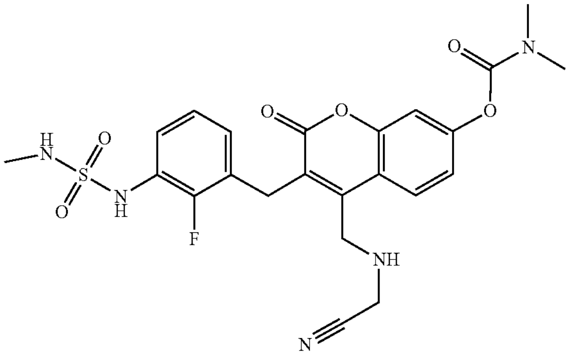 |
| 14 | 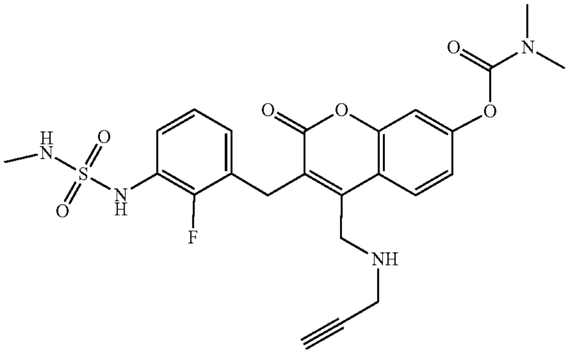 |
| 15 | 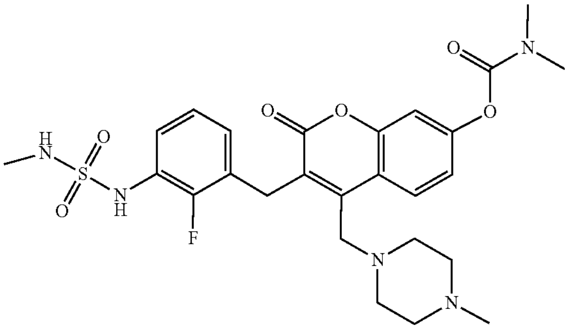 |

TABLE A-continued
| No. | Structure |
| --- | --- |
| 16 | 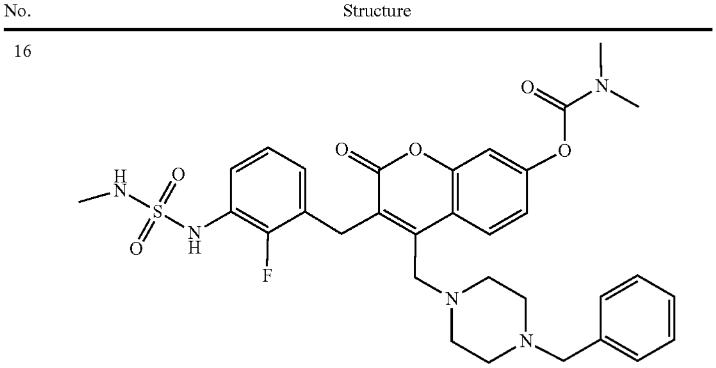 |
| 17 | 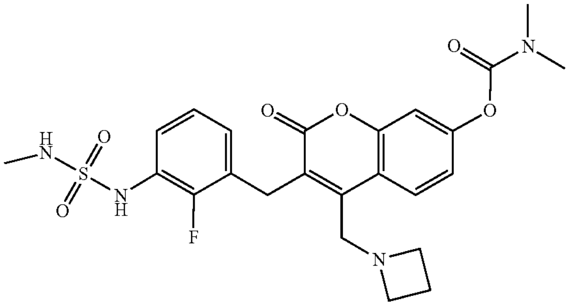 |
| 18 | 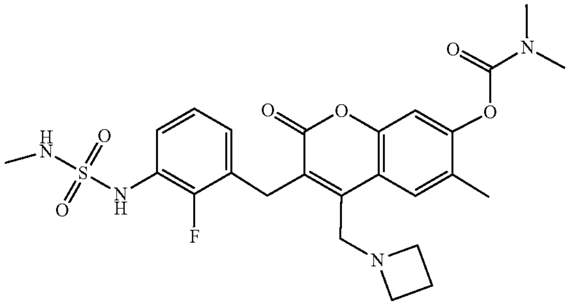 |
| 19 | 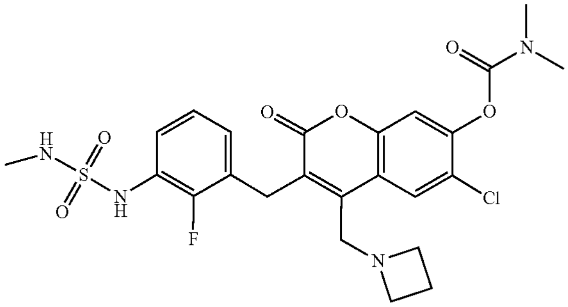 |
| 20 | 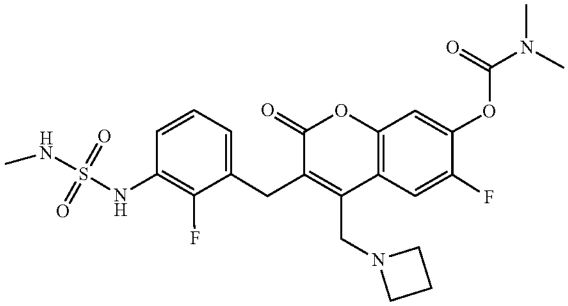 |

TABLE A-continued
| No. | Structure |
| --- | --- |
| 21 | 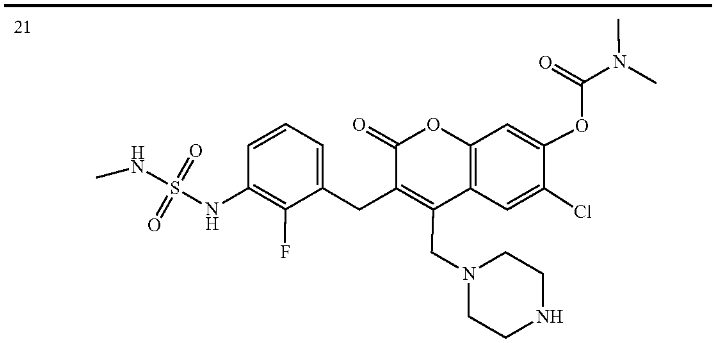 |
| 22 | 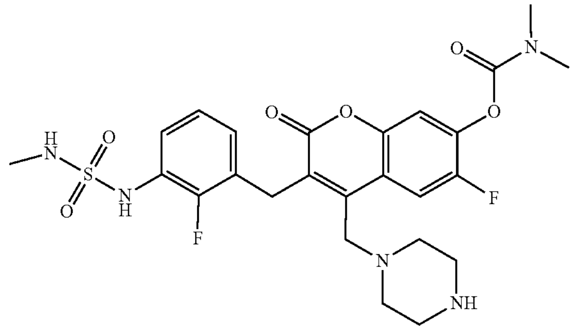 |
| 23 | 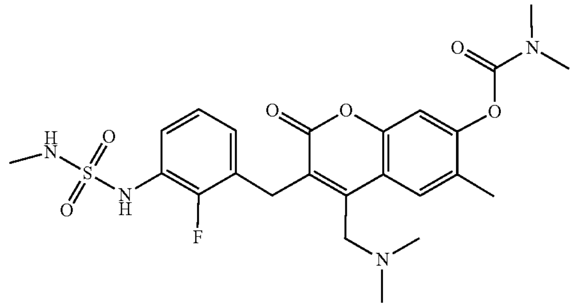 |
| 24 | 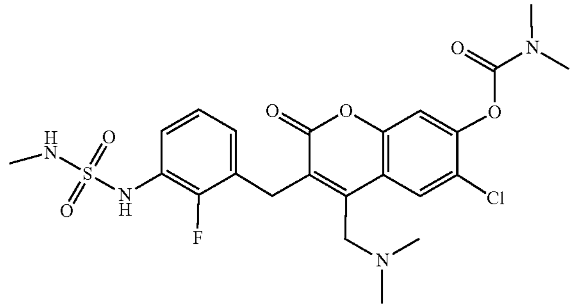 |
| 25 | 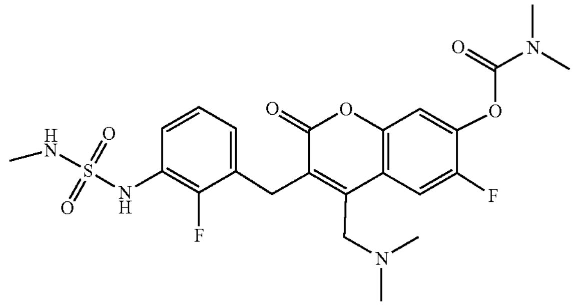 |

TABLE A-continued
| No. | Structure |
|---|---|
| 26 | 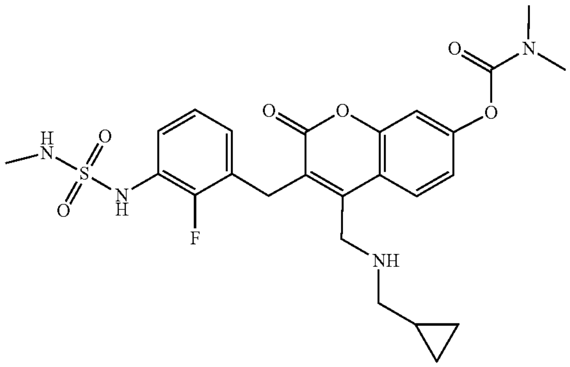 |
| 27 | 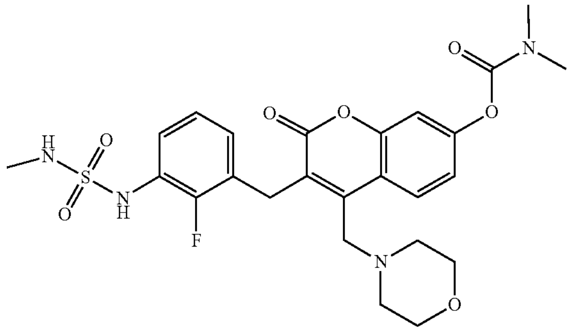 |
| 28 | 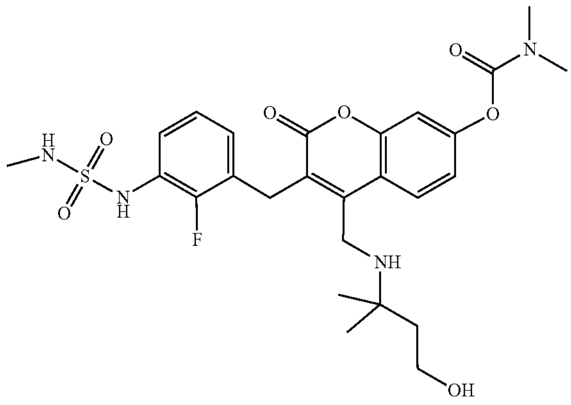 |
| 29 | 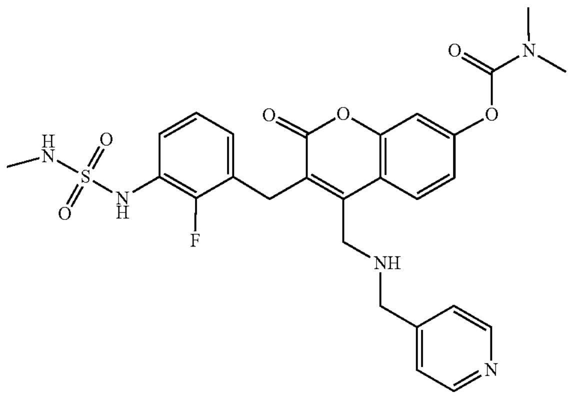 |

TABLE A-continued
| No. | Structure |
| --- | --- |
| 30 | 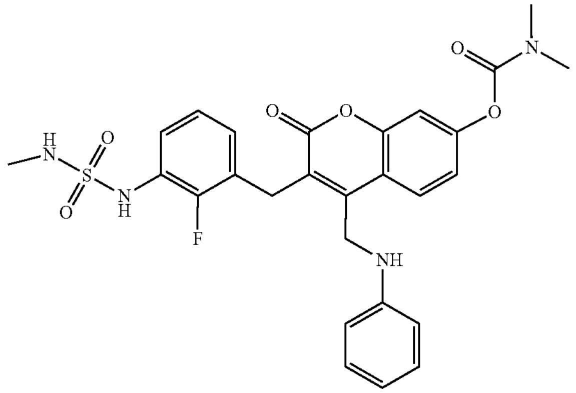 |
| 31 | 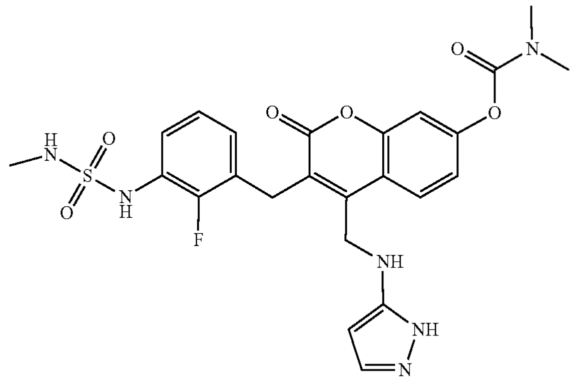 |
| 32 | 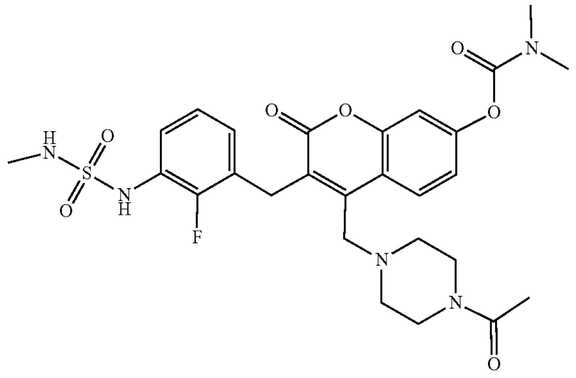 |
| 33 | 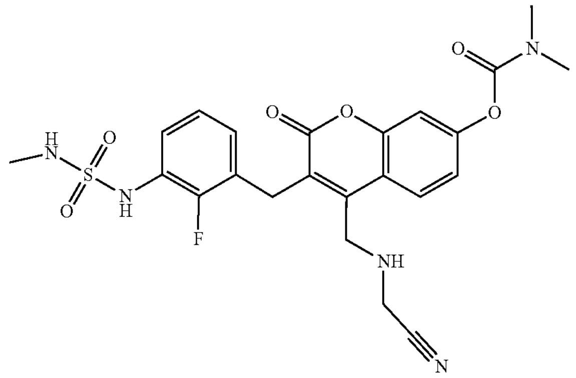 |

TABLE A-continued
| No. | Structure |
|---|---|
| 34 | 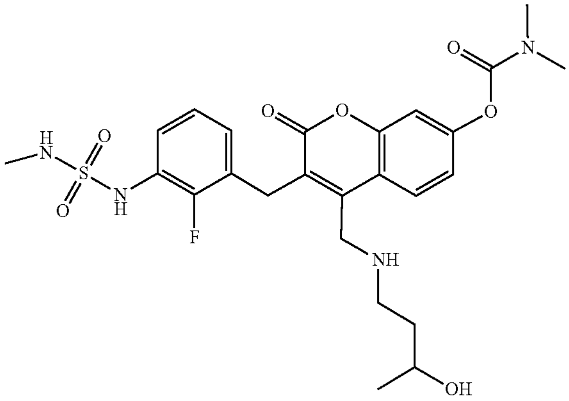 |
| 35 | 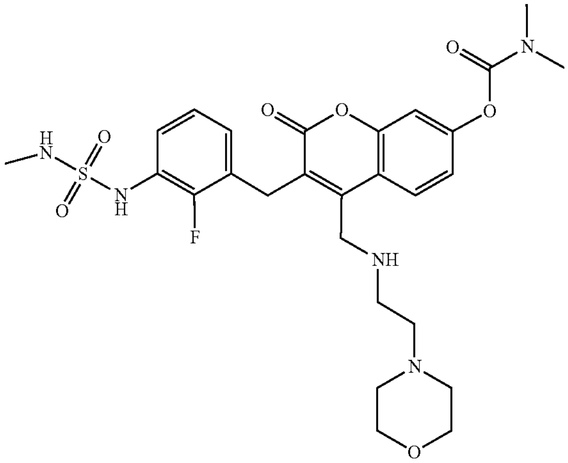 |
| 36 | 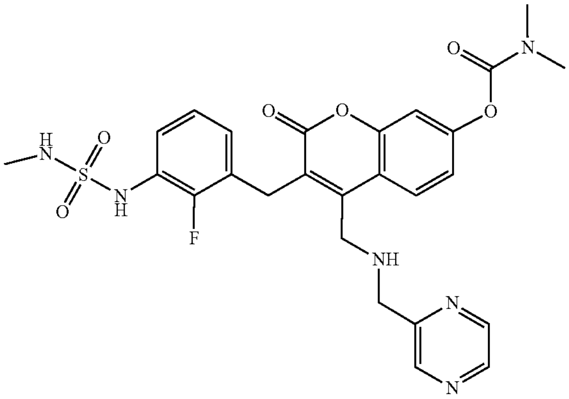 |

TABLE A-continued
| No. | Structure |
| --- | --- |
| 37 | 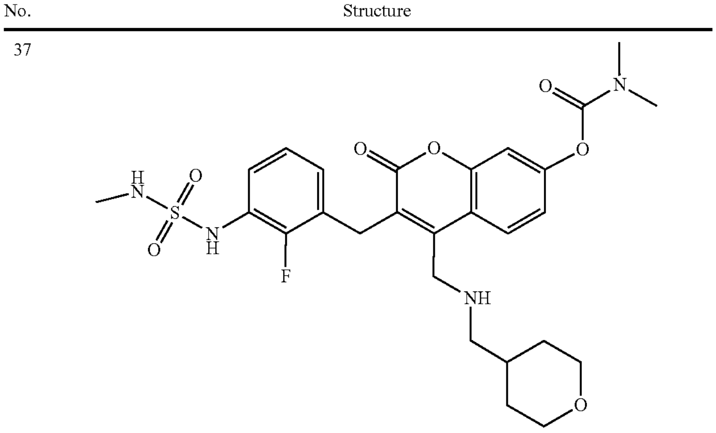 |
| 38 | 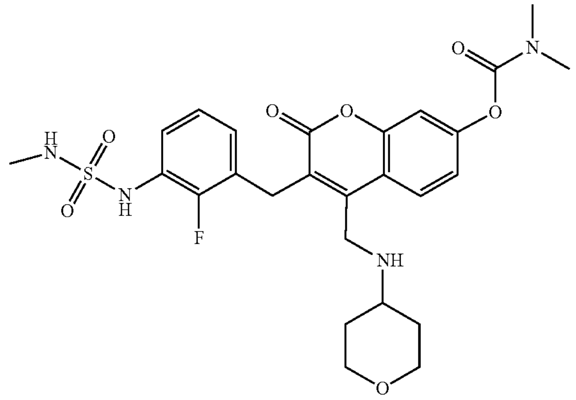 |
| 39 | 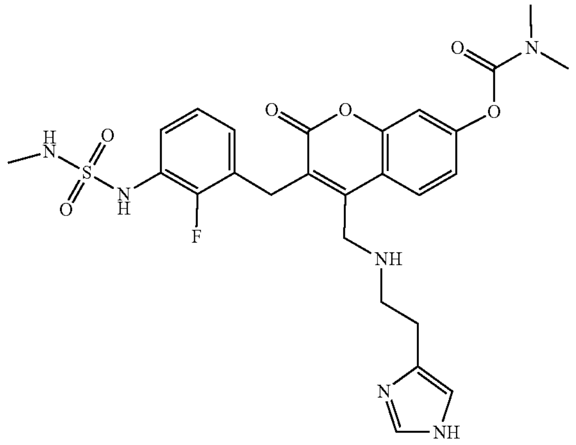 |
| 40 | 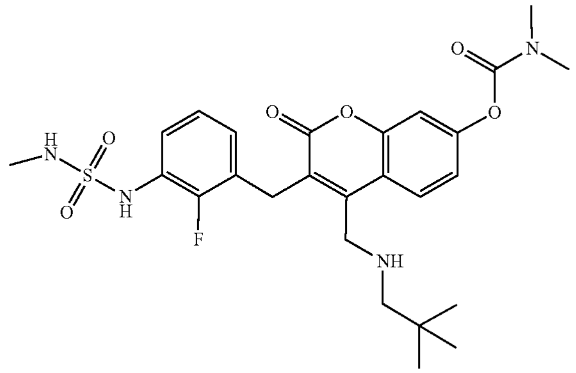 |

TABLE A-continued
| No. | Structure |
|---|---|
| 41 | 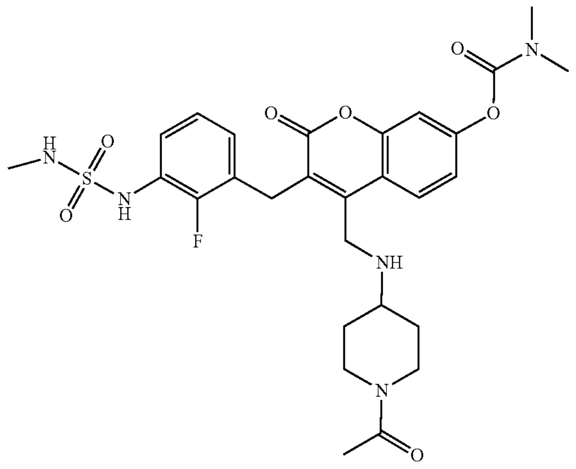 |
| 42 | 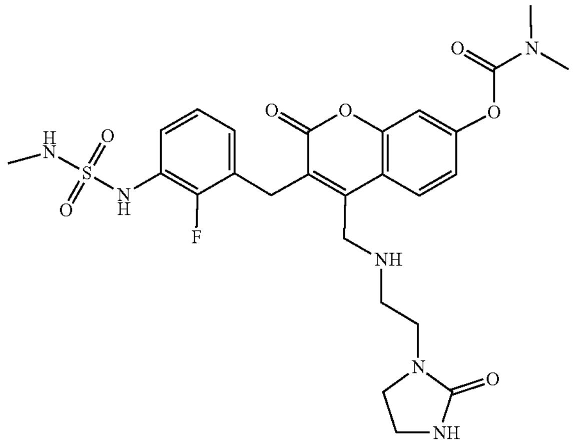 |
| 43 | 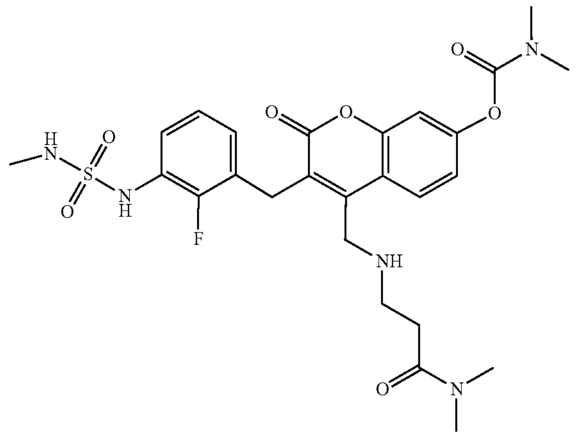 |

TABLE A-continued
| No. | Structure |
| --- | --- |
| 44 | 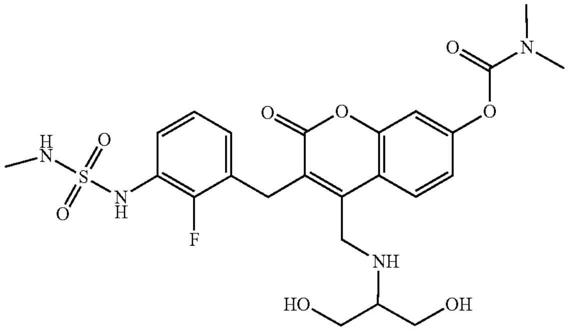 |
| 45 | 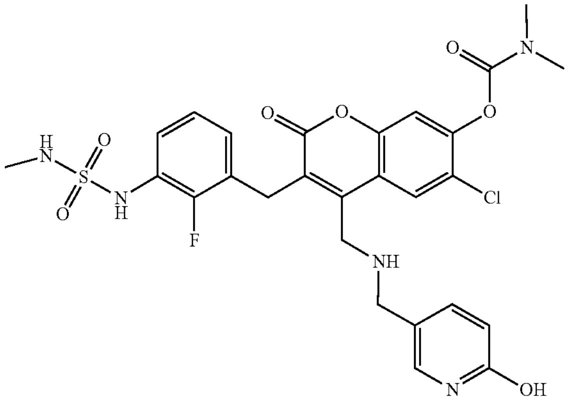 |
| 46 | 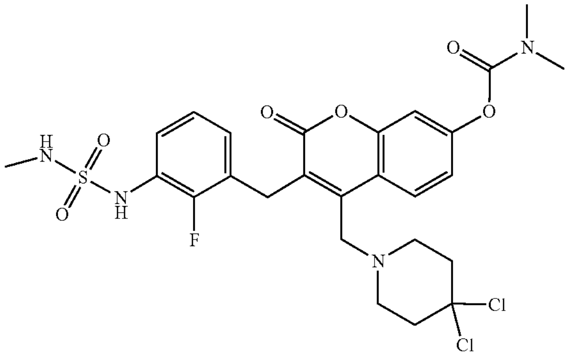 |
| 47 | 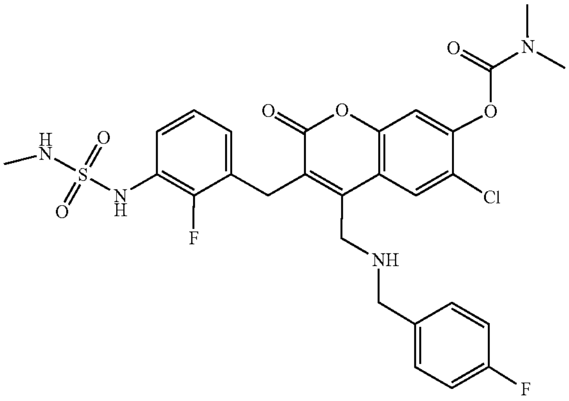 |

TABLE A-continued
| No. | Structure |
| --- | --- |
| 48 | 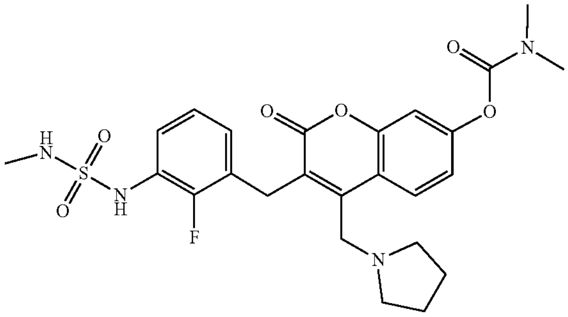 |
| 49 | 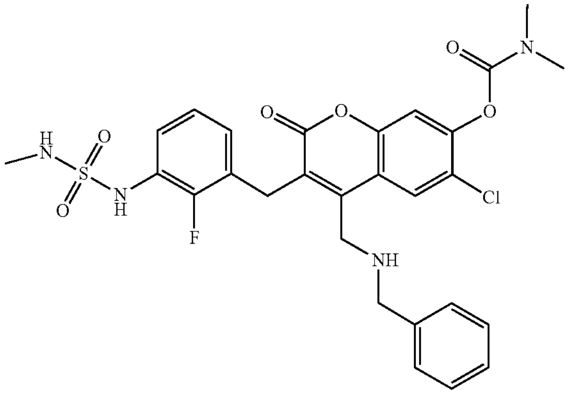 |
| 50 | 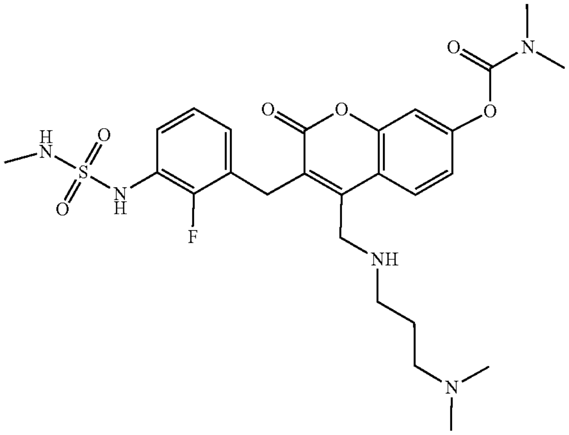 |
| 51 | 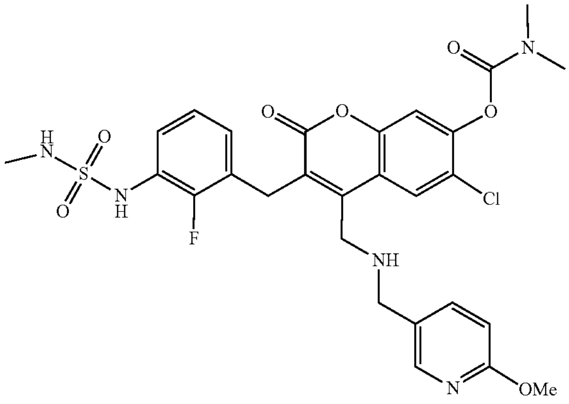 |

TABLE A-continued
| No. | Structure |
| --- | --- |
| 52 | 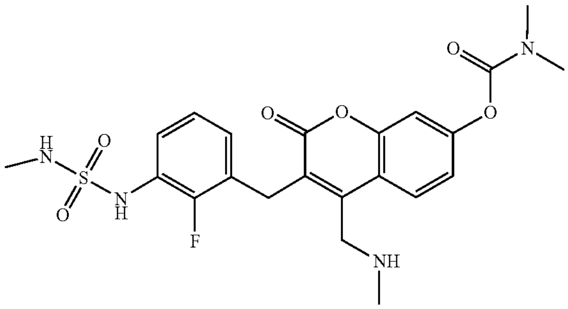 |
| 53 | 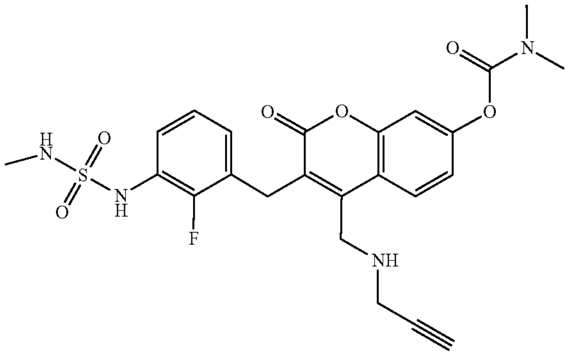 |
| 54 | 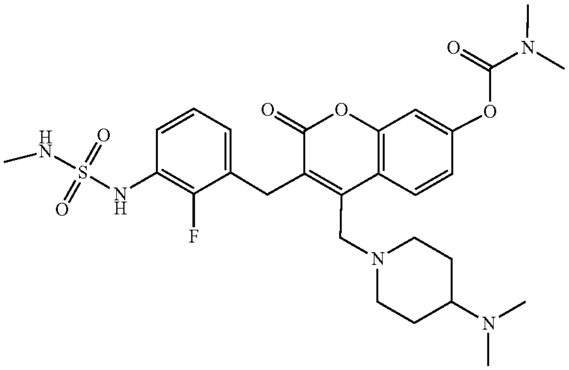 |
| 55 | 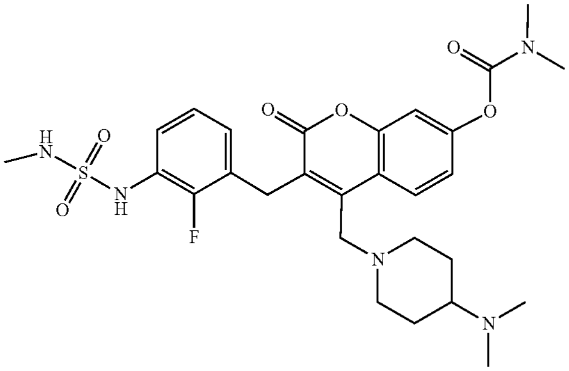 |

TABLE A-continued
| No. | Structure |
| --- | --- |
| 56 | 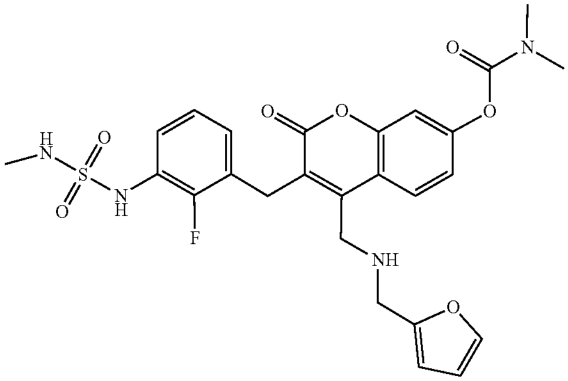 |
| 57 | 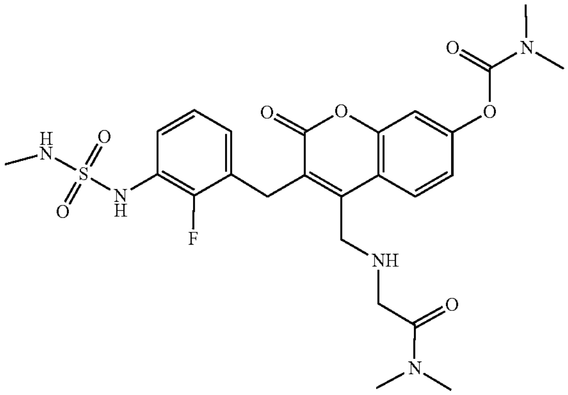 |
| 58 | 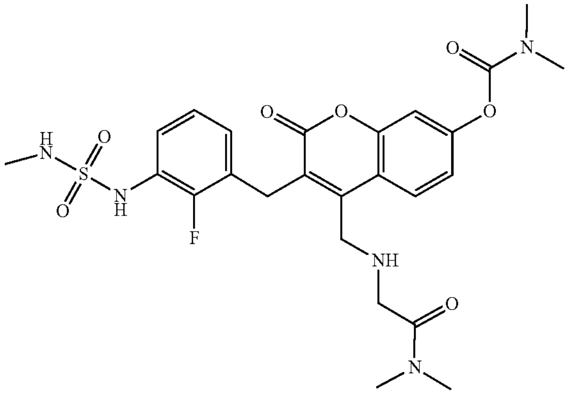 |
| 59 | 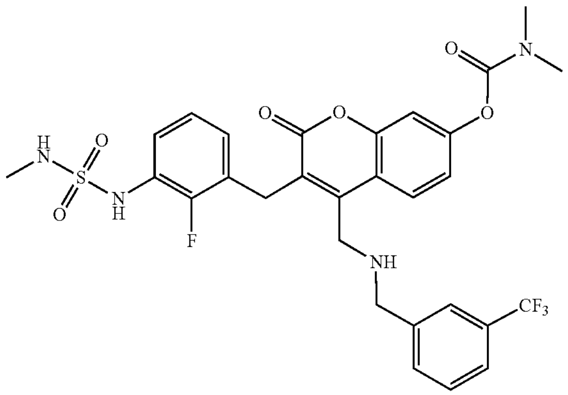 |

TABLE A-continued
| No. | Structure |
|---|---|
| 60 | 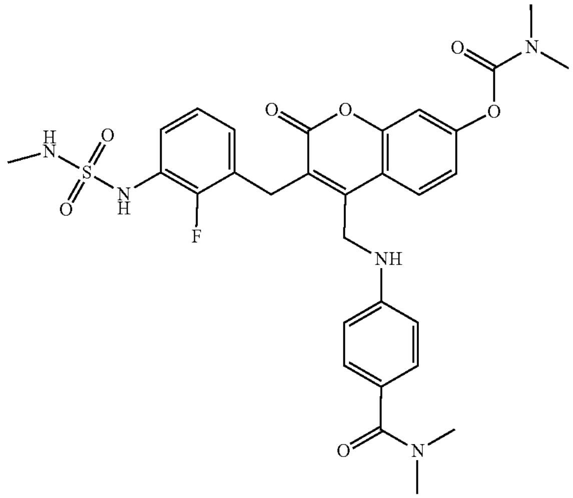 |
| 61 | 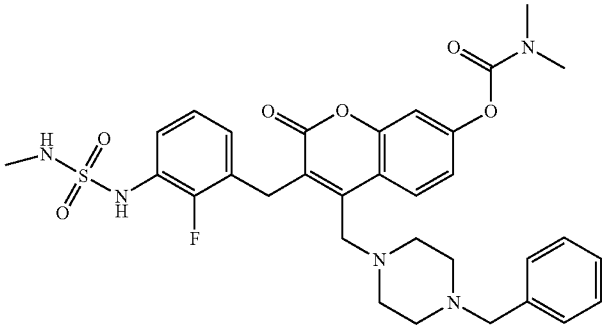 [SMILES: CNS(=O)(=O)Nc1cccc(Cc2c(CN3CCN(Cc4ccccc4)CC3)c3ccc(OC(=O)N(C)C)cc3oc2=O)c1F] |
| 62 | 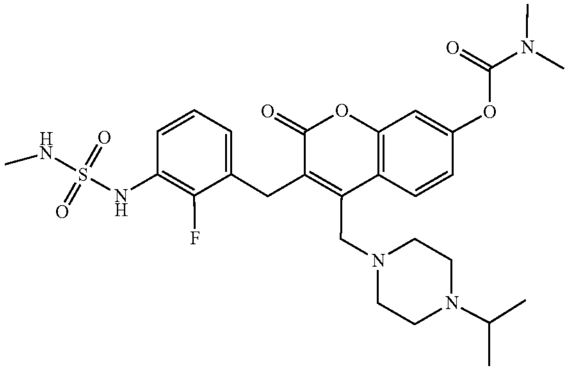 |
| 63 | 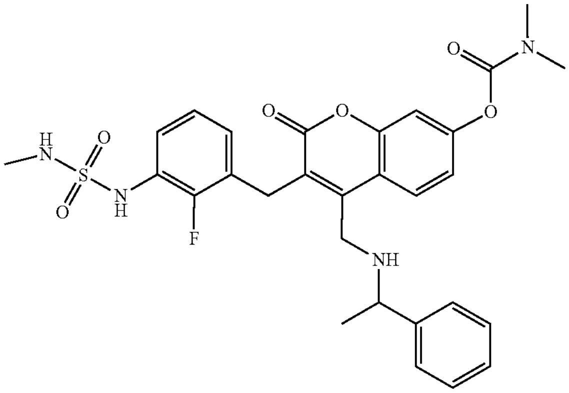 |

TABLE A-continued
| No. | Structure |
|---|---|
| 64 | 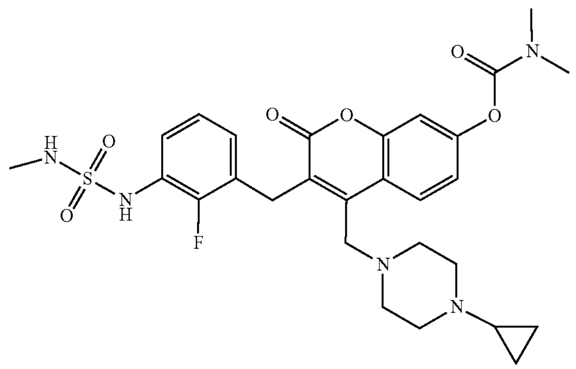 |
| 65 | 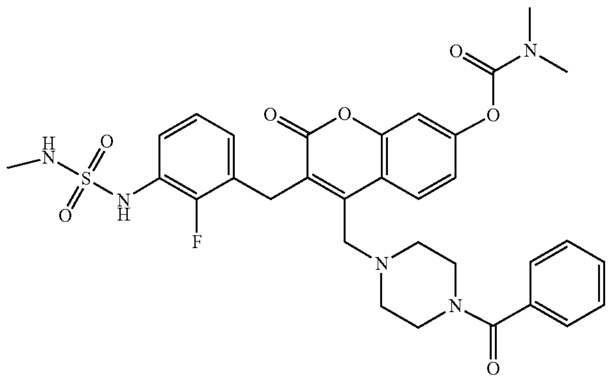 [SMILES: CNS(=O)(=O)Nc1cccc(Cc2c(CN3CCN(C(=O)c4ccccc4)CC3)c3ccc(OC(=O)N(C)C)cc3oc2=O)c1F] |
| 66 | 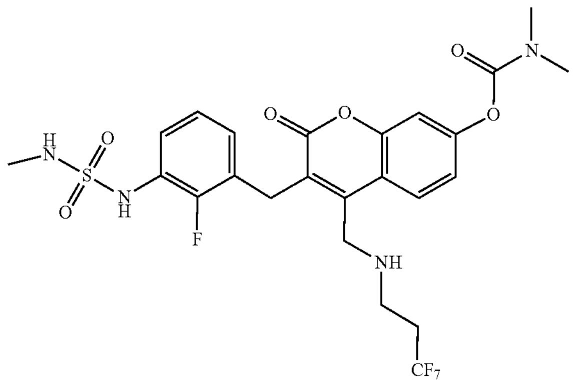 |
| 67 | 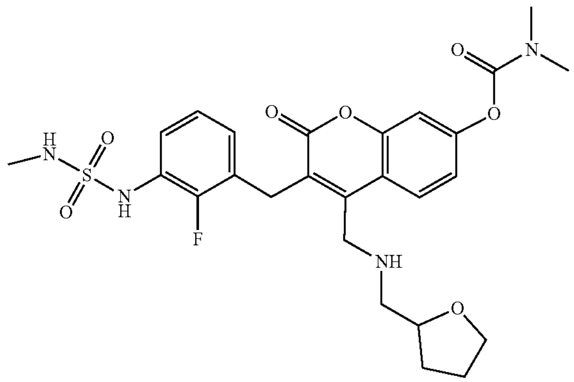 |

TABLE A-continued
| No. | Structure |
|---|---|
| 68 | 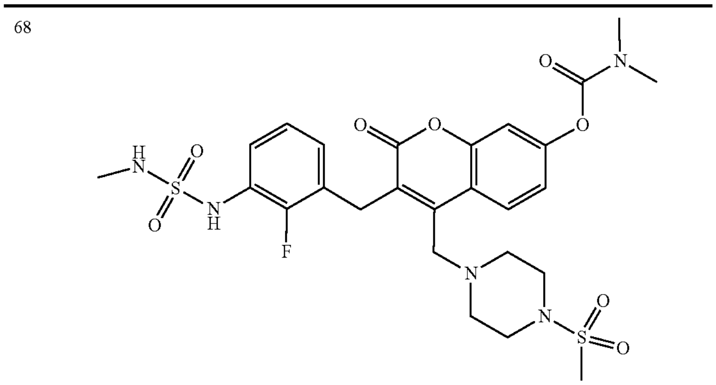 |
| 69 | 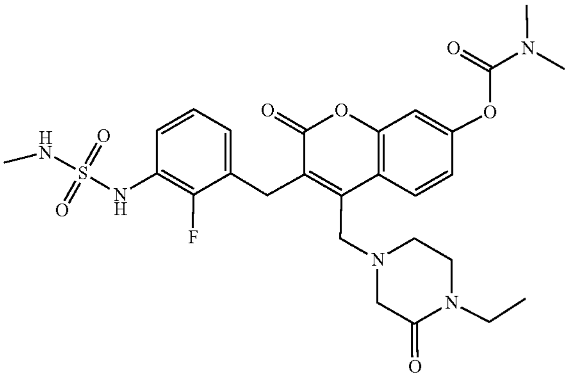 |
| 70 | 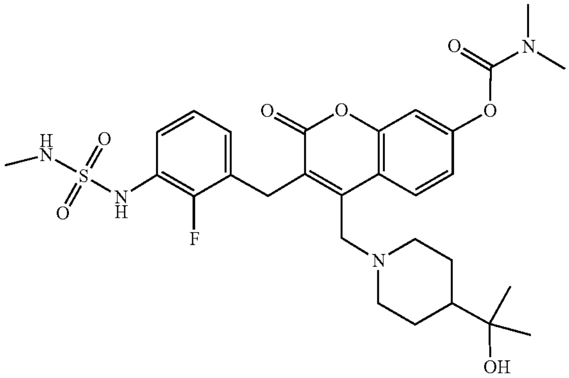 |
| 71 | 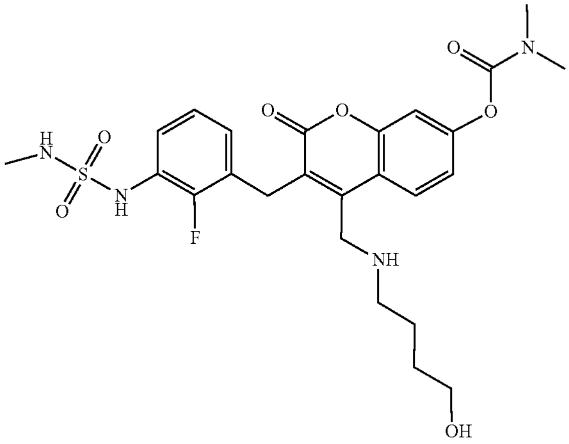 |

TABLE A-continued
| No. | Structure |
| --- | --- |
| 72 | 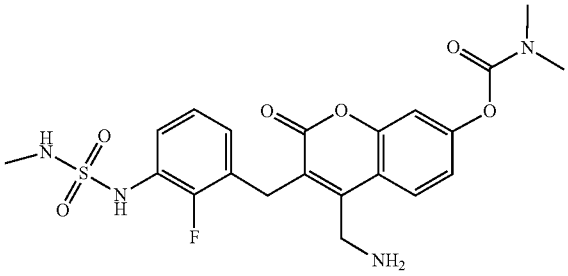 |
| 73 | 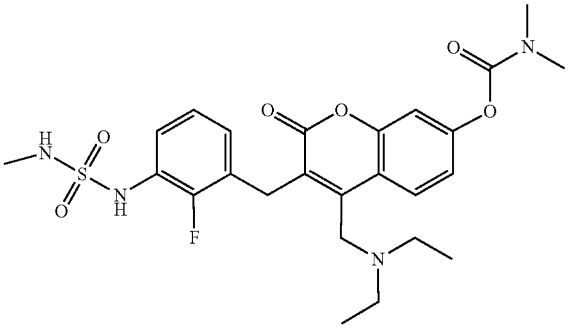 |
| 74 | 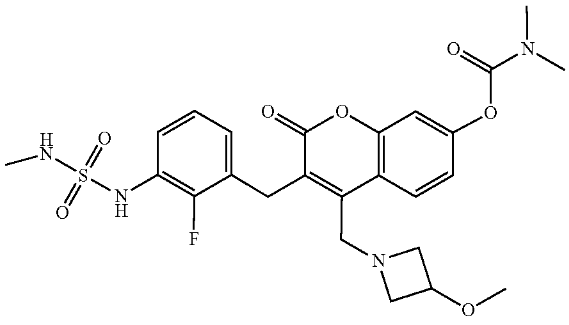 |
| 75 | 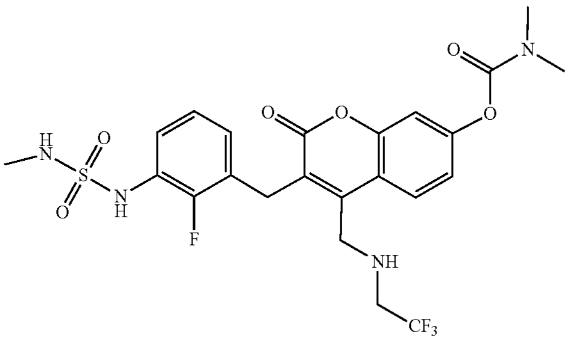 |

TABLE A-continued
| No. | Structure |
| --- | --- |
| 76 | 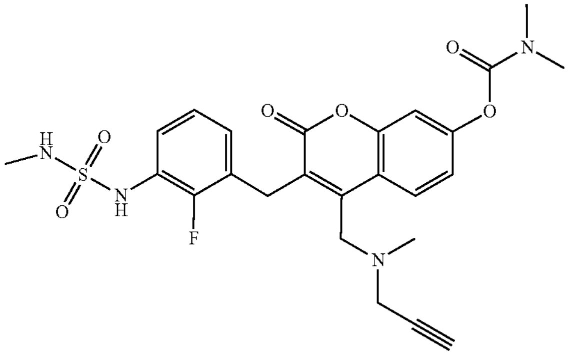 |
| 77 | 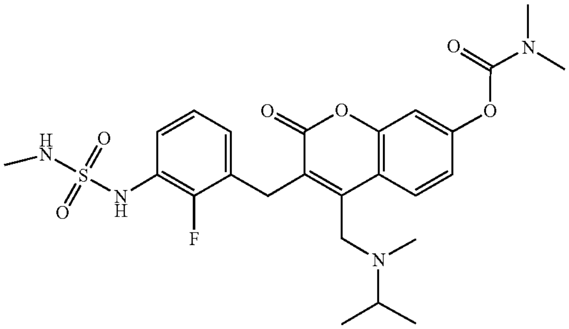 |
| 78 | 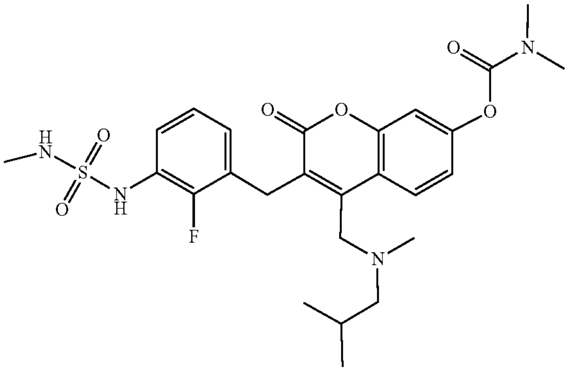 |
| 79 | 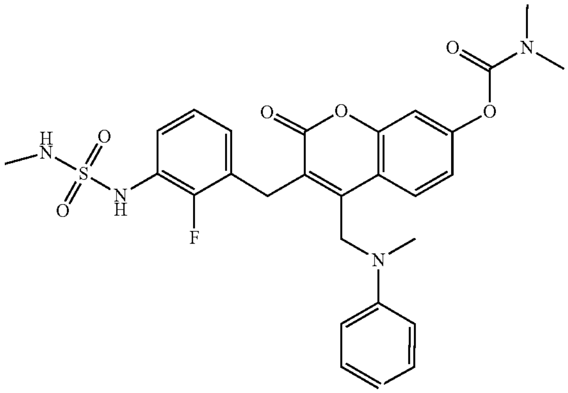 |

TABLE A-continued
| No. | Structure |
|---|---|
| 80 | 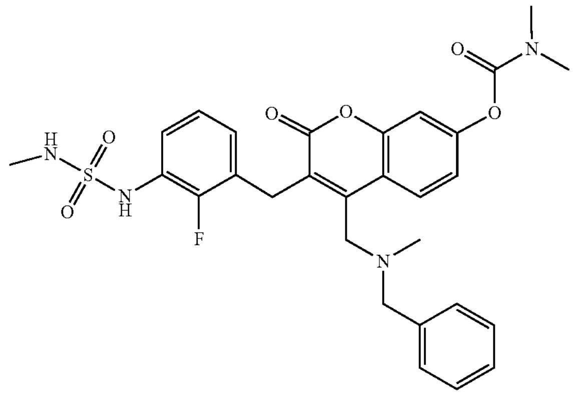 |
| 81 | 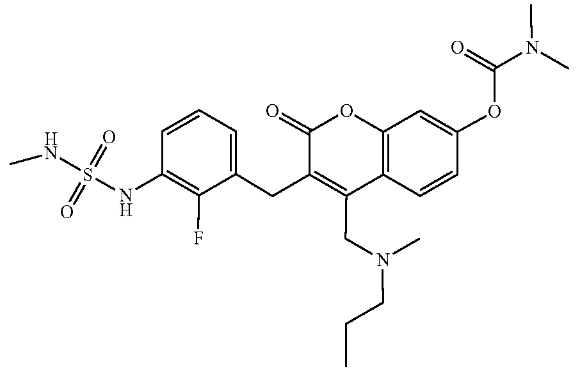 |
| 82 | 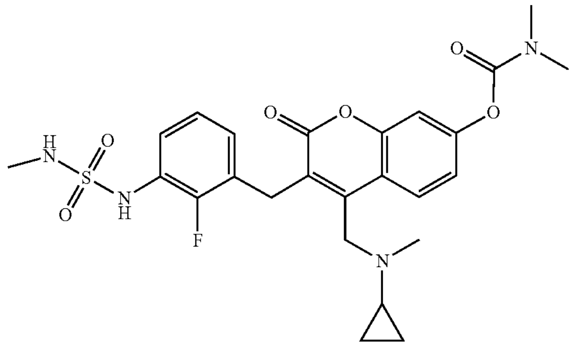 |
| 83 | 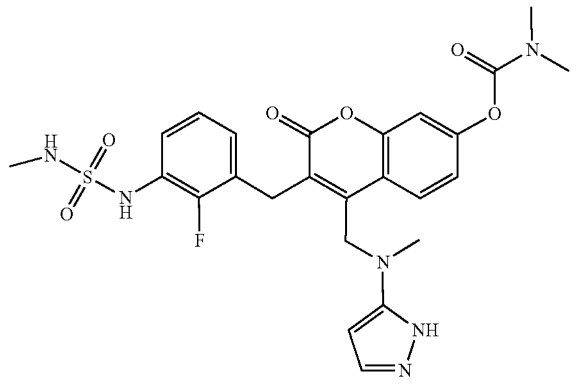 |

TABLE A-continued
| No. | Structure |
| --- | --- |
| 84 | 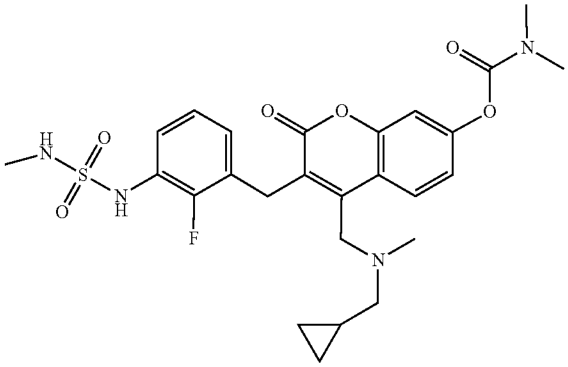 |
| 85 | 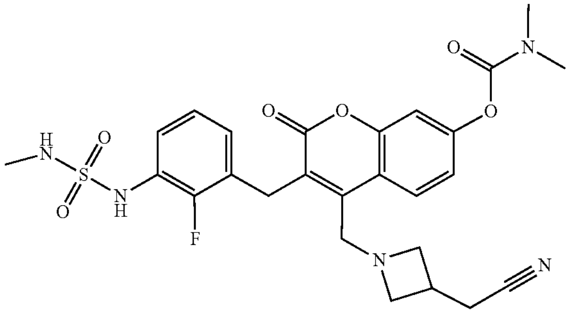 |
| 86 | 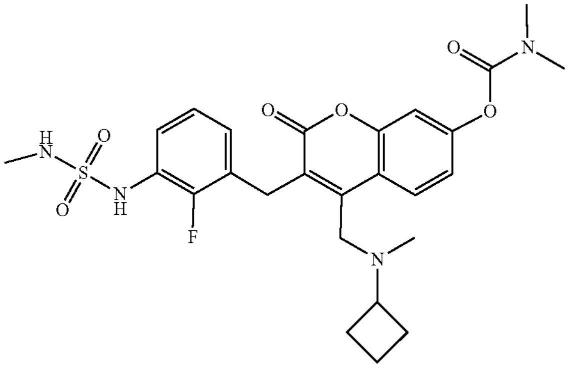 |
| 87 | 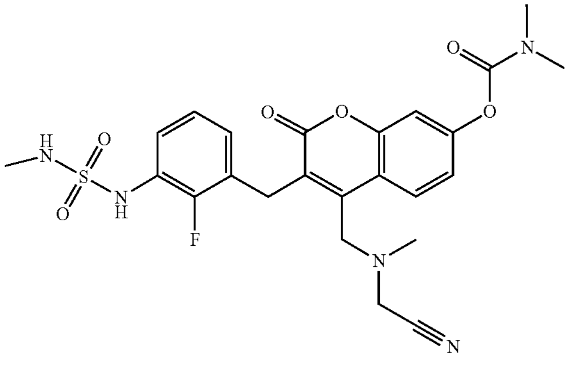 |

TABLE A-continued
| No. | Structure |
| --- | --- |
| 88 | 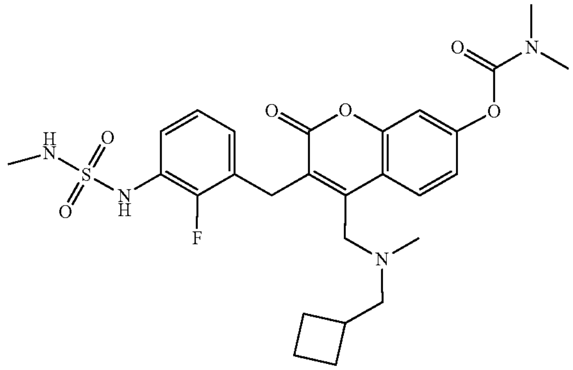 |
| 89 | 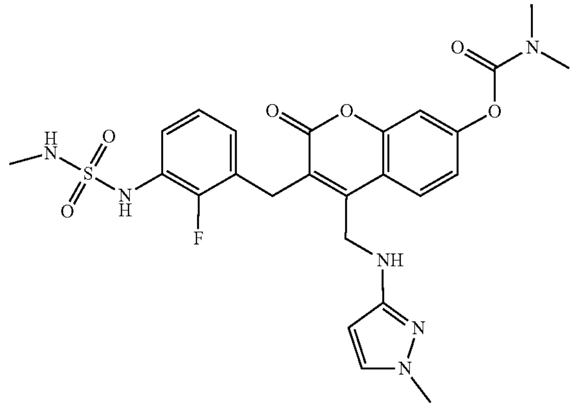 |
| 90 | 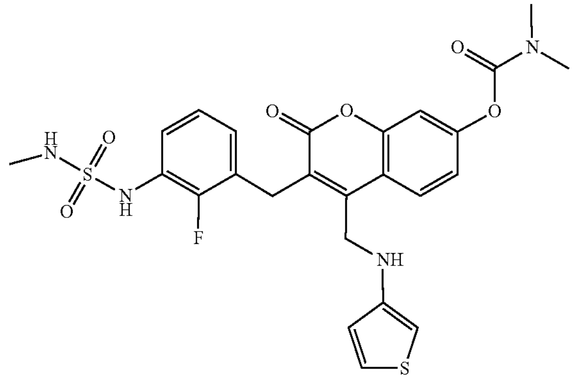 |
| 91 | 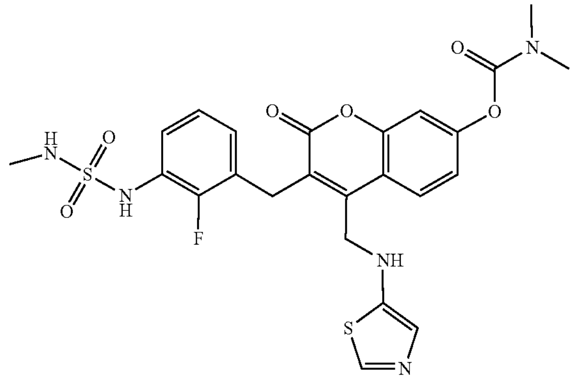 |

TABLE A-continued
| No. | Structure |
|---|---|
| 92 | 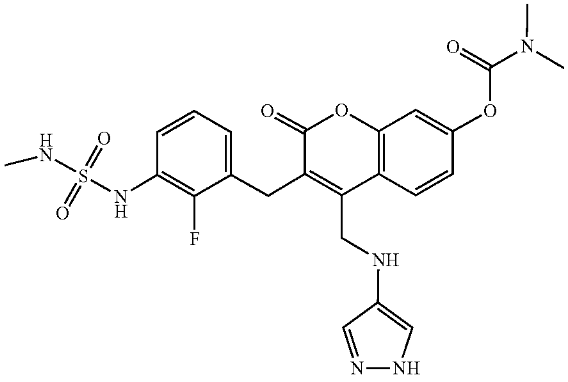 |
| 93 | 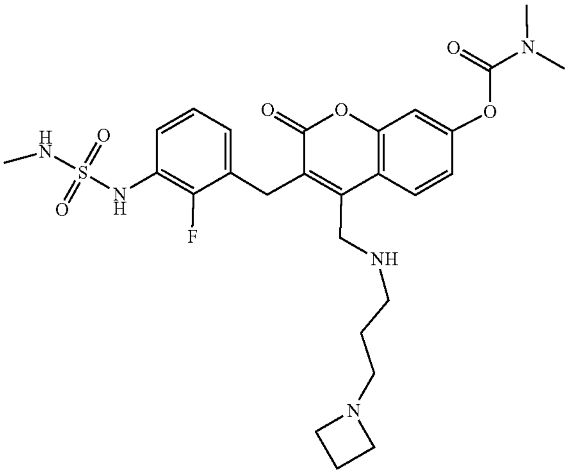 |
| 94 | 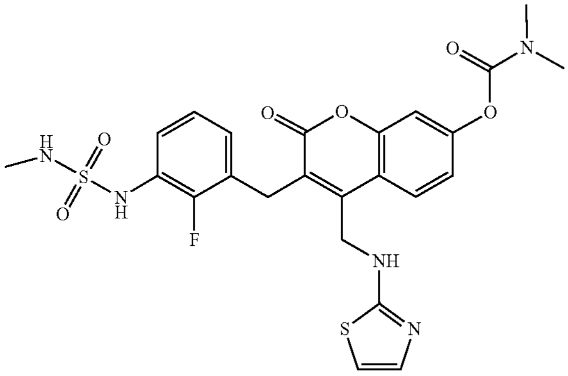 |

TABLE A-continued
| No. | Structure |
| --- | --- |
| 95 | 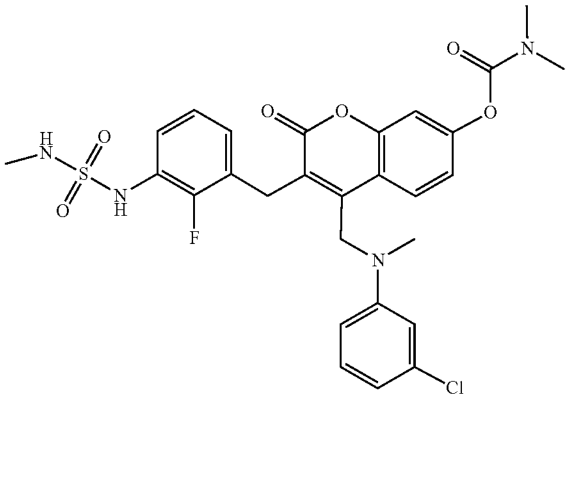 |
| 96 | 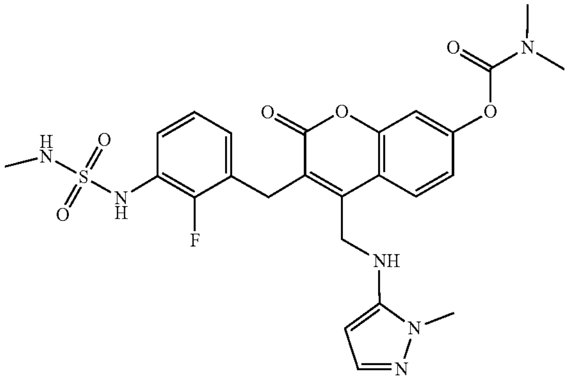 |
| 97 | 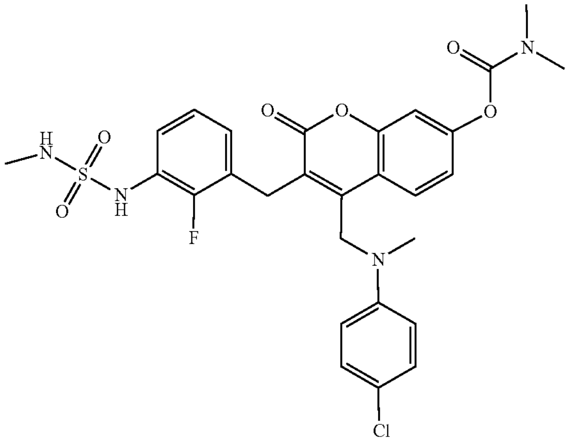 |

TABLE A-continued
| No. | Structure |
|---|---|
| 98 | 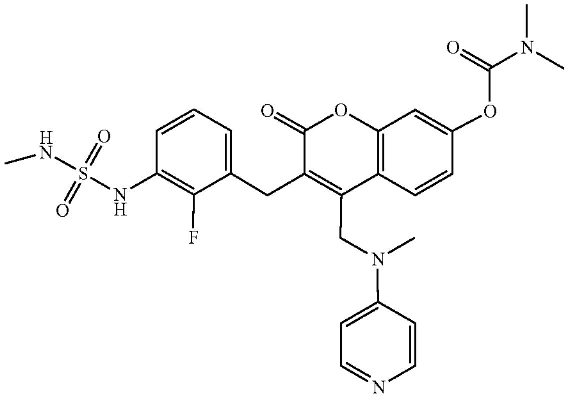 |
| 99 | 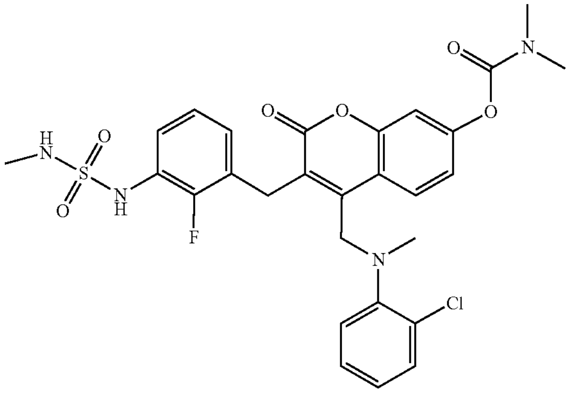 |
| 100 | 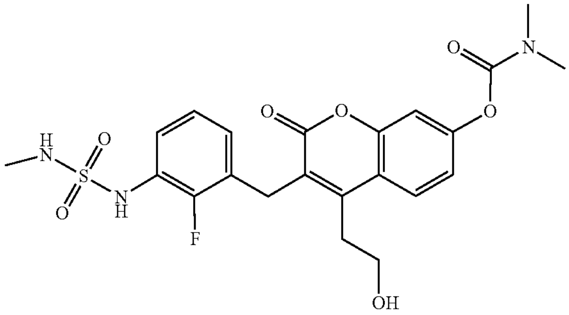 |
| 101 | 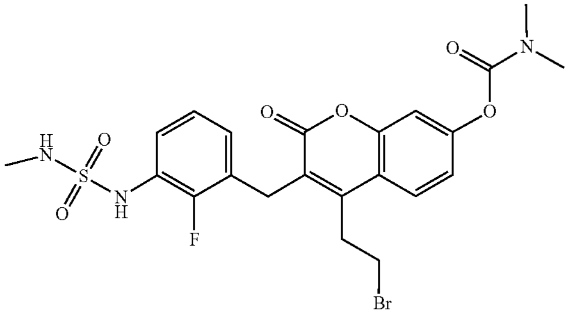 |

TABLE A-continued
| No. | Structure |
| --- | --- |
| 102 | 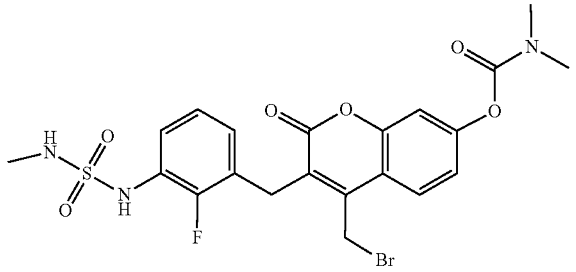 |
| 103 | 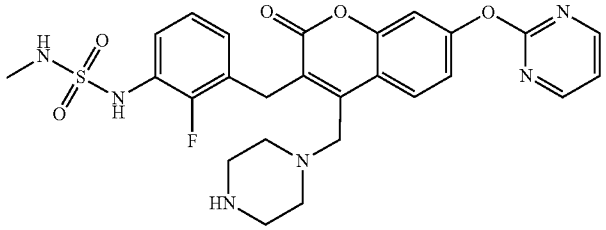 [SMILES: CNS(=O)(=O)Nc1cccc(Cc2c(CN3CCNCC3)c3ccc(Oc4ncccn4)cc3oc2=O)c1F] |
| 104 | 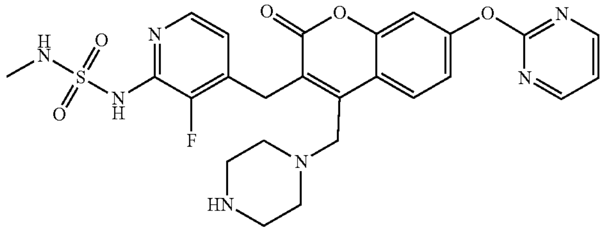 [SMILES: CNS(=O)(=O)Nc1nccc(Cc2c(CN3CCNCC3)c3ccc(Oc4ncccn4)cc3oc2=O)c1F] |
| 105 | 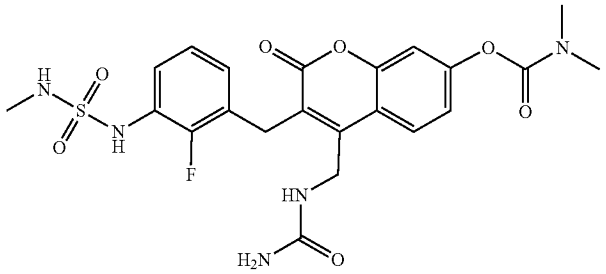 |
| 106 | 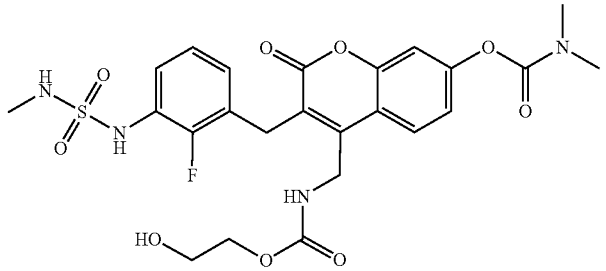 |
| 107 | 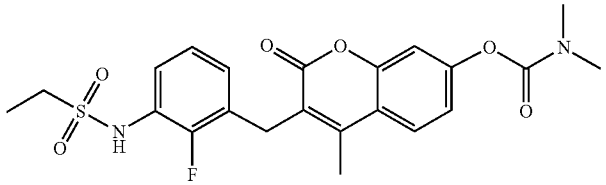 [SMILES: CCS(=O)(=O)Nc1cccc(Cc2c(C)c3ccc(OC(=O)N(C)C)cc3oc2=O)c1F] |

TABLE A-continued
| No. | Structure |
| --- | --- |
| 108 | 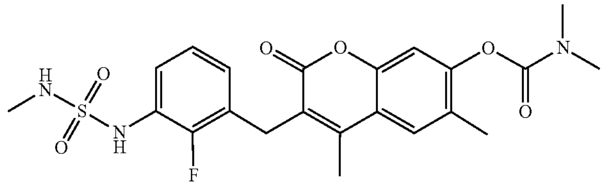 |
| 109 | 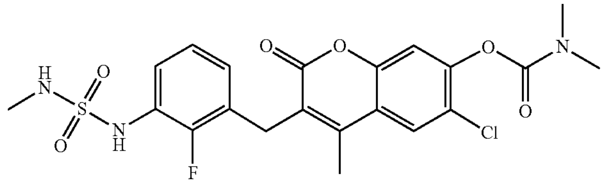 |
| 110 | 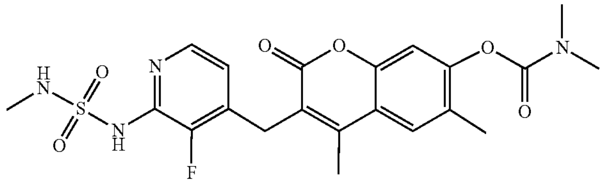 |
| 111 | 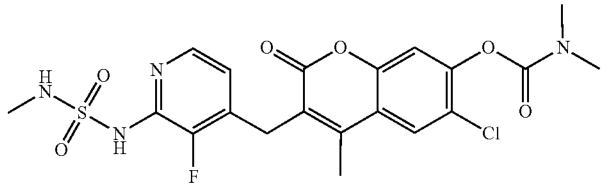 |
| 112 | 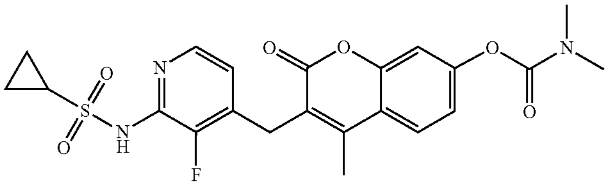 [SMILES: Cc1c(Cc2ccnc(NS(=O)(=O)C3CC3)c2F)c(=O)oc2cc(OC(=O)N(C)C)ccc12] |
| 113 | 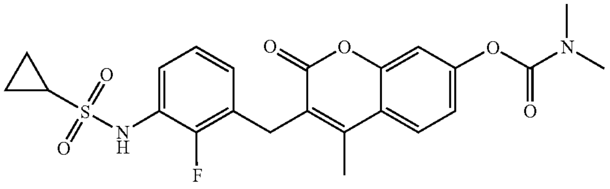 [SMILES: Cc1c(Cc2cccc(NS(=O)(=O)C3CC3)c2F)c(=O)oc2cc(OC(=O)N(C)C)ccc12] |
| 114 | 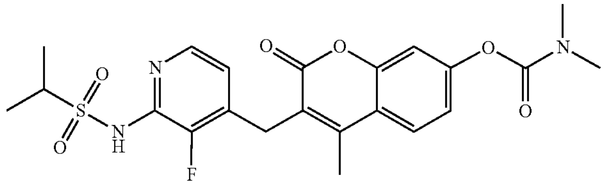 [SMILES: Cc1c(Cc2ccnc(NS(=O)(=O)C(C)C)c2F)c(=O)oc2cc(OC(=O)N(C)C)ccc12] |
| 115 | 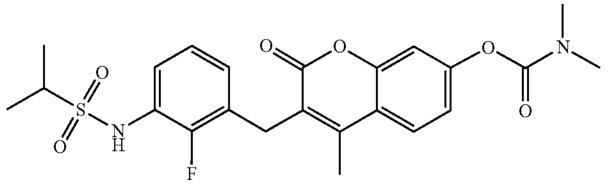 [SMILES: Cc1c(Cc2cccc(NS(=O)(=O)C(C)C)c2F)c(=O)oc2cc(OC(=O)N(C)C)ccc12] |

TABLE A-continued
| No. | Structure |
| --- | --- |
| 116 | 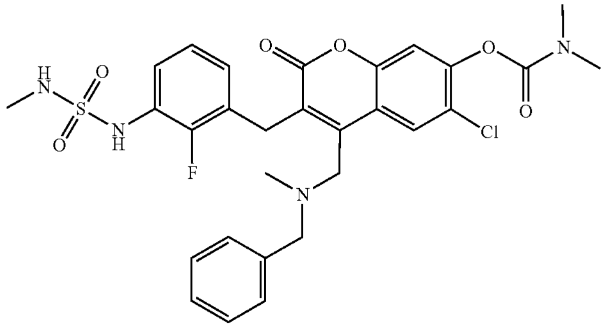 |
| 117 | 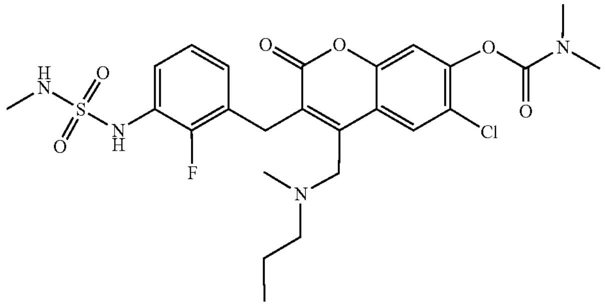 |
| 118 | 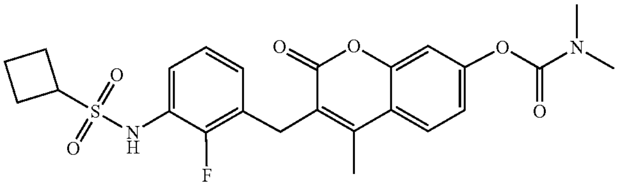 [SMILES: Cc1c(Cc2cccc(NS(=O)(=O)C3CCC3)c2F)c(=O)oc2cc(OC(=O)N(C)C)ccc12] |
| 119 | 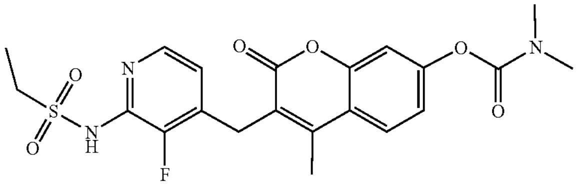 [SMILES: CCS(=O)(=O)Nc1nccc(Cc2c(C)c3ccc(OC(=O)N(C)C)cc3oc2=O)c1F] |
| 120 | 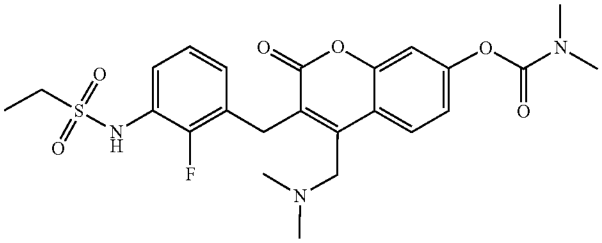 [SMILES: CCS(=O)(=O)Nc1cccc(Cc2c(CN(C)C)c3ccc(OC(=O)N(C)C)cc3oc2=O)c1F] |
| 121 | 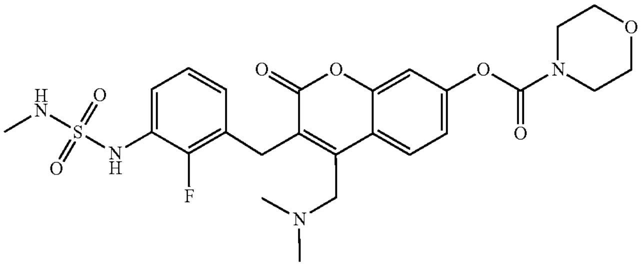 [SMILES: CNS(=O)(=O)Nc1cccc(Cc2c(CN(C)C)c3ccc(OC(=O)N4CCOCC4)cc3oc2=O)c1F] |

TABLE A-continued
| No. | Structure |
|---|---|
| 122 | 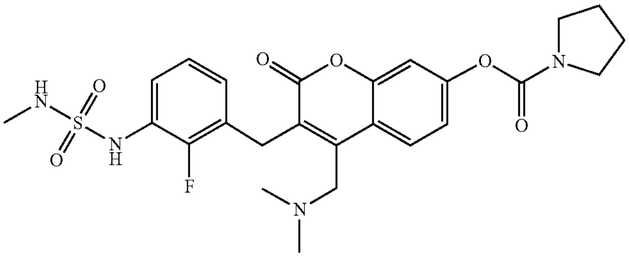 [SMILES: CNS(=O)(=O)Nc1cccc(Cc2c(CN(C)C)c3ccc(OC(=O)N4CCCC4)cc3oc2=O)c1F] |
| 123 | 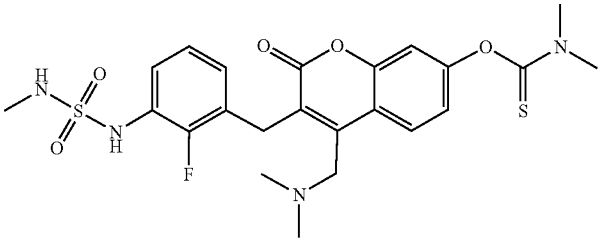 |
| 124 | 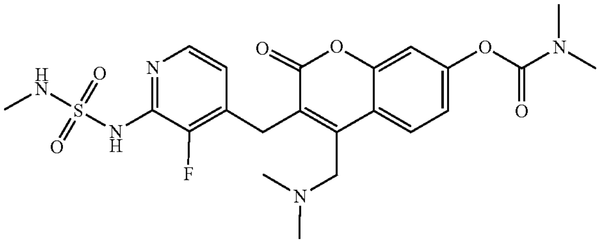 |
| 125 | 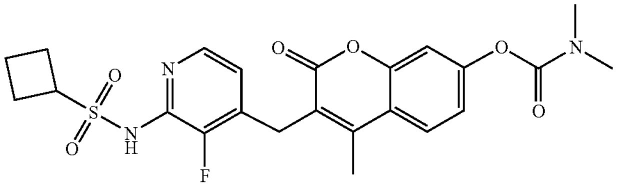 [SMILES: Cc1c(Cc2ccnc(NS(=O)(=O)C3CCC3)c2F)c(=O)oc2cc(OC(=O)N(C)C)ccc12] |
| 126 | 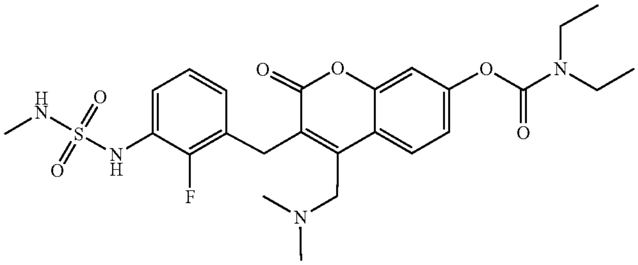 [SMILES: CCN(CC)C(=O)Oc1ccc2c(CN(C)C)c(Cc3cccc(NS(=O)(=O)NC)c3F)c(=O)oc2c1] |
| 127 | 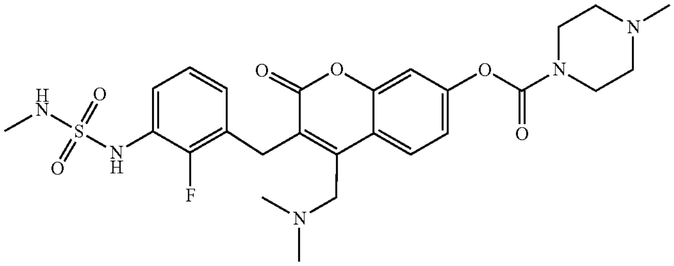 |

TABLE A-continued
| No. | Structure |
| --- | --- |
| 128 | 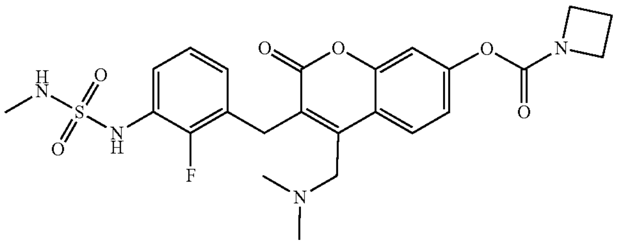 [SMILES: CNS(=O)(=O)Nc1cccc(Cc2c(CN(C)C)c3ccc(OC(=O)N4CCC4)cc3oc2=O)c1F] |
| 129 | 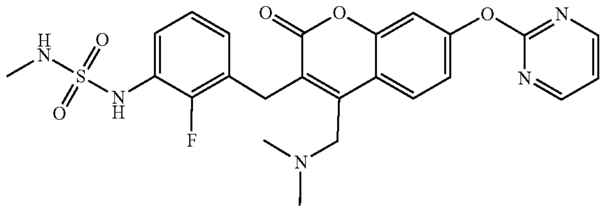 [SMILES: CNS(=O)(=O)Nc1cccc(Cc2c(CN(C)C)c3ccc(Oc4ncccn4)cc3oc2=O)c1F] |
| 130 | 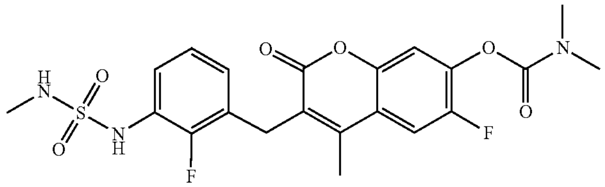 |
| 131 | 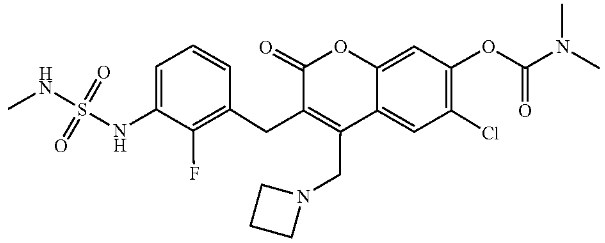 |
| 132 | 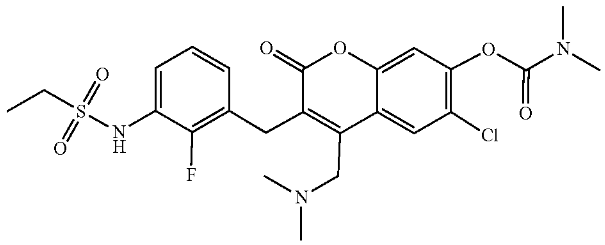 [SMILES: CCS(=O)(=O)Nc1cccc(Cc2c(CN(C)C)c3cc(Cl)c(OC(=O)N(C)C)cc3oc2=O)c1F] |
| 133 | 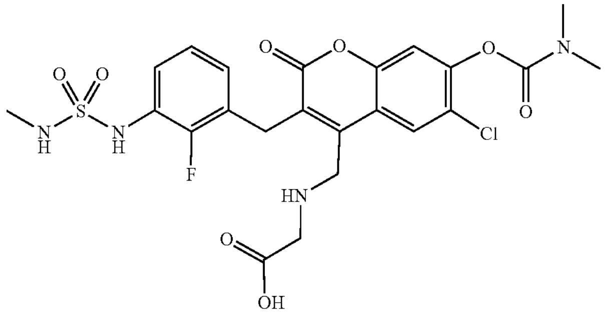 |

TABLE A-continued
| No. | Structure |
| --- | --- |
| 134 | 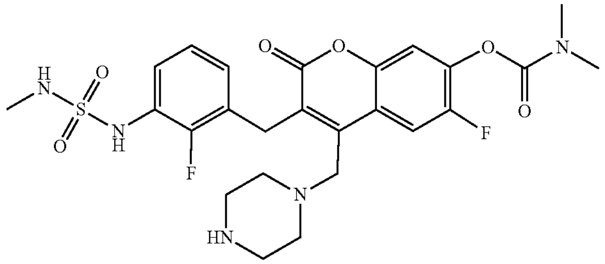 |
| 135 | 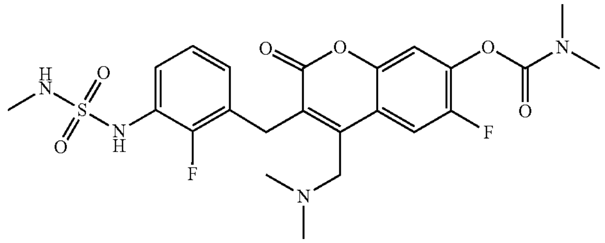 |
| 136 | 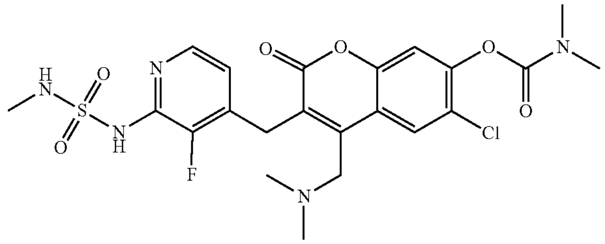 |
| 137 | 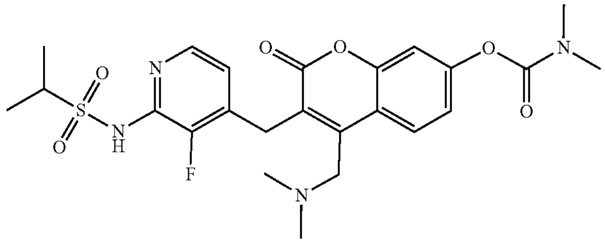 [SMILES: CC(C)S(=O)(=O)Nc1nccc(Cc2c(CN(C)C)c3ccc(OC(=O)N(C)C)cc3oc2=O)c1F] |
| 138 | 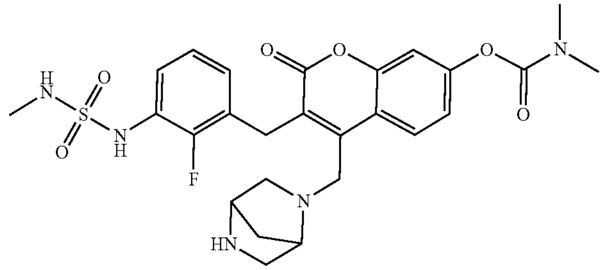 |
| 139 | 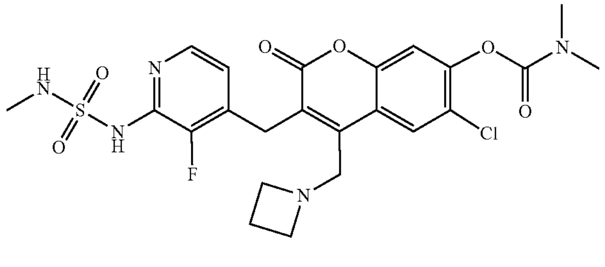 |

TABLE A-continued
| No. | Structure |
| --- | --- |
| 140 | 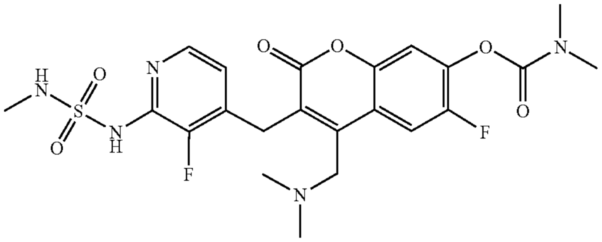 |
| 141 | 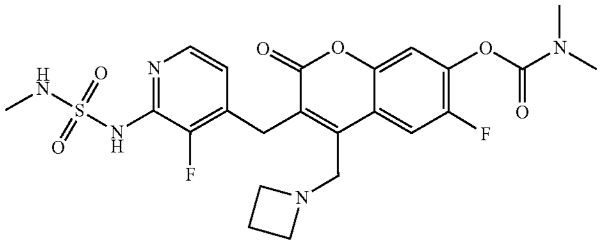 |
| 142 | 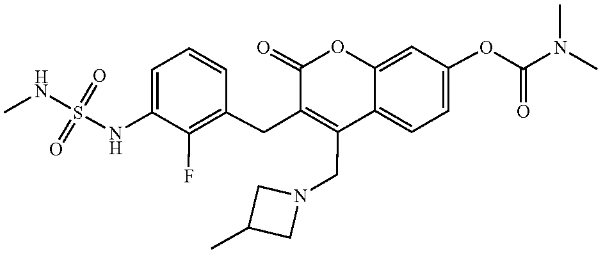 |
| 143 | 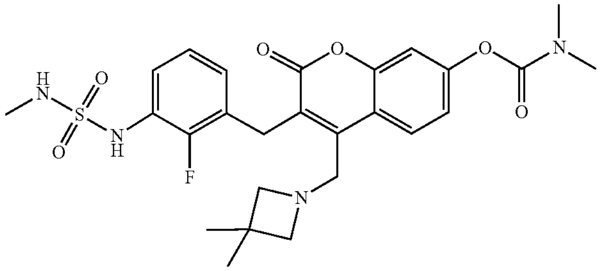 |
| 144 | 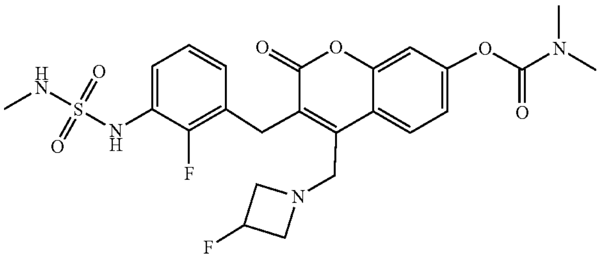 |
| 145 | 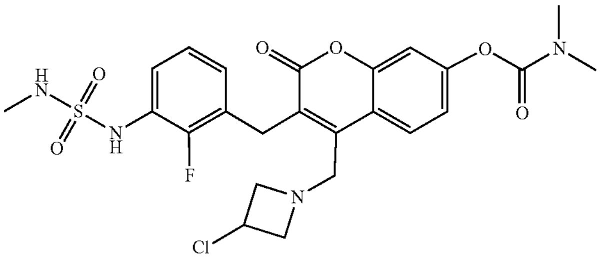 |

TABLE A-continued
| No. | Structure |
|---|---|
| 146 | 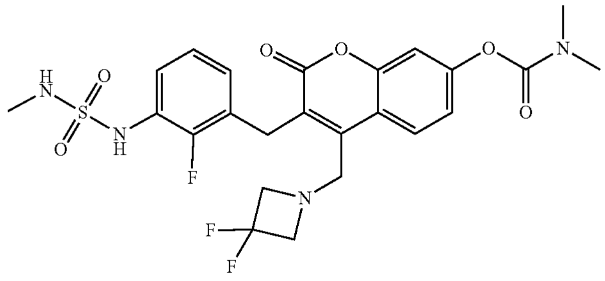 |
| 147 | 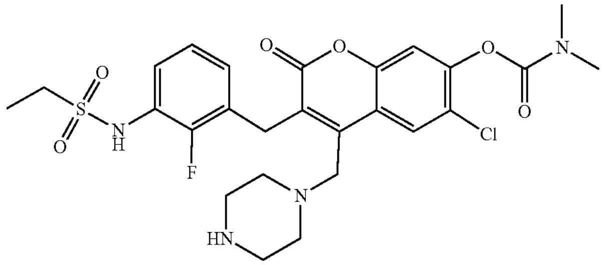 [SMILES: CCS(=O)(=O)Nc1cccc(Cc2c(CN3CCNCC3)c3cc(Cl)c(OC(=O)N(C)C)cc3oc2=O)c1F] |
| 148 | 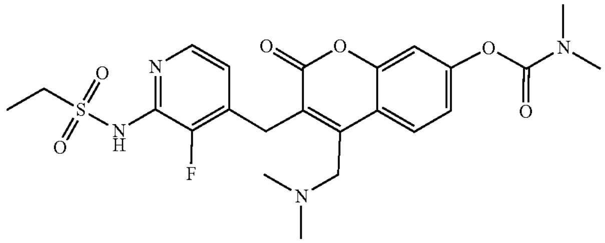 [SMILES: CCS(=O)(=O)Nc1nccc(Cc2c(CN(C)C)c3ccc(OC(=O)N(C)C)cc3oc2=O)c1F] |
| 149 | 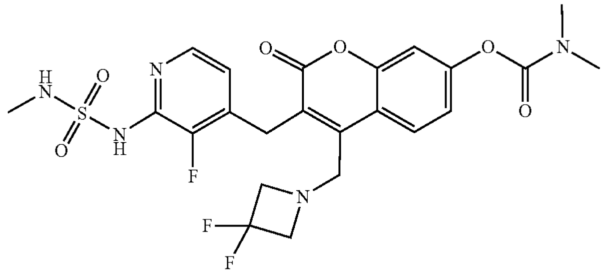 |
| 150 | 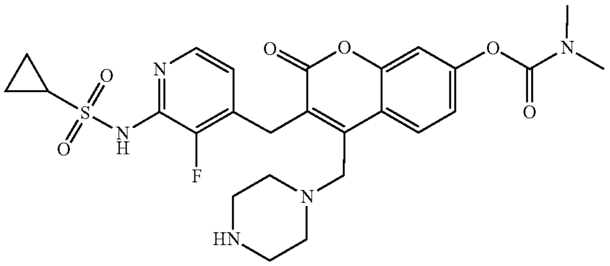 [SMILES: CN(C)C(=O)Oc1ccc2c(CN3CCNCC3)c(Cc3ccnc(NS(=O)(=O)C4CC4)c3F)c(=O)oc2c1] |

TABLE A-continued
| No. | Structure |
|---|---|
| 151 | 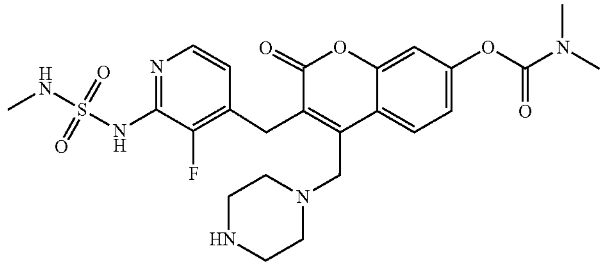 |
| 152 | 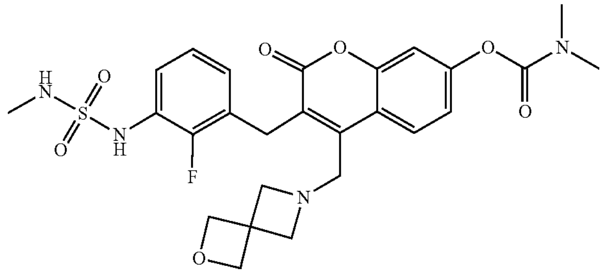 |
| 153 | 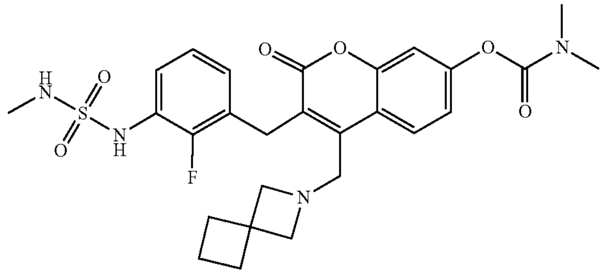 |
| 154 | 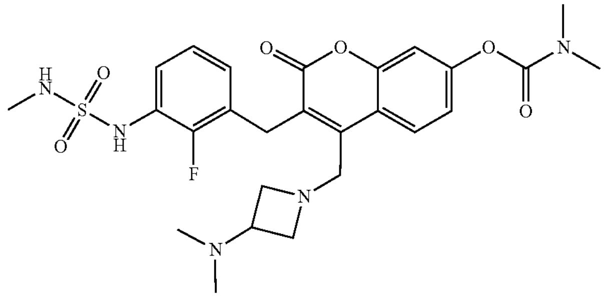 |
| 155 | 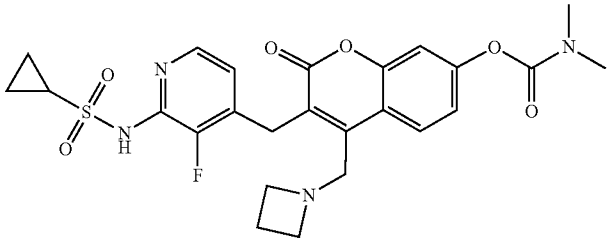 [SMILES: CN(C)C(=O)Oc1ccc2c(CN3CCC3)c(Cc3ccnc(NS(=O)(=O)C4CC4)c3F)c(=O)oc2c1] |

TABLE A-continued
| No. | Structure |
|---|---|
| 156 | 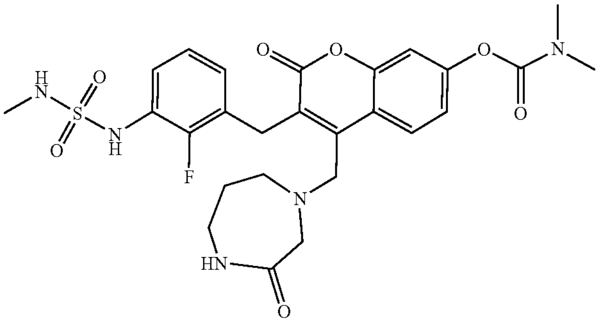 |
| 157 | 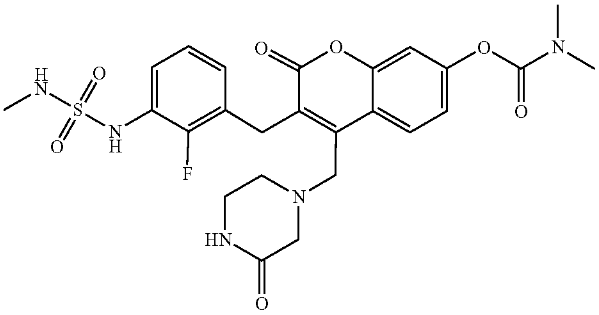 |
| 158 | 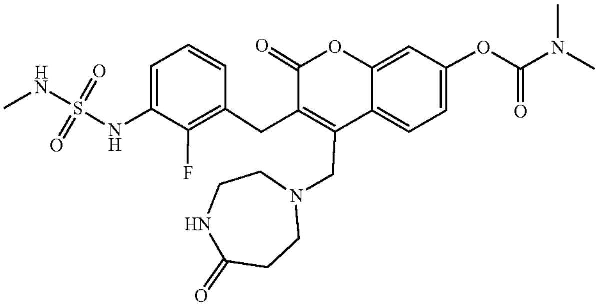 |
| 159 | 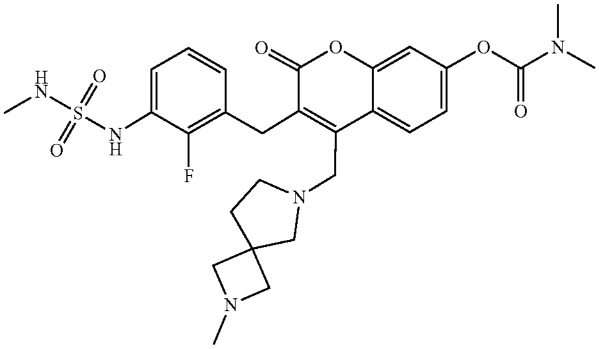 |
| 160 | 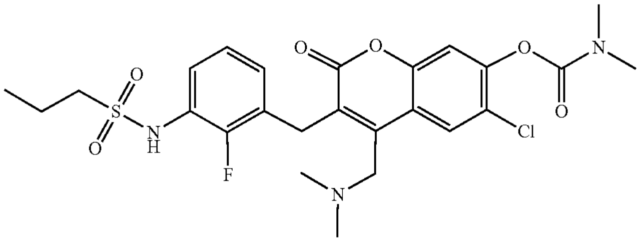 [SMILES: CCCS(=O)(=O)Nc1cccc(Cc2c(CN(C)C)c3cc(Cl)c(OC(=O)N(C)C)cc3oc2=O)c1F] |

TABLE A-continued
| No. | Structure |
|---|---|
| 161 | 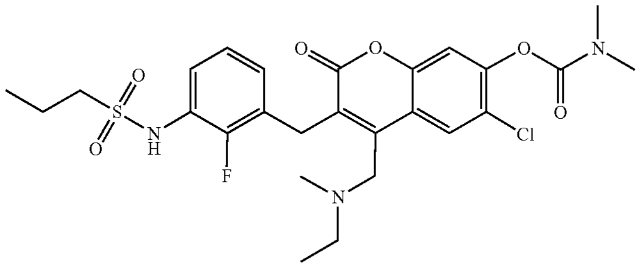 [SMILES: CCCS(=O)(=O)Nc1cccc(Cc2c(CN(C)CC)c3cc(Cl)c(OC(=O)N(C)C)cc3oc2=O)c1F] |
| 162 | 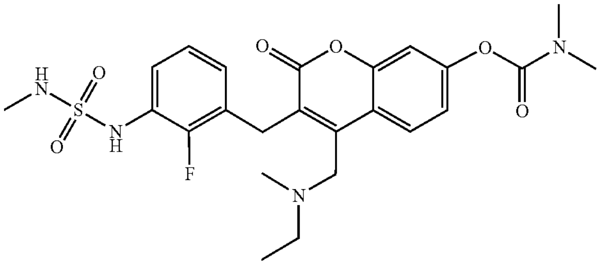 |
| 163 | 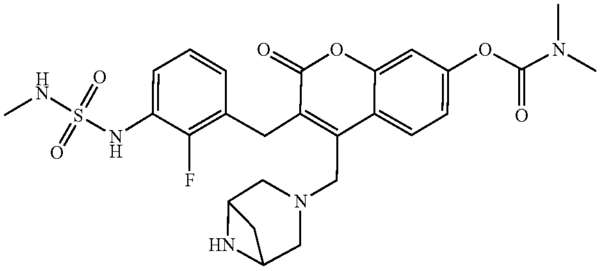 |
| 164 | 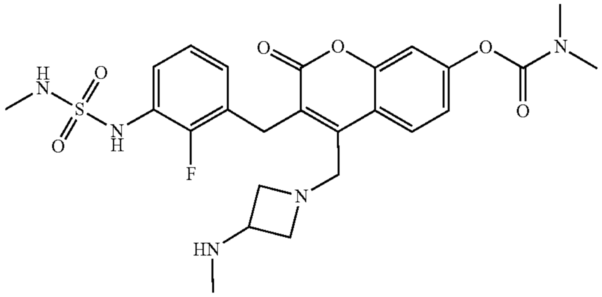 |
| 165 | 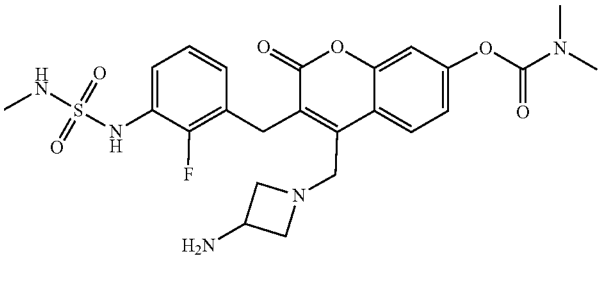 |

TABLE A-continued
| No. | Structure |
| --- | --- |
| 166 | 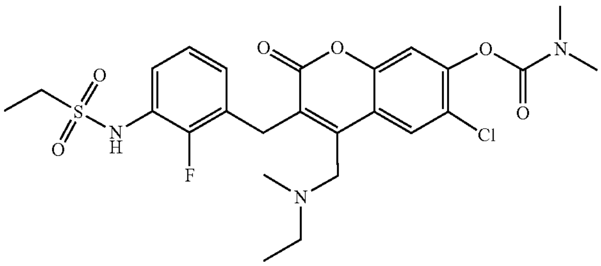 [SMILES: CCN(C)Cc1c(Cc2cccc(NS(=O)(=O)CC)c2F)c(=O)oc2cc(OC(=O)N(C)C)c(Cl)cc12] |
| 167 | 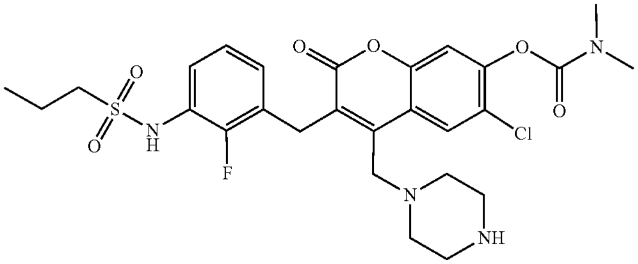 [SMILES: CCCS(=O)(=O)Nc1cccc(Cc2c(CN3CCNCC3)c3cc(Cl)c(OC(=O)N(C)C)cc3oc2=O)c1F] |
| 168 | 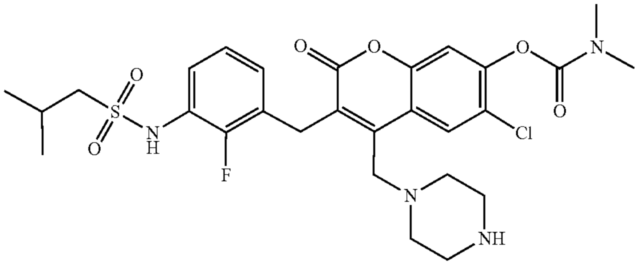 [SMILES: CC(C)CS(=O)(=O)Nc1cccc(Cc2c(CN3CCNCC3)c3cc(Cl)c(OC(=O)N(C)C)cc3oc2=O)c1F] |
| 169 | 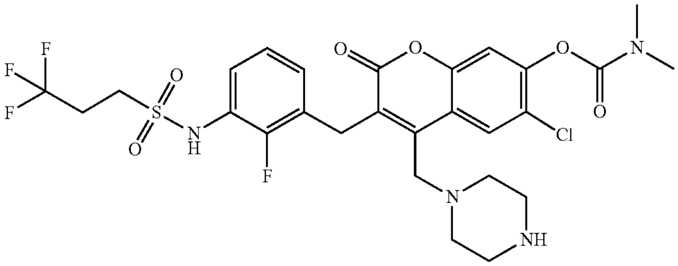 [SMILES: CN(C)C(=O)Oc1cc2oc(=O)c(Cc3cccc(NS(=O)(=O)CCC(F)(F)F)c3F)c(CN3CCNCC3)c2cc1Cl] |
| 170 | 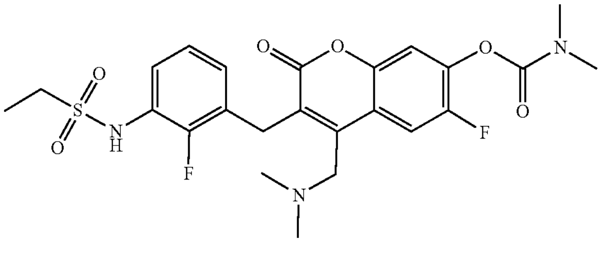 [SMILES: CCS(=O)(=O)Nc1cccc(Cc2c(CN(C)C)c3cc(F)c(OC(=O)N(C)C)cc3oc2=O)c1F] |

TABLE A-continued
| No. | Structure |
|---|---|
| 171 | 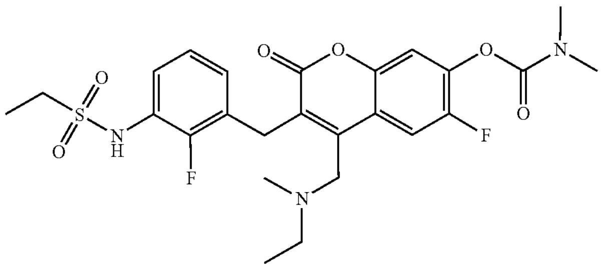 [SMILES: CCN(C)Cc1c(Cc2cccc(NS(=O)(=O)CC)c2F)c(=O)oc2cc(OC(=O)N(C)C)c(F)cc12] |
| 172 | 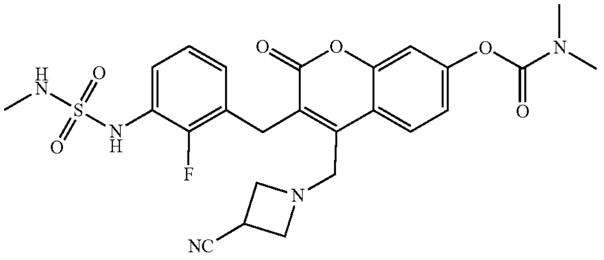 |
| 173 | 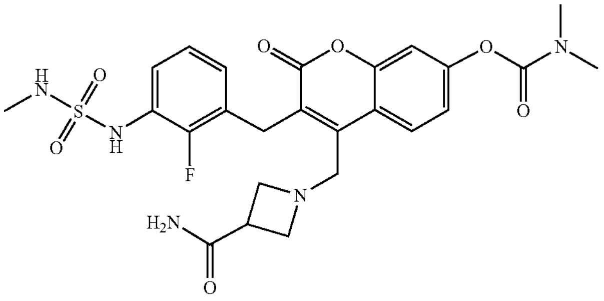 |
| 174 | 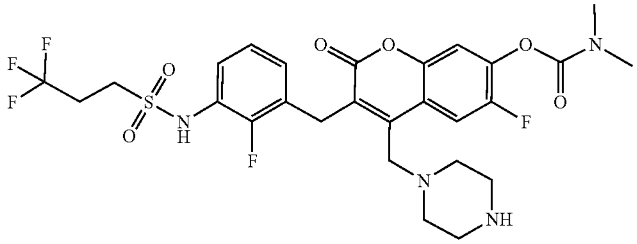 [SMILES: CN(C)C(=O)Oc1cc2oc(=O)c(Cc3cccc(NS(=O)(=O)CCC(F)(F)F)c3F)c(CN3CCNCC3)c2cc1F] |
| 175 | 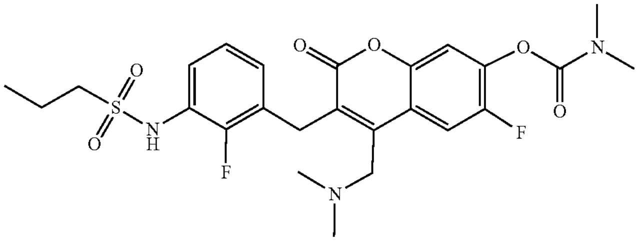 [SMILES: CCCS(=O)(=O)Nc1cccc(Cc2c(CN(C)C)c3cc(F)c(OC(=O)N(C)C)cc3oc2=O)c1F] |

TABLE A-continued
| No. | Structure |
| --- | --- |
| 176 | 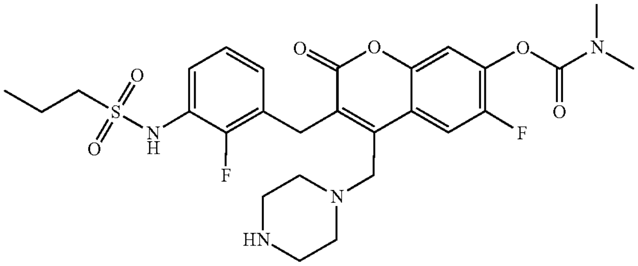 [SMILES: CCCS(=O)(=O)Nc1cccc(Cc2c(CN3CCNCC3)c3cc(F)c(OC(=O)N(C)C)cc3oc2=O)c1F] |
| 177 | 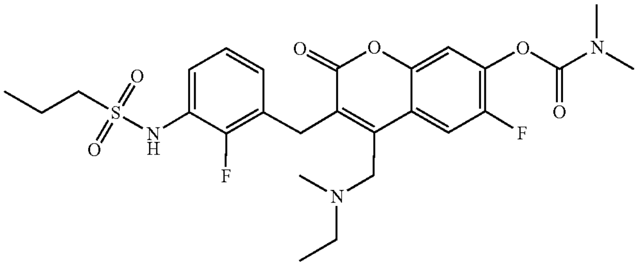 [SMILES: CCCS(=O)(=O)Nc1cccc(Cc2c(CN(C)CC)c3cc(F)c(OC(=O)N(C)C)cc3oc2=O)c1F] |
| 178 | 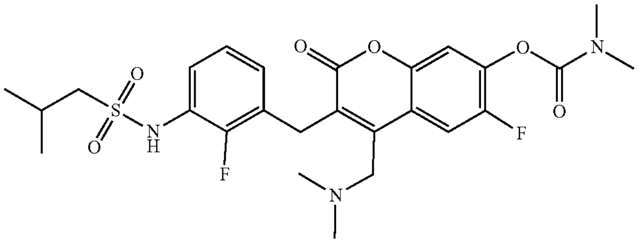 [SMILES: CC(C)CS(=O)(=O)Nc1cccc(Cc2c(CN(C)C)c3cc(F)c(OC(=O)N(C)C)cc3oc2=O)c1F] |
| 179 | 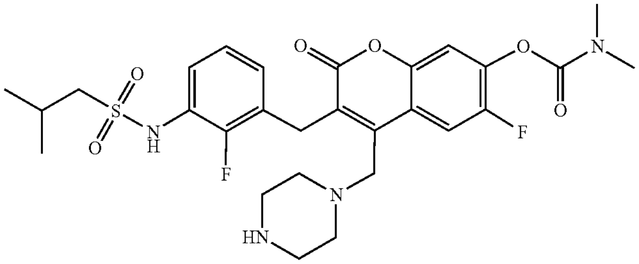 [SMILES: CC(C)CS(=O)(=O)Nc1cccc(Cc2c(CN3CCNCC3)c3cc(F)c(OC(=O)N(C)C)cc3oc2=O)c1F] |
| 180 | 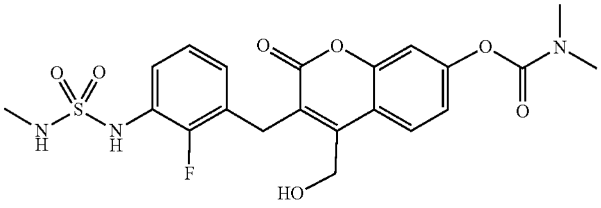 |
| 181 | 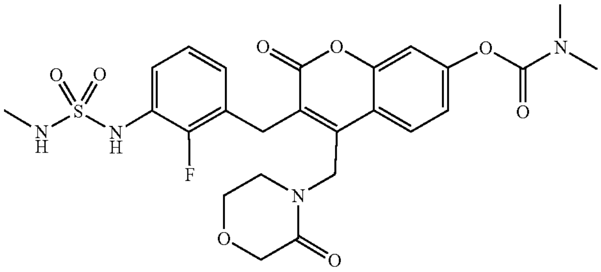 |

TABLE A-continued
| No. | Structure |
| --- | --- |
| 182 | 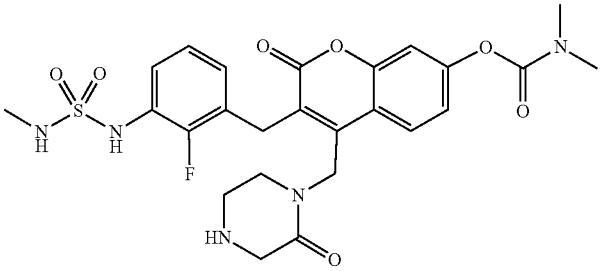 |
| 183 | 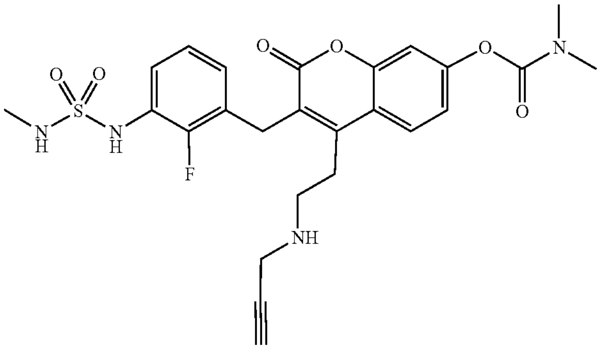 |
| 184 | 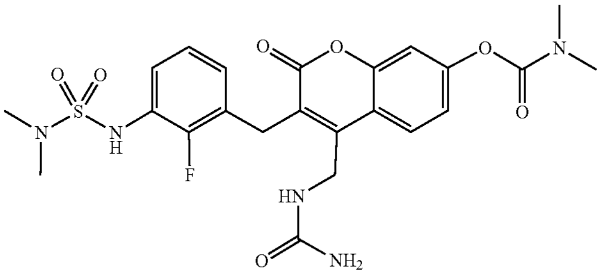 |
| 185 | 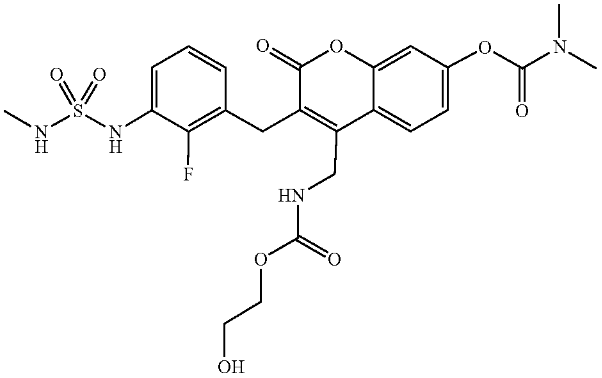 |

TABLE A-continued
| No. | Structure |
| --- | --- |
| 186 | 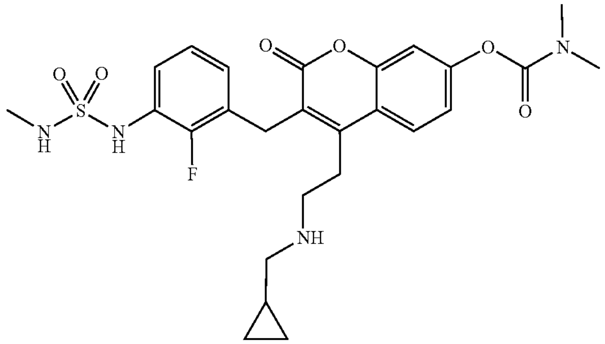 |
| 187 | 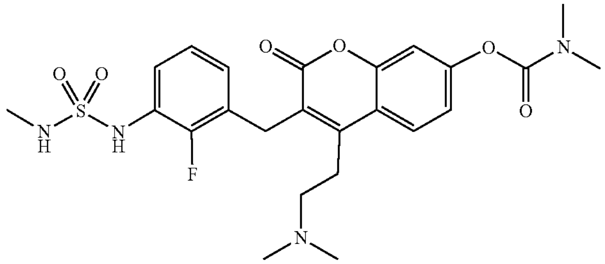 |
| 188 | 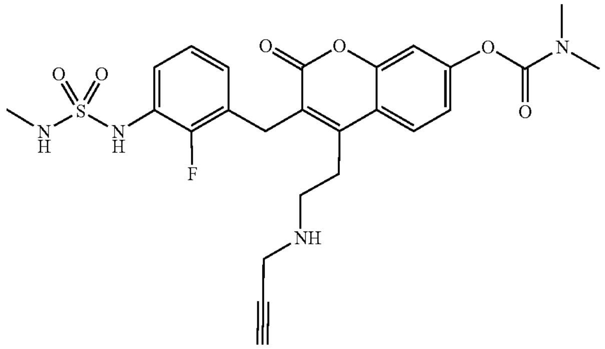 |
| 189 | 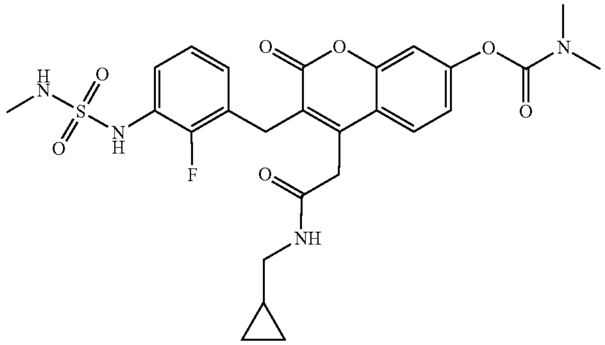 |
| 190 | 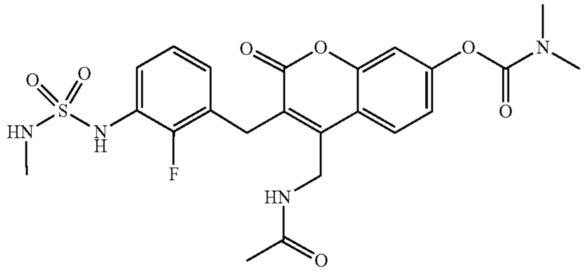 [SMILES: CNS(=O)(=O)Nc1cccc(Cc2c(CNC(C)=O)c3ccc(OC(=O)N(C)C)cc3oc2=O)c1F] |

TABLE A-continued
| No. | Structure |
| --- | --- |
| 191 | 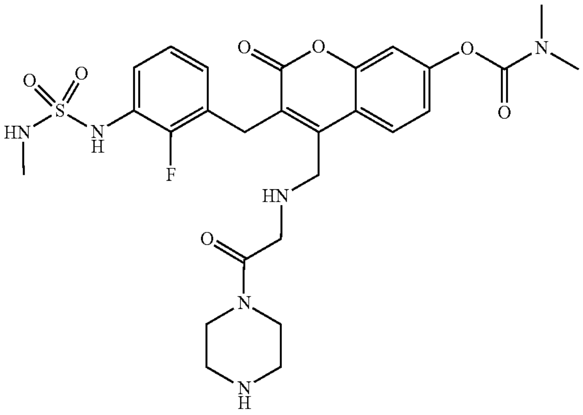 [SMILES: CNS(=O)(=O)Nc1cccc(Cc2c(CNCC(=O)N3CCNCC3)c3ccc(OC(=O)N(C)C)cc3oc2=O)c1F] |
| 192 | 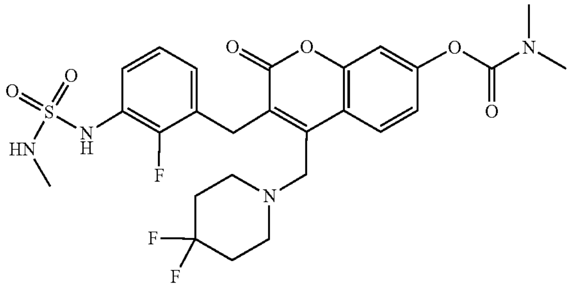 [SMILES: CNS(=O)(=O)Nc1cccc(Cc2c(CN3CCC(F)(F)CC3)c3ccc(OC(=O)N(C)C)cc3oc2=O)c1F] |
| 193 | 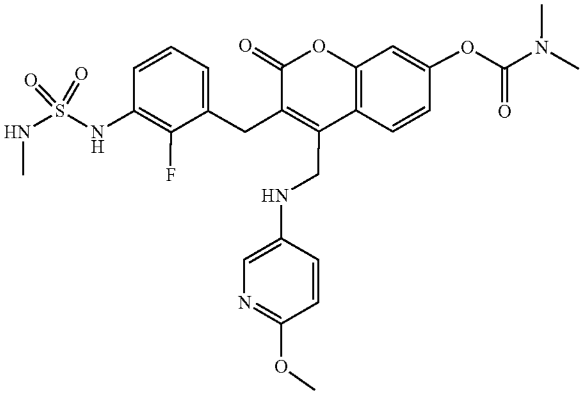 [SMILES: CNS(=O)(=O)Nc1cccc(Cc2c(CNc3ccc(OC)nc3)c3ccc(OC(=O)N(C)C)cc3oc2=O)c1F] |
| 194 | 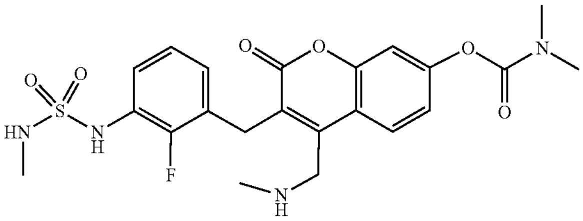 [SMILES: CNCc1c(Cc2cccc(NS(=O)(=O)NC)c2F)c(=O)oc2cc(OC(=O)N(C)C)ccc12] |

TABLE A-continued
| No. | Structure |
|---|---|
| 195 | 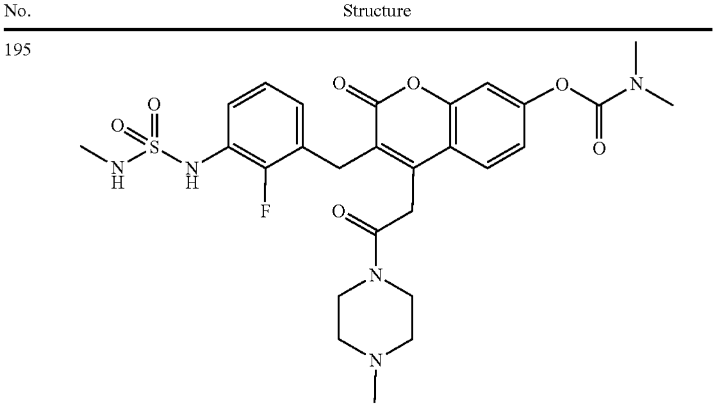 |
| 196 | 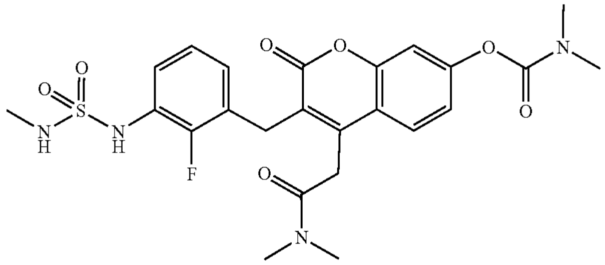 |
| 197 | 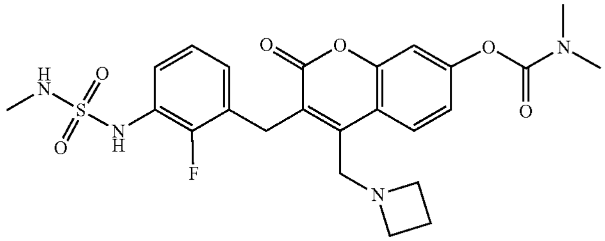 |
| 198 | 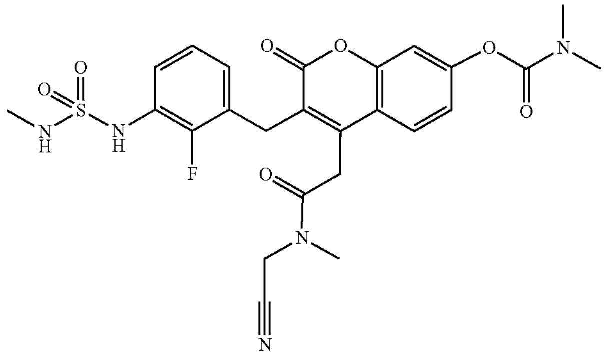 |
| 199 | 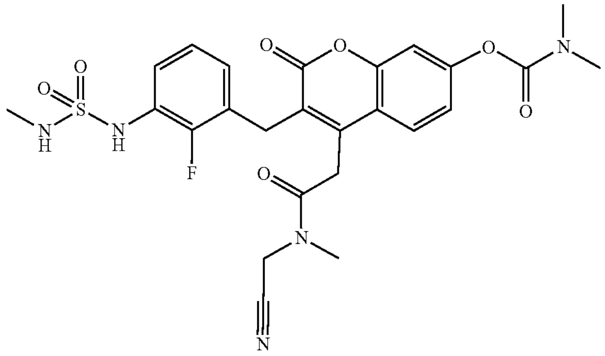 |

TABLE A-continued
| No. | Structure |
|---|---|
| 200 | 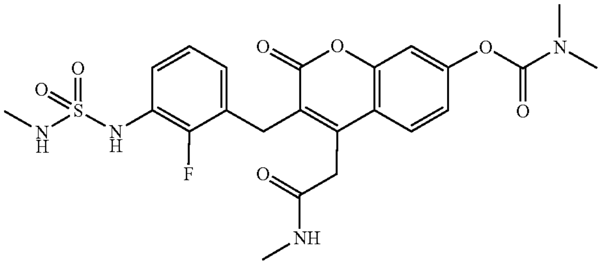 |
| 201 | 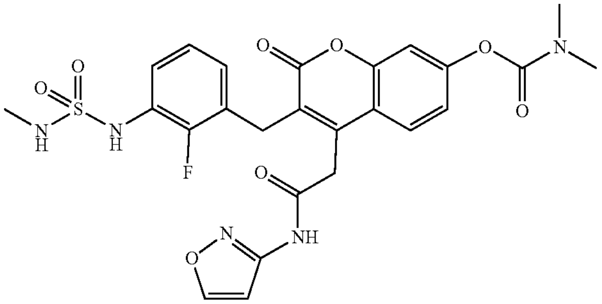 |
| 202 | 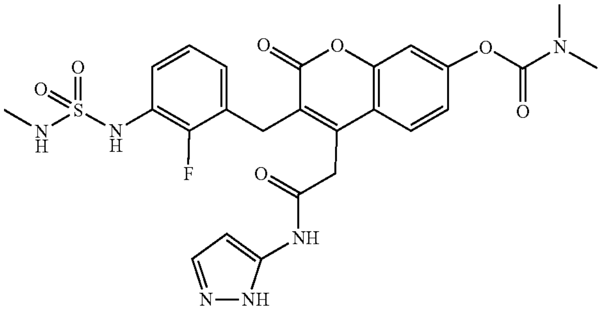 |
| 203 | 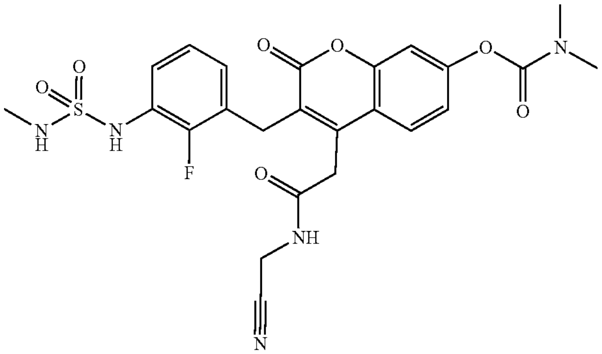 |
| 204 | 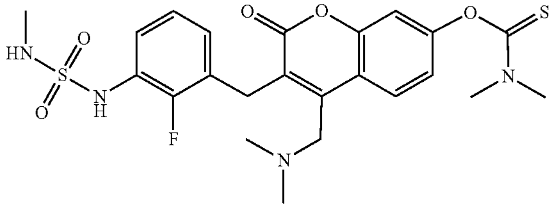 [SMILES: CNS(=O)(=O)Nc1cccc(Cc2c(CN(C)C)c3ccc(OC(=S)N(C)C)cc3oc2=O)c1F] |

TABLE A-continued
| No. | Structure |
| --- | --- |
| 205 | 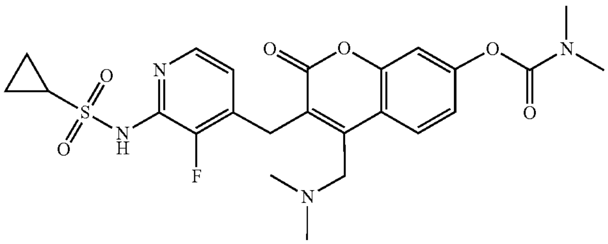 [SMILES: CN(C)Cc1c(Cc2ccnc(NS(=O)(=O)C3CC3)c2F)c(=O)oc2cc(OC(=O)N(C)C)ccc12] |
| 206 | 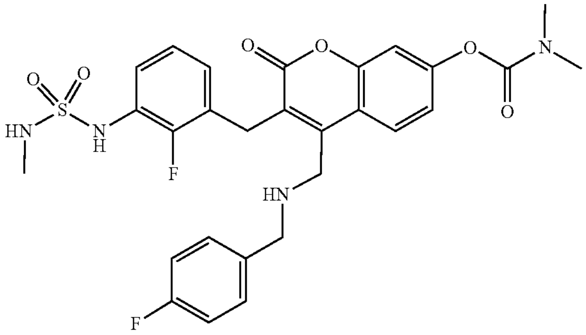 |
| 207 | 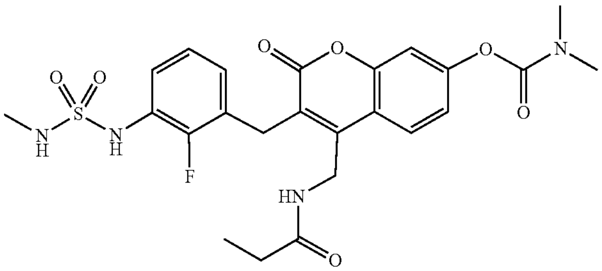 |
| 208 | 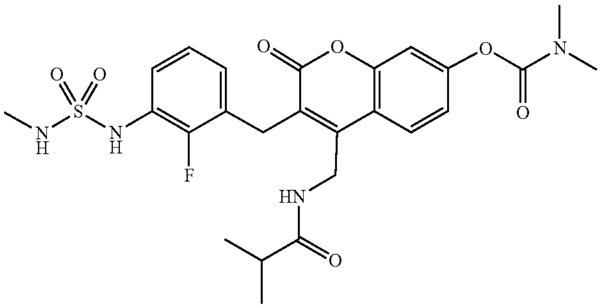 |
| 209 | 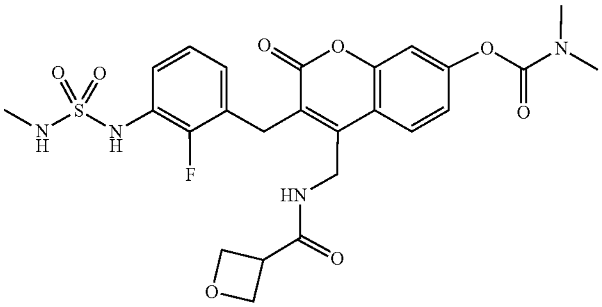 |

TABLE A-continued
| No. | Structure |
|---|---|
| 210 | 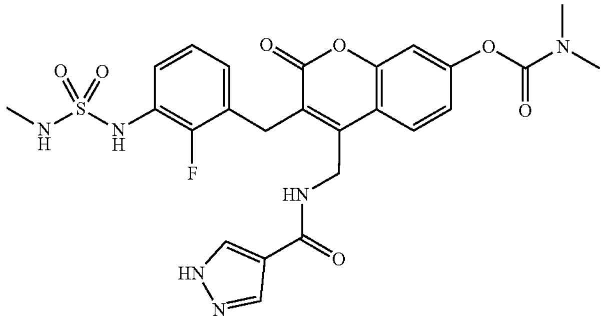 |
| 211 | 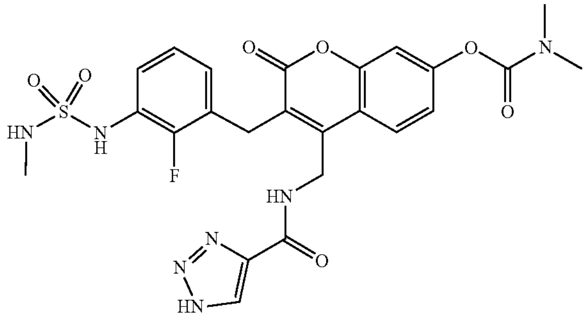 |
| 212 | 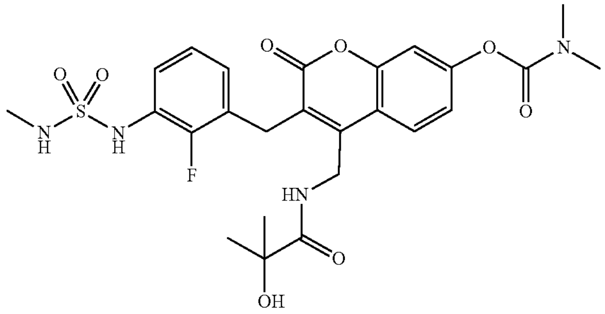 |
| 213 | 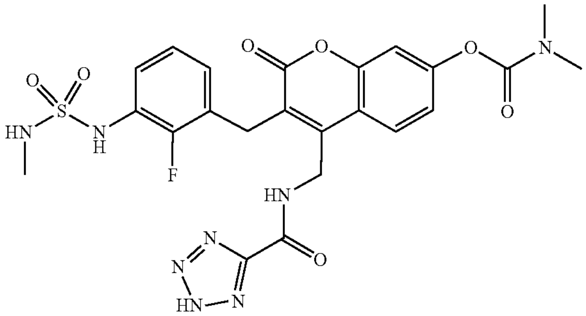 |
| 214 | 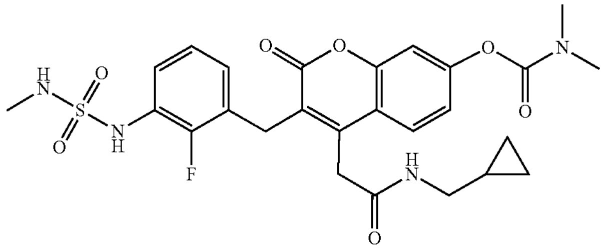 |

TABLE A-continued
| No. | Structure |
|---|---|
| 215 | 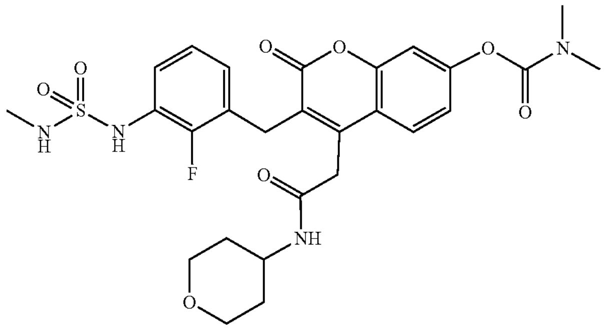 |
| 216 | 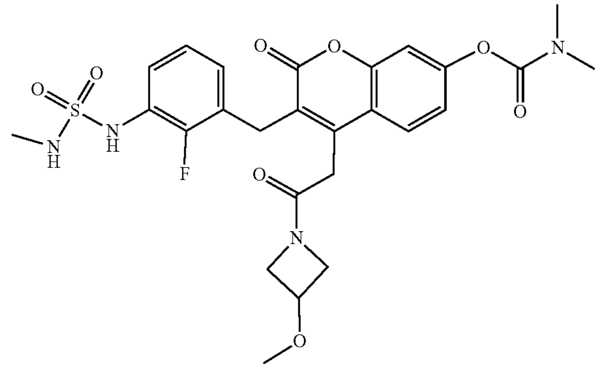 |
| 217 | 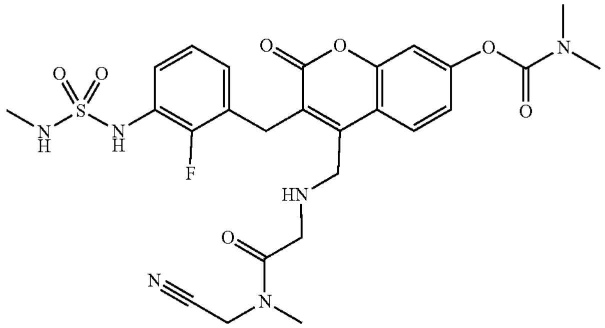 |
| 218 | 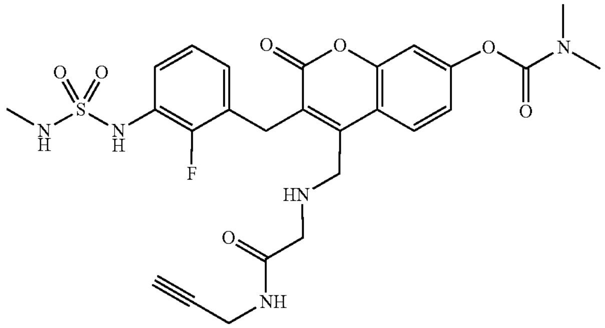 |

TABLE A-continued
| No. | Structure |
| --- | --- |
| 219 | 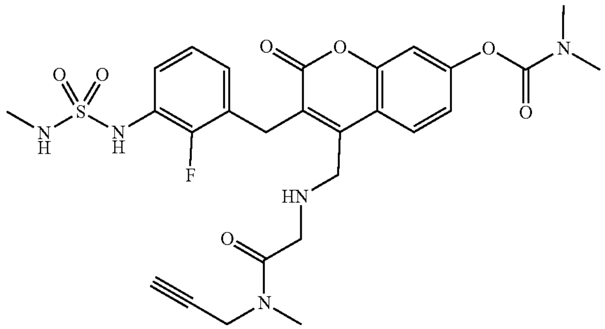 |
| 220 | 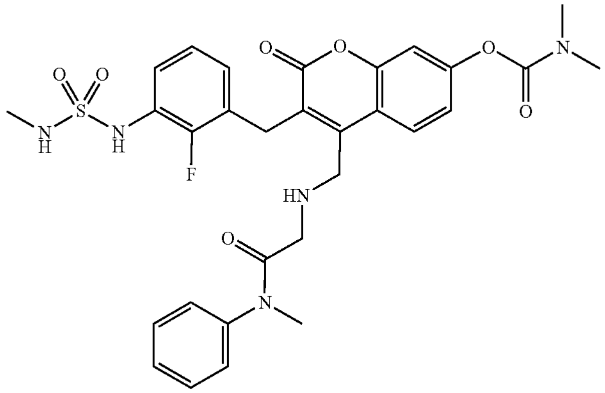 |
| 221 | 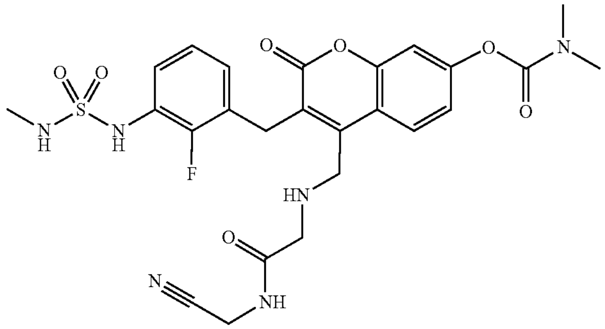 |
| 222 | 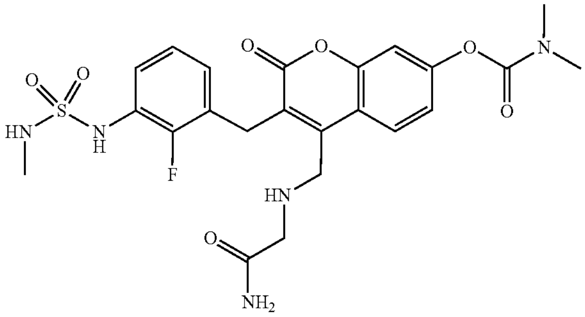 |

TABLE A-continued
| No. | Structure |
|---|---|
| 223 | 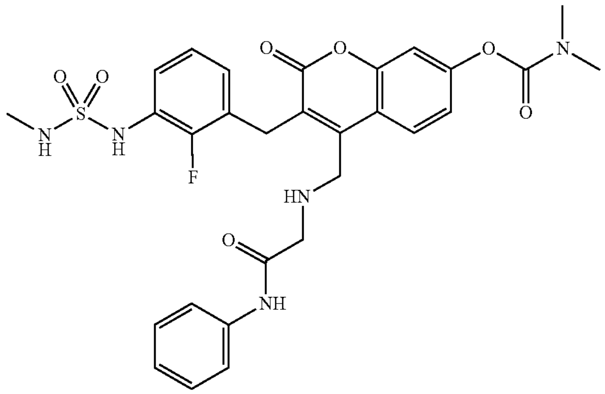 |
| 224 | 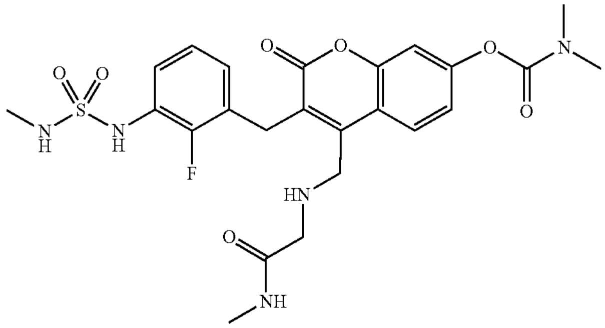 |
| 225 | 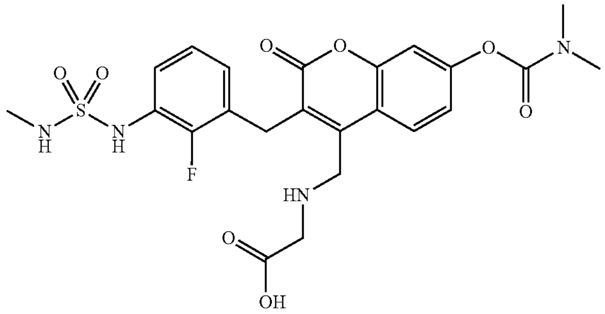 |
| 226 | 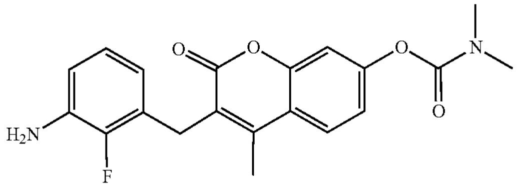 [SMILES: Cc1c(Cc2cccc(N)c2F)c(=O)oc2cc(OC(=O)N(C)C)ccc12] |
| 227 | 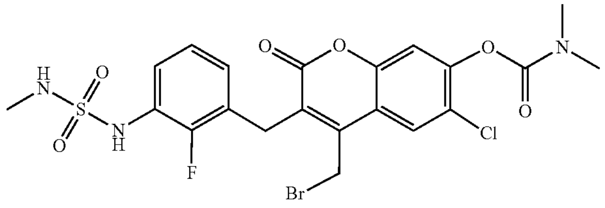 |

TABLE A-continued
| No. | Structure |
|---|---|
| 228 | 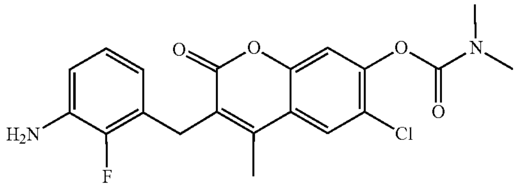 |
| 229 | 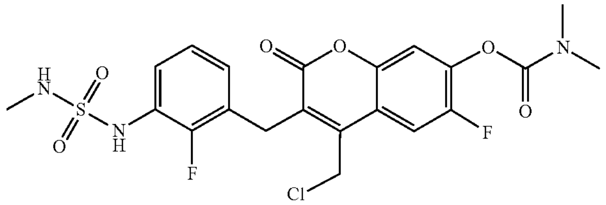 |
| 230 | 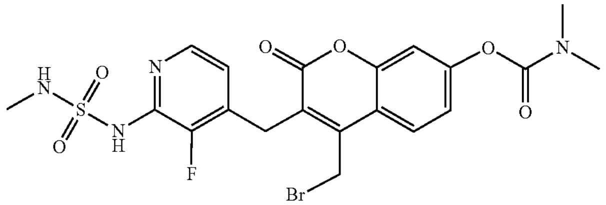 |
| 231 | 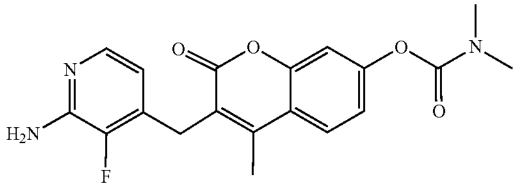 |
| 232 | 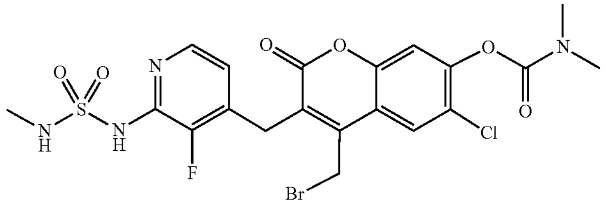 |
| 233 | 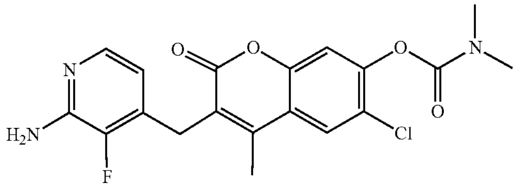 [SMILES: Cc1c(Cc2ccnc(N)c2F)c(=O)oc2cc(OC(=O)N(C)C)c(Cl)cc12] |
| 234 | 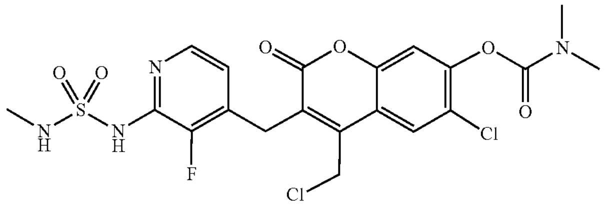 |

TABLE A-continued

| No. | Structure |
| --- | --- |
| 235 | 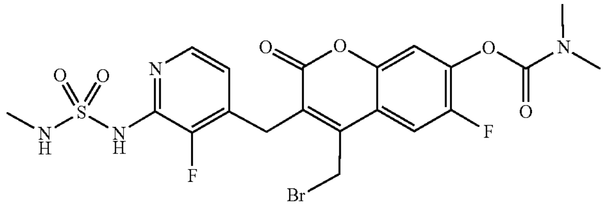 |

In some embodiments, the pharmaceutically acceptable salt can be an alkaline metal salt. In some embodiments, the pharmaceutically acceptable salt can be an alkali metal salt. In some embodiments, the pharmaceutically acceptable salt can be an alkali earth metal salt. In some embodiments, the pharmaceutically acceptable salt can be an ammonium salt.

Syntheses

Compounds of Formula (I), (Ia), (Ib), (Ic), (Id), (II), (IIa), (IIb), (IIc), (IId), or pharmaceutically acceptable salts thereof, described herein may be prepared in various ways, including those known to those skilled in the art. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. Examples of methods are described in the Examples below.

Methods of Preparation

The compounds disclosed herein may be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

Pharmaceutical Compositions

In another aspect, pharmaceutical compositions are disclosed that comprise a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition," as used herein, refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier," as used herein, refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent," as used herein, refers to chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable," as used herein, refers to a carrier or diluent that does not abrogate the biological activity and properties of the compound.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

For each of the compounds described herein, and for each genus or sub-genus of compounds described herein, also described are pharmaceutical compositions comprising the compound, alone or in a mixture with other compounds of the genus or sub-genus, or with alternative compounds described herein, or with one or more alternative pharmaceutically active compounds, and one or more pharmaceutically acceptable carrier, diluent, excipient or combination thereof. The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in any manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, PA, 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Ophthalmologica,* 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, PA (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Parenteral Pharmaceutical Composition

To prepare a parenteral pharmaceutical composition suitable for administration by injection (subcutaneous, intravenous, or the like), 0.1 mg to 120 mg of a water-soluble salt/soluble material itself/solubilized complex of a compound of a preferred embodiment is dissolved in sterile water and then mixed with 10 μL of 0.9% sterile saline. The mixture is incorporated into a dosage unit form suitable for administration by injection.

Injectable Pharmaceutical Composition

To prepare an injectable formulation, 0.1 mg to 100 mg of a compound of Formula (I), (Ia), (Ib), (Ic), (II), (IIa), (IIb), or (IIc), 2.0 mL of sodium acetate buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 0.1 mg to 120 mg of a compound of an embodiment is mixed with 750 mg of starch. The mixture is incorporated into an oral dosage unit, such as a hard gelatin capsule, or 0.1 mg to 120 mg of compound is granulated with binder solution such as starch solution along with suitable diluents such as microcrystalline cellulose or like, disintegrants such as croscaramellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 0.1 mg to 120 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weight of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 0.1 mg to 100 mg of a compound of a preferred embodiment is mixed with 50 mg of anhydrous citric acid and 100 mL of 0.9% sodium chloride solution. The mixture is incorporated into an inhalation delivery unit, such as a nebulizer, which is suitable for inhalation administration.

Nebulizer Suspension Pharmaceutical Composition

In another embodiment, a compound of a preferred embodiment (0.1 mg to 100 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Transdermal Patch Pharmaceutical Composition

To prepare a pharmaceutical composition for transdermal delivery, 0.1 mg to 100 mg of a compound of a preferred embodiment is embedded in, or deposited on, a patch with a single adhesive face. The resulting patch is then attached to the skin via the adhesive face for transdermal administration.

Topical Gel Pharmaceutical Composition

To prepare a pharmaceutical topical gel composition, 0.1 mg to 100 mg of a compound of a preferred embodiment is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution

To prepare a pharmaceutical ophthalmic solution composition, 0.1 mg to 100 mg of a compound of a preferred embodiment is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 0.1 mg to 100 mg of a compound of a preferred embodiment is mixed with 30 mL of a 0.05M phosphate buffer solution (pH 4.4). The solution is placed in a nasal administrator designed to deliver 100 μl of spray for each application.

Methods of Treatment/Uses

Aspects disclosed herein relate to administering to a subject in need an effective amount of a compound of Formula (I), (Ia), (Ib), (Ic), (Id), (II), (IIa), (IIb), (IIc), (IId), or a pharmaceutically acceptable salt thereof), or a pharmaceutical composition that includes one or more compounds as described herein (such as one or more compounds of Formula (I), (Ia), (Ib), (Ic), (Id), (II), (IIa), (IIb), (IIc), (IId), or a pharmaceutically acceptable salt thereof).

As disclosed elsewhere herein, some embodiments pertain to treating a disease or condition, such as cancer, through administration of a compound or composition as disclosed herein. A subject in need of receiving a compound or composition as disclosed herein to improve the subject's health need not always be identified prior to receiving a first treatment with the compound or composition. For example, a subject may be predetermined that they will develop a disease or condition, such as cancer, prior to showing any signs of the disease or condition. Alternatively, the subject may receive treatment prophylactically if he or she is at risk or not developing a disease or condition, such as cancer, (e.g., once a patient shows symptoms of another disease or condition associated with a cancer). Accordingly, in some embodiments, the compound or composition may be administered to the subject after the subject receives an early stage diagnosis. In some embodiments, not every subject is a candidate for such administration and identification of treatment subjects may be desirable. It is understood that patient selection depends upon a number of factors within the skill of the ordinarily skilled physician. Thus, some embodiments disclosed herein further comprise identifying a subject as one that will benefit from administering an effective amount of at least one compound or composition to increase longevity, increase survival time or increase life span.

In other aspects, the present disclosure is directed to a method for the treatment, prevention or prophylaxis of cancer can include administering to a subject in need thereof an effective amount of one or more compound described herein (such as a compound of Formula (I), (Ia), (Ib), (Ic), (Id), (II), (IIa), (IIb), (IIc), (IId), or a pharmaceutically acceptable salt thereof), or a pharmaceutical composition that includes a compound described herein (such as a compound of Formula (I), (Ia), (Ib), (Ic), (Id), (II), (IIa), (IIb), (IIc), (IId), or a pharmaceutically acceptable salt thereof). In certain embodiments, the cancer may be selected from brain cancer, breast cancer, lung cancer, ovarian cancer, pancreatic cancer, stomach cancer, prostate cancer, renal cancer, colorectal cancer or leukemia. In further or additional embodiments, the cancer is brain cancer or achenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is stomach cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer.

Some embodiments relate to a method of inhibiting proliferation of a cell having a RAS mutation, comprising administering a compound of Formula (I), (Ia), (Ib), (Ic), (Id), (II), (IL), (IIb), (IIc), (IId), or a pharmaceutically acceptable salt thereof). In some embodiments, the cancer has associated with a RAS mutation. Some embodiments relate to a method of inducing apoptosis in a cell in a cell having a RAS mutation, comprising administering a compound of Formula (I), (Ia), (Ib), (Ic), (Id), (II), (IIa), (IIb), (IIc), (IId), or a pharmaceutically acceptable salt thereof). Some embodiments relate to a method of inhibiting proliferation of a cell having a KRAS mutation, comprising administering a compound of Formula (I), (Ia), (Ib), (Ic), (Id), (II), (IL), (IIb), (IIc), (IId), or a pharmaceutically acceptable salt thereof). In some embodiments, the cancer has associated with a KRAS mutation. Some embodiments relate to a method of inducing apoptosis in a cell in a cell having a KRAS mutation, comprising administering a compound of Formula (I), (I), (Ia), (Ib), (Ic), (Id), (II), (IL), (IIb), (IIc), (IId), or a pharmaceutically acceptable salt thereof). Some embodiments relate to a method of inhibiting proliferation of a cell having a NRAS mutation, comprising administering a compound of Formula (I), (Ia), (Ib), (Ic), (Id), (II), (IIa), (IIb), (IIc), (IId), or a pharmaceutically acceptable salt thereof). In some embodiments, the cancer has associated with a NRAS mutation. Some embodiments relate to a method of inducing apoptosis in a cell in a cell having a RAS mutation, comprising administering a compound of Formula (I), (Ia), (Ib), (Ic), (Id), (II), (IL), (IIb), (IIc), (IId), or a pharmaceutically acceptable salt thereof). In some embodiments, the KRAS mutation is at codons 12, 13, 59, 61 and/or 146. In some embodiments, the mutant form of the KRAS protein has one or more amino acid substitutions selected from the group consisting of G12C, G12S, G12R, G12F, G12L, G12N, G12A, G12D, G12V, G13C, G13S, G13D, G13V, G13P, S17G, P34S, A59E, A59G, A59T, Q61K, Q61L, Q61R, and Q61H. In some embodiments, the mutant form of the KRAS protein has one or more amino acid substitutions selected from the group consisting of G12C, G12R, G12S, G12A, G12D, G12V, G13C, G13R, G13S, G13A, G13D, G13V, A59E, A59G, A59T, Q61K, Q61L, Q61R, Q61H, K117N, K117R, K117E, A146P, A146T and A146V.

In certain embodiments, the cancer is resistant to treatment of a MEK protein kinase inhibitor. In other embodiments, the cancer is resistant to treatment of a RAF protein kinase inhibitor. In still further embodiments, the resistance is acquired resistance. In other embodiments, the resistance is de novo resistance. In further or additional embodiments, the cancer is resistant to an anticancer agent.

In some aspects provided herein are a compounds or pharmaceutical compositions and methods for treating cancer comprising a therapeutically effective amount of a dual-RAF/MEK protein kinase inhibitor. In some embodiments, the administration of the dual-RAF/MEK protein kinase inhibitor provides an increase in the area under the serum concentration time curve (AUC) of the dual-RAF/MEK protein kinase inhibitor. In some embodiments, the cancer is resistant to treatment of a RAF protein kinase inhibitor. In further embodiments, the cancer is resistant to a RAF protein kinase inhibitor and the RAF protein kinase inhibitor comprises an A-RAF inhibitor, a B-RAF inhibitor, or a C-RAF inhibitor. In further embodiments, the cancer is resistant to a RAF protein kinase inhibitor, and the RAF protein kinase inhibitor comprises a B-RAF inhibitor.

In some embodiments, the resistant cancer is pancreatic, melanoma, colon, lung, or stomach cancer. In further embodiments, the resistant cancer is pancreatic. In additional embodiments, the resistant cancer is stomach. In alternative embodiments, provided are pharmaceutical combinations and methods for resensitizing cancer cells to treatment in a patient having or suspected of having a cancer resistant to an anticancer agent, comprising the step of administering to the patient a therapeutically effective amount of a dual-MEK/RAF inhibitor as disclosed herein.

Some embodiments disclosed herein relate to a method of treating a mammal having a disease that can include administering to a subject in need thereof an effective amount of one or more compound described herein (such as a compound of Formula (I), (Ia), (Ib), (Ic), (Id), (II), (IIa), (IIb), (IIc), (IId), or a pharmaceutically acceptable salt thereof), or a pharmaceutical composition that includes a compound described herein (such as a compound of Formula (I), (Ia), (Ib), (Ic), (Id), (II), (IIa), (IIb), (IIc), (IId), or a pharmaceutically acceptable salt thereof). Other embodiments disclosed herein relate to a method of treating a subject with cancer cachexia that can include administering to a subject an effective amount of one or more compounds described herein (such as a compound of Formula (I), (Ia), (Ib), (Ic), (Id), (II), (IIa), (IIb), (IIc), (IId), or a pharmaceutically acceptable salt thereof), or a pharmaceutically acceptable salt of any of the foregoing), or a pharmaceutical composition that includes a compound described herein such as a compound of Formula (I), (Ia), (Ib), (Ic), (Id), (II), (IIa), (IIb), (IIc), (IId), or a pharmaceutically acceptable salt thereof).

Some embodiments described herein relate to using one or more compounds described herein (such as a compound of Formula (I), (Ia), (Ib), (Ic), (Id), (II), (IIa), (IIb), (IIc), (IId), or a pharmaceutically acceptable salt thereof), in the manufacture of a medicament for ameliorating and/or treating cancer or conditions of cancer, such as cancer cachexia, that can include administering to a subject an effective amount of one or more compounds described herein (such as a compound of Formula (I), (Ia), (Ib), (Ic), (Id), (II), (IIa), (IIb), (IIc), (IId), or a pharmaceutically acceptable salt thereof). Still other embodiments described herein relate to one or more compounds described herein (such as a compound of Formula (I), (Ia), (Ib), (Ic), (Id), (II), (IIa), (IIb), (IIc), (IId), or a pharmaceutically acceptable salt thereof) that can be used for ameliorating and/or treating cancer or conditions of cancer, such as cancer cachexia, by administering to a subject an effective amount of one or more compounds described herein, or a pharmaceutically acceptable salt thereof.

Some embodiments disclosed herein relate to methods of ameliorating and/or treating cancer that can include contacting a cancerous cell an effective amount of one or more compounds described herein (such as a compound of Formula (I), (Ia), (Ib), (Ic), (Id), (II), (IIa), (IIb), (IIc), (IId), or a pharmaceutically acceptable salt thereof), or a pharmaceutical composition that includes one or more compounds described herein (such as a compound of Formula (I), (Ia), (Ib), (Ic), (Id), (II), (IIa), (IIb), (IIc), (IId), or a pharmaceutically acceptable salt thereof). In some embodiments, a compound of Formula (I), (Ia), (Ib), (Ic), (Id), (II), (IIa), (IIb), (IIc), (IId), or a pharmaceutically acceptable salt thereof, can act as an inhibitor of MEK. In some embodiments, a compound of Formula (I), (Ia), (Ib), (Ic), (Id), (II), (IIa), (IIb), (IIc), (IId), or a pharmaceutically acceptable salt thereof, can act as an inhibitor of ERK. In some embodiments, a compound of Formula (I), (Ia), (Ib), (Ic), (Id), (II), (IIa), (IIb), (IIc), (IId), or a pharmaceutically acceptable salt thereof, may act as a mitoSTAT3 inhibitor. In some embodiments, a compound of Formula (I), (Ia), (Ib), (Ic), (Id), (II), (IIa), (IIb), (IIc), (IId), or a pharmaceutically acceptable salt thereof, may reduce inflammatory cachexia and muscle wasting.

In some embodiments, the compound of Formula (I), (Ia), (Ib), (Ic), (Id), (II), (IIa), (IIb), (IIc), (IId), or a pharmaceutically acceptable salt thereof, may be administered in a single dose, once daily. In some embodiments, the compound of Formula (I), (Ia), (Ib), (Ic), (Id), (II), (IIa), (IIb), (IIc), (IId), or a pharmaceutically acceptable salt thereof, may be administered in multiple doses, more than once per day. In some embodiments, the compound of Formula (I), (Ia), (Ib), (Ic), (Id), (II), (IIa), (IIb), (IIc), (IId), or a pharmaceutically acceptable salt thereof, may be administered once a day. In some embodiments, the compound of Formula (I), (Ia), (Ib), (Ic), (Id), (II), (IIa), (IIb), (IIc), (IId), or a pharmaceutically acceptable salt thereof, may be administered twice a day. In some embodiments, the compound of Formula (I), (Ia), (Ib), (Ic), (Id), (II), (IIa), (IIb), (IIc), (IId), or a pharmaceutically acceptable salt thereof, may be administered trice a day. In some embodiments, the compound of Formula (I), (Ia), (Ib), (Ic), (Id), (II), (IIa), (IIb), (IIc), (IId), or a pharmaceutically acceptable salt thereof, may be administered four times a day.

In some aspects, a compound of Formula (I), (Ia), (Ib), (Ic), (Id), (II), (IIa), (IIb), (IIc), (IId), or a pharmaceutically acceptable salt thereof, may inhibit abnormal cell growth. In some embodiments, the abnormal cell growth occurs in a mammal. Methods for inhibiting abnormal cell growth may comprise administering an effective amount of a compound of Formula (I), (Ia), (Ib), (Ic), (Id), (II), (IIa), (IIb), (IIc), (IId), or a pharmaceutically acceptable salt thereof, wherein abnormal cell growth is inhibited. Methods for inhibiting abnormal cell growth in a mammal may comprise administering to the mammal a compound of Formula (I), (Ia), (Ib), (Ic), (Id), (II), (IIa), (IIb), (IIc), (IId), or a pharmaceutically acceptable salt thereof, wherein the amounts of the compound is effective in inhibiting abnormal cell growth in the mammal.

In other aspects, the present invention is directed to a method for degrading, inhibiting the growth of or killing a cancer cell comprising contacting said cell with a compound of Formula (I), (Ia), (Ib), (Ic), (Id), (II), (IIa), (IIb), (IIc), (IId), or a pharmaceutically acceptable salt thereof, effective to degrade, inhibit the growth of or to kill said cell. In some embodiments, the cancer cells comprise brain, breast, lung, ovarian, pancreatic, stomach, prostate, renal, or colorectal cancer cells.

In some embodiments, the cancer cells are degraded. In some embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded.

In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 1.0% of the cancer cells are killed. In further or additional embodiments, 20% of the cancer cells are killed. In further or additional embodiments, 25% of the cancer cells are killed. In further or additional embodiments, 30% of the cancer cells are killed. In further or =Page 70—additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In farther or additional embodiments, essentially all of the cancer cells are killed.

In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited, hi further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited.

In some embodiments, the size of a tumor is reduced by administering a therapeutically effective amount of a compound of Formula (I), (Ia), (Ib), (Ic), (Id), (II), (IIa), (IIb), (IIc), (IId), or a pharmaceutically acceptable salt thereof. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase.

In some embodiments, tumor proliferation is reduced by administering a compound of Formula (I), (Ia), (Ib), (Ic), (Id), (II), (IIa), (IIb), (IIc), (IId), or a pharmaceutically acceptable salt thereof. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

In further or additional embodiments the amount of a compound of Formula (I), (Ia), (Ib), (Ic), (Id), (II), (IIa), (IIb), (IIc), (IId), or a pharmaceutically acceptable salt thereof, may be administered in a range from about 0.001 to about 1000 mg/kg body weight/day. In further or additional embodiments, the amount a compound of Formula (I), (Ia), (Ib), (Ic), (Id), (II), (IIa), (IIb), (IIc), (IId), or a pharmaceutically acceptable salt thereof, may be administered the range of about 0.5 to about 50 mg/kg/day. In further or additional embodiments the amount a compound of Formula (I), (Ia), (Ib), (Ic), (Id), (II), (IIa), (IIb), (IIc), (IId), or a pharmaceutically acceptable salt thereof, may be administered from about 0.001 to about 7 g/day. In further or additional embodiments the amount a compound of Formula (I), (Ia), (Ib), (Ic), (Id), (II), (IIa), (IIb), (IIc), (IId), or a pharmaceutically acceptable salt thereof, may be administered from about 0.002 to about 6 g/day. In further or additional embodiments the amount a compound of Formula (I), (Ia), (Ib), (Ic), (Id), (II), (IIa), (IIb), (IIc), (IId), or a pharmaceutically acceptable salt thereof, may be administered from about 0.005 to about 5 g/day. In further or additional embodiments, the amount a compound of Formula (I), (Ia), (Ib), (Ic), (Id), (II), (IIa), (IIb), (IIc), (IId), or a pharmaceutically acceptable salt thereof, may be administered from about 0.01 to about 5 g/day. In further or additional embodiments, the amount a compound of Formula (I), (Ia), (Ib), (Ic), (Id), (II), (IIa), (IIb), (IIc), (IId), or a pharmaceutically acceptable salt thereof, may be administered from about 0.02 to about 5 g/day. In further or additional embodiments, the amount a compound of Formula (I), (Ia), (Ib), (Ic), (Id), (II), (IIa), (IIb), (IIc), (IId), or a pharmaceutically acceptable salt thereof, may be administered from about 0.05 to about 2.5 g/day. In further or additional embodiments, the amount a compound of Formula (I), (Ia), (Ib), (Ic), (Id), (II), (IIa), (IIb), (IIc), (IId), or a pharmaceutically acceptable salt thereof, may be administered from about 0.1 to about 1 g/day. In further or additional embodiments, dosage levels below the lower limit of the aforesaid range may be more than adequate.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

Administration and Pharmaceutical Compositions

The compounds are administered at a therapeutically effective dosage. While human dosage levels have yet to be specifically identified for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Second (or Other Additional) Agents

In some embodiments, the second therapeutic agent is anti-inflammatory agent. In some embodiments, the second therapeutic agent is a non-steroidal anti-inflammatory agent. In some embodiments, the second therapeutic agent is anti-cancer agent.

In some embodiments, the methods comprise administering an effective amount of a compound of Formula (I), (Ia), (Ib), (Ic), (Id), (II), (IIa), (IIb), (IIc), (IId), or a pharmaceutically acceptable salt thereof, in combination with an amount of a chemotherapeutic, wherein the amounts of the combination and the chemotherapeutic are together effective in inhibiting abnormal cell growth. Many chemotherapeutics are presently known in the art and can be used in combination. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Also described are methods for inhibiting abnormal cell growth in a mammal comprising administering to the mammal an amount of a MEK protein kinase inhibitor and/or Raf protein kinase inhibitor in combination with radiation therapy, wherein the amounts of the MEK protein kinase inhibitor and/or Raf protein kinase inhibitor in combination with the radiation therapy effective in inhibiting abnormal cell growth or treating the hyperproliferative disorder in the mammal. Techniques for administering radiation therapy are known in the art, and these techniques can be used in the combination therapy described herein.

In some embodiments, the disclosure also relates to a method of inhibiting abnormal cell growth in a mammal which may comprises a compound of Formula (I), (Ia), (Ib), (Ic), (II), (IIa), (IIb), (IIc), or a pharmaceutically acceptable salt thereof, and an amount of one or more substances selected from anti-angiogenesis agents, signal transduction inhibitors, and antiproliferative agents. Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 19911), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997). Some MMP-2 and MMP-9 inhibitors have little or no activity inhibiting MMP-1, while some selectively inhibit MMP-2 and/or AMP-9 relative to the other matrix-motalloproteinases (L e., MAP-1, NEMP-3, MMP-4, M7v1P-5, MMP-6, MMP-7, MMP-8, MMP-10, MMP-11, and MMP-13). Some specific examples of M1v1P inhibitors useful in the present invention are AG-3340, RU 32-3555, and RS 13-0830.

In some embodiments, a compound of Formula (I), (Ia), (Ib), (Ic), (Id), (II), (IIa), (IIb), (IIc), (IId), or a pharmaceutically acceptable salt thereof, is administered with at least one additional therapeutic agent. In some embodiments, the therapeutic agent is a taxol, bortezornib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epiclophyllotoxims; antineoplastic enzymes, topoisomerase inhibitors, procarbazine, mitoxantrone, platinum coordination complexes, biological response modifiers and growth inhibitors, hormonal/anti-hormonal therapeutic agents, and baematopoietic growth factors.

Many chemotherapeutics are presently known in the art and can be used in combination with the compounds and compositions of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, the combination is administered in combination with an additional therapy. In further or additional embodiments, the additional therapy is radiation therapy, chemotherapy, surgery or any combination thereof. In further or additional embodiments, the combination is administered in combination with at least one additional therapeutic agent. In further or additional embodiments, the therapeutic agent is selected from the group of cytotoxic agents, anti-angiogenesis agents and anti-neopiastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors.

In some embodiments, the second therapeutic is an agent for co-regulating MEKor RAF pathways. In some embodiments, the second therapeutic agent is a MEKor RAF inhibitor. In some embodiments, the RAF inhibitor is vemurafenib, dabrafenib, XL-281, LGX-818, CEP-32496, ARQ-736, MEK-162, Selumetinib, refametinib, E-6201, pimasertib. WX-554, and GDC-0973.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

EXAMPLES

General Procedures

Additional embodiments are disclosed in further detail in the following examples, which are not in any way intended to limit the scope of the claims.

Materials used in preparing compounds of Formula (I), (Ia), (Ib), or (Ic), described herein may be made by known methods or are commercially available. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March's Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Example 1

General Synthesis A

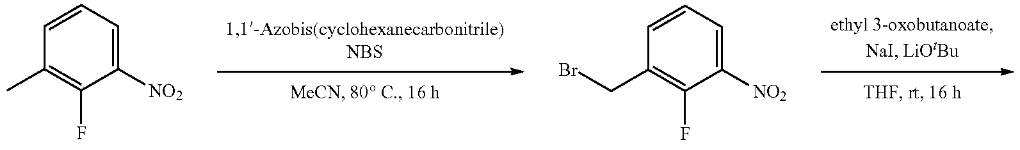

1 2

-continued

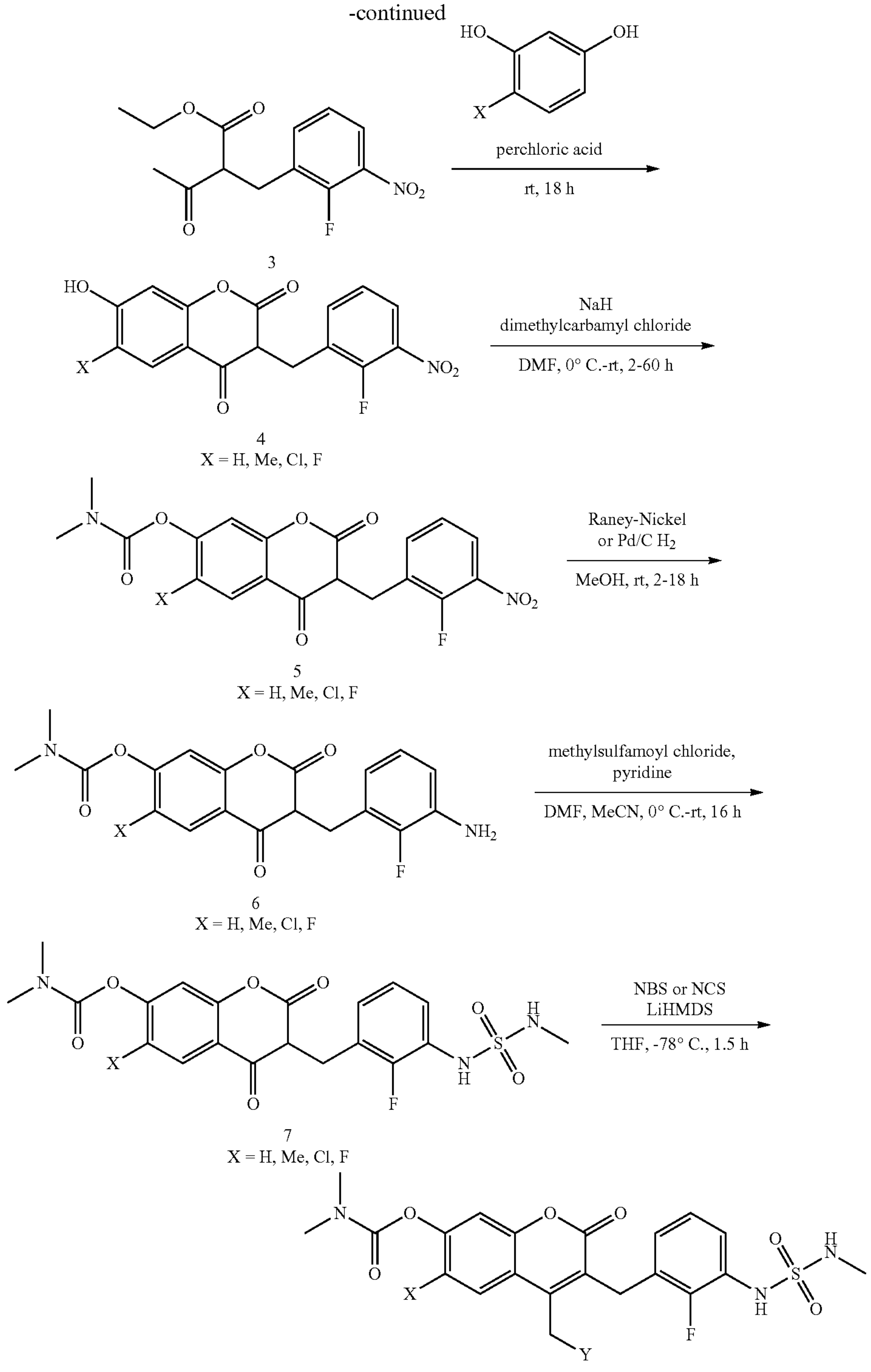

3

4
X = H, Me, Cl, F

5
X = H, Me, Cl, F

6
X = H, Me, Cl, F

7
X = H, Me, Cl, F

A
X = H, Me, Cl, F
Y = Br, Cl

Compound 2: To a solution of 2-Fluoro-3-nitrotoluene 1 (153.9 g, 268 mmol, 1.0 eq.) and NBS (57.8 g, 321 mmol, 1.20 eq.) in MeCN (1340 mL) under nitrogen atmosphere was added 1,1-azobis(cyclohexanecarbonitrile) (8.0 g, 32.1 mmol, 0.12 eq.). The formed reaction mixture was stirred at 80° C. for 16 h. The reaction mixture was allowed to cool to rt and concentrated under reduced pressure to give an orange suspension. $Et_2O$ was added and the formed suspension was stirred for 18 hours at rt. The suspension was filtered and the residue was washed with some extra $Et_2O$. Combined organic layers were washed with aqueous saturated $NaHCO_3$ and brine, dried over $Na_2SO_4$, filtered and concentrated under reduced pressure to obtain a dark red oil that crystalized upon standing. The product was recrystallized using heptane to obtain 1-(bromomethyl)-2-fluoro-3-nitrobenzene 2 (43.8 g, 186.7 mmol, yield: 70%, purity: 99%) as a white solid. LCMS (Method K): tR=1.95 min; m/z calculated for $[M+H]^+$=234.0. found=no mass; 1H NMR (400 MHz, DMSO) δ 8.14 (td, J=7.8, 7.3, 1.7 Hz, 1H), 8.01-7.93 (m, 1H), 7.50-7.40 (m, 1H), 4.81 (d, J=1.4 Hz, 2H).

Compound 3: To a solution of ethyl 2-(2-fluoro-3-nitrobenzyl) oxobutanoate 3 (1.0 eq.) in perchloric acid (10-20 eq.) the diol (1.20 eq.) was added. The formed reaction mixture was stirred for 1-18 h at rt. Water was added to the reaction mixture and the product was filtered, washed with water and $Et_2O$. The residue was dried to obtain the coumarin as a solid.

Compound 4: To a solution of the coumarin (1.0 eq.) in N,N-Dimethylformamide (dry) (0.13-0.2 M) at 0° C. under $N_2$ atmosphere, sodium hydride 60% dispersion on mineral oil (1.60 eq.) was added. The formed reaction mixture was left to stir for 10 min before dimethyl carbamoyl chloride (1.50-1.60 eq.) was added. The formed reaction mixture was allowed to warm to room temperature and left to stir for 2-60 h. Water was added to quench the reaction mixture. The formed suspension was filtered, washed with water and $Et_2O$. The residue was dried to obtain the dimethylcarbamate as a solid.

Compound 5: The dimethylcarbamate (1.0 eq.) was suspended in Methanol (0.2 M), in some cases some $CH_2Cl_2$ was added to get a solution. Argon was bubbled through the solution for 10 min. Then a 50% Raney®-Nickel slurry in water (1.0 eq.) or 10% palladium on activated carbon (0.05 eq.) was added. The formed reaction mixture was purged with hydrogen and stirred for 2-18 h at rt. The reaction mixture was filtered over kieselguhr and washed with MeCN, $CH_2Cl_2$ and MeOH. The filtrate was concentrated under reduced pressure to obtain the primary amine as a solid.

Compound 6: To an ice bath cooled (0° C.) suspension of the primary amine (1.0 eq.) and pyridine (3.00 eq.) in N,N-Dimethylformamide (0.2 M), a transparent solution of methylsulfamoyl chloride (2.50 eq.) in Acetonitrile (anhydrous) (0.2 M) was added dropwise. After complete addition the formed reaction mixture was allowed to warm-up to room temperature and stirred for 1-16 h. Water was added to the reaction mixture and the formed suspension was stirred for 1 hour. The suspension was filtered, washed with water and Et2O. The residue was dried to obtain the sulfamoyl as a solid.

Compound 7: A solution of the sulfamoyl (1.0 eq.) in Tetrahydrofuran (dry) (0.06-0.10 M) under nitrogen atmosphere was cooled to −78° C. and LiHMDS 1M in THF (3.00 eq.) was slowly added. After full addition the formed reaction mixture was in some cases diluted with some extra tetrahydrofuran (dry) and stirred for 30 min, allowed to warm to 0° C. This was added to a cooled (−78° C.) solution of NCS or NBS (1.20 eq.) in Tetrahydrofuran (dry) (0.04 M), drop-wise via a cannula over 15 minutes. The formed reaction mixture was stirred for 1 hour at −78° C. At −78° C. the reaction mixture was quenched with HCl 1M and allowed to warm to rt. Some extra water was added and the product was extracted with EtOAc. Combined organic layers were washed with brine, dried over $Na_2SO_4$, filtered and concentrated under reduced pressure. The impure product was purified by column chromatography with method 'flash' (heptane/EtOAc=1:0→0:1) to obtain the bromine or chlorine as a solid.

Example 2

General Synthesis B

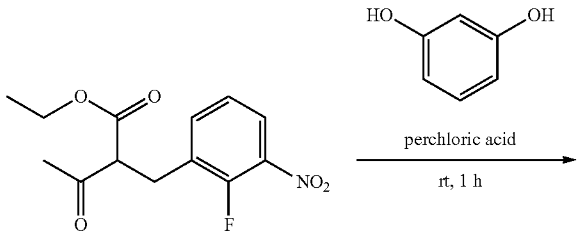

3

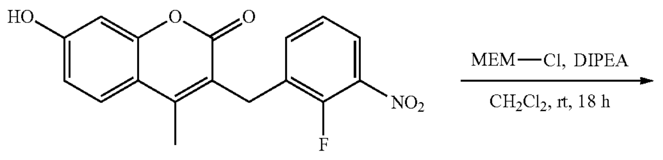

B.1

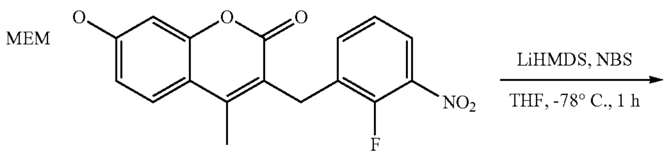

B.2

-continued

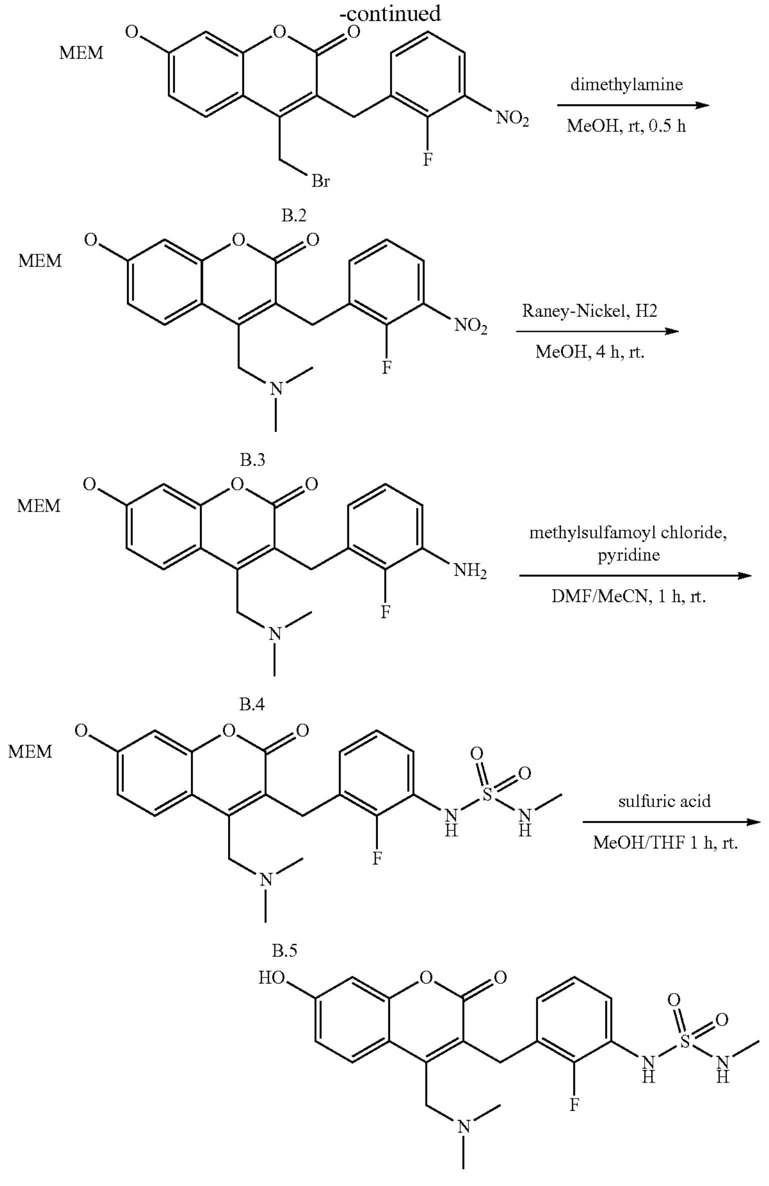

B.2

B.3

B.4

B.5

B.6

Compound B.1: To a solution of ethyl 2-(2-fluoro-3-nitrobenzyl)-3-oxobutanoate 3 (6.54 g, 23.09 mmol, 1.0 eq.) in perchloric acid (29.8 mL, 346 mmol, 15.0 eq.), resorcinol (3.05 g, 27.7 mmol, 1.20 eq.) was added. The formed reaction mixture was stirred for 1 h at rt. Water was added to the reaction mixture and the product was filtered, washed with water and $Et_2O$. The residue was dried overnight at 40° C. under reduced pressure to obtain 3-(2-fluoro-3-nitrobenzyl)-7-hydroxy-4-methyl-2H-chromen-2-one (15.224 g, 45.8 mmol, yield: 112%) as an off-white solid.

LCMS (Method I): $t_R$=1.92 min; m/z calculated for $[M+H]^+$=330.1. found=330.0; 1H NMR (400 MHz, DMSO) δ 10.51 (s, 1H), 8.03-7.92 (m, 1H), 7.69 (d, J=8.8 Hz, 1H), 7.60-7.51 (m, 1H), 7.32 (t, J=8.0 Hz, 1H), 6.83 (dd, J=8.8, 2.4 Hz, 1H), 6.72 (d, J=2.4 Hz, 1H), 4.02 (s, 2H), 2.43 (s, 3H).

Compound B.2: To a suspension of 3-(2-fluoro-3-nitrobenzyl)-7-hydroxy-4-methyl-2H-chromen-2-one (3 g, 7.74 mmol, 1.0 eq.) in $CH_2Cl_2$ (0.6 M) was added DIPEA (5 ml, 28.6 mmol, 3.70 eq.). MEM-Cl (1.8 ml, 15.90 mmol, 2.05 eq.) was added and the formed reaction mixture was stirred for 18 hours at rt. The reaction mixture was purified by column chromatography with method 'flash' (heptane/EtOAc 3:1→1:3) to obtain 3-(2-fluoro-3-nitrobenzyl)-7-((2-methoxyethoxy)methoxy)-4-methyl-2H-chromen-2-one (2.71 g, 6.49 mmol, yield: 84%) as a colorless oil.

LCMS (Method I): $t_R$=2.08 min; m/z calculated for $[M+H]^+$=418.0. found=418.0.

Compound B.3: A solution of 3-(2-fluoro-3-nitrobenzyl)-7-((2-methoxyethoxy)methoxy)-4-methyl-2H-chromen-2-one (2.71 g, 6.49 mmol, 1.0 eq.) in Tetrahydrofuran (dry) (0.04 M) was cooled to −78° C. and LiHMDS (1 M in THF, 7.79 ml, 7.79 mmol, 1.20 eq.) was slowly added. The formed reaction mixture was stirred for 30 min at −78° C. prior to slow addition of NBS (1.156 g, 6.49 mmol, 1.0 eq.) dissolved in Tetrahydrofuran (dry) (75 ml). The formed yellow solution was stirred for 30 minutes at −78° C. The reaction mixture was quenched with sat. aq. $NH_4Cl$ at −78° C. and allowed to warm to rt. The product was extracted with EtOAc. The combined organic layers were washed with brine, dried over $Na_2SO_4$, filtered and concentrated under reduced pressure to obtain a yellow oil. The impure product was purified by column chromatography with method 'flash' (heptane/EtOAc 1:0→1:3) to obtain 4-(bromomethyl)-3-(2-fluoro-3-nitrobenzyl)-7-((2-methoxyethoxy)methoxy)-2H-chromen-2-one (2.1 g, 4.23 mmol, yield: 65%) as an off-white fluffy solid.

LCMS (Method K): $t_R$=1.94 min; m/z calculated for $[M+H]^+$=496.0/498.0. found=496.0/498.0.

Compound B.4: 4-(bromomethyl)-3-(2-fluoro-3-nitrobenzyl)-7-((2-methoxyethoxy)methoxy)-2H-chromen-2-one (1.5 g, 3.02 mmol, 1.0 eq.) was suspended in dimethylamine (2.0 M in MeOH, 15 ml, 30.0 mmol, 10.0 eq.) at rt. The formed reaction mixture was stirred for 30 minutes at rt. The reaction mixture was concentrated under reduced pressure. The impure product was suspended in $Et_2O$. The solids were filtered off and the residue was washed with $Et_2O$ and dried to obtain 4-((dimethylamino)methyl)-3-(2-fluoro-3-nitrobenzyl)-7-((2-methoxyethoxy)methoxy)-2H-chromen-2-one (1.27 g, 2.59 mmol, yield: 86%) an off-white solid.

LCMS (Method I): $t_R$=2.11 min; m/z calculated for $[M+H]^+$=461.1. found=461.1.

Compound B.5: To a mixture of 4-((dimethylamino)methyl)-3-(2-fluoro-3-nitrobenzyl)-7-((2-methoxyethoxy)methoxy)-2H-chromen-2-one (1.27 g, 2.59 mmol, 1.0 eq.) in Methanol (0.26 M) was added Raney®-Nickel (50% slurry in water, 0.5 ml, 2.59 mmol, 1.0 eq.) and the formed reaction mixture was placed under a hydrogen atmosphere for 4 h. The reaction mixture was diluted with MeOH and the formed solution was filtered. The filtrate was concentrated under reduced pressure and twice stripped with toluene to obtain 3-(3-amino-2-fluorobenzyl)-4-((dimethylamino)methyl)-7-((2-methoxyethoxy)methoxy)-2H-chromen-2-one (1.116 g, 2.59 mmol, yield: 100%) as a sticky solid.

LCMS (Method U): $t_R$=2.02 min; m/z calculated for $[M+H]^+$=430.8. found=430.8.

Compound B.6: To a solution of 3-(3-amino-2-fluorobenzyl)-4-((dimethylamino)methyl)-7-((2-methoxyethoxy)methoxy)-2H-chromen-2-one (1.1 g, 2.56 mmol, 1.0 eq.) in N,N-Dimethylformamide (dry) (1.2 M) was added pyridine (0.413 ml, 5.11 mmol, 2.0 eq.) and a solution of methylsulfamoyl chloride (0.268 ml, 3.07 mmol, 1.2 eq.) in Acetonitrile (anhydrous) (1.2 M). The formed reaction mixture was stirred at rt for 1 h. 50% aq. $NaHCO_3$ was added to the reaction mixture and the product was extracted with EtOAc. The combined organic layers were washed with brine, dried over $Na_2SO_4$, filtered and concentrated under reduced pressure. The impure product was purified by column chromatography with method 'flash' (heptane/EtOAc 3:2→1:9) to obtain sulfamide (1.35 g, 2.58 mmol, yield: 101%) as a yellow oil.

LCMS (Method U): $t_R$=1.94 min; m/z calculated for $[M+H]^+$=524.2. found=524.1.

Compound B.7: To a solution of sulfamide (910 mg, 1.738 mmol, 1.0 eq.) in Methanol/THF (1:1) (0.17 mL) was added sulfuric acid (1.5 ml, 28.1 mmol, 16 eq.). The formed reaction mixture was stirred at rt for 1 h. The reaction mixture was quenched in sat. aq. $NaHCO_3$ and extracted with EtOAc. The combined organic layers were washed with brine, dried over $Na_2SO_4$, filtered and concentrated under reduced pressure. The impure product was purified by column chromatography with method 'flash' ($CH_2Cl_2$/MeOH 1:0→95:5). Desired fractions were combined and concentrated under reduced pressure. The residue was dissolved in MeCN/water and lyophilized to obtain phenol (510 mg, 1.171 mmol, yield: 67%) as a yellow solid.

LCMS (Method J): $t_R$=2.68 min; m/z calculated for $[M+H]^+$=436.1. found=436.0.

Example 3

General Synthesis C

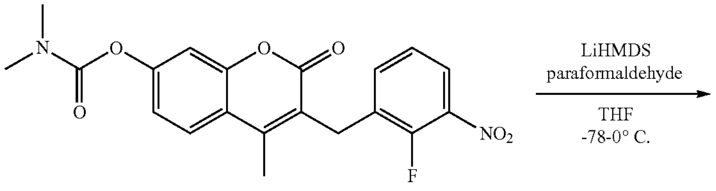

C.1

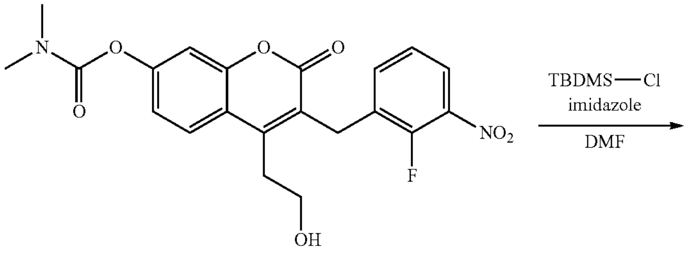

C.2

-continued

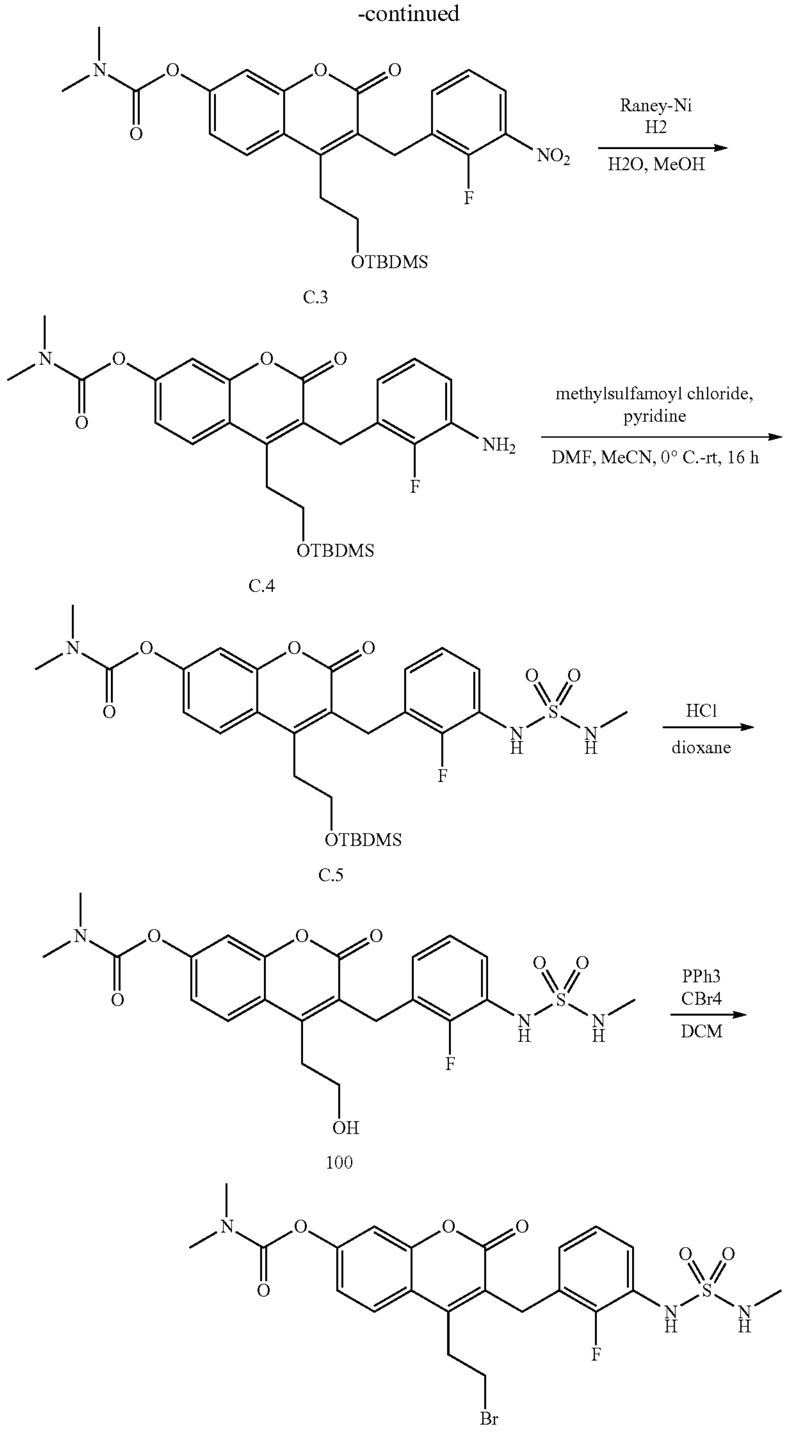

C.3

C.4

C.5

100

101

Compound C.2: A solution of $C_1$ (3.0 g, 7.49 mmol) in Tetrahydrofuran (dry) (100 mL) under nitrogen atmosphere was cooled to −78° C. and LiHMDS 1M in THF (9.7 mL, 9.7 mmol, 1.3 eq.) was slowly added. After full addition the formed reaction mixture was stirred for 30 min at −78° C. and then for 30 min at 0° C. Then, paraformaldehyde (3.4 g, 112 mmol, 15 eq.). The reaction mixture was stirred for 1 hour at 0° C. Then, the reaction mixture was quenched with HCl 1M and allowed to warm to rt and the product was extracted with EtOAc. Combined organic layers were washed with brine, dried over $Na_2SO_4$, filtered and concentrated under reduced pressure. The impure product was purified by flash column chromatography (heptane/EtOAc=1:0→3:7) to obtain C.2 (1.67 g, 3.41 mmol, purity: 88%, yield: 46%) as an off-white solid.

Compound C.3: Tert-Butyldimethylsilyl chloride (338 mg, 2.24 mmol) and imidazole (162 mg, 2.37 mmol) were dissolved in N,N-Dimethylformamide (20 mL) and 3-(2- fluoro-3-nitrobenzyl)-4-(2-hydroxyethyl)-2-oxo-2H-chromen-7-yl dimethylcarbamate (645 mg, 1.32 mmol) was added and mixture was stirred overnight. Then, the reaction mixture was quenched water and the product was extracted with EtOAc. Combined organic layers were washed with brine, dried over $Na_2SO_4$, filtered and concentrated under reduced pressure. The impure product was purified by flash column chromatography (heptane/EtOAc=1:0→1:1) to obtain C.3 (502 mg, 0.92 mmol, yield: 70%) as a colorless oil.

Compound C.4: The C.3 (2.3 g, 4.22 mmol) was dissolved in 150 mL of MeOH and argon was bubbled through the solution for 10 min. Then, 50% Raney-Ni slurry in water (2 mL, 8.44 mmol) was added. The mixture was purged with hydrogen and stirred for 1.5 h at rt. Then the reaction was quenched by purging with argon and the mixture was filtered over celite and concentrated and stripped with EtOAc and DCM to afford C.4 (2.41 g, 4.21 mmol, purity: 90%, yield: 100%) as a brown oil.

Compound C.5: To an ice bath cooled (0° C.) suspension of the primary amine (1.0 eq.) and pyridine (3.00 eq.) in N,N-Dimethylformamide (0.2 M), a transparent solution of methylsulfamoyl chloride (2.50 eq.) in Acetonitrile (anhydrous) (0.2 M) was added dropwise. After complete addition the formed reaction mixture was allowed to warm-up to room temperature and stirred for 1-16 h. Water was added to the reaction mixture and the formed suspension was stirred for 1 hour. The suspension was filtered, washed with water and Et2O. The residue was dried to obtain the sulfamoyl as a solid. 727 mg, 5.61 mmol of C.4 afforded C.5 (1.97 g, 3.24 mmol, purity: 95%, yield: 87%) as an orange foam.

Compound 100: To a stirred solution of C,5 (1.97 g, 2.92 mmol) in 5 mL of 1,4-dioxane, 2 mL of 4N HCl in 1,4-dioxane was added. After 30 min, the solvents were evaporated and stripped with DCM and purified by flash column chromatography (heptane/EtOAc=1:0→0:1) to obtain 100 (1.45 g, 2.79 mmol, yield: 96%) as an off-white foam.

Analysis: LCMS (Method P): $t_R$=1.19 min; m/z calculated for $[M+H]^+$=494.1. found=494.1; $^1H$ NMR 1H NMR (400 MHz, $CDCl_3$) δ 7.65 (d, J=8.7 Hz, 1H), 7.34 (dt, 1H), 7.14-7.07 (m, 2H), 7.02-6.90 (m, 2H), 6.81-6.73 (m, 1H), 4.79 (q, J=5.3 Hz, 1H), 4.09 (s, 2H), 3.67 (t, J=7.3 Hz, 2H), 3.17-3.08 (m, 5H), 3.03 (s, 3H), 2.75 (d, J=5.3 Hz, 3H), 2.27 (s, 1H).

Compound 101: To an ice-cooled stirred solution of 100 (100 mg, 203 mmol) and carbon tetrabromide (161 mg, 0.487 mmol, 2.4 eq) in 4 mL of DCM was added triphenylphosphine (117 mg, 0.446 mmol 2.2 eq) and the reaction was allowed to warm to rt and stirred for 5 h. The solvent was evaporated and the residue redissolved in 1 mL of DCM and purified with method 'flash' column chromatography (heptane/EtOAc=1:0→2:8) to obtain 101 (146 mg, 0.186 mmol, purity: 71% yield: 92%) as a white foam.

Example 4

General Synthesis D

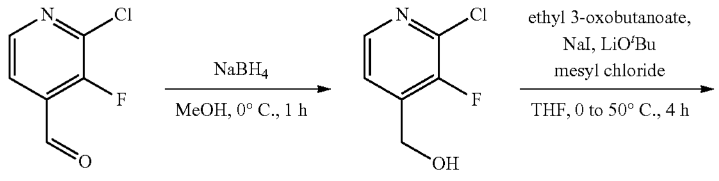

D.1 D.2

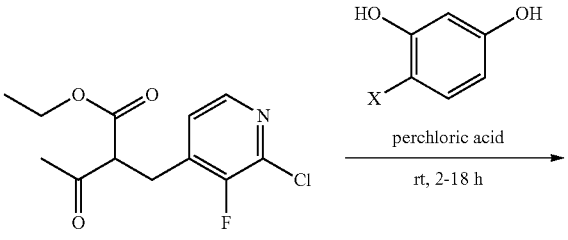

D.3

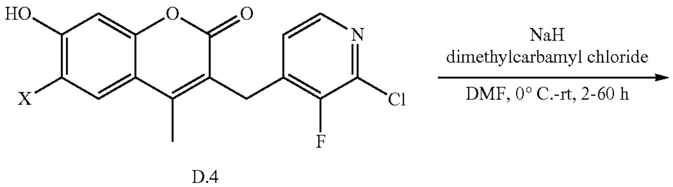

D.4
x = H, Me, Cl, F

-continued

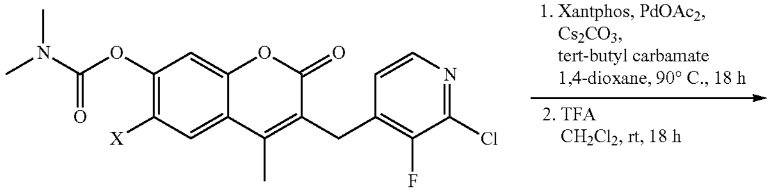

D.5
x = H, Me, Cl, F

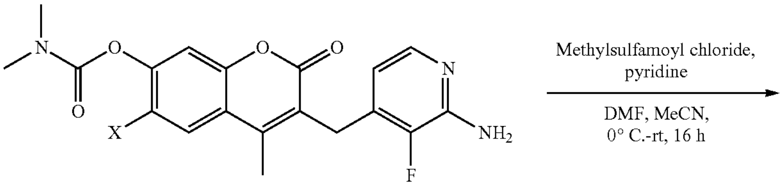

D.6
x = H, Me, Cl, F

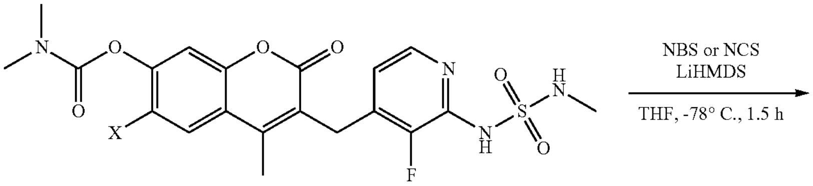

D.7
x = H, Me, Cl, F

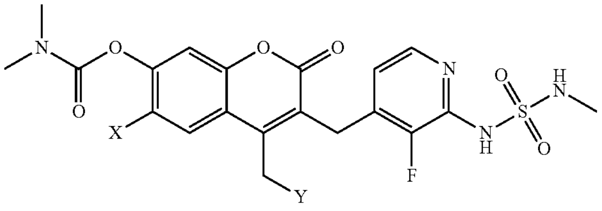

D.8
X = H, Me, Cl, F
Y = Br, Cl

Compound D.2: 2-chloro-3-fluoroisonicotinaldehyde hydrate (56.13 g, 316 mmol, 1.0 eq.) was dissolved in Methanol (630 ml) after which the solution was cooled to 0° C. sodium borohydride (11.96 g, 316 mmol, 1.0 eq.) was added in a portion-wise fashion, the formed reaction mixture was stirred for 1 hour at rt. The reaction mixture was quenched in 1000 mL of an ice water slurry and slowly acidified. The reaction mixture was extracted with EtOAc. Combined organic layers were washed with brine, dried over $Na_2SO_4$ and concentrated under reduced pressure to obtain (2-chloro-3-fluoropyridin-4-yl)methanol (66.25 g, 410 mmol, 98% yield) as an off white solid.

LCMS (Method K): $t_R$=1.20 min; m/z calculated for $[M+H]^+$=162.0. found=162.0.

Compound D.3: (2-chloro-3-fluoropyridin-4-yl)methanol (30 g, 186 mmol, 1.0 eq.) was dissolved in anhydrous Tetrahydrofuran (460 ml) and placed under a nitrogen atmosphere and cooled to 0° C. Lithium tert-butoxide (2.2 M, 89 ml, 195 mmol, 1.05 eq.) in THF was added dropwise, after which mesyl chloride (17.25 ml, 223 mmol, 1.20 eq.) was added dropwise. The formed reaction mixture was stirred for 1 hour at rt. The reaction mixture was added to a cooled (0° C.) solution of sodium iodide (27.8 g, 186 mmol, 1.0 eq.), Lithium tert-butoxide (93 ml, 204 mmol, 1.10 eq.) and Ethyl acetoacetate (47.2 ml, 371 mmol, 2.00 eq.) in 300 mL of anhydrous THF. The formed reaction mixture was stirred for 30 minutes at 0° C. and then for 3 hours at 50° C. After cooling to rt, the reaction mixture was diluted with EtOAc and washed with 0.2 M LiCl and once using brine. The organic phase was dried over $Na_2SO_4$ and concentrated under reduced pressure to obtain ethyl 2-((2-chloro-3-fluoropyridin-4-yl)methyl)-3-oxobutanoate (54.5 g, 199 mmol, 107% yield) as a yellow oil.

LCMS (Method K): $t_R$=1.91 and 2.12 min; m/z calculated for $[M+H]^+$=274.1. found=274.0.

Compound D.4: To a solution of ethyl 2-((2-chloro-3-fluoropyridin-4-yl)methyl)-3-oxobutanoate (51.2 g, 187 mmoll 1.0 eq.) in sulfuric acid (3-20 eq.) the diol 4 (2.00 eq.) was added. The formed reaction mixture was stirred for 2-18 h at rt. Water was added to the reaction mixture and the product was filtered, washed with water and $Et_2O$. The residue was recrystallized from EtOH:$H_2O$ 8:2 to obtain the coumarin as a solid.

Compound D.5: To a solution of the coumarin (1.0 eq.) in N,N-Dimethylformamide (dry) (0.15-0.4 M) at 0° C. under $N_2$ atmosphere, sodium hydride 60% dispersion on mineral oil (1.40-1.60 eq.) was added. The formed reaction mixture was left to stir for 10-20 min before dimethyl carbamoyl chloride (1.25-1.60 eq.) was added. The formed reaction mixture was allowed to warm to room temperature and left to stir for 1-24 h. Water was added to quench the reaction mixture. The formed suspension was stirred for 1 hour, filtered, washed with water and heptane. The residue was dried to obtain the dimethylcarbamate as a solid.

Compound D.6: To a solution of the dimethylcarbamate (1.0 eq.) and tert-butyl carbamate (1.40-10.0 eq.) in 1,4-Dioxane (0.1-0.2 M) under nitrogen atmosphere were added Xantphos (0.10-0.20 eq.), ceasium carbonate (1.20-1.50 eq.) and $PdOAc_2$ (0.10 eq.). after 5 additional minutes of nitrogen purging the formed reaction mixture was stirred for 18 hours at 90° C. The reaction mixture was filtered over celite and washed with $CH_2Cl_2$. The filtrated was concentrated under reduced pressure after which the residue was dissolved in $CH_2Cl_2$ (0.3-0.5 M). TFA (0.30-10.00 eq.) were added and the formed reaction mixture was stirred for 1 hour at rt. The reaction mixture was concentrated under reduced pressure and twice co-evaporated with $CH_2Cl_2$ to give an oil. The oil was purified by reversed phase chromatography method 'flash acid' to obtain the amino pyridine as a solid.

Compound D.7: To an ice bath cooled (0° C.) suspension of the amino pyridine (1.0 eq.) and pyridine (3.00 eq.) in N,N-Dimethylformamide (0.2-0.30 M), a transparent solution of methylsulfamoyl chloride (2.50 eq.) in Acetonitrile (anhydrous) (0.2 M) was added dropwise. After complete addition the formed reaction mixture was allowed to warm-up to room temperature and stirred for 16 h. Water was added to the reaction mixture and the formed suspension was stirred for 1 hour. The suspension was filtered, washed with water and $Et_2O$. The residue was dried to obtain the sulfamoyl as a solid Compound D.8: A solution of the sulfamoyl (1.0 eq.) in Tetrahydrofuran (dry) (0.06 M) under nitrogen atmosphere was cooled to −78° C. and LiHMDS 1M in THF (3.00 eq.) was slowly added. After full addition the formed reaction mixture was in some cases diluted with some extra tetrahydrofuran (dry) and stirred for 30 min, allowed to warm to 0° C. This was added to a cooled (−78° C.) solution of NCS or NBS (1.20 eq.) in Tetrahydrofuran (dry) (0.04 M), drop-wise via a cannula over 15 minutes. The formed reaction mixture was stirred for 1 hour at −78° C. At −78° C. the reaction mixture was quenched with HCl 1M and allowed to warm to rt. Some extra water was added and the product was extracted with EtOAc. Combined organic layers were washed with brine, dried over $Na_2SO_4$, filtered and concentrated under reduced pressure to obtain the bromine or chlorine as a solid.

Example 5

General Synthesis E

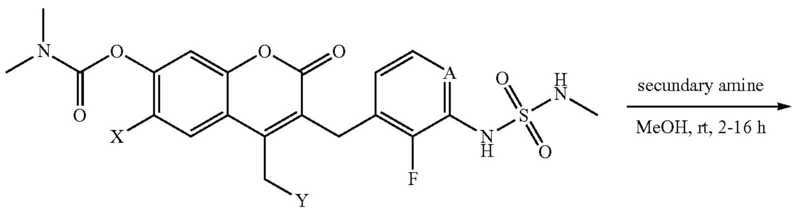

E.1

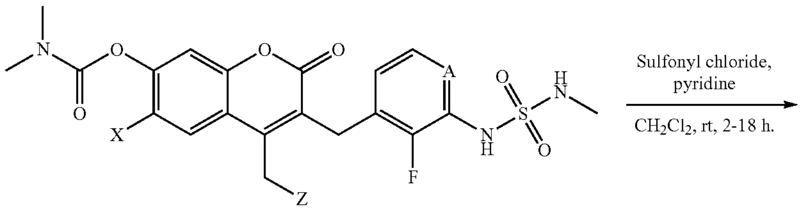

E.2
X = H, Me, Cl, F
Y = Br, Cl
Z = different amines
A = N, CH

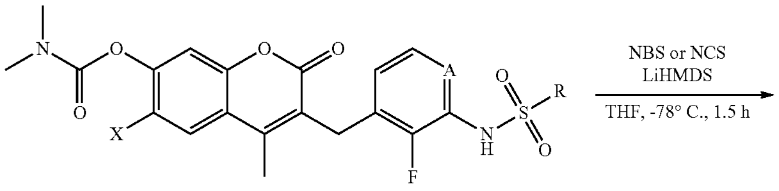

E.3
X = H, Cl
A = N, CH
R = Et, propane, cyclopropane, isopropyl(methyl), cyclobutane, 3,3,3-trifluoropropane, 3,3,3-trifluoroethane -continued

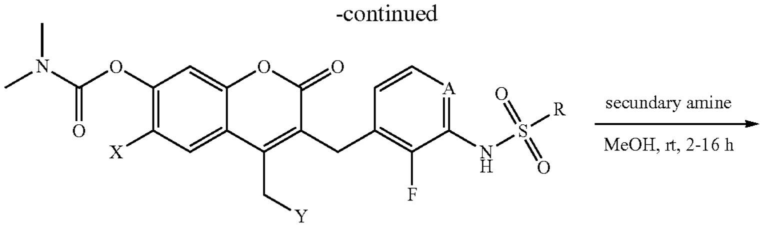

E.4
X = H, Cl
Y = Br, Cl
A = N, CH
R = Et, propane, cyclopropane, isopropyl(methyl), cyclobutane, 3,3,3-trifluoropropane, 3,3,3-trifluoroethane

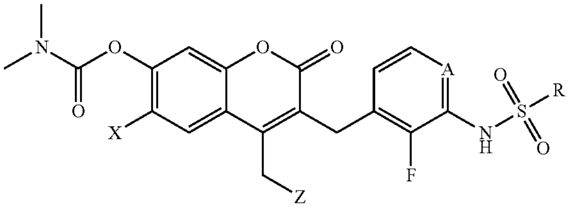

E.5

Compound E.2: The bromine or chlorine (1.0 eq.) was suspended in methanol (0.10-0.20 M). The amine (1-10 eq.) was added and the formed reaction mixture was stirred for 2-16 h at rt. The reaction mixture was filtered and purified by preparative HPLC (method: prep acid or prep base) to obtain the desired amine after freeze drying or Genevac™ as a solid.

Compound E.3: Di-methylamine E.2 (1.0 eq.) and pyridine (1.1-1.5 eq.) were dissolved in $CH_2Cl_2$ (0.2-0.8 M). The sulfonyl chloride (1.2-1.7 eq.) was added and the formed reaction mixture was stirred at rt for 2-18 h. The reaction mixture was concentrated under reduced pressure. The residue was purified by column chromatography with method 'flash' ($CH_2Cl_2$/EtOAc=1:0→6:4) to obtain the sulfamoyl E.3 as a solid.

Compound E.4: A solution of the sulfamoyl E.3 (1.0 eq.) in Tetrahydrofuran (dry) (0.06 M) under nitrogen atmosphere was cooled to −78° C. and LiHMDS 1M in THF (1-3 eq.) was slowly added. After full addition the formed reaction mixture was in some cases diluted with some extra tetrahydrofuran (dry) and stirred for 30 min, allowed to warm to 0° C. This was added to a cooled (−78° C.) solution of NCS or NBS (1.2 eq.) in Tetrahydrofuran (dry) (0.04 M), drop-wise via a cannula over 15 minutes. The formed reaction mixture was stirred for 1 hour at −78° C. At −78° C. the reaction mixture was quenched with $H_2SO_4$ 1M and allowed to warm to rt. Some extra water was added and the product was extracted with EtOAc. Combined organic layers were washed with brine, dried over $Na_2SO_4$, filtered and concentrated under reduced pressure to obtain the bromine or chlorine E.4 as a solid.

Compound E.5: The bromine or chlorine E.4 (1.0 eq.) was suspended in methanol (0.10-0.20 M). The amine (1-10 eq.) was added and the formed reaction mixture was stirred for 2-16 h at rt. The reaction mixture was filtered and purified by preparative HPLC (method: prep acid or prep base) to obtain the desired amine E.5 after freeze drying or Genevac™ as a solid.

Example 6

General Synthesis F

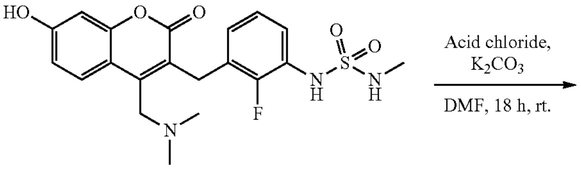

F.1

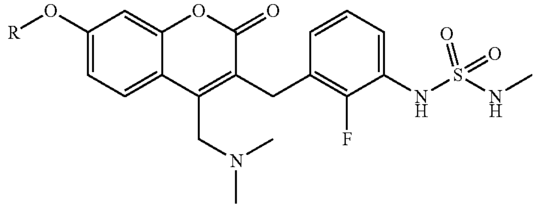

F.2

The phenol F.1 (1.0 eq.) and potassium carbonate (2.0 eq.) were dissolved in DMF (0.03-0.2 M). The acid chloride (1.0 eq.) was added and stirred for 1-18 hours at rt. The reaction mixtures were purified by preparative HPLC (method: "prep acid" or "prep basei") to obtain the desired F.2 after freeze drying or Genevac™ as a solid.

Example 7

General Synthesis G

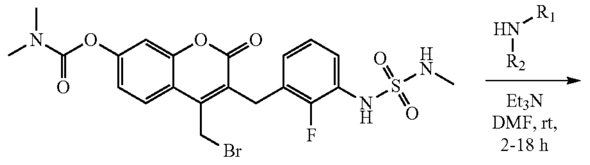

G.1

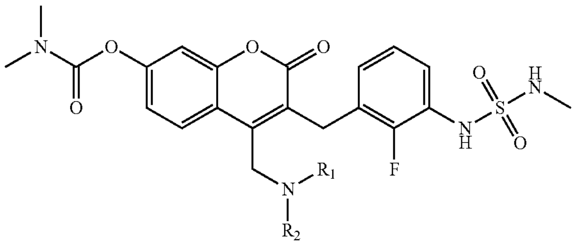

G.2

Compound G.2 To a solutions of G.1 (1.0 eq.) in DMF (0.1-0.2 M) were added the respective amines (1.5 eq.) and $Et_3N$ (2-5 eq.); each in one separate vial. The reaction mixtures were stirred for 2-18 h at rt. The reaction mixtures were then filtered and purified by preparative HPLC (method: prep acid or prep base) to obtain the desired products G.2 as solids after evaporation under vacuum at 40° C. in a Genevac™.

Example 8

Synthesis of Compound 102

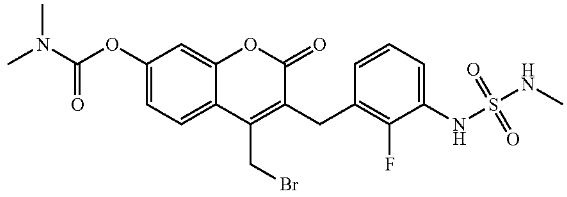

Compound 102 was prepared in 5 steps:

Step 1: Starting from ethyl 2-(2-fluoro-3-nitrobenzyl)-3-oxobutanoate 3 (48.9 g, 173 mmol) and resorcinol (1.04 eq.) following procedure General Synthesis A. After the filtration the residue was stirred in a aq. Sat. $NaHCO_3$ solution until bubbling had stopped. The suspension was again filtered washed with water, $Et_2O$ and dried to obtain the corresponding coumarin 5 (50.3 g, 153 mmol, yield: 98%) as a yellow solid.

Step 2: Following the procedure for the synthesis of Compound 4 to obtain the corresponding dimethylcarbamate 6 (70.7 g, 166 mmol, yield: 109%) as a yellow solid.

Step 3: Following the procedure for the synthesis of Compound 5, with Pd/C and EtOH/THF 1:2 (0.05 M) as solvents to obtain the corresponding primary amine 7 (50.83 g, 130 mmol, yield: 77%) as a light pink solid.

Step 4: Following the procedure for the synthesis of Compound 6 starting with 35 g, 90 mmol of 7. Methylsulfamoyl chloride was added in 2.5 eq. to obtain the corresponding sulfamoyl 8 (37.8 g, 76 mmol, yield: 84%) as a beige solid.

Step 5: Following procedure General Procedure E, using NBS and with the exception that 1N $H_2SO_4$ was used instead of 1N HCl, to obtain the title compound (23.9 g, 40.5 mmol, yield: 56%) as a white solid.

Yield: The title compound was isolated as a white solid (40% over 5 steps)

Analysis: LCMS (Method U): $t_R$=1.97 min; m/z calculated for $[M+H_2O]^+$=559.0/561.0. found=559.0/561.0.

Example 9

Synthesis of Compound 7

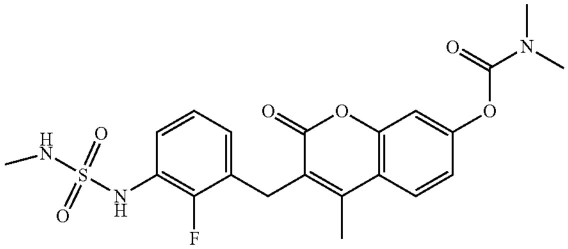

Compound 7 was prepared in 4 steps:

Step 1: Starting from ethyl 2-(2-fluoro-3-nitrobenzyl)-3-oxobutanoate (48.9 g, 173 mmol) and resorcinol (1.04 eq.) following the general synthesis of Compound 4. After the filtration the residue was stirred in a aq. Sat. $NaHCO_3$ solution until bubbling had stopped. The suspension was again filtered washed with water, $Et_2O$ and dried to obtain the corresponding coumarin 5 (50.3 g, 153 mmol, yield: 98%) as a yellow solid.

Step 2: Following the general synthesis of Compound 5 to obtain the corresponding dimethylcarbamate (70.7 g, 166 mmol, yield: 109%) as a yellow solid.

Step 3: Following the general synthesis of Compound 6, with Pd/C and EtOH/THF 1:2 (0.05 M) as solvents to obtain the corresponding primary amine (50.83 g, 130 mmol, yield: 77%) as a light pink solid.

Step 4: Following the general synthesis of Compound 7 starting with 35 g, 90 mmol of 7. Methylsulfamoyl chloride was added in 2.5 eq. to obtain the title compound (37.8 g, 76 mmol, yield: 84%) as a beige solid.

Yield: The title compound was isolated as a beige solid (69% over 4 steps).

Analysis: LCMS (Method I): $t_R$=1.98 min; m/z calculated for $[M+H]^+$=464.1. found=464.1; 1H NMR (400 MHz, $CDCl_3$) δ 7.65-7.59 (m, 1H), 7.39 (td, J=7.8, 1.7 Hz, 1H), 7.15-7.08 (m, 2H), 7.01 (t, J=7.8 Hz, 1H), 6.95 (td, J=7.9, 7.4, 1.8 Hz, 1H), 6.60 (d, J=3.0 Hz, 1H), 4.44 (q, J=5.4 Hz, 1H), 4.06 (s, 2H), 3.13 (s, 3H), 3.03 (s, 3H), 2.75 (d, J=5.3 Hz, 3H), 2.44 (s, 3H).

Example 10

Synthesis of Compound 9

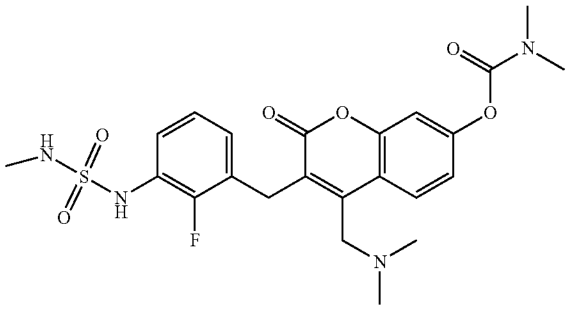

Compound 9 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (22.22 g, 34.79 mmol) and dimethylamine 2M in MeOH, following the general synthesis of Compound E.2. After full conversion the reaction was concentrated under reduced pressure. 1M HCl was added to the residue and the water layer was extracted with $CH_2Cl_2$. The water layer was made basic with solid $Na_2CO_3$. The basic water layer was extracted with $CH_2Cl_2$. The organic layer from the basic extraction was washed with brine, dried over $Na_2SO_4$, filtered and concentrated under reduced pressure to obtain the title compound (13.23 g, 25.7 mmol, yield: 74%) as a light yellow solid.

Yield: Compound 9 was isolated as a light yellow solid (74% over 1 step)

Analysis: LCMS (Method T): $t_R$=1.53 min; m/z calculated for $[M-H]^+$=507.2. found=507.2; 1H NMR (400 MHz, DMSO) δ 9.38 (s, 1H), 8.08 (d, J=8.8 Hz, 1H), 7.28 (td, J=8.0, 1.6 Hz, 1H), 7.25-7.18 (m, 2H), 7.15 (dd, J=8.8, 2.4 Hz, 1H), 7.00 (t, J=7.9 Hz, 1H), 6.90-6.77 (m, 1H), 4.04 (s, 2H), 3.64 (s, 2H), 3.06 (s, 3H), 2.93 (s, 3H), 2.52 (d, J=4.9 Hz, 3H), 2.19 (s, 6H).

Example 11

Synthesis of Compound 10

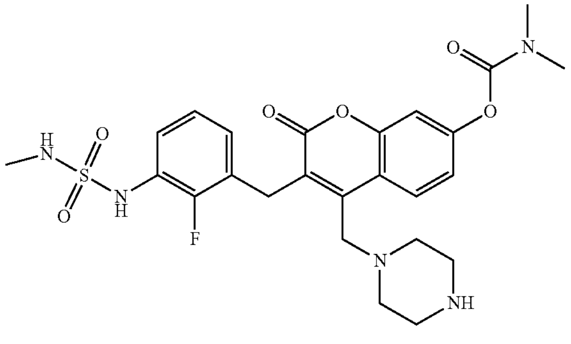

Compound 10 was prepared in 2 steps:

Step 1: Starting with 4-(bromomethyl)-3-(2-fluoro-3-((N-methylsulfamoyl)amino)benzyl)-2-oxo-2H-chromen-7-yl dimethylcarbamate (0.35 g, 0.59 mmol) and N-Boc piperazine, following the general synthesis of Compound E.2, with the addition that $NEt_3$ (1.0 eq) was added. The product was purified by prep basic. Desired fractions were combined and concentrated under reduced pressure to obtain the amine (0.414 g, 0.486 mmol, yield: 82%, purity: 76%) as a colorless oil.

Step 2: The amine was dissolved in 1,4-dioxane (3 mL) and HCl in dioxane (4M, 16.7 eq, 2.0 mL, 8.00 mmol) was added and stirred for 1 hour at rt. The reaction mixture was concentrated under reduced pressure and the twice co-evaporated with $CH_2Cl_2$. The residue was dissolved in MeCN/water and lyophilized to obtain the title compound (304 mg, 0.49 mmol, yield: 102%) as a white solid.

Yield: Compound 10 was isolated as a white solid (84% over 2 steps).

Analysis: LCMS (Method S): $t_R$=1.00 min; m/z calculated for $[M-H]^+$=548.2. found=548.2; 1H NMR (400 MHz, DMSO) δ 9.37 (s, 1H), 8.88 (s, 2H), 8.09 (d, J=8.8 Hz, 1H), 7.32-7.19 (m, 3H), 7.17 (dd, J=8.9, 2.4 Hz, 1H), 7.00 (t, J=7.8 Hz, 1H), 6.86-6.78 (m, 1H), 4.04 (s, 2H), 3.86 (s, 2H), 3.07 (s, 3H), 2.95 (d, J=14.4 Hz, 7H), 2.73 (s, 4H), 2.54 (d, J=2.8 Hz, 3H).

Example 12

Synthesis of Compound 103

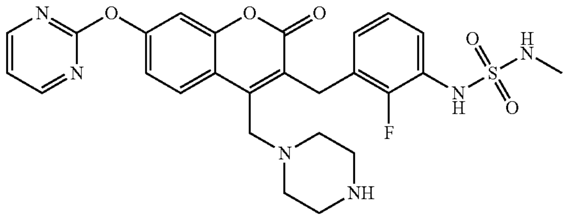 [SMILES: CNS(=O)(=O)Nc1cccc(Cc2c(CN3CCNCC3)c3ccc(Oc4ncccn4)cc3oc2=O)c1F]

Compound 103 was prepared in 5 steps:

Step 1: To a solution of 3-(2-fluoro-3-nitrobenzyl)-7-hydroxy-4-methyl-2H-chromen-2-one (700 mg, 2.126 mmol, 1.0 eq.) and 2-Bromopyrimidine (2467 mg, 15.52 mmol, 7.3 eq.) in N,N-Dimethylformamide (0.1 M) at room temperature was added potassium carbonate (588 mg, 4.25 mmol, 2.00 eq.) and the formed reaction mixture was stirred at 80° C. for 1 h. The solvent was evaporated under reduced pressure. Water was added and the product was extracted with EtOAc. Combined organic layers were washed with brine, dried over $Na_2SO_4$, filtered and concentrated under reduced pressure. The impure product was purified by column chromatography with method 'flash' (heptane/EtOAc 4:1→1:4) to obtain 3-(2-fluoro-3-nitrobenzyl)-4-methyl-7-(pyrimidin-2-yloxy)-2H-chromen-2-one (470 mg, 1.154 mmol, yield: 51%) as a light yellow solid.

Step 2: To a suspension of 3-(2-fluoro-3-nitrobenzyl)-4-methyl-7-(pyrimidin-2-yloxy)-2H-chromen-2-one (470 mg, 1.154 mmol, 1.0 eq.) in N,N-Dimethylformamide (dry) (0.11 M) was added tin(II) chloride dihydrate (1302 mg, 5.77 mmol, 5.00 eq.). The formed reaction mixture was stirred at 70° C. for 1.5 h. Reaction mixture was concentrated under reduced pressure and water was added to the residue. The product was extracted with EtOAc. Combined organic layers were washed with brine, dried over $Na_2SO_4$, filtered and concentrated under reduced pressure to obtain 3-(3-amino-2-fluorobenzyl)-4-methyl-7-(pyrimidin-2-yloxy)-2H-chromen-2-one (430 mg, 1.026 mmol, yield: 84%) as an orange oil.

Step 3: To a solution of 3-(3-amino-2-fluorobenzyl)-4-methyl-7-(pyrimidin-2-yloxy)-2H-chromen-2-one (430 mg, 1.026 mmol, 1.0 eq.) and pyridine (0.373 ml, 4.61 mmol, 4.50 eq.) in N,N-Dimethylformamide (dry) (0.1 M) at 0° C. was added a solution of methylsulfamoyl chloride (0.203 ml, 2.359 mmol, 2.30 eq.) in Acetonitrile (3 ml) and the formed reaction mixture was stirred at room temperature for 2 hours. Water was added and the product was extracted with EtOAc. Combined organic layers were washed with brine, dried over $Na_2SO_4$, filtered and concentrated under reduced pressure to obtain the sulfamoyl (493 mg, 0.912 mmol, yield: 89%) as an orange solid.

Step 4: The sulfamoyl (30 mg, 0.064 mmol, 1.0 eq.) was dissolved in Tetrahydrofuran (dry) (0.04 M), purged with argon and cooled to −78° C. Then, LiHMDS (1 M in THF, 0.191 ml, 0.191 mmol, 3.00 eq.) was added and mixture was stirred for 30 min. A solution of N-bromosuccinimide (13.62 mg, 0.077 mmol, 1.20 eq.) in Tetrahydrofuran (dry) (0.5 ml) was added dropwise. Mixture was left to stir for 30 min at −78° C. Water was added to the reaction mixture. The product was extracted with EtOAc. Combined organic layers were washed with brine, dried over $Na_2SO_4$, filtered and concentrated under reduced pressure to obtain the bromide (30 mg, 0.034 mmol, yield: 53%) as an orange solid.

Step 5: Starting with the bromine (0.02 g, 0.037 mmol) and piperazine, following procedure General Procedure P, with prep basic to obtain the title compound (11.1 mg, 0.02 mmol, yield: 54%) as a white solid.

Yield: The title compound was isolated as a white solid (11% over 5 steps)

Analysis: LCMS (Method P): $t_R$=1.12 min; m/z calculated for $[M-H]^+$=555.2. found=555.2.

Example 13

Synthesis of Compound 104

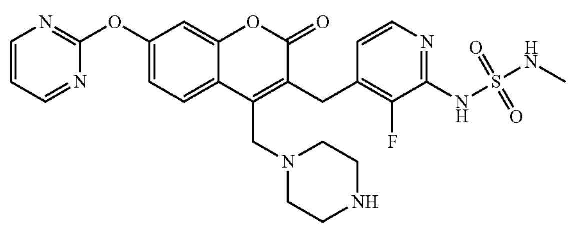 [SMILES: CNS(=O)(=O)Nc1nccc(Cc2c(CN3CCNCC3)c3ccc(Oc4ncccn4)cc3oc2=O)c1F]

Compound 104 was prepared in 2 steps:

Step 1: Sulfamide, N-[3-fluoro-4-[[4-methyl-2-oxo-7-(2-pyrimidinyloxy)-2H-1-benzopyran-3-yl]methyl]-2-pyridinyl]-N'-methyl-(20 mg, 0.042 mmol, 1.0 eq.) was dissolved in Tetrahydrofuran (dry) (0.02 M), purged with argon and cooled to −78° C. Then, LiHMDS (1 M in THF, 0.169 ml, 0.169 mmol, 4.00 eq.) was added and mixture was stirred for 30 min. A solution of N-bromosuccinimide (9 mg, 0.051 mmol, 1.20 eq.) in Tetrahydrofuran (dry) (0.5 ml) was added dropwise. Mixture was left to stir for 30 min at −78° C. 1M HCl was added to the reaction mixture. The product was extracted with EtOAc. Combined organic layers were washed with brine, dried over $Na_2SO_4$, filtered and concentrated under reduced pressure to obtain the bromide (27 mg, 0.028 mmol, yield: 66%) as an orange oil.

Step 2: Starting with the bromine (0.02 g, 0.037 mmol) and piperazine, following the general synthesis of Compound G.2, with prep basic to obtain the title compound (7.8 mg, 0.0140 mmol, yield: 38%) as a white solid.

Yield: The title compound was isolated as a white solid (25% over 2 steps)

Analysis: LCMS (Method P): $t_R$=0.83 min; m/z calculated for $[M-H]^+$=556.2. found=556.2.

Example 14

Synthesis of Compound 105

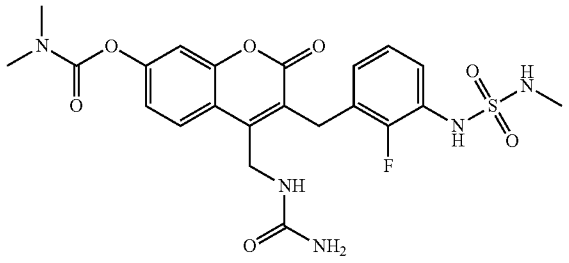

Compound 105 was prepared in 2 steps:

Step 1: 4-(bromomethyl)-3-(2-fluoro-3-((N-methylsulfamoyl)amino)benzyl)-2-oxo-2H-chromen-7-yl dimethylcarbamate (0.3 g, 0.553 mmol, 1.0 eq.) was dissolved in ammonia (0.5 M in THF, 20 mL, 10.0 mmol, 18 eq.) and stirred for 18 hours at rt. The reaction mixture was concentrated under reduced pressure to obtain 4-(aminomethyl)-3-(2-fluoro-3-((N-methylsulfamoyl)amino)benzyl)-2-oxo-2H-chromen-7-yl dimethylcarbamate hydrobromide (331 mg, 0.592 mmol, yield: 107%) as an off-white solid.

Step 2: 4-(aminomethyl)-3-(2-fluoro-3-((N-methylsulfamoyl)amino)benzyl)-2-oxo-2H-chromen-7-yl dimethylcarbamate hydrobromide (40 mg, 0.072 mmol, 1.0 eq.) was dissolved in $CH_2Cl_2$ (0.04 M). $Et_3N$ (0.08 mL, 0.572 mmol, 8.0 eq.) and Trimethylsilyl isocyanate (0.077 mL, 0.572 mmol, 8.0 eq.) were added and the formed reaction mixture was stirred for 18 hours at rt. The product was purified by prep acid to obtain the title compound (6.5 mg, 0.012 mmol, yield: 17%) as a white solid after lyophilization.

Yield: Compound 105 was isolated as a white solid (18% over 2 step)

Analysis: LCMS (Method T): $t_R$=1.20 min; m/z calculated for $[M+H]^+$=522.2. found=522.4.

Example 15

Synthesis of Compound 106

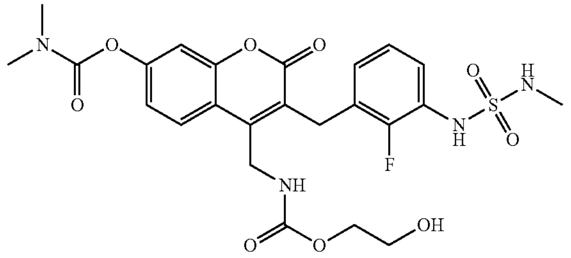

Compound 106 was prepared in 3 steps:

Step 1: 4-(bromomethyl)-3-(2-fluoro-3-((N-methylsulfamoyl)amino)benzyl)-2-oxo-2H-chromen-7-yl dimethylcarbamate (0.3 g, 0.553 mmol, 1.0 eq.) was dissolved in ammonia (0.5 M in THF, 20 mL, 10.0 mmol, 18 eq.) and stirred for 18 hours at rt. The reaction mixture was concentrated under reduced pressure to obtain 4-(aminomethyl)-3-(2-fluoro-3-((N-methylsulfamoyl)amino)benzyl)-2-oxo-2H-chromen-7-yl dimethylcarbamate hydrobromide (331 mg, 0.592 mmol, yield: 107%) as an off-white solid.

Step 2: To a solution of 4-(aminomethyl)-3-(2-fluoro-3-((N-methylsulfamoyl)amino)benzyl)-2-oxo-2H-chromen-7-yl dimethylcarbamate hydrobromide (40 mg, 0.072 mmol, 1.0 eq.) and 2-((tert-butyldimethylsilyl)oxy)ethyl (4-nitrophenyl) carbonate (31.7 mg, 0.093 mmol, 1.3 eq.) in N,N-Dimethylformamide (dry) (2 mL) was added triethylamine (0.030 mL, 0.215 mmol, 3.0 eq.) and the formed reaction mixture was stirred at room temperature for 3 days. The mixture was diluted with EtOAc and water, the layers were separated and the aqueous layer was extracted with EtOAc once. The combined organic layer was washed with water twice and brine, dried over $Na_2SO_4$ and concentrated. Water was added to the reaction mixture. The product was extracted with EtOAc. Combined organic layers were washed with brine, dried over $Na_2SO_4$, filtered and concentrated under reduced pressure. The impure product was purified by column chromatography with method ‘flash’ (heptane/EtOAc 4:1→1:4) to obtain 3-(2-fluoro-3-((N-methylsulfamoyl)amino)benzyl)-2-oxo-4-(8,8,9,9-tetramethyl-3-oxo-4,7-dioxa-2-aza-8-siladecyl)-2H-chromen-7-yl dimethylcarbamate (25 mg, 0.033 mmol, yield: 46%) as a white solid.

Step 3: To a solution of 3-(2-fluoro-3-((N-methylsulfamoyl)amino)benzyl)-2-oxo-4-(8,8,9,9-tetramethyl-3-oxo-4,7-dioxa-2-aza-8-siladecyl)-2H-chromen-7-yl dimethylcarbamate (25 mg, 0.037 mmol, 1.0 eq.) in Tetrahydrofuran (0.5 mL) was added hydrochloric acid (4N in dioxane, 0.092 mL, 0.367 mmol, 10 eq.) and the formed reaction mixture was stirred at room temperature for 30 minutes. The product was purified by prep basic to obtain the title compound (9.6 mg, 0.017 mmol, yield: 46%) as a white solid after lyophilization.

Yield: The title compound was isolated as a white solid (23% over 3 step).

Analysis: LCMS (Method T): $t_R$=1.25 min; m/z calculated for $[M+H]^+$=567.2. found=567.4; 1H NMR (400 MHz, DMSO) δ 9.38 (s, 1H), 7.94 (d, J=8.9 Hz, 1H), 7.85 (t, J=5.7 Hz, 1H), 7.32-7.22 (m, 2H), 7.19 (dd, J=8.8, 2.4 Hz, 1H), 6.97 (t, J=8.0 Hz, 1H), 6.81 (s, 1H), 4.71 (t, J=5.3 Hz, 1H), 4.41 (d, J=5.6 Hz, 2H), 4.12 (s, 2H), 3.96 (t, J=5.1 Hz, 2H), 3.50 (q, J=5.2 Hz, 2H), 3.07 (s, 3H), 2.93 (s, 3H).

Example 16

Synthesis of Compound 107

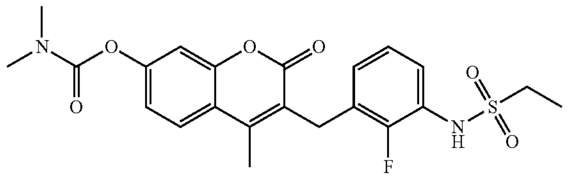 [SMILES: CCS(=O)(=O)Nc1cccc(Cc2c(C)c3ccc(OC(=O)N(C)C)cc3oc2=O)c1F]

Compound 107 was prepared in 1 step:

Step 1: Starting with 3-(3-amino-2-fluorobenzyl)-4-methyl-2-oxo-2H-chromen-7-yl dimethylcarbamate (0.1 g, 0.27 mmol) and Ethanesulfonyl chloride, following the general synthesis E.3 to obtain the title compound (46.8 mg, 0.10 mmol, yield: 37%) as a white solid.

Yield: Compound 107 was isolated as a white solid (37% over 1 step)

Analysis: LCMS (Method R): $t_R$=1.57 min; m/z calculated for $[M+H_2O]^+$=480.2. found=480.1; 1H NMR (400 MHz, DMSO) δ 9.60 (s, 1H), 7.86 (d, J=8.7 Hz, 1H), 7.29-7.22 (m, 2H), 7.19 (dd, J=8.8, 2.3 Hz, 1H), 7.03 (t, J=7.9 Hz, 1H), 6.95 (td, J=7.9, 7.5, 1.7 Hz, 1H), 3.99 (s, 2H), 3.15-3.02 (m, 5H), 2.93 (s, 3H), 2.45 (s, 3H), 1.26 (t, J=7.4 Hz, 3H).

Example 17

Synthesis of Compound 108

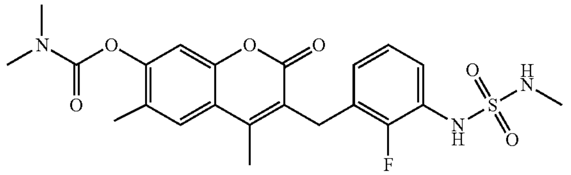

Compound 108 was prepared in 4 steps:

Step 1: Starting from ethyl 2-(2-fluoro-3-nitrobenzyl)-3-oxobutanoate (1.0 g, 3.53 mmol) and 4-methylbenzene-1,3-diol (1.20 eq.) following the general synthesis of Compound 4 to obtain the corresponding coumarin as an off white solid (1.32 g, 3.68 mmol, yield: 104%).

Step 2: Following procedure the general synthesis of Compound 5 to obtain the corresponding dimethylcarbamate (0.91 g, 2.06 mmol, yield: 54%) as a light yellow solid.

Step 3: Following the general synthesis of Compound 6. After filtration the product was purified by column chromatography with method ‘flash’ ($CH_2Cl_2$/MeOH=1:0→95:5) to obtain the corresponding primary amine (0.54 g, 0.79 mmol, purity: 56% yield: 35%) as a light yellow solid.

Step 4: Following the general synthesis of Compound 7. After filtration 576 mg of impure compound was obtained. 50 mg was further purified by preparative LC (basic) to obtain the title compound (13.2 mg, 0.027 mmol, yield: 66%) after freeze drying as a white solid.

Yield: Compound 108 was isolated as a white solid (13% over 4 steps)

Analysis: LCMS (Method T): $t_R$=1.58 min; m/z calculated for $[M-H]^+$=476.1. found=476.2; 1H NMR (400 MHz, DMSO) δ 9.38 (s, 1H), 7.76 (s, 1H), 7.30-7.24 (m, 1H), 7.22 (s, 1H), 7.13 (s, 1H), 6.99 (t, J=7.9 Hz, 1H), 6.82 (t, J=7.2 Hz, 1H), 3.96 (s, 2H), 3.09 (s, 3H), 2.94 (s, 3H), 2.44 (s, 3H), 2.23 (s, 3H).

Example 18

Synthesis of Compound 109

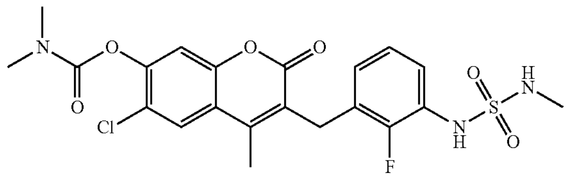

Compound 109 was prepared in 4 steps:

Step 1: Starting from ethyl 2-(2-fluoro-3-nitrobenzyl)-3-oxobutanoate 3 (1.0 g, 3.53 mmol) and 4-chlorobenzene-1,3-diol (1.20 eq.) following the general synthesis of Compound 4 to obtain the corresponding coumarin 5 (0.95 g, 2.57 mmol, yield: 73%) as an off white solid.

Step 2: Following the procedure of the general synthesis of Compound 5 to obtain the corresponding dimethylcarbamate (0.88 g, 1.95 mmol, yield: 75%) as a light yellow solid.

Step 3: Following the procedure of the general synthesis of Compound 6 to obtain the corresponding primary amine (0.51 g, 1.22 mmol, yield: 60%) as a light yellow solid.

Step 4: Following the procedure of the general synthesis of Compound 7 to obtain. After filtration, 588 mg of impure compound was obtained. 50 mg was further purified by preparative LC (basic) to obtain the title compound (28.9 mg, 0.027 mmol, yield: 44%) after freeze-drying as a white solid.

Yield: Compound 109 was isolated as a white solid (14% over 4 steps)

Analysis: LCMS (Method T): $t_R$=1.63 min; m/z calculated for $[M-H]^+$=496.1. found=496.2; 1H NMR (400 MHz, DMSO) δ 9.40 (s, 1H), 8.03 (s, 1H), 7.50 (s, 1H), 7.28 (td, J=7.9, 1.8 Hz, 1H), 7.10 (s, 1H), 6.98 (t, J=7.9 Hz, 1H), 6.84 (t, J=7.0 Hz, 1H), 3.97 (s, 2H), 3.10 (s, 3H), 2.95 (s, 3H), 2.45 (s, 3H).

Example 19

Synthesis of Compound 19

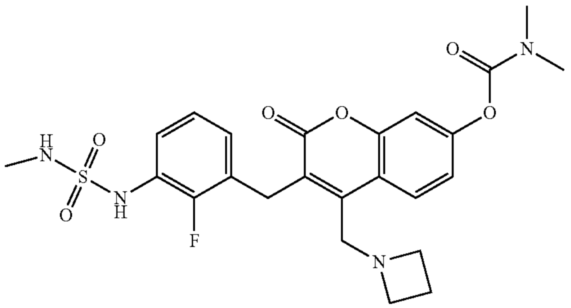

Compound 19 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (23.9 g, 44.1 mmol) and azetidine, following procedure of the general synthesis of Compound E.2, with the addition that DIPEA (2.0 eq) was added during the reaction. After full conversion the reaction mixture was concentrated under reduced pressure. The residue was purified by column chromatography with method 'flash' (heptane/EtOAc=1:0→0:1). Desired fractions were combined and concentrated under reduced pressure to obtain the title compound (11.8 g, 22.17 mmol, yield: 50%) as an off white solid.

Yield: Compound 19 was isolated as an off white solid (50% over 1 step).

Analysis: LCMS (Method T): $t_R$=1.53 min; m/z calculated for $[M-H]^+$=519.2. found=519.2; 1H NMR (400 MHz, $CDCl_3$) δ 8.01 (d, J=8.8 Hz, 1H), 7.38 (td, J=7.8, 1.6 Hz, 1H), 7.15-7.03 (m, 2H), 6.99 (t, J=8.1 Hz, 1H), 6.86 (t, J=7.7 Hz, 1H), 6.68 (s, 1H), 4.58 (q, J=5.3 Hz, 1H), 4.15 (s, 2H), 3.60 (s, 2H), 3.12 (s, 3H), 3.03 (s, 3H), 2.73 (d, J=5.3 Hz, 3H), 2.26 (s, 6H).

Example 20

Synthesis of Compound 21

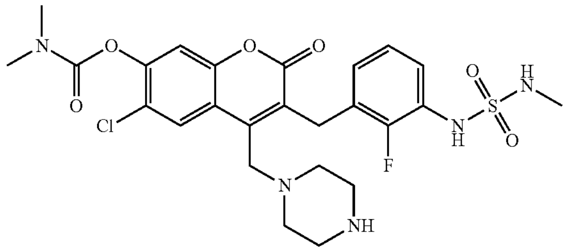

Compound 21 was prepared in 1 step:

Step 1: Starting with 6-chloro-4-(chloromethyl)-3-(2-fluoro-3-((N-methylsulfamoyl)amino)benzyl)-2-oxo-2H-chromen-7-yl dimethylcarbamate (50 mg, 0.094 mmol) and piperazine, following the general synthesis of Compound E.2. The impure product was combined with other batches and purified by prep basic to obtain the title compound (22 mg, 0.037 mmol, yield: 39%) after freeze drying as a white solid.

Yield: Compound 21 was isolated as a white solid (65% over 1 step).

Analysis: LCMS (Method R): $t_R$=1.43 min; m/z calculated for $[M+H]^+$=582.2. found=582.2; 1H NMR (400 MHz, DMSO) δ 8.30 (s, 1H), 8.27 (s, 1H), 7.48 (s, 1H), 7.31-7.19 (m, 2H), 6.99 (t, J=7.9 Hz, 1H), 6.83 (t, J=7.2 Hz, 1H), 4.03 (s, 2H), 3.70 (s, 2H), 3.10 (s, 3H), 2.95 (s, 3H), 2.64 (t, J=4.6 Hz, 4H), 2.53 (d, J=2.9 Hz, 3H), 2.40 (s, 4H).

Example 21

Synthesis of Compound 110

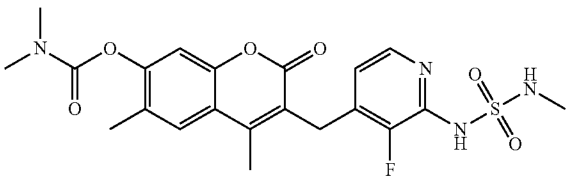

Compound 110 was prepared in 4 steps:

Step 1: Starting from ethyl 2-((2-chloro-3-fluoropyridin-4-yl)methyl)-3-oxobutanoate (1.18 g, 4.31 mmol) and 4-methylbenzene-1,3-diol (1.20 eq.) following procedure of the general synthesis of Compound D.4. After complete reaction water was added and the formed suspension was filtered. The residue co-evaporated with $Et_2O$. The residue was dried overnight at 40° C. under reduced pressure to obtain the corresponding coumarin (1.7 g, 4.53 mmol, yield: 105%, purity: 89%) as a beige solid.

Step 2: Following the procedure of the general synthesis of Compound D.5 to obtain the corresponding dimethylcarbamate (1.94 g, 4.32 mmol, yield: 95%, purity: 90%) as beige solid.

Step 3: Following the procedure of the general synthesis of Compound D.6 starting with 0.9 g, 2.22 mmol of compound D.5. The deprotection with TFA was not performed. The reaction mixture was filtered and concentrated under reduced pressure. The impure product was combined with another batch and purified by column chromatography with method 'flash' ($CH_2Cl_2$/MeOH 1:0→94:6) to obtain the corresponding primary amine D.6 (0.22 g, 0.303 mmol, yield: 14%, purity: 53%) as a brown solid.

Step 4: Following the procedure of the general synthesis of Compound D.7 After full conversion the reaction mixture was quenched with water and the product was extracted with EtOAc. Combined organic layers were washed with brine, dried over $Na_2SO_4$, filtered and concentrated under reduced pressure. The impure product was diluted with $CH_2Cl_2$ and purified by column chromatography with method 'flash' ($CH_2Cl_2$/MeOH 1:0→96:4) to give 141 mg of a yellow oil. 25 mg of the impure product was purified by prep basic to obtain the title compound (13.7 mg, 0.029 mmol, yield: 59%) after lyophilization as a white solid.

Yield: Compound 110 was isolated as a white solid (8% over 4 steps).

Analysis: LCMS (Method T): $t_R$=1.58 min; m/z calculated for $[M-H]^+$=479.1. found=479.2; 1H NMR (400 MHz, DMSO) δ 10.34 (s, 1H), 7.89 (s, 1H), 7.78 (s, 1H), 7.23 (s, 1H), 6.94 (s, 1H), 6.77 (s, 1H), 4.00 (s, 2H), 3.10 (s, 3H), 2.94 (s, 3H), 2.46 (s, 3H), 2.23 (s, 3H).

Example 22

Synthesis of Compound 111

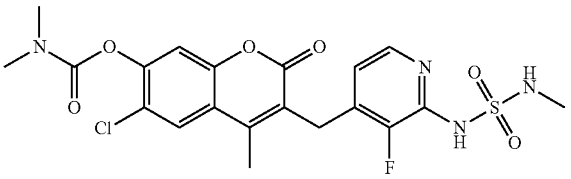

Compound 111 was prepared in 4 steps:

Step 1: Starting from ethyl 2-((2-chloro-3-fluoropyridin-4-yl)methyl)-3-oxobutanoate (15.0 g, 46.0 mmol) and 4-chlorobenzene-1,3-diol (1.20 eq.) following the procedure of the general synthesis of Compound D.4. After complete reaction water was added and the formed suspension was filtered. The residue co-evaporated with EtOH and triturated in EtOH/$Et_2O$. The solids were filtered off to obtain the corresponding coumarin (4.8 g, 13.55 mmol, yield: 29%) as a white solid.

Step 2: Following the procedure the general synthesis of Compound D.5 to obtain the corresponding dimethylcarbamate (5.48 g, 11.86 mmol, yield: 87%, purity: 92%) as a light yellow solid.

Step 3: Following the procedure of the general synthesis of Compound D.6 starting with 1.0 g, 2.35 mmol of compound D.5. The deprotection with TFA was not performed. The reaction mixture was filtered and concentrated under reduced pressure. The impure product was purified by column chromatography with method 'flash' (heptane/EtOAc 9:1→1:4) to obtain the corresponding primary amine (0.12 g, 0.281 mmol, yield: 12%) as a beige solid.

Step 4: Following procedure the general synthesis of Compound D.7 starting with 400 mg, 0.789 mmol of primary amine. After full conversion the reaction mixture was quenched with water. The product was extract with EtOAc, combined organic layers were washed with brine, dried over $Na_2SO_4$, filtered and concentrated under reduced pressure. The impure product was purified by column chromatography with method 'flash' ($CH_2Cl_2$/MeOH=1:0→96:4). The impure product was purified by prep basic to obtain the title compound (27.5 mg, 0.054 mmol, yield: 7%) after lyophilization as a white solid.

Yield: Compound 111 was isolated as a white solid (0.2% over 4 steps).

Analysis: LCMS (Method T): $t_R$=1.20 min; m/z calculated for $[M+H]^+$=499.1. found=499.2; 1H NMR (400 MHz, DMSO) δ 10.34 (s, 1H), 8.04 (s, 1H), 7.95-7.86 (m, 1H), 7.51 (s, 1H), 6.95 (s, 1H), 6.81 (s, 1H), 4.01 (s, 2H), 3.11 (s, 3H), 2.95 (s, 3H), 2.47 (s, 3H).

Example 23

Synthesis of Compound 112

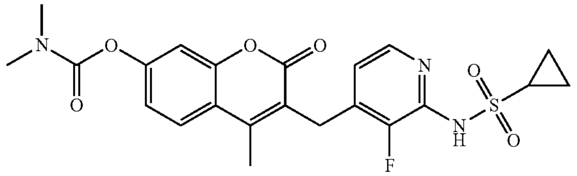 [SMILES: Cc1c(Cc2ccnc(NS(=O)(=O)C3CC3)c2F)c(=O)oc2cc(OC(=O)N(C)C)ccc12]

Compound 112 was prepared in 3 step:

Step 1: Starting from ethyl 2-((2-chloro-3-fluoropyridin-4-yl)methyl)-3-oxobutanoate (10.0 g, 24.12 mmol) and resorcinol (2.00 eq.) following the general synthesis of Compound D.4. Instead of perchloric acid, sulfuric acid was used. After complete conversion the reaction mixture was cooled (0° C.) and quenched with sat. aq. $NaHCO_3$ until basic pH. The formed white suspension was washed with water, $Et_2O$ and dried to obtain the corresponding coumarin (8.61 g, 23.4 mmol, yield: 97%, purity: 87%) as an off-white solid.

Step 2: Following the procedure of the general synthesis of Compound D.5 to obtain the corresponding dimethylcarbamate (9.33 g, 23.16 mmol, yield: 99%) as a beige solid.

Step 3: To an solution of dimethylcarbamate (200 mg, 0.512 mmol, 1.0 eq.) and cyclopropanesulfonamide (93 mg, 0.768 mmol, 1.5 eq.) in 1,4-Dioxane (extra dry) (0.1 M) under $N_2$ atmosphere were added Xantphos (59.2 mg, 0.102 mmol, 0.2 eq.), cesium carbonate (250 mg, 0.768 mmol, 1.5 eq.) and PdOAc2 (11.49 mg, 0.051 mmol, 0.1 eq.). The formed reaction mixture was stirred at 100° C. for 16 hours. The reaction mixture was filtered over a celite plug eluting with $CH_2Cl_2$. The filtrate was concentrated and purified by column chromatography with method 'flash' ($CH_2Cl_2$/EtOAc=1: 0→6:4). The impure product was further purified by prep basic to obtain the title compound (89 mg, 0.208 mmol, yield: 41%) after lyophilization as a white solid.

Yield: Compound 112 was isolated as a white solid (39% over 3 steps).

Analysis: LCMS (Method R): $t_R$=1.43 min; m/z calculated for $[M+H]^+$=476.1. found=476.2; 1H NMR (400 MHz, DMSO) δ 10.62 (s, 1H), 7.94 (d, J=5.1 Hz, 1H), 7.88 (d, J=8.8 Hz, 1H), 7.27 (d, J=2.3 Hz, 1H), 7.20 (dd, J=8.8, 2.4 Hz, 1H), 6.88 (d, J=6.0 Hz, 1H), 4.02 (s, 2H), 3.17 (s, 1H), 3.07 (s, 3H), 2.93 (s, 3H), 2.48 (s, 3H), 1.16-0.93 (m, 4H).

Example 24

Synthesis of Compound 113

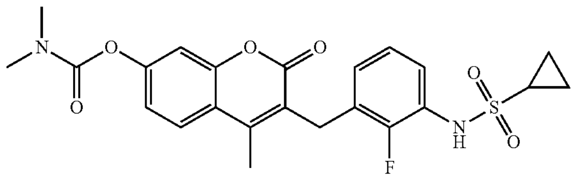 [SMILES: Cc1c(Cc2cccc(NS(=O)(=O)C3CC3)c2F)c(=O)oc2cc(OC(=O)N(C)C)ccc12]

Compound 113 was prepared in 1 step:

Step 1: Starting with 3-(3-amino-2-fluorobenzyl)-4-methyl-2-oxo-2H-chromen-7-yl dimethylcarbamate (0.1 g, 0.27 mmol) and Cyclopropanesulfonyl chloride, following the general synthesis of Compound E.3 to obtain the title compound (71.4 mg, 0.15 mmol, yield: 56%) as a white solid.

Yield: Compound 113 was isolated as a white solid (56% over 1 step).

Analysis: LCMS (Method R): $t_R$=1.58 min; m/z calculated for $[M+H_2O]^+$=492.4. found=492.1; 1H NMR (400 MHz, DMSO) δ 9.58 (s, 1H), 7.86 (d, J=8.8 Hz, 1H), 7.31-7.22 (m, 2H), 7.19 (dd, J=8.7, 2.3 Hz, 1H), 7.09-6.94 (m, 2H), 3.99 (s, 2H), 3.07 (s, 3H), 2.93 (s, 3H), 2.64 (tt, J=7.9, 4.8 Hz, 1H), 2.45 (s, 3H), 1.00-0.80 (m, 4H).

Example 25

Synthesis of Compound 114

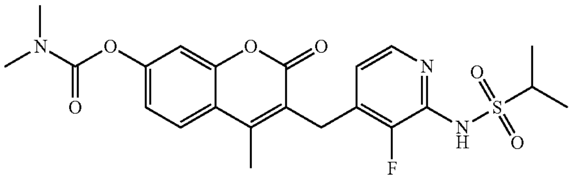 [SMILES: Cc1c(Cc2ccnc(NS(=O)(=O)C(C)C)c2F)c(=O)oc2cc(OC(=O)N(C)C)ccc12]

Compound 114 was prepared in 3 step:

Step 1: Starting from ethyl 2-((2-chloro-3-fluoropyridin-4-yl)methyl)-3-oxobutanoate (10.0 g, 24.12 mmol) and resorcinol (2.00 eq.) following the general synthesis of Compound D.4. Instead of perchloric acid, sulfuric acid was used. After complete conversion the reaction mixture was cooled (0° C.) and quenched with sat. aq. $NaHCO_3$ till basic pH. The formed white suspension was washed with water, $Et_2O$ and dried to obtain the corresponding coumarin (8.61 g, 23.4 mmol, yield: 97%, purity: 87%) as an off white solid.

Step 2: Following the procedure of the general synthesis of Compound D.5 to obtain the corresponding dimethylcarbamate (9.33 g, 23.16 mmol, yield: 99%) as a beige solid.

Step 3: To an solution of dimethylcarbamate (100 mg, 0.256 mmol, 1.0 eq.) and isopropylsulfonamide (47 mg, 0.384 mmol, 1.5 eq.) in 1,4-Dioxane (extra dry) (0.1 M) under $N_2$ atmosphere were added Xantphos (29.6 mg, 0.051 mmol, 0.2 eq.), cesium carbonate (125 mg, 0.384 mmol, 1.5 eq.) and $PdOAc_2$ (5.7 mg, 0.026 mmol, 0.1 eq.). The formed reaction mixture was stirred at 100° C. for 16 hours. The reaction mixture was filtered over a celite plug eluting with $CH_2Cl_2$. The filtrate was concentrated and purified by column chromatography with method 'flash' ($CH_2Cl_2$/EtOAc=1: 0→6:4). The impure product was further purified by prep basic to obtain the title compound (37 mg, 0.077 mmol, yield: 30%) after lyophilization as a white solid.

Yield: Compound 114 was isolated as a white solid (29% over 3 steps).

Analysis: LCMS (Method R): $t_R$=1.47 min; m/z calculated for $[M+H]^+$=478.1. found=478.2; 1H NMR (400 MHz, DMSO) δ 10.49 (s, 1H), 8.05-7.82 (m, 2H), 7.27 (d, J=2.3 Hz, 1H), 7.20 (dd, J=8.8, 2.3 Hz, 1H), 6.88 (s, 1H), 4.08-3.86 (m, 3H), 3.07 (s, 3H), 2.93 (s, 3H), 2.47 (s, 3H), 1.31 (d, J=6.8 Hz, 6H).

Example 26

Synthesis of Compound 115

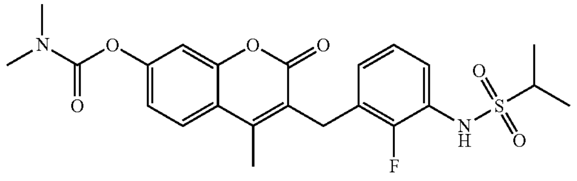 [SMILES: Cc1c(Cc2cccc(NS(=O)(=O)C(C)C)c2F)c(=O)oc2cc(OC(=O)N(C)C)ccc12]

Compound 115 was prepared in 1 step:

Step 1: Starting with 3-(3-amino-2-fluorobenzyl)-4-methyl-2-oxo-2H-chromen-7-yl dimethylcarbamate (0.1 g, 0.27 mmol) and 2-Propanesulfonyl chloride, following the general synthesis of Compound E.3. Reaction time was 3 days and the product was purified by column chromatography with method 'flash' ($CH_2Cl_2$/EtOAc=1:0→6:4). to obtain the title compound (35.8 mg, 0.074 mmol, yield: 27%) as a white solid.

Yield: Compound 115 was isolated as a white solid (27% over 1 step).

Analysis: LCMS (Method R): $t_R$=1.62 min; m/z calculated for $[M+H]^+$=477.1. found=477.2; 1H NMR (400 MHz, DMSO) δ 9.58 (s, 1H), 7.86 (d, J=8.8 Hz, 1H), 7.31-7.22 (m, 2H), 7.19 (dd, J=8.8, 2.3 Hz, 1H), 7.02 (t, J=7.9 Hz, 1H), 6.97-6.88 (m, 1H), 3.98 (s, 2H), 3.22 (p, J=6.8 Hz, 1H), 3.07 (s, 3H), 2.93 (s, 3H), 2.45 (s, 3H), 1.27 (d, J=6.8 Hz, 6H)

Example 27

Synthesis of Compound 116

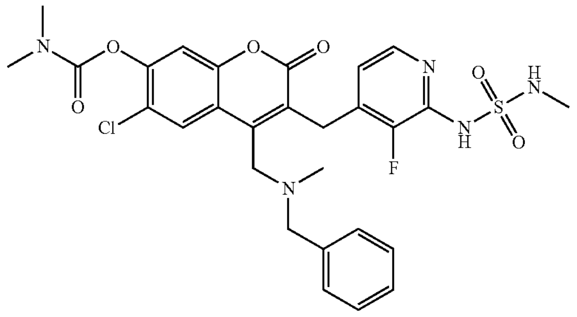

Compound 116 was prepared in 1 step:

Step 1: Starting with 4-(bromomethyl)-6-chloro-3-(2-fluoro-3-((N-methylsulfamoyl)amino)benzyl)-2-oxo-2H-chromen-7-yl dimethylcarbamate (45 mg, 0.075 mmol, py:40%) and N-Methylbenzylamine, following the general synthesis of Compound E.2, with addition of $Net_3$ 3.0 eq. The product was purified by prep basic to obtain the title compound (12.8 mg, 0.021 mmol, y: 66%) after freeze drying as a white solid.

Yield: Compound 116 was isolated as a white solid (66% over 1 step).

Analysis: LCMS (Method T): $t_R$=1.98 min; m/z calculated for $[M+H]^+$=617.2/619.2. found=617.4/619.4; 1H NMR (400 MHz, DMSO) δ 9.41 (s, 1H), 8.25 (s, 1H), 7.47 (s, 1H), 7.37-7.21 (m, 6H), 7.15 (s, 1H), 6.97 (t, J=7.9 Hz, 1H), 6.80 (t, J=7.2 Hz, 1H), 4.05 (s, 2H), 3.76 (s, 2H), 3.56 (s, 2H), 3.11 (s, 3H), 2.95 (s, 3H), 2.52 (d, J=4.0 Hz, 3H), 2.06 (s, 3H).

Example 28

Synthesis of Compound 117

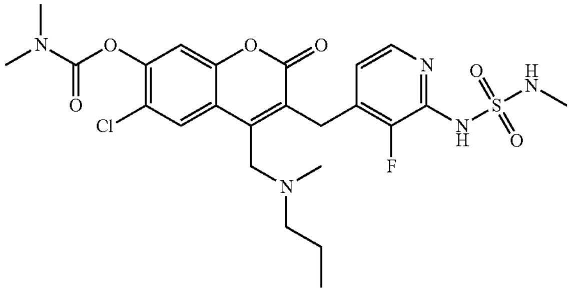

Compound 117 was prepared in 1 step:

Step 1: Starting with 4-(bromomethyl)-6-chloro-3-(2-fluoro-3-((N-methylsulfamoyl)amino)benzyl)-2-oxo-2H-chromen-7-yl dimethylcarbamate (45 mg, 0.075 mmol, py:40%) and N-Methylpropylamine, following the general synthesis of Compound E.2, with addition of $Net_3$ 3.0 eq. The product was purified by prep basic followed by prep acid to obtain the title compound (3.8 mg, 0.007 mmol, y: 21%) after freeze drying as a white solid.

Yield: Compound 117 was isolated as a white solid (21% over 1 step).

Analysis: LCMS (Method T): $t_R$=1.94 min; m/z calculated for $[M+H]^+$=569.2/571.2. found=569.4/571.4; 1H NMR (400 MHz, DMSO) δ 9.41 (s, 1H), 8.29 (s, 1H), 7.48 (s, 1H), 7.28 (t, J=7.7 Hz, 1H), 7.15 (s, 1H), 6.98 (t, J=7.9 Hz, 1H), 6.81 (t, J=7.2 Hz, 1H), 4.04 (s, 2H), 3.71 (s, 2H), 3.10 (s, 3H), 2.95 (s, 3H), 2.52 (s, 3H), 2.35 (t, J=7.0 Hz, 2H), 2.06 (s, 3H), 1.44 (h, J=7.3 Hz, 2H), 0.82 (t, J=7.3 Hz, 3H).

Example 29

Synthesis of Compound 118

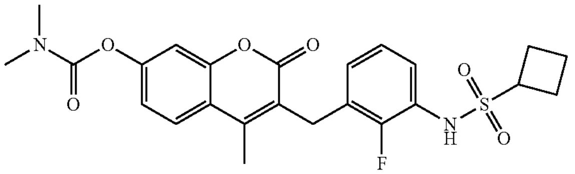 [SMILES: Cc1c(Cc2cccc(NS(=O)(=O)C3CCC3)c2F)c(=O)oc2cc(OC(=O)N(C)C)ccc12]

Compound 117 was prepared in 1 step:

Step 1: Starting with 3-(3-amino-2-fluorobenzyl)-4-methyl-2-oxo-2H-chromen-7-yl dimethylcarbamate (0.1 g, 0.27 mmol) and cyclobutanesulfonyl chloride, following the general synthesis of Compound E.3. Reaction mixture was purified with method 'prep base' to obtain the title compound (8.0 mg, 0.016 mmol, yield: 6%) after lyophilization as a white solid.

Yield: Compound 117 was isolated as a white solid (6% over 1 step).

Analysis: LCMS (Method R): $t_R$=1.65 min; m/z calculated for $[M+H]^+$=489.1. found=489.4; 1H NMR (400 MHz, DMSO) δ 9.51 (s, 1H), 7.86 (d, J=8.8 Hz, 1H), 7.28-7.15 (m, 3H), 7.06-6.88 (m, 2H), 3.98 (s, 2H), 3.90 (p, J=8.2 Hz, 1H), 3.07 (s, 3H), 2.93 (s, 3H), 2.45 (s, 3H), 2.36-2.13 (m, 4H), 1.97-1.80 (m, 2H).

Example 30

Synthesis of Compound 119

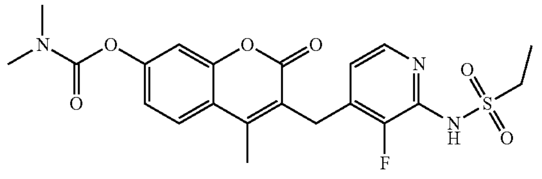 [SMILES: CCS(=O)(=O)Nc1nccc(Cc2c(C)c3ccc(OC(=O)N(C)C)cc3oc2=O)c1F]

Compound 119 was prepared in 1 step:

Step 1: Starting with 3-((2-amino-3-fluoropyridin-4-yl)methyl)-4-methyl-2-oxo-2H-chromen-7-yl dimethylcarbamate (0.05 g, 0.135 mmol) and Ethanesulfonyl chloride, following the general synthesis of Compound E.3. Reaction mixture was purified with method 'prep base' to obtain the title compound (3.6 mg, 0.007 mmol, yield: 6%) after lyophilization as a white solid.

Yield: Compound 119 was isolated as a white solid (6% over 1 step).

Analysis: LCMS (Method R): $t_R$=1.42 min; m/z calculated for $[M+H]^+$=464.1. found=464.2; 1H NMR (400 MHz, DMSO) δ 10.54 (s, 1H), 8.01-7.80 (m, 2H), 7.27 (d, J=2.3 Hz, 1H), 7.20 (dd, J=8.8, 2.4 Hz, 1H), 6.88 (s, 1H), 4.02 (s, 2H), 3.63-3.42 (m, 2H), 3.07 (s, 3H), 2.93 (s, 3H), 2.47 (s, 3H), 1.26 (t, J=7.4 Hz, 3H).

Example 31

Synthesis of Compound 120

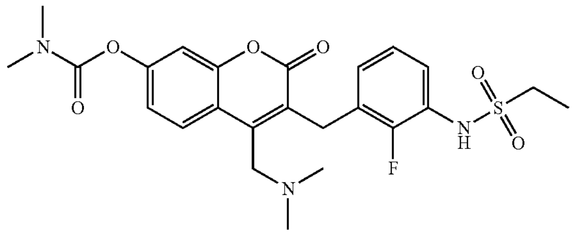 [SMILES: CCS(=O)(=O)Nc1cccc(Cc2c(CN(C)C)c3ccc(OC(=O)N(C)C)cc3oc2=O)c1F]

Compound 120 was prepared in 3 steps:

Step 1: Starting with 3-(3-amino-2-fluorobenzyl)-4-methyl-2-oxo-2H-chromen-7-yl dimethylcarbamate (0.516 g, 1.115 mmol) and ethanesulfonyl chloride, following the general synthesis of Compound E.3 to obtain the sulfamoyl (320 mg, 0.678 mmol, yield: 61%) as a white solid.

Step 2: Following the procedure of the general synthesis of Compound E.4 using NBS. After extraction the impure product was purified by column chromatography with method 'flash' (heptane/EtOAc=1:0→0:1) to obtain the corresponding bromine compound (324 mg, 0.53 mmol, yield: 79%, purity: 89%) as a white solid.

Step 3: Following the procedure of the general synthesis of Compound E.5 starting with 10 mg, 0.016 mmol of the bromine compound and dimethylamine 2M in MeOH. The impure product was purified by prep basic followed by SFC CEL-2 gradient to obtain the title compound (2.8 mg, 0.005 mmol, yield: 33%) as a white solid.

Yield: Compound 120 was isolated as a white solid (16% over 3 steps).

Analysis: LCMS (Method T): $t_R$=1.61 min; m/z calculated for $[M+H]^+$=506.2. found=506.4; 1H NMR (400 MHz, $CDCl_3$) δ 8.01 (d, J=8.8 Hz, 1H), 7.44 (td, J=7.7, 1.2 Hz, 1H), 7.14-7.05 (m, 2H), 7.01 (t, J=7.9 Hz, 1H), 6.90 (t, J=7.2 Hz, 1H), 6.49-6.43 (m, 1H), 4.16 (s, 2H), 3.60 (s, 2H), 3.16 (q, J=7.4 Hz, 3H), 3.13 (s, 2H), 3.04 (s, 3H), 2.27 (s, 6H), 1.40 (t, J=7.4 Hz, 3H).

Example 32

Synthesis of Compound 121

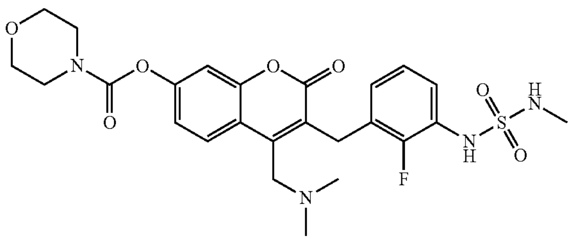 [SMILES: CNS(=O)(=O)Nc1cccc(Cc2c(CN(C)C)c3ccc(OC(=O)N4CCOCC4)cc3oc2=O)c1F]

Compound 121 was prepared in 1 step:

Step 1: Starting with phenol (20 mg, 0.046 mmol) and 4-Morpholinecarbonyl chloride, following the general synthesis of Compound F.2. Purification with method 'prep base' to obtain the title compound (16 mg, 0.029 mmol, yield: 64%) as a white solid after lyophilization.

Yield: Compound 121 was isolated as a white solid (64% over 1 step).

Analysis: LCMS (Method P): $t_R$=1.39 min; m/z calculated for $[M+H]^+$=549.2. found=549.1; 1H NMR (400 MHz, $CDCl_3$) δ 8.03 (d, J=8.8 Hz, 1H), 7.39 (td, J=7.9, 1.6 Hz, 1H), 7.14-7.05 (m, 2H), 7.00 (td, J=8.0, 1.2 Hz, 1H), 6.92-6.84 (m, 1H), 6.61 (d, J=3.2 Hz, 1H), 4.43 (t, J=5.3 Hz, 1H), 4.15 (s, 2H), 3.77 (dd, J=5.5, 4.0 Hz, 4H), 3.70 (d, J=7.4 Hz, 2H), 3.60 (d, J=12.2 Hz, 4H), 2.76 (d, J=5.3 Hz, 3H), 2.28 (s, 6H).

Example 33

Synthesis of Compound 122

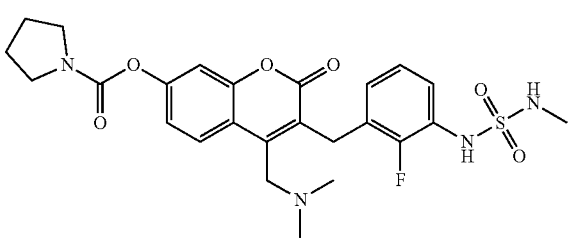 [SMILES: CNS(=O)(=O)Nc1cccc(Cc2c(CN(C)C)c3ccc(OC(=O)N4CCCC4)cc3oc2=O)c1F]

Compound 122 was prepared in 1 step:

Step 1: Starting with phenol (20 mg, 0.046 mmol) and 4-Morpholinecarbonyl chloride, following the general synthesis of Compound F.2. Purification with method 'prep base' to obtain the title compound (16 mg, 0.029 mmol, yield: 64%) as a white solid after lyophilization.

Yield: Compound 122 was isolated as a white solid (64% over 1 step).

Analysis: LCMS (Method P): $t_R$=1.39 min; m/z calculated for $[M+H]^+$=549.2. found=549.1; 1H NMR (400 MHz, $CDCl_3$) δ 8.03 (d, J=8.8 Hz, 1H), 7.39 (td, J=7.9, 1.6 Hz, 1H), 7.14-7.05 (m, 2H), 7.00 (td, J=8.0, 1.2 Hz, 1H), 6.92-6.84 (m, 1H), 6.61 (d, J=3.2 Hz, 1H), 4.43 (t, J=5.3 Hz, 1H), 4.15 (s, 2H), 3.77 (dd, J=5.5, 4.0 Hz, 4H), 3.70 (d, J=7.4 Hz, 2H), 3.60 (d, J=12.2 Hz, 4H), 2.76 (d, J=5.3 Hz, 3H), 2.28 (s, 6H).

Example 34

Synthesis of Compound 123

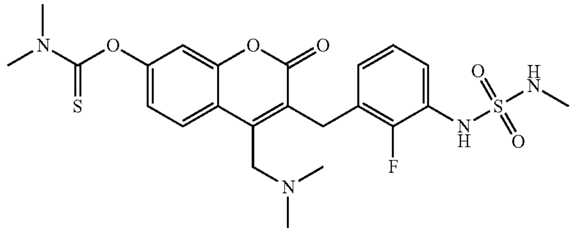

Compound 123 was prepared in 1 step.

Step 1: Starting at general synthesis step D.4 (155 mg, 0.356 mmol) was dissolved in MeCN (1.8 mL) and DMAP (130 mg, 1.07 mmol, 3 eq) and dimethylthiocarbamoyl chloride (66 mg, 0.53 mmol, 1.5 eq) were added. This mixture was stirred overnight at rt and for 4 h at 40° C. The reaction as such was purified with method "prep acid" to give the title compound (163 mg, 0.31 mmol, yield: 86%) as a white solid after lyophilzation.

Analysis: LCMS (Method R): $t_R$=0.951 min; m/z calculated for $[M-H]^+$=523.2. found=523.4; 1H NMR (400 MHz, DMSO) δ 9.38 (s, 1H), 8.08 (d, J=8.9 Hz, 1H), 7.33-7.16 (m, 3H), 7.11 (dd, J=8.8, 2.4 Hz, 1H), 7.00 (t, J=7.9 Hz, 1H), 6.84 (t, J=7.1 Hz, 1H), 4.05 (s, 2H), 3.65 (s, 2H), 3.41-3.30 (m, 6H), 2.55-2.52 (m, 3H), 2.20 (s, 6H).

Example 35

Synthesis of Compound 124

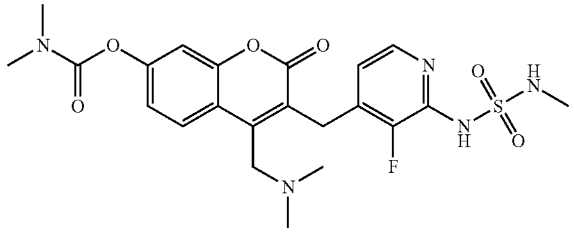

Compound 124 was prepared in 1 step:

Step 1: Starting with 4-(chloromethyl)-3-((3-fluoro-2-((N-methylsulfamoyl)amino)pyridin-4-yl)methyl)-2-oxo-2H-chromen-7-yl dimethylcarbamate (390 mg g, 0.391 mmol, purity: 50%) and dimethylamine 2M in MeOH, following the general synthesis of Compound E.2. The product was purified with method "prep acid" to obtain the title compound (80 g, 0.155 mmol, yield: 40%) as an off white solid after lyophilization.

Yield: Compound 124 was isolated as an off white solid (40% over 1 step).

Analysis: LCMS (Method R): $t_R$=0.80 min; m/z calculated for $[M-H]^+$=508.2. found=508.4; 1H NMR (400 MHz, DMSO) δ 10.34 (s, 1H), 8.09 (d, J=8.9 Hz, 1H), 7.90 (d, J=5.1 Hz, 1H), 7.24 (d, J=2.3 Hz, 1H), 7.16 (dd, J=8.8, 2.4 Hz, 1H), 6.96 (s, 1H), 6.79 (t, J=5.1 Hz, 1H), 4.07 (s, 2H), 3.66 (s, 2H), 3.07 (s, 3H), 2.93 (s, 3H), 2.20 (s, 6H).

Example 36

Synthesis of Compound 125

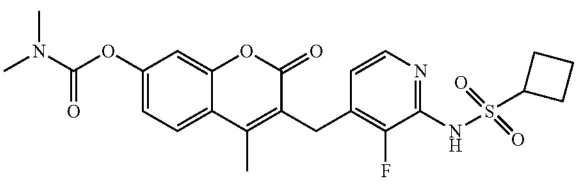 [SMILES: Cc1c(Cc2ccnc(NS(=O)(=O)C3CCC3)c2F)c(=O)oc2cc(OC(=O)N(C)C)ccc12]

Compound 125 was prepared in 3 step:

Step 1: Starting from ethyl 2-((2-chloro-3-fluoropyridin-4-yl)methyl)-3-oxobutanoate (10.0 g, 24.12 mmol) and resorcinol (2.00 eq.) following the general synthesis of Compound D.4. Instead of perchloric acid, sulfuric acid was used. After complete conversion the reaction mixture was cooled (0° C.) and quenched with sat. aq. $NaHCO_3$ till basic pH. The formed white suspension was washed with water, $Et_2O$ and dried to obtain the corresponding coumarin (8.61 g, 23.4 mmol, yield: 97%, purity: 87%) as an off white solid.

Step 2: Following the procedure of the general synthesis of Compound D.5 to obtain the corresponding dimethylcarbamate (9.33 g, 23.16 mmol, yield: 99%) as a beige solid.

Step 3: To an solution of dimethylcarbamate (200 mg, 0.512 mmol, 1.0 eq.) and cyclobutanesulfonamide (104 mg, 0.768 mmol, 1.5 eq.) in 1,4-Dioxane (extra dry) (0.1 M) under $N_2$ atmosphere were added Xantphos (59.2 mg, 0.102 mmol, 0.2 eq.), cesium carbonate (250 mg, 0.768 mmol, 1.5 eq.) and PdOAc2 (11.5 mg, 0.051 mmol, 0.1 eq.). The formed reaction mixture was stirred at 100° C. for 16 hours. The reaction mixture was filtered over a celite plug eluting with $CH_2Cl_2$. The filtrate was concentrated and purified by prep basic to obtain the title compound (53 mg, 0.107 mmol, yield: 21%) after lyophilization as a white solid.

Yield: Compound 125 was isolated as a white solid (20% over 3 steps).

Analysis: LCMS (Method L): $t_R$=3.71 min; m/z calculated for $[M+H]^+$=490.2. found=490.1; 1H NMR (400 MHz, DMSO) δ 10.53 (bs, 1H), 8.00-7.79 (m, 2H), 7.26 (d, J=2.3 Hz, 1H), 7.20 (dd, J=8.7, 2.3 Hz, 1H), 6.84 (s, 1H), 4.50 (bs, 1H), 4.00 (s, 2H), 3.07 (s, 3H), 2.93 (s, 3H), 2.48-2.34 (m, 5H), 2.29-2.17 (m, 2H), 2.01-1.83 (m, 2H).

Example 37

Synthesis of Compound 126

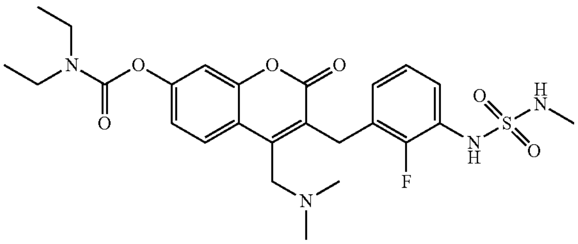 [SMILES: CCN(CC)C(=O)Oc1ccc2c(CN(C)C)c(Cc3cccc(NS(=O)(=O)NC)c3F)c(=O)oc2c1]

Compound 125 was prepared in 1 step:

Step 1: Starting with phenol (20 mg, 0.046 mmol) and diethylcarbamyl chloride, following the general synthesis of Compound F.2. Purification with method 'prep base' to obtain the title compound (9.7 mg, 0.018 mmol, yield: 39%) as a white solid after lyophilization.

Yield: Compound 125 was isolated as a white solid (39% over 1 step)

Analysis: LCMS (Method P): $t_R$=1.65 min; m/z calculated for $[M+H]^+$=535.2. found=535.1; no HNMR, compound was made in library.

Example 38

Synthesis of Compound 127

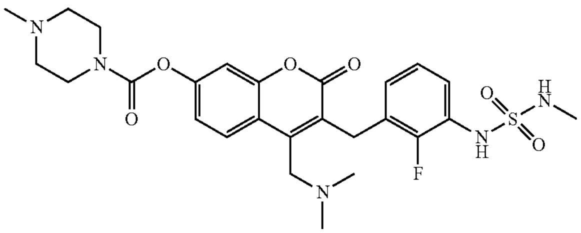

Compound 126 was prepared in 1 step:

Step 1: Starting with phenol (20 mg, 0.046 mmol) and 4-Methyl-1-piperazinecarbonyl chloride, following the general synthesis of Compound F.2. Purification with method 'prep base' to obtain the title compound (17.8 mg, 0.032 mmol, yield: 70%) as a white solid after lyophilization.

Yield: Compound 126 was isolated as a white solid (70% over 1 step).

Analysis: LCMS (Method P): $t_R$=1.33 min; m/z calculated for $[M+H]^+$=562.2. found=562.1; no HNMR, compound was made in library.

Example 39

Synthesis of Compound 128

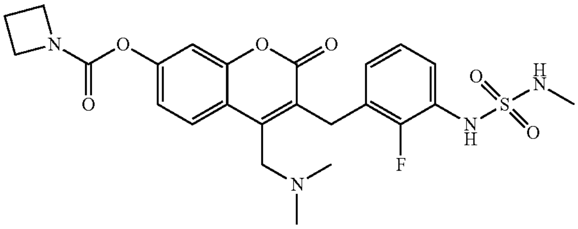 [SMILES: CNS(=O)(=O)Nc1cccc(Cc2c(CN(C)C)c3ccc(OC(=O)N4CCC4)cc3oc2=O)c1F]

Compound 128 was prepared in 1 step:

Step 1: Starting with phenol (50 mg, 0.115 mmol) and azetidine-1-carbonyl chloride, following the general synthesis of Compound F.2, DMAP (0.6 eq.) and $Et_3N$ (1.1 eq.) were added and the reaction was performed in $CH_2Cl_2$ (0.11 M). After full conversion the reaction mixture was concentrated and water was added to the residue. The product was extracted with $CH_2Cl_2$. Combined organic layers were washed with brine, dried over $Na_2SO_4$, filtered and concentrated under reduced pressure. The impure product was purified with method 'prep base' to obtain the title compound (6 mg, 0.012 mmol, yield: 10%) as a white solid after lyophilization.

Yield: Compound 128 was isolated as a white solid (10% over 1 step).

Analysis: LCMS (Method T): $t_R$=1.44 min; m/z calculated for $[M+H]^+$=519.2. found=519.1; 1H NMR (400 MHz, $CDCl_3$) δ 8.00 (d, J=8.8 Hz, 1H), 7.39 (td, J=7.9, 1.6 Hz, 1H), 7.15-7.05 (m, 2H), 7.03-6.96 (m, 1H), 6.90-6.83 (m, 1H), 6.61 (s, 1H), 4.44 (q, J=5.4 Hz, 1H), 4.25 (s, 2H), 4.15 (s, 4H), 3.59 (s, 2H), 2.75 (d, J=5.3 Hz, 3H), 2.36 (p, J=7.7 Hz, 2H), 2.27 (s, 6H).

Example 40

Synthesis of Compound 129

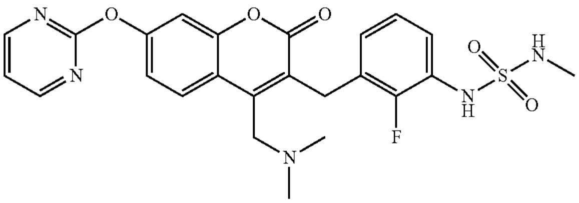 [SMILES: CNS(=O)(=O)Nc1cccc(Cc2c(CN(C)C)c3ccc(Oc4ncccn4)cc3oc2=O)c1F]

Compound 129 was prepared in 1 step:

Step 1: To a solution of Phenol derivate (50 mg, 0,115 mmol, 1.0 eq.) and 2-Bromopyrimidine (30 mg, 0.19 mmol, 1.6 eq.) in N,N-Dimethylformamide (dry) (2 ml) was added potassium carbonate (26 mg, 0.19 mmol, 1.6 eq.) The formed reaction mixture was stirred for 5 hours at 80° C. Water was added and the product was extracted with EtOAc. Combined organic layers were washed with brine, dried over $Na_2SO_4$, filtered and concentrated under reduced pressure. The impure product was purified with method 'prep base' to obtain the title compound (8.0 mg, 0.016 mmol, yield: 14%) as a white solid after lyophilization.

Yield: The title compound was isolated as a white solid (14% over 1 step).

Analysis: LCMS (Method T): $t_R$=1.34 min; m/z calculated for $[M+H]^+$=514.2. found=514.1; 1H NMR (400 MHz, $CDCl_3$) δ 8.60 (d, J=4.7 Hz, 2H), 8.11 (d, J=8.8 Hz, 1H), 7.40 (td, J=7.8, 1.6 Hz, 1H), 7.22 (d, J=2.4 Hz, 1H), 7.17 (dd, J=8.8, 2.4 Hz, 1H), 7.12 (t, J=4.8 Hz, 1H), 7.01 (t, J=8.0 Hz, 1H), 6.91-6.81 (m, 1H), 6.61 (s, 1H), 4.43 (q, J=5.4 Hz, 1H), 4.17 (s, 2H), 3.62 (s, 2H), 2.77 (d, J=5.2 Hz, 3H), 2.29 (s, 6H).

Example 41

Synthesis of Compound 130

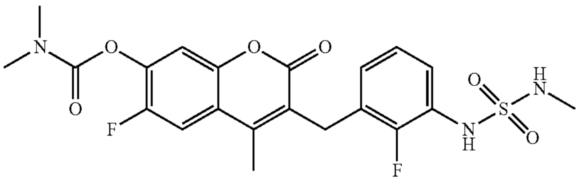

Compound 130 was prepared in 4 steps:

Step 1: Starting from ethyl 2-(2-fluoro-3-nitrobenzyl)-3-oxobutanoate (2.0 g, 7.06 mmol) and 4-fluorobenzene-1,3-diol (1.20 eq.) following the general synthesis of Compound 4 to obtain the corresponding coumarin compound (2.85 g, 8.13 mmol, yield: 115%) as an off white solid.

Step 2: Following the procedure of the general synthesis of Compound 5. With a reaction time of 2.5 days, to obtain the corresponding dimethylcarbamate (2.28 g, 5.01 mmol, purity: 92%, yield: 61%) as a beige solid.

Step 3: Following the procedure of the general synthesis of Compound 6 to obtain the corresponding primary amine (1.28 g, 3.11 mmol, yield: 57%) as a light yellow solid.

Step 4: Following the procedure of the general synthesis of Compound 7. After filtration the impure product was purified by flash column chromatography ($CH_2Cl_2$/MeOH=1:0→97:3) to obtain the title compound (1.043 g, 2.15 mmol, yield: 65%) as an off white solid.

Yield: Compound 130 was isolated as an off white solid (26% over 4 steps).

Analysis: LCMS (Method R): $t_R$=1.55 min; m/z calculated for $[M-H]^+$=480.1. found=480.2; 1H NMR (400 MHz, DMSO) δ 9.37 (s, 1H), 7.86 (d, J=11.2 Hz, 1H), 7.49 (d, J=6.8 Hz, 1H), 7.28 (td, J=7.8, 1.6 Hz, 1H), 7.21 (q, J=5.1 Hz, 1H), 7.01 (t, J=7.9 Hz, 1H), 6.91-6.83 (m, 1H), 3.98 (s, 2H), 3.08 (s, 3H), 2.94 (s, 3H), 2.53 (s, 3H), 2.43 (s, 3H).

Example 42

Synthesis of Compound 131

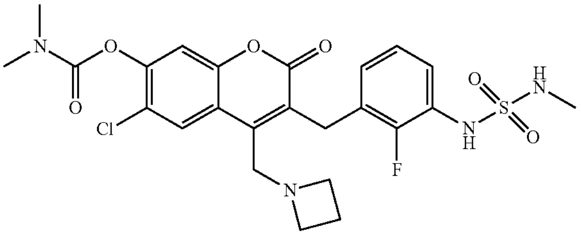

Compound 131 was prepared in 1 step:

Step 1: Starting with 6-chloro-4-(chloromethyl)-3-(2-fluoro-3-((N-methylsulfamoyl)amino)benzyl)-2-oxo-2H-chromen-7-yl dimethylcarbamate (20 mg, 0.038 mmol) and azetidine, following procedure the general synthesis of Compound E.2, with addition of potassium carbonate 3.0 eq. The impure product was combined with other batches and purified by prep basic to obtain the title compound (44 mg, 0.076 mmol, yield: 65%) after freeze drying as a white solid.

Yield: The title compound was isolated as a white solid (65% over 1 step)

Analysis: LCMS (Method R): $t_R$=0.95 min; m/z calculated for $[M+H]^+$=553.1. found=553.2; 1H NMR (400 MHz, DMSO) δ 9.39 (s, 1H), 8.20 (s, 1H), 7.48 (s, 1H), 7.33-7.19 (m, 2H), 7.00 (t, J=8.0 Hz, 1H), 6.81 (t, J=7.1 Hz, 1H), 4.09 (s, 2H), 3.82 (s, 2H), 3.16 (t, J=6.9 Hz, 4H), 3.10 (s, 3H), 2.95 (s, 3H), 2.53 (d, J=4.8 Hz, 3H), 1.91 (p, J=7.0 Hz, 2H).

Example 43

Synthesis of Compound 132

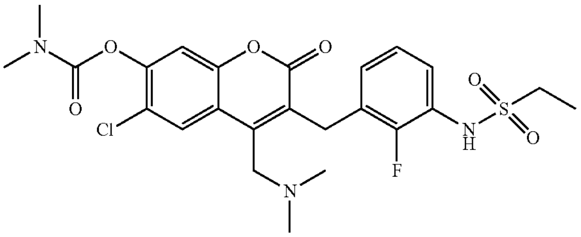 [SMILES: CCS(=O)(=O)Nc1cccc(Cc2c(CN(C)C)c3cc(Cl)c(OC(=O)N(C)C)cc3oc2=O)c1F]

Compound 132 was prepared in 3 steps:

Step 1: Starting with 3-(3-amino-2-fluorobenzyl)-6-chloro-4-methyl-2-oxo-2H-chromen-7-yl dimethylcarbamate (0.320 g, 0.585 mmol) and ethanesulfonyl chloride, following the general synthesis of Compound E.3. During work-up the reaction mixture was combined with another batch to obtain the sulfamoyl (350 mg, 0.704 mmol, yield: 92%) as a white solid.

Step 2: Following the procedure of the general synthesis of Compound E.4 using NBS. After extraction the impure product was purified by column chromatography with method 'flash' (heptane/EtOAc=1:0→0:1) followed by prep acid to obtain the corresponding bromine (65 mg, 0.113 mmol, yield: 19%) as a beige solid.

Step 3: Following the procedure of the general synthesis of Compound E.5 using dimethylamine 2M in MeOH. The reaction mixture was quenched with water and the product was extracted with $CH_2Cl_2$. Combined organic layers were dried over $Na_2SO_4$, filtered and concentrated under reduced pressure. The residue was purified by prep acid to obtain the title compound (39 mg, 0.073 mmol, yield: 65%) as a white solid after lyophilization.

Yield: Compound 132 was isolated as a white solid (11% over 3 steps).

Analysis: LCMS (Method V): $t_R$=3.92 min; m/z calculated for $[M+H]^+$=540.1/542.1. found=540.1/542.1; 1H NMR (400 MHz, DMSO) δ 9.67 (s, 1H), 8.21 (s, 1H), 7.48 (s, 1H), 7.25 (td, J=7.8, 1.7 Hz, 1H), 7.03 (t, J=7.8 Hz, 1H), 6.98-6.88 (m, 1H), 4.05 (s, 2H), 3.66 (s, 2H), 3.14-3.07 (m, 5H), 2.95 (s, 3H), 2.18 (s, 6H), 1.26 (t, J=7.3 Hz, 3H).

Example 44

Synthesis of Compound 133

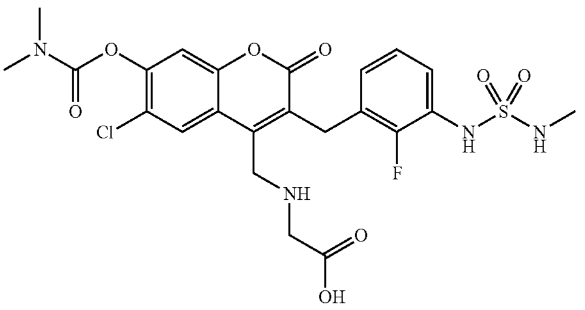

Compound 133 was prepared analogously to compound 225 with the chloride instead of the bromide.

Step-1: 6-chloro-4-(chloromethyl)-3-(2-fluoro-3-((N-methylsulfamoyl)amino)benzyl)-2-oxo-2H-chromen-7-yl dimethylcarbamate (300 mg, 0.564 mmol) and triethylamine (236 uL, 1.69 mmol, 3 eq) was stirred at 40° C. in DCM (7 mL) and tert-butyl glycinate (308 uL, 2.25 mmol, 4 eq) was added. The next day, water was added and the product was extracted with DCM (2×). The combined extract was dried over brine and sodium sulfate and evaporated. The residue was redissolved in 1 mL of DCM and purified by column chromatography with method 'prep base' to obtain the intermediate tert-butylester (126 mg, 0.20 mmol, yield: 35%).

Step-2: The intermediate of the previous step (126 mg, 0.20 mmol) was stirred in 2 mL of DCM and 2 mL of 4 N HCl in dioxane (58 mmol, 287 eq). The next day, the volatiles were evaporated and the residue was stripped with DCM and the crude product was redissolved in MeCN and purifined with method 'prep base' to give the title compound (94 mg, 0.16 mmol, yield: 81%) as an off-white solid.

Example 45

Synthesis of Compound 134

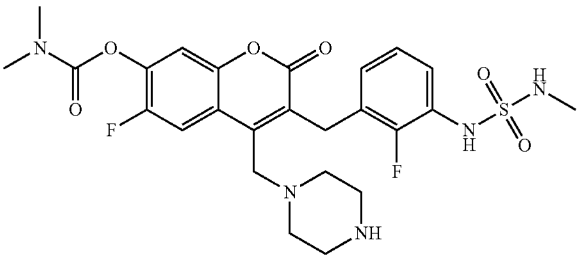

Compound 134 was prepared in 1 step:

Step 1: Starting with 4-(chloromethyl)-6-fluoro-3-(2-fluoro-3-((N-methylsulfamoyl)amino)benzyl)-2-oxo-2H-chromen-7-yl dimethylcarbamate (30 mg, 0.058 mmol) and piperazine, following the general synthesis of Compound E.2. With the addition of $Et_3N$ 3.0 eq. The impure product was purified by prep basic to obtain the title compound (17.3 mg, 0.029 mmol, yield: 51%) after freeze drying as a white solid.

Yield: Compound 134 was isolated as a white solid (51% over 1 step)

Analysis: LCMS (Method T): $t_R$=1.39 min; m/z calculated for $[M+H]^+$=566.2. found=566.4; 1H NMR (400 MHz, DMSO) δ 8.04 (d, J=11.8 Hz, 1H), 7.47 (d, J=6.9 Hz, 1H), 7.28 (td, J=7.9, 1.7 Hz, 1H), 7.24-7.12 (m, 1H), 6.99 (t, J=7.9 Hz, 1H), 6.82 (t, J=7.1 Hz, 1H), 4.03 (s, 2H), 3.66 (s, 2H), 3.08 (s, 3H), 2.94 (s, 3H), 2.63-2.55 (m, 4H), 2.55-2.52 (m, 3H), 2.41-2.28 (m, 4H).

Example 46

Synthesis of Compound 135

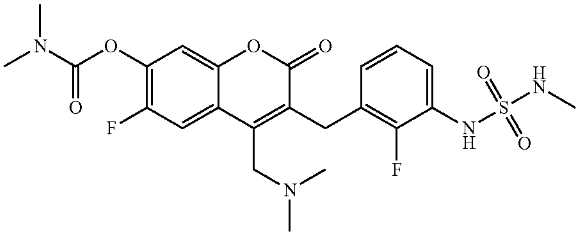

Compound 135 was prepared in 1 step:

Step 1: Starting with 4-(chloromethyl)-6-fluoro-3-(2-fluoro-3-((N-methylsulfamoyl)amino)benzyl)-2-oxo-2H-chromen-7-yl dimethylcarbamate (50 mg, 0.097 mmol) and dimethylamine 2M in MeOH, following the general synthesis of Compound E.2. The product was combined with another batch and purified by prep basic to obtain the title compound (9.1 mg, 0.017 mmol, yield: 18%) after freeze drying as a white solid.

Yield: The title compound was isolated as a white solid (18% over 1 step).

Analysis: LCMS (Method T): $t_R$=1.63 min; m/z calculated for $[M+H]^+$=525.2. found=525.2; 1H NMR (400 MHz, DMSO) δ 9.38 (s, 1H), 8.00 (d, J=11.7 Hz, 1H), 7.46 (d, J=6.9 Hz, 1H), 7.32-7.25 (m, 1H), 7.18 (s, 1H), 6.99 (t, J=7.9 Hz, 1H), 6.82 (t, J=7.2 Hz, 1H), 4.04 (s, 2H), 3.63 (s, 2H), 3.08 (s, 3H), 2.94 (s, 3H), 2.54-2.51 (m, 3H), 2.18 (s, 6H).

Example 47

Synthesis of Compound 136

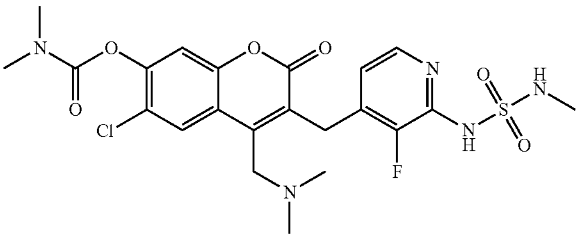

Compound 136 was prepared in 1 step:

Step 1: Starting with 4-(bromomethyl)-6-chloro-3-((3-fluoro-2-((N-methylsulfamoyl)amino)pyridin-4-yl)methyl)-2-oxo-2H-chromen-7-yl dimethylcarbamate (151 mg, 0.055 mmol, purity: 21%) and dimethylamine 2M in MeOH (109 eq.), following the general synthesis of Compound E.2. The reaction was performed neat. The product was purified by prep acid to obtain the title compound (12 mg, 0.022 mmol, yield: 40%) after lyophilization as a light yellow solid.

Yield: Compound 136 was isolated as a light yellow solid (40% over 1 step)

Analysis: LCMS (Method V): $t_R$=2.96 min; m/z calculated for $[M+H]^+$=542.1. found=542.1; 1H NMR (400 MHz, DMSO) δ 8.22 (s, 1H), 7.89 (d, J=5.2 Hz, 1H), 7.50 (s, 1H), 6.78 (t, J=5.1 Hz, 1H), 4.07 (s, 2H), 3.67 (s, 2H), 3.10 (s, 3H), 2.95 (s, 3H), 2.51 (s, 3H), 2.20 (s, 6H).

Example 48

Synthesis of Compound 205

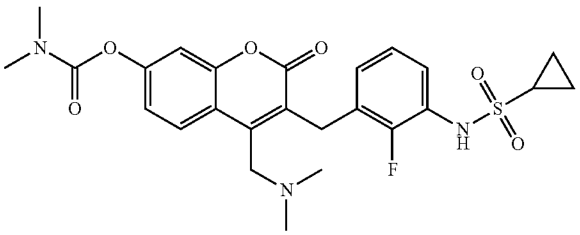 [SMILES: CN(C)Cc1c(Cc2cccc(NS(=O)(=O)C3CC3)c2F)c(=O)oc2cc(OC(=O)N(C)C)ccc12]

Compound 205 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method 'flash' ($CH_2Cl_2$/MeOH=1:0→9:1). The still impure product was purified by prep basic to obtain 3-((2-(ethylsulfonamido)-3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5 starting with 33 mg, 0.040 mmol of bromine and dimethylamine 2M in MeOH. The impure product was purified prep acid to obtain the title compound (8.4 mg, 0.016 mmol, yield: 40%) as a white solid.

Yield: Compound 205 was isolated as a white solid (1% over 3 steps).

Analysis: LCMS (Method L): $t_R$=2.32 min; m/z calculated for $[M+H]^+$=519.2. found=519.2; 1H NMR (400 MHz, DMSO-d6) δ 8.25 (s, 1H), 8.08 (d, J=8.9 Hz, 1H), 7.78 (s, 1H), 7.24 (d, J=2.3 Hz, 1H), 7.15 (dd, J=8.8, 2.4 Hz, 1H), 6.57 (s, 1H), 4.03 (s, 2H), 3.65 (s, 2H), 3.07 (s, 3H), 2.93 (s, 3H), 2.21 (s, 7H), 0.92 (d, J=41.0 Hz, 4H).

Example 49

Synthesis of Compound 137

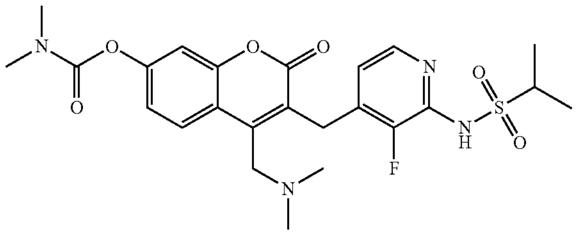 [SMILES: CC(C)S(=O)(=O)Nc1nccc(Cc2c(CN(C)C)c3ccc(OC(=O)N(C)C)cc3oc2=O)c1F]

Compound 137 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method 'flash' ($CH_2Cl_2$/MeOH=1:0→9:1). The still impure product was purified by prep basic to obtain 3-((2-(ethylsulfonamido)-

3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5 starting with 106 mg, 0.078 mmol of bromine and dimethylamine 2M in MeOH. The impure product was purified twice with prep acid to obtain the title compound (23 mg, 0.044 mmol, yield: 57%) as a white solid.

Yield: Compound 137 was isolated as a white solid (1% over 3 steps)

Analysis: LCMS (Method L): $t_R$=2.38 min; m/z calculated for $[M+H]^+$=521.2. found=521.2; 1H NMR (400 MHz, DMSO-d6) δ 8.09 (d, J=8.8 Hz, 1H), 7.87 (d, J=5.0 Hz, 1H), 7.24 (d, J=2.3 Hz, 1H), 7.16 (dd, J=8.7, 2.4 Hz, 1H), 6.76 (s, 1H), 4.06 (s, 2H), 3.91 (s, 1H), 3.66 (s, 2H), 3.07 (s, 3H), 2.93 (s, 3H), 2.54 (s, 1H), 2.20 (s, 6H), 1.29 (d, J=6.8 Hz, 6H).

Example 50

Synthesis of Compound 138

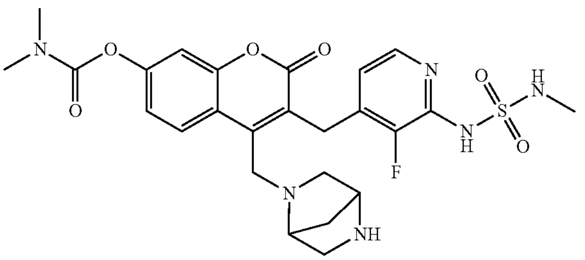

Compound 138 was prepared in 2 steps:

Step 1: Starting with 4-(bromomethyl)-3-(2-fluoro-3-((N-methylsulfamoyl)amino)benzyl)-2-oxo-2H-chromen-7-yl dimethylcarbamate (100 mg, 0.184 mmol) and tert-butyl 2,5-diazabicyclo[2.2.1]heptane-2-carboxylate, following the general synthesis of Compound E.2, with the exception that the reaction was performed in $CH_2Cl_2$ and $Et_3N$ (1.8 eq) was added. After full conversion water was added and the product was extracted with $CH_2Cl_2$. Combined organic layers were washed with brine, dried over $Na_2SO_4$, filtered and concentrated under reduced pressure. The impure product was purified by column chromatography with method 'flash' (heptane/EtOAc=1:0→1:9). Desired fractions were combined and concentrated under reduced pressure to obtain the Boc-amine (73 mg, 0.111 mmol, 120%) as a colorless oil.

Step 2: The Boc-amine was dissolved in $CH_2Cl_2$ (0.05 M) and TFA (341 μL, 4.43 mmol, 40 eq.) was added. The formed reaction mixture was stirred for 18 hours at rt. Water was added to the reaction mixture followed by some sat. aq. $Na_2CO_3$. The product was extracted with $CH_2Cl_2$. Combined organic layers were washed with brine, dried over $Na_2SO_4$, filtered and concentrated under reduced pressure. The impure product was purified by prep acid to obtain the title compound (25.4 mg, 0.045 mmol, yield: 40%) after lyophilization as a white solid.

Yield: Compound 138 was isolated as a white solid (83% over 2 steps).

Analysis: LCMS (Method T): $t_R$=1.28 min; m/z calculated for $[M+H]^+$=560.2. found=560.2; 1H NMR (400 MHz, $CDCl_3$) δ 8.49 (s, 1H), 7.94 (d, J=8.8 Hz, 1H), 7.33 (dd, J=8.3, 6.5 Hz, 1H), 7.14 (d, J=2.3 Hz, 1H), 7.08 (dd, J=8.9, 2.4 Hz, 1H), 6.99 (t, J=7.9 Hz, 1H), 6.92 (t, J=6.9 Hz, 1H), 4.22-4.08 (m, 2H), 4.06-3.94 (m, 2H), 3.85 (d, J=13.6 Hz, 1H), 3.26 (s, 1H), 3.13 (s, 3H), 3.03 (s, 3H), 2.93 (t, J=11.5 Hz, 2H), 2.87-2.79 (m, 2H), 2.77 (s, 3H), 1.88-1.73 (m, 2H).

Example 51

Synthesis of Compound 139

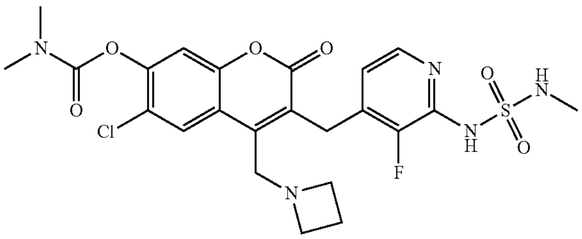

Compound 139 was prepared in 1 step:

Step 1: Starting with 6-chloro-4-(chloromethyl)-3-((3-fluoro-2-((N-methylsulfamoyl)amino)pyridin-4-yl)methyl)-2-oxo-2H-chromen-7-yl dimethylcarbamate (100 mg, 0.12 mmol, purity: 64%) and azetidine, following the general synthesis of Compound E.2. The reaction was performed in THF 0.12 M and with the addition of NaI 2.0 eq. The product was purified by prep acid followed by an purification on prep basic to obtain the title compound (6.5 mg, 0.011 mmol, yield: 9%) after lyophilization as a white solid.

Yield: Compound 139 was isolated as a white solid (9% over 1 step).

Analysis: LCMS (Method T): $t_R$=1.25 min; m/z calculated for $[M+H]^+$=554.1. found=554.2; 1H NMR (400 MHz, DMSO) δ 8.21 (s, 1H), 7.83 (s, 1H), 7.49 (s, 1H), 7.09-6.43 (m, 2H), 4.09 (s, 2H), 3.84 (s, 2H), 3.18 (t, J=6.9 Hz, 4H), 3.11 (s, 3H), 2.95 (s, 3H), 2.47 (s, 3H), 1.91 (p, J=6.8 Hz, 2H).

Example 52

Synthesis of Compound 140

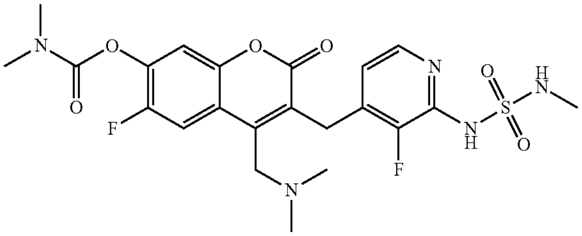

Compound 140 was prepared in 1 step:

Step 1: Starting with 4-(bromomethyl)-6-fluoro-3-((3-fluoro-2-((N-methylsulfamoyl)amino)pyridin-4-yl) methyl)-2-oxo-2H-chromen-7-yl dimethylcarbamate (50 mg, 0.050 mmol, purity: 56%) and dimethylamine 2M in MeOH, following the general synthesis of Compound E.2. The reaction was performed in THF instead of MeOH. The product was purified by prep acid followed by purification by prep basic to obtain the title compound (5.8 mg, 0.011 mmol, yield: 22%) after lyophilization as a white solid.

Yield: Compound 140 was isolated as a white solid (22% over 1 step).

Analysis: LCMS (Method T): $t_R$=1.17 min; m/z calculated for $[M+H]^+$=526.2. found=526.2; 1H NMR (400 MHz, DMSO) δ 10.35 (s, 1H), 8.02 (d, J=11.7 Hz, 1H), 7.91 (d, J=5.1 Hz, 1H), 7.48 (d, J=6.8 Hz, 1H), 6.98 (d, J=5.4 Hz, 1H), 6.81 (t, J=5.1 Hz, 1H), 4.07 (s, 2H), 3.65 (s, 2H), 3.08 (s, 3H), 2.94 (s, 3H), 2.20 (s, 6H).

Example 53

Synthesis of Compound 141

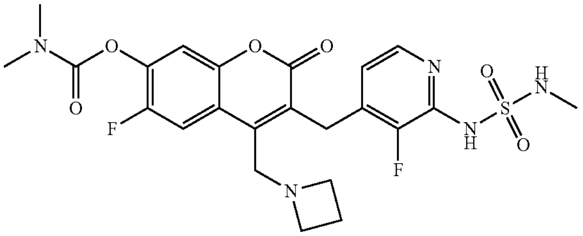

Compound 141 was prepared in 1 step:

Step 1: Starting with 4-(bromomethyl)-6-fluoro-3-((3-fluoro-2-((N-methylsulfamoyl)amino)pyridin-4-yl) methyl)-2-oxo-2H-chromen-7-yl dimethylcarbamate (50 mg, 0.05 mmol, purity: 56%) and azetidine, following the general synthesis of Compound E.2. The reaction was performed in THF 0.05 M. The product was purified by prep acid followed by an purification on prep basic to obtain the title compound (4.6 mg, 0.008 mmol, yield: 16%) after lyophilization as a white solid.

Yield: Compound 141 was isolated as a white solid (16% over 1 step).

Analysis: LCMS (Method T): $t_R$=1.16 min; m/z calculated for $[M+H]^+$=538.2. found=538.2; 1H NMR (400 MHz, DMSO) δ 10.36 (s, 1H), 8.03 (d, J=11.6 Hz, 1H), 7.89 (s, 1H), 7.47 (d, J=6.8 Hz, 1H), 6.95 (s, 1H), 6.75 (s, 1H), 4.11 (s, 2H), 3.82 (s, 2H), 3.18 (t, J=6.9 Hz, 4H), 3.09 (s, 3H), 2.95 (s, 3H), 1.90 (dd, J=7.9, 6.0 Hz, 2H).

Example 54

Synthesis of Compound 142

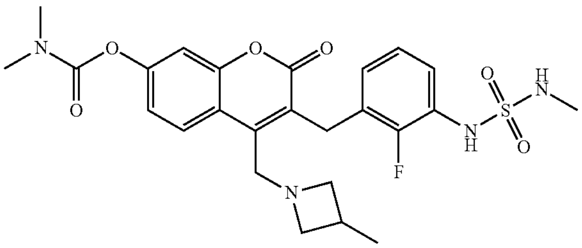

Compound 142 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (33 mg, 0.061 mmol) and 3-methylazetidine hydrochloride, following the general synthesis of Compound E.2 with the exception that the reaction was performed in MeCN and potassium carbonate (1.3 eq) was added. The product was purified by prep acid to obtain the title compound (24 mg, 0.045 mmol, yield: 74%) after lyophilization as a white solid.

Yield: Compound 142 was isolated as a white solid (74% over 1 step).

Analysis: LCMS (Method L): $t_R$=2.44 min; m/z calculated for $[M+H]^+$=533.2. found=533.2; 1H NMR (400 MHz, DMSO-d6) δ 9.39 (s, 1H), 8.06 (d, J=8.9 Hz, 1H), 7.32-7.25 (m, 1H), 7.25-7.19 (m, 2H), 7.00 (t, J=7.9 Hz, 1H), 6.81 (t, J=7.2 Hz, 1H), 4.07 (s, 2H), 3.80 (s, 2H), 3.06 (s, 3H), 2.93 (s, 3H), 2.74 (t, J=6.8 Hz, 2H), 2.53 (d, J=5.0 Hz, 3H), 2.42-2.34 (m, 1H), 1.04 (d, J=6.7 Hz, 3H).

Example 55

Synthesis of Compound 143

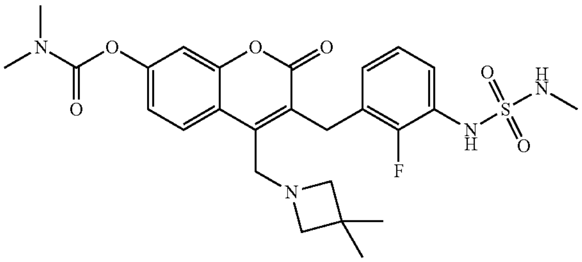

Compound 143 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (33 mg, 0.061 mmol) and 3,3-dimethylazetidine hydrochloride, following the general synthesis of Compound E.2, with the exception that the reaction was performed in MeCN and potassium carbonate (1.3 eq) was added. The product was purified by prep acid to obtain the title compound (26.2 mg, 0.048 mmol, yield: 78%) after lyophilization as a white solid.

Yield: Compound 143 was isolated as a white solid (78% over 1 step).

Analysis: LCMS (Method L): $t_R$=2.52 min; m/z calculated for $[M+H]^+$=547.2. found=547.2; 1H NMR (400 MHz, DMSO-d6) δ 8.10 (d, J=8.8 Hz, 1H), 7.31-7.25 (m, 1H), 7.22 (t, J=2.9 Hz, 2H), 7.17 (dd, J=8.8, 2.4 Hz, 1H), 6.99 (t, J=7.9 Hz, 1H), 6.81 (t, J=7.1 Hz, 1H), 4.06 (s, 2H), 3.83 (s, 2H), 3.06 (s, 3H), 2.92 (d, J=9.8 Hz, 7H), 2.53 (s, 3H), 1.09 (s, 6H).

Example 56

Synthesis of Compound 144

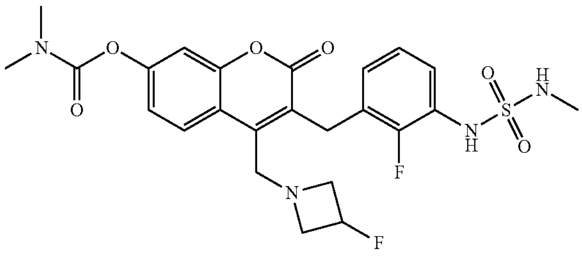

Compound 144 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (33 mg, 0.061 mmol) and 3-fluoroazetidine, hydrochloride, following the general synthesis of Compound E.2, with the exception that the reaction was performed in MeCN and potassium carbonate (1.3 eq) was added. The product was purified by prep acid to obtain the title compound (23.8 mg, 0.044 mmol, yield: 72%) after lyophilization as a white solid.

Yield: Compound 144 was isolated as a white solid (72% over 1 step).

Analysis: LCMS (Method L): $t_R$=2.69 min; m/z calculated for $[M+H]^+$=537.2. found=537.1; 1H NMR (1H NMR (400 MHz, DMSO-d6) δ 9.39 (s, 1H), 8.06 (d, J=8.8 Hz, 1H), 7.31-7.25 (m, 1H), 7.23 (d, J=2.4 Hz, 1H), 7.16 (dd, J=8.8, 2.4 Hz, 1H), 6.99 (t, J=7.9 Hz, 1H), 6.80 (s, 1H), 5.08 (dt, J=57.6, 5.1 Hz, 1H), 4.08 (s, 2H), 3.94 (s, 2H), 3.61-3.51 (m, 2H), 3.25 (dd, J=9.1, 4.5 Hz, 3H), 3.22-3.14 (m, 2H), 3.06 (s, 3H), 2.93 (s, 3H), 2.53 (s, 1H).

Example 57

Synthesis of Compound 145

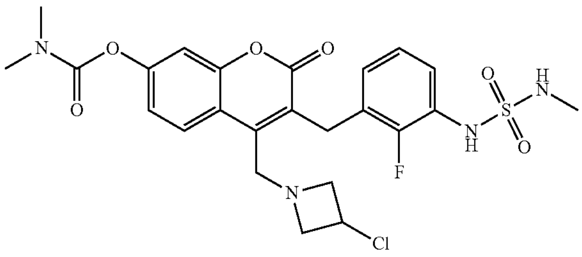

Compound 145 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (33 mg, 0.061 mmol) and 3-chloroazetidine hydrochloride, following the general synthesis of Compound E.2, with the exception that the reaction was performed in MeCN and potassium carbonate (1.3 eq) was added. The product was purified by prep acid to obtain the title compound (10.9 mg, 0.019 mmol, yield: 32%) after lyophilization as a white solid.

Yield: Compound 145 was isolated as a white solid (32% over 1 step).

Analysis: LCMS (Method L): $t_R$=3.08 min; m/z calculated for $[M+H]^+$=553.2/555.2. found=553.1/555.1; 1H NMR (400 MHz, DMSO-d6) δ 8.04 (d, J=8.8 Hz, 1H), 7.27 (t, J=7.9 Hz, 1H), 7.23 (d, J=2.3 Hz, 1H), 7.17 (dd, J=8.7, 2.4 Hz, 1H), 6.96 (s, 1H), 6.75 (s, 1H), 4.51 (t, J=5.9 Hz, 1H), 4.07 (s, 2H), 3.94 (s, 2H), 3.72 (dd, J=8.3, 6.3 Hz, 2H), 3.29-3.23 (m, 7H), 3.06 (s, 3H), 2.93 (s, 3H).

Example 58

Synthesis of Compound 146

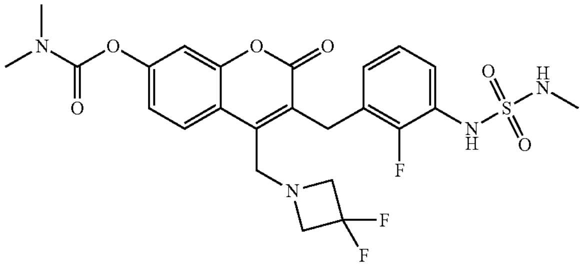

Compound 146 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (26 mg, 0.048 mmol) and 3,3-Difluoroazetidine hydrochloride, following the general synthesis of Compound E.2, with the exception that the reaction was performed in MeCN and potassium carbonate (1.4 eq) was added. The product was purified by SFC 2-PIC gradient to obtain the title compound (7 mg, 0.013 mmol, yield: 26%) after lyophilization as a white solid.

Yield: Compound 146 was isolated as a white solid (26% over 1 step).

Analysis: LCMS (Method L): $t_R$=3.67 min; m/z calculated for $[M+H]^+$=555.2. found=555.1; 1H-NMR (400 MHz, DMSO-d6) δ 9.30 (s, 1H), 8.10 (d, J=8.9 Hz, 1H), 7.28 (t, J=7.8 Hz, 1H), 7.23 (d, J=2.4 Hz, 1H), 7.18 (dd, J=8.8, 2.4 Hz, 1H), 6.97 (t, J=8.0 Hz, 1H), 6.76 (s, 1H), 4.08 (d, J=12.0 Hz, 4H), 3.65 (t, J=12.1 Hz, 4H), 3.07 (s, 3H), 2.93 (s, 3H), 2.54 (s, 3H), 1.25 (d, J=8.9 Hz, 1H).

Example 59

Synthesis of Compound 147

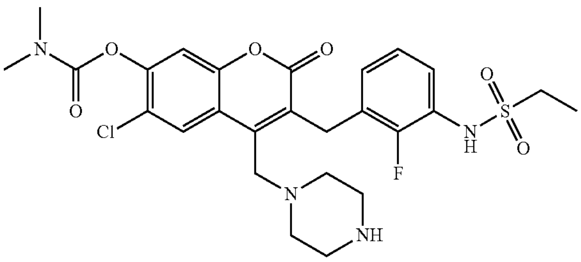 [SMILES: CCS(=O)(=O)Nc1cccc(Cc2c(CN3CCNCC3)c3cc(Cl)c(OC(=O)N(C)C)cc3oc2=O)c1F]

Compound 147 was prepared in 3 steps:

Step 1: Starting with 3-(3-amino-2-fluorobenzyl)-6-chloro-4-methyl-2-oxo-2H-chromen-7-yl dimethylcarbamate (0.320 g, 0.585 mmol) and ethanesulfonyl chloride, following the general synthesis of Compound E.3. During work-up the reaction mixture was combined with another batch to obtain the sulfamoyl (350 mg, 0.704 mmol, yield: 92%) as a white solid.

Step 2: Following the procedure of the general synthesis of Compound E.4 using NBS. After extraction the impure product was purified by column chromatography with method 'flash' (heptane/EtOAc=1:0→0:1) followed by prep acid to obtain the corresponding bromine (65 mg, 0.113 mmol, yield: 19%) as a beige solid.

Step 3: Following the procedure of the general synthesis of Compound E.5, starting with 0.2 g, 0.16 mmol of bromine using piperazine and $Et_3N$ (2.0 eq.). The impure product was purified by prep basic followed by prep acid to obtain the title compound (21 mg, 0.036 mmol, yield: 22%) as a white solid after lyophilization.

Yield: Compound 147 was isolated as a white solid (4% over 3 steps).

Analysis: LCMS (Method T): $t_R$=1.47 min; m/z calculated for $[M+H]^+$=581.2/583.2. found=581.2/583.2; 1H NMR (400 MHz, DMSO) δ 8.25 (d, J=3.1 Hz, 2H), 7.49 (s, 1H), 7.25 (td, J=7.8, 1.7 Hz, 1H), 7.02 (t, J=7.9 Hz, 1H), 6.95-6.88 (m, 1H), 4.04 (s, 2H), 3.74 (s, 2H), 3.13-3.07 (m, 6H), 2.95 (s, 3H), 2.71 (t, J=4.9 Hz, 4H), 2.46 (s, 4H), 1.26 (t, J=7.3 Hz, 3H).

Example 60

Synthesis of Compound 148

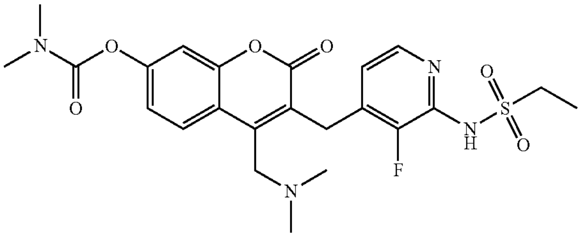

Compound 148 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method 'flash' ($CH_2Cl_2$/MeOH=1:0→9:1). The still impure product was purified by prep basic to obtain 3-((2-(ethylsulfonamido)-3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5 starting with 27 mg, 0.029 mmol of bromine and dimethylamine 2M in MeOH. The impure product was purified by SFC 2-PIC gradient followed by prep basic to obtain the title compound (3.5 mg, 0.007 mmol, yield: 24%) as a white solid.

Yield: Compound 148 was isolated as a white solid (1% over 3 steps).

Analysis: LCMS (Method R): $t_R$=0.83 min; m/z calculated for $[M+H]^+$=507.2. found=507.2; 1H NMR (400 MHz, DMSO-d6) δ 8.37 (s, 2H), 8.06 (d, J=8.9 Hz, 1H), 7.59 (s, 1H), 7.22 (d, J=2.4 Hz, 1H), 7.14 (dd, J=8.8, 2.4 Hz, 1H), 6.23 (s, 1H), 3.96 (s, 2H), 3.63 (s, 2H), 3.07 (s, 4H), 2.93 (s, 3H), 2.20 (s, 6H), 1.10 (t, J=7.4 Hz, 3H).

Example 61

Synthesis of Compound 149

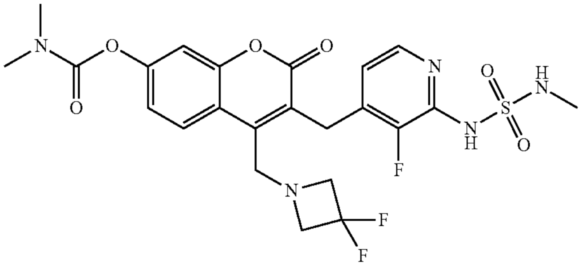

Compound 149 was prepared in 1 step:

Step 1: Starting with 4-(bromomethyl)-3-((3-fluoro-2-((N-methylsulfamoyl)amino)pyridin-4-yl)methyl)-2-oxo-2H-chromen-7-yl dimethylcarbamate (30 mg, 0.055 mmol) and 3,3-difluoroazetidine hydrochloride, following the general synthesis of Compound E.2. With the exception that the reaction was performed in $CH_2Cl_2$ and $Et_3N$ was added. After stirring for 24 hours NaI (2.00 eq.), 3,3-difluoroazetidine hydrochloride (1.00 eq.) and $Et_3N$ (1.00 eq.) were added and stirred for 1 hour at rt. $K_2CO_3$ (1.00 eq.) and 3,3-difluoroazetidine hydrochloride (1.00 eq.) were added and stirred for 24 hours at rt. The product was purified by SFC 2-PIC gradient to obtain the title compound (3.4 mg, 0.006 mmol, y: 11%) after freeze drying as a white solid.

Yield: Compound 149 was isolated as a white solid (11% over 1 step).

Analysis: LCMS (Method R): $t_R$=1.52 min; m/z calculated for $[M+H]^+$=556.2. found=556.2; 1H NMR (400 MHz, DMSO-d6) δ 8.45 (s, 2H), 8.08 (d, J=8.8 Hz, 1H), 7.56 (d, J=5.3 Hz, 1H), 7.23 (d, J=2.4 Hz, 1H), 7.17 (dd, J=8.8, 2.4 Hz, 1H), 6.14 (s, 1H), 4.03 (d, J=16.4 Hz, 4H), 3.66 (t, J=12.1 Hz, 4H), 3.07 (s, 3H), 2.93 (s, 3H), 2.31 (s, 3H), 1.24 (s, 1H).

Example 62

Synthesis of Compound 150

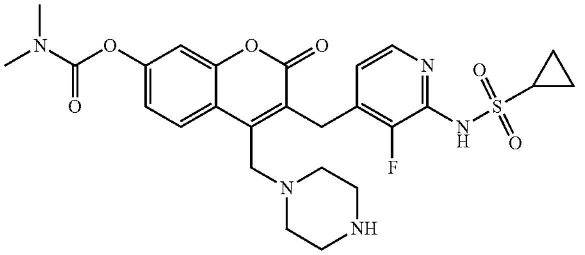 [SMILES: CN(C)C(=O)Oc1ccc2c(CN3CCNCC3)c(Cc3ccnc(NS(=O)(=O)C4CC4)c3F)c(=O)oc2c1]

Compound 150 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method ‘flash’ ($CH_2Cl_2$/MeOH=1:0→9:1). The still impure product was purified by prep basic to obtain 3-((2-(ethylsulfonamido)-3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5, starting with 33 mg, 0.040 mmol of bromine and piperazine in THF. The impure product was purified by SFC BEH gradient followed by prep acid to obtain the title compound (5.75 mg, 0.010 mmol, yield: 25%) as a white solid.

Yield: Compound 150 was isolated as a white solid (1% over 3 steps).

Analysis: LCMS (Method R): $t_R$=0.91 min; m/z calculated for $[M+H]^+$=560.2. found=560.2; 1H NMR (400 MHz, DMSO-d6) δ 8.33 (s, 2H), 8.08 (d, J=8.9 Hz, 1H), 7.66 (d, J=5.3 Hz, 1H), 7.24 (d, J=2.3 Hz, 1H), 7.16 (dd, J=8.8, 2.4 Hz, 1H), 6.33 (s, 1H), 3.97 (s, 2H), 3.71 (s, 2H), 3.07 (s, 3H), 2.93 (s, 3H), 2.73-2.63 (m, 4H), 0.88 (s, 2H), 0.75 (d, J=8.4 Hz, 2H).

Example 63

Synthesis of Compound 151

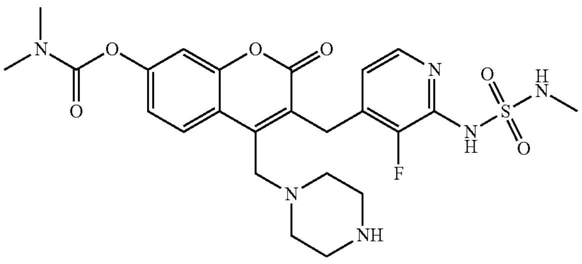

Compound 151 was prepared in 1 step:

Step 1: Starting with 4-(chloromethyl)-3-((3-fluoro-2-((N-methylsulfamoyl)amino)pyridin-4-yl)methyl)-2-oxo-2H-chromen-7-yl dimethylcarbamate (50 mg g, 0.064 mmol, purity: 70%) and piperazine, following the general synthesis of Compound E.2. With the exception that THF was used. The product was purified with SFC BEH gradient followed by prep acid to obtain the title compound (4 mg, 0.007 mmol, yield: 10%) as an off white solid after lyophilization.

Yield: Compound 151 was isolated as an off white solid (10% over 1 step).

Analysis: LCMS (Method R): $t_R$=1.01 min; m/z calculated for $[M+H]^+$=549.2. found=549.2; 1H NMR (400 MHz, DMSO-d6) δ 8.38 (s, 2H), 8.08 (d, J=8.9 Hz, 1H), 7.66 (d, J=5.2 Hz, 1H), 7.24 (d, J=2.3 Hz, 1H), 7.16 (dd, J=8.9, 2.3 Hz, 1H), 6.34 (s, 1H), 3.98 (s, 2H), 3.69 (s, 2H), 3.07 (s, 3H), 2.93 (s, 3H), 2.37 (s, 3H).

Example 64

Synthesis of Compound 152

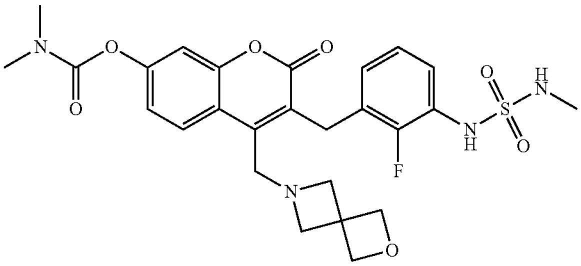

Compound 152 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (18 mg, 0.033 mmol) and 2-Oxa-6-azaspiro[3.3]heptane, following the general synthesis of Compound E.2, with the exception that the reaction was performed in $CH_2Cl_2$ and $Et_3N$ (1.8 eq) was added. The product was purified by prep acid to obtain the title compound (13.2 mg, 0.023 mmol, yield: 68%) after lyophilization as a white solid.

Yield: Compound 162 was isolated as a white solid (68% over 1 step).

Analysis: LCMS (Method T): $t_R$=1.37 min; m/z calculated for $[M+H]^+$=561.2. found=561.2; 1H NMR (400 MHz, DMSO-d6) δ 8.02 (d, J=8.8 Hz, 1H), 7.36-7.24 (m, 1H), 7.24-7.12 (m, 3H), 6.99 (t, J=7.9 Hz, 1H), 6.79 (t, J=7.1 Hz, 1H), 4.52 (s, 4H), 4.06 (s, 2H), 3.80 (s, 2H), 3.06 (s, 3H), 2.93 (s, 3H), 2.54 (s, 2H), 2.53 (s, 2H).

Example 65

Synthesis of Compound 153

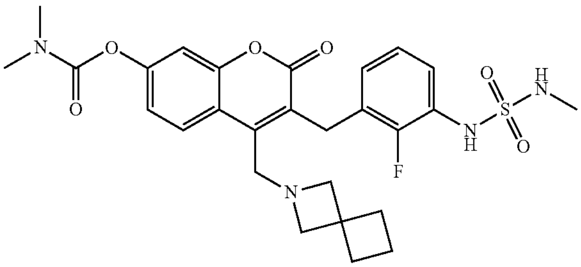

Compound 153 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (40 mg, 0.074 mmol) and 2-azaspiro[3.3]heptane hydrochloride, following the general synthesis of Compound E.2, with the exception that the reaction was performed in MeCN and potassium carbonate (1.3 eq) was added. The product was purified by prep basic followed by prep acid to obtain the title compound (15.8 mg, 0.028 mmol, yield: 38%) after lyophilization as a white solid.

Yield: Compound 153 was isolated as a white solid (38% over 1 step).

Analysis: LCMS (Method R): $t_R$=0.96 min; m/z calculated for $[M+H]^+$=559.2. found=559.2; 1H NMR (400 MHz, DMSO) δ 9.38 (s, 1H), 8.04 (d, J=8.9 Hz, 1H), 7.31-7.20 (m, 3H), 7.16 (dd, J=8.8, 2.4 Hz, 1H), 6.99 (t, J=7.8 Hz, 1H), 6.84-6.76 (m, 1H), 4.05 (s, 2H), 3.78 (s, 2H), 3.14 (s, 4H), 3.06 (s, 3H), 2.93 (s, 3H), 2.53 (d, J=4.8 Hz, 3H), 1.96 (t, J=7.6 Hz, 4H), 1.74-1.63 (m, 2H).

Example 66

Synthesis of Compound 154

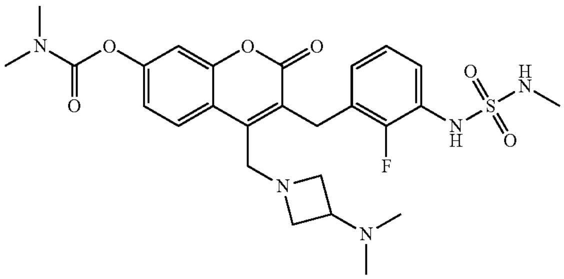

Compound 154 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (40 mg, 0.074 mmol) and N,N-dimethylazetidin-3-amine dihydrochloride, following the general synthesis of Compound E.2, with the exception that the reaction was performed in MeCN and potassium carbonate (1.3 eq) was added. The product was purified by prep basic followed by prep acid to obtain the title compound (19.5 mg, 0.035 mmol, yield: 47%) after lyophilization as a white solid.

Yield: Compound 154 was isolated as a white solid (47% over 1 step).

Analysis: LCMS (Method R): $t_R$=0.92 min; m/z calculated for $[M+H]^+$=562.2. found=562.2; 1H NMR (400 MHz, DMSO) δ 9.38 (s, 1H), 8.30 (s, 1H), 8.05 (d, J=8.9 Hz, 1H), 7.35-7.25 (m, 2H), 7.23 (d, J=2.3 Hz, 1H), 7.16 (dd, J=8.8, 2.4 Hz, 1H), 7.00 (t, J=7.9 Hz, 1H), 6.86-6.77 (m, 1H), 4.06 (s, 2H), 3.81 (s, 2H), 3.31 (d, J=6.4 Hz, 2H), 3.07 (s, 3H), 2.93 (s, 3H), 2.75 (d, J=6.6 Hz, 2H), 2.66 (p, J=6.3 Hz, 1H), 2.55 (d, J=4.7 Hz, 3H), 1.92 (s, 6H).

Example 67

Synthesis of Compound 155

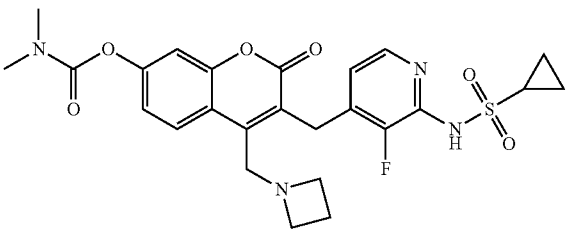 [SMILES: CN(C)C(=O)Oc1ccc2c(CN3CCC3)c(Cc3ccnc(NS(=O)(=O)C4CC4)c3F)c(=O)oc2c1]

Compound 155 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method 'flash' ($CH_2Cl_2$/MeOH=1:0→9:1). The still impure product was purified by prep basic to obtain 3-((2-(ethylsulfonamido)-3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5, starting with 33 mg, 0.040 mmol of bromine and azetidine. The impure product was purified prep acid followed by SFC BEH gradient to obtain the title compound (17.4 mg, 0.030 mmol, yield: 73%, purity: 90%) as a white solid.

Yield: Compound 155 was isolated as a white solid (2.5% over 3 steps).

Analysis: LCMS (Method T): $t_R$=1.09 min; m/z calculated for $[M+H]^+$=531.2. found=531.2; 1H NMR (400 MHz, Chloroform-d) δ 8.03-7.95 (m, 1H), 7.90 (s, 1H), 7.14-7.09 (m, 2H), 6.76 (t, J=5.3 Hz, 1H), 4.18 (s, 2H), 3.73 (s, 2H), 3.25 (t, J=6.9 Hz, 4H), 3.19 (d, J=7.1 Hz, 1H), 3.13 (d, J=2.2 Hz, 3H), 3.03 (d, J=2.4 Hz, 3H), 2.04 (p, J=6.9 Hz, 2H), 1.40 (dt, J=7.0, 3.4 Hz, 2H), 1.12-1.05 (m, 2H), 0.86 (d, J=18.2 Hz, 1H).

Example 68

Synthesis of Compound 156

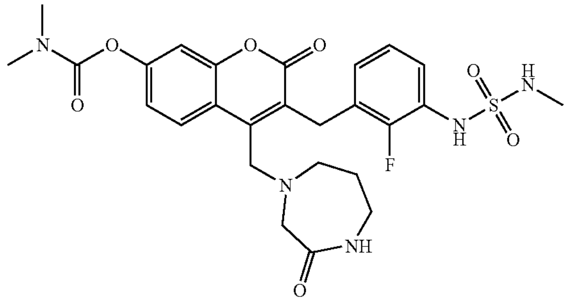

Compound 156 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.092 mmol) and 1,4-Diazepan-2-one, following the general synthesis of Compound E.2, with the exception that the reaction was performed in MeCN and $Et_3N$ (1.8 eq) was added. The product was purified by prep acid to obtain the title compound (29.3 mg, 0.051 mmol, yield: 55%) after lyophilization as a white solid.

Yield: Compound 156 was isolated as a white solid (55% over 1 step)

Analysis: LCMS (Method R): $t_R$=1.33 min; m/z calculated for $[M-H]^+$=574.2. found=574.2; 1H NMR (400 MHz, Chloroform-d) δ 7.92 (d, J=8.9 Hz, 1H), 7.33 (td, J=7.9, 1.7 Hz, 1H), 7.14 (d, J=2.3 Hz, 1H), 7.09 (dd, J=8.9, 2.4 Hz, 1H), 7.05-6.95 (m, 1H), 6.84 (t, J=7.3 Hz, 1H), 6.59 (s, 1H), 6.14 (s, 1H), 5.38 (q, J=5.2 Hz, 1H), 4.14 (s, 2H), 3.91 (s, 2H), 3.47 (s, 2H), 3.20 (q, J=5.2 Hz, 2H), 3.13 (s, 3H), 3.04 (s, 3H), 2.78 (dd, J=15.3, 5.5 Hz, 5H), 0.83 (s, 1H).

Example 69

Synthesis of Compound 157

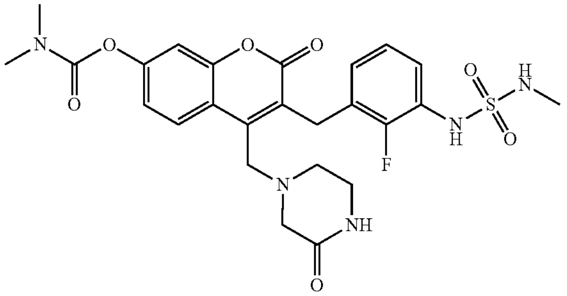

Compound 157 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.092 mmol) and piperazin-2-one, following the general synthesis of Compound E.2, with the exception that the reaction was performed in MeCN and $Et_3N$ (1.8 eq) was added. The product was purified by prep acid to obtain the title compound (27.3 mg, 0.049 mmol, yield: 53%) after lyophilization as a white solid.

Yield: Compound 157 was isolated as a white solid (53% over 1 step)

Analysis: LCMS (Method R): $t_R$=1.27 min; m/z calculated for $[M+H]^+$=562.2. found=562.2; 1H NMR (400 MHz, Chloroform-d) δ 7.93 (d, J=8.9 Hz, 1H), 7.40 (td, J=7.9, 1.7 Hz, 1H), 7.14 (d, J=2.3 Hz, 1H), 7.09 (dd, J=8.9, 2.4 Hz, 1H), 7.05-6.98 (m, 1H), 6.97-6.90 (m, 1H), 5.92 (s, 1H), 4.92 (d, J=5.3 Hz, 1H), 4.14 (s, 2H), 3.78 (s, 2H), 3.21-3.14 (m, 2H), 3.13 (s, 3H), 3.09 (s, 2H), 3.04 (s, 3H), 2.75 (d, J=5.2 Hz, 3H), 2.60 (t, J=5.4 Hz, 2H).

Example 70

Synthesis of Compound 158

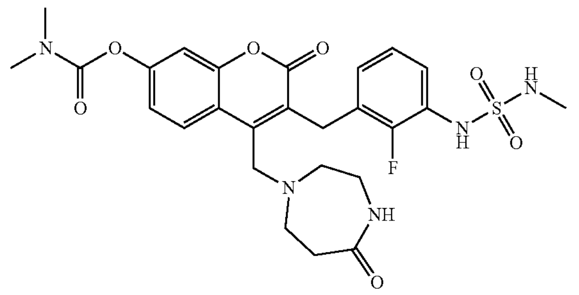

Compound 158 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (19 mg, 0.035 mmol) and 1,4-diazepan-5-one, following the general synthesis of Compound E.2, with the exception that the reaction was performed in MeCN and $K_2CO_3$ (1.8 eq) was added. The product was purified by prep acid followed by a second prep acid to obtain the title compound (5.1 mg, 0.009 mmol, yield: 25%) after lyophilization as a white solid.

Yield: Compound 158 was isolated as a white solid (25% over 1 step).

Analysis: LCMS (Method T): $t_R$=1.30 min; m/z calculated for $[M+H]^+$=576.2. found=576.2; 1H NMR (400 MHz, DMSO-d6) δ 9.36 (s, 1H), 8.50 (s, 1H), 8.11 (d, J=8.9 Hz, 1H), 7.53 (t, J=5.6 Hz, 1H), 7.29-7.21 (m, 2H), 7.15 (dd, J=8.8, 2.4 Hz, 1H), 6.95 (s, 1H), 6.74 (s, 1H), 4.02 (s, 2H), 3.81 (s, 2H), 3.06 (s, 3H), 2.99 (s, 2H), 2.93 (s, 3H), 2.63-2.51 (m, 7H), 2.29 (d, J=7.5 Hz, 2H).

Example 71

Synthesis of Compound 159

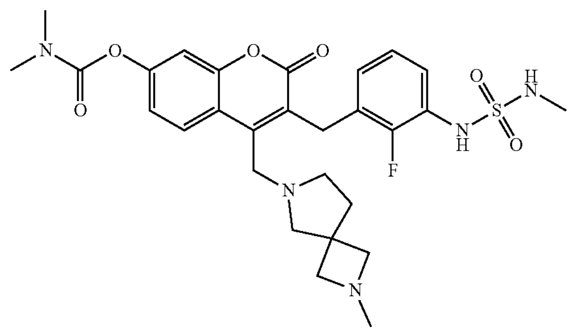

Compound 159 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.092 mmol) and 2-methyl-2,6-diazaspiro[3.4]octane dihydrochloride, following the general synthesis of Compound E.2, with the exception that the reaction was performed in MeCN and $K_2CO_3$ (1.8 eq) was added. After full conversion the reaction mixture was diluted with MeOH and $CH_2Cl_2$. Solids were filtered off and the filtrate was concentrated under reduced pressure. Water was added and the product was extracted with $CH_2Cl_2$. Combined organic layers were washed with brine, dried over $Na_2sO_4$, filtered and concentrated under reduced pressure. The product was purified with method 'prep base' to obtain the title compound (4.7 mg, 0.008 mmol, yield: 8%) after lyophilization as a white solid.

Yield: Compound 159 was isolated as a white solid (8% over 1 step).

Analysis: LCMS (Method R): $t_R$=0.84 min; m/z calculated for $[M+H]^+$=588.2. found=588.4; 1H NMR (400 MHz, DMSO-d6) δ 8.09 (d, J=8.9 Hz, 1H), 7.31-7.19 (m, 2H), 7.14 (dd, J=8.8, 2.4 Hz, 1H), 6.97 (t, J=8.0 Hz, 1H), 6.79 (s, 1H), 4.04 (s, 2H), 3.80 (s, 2H), 3.06 (s, 3H), 2.99 (d, J=6.8 Hz, 2H), 2.93 (s, 3H), 2.88 (d, J=6.8 Hz, 2H), 2.61 (s, 2H), 2.47 (d, J=7.1 Hz, 4H), 2.11 (s, 3H), 1.79 (t, J=6.9 Hz, 2H).

Example 72

Synthesis of Compound 160

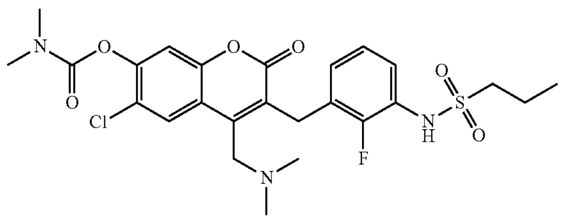 [SMILES: CCCS(=O)(=O)Nc1cccc(Cc2c(CN(C)C)c3cc(Cl)c(OC(=O)N(C)C)cc3oc2=O)c1F]

Compound 160 was prepared in 3 steps:

Step 1: A suspension of 3-(3-amino-2-fluorobenzyl)-6-chloro-4-methyl-2-oxo-2H-chromen-7-yl dimethylcarbamate (0.500 g, 0.914 mmol, 1.0 eq.) and propane-1-sulfonyl chloride (257 μL, 2.285 mmol, 2.50 eq.) in pyridine (2.8 mL, 34.7 mmol, 38 eq.) was stirred for 18 hours at rt. 1M HCl was added and the product was extracted with EtOAc. Combined organic layers were washed with brine, dried over $Na_2SO_4$, filtered and concentrated under reduced pressure. The impure product was purified by column chromatography with method 'flash' (heptane/EtOAc=1:0→0:1). Desired fractions were combined and concentrated under reduced pressure to obtain 6-chloro-3-(2-fluoro-3-(propylsulfonamido)benzyl)-4-methyl-2-oxo-2H-chromen-7-yl dimethylcarbamate (476 mg, 0.932 mmol, yield: 102%) as a light yellow foam.

Step 2: Following the procedure of the general synthesis of Compound E.4 using NBS. Reaction mixture was quenched with HCl 1M. After extraction the impure product was purified by column chromatography with method 'flash' (heptane/EtOAc=1:0→1:1) to obtain a mixture of chloride and bromine (110 mg, 0.186 mmol, yield: 20%) as a light yellow solid.

Step 3: Following the procedure of the general synthesis of Compound E.5, starting with 50 mg, 0.092 mmol of Compound E.4 and using dimethylamine 2M in MeOH. The reaction mixture stirred for 2 days. The product was purified with method 'prep acid' to obtain the title compound (12 mg, 0.022 mmol, yield: 23%) as a white solid after lyophilization.

Yield: Compound 160 was isolated as a white solid (5% over 3 steps).

Analysis: LCMS (Method R): $t_R$=1.09 min; m/z calculated for $[M+H]^+$=554.1/556.1. found=554.2/556.2; 1H NMR (400 MHz, DMSO) δ 9.67 (s, 1H), 8.21 (s, 1H), 7.48 (s, 1H), 7.29-7.20 (m, 1H), 7.01 (t, J=7.8 Hz, 1H), 6.91 (t, J=6.8 Hz, 1H), 4.05 (s, 2H), 3.65 (s, 2H), 3.10 (s, 3H), 3.08-3.01 (m, 2H), 2.95 (s, 3H), 2.18 (s, 6H), 1.81-1.67 (m, 2H), 0.96 (t, J=7.4 Hz, 3H).

Example 73

Synthesis of Compound 161

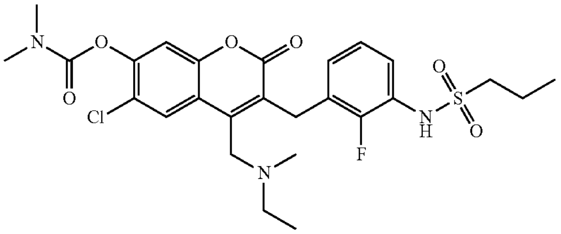 [SMILES: CCCS(=O)(=O)Nc1cccc(Cc2c(CN(C)CC)c3cc(Cl)c(OC(=O)N(C)C)cc3oc2=O)c1F]

Compound 161 was prepared in 3 steps:

Step 1: A suspension of 3-(3-amino-2-fluorobenzyl)-6-chloro-4-methyl-2-oxo-2H-chromen-7-yl dimethylcarbamate (0.500 g, 0.914 mmol, 1.0 eq.) and propane-1-sulfonyl chloride (257 μL, 2.285 mmol, 2.50 eq.) in pyridine (2.8 mL, 34.7 mmol, 38 eq.) was stirred for 18 hours at rt. 1M HCl was added and the product was extracted with EtOAc. Combined organic layers were washed with brine, dried over $Na_2SO_4$, filtered and concentrated under reduced pressure. The impure product was purified by column chromatography with method 'flash' (heptane/EtOAc=1:0→0:1). Desired fractions were combined and concentrated under reduced pressure to obtain 6-chloro-3-(2-fluoro-3-(propylsulfonamido)benzyl)-4-methyl-2-oxo-2H-chromen-7-yl dimethylcarbamate (476 mg, 0.932 mmol, yield: 102%) as a light yellow foam.

Step 2: Following the procedure of the general synthesis of Compound E.4 using NBS. Reaction mixture was quenched with HCl 1M. After extraction the impure product was purified by column chromatography with method 'flash' (heptane/EtOAc=1:0→1:1) to obtain a mixture of chloride and bromine (110 mg, 0.186 mmol, yield: 20%) as a light yellow solid.

Step 3: Following the procedure of the general synthesis of Compound E.5 starting with 50 mg, 0.092 mmol of Compound E.4 and using n-ethylamine. The reaction mixture stirred for 2 days. The product was purified with method 'prep acid' to obtain the title compound (2 mg, 0.003 mmol, yield: 4%) as a white solid after lyophilization.

Yield: Compound 161 was isolated as a white solid (1% over 3 steps).

Analysis: LCMS (Method R): $t_R$=1.13 min; m/z calculated for $[M+H]^+$=568.1/570.1. found=568.2/570.2; 1H NMR (400 MHz, DMSO) δ 9.66 (s, 1H), 8.26 (s, 1H), 7.48 (s, 1H), 7.23 (t, J=7.7 Hz, 1H), 6.99 (t, J=7.8 Hz, 1H), 6.86 (s, 1H), 4.04 (s, 2H), 3.71 (s, 2H), 3.10 (s, 3H), 3.02 (t, J=7.6 Hz, 2H), 2.95 (s, 3H), 2.44 (t, J=7.1 Hz, 2H), 2.09 (s, 3H), 1.72 (h, J=7.5 Hz, 2H), 1.01 (t, J=7.1 Hz, 3H), 0.95 (t, J=7.5 Hz, 3H).

Example 74

Synthesis of Compound 162

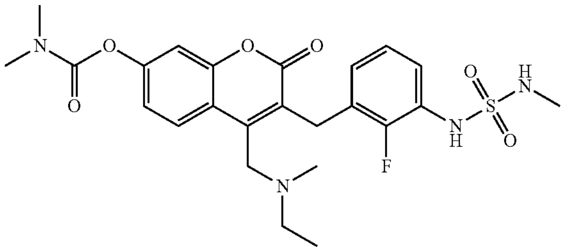

Compound 162 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.092 mmol) and N-ethylmethylamine, in $CH_2Cl_2$ and with DIPEA (1.0 eq.) following procedure the general synthesis of Compound E.2. After full conversion the reaction was concentrated under reduced pressure. The impure product was purified by column chromatography with method 'flash' (heptane/EtOAc=4:1→3:7) to obtain the title compound (30 mg, 0.058 mmol, yield: 62%) as a white solid.

Yield: Compound 162 was isolated as a white solid (62% over 1 step).

Analysis: LCMS (Method H): $t_R$=2.34 min; m/z calculated for $[M-H]^+$=521.4. found=521.4; 1H NMR (400 MHz, DMSO) δ 9.38 (s, 1H), 8.11 (d, J=8.9 Hz, 1H), 7.28 (td, J=7.8, 1.6 Hz, 1H), 7.24-7.18 (m, 2H), 7.15 (dd, J=8.8, 2.4 Hz, 1H), 6.99 (t, J=7.9 Hz, 1H), 6.85-6.79 (m, 1H), 4.04 (s, 2H), 3.69 (s, 2H), 3.06 (s, 3H), 2.93 (s, 3H), 2.52 (d, J=4.8 Hz, 3H), 2.45 (q, J=7.1 Hz, 2H), 2.10 (s, 3H), 1.00 (t, J=7.1 Hz, 3H).

Example 75

Synthesis of Compound 163

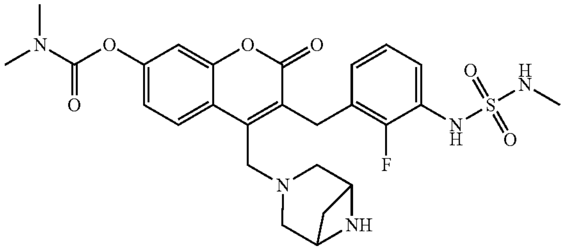

Compound 163 was prepared in 2 steps:

Step 1: Starting with 4-(bromomethyl)-3-(2-fluoro-3-((N-methylsulfamoyl)amino)benzyl)-2-oxo-2H-chromen-7-yl dimethylcarbamate (100 mg, 0.184 mmol) and tert-butyl 3,6-diazabicyclo[3.1.1]heptane-6-carboxylate, following procedure the general synthesis of Compound E.2, with the exception that the reaction was performed in $CH_2Cl_2$ and $Et_3N$ (1.8 eq) was added. After full conversion water was added and the product was extracted with $CH_2Cl_2$. Combined organic layers were washed with brine, dried over $Na_2SO_4$, filtered and concentrated under reduced pressure to obtain the Boc-amine (100.8 mg, 0.153 mmol, 83%) as an off-white solid.

Step 2: The Boc-amine was dissolved in $CH_2Cl_2$ (0.05 M) and TFA (374 μL, 4.85 mmol, 40 eq.) was added. The formed reaction mixture was stirred for 2 hours at rt. Water was added to the reaction mixture and the product was extracted with EtOAc. Combined organic layers were washed with brine, dried over $Na_2SO_4$, filtered and concentrated under reduced pressure. The impure product was purified with method 'prep acid' to obtain the title compound (56 mg, 0.100 mmol, yield: 83%) after lyophilization as a white solid.

Yield: Compound 163 was isolated as a white solid (69% over 2 steps).

Analysis: LCMS (Method R): $t_R$=0.95 min; m/z calculated for $[M+H]^+$=560.2. found=560.2; 1H NMR (400 MHz, DMSO) δ 8.35 (d, J=1.6 Hz, 1H), 8.08 (d, J=8.9 Hz, 1H), 7.33-7.18 (m, 3H), 7.18-7.12 (m, 1H), 7.00 (t, J=7.9 Hz, 1H), 6.82 (t, J=7.2 Hz, 1H), 4.09 (s, 2H), 3.99 (s, 2H), 3.79 (d, J=5.7 Hz, 2H), 3.10 (d, J=10.8 Hz, 2H), 3.06 (s, 3H), 2.93 (s, 3H), 2.90 (d, J=11.2 Hz, 2H), 2.53 (s, 3H).

Example 76

Synthesis of Compound 164

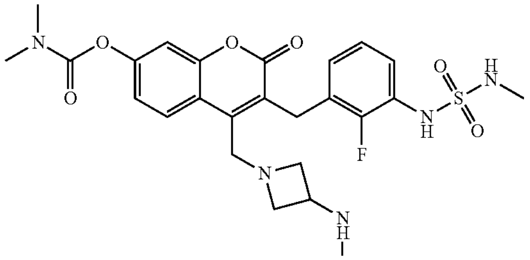

Compound 164 was prepared in 2 steps:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.092 mmol) and tert-butyl azetidin-3-yl(methyl)carbamate, following the general synthesis of Compound E.2, with the exception that the reaction was performed in $CH_2Cl_2$ and $Et_3N$ (1.8 eq) was added. After full conversion water was added and the product was extracted with $CH_2Cl_2$. Combined organic layers were washed with brine, dried over $Na_2SO_4$, filtered and concentrated under reduced pressure. The impure product was purified by column chromatography with method 'flash' (heptane/EtOAc=1:0→1:9) to obtain the Boc-protected amine 10 (44 mg, 0.068 mmol, yield: 74%) as a colorless oil.

Step 2: The Boc-protected amine 10 was dissolved in $CH_2Cl_2$ (0.05 M) and TFA (40 eq.) was added. The formed reaction mixture was 18 hours at rt. Water was added to the reaction mixture and made basic with solid $Na_2CO_3$. The product was extracted with $CH_2Cl_2$. Combined organic layers were washed with brine, dried over $Na_2SO_4$, filtered and concentrated under reduced pressure. The impure product was purified with method 'prep acid' to obtain the title compound (16 mg, 0.029 mmol, yield: 43%) after lyophilization as a white solid.

Yield: Compound 164 was isolated as a white solid (35% over 1 step).

Analysis: LCMS (Method R): $t_R$=1.98 min; m/z calculated for $[M+H]^+$=592.2. found=592.2; 1H NMR (400 MHz, $CDCl_3$) δ 8.35 (s, 1H), 7.99 (d, J=8.8 Hz, 1H), 7.35-7.29 (m, 1H), 7.12 (d, J=2.3 Hz, 1H), 7.09-7.01 (m, 3H), 4.13 (s, 2H), 3.79 (s, 2H), 3.44-3.31 (m, 3H), 3.13 (s, 3H), 3.03 (s, 3H), 2.86 (s, 3H), 2.60 (t, J=6.7 Hz, 2H).

Example 77

Synthesis of Compound 165

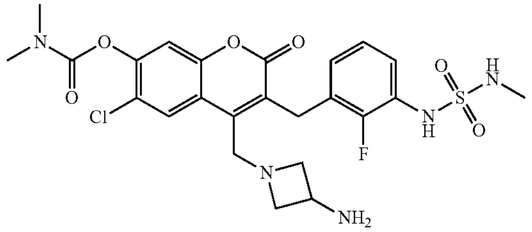

Compound 165 was prepared in 2 steps:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.069 mmol, py:75%) and tert-butyl azetidin-3-ylcarbamate hydrochloride, following the general synthesis of Compound E.2, with addition of $K_2CO_3$ (1.80 eq.). The formed reaction mixture was stirred for 3 days at rt. The reaction mixture was filtered and concentrated under reduced pressure to obtain the Boc-protected amine as a yellow oil. Used as such in subsequent reaction.

Step 2: The yellow oil from step 1 (unknown purity and mass) was dissolved in $CH_2Cl_2$ and TFA (0.209 mL, 2.71 mmol) was added and stirred for 18 hours at rt. The reaction mixture was purified by prep basic to obtain the title compound (13.7 mg, 0.025 mmol, y: 37%) after freeze drying as a white solid.

Yield: Compound 165 was isolated as a white solid (37% over 2 steps)

Analysis: LCMS (Method R): $t_R$=0.87 min; m/z calculated for $[M+H]^+$=534.2. found=534.2; 1H-NMR (400 MHz, DMSO-d6) δ 8.04 (d, J=8.8 Hz, 1H), 7.26 (t, J=7.8 Hz, 1H), 7.21 (d, J=2.4 Hz, 1H), 7.16 (dd, J=8.8, 2.4 Hz, 1H), 6.92 (t, J=7.9 Hz, 1H), 6.66 (s, 1H), 4.06 (s, 2H), 3.80 (s, 2H), 3.46 (t, J=6.6 Hz, 3H), 3.29-3.25 (m, 4H), 3.06 (s, 3H), 2.93 (s, 3H), 2.72 (t, J=6.9 Hz, 2H), 2.51 (s, 3H).

Example 78

Synthesis of Compound 166

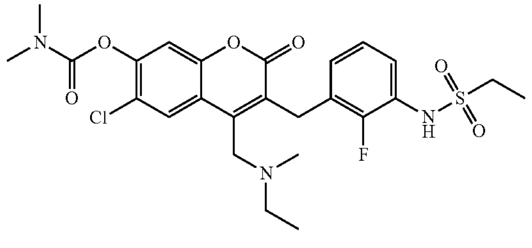 [SMILES: CCN(C)Cc1c(Cc2cccc(NS(=O)(=O)CC)c2F)c(=O)oc2cc(OC(=O)N(C)C)c(Cl)cc12]

Compound 166 was prepared in 3 steps:

Step 1: A suspension of 3-(3-amino-2-fluorobenzyl)-6-chloro-4-methyl-2-oxo-2H-chromen-7-yl dimethylcarbamate (0.250 g, 0.457 mmol, 1.0 eq.) and ethanesulfonyl chloride (59.9 mg, 0.548 mmol, 1.20 eq.) in pyridine (1.4 mL, 17.37 mmol, 38 eq.) was stirred for 18 hours at rt. 1M HCl was added and the product was extracted with EtOAc. Combined organic layers were washed with brine, dried over $Na_2SO_4$, filtered and concentrated under reduced pressure. The impure product was purified by column chromatography with method 'flash' (heptane/EtOAc=1:0→0:1). Desired fractions were combined and concentrated under reduced pressure to obtain 6-chloro-3-(3-(ethylsulfonamido)-2-fluorobenzyl)-4-methyl-2-oxo-2H-chromen-7-yl dimethylcarbamate (183 mg, 0.368 mmol, yield: 81%) as a light yellow foam.

Step 2: Following the procedure of the general synthesis of Compound E.4 using NBS. After extraction the impure product was purified by column chromatography with method 'flash' (heptane/EtOAc=1:0→1:1) to obtain the corresponding bromine (213 mg, 0.370 mmol, yield: 100%) as a light yellow solid.

Step 3: Following the procedure of the general synthesis of Compound E.5, using N-ethylmethylamine. The product was purified with method 'prep acid' to obtain the title compound (25 mg, 0.045 mmol, yield: 12%) as a white solid after lyophilization.

Yield: Compound 166 was isolated as a white solid (10% over 3 steps).

Analysis: LCMS (Method R): $t_R$=1.06 min; m/z calculated for $[M+H]^+$=554.1/556.1. found=554.2/556.2; 1H NMR (400 MHz, DMSO) δ 9.68 (s, 1H), 8.27 (s, 1H), 7.48 (s, 1H), 7.25 (td, J=7.8, 1.8 Hz, 1H), 7.01 (t, J=7.9 Hz, 1H), 6.96-6.85 (m, 1H), 4.05 (s, 2H), 3.71 (s, 2H), 3.09 (d, J=8.6 Hz, 5H), 2.95 (s, 3H), 2.45 (q, J=7.0 Hz, 2H), 2.09 (s, 3H), 1.26 (t, J=7.3 Hz, 3H), 1.01 (t, J=7.0 Hz, 3H).

Example 79

Synthesis of Compound 167

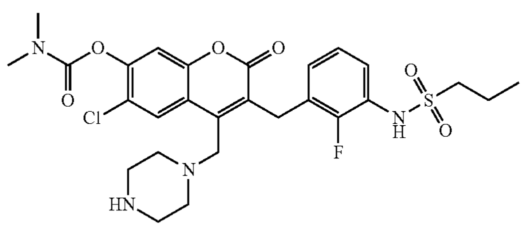 [SMILES: CCCS(=O)(=O)Nc1cccc(Cc2c(CN3CCNCC3)c3cc(Cl)c(OC(=O)N(C)C)cc3oc2=O)c1F]

Compound 167 was prepared in 3 steps:

Step 1: Starting with 3-(3-amino-2-fluorobenzyl)-6-chloro-4-methyl-2-oxo-2H-chromen-7-yl dimethylcarbamate (0.300 g, 0.548 mmol, py: 74%) and propane-1-sulfonyl chloride, following the general synthesis of Compound E.3. Pyridine was used as solvent in 38 eq. After full conversion water was added to the reaction mixture and the product was extracted with $CH_2Cl_2$. The layers were separated using a phase separator. The organic layer was concentrated under reduced pressure and the residue was purified by column chromatography with method 'flash' (heptane/EtOAc=1:0→0:1). Desired fraction were combined and concentrated under reduced pressure to obtain the sulfamoyl (273 mg, 0.534 mmol, y: 97%) as a white solid.

Step 2: Following the procedure of the general synthesis of Compound E.4 using NBS. After extraction the impure product was purified with method 'prep acid' to obtain the corresponding bromine (115 mg, 0.195 mmol, y: 36%) as a white solid.

Step 3: Following the procedure of the general synthesis of Compound E.5, starting with 41 mg, 0.070 mmol of the bromine and tert-butyl piperazine-1-carboxylate. The reaction was performed in THF. After full conversion HCl (4M in dioxane, 8.00 eq.) was added and the formed reaction mixture was stirred for 1 hour at rt. The impure product was purified by prep basic to obtain the title compound (34 mg, 0.057 mmol, y: 82%) as a white solid.

Yield: Compound 167 was isolated as a white solid (29% over 3 steps).

Analysis: LCMS (Method T): $t_R$=1.57 min; m/z calculated for $[M+H]^+$=595.2/597.2. found=595.2/597.2; 1H NMR (400 MHz, DMSO) δ 8.23 (d, J=5.2 Hz, 1H), 7.50 (s, 1H), 7.25 (td, J=7.8, 1.7 Hz, 1H), 7.02 (t, J=7.9 Hz, 1H), 6.93 (t, J=6.8 Hz, 1H), 4.04 (s, 2H), 3.78 (s, 2H), 3.10 (s, 3H), 3.10-3.04 (m, 3H), 2.95 (s, 3H), 2.80 (d, J=5.1 Hz, 4H), 2.58-2.53 (m, 4H), 1.80-1.68 (m, 2H), 0.97 (t, J=7.4 Hz, 3H).

Example 80

Synthesis of Compound 168

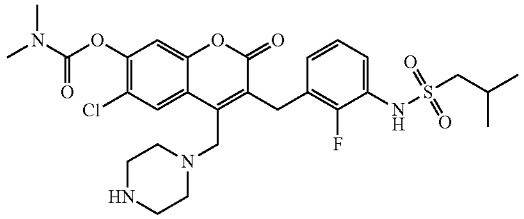

Compound 168 was prepared in 3 steps:

Step 1: Starting with 3-(3-amino-2-fluorobenzyl)-6-chloro-4-methyl-2-oxo-2H-chromen-7-yl dimethylcarbamate (0.300 g, 0.548 mmol, py: 74%) and 2-methylpropane-1-sulfonyl chloride, following the general synthesis of Compound E.3. Pyridine was used as solvent in 38 eq. After full conversion water was added to the reaction mixture and the product was extracted with $CH_2Cl_2$. The layers were separated using a phase separator. The organic layer was concentrated under reduced pressure and the residue was purified by column chromatography with method 'flash' (heptane/EtOAc=1:0→1:9). Desired fraction were combined and concentrated under reduced pressure to obtain the sulfamoyl (253 mg, 0.482 mmol, y: 88%) as a yellow solid.

Step 2: Following the procedure of the general synthesis of Compound E.4 using NBS. After extraction the impure product was purified by prep acid to obtain the corresponding bromine (104 mg, 0.172 mmol, y: 36%) as a white solid.

Step 3: Following the procedure of the general synthesis of Compound E.5 starting with 50 mg, 0.083 mmol of the bromine and tert-butyl piperazine-1-carboxylate.

The reaction was performed in THF. After full conversion HCl (4M in dioxane, 8.00 eq.) was added and the formed reaction mixture was stirred for 1 hour at rt. The impure product was purified by prep basic to obtain the title compound (33 mg, 0.054 mmol, y: 65%) as a white solid.

Yield: Compound 168 was isolated as a white solid (17% over 3 steps)

Analysis: LCMS (Method T): $t_R$=1.68 min; m/z calculated for $[M+H]^+$=609.2/611.2. found=609.4/611.4; 1H NMR (400 MHz, DMSO) δ 8.24 (d, J=5.0 Hz, 2H), 7.49 (s, 1H), 7.25 (td, J=7.9, 1.7 Hz, 1H), 7.02 (t, J=7.8 Hz, 1H), 6.93 (t, J=7.1 Hz, 1H), 4.04 (s, 2H), 3.75 (s, 2H), 3.10 (s, 4H), 2.98 (d, J=6.4 Hz, 2H), 2.95 (s, 3H), 2.77-2.66 (m, 4H), 2.54 (s, 1H), 2.48-2.44 (m, 3H), 2.17 (hept, J=6.5 Hz, 1H), 1.01 (d, J=6.7 Hz, 6H).

Example 81

Synthesis of Compound 169

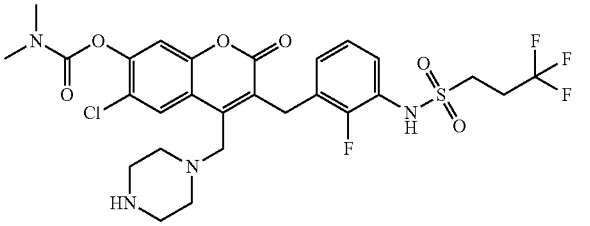 [SMILES: CN(C)C(=O)Oc1cc2oc(=O)c(Cc3cccc(NS(=O)(=O)CCC(F)(F)F)c3F)c(CN3CCNCC3)c2cc1Cl]

Compound 169 was prepared in 3 steps:

Step 1: Starting with 3-(3-amino-2-fluorobenzyl)-6-chloro-4-methyl-2-oxo-2H-chromen-7-yl dimethylcarbamate (0.300 g, 0.741 mmol) and 3,3,3-trifluoropropane-1-sulfonyl chloride, following the general synthesis of Compound E.3. Pyridine was used as solvent in 38 eq. After full conversion water was added to the reaction mixture and the product was extracted with $CH_2Cl_2$. The layers were separated using a phase separator. The organic layer was concentrated under reduced pressure and the residue was purified by column chromatography with method 'flash' (heptane/EtOAc=1:0→1:9). Desired fraction were combined and concentrated under reduced pressure to obtain the sulfamoyl (315 mg, 0.558 mmol, y: 75%) as a yellow solid.

Step 2: Following the procedure of the general synthesis of Compound E.4 using NBS. After extraction the impure product was purified by column chromatography with method 'flash' (heptane/EtOAc=1:0→1:1). Desired fractions were combined and concentrated under reduced pressure to obtain the corresponding bromine (230 mg, 0.322 mmol, y: 58%, py: 90%) as a white solid.

Step 3: Following the procedure of the general synthesis of Compound E.5, starting with 50 mg, 0.078 mmol of the bromine and piperazine. 3.00 eq of $NEt_3$ was added to the reaction mixture. After full conversion the impure product was purified by prep basic to obtain the title compound (28 mg, 0.043 mmol, y: 55%) as a white solid.

Yield: Compound 169 was isolated as a white solid (24% over 3 steps).

Analysis: LCMS (Method T): $t_R$=1.44 min; m/z calculated for $[M+H]^+$=649.2/651.2. found=649.2/651.2; 1H NMR (400 MHz, DMSO) δ 8.23 (s, 1H), 7.48 (s, 1H), 7.23-7.14 (m, 1H), 6.89 (t, J=7.8 Hz, 1H), 6.66 (t, J=7.1 Hz, 1H), 4.00 (s, 2H), 3.73 (s, 2H), 3.16-3.08 (m, 5H), 2.95 (s, 3H), 2.79-2.60 (m, 6H), 2.50-2.45 (m, 4H).

Example 82

Synthesis of Compound 170

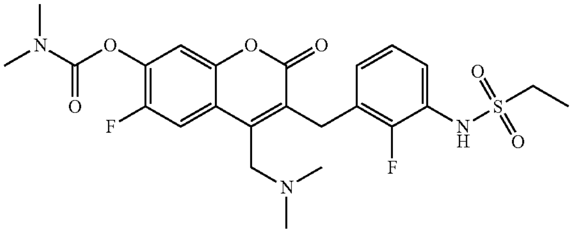 [SMILES: CCS(=O)(=O)Nc1cccc(Cc2c(CN(C)C)c3cc(F)c(OC(=O)N(C)C)cc3oc2=O)c1F]

Compound 170 was prepared in 3 steps:

Step 1: Starting with 3-(3-amino-2-fluorobenzyl)-6-fluoro-4-methyl-2-oxo-2H-chromen-7-yl dimethylcarbamate (1.00 g, 2.57 mmol) and ethanesulfonyl chloride, following the procedure of the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The impure product was purified by column chromatography with method 'flash' (heptane/EtOAc=1:0→0:1). Desired fraction were combined and concentrated under reduced pressure to obtain the sulfamoyl (997 mg, 2.013 mmol, y: 78%) as a white solid.

Step 2: Following the procedure of the general synthesis of Compound E.4 using NBS. After extraction the impure product was purified by column chromatography with method 'flash' (heptane/EtOAc=1:0→0:1). Desired fractions were combined and concentrated under reduced pressure to obtain the corresponding bromine (237 mg, 0.339 mmol, y: 54%, py: 80%) as a brown solid.

Step 3: Following the procedure of the general synthesis of Compound E.5, starting with 50 mg, 0.072 mmol (py: 80%) of bromine and dimethylamine 2M in MeOH. 3.00 eq of $NEt_3$ was added to the reaction mixture. After full conversion the impure product was purified by prep basic to obtain the title compound (22 mg, 0.041 mmol, y: 58%) as an off-white solid.

Yield: Compound 170 was isolated as a white solid (24% over 3 steps).

Analysis: LCMS (Method T): $t_R$=1.66 min; m/z calculated for $[M+H]^+$=524.2. found=524.2; 1H NMR (400 MHz, DMSO) δ 9.62 (s, 1H), 8.00 (d, J=11.7 Hz, 1H), 7.46 (d, J=6.9 Hz, 1H), 7.23 (t, J=7.8 Hz, 1H), 7.03-6.91 (m, 1H), 6.88-6.72 (m, 1H), 4.04 (s, 2H), 3.63 (s, 2H), 3.08 (s, 3H), 3.06-2.99 (m, 2H), 2.94 (s, 3H), 2.18 (s, 6H), 1.24 (t, J=7.3 Hz, 3H).

Example 83

Synthesis of Compound 171

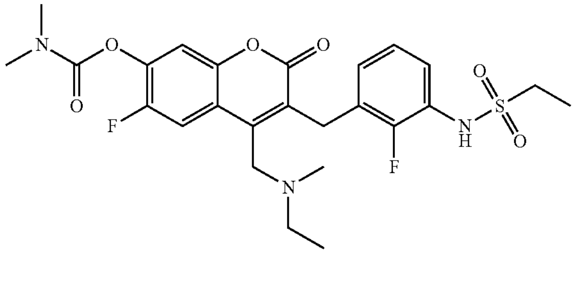 [SMILES: CCN(C)Cc1c(Cc2cccc(NS(=O)(=O)CC)c2F)c(=O)oc2cc(OC(=O)N(C)C)c(F)cc12]

Compound 170 was prepared in 3 steps:

Step 1: Starting with 3-(3-amino-2-fluorobenzyl)-6-fluoro-4-methyl-2-oxo-2H-chromen-7-yl dimethylcarbamate (1.00 g, 2.57 mmol) and ethanesulfonyl chloride, following procedure the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The impure product was purified by column chromatography with method 'flash' (heptane/EtOAc=1:0→0:1). Desired fraction were combined and concentrated under reduced pressure to obtain the sulfamoyl (997 mg, 2.013 mmol, y: 78%) as a white solid.

Step 2: Following the procedure of the general synthesis of Compound E.4 using NBS. After extraction the impure product was purified by column chromatography with method 'flash' (heptane/EtOAc=1:0→0:1). Desired fractions were combined and concentrated under reduced pressure to obtain the corresponding bromine (237 mg, 0.339 mmol, y: 54%, py: 80%) as a brown solid.

Step 3: Following the procedure of the general synthesis of Compound E.5, starting with 50 mg, 0.072 mmol (py: 80%) of the bromine and N-methylethanamine. 3.00 eq of $NEt_3$ was added to the reaction mixture. After full conversion the impure product was purified by prep basic to obtain the title compound (26 mg, 0.048 mmol, y: 67%) as an off-white solid.

Yield: Compound 171 was isolated as a white solid (28% over 3 steps).

Analysis: LCMS (Method T): $t_R$=1.79 min; m/z calculated for $[M+H]^+$=538.2. found=538.2; 1H NMR (400 MHz, DMSO) δ 9.60 (s, 1H), 8.04 (d, J=11.8 Hz, 1H), 7.47 (d, J=6.9 Hz, 1H), 7.24 (td, J=7.9, 1.7 Hz, 1H), 7.01 (t, J=7.9 Hz, 1H), 6.93-6.85 (m, 1H), 4.05 (s, 2H), 3.69 (s, 2H), 3.13-3.03 (m, 5H), 2.94 (s, 3H), 2.46-2.39 (m, 2H), 2.09 (s, 3H), 1.25 (t, J=7.3 Hz, 3H), 0.99 (t, J=7.1 Hz, 3H).

Example 84

Synthesis of Compound 172

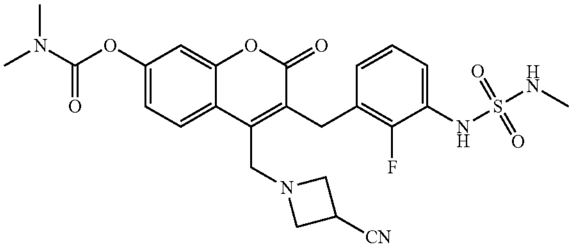

Compound 172 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (50 mg, 0.069 mmol, purity: 75%) and 3-Azetidinecarbonitrile hydrochloride, following the general synthesis of Compound E.2, with the exception that the reaction was performed in MeCN and potassium carbonate (1.3 eq) was added. The product was purified by prep basic followed with method 'prep acid' to obtain the title compound (6.2 mg, 0.011 mmol, yield: 16%) after lyophilization as a white solid.

Yield: Compound 172 was isolated as a white solid (16% over 1 step).

Analysis: LCMS (Method T): $t_R$=1.48 min; m/z calculated for $[M+H]^+$=544.2. found=544.2; 1H NMR (400 MHz, Chloroform-d) δ 7.92 (d, J=8.7 Hz, 1H), 7.45-7.34 (m, 1H), 7.16-7.08 (m, 2H), 7.03 (dd, J=15.8, 7.8 Hz, 1H), 6.91 (t, J=7.3 Hz, 1H), 6.58 (s, 1H), 4.52 (d, J=5.3 Hz, 1H), 4.15 (s, 2H), 3.83 (s, 2H), 3.53 (t, J=7.2 Hz, 2H), 3.28 (t, J=7.0 Hz, 2H), 3.19 (d, J=7.3 Hz, 1H), 3.13 (s, 3H), 3.04 (s, 3H), 2.79 (d, J=5.3 Hz, 3H).

Example 85

Synthesis of Compound 173

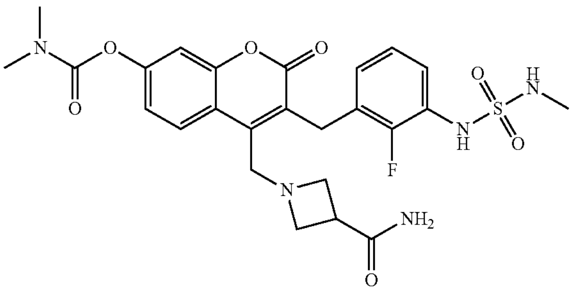

Compound 173 was prepared in 1 step:

Step 1: Starting with 4-(bromomethyl)-3-(2-fluoro-3-((N-methylsulfamoyl)amino)benzyl)-2-oxo-2H-chromen-7-yl dimethylcarbamate (70 mg, 0.129 mmol) and azetidine-3-carboxamide, following the general synthesis of Compound E.2, with the exception that the reaction was performed in $CH_2CL_2$ and $Et_3N$ (1.8 eq) was added. After full conversion sat. aq. $NaHCO_3$ was added and the product was extracted with $CH_2Cl_2$.

Combined organic layers were washed with brine, dried over $Na_2SO_4$, filtered and concentrated under reduced pressure. The impure product was purified by prep basic to obtain the title compound (29.5 mg, 0.052 mmol, yield: 41%) after lyophilization as a white solid.

Yield: Compound 173 was isolated as a white solid (41% over 1 step).

Analysis: LCMS (Method T): $t_R$=1.22 min; m/z calculated for $[M+H]^+$=562.2. found=562.2; 1H NMR (400 MHz, Chloroform-d) δ 7.99 (d, J=8.8 Hz, 1H), 7.41 (td, J=7.9, 1.8 Hz, 1H), 7.16-7.05 (m, 2H), 7.04-6.98 (m, 1H), 6.95 (d, J=7.2 Hz, 1H), 6.72 (s, 1H), 5.62 (s, 1H), 5.29 (s, 1H), 4.97 (d, J=5.4 Hz, 1H), 4.15 (s, 2H), 3.84 (s, 2H), 3.40 (t, J=7.4 Hz, 2H), 3.19 (t, J=6.7 Hz, 2H), 3.13 (s, 3H), 3.04 (s, 4H), 2.81 (d, J=5.3 Hz, 3H).

Example 86

Synthesis of Compound 174

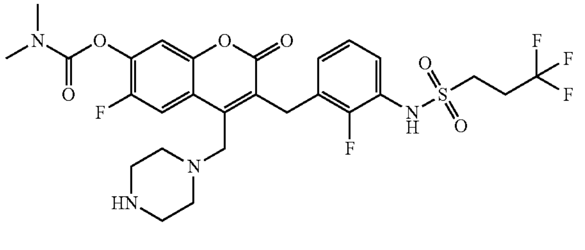 [SMILES: CN(C)C(=O)Oc1cc2oc(=O)c(Cc3cccc(NS(=O)(=O)CCC(F)(F)F)c3F)c(CN3CCNCC3)c2cc1F]

Compound 173 was prepared in 3 steps:

Step 1: Starting with 3-(3-amino-2-fluorobenzyl)-6-fluoro-4-methyl-2-oxo-2H-chromen-7-yl dimethylcarbamate (0.700 g, 1.802 mmol) and 3,3,3-trifluoropropane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (526 mg, 0.959 mmol, yield: 53%) as a white solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (675 mg, 0.570 mmol, yield: 66%, purity: 53%) as a brown solid.

Step 3: Following the procedure of the general synthesis of Compound E.5, starting with 100 mg, 0.084 mmol of the bromine and piperazine. 3.00 eq of $NEt_3$ was added to the reaction mixture. After full conversion the impure product was purified by prep basic to obtain the title compound (36 mg, 0.056 mmol, yield: 67%) as an off-white solid.

Yield: Compound 174 was isolated as an off-white solid (23% over 3 steps).

Analysis: LCMS (Method T): $t_R$=1.34 min; m/z calculated for $[M+H]^+$=633.2. found=633.4; 1H NMR (400 MHz, DMSO) δ 8.01 (d, J=11.7 Hz, 1H), 7.47 (d, J=6.9 Hz, 1H), 7.22-7.13 (m, 1H), 6.89 (t, J=7.8 Hz, 1H), 6.65 (t, J=7.1 Hz, 1H), 4.00 (s, 2H), 3.70 (s, 2H), 3.15-3.10 (m, 2H), 3.08 (s, 3H), 2.94 (s, 3H), 2.78-2.71 (m, 4H), 2.71-2.61 (m, 2H), 2.48-2.44 (m, 4H).

Example 87

Synthesis of Compound 175

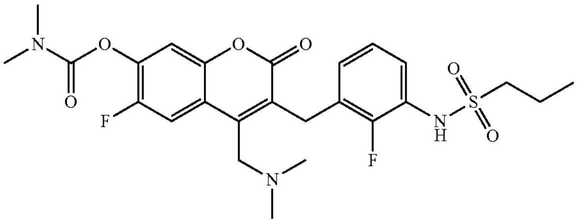 [SMILES: CCCS(=O)(=O)Nc1cccc(Cc2c(CN(C)C)c3cc(F)c(OC(=O)N(C)C)cc3oc2=O)c1F]

Compound 175 was prepared in 3 steps:

Step 1: Starting with 3-(3-amino-2-fluorobenzyl)-6-fluoro-4-methyl-2-oxo-2H-chromen-7-yl dimethylcarbamate (1.00 g, 2.57 mmol) and propane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (973 mg, 1.948 mmol, yield: 76%) as a white solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (661 mg, 0.980 mmol, yield: 50%, purity: 85%) as a white solid.

Step 3: Following the procedure of the general synthesis of Compound E.5, starting with 220 mg, 0.384 mmol of the bromine and dimethylamine 2M in MeOH. After full conversion the impure product was purified by prep basic to obtain the title compound (92.5 mg, 0.172 mmol, yield: 45%) as an off-white solid.

Yield: Compound 175 was isolated as an off-white solid (17% over 3 steps)

Analysis: LCMS (Method T): $t_R$=1.75 min; m/z calculated for $[M+H]^+$=538.2. found=538.2; 1H NMR (400 MHz, $CDCl_3$) δ 7.89 (d, J=11.3 Hz, 1H), 7.45 (td, J=7.8, 1.6 Hz, 1H), 7.19 (d, J=6.6 Hz, 1H), 7.06-6.98 (m, 1H), 6.91-6.85 (m, 1H), 6.47 (s, 1H), 4.15 (s, 2H), 3.56 (s, 2H), 3.15 (s, 3H), 3.13-3.06 (m, 2H), 3.04 (s, 3H), 2.25 (s, 6H), 1.92-1.82 (m, 2H), 1.05 (t, J=7.4 Hz, 3H).

Example 88

Synthesis of Compound 176

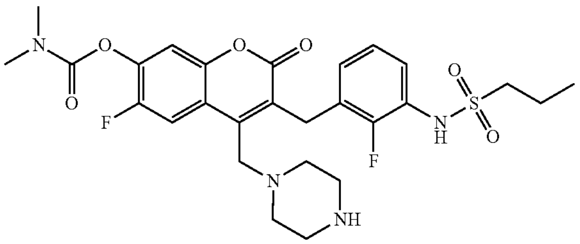 [SMILES: CCCS(=O)(=O)Nc1cccc(Cc2c(CN3CCNCC3)c3cc(F)c(OC(=O)N(C)C)cc3oc2=O)c1F]

Compound 176 was prepared in 3 steps:

Step 1: Starting with 3-(3-amino-2-fluorobenzyl)-6-fluoro-4-methyl-2-oxo-2H-chromen-7-yl dimethylcarbamate (1.00 g, 2.57 mmol) and propane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (973 mg, 1.948 mmol, yield: 76%) as a white solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (661 mg, 0.980 mmol, yield: 50%, purity: 85%) as a white solid.

Step 3: Following the procedure of the general synthesis of Compound E.5, starting with 220 mg, 0.384 mmol of the bromine and piperazine. After full conversion the impure product was purified by prep basic to obtain the title compound (147.2 mg, 0.247 mmol, yield: 64%) as an off-white solid.

Yield: Compound 176 was isolated as an off-white solid (24% over 3 steps).

Analysis: LCMS (Method T): $t_R$=1.45 min; m/z calculated for $[M+H]^+$=579.2. found=579.4; 1H NMR (400 MHz, $CDCl_3$) δ 7.90 (d, J=11.3 Hz, 1H), 7.44 (td, J=7.9, 1.6 Hz, 1H), 7.19 (d, J=6.6 Hz, 1H), 7.02 (td, J=8.0, 1.2 Hz, 1H), 6.92-6.85 (m, 1H), 4.14 (s, 2H), 3.62 (s, 2H), 3.15 (s, 3H), 3.13-3.07 (m, 2H), 3.05 (s, 3H), 2.82 (t, J=4.8 Hz, 4H), 2.44 (s, 5H), 1.94-1.82 (m, 3H), 1.05 (t, J=7.4 Hz, 3H).

Example 89

Synthesis of Compound 177

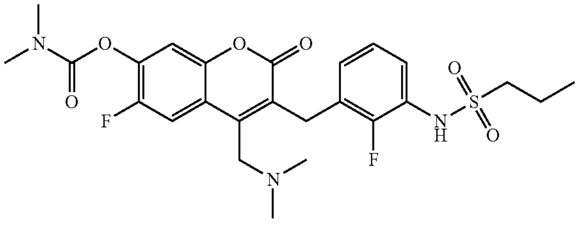

Compound 177 was prepared in 3 steps:

Step 1: Starting with 3-(3-amino-2-fluorobenzyl)-6-fluoro-4-methyl-2-oxo-2H-chromen-7-yl dimethylcarbamate (1.00 g, 2.57 mmol) and propane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (973 mg, 1.948 mmol, yield: 76%) as a white solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (661 mg, 0.980 mmol, yield: 50%, purity: 85%) as a white solid.

Step 3: Following the procedure of the general synthesis of Compound E.5, starting with 220 mg, 0.384 mmol of the bromine and N-methylethanamine. After full conversion the impure product was purified by prep basic to obtain the title compound (146.5 mg, 0.266 mmol, yield: 69%) as an off-white solid.

Yield: Compound 177 was isolated as an off-white solid (26% over 3 steps).

Analysis: LCMS (Method T): $t_R$=1.87 min; m/z calculated for $[M+H]^+$=552.2. found=552.4; 1H NMR (400 MHz, $CDCl_3$) δ 7.97 (d, J=11.3 Hz, 1H), 7.44 (td, J=7.9, 1.6 Hz, 1H), 7.19 (d, J=6.7 Hz, 1H), 7.05-6.98 (m, 1H), 6.91-6.84 (m, 1H), 6.47 (s, 1H), 4.15 (s, 2H), 3.61 (s, 2H), 3.15 (s, 3H), 3.12-3.06 (m, 2H), 3.05 (s, 3H), 2.47 (q, J=7.1 Hz, 2H), 2.16 (s, 3H), 1.94-1.82 (m, 2H), 1.09 (t, J=7.1 Hz, 3H), 1.05 (t, J=7.4 Hz, 3H).

Example 90

Synthesis of Compound 178

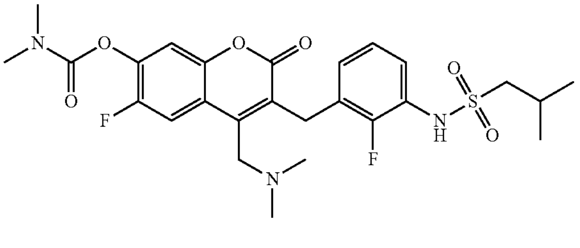 [SMILES: CC(C)CS(=O)(=O)Nc1cccc(Cc2c(CN(C)C)c3cc(F)c(OC(=O)N(C)C)cc3oc2=O)c1F]

Compound 178 was prepared in 3 steps:

Step 1: Starting with 3-(3-amino-2-fluorobenzyl)-6-fluoro-4-methyl-2-oxo-2H-chromen-7-yl dimethylcarbamate (0.70 g, 1.802 mmol) and 2-methylpropane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (648 mg, 1.274 mmol, yield: 71%) as a beige solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (162 mg, 0.207 mmol, yield: 18%, purity: 75%) as a white solid.

Step 3: Following the procedure of the general synthesis of Compound E.5, starting with 220 mg, 0.375 mmol of the bromine and dimethylamine 2M in MeOH. After full conversion the impure product was purified by prep basic to obtain the title compound (43 mg, 0.078 mmol, yield: 21%) as an off-white solid.

Yield: Compound 178 was isolated as an off-white solid (3% over 3 steps).

Analysis: LCMS (Method T): $t_R$=1.84 min; m/z calculated for $[M+H]^+$=552.2. found=552.4; 1H NMR (400 MHz, $CDCl_3$) δ 7.89 (d, J=11.3 Hz, 1H), 7.44 (td, J=7.9, 1.6 Hz, 1H), 7.19 (d, J=6.6 Hz, 1H), 7.02 (td, J=8.0, 1.2 Hz, 1H), 6.92-6.85 (m, 1H), 6.48 (s, 1H), 4.15 (s, 2H), 3.56 (s, 2H), 3.15 (s, 3H), 3.04 (s, 3H), 3.01 (d, J=6.6 Hz, 2H), 2.32 (dt, J=13.3, 6.7 Hz, 1H), 2.25 (s, 6H), 1.10 (d, J=6.7 Hz, 6H).

Example 91

Synthesis of Compound 179

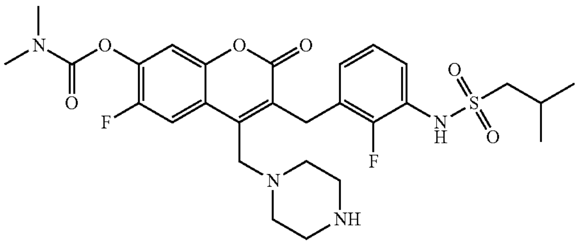 [SMILES: CC(C)CS(=O)(=O)Nc1cccc(Cc2c(CN3CCNCC3)c3cc(F)c(OC(=O)N(C)C)cc3oc2=O)c1F]

Compound 179 was prepared in 3 steps:

Step 1: Starting with 3-(3-amino-2-fluorobenzyl)-6-fluoro-4-methyl-2-oxo-2H-chromen-7-yl dimethylcarbamate (0.70 g, 1.802 mmol) and 2-methylpropane-1-sulfonyl chloride, following the general synthesis of Compound E.3. After full conversion water was added to the reaction mixture and the product was extracted with $CH_2Cl_2$. Combined organic layers were washed with brine, dried over $Na_2SO_4$, filtered and concentrated under reduced pressure. The residue was purified by flash column chromatography (heptane/EtOAc=1:0→0:1). Desired fraction were combined and concentrated under reduced pressure to obtain the sulfamoyl (648 mg, 1.274 mmol, yield: 71%) as a beige solid.

Step 2: Following the procedure of the general synthesis of Compound E.4 using NBS. After extraction the impure product was purified by flash column chromatography (heptane/EtOAc=1:0→0:1). Desired fractions were combined and concentrated under reduced pressure to obtain the corresponding bromine (162 mg, 0.207 mmol, yield: 18%, purity: 75%) as a white solid.

Step 3: Following the procedure of the general synthesis of Compound E.5, starting with 220 mg, 0.375 mmol of the bromine and piperazine. After full conversion the impure product was purified by prep basic to obtain the title compound (51 mg, 0.084 mmol, yield: 22%) as an off-white solid.

Yield: Compound 179 was isolated as an off-white solid (3% over 3 steps).

Analysis: LCMS (Method T): $t_R$=1.56 min; m/z calculated for $[M+H]^+$=593.2. found=593.4; 1H NMR (400 MHz, $CDCl_3$) δ 7.90 (d, J=11.2 Hz, 1H), 7.43 (t, J=7.5 Hz, 1H), 7.19 (d, J=6.7 Hz, 1H), 7.03 (t, J=7.9 Hz, 1H), 6.88 (t, J=7.4 Hz, 1H), 4.14 (s, 2H), 3.62 (s, 2H), 3.15 (s, 3H), 3.05 (s, 3H), 3.01 (d, J=6.5 Hz, 2H), 2.82 (t, J=4.8 Hz, 4H), 2.44 (s, 4H), 2.32 (dt, J=13.3, 6.6 Hz, 1H), 1.10 (d, J=6.7 Hz, 6H).

Example 92

Synthesis of Compound 180

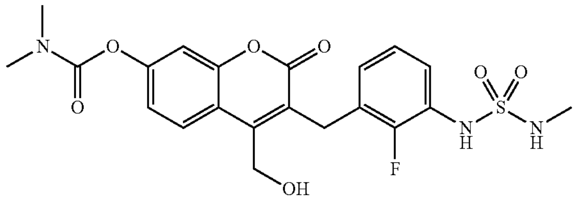

Compound 180 was prepared in 2 steps:

Step-1: 4-(bromomethyl)-3-(2-fluoro-3-((N-methylsulfamoyl)amino)benzyl)-2-oxo-2H-chromen-7-yl dimethylcarbamate (2.715 g, 3.30 mmol) was suspended in MeCN (60 mL) and silver acetate (1 g, 5.99 mmol, 1.8 eq) was added. The next day, water was added and the product was extracted with DCM (2×). The combined extract was dried over brine and sodium sulfate and evaporated. The crude was purified with method 'flash' column chromatography (heptane/EtOAc=9:1→5:5) to obtain the intermediate acetate (1.40 g, 2.68 mmol, yield: 81%) as an off-white solid.

Step-2: To a solution of the above acetate (1.21 g, 2.52 mmol) in MeOH (27 mL), potassium carbonate (0.445 g, 3.22 mmol, 1.2 eq) was added. After 2 h, HCl (1 N in water) was added until the mixture was slightly acidic. Then water and DCM were added. The aqueous layer was extracted with DCM (2×), the combined extract was dried over brine and sodium sulfate and evaporated to give the title compound (1.21 g, 2.52 mmol, yield: 94%) as an off-white solid.

Example 93

Synthesis of Compound 181

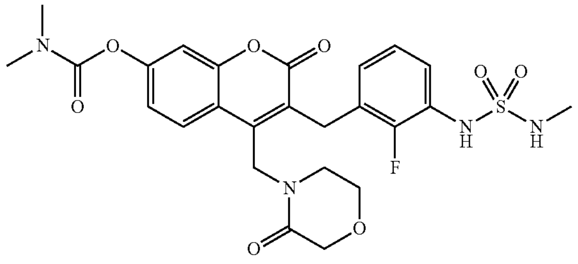

Compound 181 was prepared in one step:

Step 1: Sodium hydride (60% w/w/in mineral oil, 8 mg, 0.20 mmol, 2.1 eq) was suspended in dry DMF (1 mL) and morpholin-3-one (20 mg, 0.198 mmol, 2.1 eq) was added. After 30 min, this solution was slowly added to 4-(bromomethyl)-3-(2-fluoro ((N-methylsulfamoyl) amino)benzyl)-2-oxo-2H-chromen-7-yl dimethylcarbamate (50 mg, 0.092 mmol) in dry DMF (1 mL). After 30 min, the reaction was quenched with 1 N HCl and the product extracted with EtOAc (2×). The combined extract was dried over brine and sodium sulfate evaporated and purified with method 'flash' column chromatography (heptane/EtOAc=9:1→0:1). Product fractions were collected and evaporated and stripped with $Et_2O$ to give the title compound (33 mg, 0.059 mmol, yield: 64%) as a white solid.

Analysis: LCMS (Method R): $t_R$=1.31 min; m/z calculated for $[M+H]^+$=563.1. found=563.4; $^1H$ NMR (400 MHz, DMSO) δ 9.37 (s, 1H), 7.91 (d, J=8.9 Hz, 1H), 7.33-7.25 (m, 2H), 7.24-7.15 (m, 2H), 7.00 (t, J=7.9 Hz, 1H), 6.86 (t, J=6.4 Hz, 1H), 4.95 (s, 2H), 4.06 (s, 2H), 3.96 (s, 2H), 3.66-3.57 (m, 2H), 3.17 (t, J=5.2 Hz, 2H), 3.06 (s, 3H), 2.93 (s, 3H), 2.52 (d, J=4.9 Hz, 3H).

Example 94

Synthesis of Compound 182

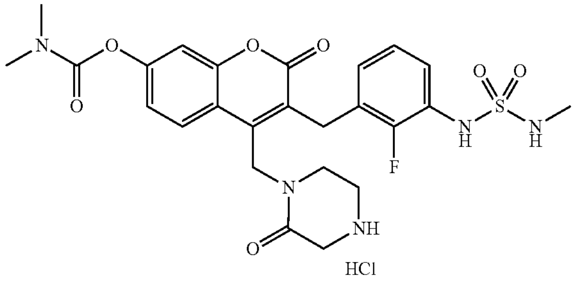

Compound 182 was prepared in two steps:

Step-1: The first step was executed analogous to that of the preparation of compound 180 taking tert-butyl 3-oxopiperazine-1-carboxylate (40 mg, 0.20 mmol, 2.2 eq) instead of the morpholin-3-one giving the Boc-protected intermediate (35 mg, 0.048 mmol, purity: 90%, yield: 52%) as a white solid.

Step-2: The Boc-protected intermediate (32 mg, 0.048 mmol) was dissolved in dry dioxane (2 mL) and 4 N HCl in dioxane (0.48 mL, 1.90 mmol, 40 eq) was added. After 1 h, the volatiles were evaporated and the residue was redissolved in water/MeCN and lyophillized to give the title compound (20 mg, 0.033 mmol, purity: 94%, yield: 70%) as an off-white solid.

Analysis: LCMS (Method T): $t_R$=1.17 min; m/z calculated for $[M+H]^+$=562.1. found=562.4 (free base); $^1H$ NMR (400 MHz, DMSO) δ 9.38 (s, 1H), 9.33 (s, 2H), 7.86 (d, J=8.9 Hz, 1H), 7.33-7.26 (m, 2H), 7.23 (q, J=5.0 Hz, 1H), 7.17 (dd, J=8.8, 2.4 Hz, 1H), 7.01 (t, J=7.9 Hz, 1H), 6.89 (t, J=6.9 Hz, 1H), 4.94 (s, 2H), 4.07 (s, 2H), 3.72 (s, 2H), 3.18 (t, J=5.6 Hz, 2H), 3.06 (s, 3H), 2.93 (s, 3H), 2.52 (d, J=4.9 Hz, 3H).

Example 95

Synthesis of Compound 183

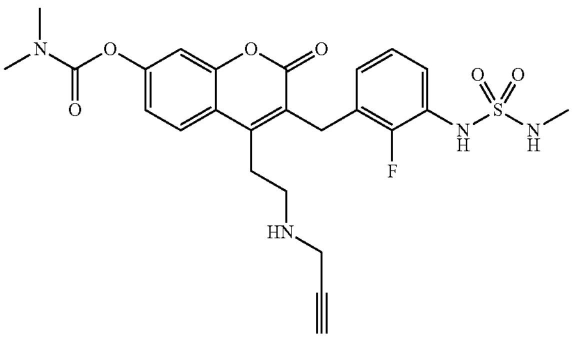

Compound 183 was prepared in one step:

Step 1: To a stirred solution of Compound 17 (30 mg, 0.038 mmol) in N,N-dimethylformamide (1.0 mL), propargylamone (3.1 uL, 0.049 mmol, 1.3 eq) and triethylamine (16 uL, 0.113 mmol, 3 eq) were added. The next day, the mixture was purified with method 'prep base'. Product fractions were lyophillized to obtain the title compound (3.5 mg, 6.60 umol, yield: 17%).

Analysis: LCMS (Method P): $t_R$=1.30 min; m/z calculated for $[M+H]^+$=531.2. found=531.1; 1H NMR (400 MHz, $CDCl_3$) δ 7.67 (d, J=8.6 Hz, 1H), 7.39 (td, J=7.7, 1.8 Hz, 1H), 7.16-7.09 (m, 2H), 7.08-6.90 (m, 2H), 5.05-4.82 (m, 1H), 4.11 (s, 2H), 3.41 (d, J=2.5 Hz, 2H), 3.13 (s, 3H), 3.06-2.97 (m, 5H), 2.81-2.71 (m, 5H), 2.21 (t, J=2.4 Hz, 1H).

Example 96

Synthesis of Compound 184

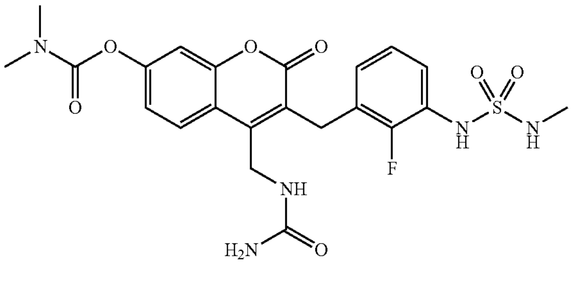

Compound 184 was prepared in one step:

Step 1: To a solution of compound 182 (40 mg, 0.072 mmol) in DCM (2 mL) and triethylamine (80 uL, 0.57 mmol, 8 eq) was added trimethylsilyl isocyanate (77 uL, 0.57 mmol, 8 eq). The next day, the solvents were evaporated and the residue redissolved in DMSO abd purified by method 'prep acid'. Product fractions were lyophillized to obtain the title compound (6.5 mg, 0.012 mmol, yield: 17%).

Example 97

Synthesis of Compound 185

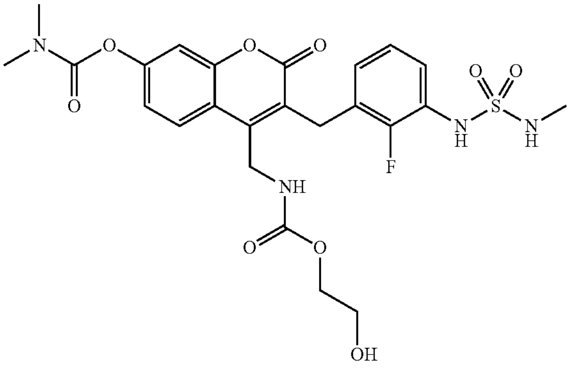

Compound 185 was prepared in three steps:

Step-1: To a solution of bis(4-nitrophenyl) carbonate (500 mg, 1.64 mmol) and triethylamine (344 uL, 2.47 mmol, 1.5 eq) in DCM (10 mL) was slowly added 2-(t-Butyldimethylsiloxy)ethanol. The next day, water was added and the product was extracted with DCM. The extract was dried over brine and sodium sulfate and evaporated. The impure product was purified by column chromatography with method 'flash' (heptane/EtOAc=98:2→6:4) to give 2-((tert-butyldimethylsilyl)oxy)ethyl (4-nitrophenyl) carbonate (360 mg, 1.05 mmol, yield: 64%).

Step-2: To a solution of Compound 181 (40 mg, 0.072 mmol) and triethylamine (30 uL, 0.22 mmol, 3 eq) in dry DMF (2 mL) was added 2-((tert-butyldimethylsilyl)oxy)ethyl (4-nitrophenyl) carbonate (39 mg, 0.11 mmol, 1.5 eq). The next day, the reaction was diluted with water and extracted with EtOAc. The extract was washed with water (2×) and dried over brine and sodium sulfate and evaporated. The impure product was purified by column chromatography with method 'flash' (heptane/EtOAc=8:2→2:8) to give the protected product 3-(2-fluoro-3-((N-methylsulfamoyl)amino)benzyl)-2-oxo (8,8,9,9-tetramethyl-3-oxo-4,7-dioxa-2-aza-8-siladecyl)-2H-chromen-7-yl dimethylcarbamate (25 mg, 0.033 mmol, purity: 89%, yield: 46%).

Step-3: To a solution of the protected product (25 mg, 0.033 mmol) was added 4N HCl in dioxane (92 uL, 0.37 mmol, 10 eq). After 1 h, the solvent was evaporated and the crude product was purified with method 'prep acid' to obtain the title compound (9.6 mg, 0.017 mmol, yield: 46%) as a white solid after lyophilization.

Analysis: LCMS (Method T): $t_R$=1.25 min; m/z calculated for $[M+H]^+$=567.1. found=567.4; $^1H$ NMR (400 MHz, DMSO): δ 9.38 (s, 1H), 7.94 (d, J=8.9 Hz, 1H), 7.85 (t, J=5.7 Hz, 1H), 7.31-7.23 (m, 2H), 7.19 (dd, J=8.8, 2.4 Hz, 1H), 6.97 (t, J=8.0 Hz, 1H), 6.81 (s, 1H), 4.71 (t, J=5.3 Hz, 1H), 4.41 (d, J=5.6 Hz, 2H), 4.12 (s, 2H), 3.96 (t, J=5.1 Hz, 2H), 3.50 (q, J=5.2 Hz, 2H), 3.07 (s, 3H), 2.93 (s, 3H), 2.52 (s, 3H).

Example 98

Synthesis of Compound 186

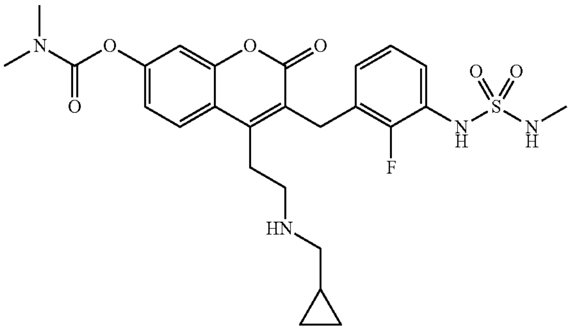

To a stirred solution of Compound 100 (30 mg, 0.055 mmol) in dichloromethane (1.0 mL), Dess-Martin periodane (35 mg, 0.082 mmol, 1.5 eq.) was added at rt. After 1 h, the reaction was quenched with MeOH (1 mL). After 30 min, aminomethylcyclopropane (7.8 mg, 0.11 mmol, 2 eq.) was added. After 20 min, sodium triacetoxy borohydride (46 mg, 0.22 mmol) was added. The next day, sodium borohydride (1.0 mg, 0.27 mmol) was added. After 30 min, the solvent was evaporated and the residue was redissolved in DMSO and purified by method 'prep base'. Product fractions were lyophillized to obtain the title compound (2.7 mg, 4.94 umol, yield: 9%).

Analysis: LCMS (Method P): $t_R$=1.38 min; m/z calculated for $[M+H]^+$=547.2. found=547.2; 1H NMR (400 MHz, $CDCl_3$) δ 7.63 (d, J=8.7 Hz, 1H), 7.42-7.35 (m, 1H), 7.16-7.09 (m, 2H), 7.02 (t, J=7.9 Hz, 1H), 6.94 (t, J=7.0 Hz, 1H), 5.22 (s, 1H), 4.11 (s, 2H), 3.13 (s, 3H), 3.06-2.96 (m, 5H), 2.78 (s, 3H), 2.65-2.58 (m, 2H), 2.43 (d, J=6.9 Hz, 2H), 0.91-0.86 (m, 1H), 0.52-0.44 (m, 2H), 0.13-0.06 (m, 2H).

Example 99

Synthesis of Compound 187

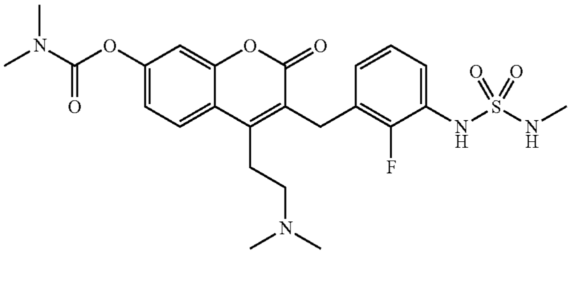

Compound 187 was prepared in one step:

Step 1: To a stirred solution of Compound 100 (30 mg, 0.055 mmol) in dichloromethane (1.0 mL), Dess-Martin periodane (46 mg, 0.109 mmol, 2.0 eq.) was added at rt. After 1 h, the reaction was quenched with MeOH (1 mL). After 30 min, dimethylamine 2M in THF (219 uL, 0.22 mmol, 4 eq.) was added. After 20 min sodium borohydride (27 mg, 0.711 mmol, 13 eq) was added. The next day, solvent was evaporated and the residue was redissolved in DMSO and purified with method 'prep base'. Product fractions were lyophillized to obtain the title compound (2.1 mg, 3.74 umol, purity: 92.6%, yield: 6.8%).

Analysis: LCMS (Method P): $t_R$=1.30 min; m/z calculated for $[M+H]^+$=521.2. found=521.2; 1H NMR (400 MHz, $CDCl_3$) δ 7.59 (d, J=8.7 Hz, 1H), 7.41 (td, J=7.8, 1.7 Hz, 1H), 7.17-7.09 (m, 2H), 7.07-7.00 (m, 1H), 6.99-6.92 (m, 1H), 5.40-5.25 (m, 1H), 4.10 (s, 2H), 3.13 (s, 3H), 3.04 (s, 3H), 2.99-2.90 (m, 2H), 2.78 (d, J=4.5 Hz, 3H), 2.24-2.16 (m, 8H).

Example 100

Synthesis of Compound 188

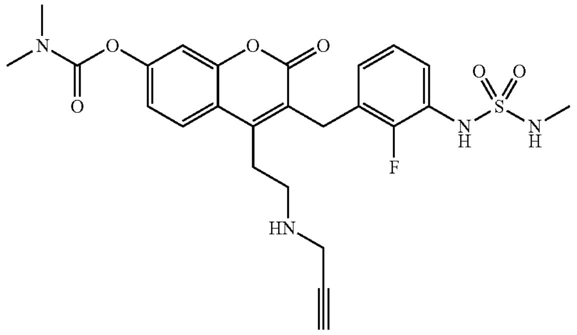

Compound 188 was prepared in one step:

Step 1: To a stirred solution of Compound 17 (30 mg, 0.038 mmol) in N,N-dimethylformamide (1.0 mL), propargylamone (3.1 uL, 0.049 mmol, 1.3 eq) and triethylamine (16 uL, 0.113 mmol, 3 eq) were added. The next day, the mixture was purified with method 'prep base'. Product fractions were lyophillized to obtain the title compound (3.5 mg, 6.60 umol, yield: 17%).

Analysis: LCMS (Method P): $t_R$=1.30 min; m/z calculated for $[M+H]^+$=531.2. found=531.1; 1H NMR (400 MHz, $CDCl_3$) δ 7.67 (d, J=8.6 Hz, 1H), 7.39 (td, J=7.7, 1.8 Hz, 1H), 7.16-7.09 (m, 2H), 7.08-6.90 (m, 2H), 5.05-4.82 (m, 1H), 4.11 (s, 2H), 3.41 (d, J=2.5 Hz, 2H), 3.13 (s, 3H), 3.06-2.97 (m, 5H), 2.81-2.71 (m, 5H), 2.21 (t, J=2.4 Hz, 1H).

Example 101

Synthesis of Compound 189

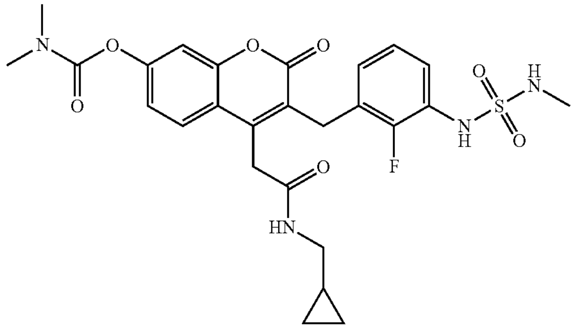

Compound 189 was prepared in one step:

Step 1: The amide-product was formed by amide-coupling of Compound C.6 (20 mg, 0.039 mmol) with the respective amines (1.2 eq) using EDC-HCl (1.1 eq) and HOAt (0.2 eq) in DCM. After reaction, the DCM was evaporated and the residues were redissolved in DMSO and purified with method 'prep base'. The products were obtained as solids after evaporation under vacuum at 40° C. in a Genevac™.

Example 102

Synthesis of Compound 190

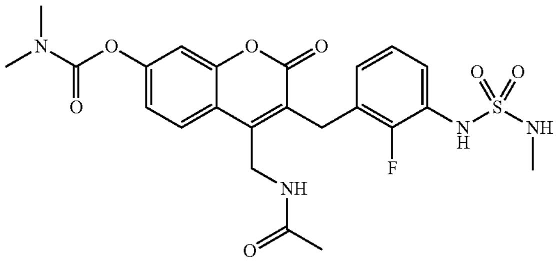

Compound 190 was prepared in one step:

Step 1: The amide-products were formed by amide-coupling of Compound 182-HBr salt (34 mg, 0.047 mmol) with the respective acids (1.4 eq) using EDC-HCl (1.1 eq) and Ethyl cyano(hydroxyimino)acetate (0.2 eq) abd triethylamine 3 eq) in DCM. After reaction, the DCM was evaporated and the residues were redissolved in DMSO and purified with method 'prep base'. The products were obtained as solids after evaporation under vacuum at 40° C. in a Genevac™.

Analysis: LCMS (Method T): $t_R$=1.27 min; m/z calculated for $[M+H]^+$=521.1. found=521.2; $^1$H NMR (400 MHz, $CDCl_3$) δ 7.68 (d, J=8.7 Hz, 1H), 7.38 (td, J=7.8, 1.7 Hz, 1H), 7.14 (d, J=2.3 Hz, 1H), 7.10 (dd, J=8.7, 2.4 Hz, 1H), 7.02 (t, J=6.5 Hz, 1H), 6.94 (t, J=6.5 Hz, 1H), 6.64 (s, 1H), 5.53 (t, J=5.2 Hz, 1H), 4.90 (q, J=5.3 Hz, 1H), 4.62 (d, J=5.4 Hz, 2H), 4.14 (s, 2H), 3.13 (s, 3H), 3.03 (s, 3H), 2.78 (d, J=5.2 Hz, 3H), 1.83 (s, 3H).

Example 103

Synthesis of Compound 191

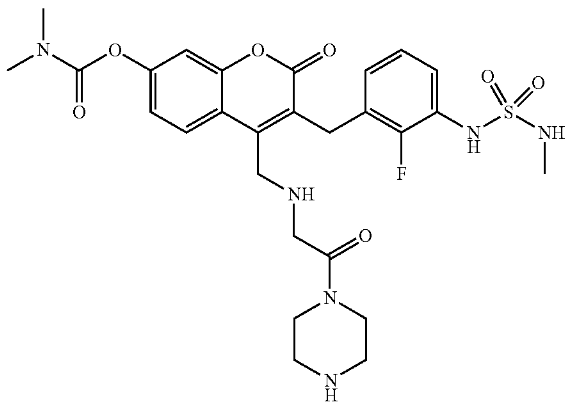

Compound 191 was prepared in three steps:

Step 1: 4-(bromomethyl)-3-(2-fluoro-3-((N-methylsulfamoyl)amino)benzyl)-2-oxo-2H-chromen-7-yl dimethylcarbamate (900 mg, 1.00 mmol) and triethylamine (416 uL, 3.00 mmol, 3 eq) was stirred in DCM (5 mL) and tert-butyl glycinate (680 uL, 5.00 mmol, 5 eq) was added. The next day, water was added and the product was extracted with DCM (2×). The combined extract was dried over brine and sodium sulfate and evaporated. The residue was redissolved in 1 mL of DCM and purified by column chromatography with method 'flash' (heptane/EtOAc=0:0→3:7) to obtain the intermediate tert-butylester (480 mg, 0.61 mmol, purity: 75%, yield: 61%).

Step 2: The intermediate of the previous step (480 mg, 0.61 mmol) was stirred in 4 N HCl in dioxane (7.6 mL, 30.4 mmol, 50 eq). The next day, the volatiles were evaporated and the residue was stripped with DCM to give the glyceryl HCl-salt (540 mg, 0.57 mmol, purity: 60%, yield: 93%) as an off-white solid. This was used as such.

Step 3: The amide-product was formed by glyceryl HCL-salt of step 2 (20 mg, 0.041 mmol) with the respective amines (1.2 eq) using HATU (1.2 eq) and DIPEA (4 eq) in DMF. After reaction, the reaction solutions were purified with method 'prep base'. The products were obtained as solids after evaporation under vacuum at 40° C. in a Genevac™.

Analysis: LCMS (Method P): $t_R$=1.06 min; m/z calculated for $[M+H]^+$=605.2. found=605.1; 1H NMR (400 MHz, $CDCl_3$) δ 7.99 (d, J=8.6 Hz, 1H), 7.43-7.36 (m, 1H), 7.15-7.08 (m, 2H), 7.05-6.96 (m, 2H), 5.02 (s, 1H), 4.15 (s, 2H), 3.96 (s, 2H), 3.58 (t, J=5.2 Hz, 2H), 3.37 (s, 2H), 3.31-3.23 (m, 2H), 3.13 (s, 3H), 3.03 (s, 3H), 2.89-2.79 (m, 4H), 2.74 (s, 3H).

Example 104

Synthesis of Compound 205

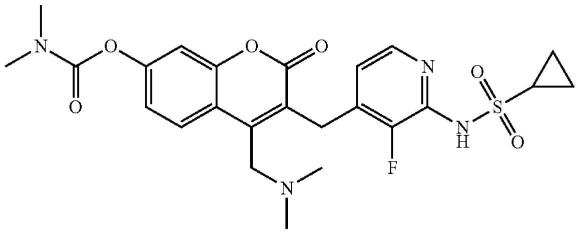 [SMILES: CN(C)Cc1c(Cc2ccnc(NS(=O)(=O)C3CC3)c2F)c(=O)oc2cc(OC(=O)N(C)C)ccc12]

Compound 205 was prepared in 3 steps:

Step 1: To a solution of 3-((2-chloro-3-fluoropyridin-4-yl)methyl)-4-methyl-2-oxo-2H-chromen-7-yl dimethylcarbamate (0.5 g, 1.279 mmol, 1.0 eq.) and ethanesulfonamide (1.41 g, 12.92 mmol, 10.1 eq.) in 1,4-dioxane (0.1 M) under inert atmosphere were added Xantphos (0.148 g, 0.256 mmol, 0.2 eq.), cesium carbonate (0.625 g, 1.919 mmol, 1.5 eq.) and PdOAc2 (0.049 g, 0.218 mmol, 0.17 eq.). The formed reaction mixture was stirred for 24 hours at 100° C. The reaction mixture was filtered over celite and washed with $H_2O$ and $CH_2Cl_2$. The layers of the filtrate were separated and the organic layer was washed with brine. Dried over $Na_2SO_4$, filtered and concentrated under reduced pressure. The impure product was purified by column chromatography with method 'flash' ($CH_2Cl_2$/MeOH=1:0→9:1). The still impure product was purified by prep basic to obtain 3-((2-(ethylsulfonamido)-3-fluoropyridin-4-yl)methyl)-4-methyl-2-oxo-2H-chromen-7-yl dimethylcarbamate (32 mg, 0.068 mmol, yield: 5.3%) as an off-white solid.

Step 2: Following the procedure of the general synthesis of Compound E.4 using NBS. The reaction was quenched with 1N $H_2SO_4$ and the THF was removed under reduced pressure. The product was extracted with EtOAc. Combined organic layers were washed with brine, dried over $Na_2SO_4$, filtered and concentrated under reduced pressure to obtain the corresponding bromine (42 mg, 0.046 mmol, yield: 64%, purity: 59%) as a sticky yellow solid.

Step 3: Following the procedure of the general synthesis of Compound E.5 starting with 33 mg, 0.040 mmol of bromine and dimethylamine 2M in MeOH. The impure product was purified prep acid to obtain the title compound (8.4 mg, 0.016 mmol, yield: 40%) as a white solid.

Yield: Compound 205 was isolated as a white solid (1% over 3 steps).

Analysis: LCMS (Method L): $t_R$=2.32 min; m/z calculated for $[M+H]^+$=519.2. found=519.2; 1H NMR (400 MHz, DMSO-d6) δ 8.25 (s, 1H), 8.08 (d, J=8.9 Hz, 1H), 7.78 (s, 1H), 7.24 (d, J=2.3 Hz, 1H), 7.15 (dd, J=8.8, 2.4 Hz, 1H), 6.57 (s, 1H), 4.03 (s, 2H), 3.65 (s, 2H), 3.07 (s, 3H), 2.93 (s, 3H), 2.21 (s, 7H), 0.92 (d, J=41.0 Hz, 4H).

Example 105

Synthesis of Compound 228

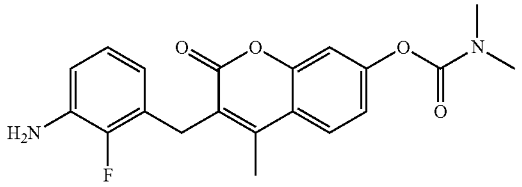 [SMILES: Cc1c(Cc2cccc(N)c2F)c(=O)oc2cc(OC(=O)N(C)C)ccc12]

Compound 228 was prepared in 3 steps:

Step 1: Starting from ethyl 2-(2-fluoro-3-nitrobenzyl)-3-oxobutanoate 3 (48.9 g, 173 mmol) and resorcinol (1.04 eq.) following the general synthesis of Compound 4. After the filtration the residue was stirred in a aq. Sat. $NaHCO_3$ solution until bubbling had stopped. The suspension was again filtered washed with water, $Et_2O$ and dried to obtain the corresponding coumarin 5 (50.3 g, 153 mmol, yield: 98%) as a yellow solid.

Step 2: Following the general synthesis of Compound 5 to obtain the corresponding dimethylcarbamate 6 (70.7 g, 166 mmol, yield: 109%) as a yellow solid.

Step 3: Following procedure General Procedure C, with Pd/C and EtOH/THF 1:2 (0.05 M) as solvents to obtain the title compound (50.83 g, 130 mmol, yield: 77%) as a light pink solid.

Yield: Compound 228 was isolated as a white solid (43% over 3 steps)

Analysis: LCMS (Method U): $t_R$=1.95 min; m/z calculated for $[M+H]^+$=371.1. found=371.2.

Example 106

Synthesis of Compound 227

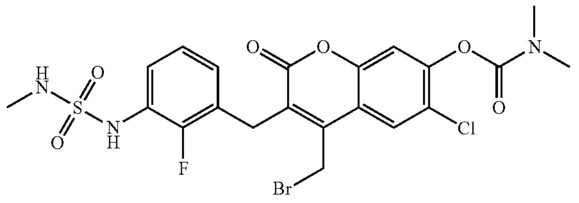

Compound 229 was prepared in 5 steps:

Step 1: Starting from ethyl 2-(2-fluoro-3-nitrobenzyl)-3-oxobutanoate 3 (1.0 g, 3.53 mmol) and 4-chlorobenzene-1,3-diol (1.20 eq.) following the general synthesis of Compound 4 to obtain the corresponding coumarin 5 (0.95 g, 2.57 mmol, yield: 73%) as an off white solid.

Step 2: Following the general synthesis of Compound 5 to obtain the corresponding dimethylcarbamate 6 (0.88 g, 1.95 mmol, yield: 75%) as a light yellow solid.

Step 3: Following the general synthesis of Compound 6 to obtain the corresponding primary amine 7 (0.51 g, 1.22 mmol, yield: 60%) as a light yellow solid.

Step 4: Following the general synthesis of Compound 7 to obtain the corresponding sulfamoyl 8 (0.54 g, 1.03 mmol, yield: 81%) as a beige solid.

Step 5: Following procedure the general synthesis of Compound 8, starting with 280 mg, 0.56 mmol of 8 and using NBS to obtain the title compound (0.17 g, 0.12 mmol, purity: 40%, yield: 20%) as an off white solid.

Yield: Compound 229 was isolated as an off white solid (5% over 5 steps).

Analysis: LCMS (Method I): $t_R$=2.06 min; m/z calculated for $[M+H_2O]^+$=574.0/576.0. found=573.9/575.9.

Example 107

Synthesis of Compound 228

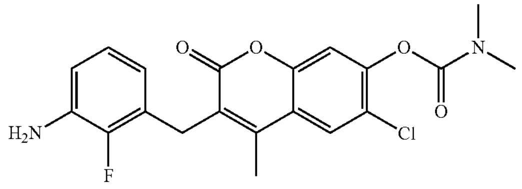

Compound 230 was prepared in 3 steps:

Step 1: Starting from ethyl 2-(2-fluoro-3-nitrobenzyl)-3-oxobutanoate 3 (1.0 g, 3.53 mmol) and 4-chlorobenzene-1,3-diol (1.20 eq.) following the general synthesis of Compound 4 to obtain the corresponding coumarin 5 (0.95 g, 2.57 mmol, yield: 73%) as an off white solid.

Step 2: Following the general synthesis of Compound 5 to obtain the corresponding dimethylcarbamate 6 (0.88 g, 1.95 mmol, yield: 75%) as a light yellow solid.

Step 3: Following the general synthesis of Compound 6 to obtain the title compound (0.51 g, 1.22 mmol, yield: 60%) as a light yellow solid.

Yield: The title compound was isolated as a white solid (33% over 3 steps).

Analysis: LCMS (Method U): $t_R$=2.08 min; m/z calculated for $[M+H]^+$=405.1/407.1. found=405.1/407.1.

Example 108

Synthesis of Compound 229

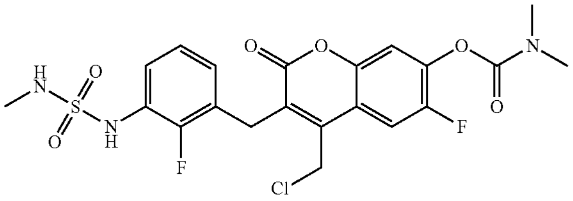

Compound 231 was prepared in 5 steps:

Step 1: Starting from ethyl 2-(2-fluoro-3-nitrobenzyl)-3-oxobutanoate 3 (2.0 g, 7.06 mmol) and 4-fluorobenzene-1,3-diol (1.20 eq.) following the general synthesis of Compound 4 to obtain the corresponding coumarin 5 (2.85 g, 8.13 mmol, yield: 115%) as an off white solid.

Step 2: Following the general synthesis of Compound 5. With a reaction time of 2.5 days, to obtain the corresponding dimethylcarbamate 6 (2.28 g, 5.01 mmol, purity: 92%, yield: 61%) as a beige solid.

Step 3: Following the general synthesis of Compound 6 to obtain the corresponding primary amine 7 (1.28 g, 3.11 mmol, yield: 57%) as a light yellow solid.

Step 4: Following the general synthesis of Compound 7. After filtration the impure product was purified by column chromatography with method 'flash' ($CH_2Cl_2$/MeOH=1:0→97:3) to obtain the corresponding sulfamoyl 8 (1.04 g, 2.15 mmol, yield: 65%) as a beige solid.

Step 5: Following the general synthesis of Compound 8, using NCS and without flash column chromatography to obtain the title compound (1.22 g, 2.13 mmol, purity: 90%, yield: 98%) as an off-white solid.

Yield: The title compound was isolated as an off-white solid (25% over 5 steps)

Analysis: LCMS (Method I): $t_R$=2.06 min; m/z calculated for $[M+H_2O]$+=533.1/535.1. found=533.1/535.0.

Example 109

Synthesis of Compound 230

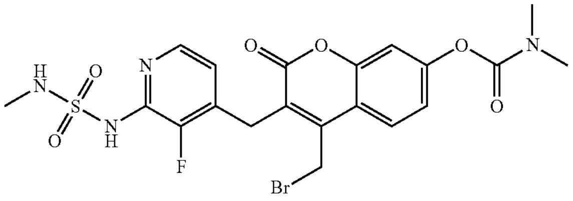

Compound 232 was prepared in 5 steps:

Step 1: Starting from ethyl 2-((2-chloro-3-fluoropyridin-4-yl)methyl)-3-oxobutanoate (10.0 g, 24.12 mmol) and resorcinol (2.00 eq.) following the general synthesis of Compound D.4. Instead of perchloric acid, sulfuric acid was used. After complete conversion the reaction mixture was cooled (0° C.) and quenched with sat. aq. $NaHCO_3$ till basic pH. The formed white suspension was washed with water, $Et_2O$ and dried to obtain the corresponding coumarin (8.61 g, 23.4 mmol, yield: 97%, purity: 87%) as an off-white solid.

Step 2: Following the general synthesis of Compound D.5 to obtain the corresponding dimethylcarbamate (9.33 g, 23.16 mmol, yield: 99%) as a beige solid.

Step 3: Following the general synthesis of Compound D.6, starting with 0.7 g, 1.79 mmol of compound D.5. In the second step first 4N HCl in 1,4-dioxane was used but later TFA was added to give full conversion. After concentrating the reaction mixture the residue was coated onto hydro matrix and purified by column chromatography with method 'flash' ($CH_2Cl_2$/MeOH+1.5% (v/v) $Et_3N$=1:0→9:1) to obtain the corresponding primary amine (0.37 g, 0.986 mmol, yield: 55%) as a beige solid.

Step 4: Following the general synthesis of Compound D.7. After full conversion the reaction mixture was quenched with water. The product was extract with EtOAc, combined organic layers were washed with brine, dried over $Na_2SO_4$, filtered and concentrated under reduced pressure. The impure product was purified by column chromatography with method 'flash' ($CH_2Cl_2$/MeOH=1:0→9:1) to obtain the corresponding sulfamoyl 0.236 g, 0.462 mmol, yield: 49%) as a green/white solid.

Step 5: Following the general synthesis of Compound D.8, using NBS and with the exception that 1N $H_2SO_4$ was used instead of 1N HCl to quench the reaction, to obtain the title compound (0.265 g, 0.341 mmol, yield: 67%, purity: 70%) as a yellow sticky solid.

Yield: The title compound was isolated as sticky yellow solid (17% over 5 steps)

Analysis: LCMS (Method K): $t_R$=1.91 min; m/z calculated for $[M+H]^+$=543.0/545.0. found=543.0/545.0.

Example 110

Synthesis of Compound 231

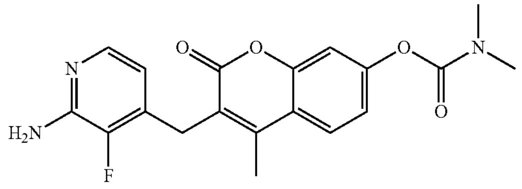

Compound 233 was prepared in 3 steps:

Step 1: Starting from ethyl 2-((2-chloro-3-fluoropyridin-4-yl)methyl)-3-oxobutanoate (10.0 g, 24.12 mmol) and resorcinol (2.00 eq.) following the general synthesis of Compound D.4. Instead of perchloric acid, sulfuric acid was used. After complete conversion the reaction mixture was cooled (0° C.) and quenched with sat. aq. $NaHCO_3$ till basic pH. The formed white suspension was washed with water, $Et_2O$ and dried to obtain the corresponding coumarin (8.61 g, 23.4 mmol, yield: 97%, purity: 87%) as an off white solid.

Step 2: Following the general synthesis of Compound D.5 to obtain the corresponding dimethylcarbamate (9.33 g, 23.16 mmol, yield: 99%) as a beige solid.

Step 3: Following the general synthesis of Compound D.6, starting with 0.7 g, 1.79 mmol of compound D.5. In the second step first 4N HCl in 1,4-dioxane was used but later TFA was added to give full conversion. After concentrating the reaction mixture the residue was coated onto hydro matrix and purified by column chromatography with method 'flash' ($CH_2Cl_2$/MeOH+1.5% (v/v) $Et_3N$=1:0→9:1) to obtain the compound 108 (0.37 g g, 0.986 mmol, yield: 55%) as a beige solid.

Yield: The title compound was isolated as a beige solid (53% over 3 steps)

Analysis: LCMS (Method I): $t_R$=1.85 min; m/z calculated for $[M+H]^+$=372.1. found=372.1.

Example 111

Synthesis of Compound 22

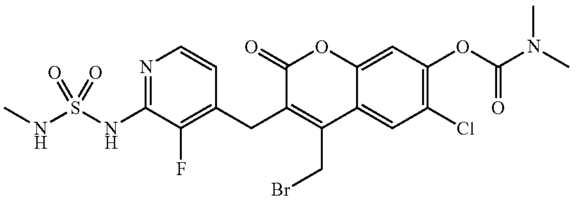

Compound 234 was prepared in 5 steps:

Step 1: Starting from ethyl 2-((2-chloro-3-fluoropyridin-4-yl)methyl)-3-oxobutanoate (15.0 g, 46.0 mmol) and 4-chlorobenzene-1,3-diol (1.20 eq.) following the general synthesis of Compound D.4. After complete reaction water was added and the formed suspension was filtered. The residue co-evaporated with EtOH and triturated in EtOH/$Et_2O$. The solids were filtered off to obtain the corresponding coumarin (4.8 g, 13.55 mmol, yield: 29%) as a white solid.

Step 2: Following the general synthesis of Compound D.5 to obtain the corresponding dimethylcarbamate (5.48 g, 11.86 mmol, yield: 87%, purity: 92%) as a light yellow solid.

Step 3: Following the general synthesis of Compound D.6, starting with 1.0 g, 2.35 mmol of compound. The deprotection with TFA was not performed. The reaction mixture was filtered and concentrated under reduced pressure. The impure product was purified by column chromatography with method 'flash' (heptane/EtOAc 9:1→1:4) to obtain the corresponding primary amine (0.12 g, 0.281 mmol, yield: 12%) as a beige solid.

Step 4: Following the general synthesis of Compound D.7. After full conversion the reaction mixture was quenched with water. The product was extract with EtOAc, combined organic layers were washed with brine, dried over $Na_2SO_4$, filtered and concentrated under reduced pressure. The impure product was purified by column chromatography with method 'flash' ($CH_2Cl_2$/MeOH=1:0→96:4) to obtain the corresponding sulfamoyl (0.100 g, 0.198 mmol, yield: 67%) as a clear oil.

Step 5: Following the general synthesis of Compound D.8, starting with 200 mg, 0.401 mmol of D.7 and using NBS. For work-up the reaction mixture was quenched with potassium hydrogen sulfate (0.5 M) at −78° C. Some extra water was added and the product was extracted with EtOAc. Combined organic layers were washed with brine, dried over $Na_2SO_4$, filtered and concentrated under reduced pressure to obtain the Compound 109 (0.151 g, 0.055 mmol, yield: 14%, purity: 21%) as a yellow oil.

Yield: The title compound was isolated as a beige solid (0.3% over 5 steps)

Analysis: LCMS (Method I): $t_R$=1.77 min; m/z calculated for $[M+H]^+$=577.0/579.0. found=576.9/578.9.

Example 112

Synthesis of Compound 233

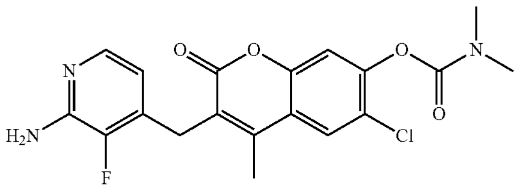

Compound 235 was prepared in 3 steps:

Step 1: Starting from ethyl 2-((2-chloro-3-fluoropyridin-4-yl)methyl)-3-oxobutanoate (15.0 g, 46.0 mmol) and 4-chlorobenzene-1,3-diol (1.20 eq.) following the general synthesis of Compound D.4. After complete reaction water was added and the formed suspension was filtered. The residue co-evaporated with EtOH and triturated in EtOH/$Et_2O$. The solids were filtered off to obtain the corresponding coumarin (4.8 g, 13.55 mmol, yield: 29%) as a white solid.

Step 2: Following the general synthesis of Compound D.5 to obtain the corresponding dimethylcarbamate (5.48 g, 11.86 mmol, yield: 87%, purity: 92%) as a light yellow solid.

Step 3: Following the general synthesis of Compound D.6, starting with 1.0 g, 2.35 mmol of compound D.5. The deprotection with TFA was not performed. The reaction mixture was filtered and concentrated under reduced pressure. The impure product was purified by column chromatography with method 'flash' (heptane/EtOAc 9:1→1:4) to obtain the title compound (0.12 g, 0.281 mmol, yield: 12%) as a beige solid.

Yield: The title compound was isolated as a beige solid (3% over 3 steps)

Analysis: LCMS (Method I): $t_R$=1.92 min; m/z calculated for $[M+H]^+$=406.1/408.1. found=406.0/408.0.

Example 113

Synthesis of Compound 234

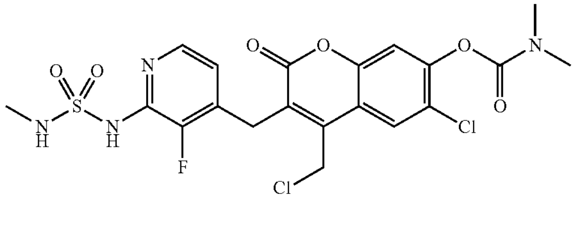

Compound 236 was prepared in 5 steps:

Step 1: Starting from ethyl 2-((2-chloro-3-fluoropyridin-4-yl)methyl)-3-oxobutanoate (15.0 g, 46.0 mmol) and 4-chlorobenzene-1,3-diol (1.20 eq.) following the general synthesis of Compound D.4. After complete reaction water was added and the formed suspension was filtered. The residue co-evaporated with EtOH and triturated in EtOH/$Et_2O$. The solids were filtered off to obtain the corresponding coumarin (4.8 g, 13.55 mmol, yield: 29%) as a white solid.

Step 2: Following the general synthesis of Compound D.5 to obtain the corresponding dimethylcarbamate (5.48 g, 11.86 mmol, yield: 87%, purity: 92%) as a light yellow solid.

Step 3: Following the general synthesis of Compound D.6, starting with 1.0 g, 2.35 mmol of compound D.5. The deprotection with TFA was not performed. The reaction mixture was filtered and concentrated under reduced pressure. The impure product was purified by column chromatography with method 'flash' (heptane/EtOAc 9:1→1:4) to obtain the corresponding primary amine (0.12 g, 0.281 mmol, yield: 12%) as a beige solid.

Step 4: Following the general synthesis of Compound D.7. After full conversion the reaction mixture was quenched with water. The product was extract with EtOAc, combined organic layers were washed with brine, dried over $Na_2SO_4$, filtered and concentrated under reduced pressure. The impure product was purified by column chromatography with method 'flash' ($CH_2Cl_2$/MeOH=1:0→96:4) to obtain the corresponding sulfamoyl (0.100 g, 0.198 mmol, yield: 67%) as a clear oil.

Step 5: Following the general synthesis of Compound D.8, starting with 80 mg, 0.16 mmol of D.7 and using NCS to obtain the title compound (0.044 g, 0.064 mmol, yield: 40%, purity: 77%) as a beige solid.

Yield: Compound 236 was isolated as a beige solid (1% over 5 steps)

Analysis: LCMS (Method I): $t_R$=1.76 min; m/z calculated for $[M+H]^+$=561.2/563.2. found=561.0/563.0.

Example 114

Synthesis of Compound 235

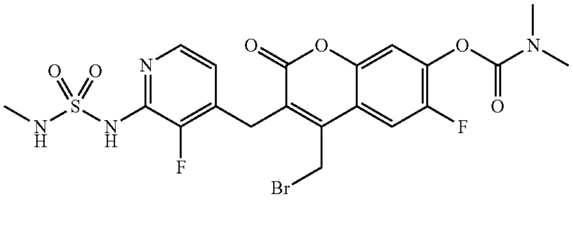

Compound 237 was prepared in 5 steps:

Step 1: Starting from ethyl 2-((2-chloro-3-fluoropyridin-4-yl)methyl)-3-oxobutanoate (6.0 g, 18.42 mmol) and 4-fluorobenzene-1,3-diol (1.27 eq.) following the general synthesis of Compound D.4. After complete reaction water was added and the formed suspension was filtered. The residue co-evaporated with EtOH and triturated in EtOH/$Et_2O$. The solids were filtered off to obtain the corresponding coumarin (1.89 g, 4.53 mmol, yield: 25%, purity: 81%) as an off white solid.

Step 2: Following the general synthesis of Compound D.5, starting with 2.0 g, 5.92 mmol of coumarin. After full conversion the reaction mixture was poured into 0.1 M HCl. The formed suspension was filtered, and the residue was co-evaporated with EtOH. The residue was triturated with DIPE overnight and filtered to obtain the corresponding dimethylcarbamate (1.54 g, 3.77 mmol, yield: 64%) as a beige solid.

Step 3: Following the general synthesis of Compound D.6, starting with 0.75 g, 1.83 mmol of compound D.5. The deprotection with TFA was stirred for 48 hours. The reaction mixture was poured into sat. aq. $NaHCO_3$ and was extracted with EtOAc. The combined organic layers were washed with brine, dried over $Na_2SO_4$, filtered and concentrated under reduced pressure to obtain a yellow oil. The product was purified by column chromatography with method 'flash' (MeOH/DCM 1:0→96:4) to obtain a yellow oil. This was dissolved in $CH_2Cl_2$ (0.12 M) and TFA (5.0 eq) was added and stirred for 1 hour at rt. The reaction mixture was concentrated and twice stripped with $CH_2Cl_2$ to obtain the corresponding primary amine (0.45 g, 1.05 mmol, yield: 58%, purity: 91%) as a yellow solid.

Step 4: Following the general synthesis of Compound D.7. After full conversion the reaction mixture was quenched with sat. aq. $NH_4Cl$. The product was extract with EtOAc, combined organic layers were washed with brine, dried over $Na_2SO_4$, filtered and concentrated under reduced pressure. The impure product was purified by column chromatography with method 'flash' (heptane/EtOAc 9:1→0:1) to obtain the corresponding sulfamoyl 17 (0.100 g, 0.203 mmol, yield: 17%) as a yellow solid.

Step 5: Following the general synthesis of Compound D.8. Reaction was quenched with 1 M sulfuric acid instead of 1 M HCl. After extraction the compound was purified by column chromatography with method 'flash' (heptane/EtOAc 9:1→0:1 to obtain the title compound (0.10 g, 0,102 mmol, yield: 49%, purity: 57%) as a beige solid.

Yield: Compound 237 was isolated as a beige solid (1% over 5 steps)

Analysis: LCMS (Method I): $t_R$=1.91 min; m/z calculated for $[M+H]^+$=533.0/535.0. found=533.0/535.0.

Example 115

Materials & Methods

Media components, reagents and buffers for Western Blot: All cell culture media components were obtained from ThermoFisher Scientific. Cell lysis/Protein Extraction Reagent (Cell Signal Technology, Cat No: 9803). 20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM Na, $VO_4$, 1 μg/ml leupeptin, Protease inhibitors (Roche, Cat no. 11873580001), Phosphatase inhibitors (Cell Signaling Technologies, Cat No. 5870). Coomassie protein assay reagent (ThermoFisher Scientific, Cat. No. 1856209). Laemmli sample loading 4× buffer (ThermoFisher Scientific, Cat No. NP0007). MOPS/SDS electrophoresis running buffer (GenScript, Cat No. M00138). Tris-buffered saline with Tween 20 (TBST buffer): 20 mM Tris-HCl (pH 7.5), 150 mM NaCl, 0.1% Tween 20 NuPAGE gels, 4-12% (ThermoFisher Scientific, Cat No. NP0322BOX). iBLOT nitrocellulose transfer kit (ThermoFisher Scientific Cat No. IB301002). Blocking Buffer (LICOR Cat No. 927-50000).

Antibodies: Phospho-STAT3 (S727), mouse polyclonal antibodies were obtained from BD Biosciences (Cat No. 612542), following 5 antibodies were obtained from Cell Signaling Technologies. Anti-STAT3, rabbit monoclonal antibodies (Cat No. 12640), Anti-phospho-MEK1/2 (S218/S222), rabbit polyclonal antibodies (Cat No: 9121), Anti MEK-1/2, rabbit monoclonal antibodies (Cat No: 9122), Anti-ERK, mouse monoclonal antibodies (Cat No: 9107), and Anti-phospho-ERK, rabbit monoclonal antibodies (Cat No. 4377).

Secondary antibodies: IRDye 800CW goat anti-rabbit antibodies (LICOR Cat No. 926-32211), IRDye 680RD goat anti-rabbit antibodies (LICOR Cat No. 926-68071), IRDye 800CW goat anti-mouse antibodies (LICOR Cat No. 926-32210) and IRDye 680RD goat anti-mouse antibodies (LICOR Cat No. 926-68070).

Tumor Cell Lines: Cell Lines and Tissue Culture conditions: The A549 (Cat No. CCL-185) cell line was obtained from American Type Culture Collection (ATCC) and grown in T75 flasks in DMEM containing 10% FBS and Pen-Strep at 37° C. in a humidified, 5% $CO_2$ incubator.

The Colon26 syngeneic adenocarcinoma cell line was obtained from the National Cancer Institute. Colon26 tumor cells were maintained as exponentially growing cultures in RPMI-1640 medium containing 10% fetal bovine serum, 2 mM glutamine, 100 units/mL penicillin G sodium, 100 μg/mL streptomycin sulfate, 25 ∫ g/mL gentamicin, 10 mM HEPES, and 0.075% sodium bicarbonate. The tumor cells were grown in tissue culture flasks in a humidified incubator at 37° C., in an atmosphere of 5% CO2 and 95% air.

Subculture conditions: Adherent cells were grown to approximately 90% confluency, culture medium was aspirated and the cell layer was rinsed with PBS. Two mL trypsin solution (0.25%) was added to the flask and observed under an inverted microscope until cell layer is dispersed. Eight mL media was added, cells were spun down at 1000×g for 5 minutes. Cell pellet was re-suspended in 10 mL media and an appropriate volume was inoculated into a new culture flask.

Compound (drug) treatment: Cells were plated in a 6-well plate at a density of 250,000-300,000 cells/well in 3 mL media and incubated 37.0 in a humidified, 5% $CO_2$ incubator. Next day, 10 mM stock solutions of compounds were diluted 10- and 100-fold in DMSO to yield 100 and 10 uM solutions, respectively. These solutions were added to the cells (3 uL/well), mixed by swirling the plate, and incubated at 37° C. in a humidified, 5% $CO_2$ incubator for 2 hours.

Cell lysis and protein estimation: Cells were washed with PBS, and scraped in 50 uL of lysis buffer containing protease and phosphatase inhibitors. Cell lysates were stored at −20° C. Cell lysates were thawed and spun at 12,000 rpm for one minute, 3 ul of the supernatant was added to 500 uL of Coomassie blue reagent following by 500 uL of water. Absorbance was read at 595 nm after 10 minutes of incubation. Protein standards were used (0-20 mg/mL) to calculate protein concentrations of test samples.

Western Blotting: For electrophoresis 20 ug of protein was mixed with 5 ul of 4× Laemmle's sample buffer and 1 ul of 0.4 M DTT in a volume of 20 ul made up with lysis buffer. All samples were heated at 95° C. for 5 minutes, cooled to room temperature and spun down. Protein samples were loaded onto 4-12% polyacrylamide gels and run at 100V for approximately 1.5 hours till the blue dye reached the bottom. After the run, gel was removed and protein transfer was done using iBlot for 7 minutes, as per manufacturer's recommendations. After the transfer, nitrocellulose membrane was incubated on a shaker in 5 mL of blocking buffer at room temperature for 1 hr. The blot was then incubated overnight on a shaker in 5 ml of blocking buffer containing 0.2% Tween-20 and primary antibody, at room temperature. Anti-phospho-STAT3 antibody was used at a dilution of 1:500, the other 3 primary antibodies were used at a dilution of 1:1000.

Next day, the blot was washed 3 times for 10 min each with 10 mL of TBST followed by incubation on a shaker in 5 ml of blocking buffer containing 0.2% Tween-20 and 0.5 ul of the IRDye labeled secondary antibodies, diluted 1:10000, at room temperature for 1 hr. The blot was then washed 3 times for 10 min each with 10 mL of TBST and dried between sheets of paper towels. Imaging was done using LICOR's Odyssey imaging system, quantitation was done using their software, Image Studio version 3.1.

Animal Studies: Female BALB/c mice (BALB/cAnNCrl, Charles River) were eleven weeks old on Day 1 of the study and had a body weight (BW) range of 15.8 to 21.4 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. Charles River Discovery Services North Carolina (CR Discovery Services) specifically complies with the recommendations of the *Guide for Care and Use of Laboratory Animals* with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

In Vivo Implantation and Growth: Colon26 tumor cells used for implantation were harvested during log phase growth and re-suspended at a concentration of $1\times10^7$ cells/mL in cold phosphate buffered saline (PBS). Each mouse was injected subcutaneously in the right flank with $1\times10^6$ tumor cells (in a 0.1 mL cell suspension). The tumors were measured with a caliper in two dimensions to monitor size as the mean volume approached the desired 80 to 120 mm3 range. Tumor size was calculated using the formula: Tumor volume ($mm^3$)=$w^2\cdot l$)/2, where w=width and l=length, in mm, of a tumor. Tumor weight may be estimated with the assumption that 1 mg is equivalent to 1 $mm^3$ of tumor volume. Tumors were measured with a caliper twice weekly for the duration of the study.

Treatment: Tumor bearing BALB/c mice were randomized into treatment groups once target range was reached (n=5 per group). All treatments were administered orally (p.o.) once a day for fourteen days (QD×14) in a volume of 10 mL/kg (0.2 mL per 20 g mouse), adjusted to the BW of each animal.

Sampling for Pharmacokinetic analysis: Blood, skeletal muscle, livers and tumors were collected from three animals each from the designated groups two hours after animals received a single dose. Full blood volume was collected by terminal cardiac puncture under isoflurane anesthesia, processed for plasma and the presence of $K^2$EDTA anti-coagulant and stored at −80° C. Skeletal muscle groups composed of right and left gastrocnemius, tibialis and soleus muscles were collected as a unit, snap frozen and stored at −80° C. Livers were collected were snap frozen and shipped to CRL-Worcester for bioanalytical analysis. Sample inventories are appended.

Data Analysis: Tumors were measured using calipers twice per week with the data being expressed as either median+/−interquartile range or as individual plots in days. Tumor growth inhibition (TGI) was calculated as follows: % TGI=1−(T/C)×100, where: T=median Tumor volume for a treatment group, and C=median Tumor volume for the designated control group.

Example 116

Pharmacokinetic Properties

Figure 3:
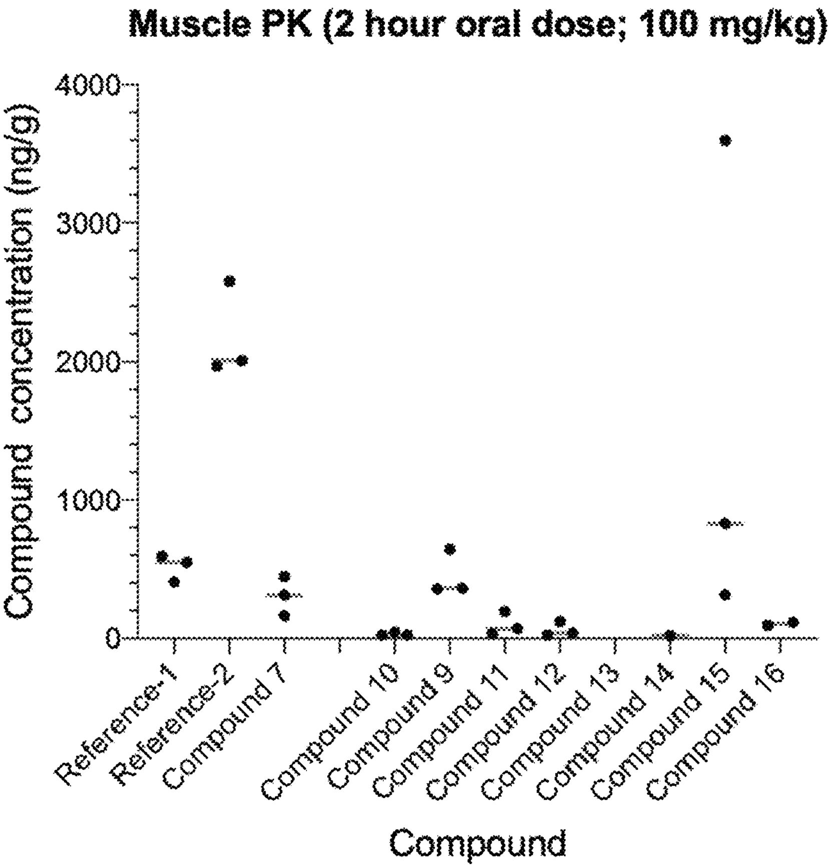
FIG. 3 illustrates a gastrocnemius pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16.

FIG. 3 illustrates a gastrocnemius pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16. Colon26 tumor bearing mice received a single dose (3 mice/treatment) and 2 hour post dose humanely euthanized. Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Waters HSS T3 2.1×50 mm (1.8 um) LC column, and an API-6500 Electrospray MS unit).

Figure 4:
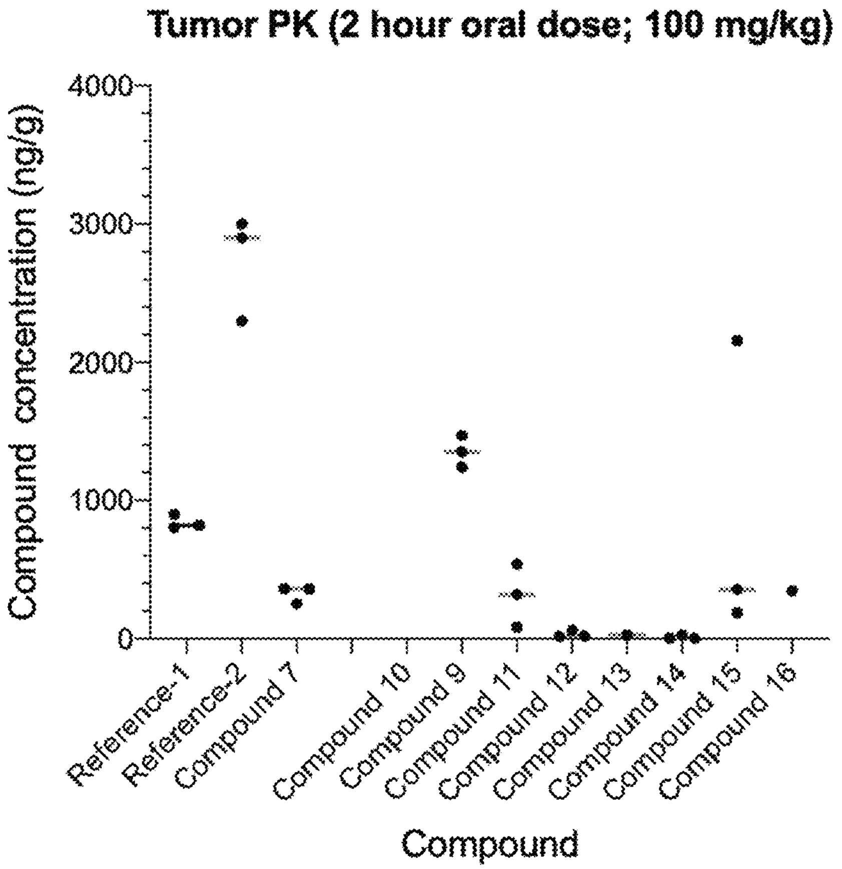
FIG. 4 illustrates a tumor pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16.

FIG. 4 illustrates a tumor pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16. Colon26 tumor bearing mice received a single dose (3 mice/treatment) and 2 hour post dose humanely euthanized. Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Waters HSS T3 2.1×50 mm (1.8 um) LC column, and an API-6500 Electrospray MS unit).

Figure 5:
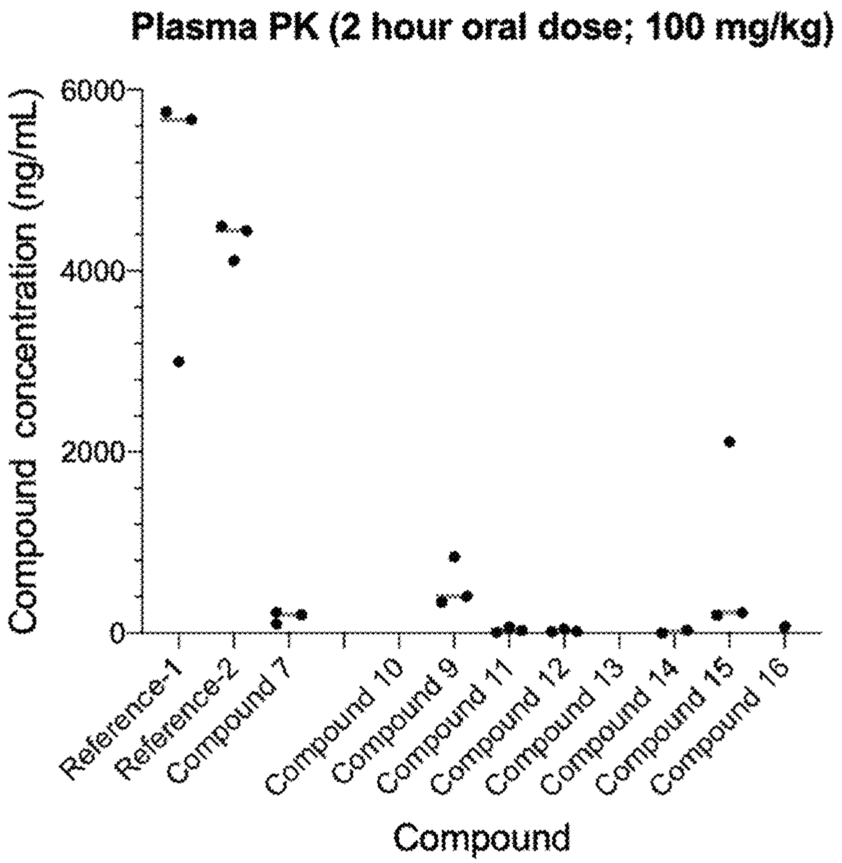
FIG. 5 illustrates a plasma pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16.

FIG. 5 illustrates a plasma pharmacokinetic (PK) results from a single 2 hour timepoint in a C26 tumor model for Reference-1, Reference-2, Compound-7, Compound-10, Compound-9, Compound-11, Compound-12, Compound-13, Compound-14, Compound-15, and Compound-16. Colon26 tumor bearing mice received a single dose (3 mice/treatment) and 2 hour post dose humanely euthanized. Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Waters HSS T3 2.1×50 mm (1.8 um) LC column, and an API-6500 Electrospray MS unit).

Figure 6:
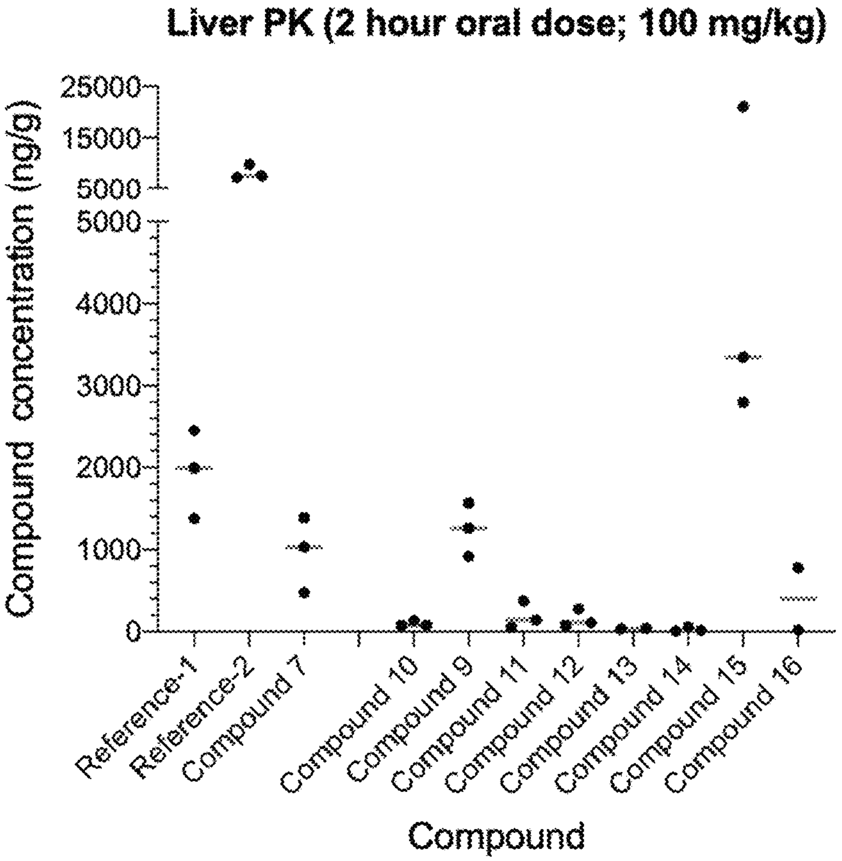
FIG. 6 illustrates a liver pharmacokinetic (PK) results from a single 2 h timepoint in a C26 tumor model for Reference-1, Reference-2, Compound-7, Compound-10, Compound-9, Compound-11, Compound-12, Compound-13, Compound-14, Compound-15, and Compound-16.

FIG. 6 illustrates a liver pharmacokinetic (PK) results from a single 2 h timepoint in a C26 tumor model for Reference-1, Reference-2, Compound-7, Compound-10, Compound-9, Compound-11, Compound-12, Compound-13, Compound-14, Compound-15, and Compound-16. Colon26 tumor bearing mice received a single dose (3 mice/treatment) and 2 hour post dose humanely euthanized. Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Waters HSS T3 2.1×50 mm (1.8 um) LC column, and an API-6500 Electrospray MS unit).

Figure 7A:
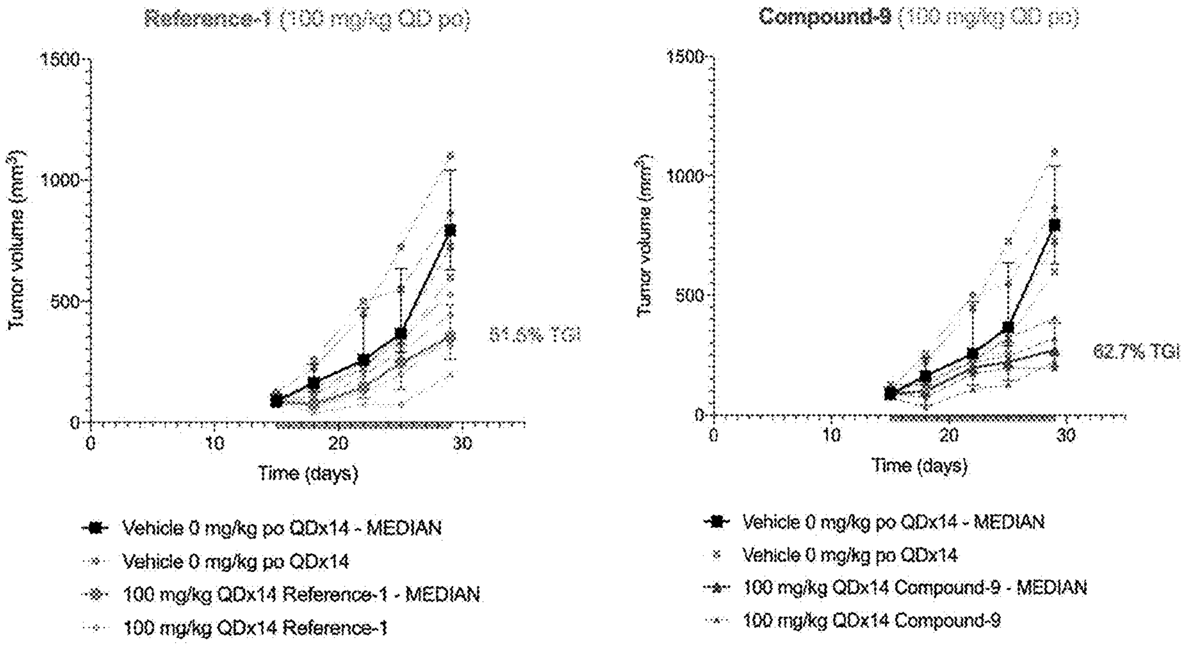
FIG. 7A illustrates a C26 tumor-bearing MTD study comparison between Reference-1 and Compound-9 100 mg/kg QD.

FIG. 7A illustrates a C-26 tumor-bearing MTD study comparison between Reference-1 and Compound-9 100 mg/kg QD. Efficacy of Reference-1 and Compound-9 in established Colon26 syngeneic (C26) tumor allograft after p.o. administration (once daily (QD) for 14 days to mice at 100 mg/kg. Each solid bold line is median tumor volumes±interquartile range of n=5 animals. Dotted lines of the same color (with the same smaller data symbols) represent the individual tumor volumes of mice corresponding to the same treatment group. Shaded area under x-axis is the days of dosing. Tumor growth inhibition (TGI) calculated as 1−T/C, where T=median tumor volume of treated group and C=median tumor volume of control treated group and expressed as a percentage.

Figure 7B:
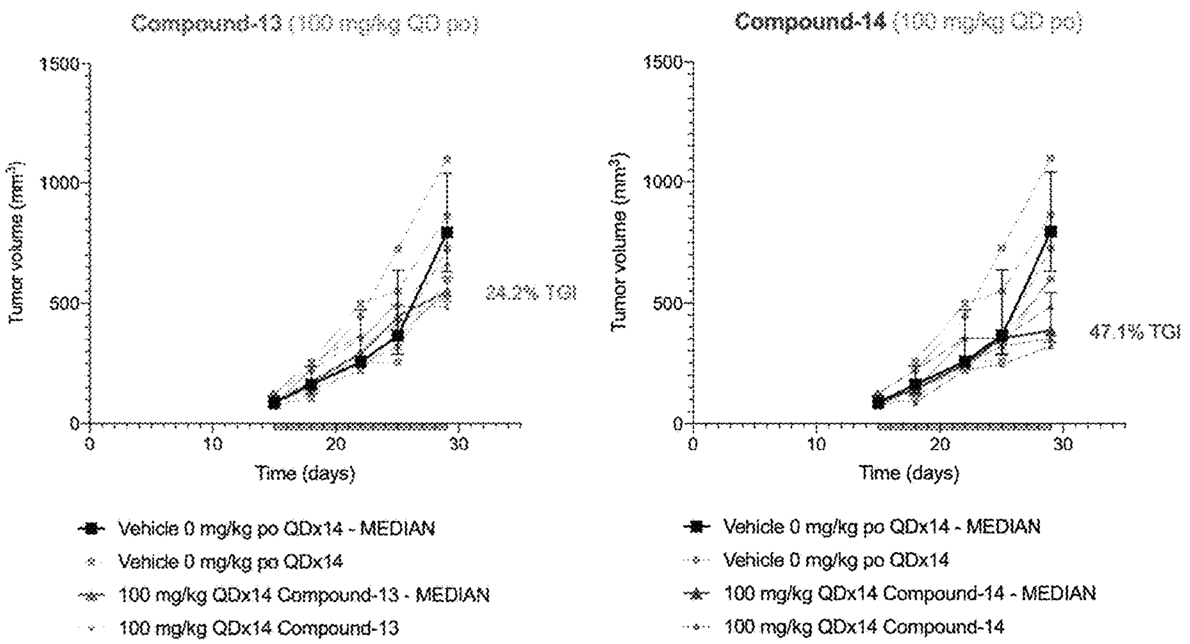
FIG. 7B illustrates a C26 tumor-bearing MTD study comparison between Compound 13 and Compound 14 100 mg/kg QD.

FIG. 7B illustrates a C26 tumor-bearing MTD study comparison between Compound-13 and Compound-14 100 mg/kg QD. Efficacy of Compound-13 and Compound-14 in established Colon26 syngeneic (C26) tumor allograft after p.o. administration (once daily (QD) for 14 days to mice at 100 mg/kg. Each solid bold line is median tumor volumes±interquartile range of n=5 animals. Dotted lines of the same color (with the same smaller data symbols) represent the individual tumor volumes of mice corresponding to the same treatment group. Shaded area under x-axis is the days of dosing. Tumor growth inhibition (TGI) calculated as 1−T/C, where T=median tumor volume of treated group and C=median tumor volume of control treated group and expressed as a percentage.

Figure 8A:
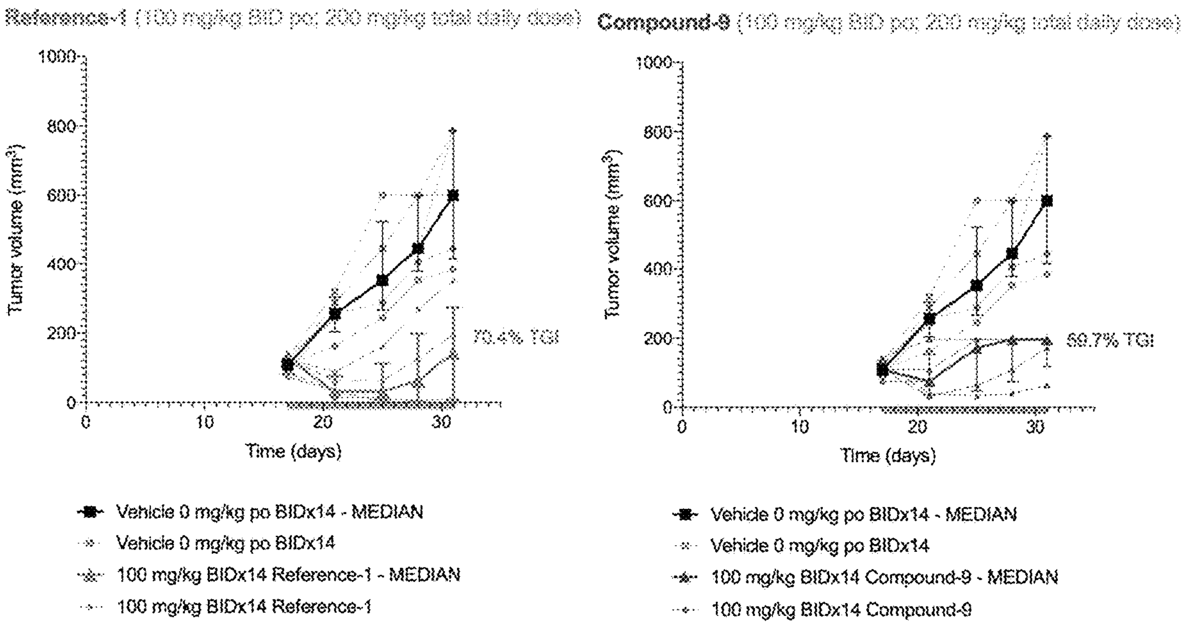
FIG. 8A illustrates a C26 tumor-bearing MTD study comparison between Reference-1 and Compound-9 at 100 mg/kg BID.

FIG. 8A illustrates a C26 tumor-bearing MTD study comparison between Reference-1 and Compound-9 at 100 mg/kg BID. Efficacy of Reference-1 and Compound-9 in established Colon26 syngeneic (C26) tumor allograft after p.o. administration (twice daily (BID) for 14 days to mice at 100 mg/kg (200 mg/kg total daily dose, with a minimum of 8 h between daily doses). Each solid bold line is median tumor volumes±interquartile range of n=5 animals. Dotted lines of the same color (with the same smaller data symbols) represent the individual tumor volumes of mice corresponding to the same treatment group. Shaded area under x-axis is the days of dosing. Tumor growth inhibition (TGI) calculated as 1−T/C, where T=median tumor volume of treated group and C=median tumor volume of control treated group and expressed as a percentage.

Figure 8B:
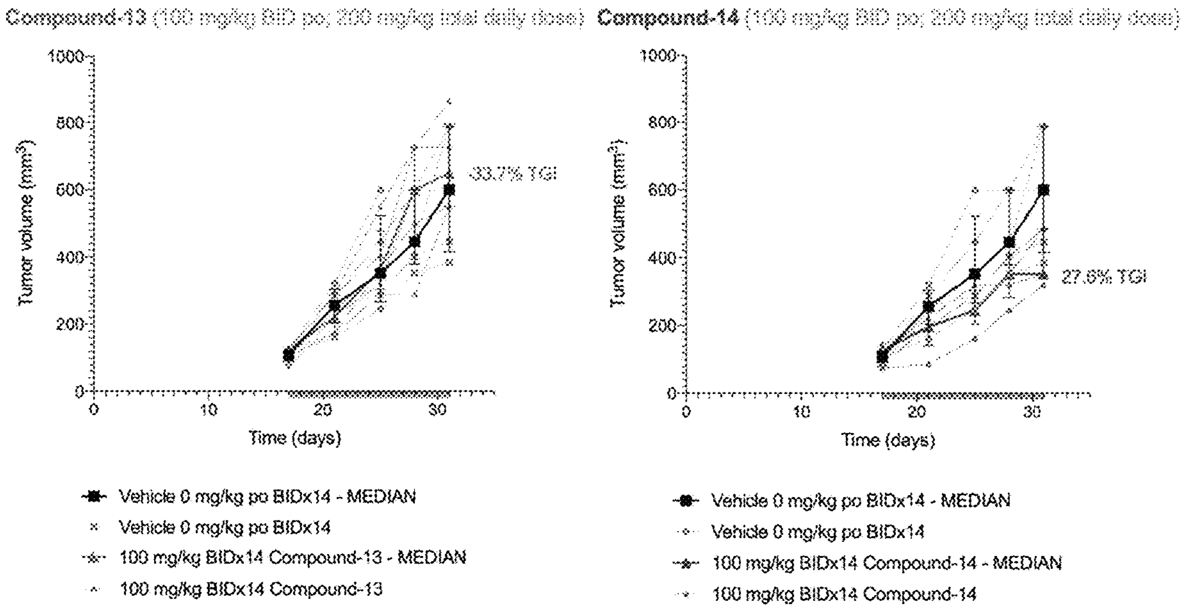
FIG. 8B illustrates a C26 tumor-bearing MTD study comparison between Compound-13 and Compound-14 100 mg/kg BID.

FIG. 8B illustrates a C26 tumor-bearing MTD study comparison between Compound-13 and Compound-14 100 mg/kg BID. Efficacy of Compound-13 and Compound-14 in established Colon26 syngeneic (C26) tumor allograft after p.o. administration (twice daily (BID) for 14 days to mice at 100 mg/kg (200 mg/kg total daily dose, with a minimum of 8 h between daily doses). Each solid bold line is median tumor volumes±interquartile range of n=5 animals. Dotted lines of the same color (with the same smaller data symbols) represent the individual tumor volumes of mice corresponding to the same treatment group. Shaded area under x-axis is the days of dosing. Tumor growth inhibition (TGI) calculated as 1−T/C, where T=median tumor volume of treated group and C=median tumor volume of control treated group and expressed as a percentage.

TABLE 1

Physicochemical Properties: Absorption & Efflux

| Compound (10 μM; Caco-2; 2 hrs) | Mean $P_{app}$ A-B ($10^{-6}$ cm/s) | Mean $P_{app}$ B-A ($10^{-6}$ cm/s) | Mean (B-A/A-B) (Efflux Ratio)^ | A-B Permeability Ranking* |
|---|---|---|---|---|
| Reference-1 | 8.83 | 28.2 | 3.19 | High |
| Reference-2 | 18.1 | 20.9 | 1.16 | High |
| Reference-7 | 14.4 | 10.0 | 0.695 | High |
| Compound 9 | 13.0 | 21.0 | 1.62 | High |
| Compound 10 | 0.0676 | 3.80 | 56.3 | Low |
| Compound 11 | 9.18 | 19.7 | 2.15 | High |
| Compound 12 | 1.06 | 17.9 | 16.9 | High |
| Compound 13 | 3.59 | 20.0 | 5.57 | High |
| Compound 14 | 9.34 | 26.1 | 2.80 | High |
| Compound 15 | 1.19 | 34.9 | 29.3 | High |
| Compound 16 | 7.55 | 5.61 | 0.743 | High |
| Controls | | | | |
| Ranitidine | 0.347 | 1.41 | 4.06 | Low |
| Talinolal | 0.375 | 8.20 | 21.8 | Effluxed |
| Talinolal + Verapamil (2.5 uM) | 0.766 | 3.07 | 4.01 | Inhibited Efflux |
| Warfarin | 36.6 | 26.6 | 0.726 | High |

Reference 1 is Selumetinib.

Reference 2 is

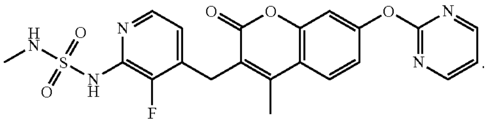 [SMILES: CNS(=O)(=O)Nc1nccc(Cc2c(C)c3ccc(Oc4ncccn4)cc3oc2=O)c1F]

^An efflux ratio > 2 indicates potential for the compound to be a substrate for Pgp or other active transporter.

*Permeability Ranking: lower is <1 x 10 = 6 cm/s; higher is >1 x 10-6 cm/s

TABLE 2

| Physicochemical Properties: hERG Channel | |
|---|---|
| Compound (30 to 0.01 μM dose range) | hERG IC50 [μM] |
| Reference-1 | >30 |
| Reference-2 | >30 |
| Compound 7 | 28.6 |
| Compound 9 | 26.2 |
| Compound 10 | >30 |
| Compound 11 | 1.1 |
| Compound 12 | >30 |
| Compound 13 | >30 |
| Compound 14 | 19.4 |
| Compound 15 | 6.5 |
| Compound 16 | 0.1 |
| Controls | |
| Cisapride | 0.01 |

Reference 1 is Selumetinib.

Reference 2 is

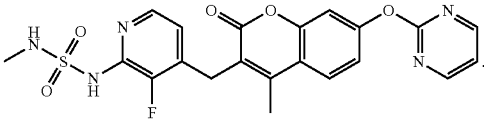 [SMILES: CNS(=O)(=O)Nc1nccc(Cc2c(C)c3ccc(Oc4ncccn4)cc3oc2=O)c1F]

TABLE 3

| Physicochemical Properties: Microsome Stability | | | | |
|---|---|---|---|---|
| Compound [2 μM] | Human (% Reamining @ 1 hour) | Beagle Dog (% Reamining @ 1 hour) | SD Rat (% Remaining @ 1 hour) | CD-1 Mouse (% Reamining @ 1 hour) |
| Reference-1 | 75.8 | 97.5 | 54.6 | 13.9 |
| Reference-2 | 107.1 | 111.6 | 102.0 | 96.0 |
| Compound 7 | 61.1 | 57.0 | 2.7 | 29.6 |
| Compound 9 | 51.7 | 76.5 | 28.8 | 54.3 |
| Compound 10 | 80.1 | 73.9 | 83.1 | 91.3 |
| Compound 11 | 28.9 | 4.9 | 1.1 | 7.0 |
| Compound 12 | 32.9 | 42.8 | 7.9 | 28.2 |
| Compound 13 | 57.7 | 69.6 | 18.0 | 16.8 |
| Compound 14 | 38.1 | 51.6 | 2.6 | 13.2 |
| Compound 15 | 75.8 | 46.0 | 57.4 | 77.6 |
| Compound 16 | 1.4 | 0.4 | 0.5 | 0.6 |
| Controls | | | | |
| Verapamil | 5.8 | 6.0 | 0.7 | 0.8 |

Reference 1 is Selumetinib.
Reference 2 is

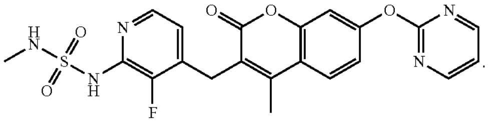 [SMILES: CNS(=O)(=O)Nc1nccc(Cc2c(C)c3ccc(Oc4ncccn4)cc3oc2=O)c1F]

TABLE 4

| Physicochemical Properties: Plasma Stability | | | | |
|---|---|---|---|---|
| Compound [2 μM] | Human (% Reamining @ 2 hour) | Beagle Dog (% Reamining @ 2 hour) | SD Rat (% Remaining @ 2 hour) | CD-1 Mouse (% Reamining @ 2 hour) |
| Reference-1 | 98.1 | 100.4 | 94.9 | 104.8 |
| Reference-2 | 91.1 | 99.8 | 99.8 | 92.9 |
| Compound 7 | 88.1 | 99.8 | 77.3 | 56.5 |
| Compound 9 | 95.1 | 96.8 | 106.4 | 90.6 |
| Compound 10 | 92.1 | 96.2 | 97.2 | 97.7 |
| Compound 11 | 93.7 | 97.8 | 97.4 | 81.4 |
| Compound 12 | 100.5 | 102.6 | 98.4 | 86.6 |
| Compound 13 | 87.3 | 95.9 | 100.5 | 87.1 |
| Compound 14 | 96.0 | 91.2 | 106.0 | 95.0 |
| Compound 15 | 98.1 | 89.1 | 90.7 | 87.1 |
| Compound 16 | 99.0 | 101.2 | 96.5 | 92.7 |
| Controls | | | | |
| Propantheline | 5.7 | 58.4 | 92.6 | 27.1 |
| Lovastatin | 81.8 | 94.1 | 0.6 | 0.6 |

Reference 1 is Selumetinib.
Reference 2 is

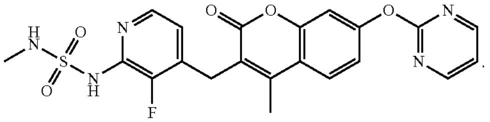 [SMILES: CNS(=O)(=O)Nc1nccc(Cc2c(C)c3ccc(Oc4ncccn4)cc3oc2=O)c1F]

TABLE 5

| Physicochemical Properties: CYP450 Panel | | | | | | | | |
|---|---|---|---|---|---|---|---|---|
| Compound [10 μM] | 1A2* | 2B6* | 2C8* | 2C9* | 2C19* | 2D6* | 3A4* | 3A4^ |
| Reference-1 | 8.3 | 30.2 | 18.9 | 14.1 | 13.9 | 5.0 | 25.9 | 21.4 |
| Reference-2 | 0.8 | 13.6 | 41.5 | −1.6 | −0.9 | 3.4 | 16.6 | 15.7 |
| Compound 7 | 0.3 | 28.5 | 14.4 | 33.8 | 11.6 | −7.4 | 29.9 | 59.7 |
| Compound 9 | 4.8 | 14.8 | 4.0 | 6.8 | 8.2 | −3.7 | 16.3 | 26.8 |
| Compound 10 | 0.4 | 22.4 | −1.0 | 1.8 | 4.8 | −3.4 | 17.3 | 16.2 |
| Compound 11 | 6.9 | 12.1 | 0.8 | 12.9 | 9.7 | 9.8 | 36.1 | 44.8 |
| Compound 12 | 13.0 | 14.9 | 2.4 | 8.4 | 16.0 | 4.5 | 29.2 | 31.9 |
| Compound 13 | 6.5 | 15.8 | 6.2 | −4.6 | 6.2 | −2.6 | 25.7 | 34.9 |
| Compound 14 | 6.3 | 15.6 | 8.4 | 8.2 | 4.0 | 6.6 | 26.7 | 39.3 |
| Compound 15 | 7.8 | 16.3 | −16.9 | 3.0 | 4.3 | 0.5 | 21.3 | 20.5 |
| Compound 16 | 6.9 | 11.6 | 45.5 | 42.4 | 88.4 | 55.0 | 75.1 | 92.1 |
| Controls | | | | | | | | |
| Fluvoxamine | 100.2 | — | — | — | — | — | — | — |
| Ticlopidine | — | 101.5 | — | — | — | — | — | — |
| Quercetin | — | — | 93.1 | — | — | — | — | — |
| Sulfaphenazole | — | — | — | 101.2 | — | — | — | — |
| Omeprazole | — | — | — | — | 61.6 | — | — | — |
| Quinidine | — | — | — | — | — | 99.7 | — | — |
| Ketoconazole | — | — | — | — | — | — | 110.1 | — |
| Ketoconazole | — | — | — | — | — | — | — | 105.5 |

Reference 1 is Selumetinib.
Reference 2 is

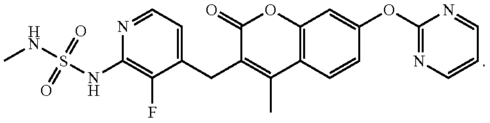 [SMILES: CNS(=O)(=O)Nc1nccc(Cc2c(C)c3ccc(Oc4ncccn4)cc3oc2=O)c1F]

*1A2 (phenacetin), 2B6 (bupropion), 2C8 (amodiaquine), 2C9 (Diclofenac), 2C19 (mephenytoin), 2D6 (dextromethophan), 3A4 (midazolam)

^3A4 (testosterone)

Example 117

Cell-Based pERK Dose Response Study

Materials and Methods: A549 or A375 cells were seeded in 6-well plates at an appropriate seeding density on day 0. On day 2 or 3, after checking the health and confluency of cells, the media was aspirated and replaced with 1 mL media containing a predetermined concentration of compound and incubated for 2 hours. After 2 hours, the media was aspirated, and the cells washed 2 times with cold PBS. Cells were lysed on ice, with 50 uL 1×CST lysis buffer+1 mM PMSF for 5 minutes. After 5 minutes, cells were removed using a scraper and transferred to cold 1.5 mL tubes, and centrifuged for 10 min, 4° C., 14,000×g. Supernatant was gently removed and snap frozen in liquid nitrogen. Protein concentration of the lysate was determined using Bradford Reagent (analyzed using SpectraMax M2E) and diluted to 1 mg/mL or pERK or 1.5 mg/mL for pMEK analysis. Cell lysates were then analyzed for phosphor-ERK/total-ERK levels on a Jess system (ProteinSimple; Cat #J53346) using the following antibodies: tERK1/2 (CST 4696; 1:50) and pERK1/2 (CST 4377; 1:50). For pMEK/tMEK, the following antibodies were used: tMEK1/2 (CST 4694; 1:15) and pMEK1/2 (CST 9154; 1:400). All dilutions were in Milk-free antibody diluent.

Mouse & Human Microsome ($t_{1/2}$ Min), Mouse & Human $Cl_{int}$ (μl/Min/Mg)

Test compounds were dissolved in DMSO to a concentration of 10 mM and further diluted to 100 μM using acetonitrile. Liver microsomes from selected species were incubated in duplicate with the test compound at a final concentration of 1 μM in 0.1 M potassium phosphate buffer (pH 7.4) containing 3.3 mM MgCl2, 0.5 mg/ml microsomal protein, in the presence or absence of NADPH (1 mM). Incubations were performed at 37° C. in a total volume of 500 μl. Control incubations with reference substances were included for each experiment.

At different time points (t=0, 5, 15, 30, 45 min), 50 μl of the incubation mixture was transferred into a quench plate containing acetonitrile and internal standard (200 nM labetalol) cooled to 4° C. After the last time point, the quench plates were mixed thoroughly and centrifuged for 15 minutes at 3700 rpm and 10° C. (Eppendorf 5804R). The supernatant was transferred to new 96 well plates and subjected to LC-MS analysis. The disappearance of the parent compound was determined.

All sample analysis was performed using a Vanquish Horizon UHPLC-system equipped with an autosampler, a binary pump, a column compartment and a diode array detector coupled to a Q Exactive focus hybrid quadrupole-Orbitrap mass spectrometer (Thermo Fisher Scientific) equipped with heated electrospray ion source.

The percentage of test compound remaining was defined as the ratio of test compound peak area at a specific time point and the peak area in the t=0 min samples multiplied by 100%.

The metabolic stability was evaluated by plotting the natural logarithm of the percentage test compound remaining versus time and performing linear regression. Using this graph, the following parameters were calculated: elimination constant k ($min^{-1}$)=−slope, in vitro half-life ($t_{1/2}$)=ln (2)/k, in vitro intrinsic clearance $Cl_{int}$ (in μl/min/mg protein)=[ln(2)×incubation volume in μl/mg protein]/$t_{1/2}$.

Kinetic Solubility (PBS pH=7.4; 4 hr)

Test compounds were dissolved in DMSO to a concentration of 10 mM and further diluted to 100 μM in buffer (10 mM PBS, pH 7.4) in a 96 well plate at a final DMSO concentration of 1%. The plates were shaken for 4 h at room temperature in an Eppendorf Thermomixer. After incubation, the plates were centrifuged for 20 minutes at 4680 rpm. From the supernatant, 150 μL was transferred to a new 96 well plate and 50 μL DMSO was added to ensure continued dissolution. Samples were measured on LC-UV at injection volumes of 1 and 8 μL. Peak areas were determined and compared to peak areas obtained using calibration curves of the test compounds in DMSO. All sample analysis was performed using an Agilent 1290 HPLC-system equipped with an autosampler, a binary pump, a column compartment and a diode array detector.

e Log D (Lipophilicity; pH=7.4)

Test compounds were dissolved in DMSO at a concentration of 10 mM and further diluted with methanol:water 1:1. Samples were analyzed using gradient HPLC with three different isocratic mobile phases of 0.25% octanol in methanol (60, 65 and 70%) and 20 mM MOPS buffer (pH 7.4) with decylamine. If needed, (for low E log Doct compounds) the isocratic mobile phases were adjusted to e.g. 40, 45 and 50% methanol. Peaks were detected using a diode array at absorbance 220-320 nm.

Capacity factors data (k'_=(tr−_t0)/t0) obtained at various amounts of methanol were extrapolated to 0% methanol and k'w values are determined using a linear procedure. E log Doct (7.4) is calculated using a series of reference standards with known Log D values. Each experiment was performed in triplicate.

All sample analysis was performed using an Agilent HPLC-system equipped with an autosampler, a binary pump, a column compartment and a diode array detector.

PAMPA (pH=7.4; Papp 10-6 cm/s)

PAMPA studies were conducted using the PAMPA Explorer kit (pION Inc.) and the double sink protocol (Avdeef, 2005). Stock solutions of all test compounds were dissolved in DMSO to a concentration of 10 mM. Each stock solution was diluted to 50 μM in pH 7.4 Prisma HT buffer (pION) and 200 μl was added to each well of the donor plate in triplicate. The polyvinylidene fluoride (PVDF, 0.45 μm) filter membrane on the acceptor plate was coated with 5 μl gastrointestinal tract lipid formulation (GIT-0, pION) and to each well of the acceptor plate, 200 μl of acceptor sink buffer (pION) was added. The acceptor filter plate was then carefully placed on top of the donor plate to form a sandwich. The sandwich was incubated at 25° C. for 4 h without stirring. UV-vis spectra of the solutions in the blank, reference, acceptor and donor plates were measured using a microplate reader (Tecan Infinite 200PRO M Nano Plus). Permeability values were calculated using the PAMPA explorer software v. 3.8.0.2 (pION). Control incubations with ketoprofen (low permeability) and verapamil (high permeability) were included in each experiment.

Figure 9:
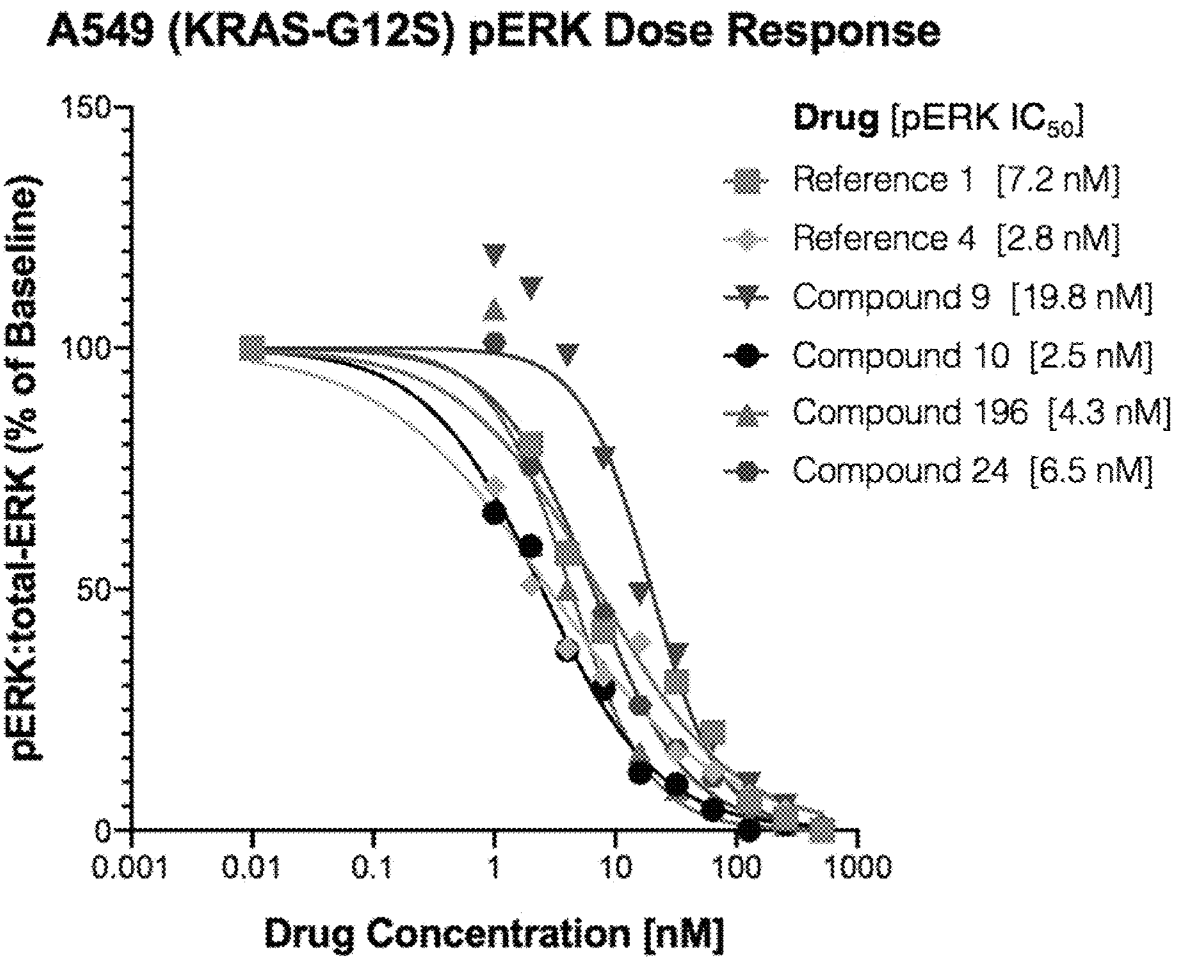
FIG. 9 illustrates an A549 (KRAS-G12S) pERK dose response.
Figure 10:
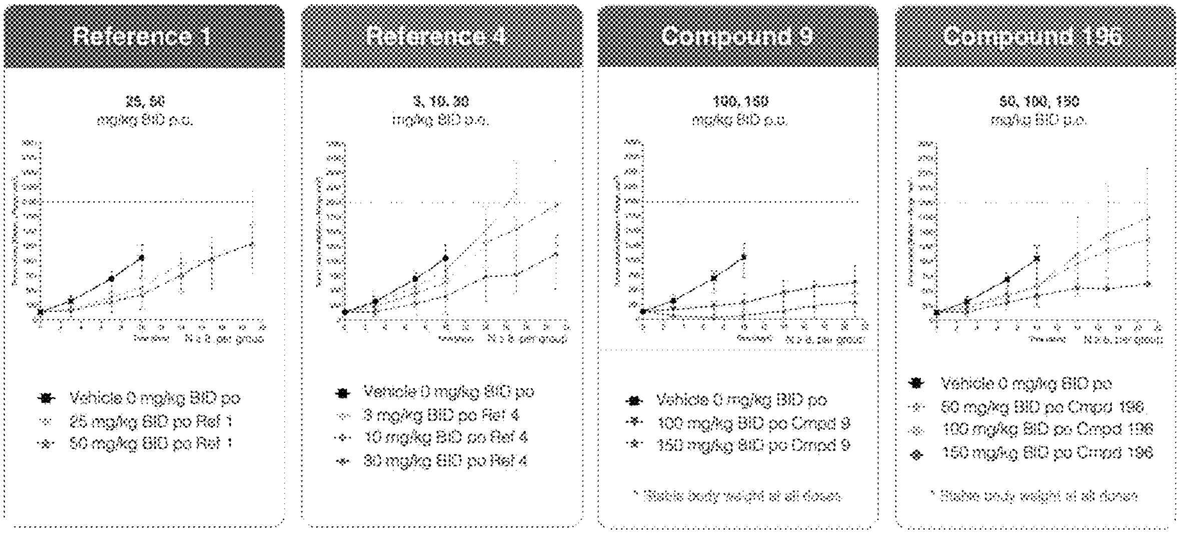
FIG. 10 illustrates a graph of a colon-26 model for KRAS G12D CRC efficacy and safety.
Figure 11A:
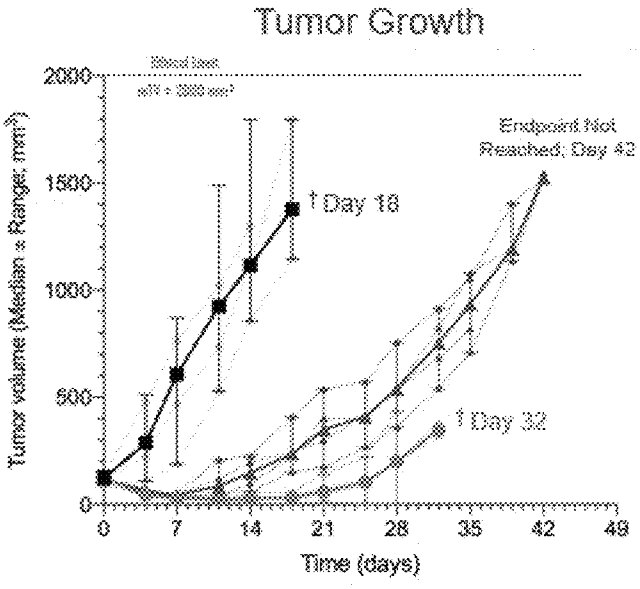
FIG. 11A illustrates a graph of C-26 pharmacology study KRAS G12D CRC tumor growth.
Figure 11B:
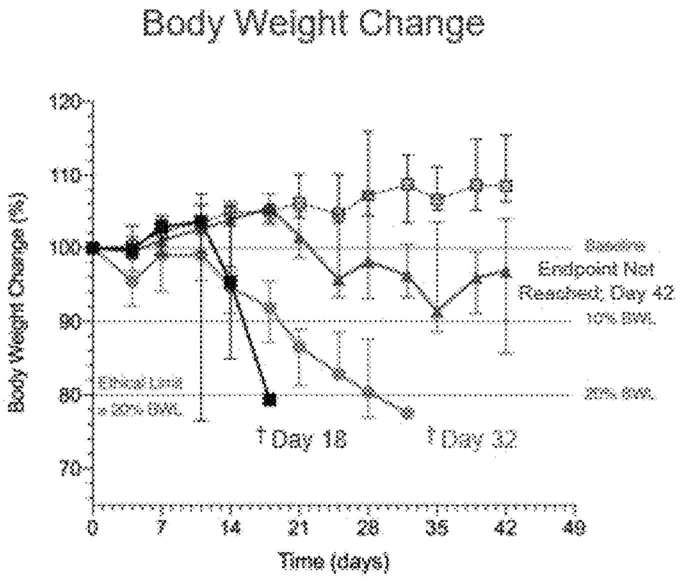
FIG. 11B illustrates a graph of C-26 pharmacology study KRAS G12D CRC weight loss.
Figure 12:
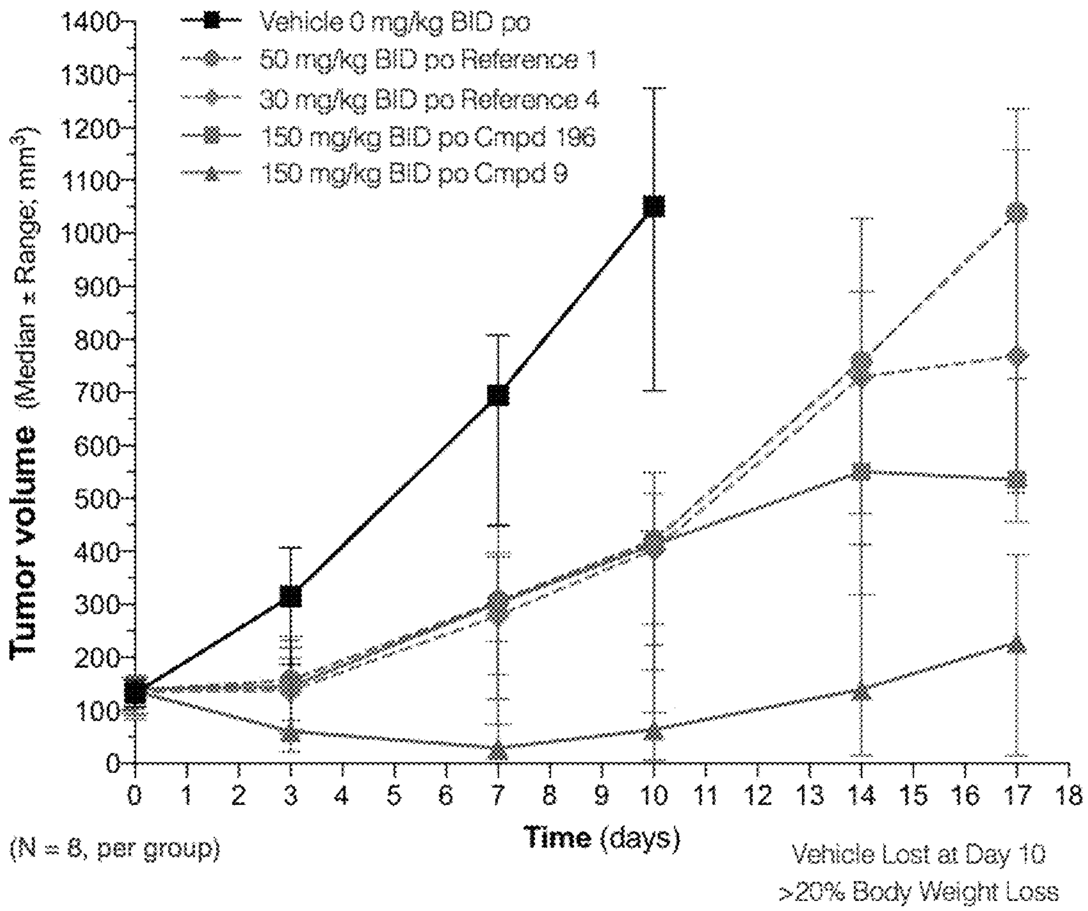
FIG. 12 illustrates a graph of activity in a Colon-26 KRAS mutant CRC model.
Figure 13:
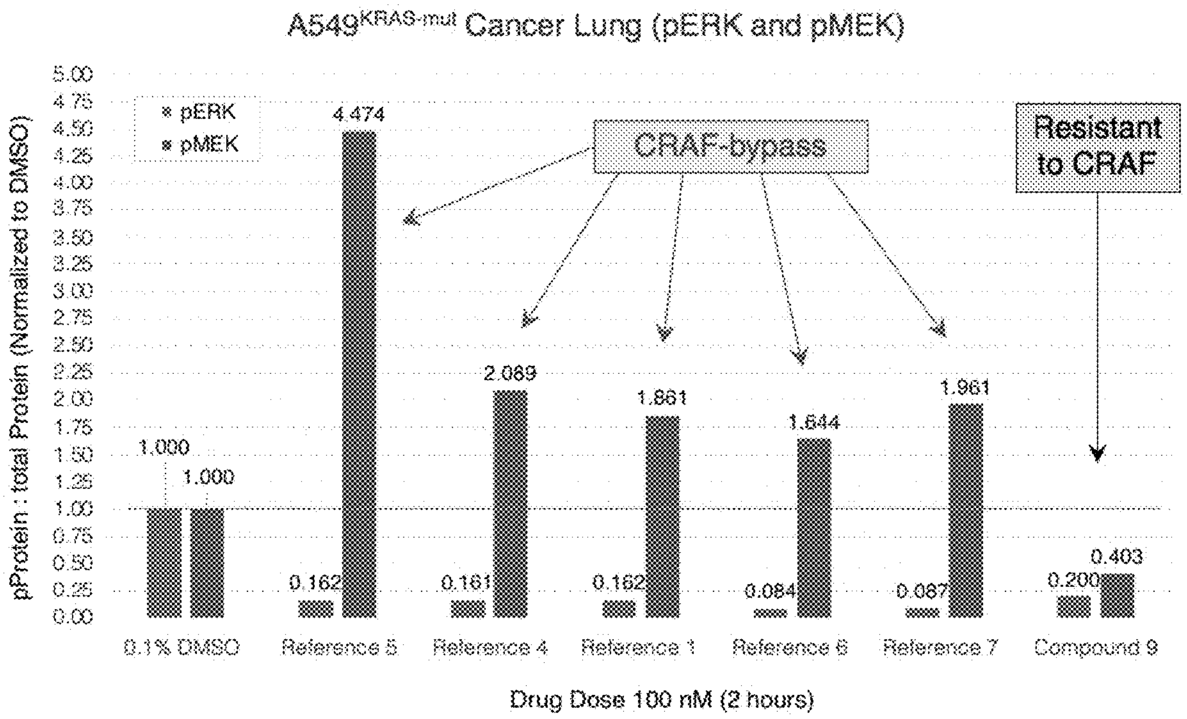
FIG. 13 illustrates a graph of dual-RAF/MEK resistance to CRAF-bypass.
Figure 14A:
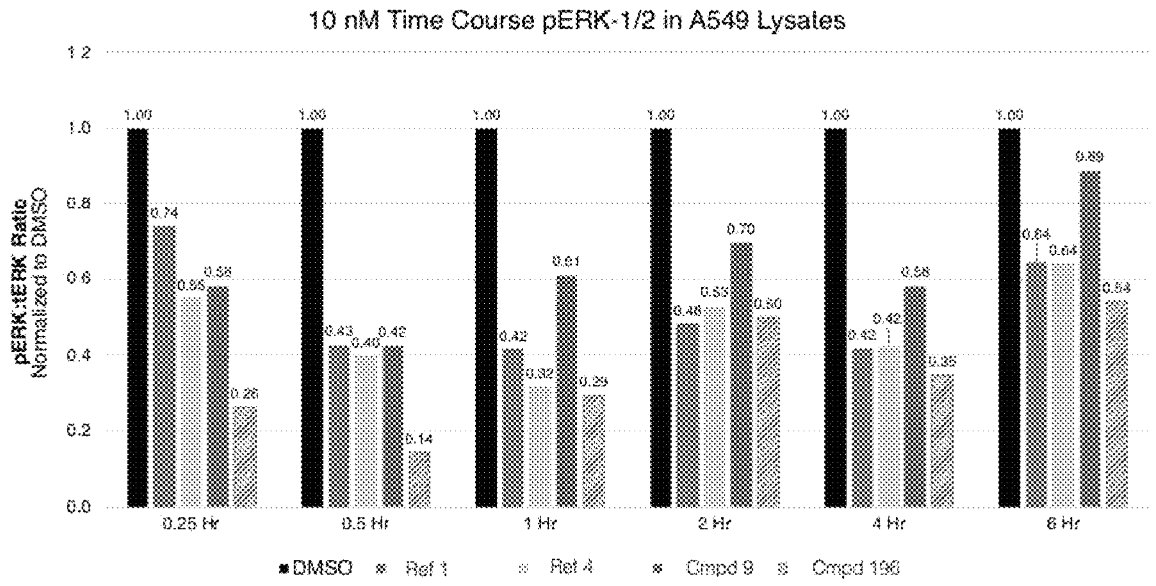
FIG. 14A illustrates a graph of a dual-RAF/MEK: CRAF-bypass time course for A459 KRAS pERK:total ERK.
Figure 14B:
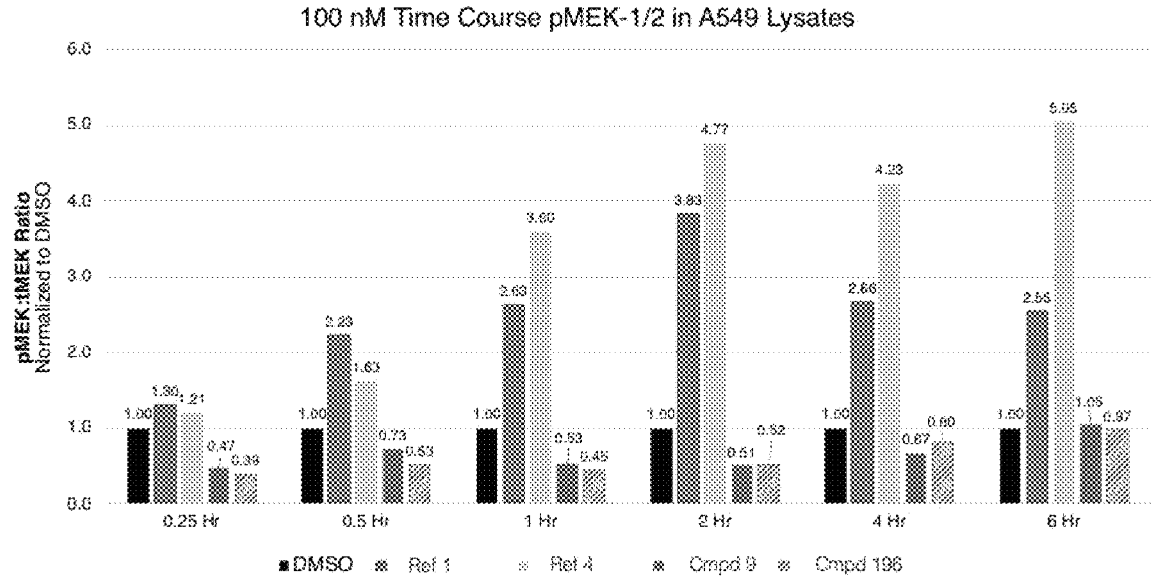
FIG. 14B illustrates pMEK:total MEK in the NSCLC model A549 KRAS(G12S).
Figure 15A:
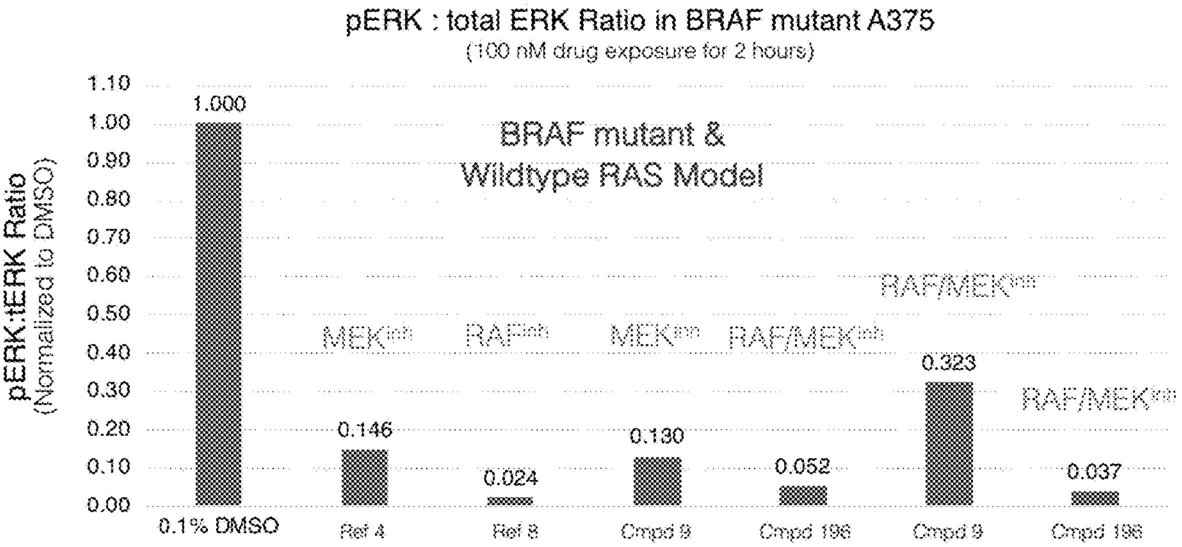
FIG. 15A illustrates a graph of pERK:total ERK (activation) in the BRAF V600E mutant A375 melanoma model.
Figure 15B:
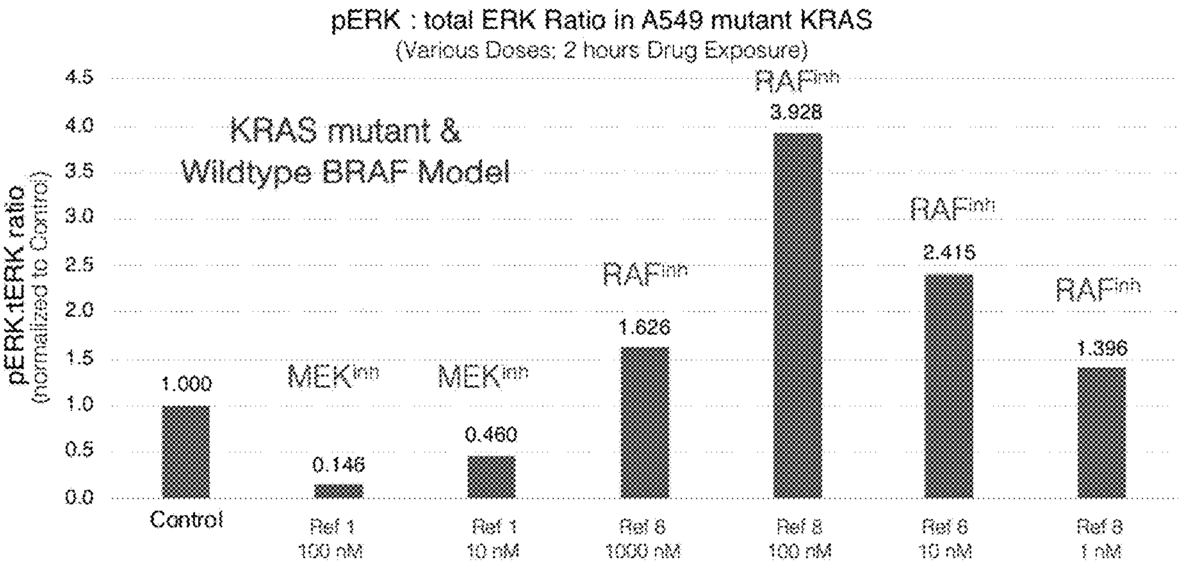
FIG. 15B illustrates pERK:total ERK in the KRAS G12S mutant A549 model and paradoxical activation by a RAF inhibitor.

FIG. 9 illustrates a A549 (KRAS-G125) pERK Dose Response study. The results are also represented in Table 6.

TABLE 6

| Attribute | Reference 1 | Compound 9 | Compound 197 |
|---|---|---|---|
| pERK IC50 (A549) [12-point dose] | 7.2 nM | 19.8 nM | 4.3 nM |
| A549 pERK:tERK ratio [10 nM; 2 hr] | 0.56 | 0.62 | 0.32 |
| A375 pERK:tERK ratio [10 nM; 2 hr] | 0.59 | 0.71 | 0.44 |

TABLE 6-continued

| Attribute | Reference 1 | Compound 9 | Compound 197 |
|---|---|---|---|
| CRAF A549 pMEK:tMEK [100 nM; 2 hr] | 2.09 | 0.47 | 0.49 |
| Mouse Microsome ($t_{1/2}$ min) | 18 min | 44 min | 53 min |
| Mouse Clint (µl/min/mg) | 78 | 32 | 26 |
| Human Microsome ($t_{1/2}$ min) | >90 min | 35 min | 38 min |
| Kinetic Solubility (PBS pH = 7.4; 4 hr) | 36 µM | >80 µM | >80 µM |
| eLogD (lipophilicity; pH = 7.4) | 3.6 | 3.0 | 2.9 |
| PAMPA (pH = 7.4; $P_{app}$ $10^{-6}$ cm/s) | 29 | 37 | 51 |

Reference 1 is Selumetinib

The results of a phospho-ERK Screen in A549 (KRAS G12S) study is described in Table 7, 7A, 7B, and 8 below.

TABLE 7

| Phospho-ERK Screen in A549 (KRAS G12S): 10 µM for 2 hours | |
|---|---|
| Compound | pERK: total ERK (% relative to vehicle) |
| Vehicle | 100.00% |
| Reference 1 | 0.48% |
| Reference 2 | 1.26% |
| Compound 7 | 0.53% |
| Compound 9 | 0.60% |
| Compound 100 | 0.82% |
| Compound 106 | 27.88% |
| Compound 181 | 22.23% |
| Compound 182 | 6.77% |
| Compound 185 | 7.39% |
| Compound 186 | 0.74% |
| Compound 187 | 0.91% |
| Compound 188 | 0.82% |
| Compound 190 | 15.28% |
| Compound 191 | 7.34% |
| Compound 207 | 11.35% |
| Compound 208 | 23.64% |
| Compound 209 | 34.23% |
| Compound 210 | 78.26% |
| Compound 211 | 70.75% |
| Compound 212 | 13.03% |

TABLE 7-continued

| Phospho-ERK Screen in A549 (KRAS G12S): 10 µM for 2 hours | |
|---|---|
| Compound | pERK: total ERK (% relative to vehicle) |
| Compound 215 | 11.77% |
| Compound 216 | 4.51% |

Reference 1 is Selumetinib.
Reference 2 is

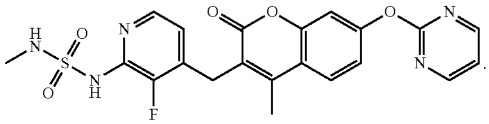 [SMILES: CNS(=O)(=O)Nc1nccc(Cc2c(C)c3ccc(Oc4ncccn4)cc3oc2=O)c1F]

.

TABLE 7A

| Phospho-ERK Screen in A549 (KRAS G12S): 10 µM for 2 hours | |
|---|---|
| Compound | pERK: total ERK (% relative to vehicle) |
| Vehicle | 100.00% |
| Reference 1 | 2.40% |
| Reference 2 | 2.59% |
| Compound 7 | 3.33% |
| Compound 9 | 1.81% |
| Compound 57 | 7.33% |
| Compound 134 | 23.41% |
| Compound 191 | 8.60% |
| Compound 213 | 70.14% |
| Compound 217 | 11.20% |
| Compound 218 | 9.46% |
| Compound 219 | 13.94% |
| Compound 220 | 4.28% |
| Compound 221 | 17.24% |
| Compound 222 | 9.32% |
| Compound 223 | 3.04% |
| Compound 224 | 28.27% |

Reference 1 is Selumetinib
Reference 2 is

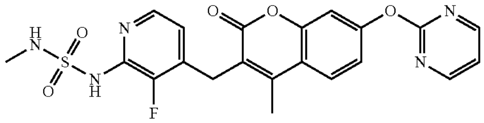 [SMILES: CNS(=O)(=O)Nc1nccc(Cc2c(C)c3ccc(Oc4ncccn4)cc3oc2=O)c1F]

Example 118

Metabolite ID Study

Animal Studies: Compound 9 was tested using six species hepatocytes in a metabolite ID study (T=60 min). The results of the study are represented in Table 8.

TABLE 8

| m/z of | Retention Time | % of total compound related material based on peak area | | | | | |
|---|---|---|---|---|---|---|---|
| [M + H] + ion | Rt (min) | Mouse | Rat | Rabbit | Dog | Monkey | Human |
| Parent Molecule | 4.2 | 97 | 95 | 93 | 96 | 95 | 99 |
| Met-ID 1 | 3.8 | 0.8* | 0.8* | 0.2* | 0.8* | ***1.4**** | ***0.9**** |
| Met-ID 2 | 2.9 | 0.4* | 0.3* | ***3.2**** | 0.8* | 0.5 | 0.7* |
| Met-ID 3 | 3.7 | 0.4 | 1.0 | 0.1 | 0.0 | **0.9** | 0.3 |
| Met-ID 4 | 3.4 | 0.2 | 0.3 | 2.1 | 0.2 | 0.7 | 0.2 |
| Met-ID 5 | 3.6 | 0.1 | 0.2 | 0.0 | 0.0 | 0.0 | 0.0 |
| Met-ID 6 | 3.9 | 0.0 | 0.1 | 0.0 | 0.0 | 0.0 | 0.2 |

TABLE 8-continued

| m/z of [M + H] + ion | Retention Time Rt (min) | % of total compound related material based on peak area Mouse | Rat | Rabbit | Dog | Monkey | Human |
|---|---|---|---|---|---|---|---|
| Met-ID 7 | 2.7 | ***1.3*** * | ***1.3*** * | 1.0* | ***1.5*** * | 0.5 | ***0.9*** * |
| Met-ID 8 | 3.5 | 0.3* | 0.5* | 0.5* | 0.4* | 0.4 | 0.4* |

Bold and italic: main mass observed in that species
*also present in buffer incubations Test compounds were dissolved in DMSO to a concentration of 10 mM, and further diluted to a 100 µM solution in DMSO:MQ 1:1. Cryopreserved hepatocytes from a selected species were thawed and incubated in duplicate with 10 µM compound 9 in Krebs-Henseleit buffer. Incubations were performed in a total volume of 350 µl, with 0.5×106 cells/ml. Control incubations with the reference substances verapamil, 7-hydroxycoumarin, propranolol and diltiazem were included for each species. Viability of hepatocytes was >70% after thawing.

At different time points, 50 µl of the incubation mixture was transferred into a quench plate containing acetonitrile and internal standard and cooled to 4° C. After the last time point (t=60 minutes), the quench plates were mixed thoroughly and centrifuged for 15 minutes at 3700 rpm and 10° C. (Eppendorf 5804R). The supernatant was transferred to new 96 well plates and subjected to LC-MS analysis. The disappearance of the parent compound was determined, and the formation of metabolites was evaluated. Metabolites present at >1% of total compound related material (based on peak area) were identified by interpretation of the LC-MS/MS data.

All sample analysis was performed using a Vanquish Horizon UHPLC-system equipped with an autosampler, a binary pump, a column compartment and a diode array detector coupled to a Q Exactive focus hybrid quadrupole-Orbitrap mass spectrometer (Thermo Fisher Scientific) equipped with heated electrospray ion source. MS settings were optimized for the flow rate. Full scan spectra were acquired in combination with data dependent MS2.

The formation and identification of metabolites was evaluated according to the following approach:

The spectra obtained from all samples were screened for the presence of m/z values that are absent in the blank incubations (incubations with hepatocytes without compound and with vehicle control, and incubations of compound in buffer without hepatocytes). T=60 min incubations were used as an initial screening. All possible metabolites observed were semi-quantified by MS response (peak area). MS2 spectra were interpreted to determine possible location of the metabolism reaction. The presence of metabolites identified was compared across the selected species.

Compound 9 was not extensively metabolized in hepatocytes from different species. As a percentage of total compound-related material in MS chromatograms of the hepatocyte incubations, approximately 92 to 98% of the parent compound was remaining (based on peak area). Primary metabolite shown for each species in bold font. Several masses found were also present in incubations with compound in buffer and were considered not to be metabolites.

Example 119

Colon-26 Model (KRAS G12D CRC): Efficacy & Safety

Female athymic BALB/c nude or BALB/c mice (Beijing Vital River Laboratory Animal Technology Co., Ltd.), approximately 8-10 weeks old were used in these studies. Animals were maintained in individually vented cages on a 12-h light-dark cycle. Food and water were available ad libitum. The Colon-26 tumor cells were maintained in vitro with RPMI1640 medium supplemented with 10% fetal bovine serum at 37° C. in an atmosphere of 5% CO2 in air. The cells in exponential growth phase were harvested and quantitated by cell counter before tumor inoculation. Each mouse was inoculated subcutaneously in the right flank region with Colon-26 tumor cells (5×105) in 0.1 mL of PBS. Randomization was started when the mean tumor size reached approximately 125 mm3. A total of 84 tumor-bearing mice were enrolled in the study and allocated into 7 treatment groups (12 mice per group). Also 12 non-tumor-bearing mice were assigned as un-treated group.

Animals were treated with either vehicle (10% DMSO/90% [20% SBE-β-CD in saline], pH 5) or vehicle containing compounds at the indicated doses by gavage (p.o.) twice daily for approximately 28-42 days (BID×28-42 p.o.), or to ethical endpoints (BWL>20%; Median Tumor Volume (MTV)>2000 mm3; Individual TV>3000 mm3; clinical signs of unwell). Clinical signs of unwell was characterized, but not limited to the following. Severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice. Dosing as well as tumor and body weight measurements were conducted in a Laminar Flow Cabinet.

Animals were checked daily for morbidity and mortality. During routine monitoring, the animals were checked for any effects of tumor growth and treatments on behavior such as mobility, food and water consumption, body weight gain/loss (body weights were measured twice per week after randomization), eye/hair matting and any other abnormalities. Mortality and observed clinical signs were recorded for individual animals in detail.

Tumor volumes were measured twice per week after randomization in two dimensions using a caliper, and the volume was expressed in mm3 using the formula: V=(L×W×W)/2, where V is tumor volume, L is tumor length (the longest tumor dimension) and W is tumor width (the longest tumor dimension perpendicular to L). Results were presented as the median tumor volume, expressed in mm3+/−interquartile range, of each group. Tumor Growth Inhibition; TGI %=[1−(Ti/(Ci)]×100; where Ti as the median tumor volume of the treatment group on the measurement day, Ci as the median tumor volume of control group at the measurement day.

The body weights and tumor volumes were measured by using StudyDirector™ software (version 3.1.399.19).

The protocol and any amendment(s) or procedures involving the care and use of animals in this study were reviewed and approved by the Institutional Animal Care and Use Committee (IACUC) of CrownBio prior to execution. During the study, the care and use of animals were conducted in accordance with the regulations of the Association for Assessment and Accreditation of Laboratory Animal Care (AAALAC).

Table 9 and FIGS. 10, 11A, 11B, and 12 illustrate the results of this study.

TABLE 9

| Colon-26 KRAS-G12D in Balb/c | | | | |
|---|---|---|---|---|
| Drug | Dose (mg/kg BID po) | TGI (Day 10) | BWL (Day 14) | BWL (Day 17) |
| Vehicle | 0 | n/a | −26% | n/a |
| Reference 1 | 50 | 60.0% | 0% | −2% |
| Reference 2 | 50 | 61.6% | −2% | −2% |
| Compound 9 | 150 | 93.9% | 0% | 0% |

Reference 1 is Selumetinib.
Reference 2 is

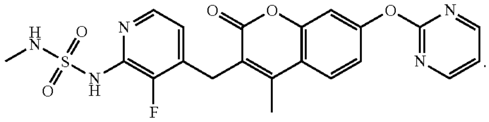 [SMILES: CNS(=O)(=O)Nc1nccc(Cc2c(C)c3ccc(Oc4ncccn4)cc3oc2=O)c1F]

Example 120

Dual-RAF/MEK Resistant to CRAF-bypass

A549 or 375 cells were treated in duplicate for two hours with compounds at varying concentrations. After two hours, the cells were lysed, snap frozen, and stored at −80° C. After storage, the lysate was quantified with the Bradford assay. Before the lysates were prepared to run on the Jess, the lysates were diluted to 1 mg/mL for pERK analysis and 1.5 mg/mL pMEK analysis using quantitative Western blotting. ERK and MEK phosphorylation levels were estimated by taking the ratio of phospho-protein to total protein and normalizing to the DMSO control. FIGS. 13, 14A, 14B, 15A, and 15B illustrate the results of this study.

Example 121

Dose-Response Curves

A549 (Cat No. CCL-185) cell line was obtained from American Type Culture Collection (ATCC). They were grown in T75 flasks in DMEM containing 10% FBS and Pen-Strep. at 37° C. in a humidified, 5% $CO_2$ incubator. The adherent cells were grown to about 90% confluency, culture medium was aspirated, and the cell layer was rinsed with PBS. Two mL trypsin solution (0.25%) was added to the flask and observed under an inverted microscope until cell layer is dispersed. Eight mL media was added, cells were spun down at 1000 g for 5 minutes. Cell pellet was re-suspended in 10 mL media and an appropriate volume was inoculated into a new culture flask. Cells were plated in a 6-well plate at a density of 250,000-300,000 cells/well in 3 mL media and incubated 37° C. in a humidified, 5% $CO_2$ incubator. Next day, 10 mM stock solutions of compounds were diluted 10- and 100-fold in DMSO to yield 100 and 10 μM solutions, respectively. These solutions were added to the cells (3 μL/well), mixed by swirling the plate, and incubated at 37° C. in a humidified, 5% $CO_2$ incubator for 2 hours. Cells were washed with PBS and scraped in 50 μL of lysis buffer containing protease and phosphatase inhibitors. Cell lysates were stored at −20° C. Cell lysates were thawed and spun at 12,000 rpm for one minute, 3 1 of the supernatant was added to 500 μL of Coomassie blue reagent following by 500 μL of water. Absorbance was read at 595 nm after 10 minutes of incubation. Protein standards were used (0-20 mg/mL) to calculate protein concentrations of test samples. For electrophoresis 20 μg of protein was mixed with 5 μl of 4× Laemmle's sample buffer and 1 μl of 0.4 M DTT in a volume of 20 μl made up with lysis buffer. All samples were heated at 95° C. for 5 minutes, cooled to room temperature and spun down. Protein samples were loaded onto 4-12% polyacrylamide gels and run at 100V for about 1.5 hours till the blue dye reached the bottom. After the run, gel was removed and protein transfer was done using iBlot for 7 minutes, as per manufacturer's recommendations. After the transfer, nitrocellulose membrane was incubated on a shaker in 5 mL of blocking buffer at room temperature for 1 hr. The blot was then incubated overnight on a shaker in 5 ml of blocking buffer containing 0.2% Tween-20 and primary antibody, at room temperature. Anti-phospho-STAT3 antibody was used at a dilution of 1:500, the other 3 primary antibodies were used at a dilution of 1:1000. Next day, the blot was washed 3 times for 10 min each with 10 mL of TBST followed by incubation on a shaker in 5 ml of blocking buffer containing 0.2% Tween-20 and 0.5 μl of the IRDye labeled secondary antibodies, diluted 1:10000, at room temperature for 1 hr. The blot was then washed 3 times for 10 min each with 10 mL of TBST and dried between sheets of paper towels.

Antibodies: Phospho-STAT3 (S727), mouse polyclonal antibodies were obtained from BD Biosciences (Cat No. 612542), following 3 antibodies were obtained from Cell Signaling Technologies. Anti-STAT3, rabbit monoclonal antibodies (Cat No. 12640), Anti-ERK, mouse monoclonal antibodies (Cat No: 9107), and Anti-phospho-ERK, rabbit monoclonal antibodies (Cat No. 4377).

Secondary antibodies: IRDye 800CW goat anti-rabbit antibodies (LICOR Cat No. 926-32211), IRDye 680RD goat anti-rabbit antibodies (LICOR Cat No. 926-68071), IRDye 800CW goat anti-mouse antibodies (LICOR Cat No. 926-32210) and IRDye 680RD goat anti-mouse antibodies (LI-COR Cat No. 926-68070)

Imaging was done using LICOR's Odyssey imaging system, quantitation was done using their software, Image Studio version 3.1.

Example 122

Pharmacokinetics

Female mice (either athymic BALC/c nude, or BALB/c mice) were inoculated with a single subcutaneous injection of 0.2 ml of mouse Colon-26 cell suspension (1×105 cells per animal) in the inguinal region. Colon26 (C26) tumor bearing mice received a single dose (3 mice/treatment) of vehicle (10% DMSO/90% [20% SBE-β-CD in saline], pH 5) containing compounds at 100 mg/kg by gavage (p.o.) and 2-hour post dose humanely euthanized.

Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Waters HSS T3 2.1×50 mm (1.8 um) LC column, and an API-6500 Electrospray MS unit). The results of this study are represented in Table 10.

TABLE 10

| Pharmacokinetics Summary | | | | |
|---|---|---|---|---|
| Compound | Plasma | Liver | Tumor | Muscle |
| Reference 2 | 5670 ng/ml | 1990 ng/g | 819 ng/g | 550 ng/g |
| Compound 9 | 407 ng/ml | 1260 ng/g | 1350 ng/g | 363 ng/g |
| Compound 13 | BQL | 36.65 ng/g | 26 ng/g | BQL |
| Compound 14 | 18.46 ng/ml | 17.8 ng/g | 2.68 ng/g | 19 ng/g |

Reference 2 is

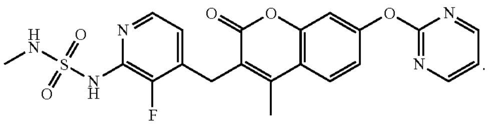 [SMILES: CNS(=O)(=O)Nc1nccc(Cc2c(C)c3ccc(Oc4ncccn4)cc3oc2=O)c1F]

Example 123

Pharmacokinetic Profile for Compound 9 and 197

Figure 16:
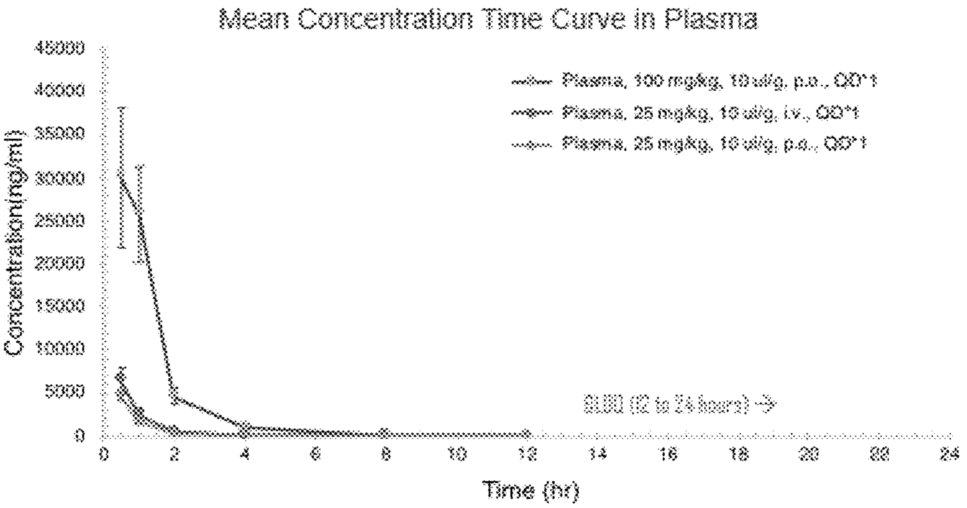
FIG. 16 illustrates a graph of a single dose pharmacokinetic profile in plasma.
Figure 17:
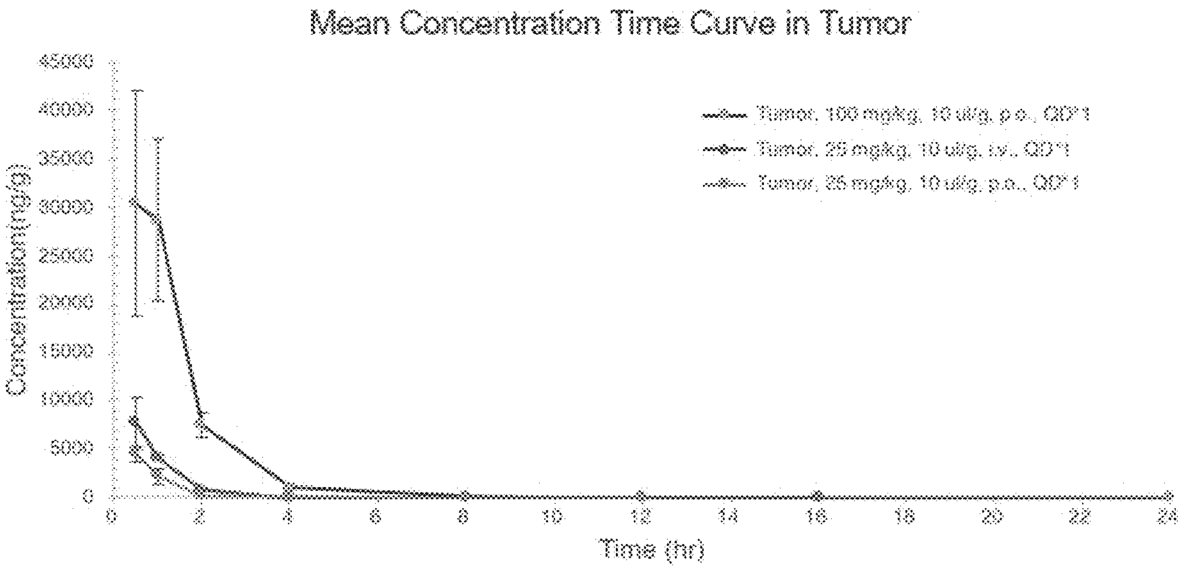
FIG. 17 illustrates a graph of a single dose pharmacokinetic profile in the CRC model Colon-26 tumor.

Female mice (either athymic BALC/c nude, or BALB/c mice) were inoculated with a single subcutaneous injection of 0.1 ml of mouse Colon-26 cell suspension (1×105 cells per animal) in the right flank region. Colon26 (C26) tumor bearing mice received a single dose (3-4 mice/treatment) of vehicle (10% DMSO/90% [20% SBE-β-CD in saline], pH 5) containing compounds at indicated dose by gavage (p.o.) or intravenous administration (i.v.) and at various time points (0.16, 0.5, 1, 2, 4, 8, 12, 16, 24-hour) post dose humanely euthanized. Blood was obtained through cardiac puncture into K+EDTA tubes, mixed by inversion and centrifuged to obtain the plasma. Tissues were excised, cleaned of surrounding tissues. All samples immediately snap frozen in liquid N2 prior to LC-MS/MS analysis (using Agilent Poroshell-120 EC-C18 (4.0 μm) 2.1×50 mm, and a Water+ API-4000 Electrospray MS unit). The results of this study are illustrated in FIGS. 16, and 17. Tables 11 describes a single does PK profile (plasma) and Table 12 describes a single dose PK profile (tumor).

TABLE 11

| Single Dose PK Profile (Plasma), compound 9/compound 197 | | | |
|---|---|---|---|
| PK Parameter | 25 mpk i.v. | 25 mpk p.o. | 100 mpk p.o. |
| $T_{1/2}$ (hr) | 0.63/2.39 | 1.32/1.23 | 1.22/1.38 |
| $T_{max}$ (hr) | 0.50/0.16 | 0.50/0.50 | 0.50/0.16 |
| $C_{max}$ (ng/mL) | 6,520/10,930 | 4,640/2,317 | 30,067/14,200 |
| $AUC_{0-4}$ (ng · hr/mL) | 5,807/7,730 | 4,392/3,645 | 44,548/31,063 |
| $AUC_{0-\infty}$ (ng · hr/mL) | 5,808/7,735 | 4,404/3,650 | 44,566/31,071 |
| Bioavailability (%) | n/a/n/a | 75.6/47.0 | 191.8/100.0 |

TABLE 12

| Single Dose PK Profile (Tumor), Compound 9/Compound 197 | | | |
|---|---|---|---|
| PK Parameter | 25 mpk i.v. | 25 mpk p.o. | 100 mpk p.o. |
| $T_{1/2}$ (hr) | 3.46/— | 1.28/— | 1.97/— |
| $T_{max}$ (hr) | 0.50/0.50 | 0.50/1.00 | 0.50/1.00 |
| $C_{max}$ (ng/mL) | 7,790/6,750 | 4,577/1,917 | 30,333/12,560 |
| $AUC_{0-4}$ (ng · hr/mL) | 8,278/8,315 | 4,892/3,461 | 51,661/36,856 |
| $AUC_{0-\infty}$ (ng · hr/mL) | 8,288/8,363 | 4,903/— | 51,711/37,087 |
| Bioavailability (%) | n/a/n/a | 59.1/42.0 | 156.0/111.0 |

Example 124

A549 Xenograft Body Weight (23 Days BID p.o. Dosing

Female, athymic BALB/c nude mice (Beijing Anikeeper Biotech Co., Ltd (Beijing, China)), approximately 8-9 weeks old were used in these studies. Animals were maintained in individually vented cages on a 12-h light-dark cycle. Food and water were available ad libitum. The A549 tumor cells were maintained in vitro with Ham's F12K medium supplemented with 10% fetal bovine serum at 37° C. in an atmosphere of 5% $CO_2$ in air. The cells in exponential growth phase were harvested and quantitated by cell counter before tumor inoculation. Each mouse was inoculated subcutaneously in the right flank region with A549 tumor cells ($5\times10^5$) in 0.1 mL of PBS. Randomization for inoculation was started when the mean tumor size reaches approximately 144 $mm^3$. A total of 48 mice were enrolled in the study and allocated into 8 groups as shown in Section 4, with 6 mice per group.

Animals were treated with either vehicle (10% DMSO/90% [20% SBE-β-CD in saline], pH 5) or vehicle containing compounds at the indicated doses by gavage (p.o.) twice daily for 23 days (BID×23 p.o.), or to ethical endpoints (BWL>20%; Median Tumor Volume (MTV)>2000 mm3; Individual TV>3000 mm3; clinical signs of unwell). Clinical signs of unwell was characterized, but not limited to the following. Severe dehydration, hypothermia, abnormal/labored respiration, lethargy, obvious pain, diarrhea, skin lesions, neurological symptoms, impaired mobility (not able to eat or drink) due to significant ascites and enlarged abdomen, astasia, continuous prone or lateral position, signs of muscular atrophy, paralytic gait, clonic convulsions, tonic convulsions, persistent bleeding from body orifice. Dosing as well as tumor and body weight measurements were conducted in a Laminar Flow Cabinet.

Animals were checked daily for morbidity and mortality. During routine monitoring, the animals were checked for any effects of tumor growth and treatments on behavior such as mobility, food and water consumption, body weight gain/loss (body weights were measured twice per week after randomization), eye/hair matting and any other abnormalities. Mortality and observed clinical signs were recorded for individual animals in detail.

Tumor volumes were measured twice per week after randomization in two dimensions using a caliper, and the volume was expressed in mm3 using the formula: V=(L×W×W)/2, where V is tumor volume, L is tumor length (the longest tumor dimension) and W is tumor width (the longest tumor dimension perpendicular to L). Results were presented as the median tumor volume, expressed in mm3+/− interquartile range, of each group. Tumor Growth Inhibition; TGI %=[1−(Ti/(Ci)]×100; where Ti as the median tumor volume of the treatment group on the measurement day, Ci as the median tumor volume of control group at the measurement day.

The body weights and tumor volumes were measured by using StudyDirector™ software (version 3.1.399.19).

Figure 18:
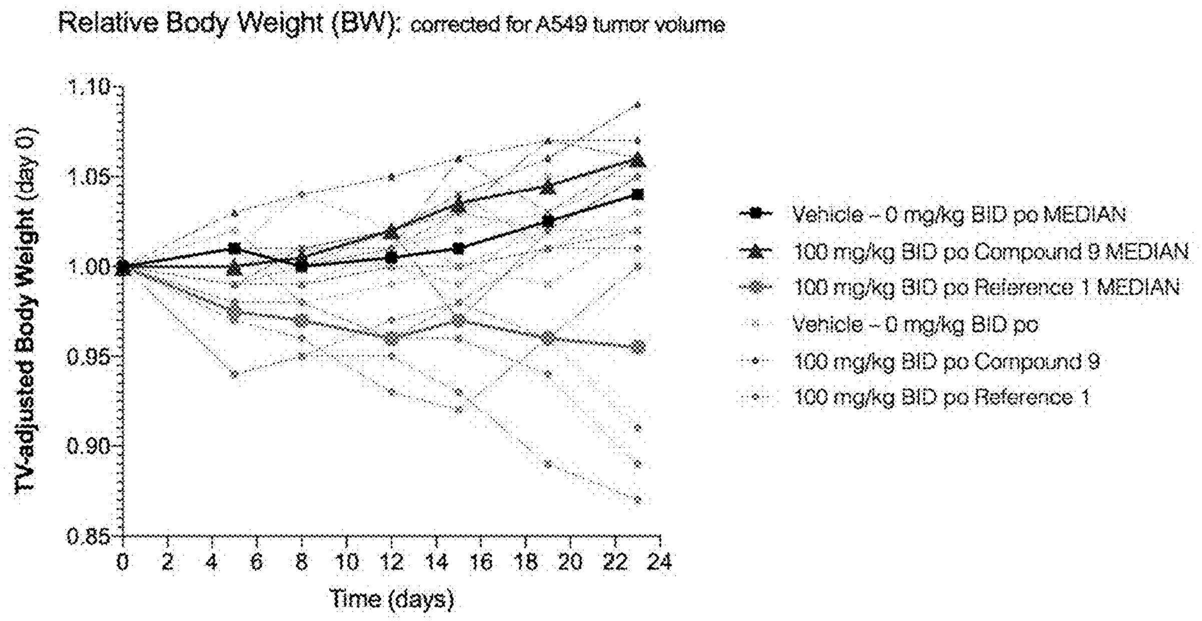
FIG. 18 illustrates a graph of relative body weight corrected for the NSCLC model A549 tumor volume.

The protocol and any amendment(s) or procedures involving the care and use of animals in this study were reviewed and approved by the Institutional Animal Care and Use Committee (IACUC) of CrownBio prior to execution. During the study, the care and use of animals were conducted in accordance with the regulations of the Association for Assessment and Accreditation of Laboratory Animal Care (AAALAC). The results are described in FIG. 18.

Example 125

Drug Profiles

Table 13 describes the attributes of two compounds and a reference compound.

TABLE 13

| Attribute | Reference 2 | Compound 9 | Compound 19 |
|---|---|---|---|
| pERK IC50 (A549) [12-point dose] | 7.2 nM | 19.8 nM | 40-50 nM |
| A549 pERK:tERK ratio [10 nm; 2 hr] | 0.56 | 0.62 | n.t. |
| A375 pERK:tERK ratio [10 nM; 2 hr] | 0.59 | 0.71 | n.t. |
| CRAF A549 pMEK:tMEK [100 nM; 2 hr] | 2.09 | 0.47 | n.t. |
| Mouse Microsome ($t_{1/2}$ min) | 18 min | 44 min | 53 min |
| Mouse Clint (µl/min/mg) | 78 | 32 | 26 |
| Human Microsome ($t_{1/2}$ min) | >90 min | 35 min | 38 min |
| Human Clint (µl/min/mg) | <15 | 40 | 37 |
| Kinetic Solubility (PBS pH = 7.4; 4 hr) | 36 µM | >80 µM | >80 µM |
| eLogD (lipophilicity; pH = 7.4) | 3.6 | 3.0 | 2.9 |
| PAMPA (pH = 7.4; Papp 10-6 cm/s) | 29 | 37 | 51 |

Example 126

A549-pERK 10 nM

A549 or 375 cells were treated in duplicate for two hours with compounds at varying concentrations. After two hours, the cells were lysed, snap frozen, and stored at −80° C. After storage, the lysate was quantified with the Bradford assay. Before the lysates were prepared to run on the Jess, the lysates were diluted to 1 mg/mL for pERK analysis and 1.5 mg/mL pMEK analysis using quantitative Western blotting. ERK and MEK phosphorylation levels were estimated by taking the ratio of phospho-protein to total protein and normalizing to the DMSO control. The results of this study are described in Tables 14-16.

TABLE 14

A549-pERK 10 nM, 2 h

| Compound | A549-pERK (10 nM, 2 h) |
|---|---|
| Compound 9 | 63.0 (mean, n = 20) |
| Compound 10 | 27.7 (mean, n = 2) |
| Compound 14 | 64 |
| Compound 15 | 73.8 |
| Compound 16 | 91.6 |
| Compound 19 | 59.9 |
| Compound 21 | 20.4 (mean, n = 2) |
| Compound 24 | 42.4 (mean, n = 3) |
| Compound 25 | 66.2 (mean, n = 2) |
| Compound 26 | 94.2 |
| Compound 29 | 96 |
| Compound 30 | 54.3 |
| Compound 31 | 66.7 |
| Compound 33 | 55.4 |
| Compound 48 | 94.3 |
| Compound 50 | 103 |
| Compound 56 | 92.9 |
| Compound 57 | 106 |
| Compound 57 | 119 |

TABLE 14-continued

A549-pERK 10 nM, 2 h

| Compound | A549-pERK (10 nM, 2 h) |
|---|---|
| Compound 58 | 98.7 |
| Compound 58 | 108 |
| Compound 59 | 105 |
| Compound 60 | 91.1 |
| Compound 62 | 73 |
| Compound 63 | 88 |
| Compound 64 | 73 |
| Compound 65 | 100 |

TABLE 14-continued

A549-pERK 10 nM, 2 h

| Compound | A549-pERK (10 nM, 2 h) |
|---|---|
| Compound 66 | 104 |
| Compound 67 | 112 |
| Compound 68 | 68.9 |
| Compound 69 | 101 |
| Compound 70 | 103 |
| Compound 71 | 99.4 |
| Compound 72 | 85.4 |
| Compound 73 | 77.7 |
| Compound 74 | 75.3 |
| Compound 75 | 69.3 |
| Compound 76 | 62.1 |
| Compound 77 | 67.2 |
| Compound 78 | 78.6 |
| Compound 79 | 49.4 |
| Compound 79 | 75.6 (mean, n = 2) |
| Compound 80 | 56.4 |
| Compound 81 | 57.6 |
| Compound 82 | 64.9 |
| Compound 83 | 59.5 |
| Compound 84 | 83.2 |
| Compound 86 | 96.4 |
| Compound 87 | 63.8 |
| Compound 88 | 142 |
| Compound 89 | 83.7 |
| Compound 90 | 72.4 (mean, n = 2) |
| Compound 91 | 74.6 |
| Compound 92 | 93.8 |
| Compound 93 | 108 |
| Compound 94 | 93.5 |
| Compound 95 | 80.2 |
| Compound 96 | 102 |
| Compound 97 | 56.5 (mean, n = 2) |
| Compound 99 | 98.9 |
| Compound 100 | 63.1 (mean, n = 2) |
| Compound 104 | 77.3 |
| Compound 107 | 18.0 (mean, n = 2) |
| Compound 108 | 5.78 (mean, n = 2) |
| Compound 109 | 4.51 (mean, n = 2) |
| Compound 110 | 5.92 (mean, n = 2) |

TABLE 14-continued

A549-pERK 10 nM, 2 h

| Compound | A549-pERK (10 nM, 2 h) |
| --- | --- |
| Compound 111 | 4.63 (mean, n = 2) |
| Compound 112 | 46.3 (mean, n = 2) |
| Compound 113 | 24.7 (mean, n = 2) |
| Compound 114 | 36.6 (mean, n = 2) |
| Compound 115 | 13.5 (mean, n = 2) |
| Compound 116 | 52.8 (mean, n = 2) |
| Compound 117 | 58.6 (mean, n = 3) |
| Compound 118 | 21.1 (mean, n = 2) |
| Compound 119 | 64.8 (mean, n = 2) |
| Compound 120 | 77.2 |
| Compound 121 | 92.5 |
| Compound 122 | 116 |
| Compound 124 | 94.6 |
| Compound 125 | 54.4 (mean, n = 2) |
| Compound 126 | 91.4 |
| Compound 127 | 110 |
| Compound 128 | 66.3 (mean, n = 2) |
| Compound 129 | 92.2 |
| Compound 130 | 10.7 (mean, n = 2) |
| Compound 132 | 62.6 |
| Compound 133 | 88.1 |
| Compound 134 | 33.1 (mean, n = 2) |
| Compound 136 | 50.7 (mean, n = 2) |
| Compound 137 | 69.3 |
| Compound 138 | 96.9 |
| Compound 139 | 53.5 (mean, n = 2) |
| Compound 140 | 65.0 (mean, n = 2) |
| Compound 141 | 77.8 (mean, n = 2) |
| Compound 142 | 94.6 |
| Compound 143 | 104 |
| Compound 144 | 129 |
| Compound 145 | 104 |
| Compound 146 | 114 |
| Compound 147 | 21.7 |
| Compound 148 | 49.6 |
| Compound 149 | 69.1 |
| Compound 150 | 47.4 |
| Compound 151 | 54.2 |
| Compound 152 | 70.5 |
| Compound 153 | 50.2 |
| Compound 154 | 64 |
| Compound 155 | 84.9 |
| Compound 156 | 94.4 |
| Compound 157 | 63.9 |
| Compound 158 | 80 |
| Compound 159 | 82.7 |
| Compound 160 | 72.9 |
| Compound 161 | 79.6 |
| Compound 162 | 72.9 |
| Compound 163 | 104 |
| Compound 164 | 102 |
| Compound 165 | 104 |
| Compound 166 | 60.9 |
| Compound 172 | 111 |
| Compound 173 | 97.7 |
| Compound 180 | 75 |
| Compound 181 | 100 |
| Compound 182 | 117 |
| Compound 183 | 32.4 (mean, n = 2) |
| Compound 187 | 85.9 (mean, n = 2) |
| Compound 190 | 107 |
| Compound 186 | 80.1 (mean, n = 2) |
| Compound 191 | 131 |
| Compound 193 | 90.7 |
| Compound 194 | 83 |
| Compound 195 | 113 |
| Compound 196 | 106 |
| Compound 197 | 31.7 (mean, n = 2) |
| Compound 198 | 109 |
| Compound 199 | 118 |
| Compound 200 | 112 |
| Compound 201 | 119 |
| Compound 202 | 119 |
| Compound 203 | 115 |
| Compound 204 | 83.4 |

TABLE 14-continued

A549-pERK 10 nM, 2 h

| Compound | A549-pERK (10 nM, 2 h) |
| --- | --- |
| Compound 205 | 73.7 |
| Compound 207 | 97.4 |
| Compound 208 | 105 |
| Compound 209 | 78.5 |
| Compound 210 | 81.9 |
| Compound 211 | 121 |
| Compound 212 | 100 |
| Compound 213 | 100 |
| Compound 214 | 98.6 |
| Compound 215 | 100 |
| Compound 216 | 89.5 |
| Compound 217 | 96.7 |
| Compound 218 | 113 |
| Compound 219 | 85.9 |
| Compound 220 | 109 |
| Compound 221 | 114 |
| Compound 222 | 150 |
| Compound 223 | 119 |
| Compound 224 | 119 |

TABLE 15

A549-pERK 10 μM, 2 h

| Compound | A549-pERK 10 uM, 2 h |
| --- | --- |
| Compound 9 | 1.205 (mean, n = 2) |
| Compound 57 | 7.33 |
| Compound 100 | 0.82 |
| Compound 105 | 7.39 |
| Compound 106 | 27.88 |
| Compound 133 | 23.41 |
| Compound 181 | 22.23 |
| Compound 182 | 6.77 |
| Compound 183 | 0.82 |
| Compound 186 | 0.74 |
| Compound 187 | 0.91 |
| Compound 190 | 15.28 |
| Compound 191 | 8.6 |
| Compound 207 | 11.35 |
| Compound 208 | 23.64 |
| Compound 209 | 34.23 |
| Compound 210 | 78.26 |
| Compound 211 | 70.75 |
| Compound 212 | 13.03 |
| Compound 213 | 70.14 |
| Compound 214 | 7.34 |
| Compound 215 | 11.77 |
| Compound 216 | 4.51 |
| Compound 217 | 11.2 |
| Compound 218 | 9.46 |
| Compound 219 | 13.94 |
| Compound 220 | 4.28 |
| Compound 221 | 17.24 |
| Compound 222 | 9.32 |
| Compound 223 | 3.04 |
| Compound 224 | 28.27 |

TABLE 16

A549-CAR BP 100 nM, 2 h

| Compound | A549-CRAF BP 100 nM, 2 h |
| --- | --- |
| Compound 9 | 44.9 (mean, n = 8) |
| Compound 10 | 42.2 |
| Compound 14 | 59.1 |
| Compound 19 | 51.9 |

TABLE 16-continued

| A549-CAR BP 100 nM, 2 h | |
|---|---|
| Compound | A549-CRAF BP 100 nM, 2 h |
| Compound 21 | 47.9 (mean, n = 2) |
| Compound 24 | 55.9 (mean, n = 2) |
| Compound 25 | 71 |
| Compound 33 | 51.4 |
| Compound 73 | 33.9 |
| Compound 74 | 59.2 |
| Compound 75 | 66.5 |
| Compound 76 | 53.9 |
| Compound 77 | 78 |
| Compound 78 | 64.2 |
| Compound 79 | 45.2 |
| Compound 79 | 64.9 |
| Compound 80 | 56.1 |
| Compound 81 | 78.3 |
| Compound 82 | 72.3 |
| Compound 83 | 68.4 |
| Compound 84 | 87.3 |
| Compound 86 | 53.2 |
| Compound 87 | 95.8 |
| Compound 88 | 53.6 |
| Compound 90 | 71 |
| Compound 91 | 84.2 |
| Compound 97 | 52.1 (mean, n = 2) |
| Compound 100 | 65.3 |
| Compound 107 | 39.9 |
| Compound 108 | 47.9 (mean, n = 2) |
| Compound 109 | 41.9 (mean, n = 2) |
| Compound 110 | 56.6 (mean, n = 2) |
| Compound 111 | 48.6 (mean, n = 2) |
| Compound 112 | 52.9 (mean, n = 2) |
| Compound 113 | 48.0 (mean, n = 2) |
| Compound 114 | 59.9 (mean, n = 3) |
| Compound 115 | 39.2 (mean, n = 2) |
| Compound 116 | 53.9 (mean, n = 2) |
| Compound 117 | 56.8 (mean, n = 2) |
| Compound 118 | 39.1 (mean, n = 2) |
| Compound 119 | 66.1 |
| Compound 125 | 41.7 |
| Compound 128 | 37.7 |
| Compound 130 | 36.9 |
| Compound 132 | 57.8 |
| Compound 134 | 26.9 |
| Compound 136 | 44.4 (mean, n = 2) |
| Compound 139 | 62.1 |
| Compound 140 | 70.3 |
| Compound 144 | 80.3 |
| Compound 147 | 46.4 |
| Compound 148 | 56.5 |
| Compound 150 | 90.2 |
| Compound 151 | 70.9 |
| Compound 153 | 54.1 |
| Compound 183 | 65.9 (mean, n = 2) |
| Compound 197 | 48.5 (mean, n = 2) |

Accordingly, some aspects described herein relate to the following numbered alternatives:

1. A compound having the structure of Formula (I):

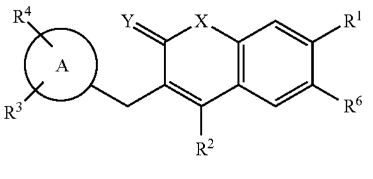

(I)

including pharmaceutically acceptable salts thereof, wherein:

Ring A is

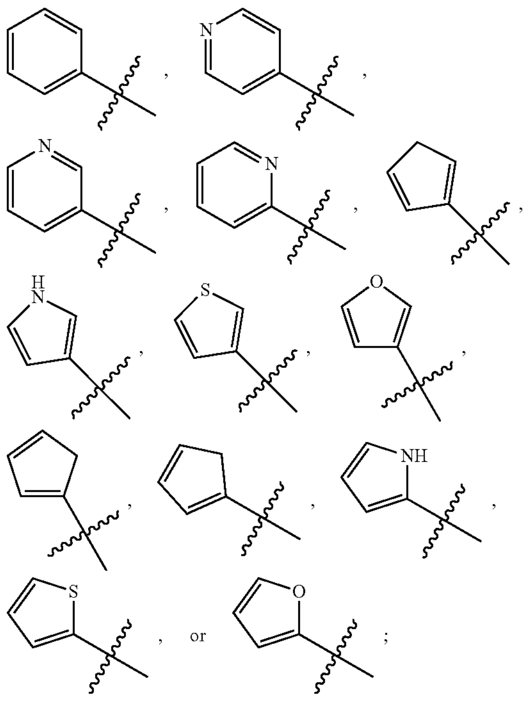

$R^1$, $R^2$, $R^3$, and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, and L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

X is $C(R^5)_2$, $CH(R^5)$, $CH_2$, —O—,

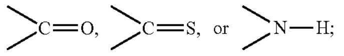

L is $—Z_1—Z_2$ or $—Z_1—Z_2—Z_3$;

$Z_1$, $Z_2$, and $Z_3$ are independently selected from the group consisting of $—CH_2—$, —O—, —S—, S═O, $—SO_2—$, C═O, $—CO_2—$, $—NO_2$, —NH—, $—CH_2CCH$, $—CH_2CN$, $—NR^5R^{5'}$, —NH(CO)—, —(CO)NH—, —(CO)NR$^5$R$^{5'}$, —NH—SO$_2$—, —SO$_2$—NH—, —R$^5$CH$_2$—, —R$^5$O—, —R$^5$S—, R$^5$—S═O, —R$^5$SO$_2$—, R$^5$—C═O, —R$^5$CO$_2$—, —R$^5$NH—, —R$^5$NH(CO)—, —R$^5$(CO)NH—, —R$^5$NH—SO$_2$—, —R$^5$SO$_2$—NH—, —NHCH$_2$CO—, —CH$_2$R$^5$—, —OR$^5$—, —SR$^5$—, S═O—R$^5$, —SO$_2$R$^5$—, C═O—R$^5$, —CO$_2$R$^5$—, —NHR$^5$—, —NH(CO)R$^5$—, —(CO)NHR$^5$—, —NH—SO$_2$R$^5$—, —SO$_2$—NHR$^5$—, optionally substituted C$_1$ to C$_6$ alkyl, optionally substituted C$_3$ to C$_8$ cycloalkyl, optionally substituted C$_6$ to C$_{10}$ aryl, optionally substituted C$_3$ to C$_8$ heterocyclyl, optionally substituted C$_3$ to C$_{10}$ heteroaryl, —CH$_2$-(optionally substituted aryl), —CH$_2$-(optionally substituted C$_3$ to C$_8$ cycloalkyl), and —CH$_2$-(optionally substituted C$_3$ to C$_{10}$ heteroaryl);

each R$^5$ and R$^{5'}$ are independently selected from H, deuterium, optionally substituted C$_1$ to C$_6$ alkyl, optionally substituted C$_2$ to C$_6$ alkenyl, optionally substituted C$_2$ to C$_6$ alkynyl, optionally substituted C$_3$ to C$_8$ carbocyclyl, optionally substituted C$_6$ to C$_{10}$ aryl, optionally substituted C$_3$ to C$_8$ heterocyclyl, and optionally substituted C$_3$ to C$_{10}$ heteroaryl; and Y is CH$_2$, NH, or O, with the proviso that R$^1$ is not pyrimidyl.

2. The compound of alternative 1, wherein the Ring A is

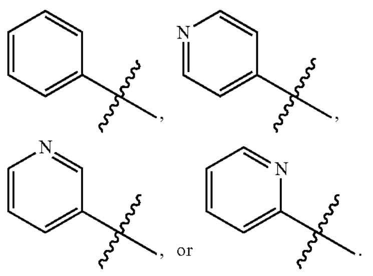

3. The compound of alternative 1 or 2, wherein R$^2$ is —CH$_3$.

4. The compound of alternative 1 or 2, wherein R$^2$ is L.

5. The compound of alternative 4, wherein L is —Z$_1$—Z$_2$.

6. The compound of alternative 5, wherein Z$_1$ is —CH$_2$—.

7. The compound of alternative 5 or 6, wherein Z$_2$ is selected from optionally substituted C$_3$ to C$_8$ cycloalkyl, optionally substituted C$_3$ to C$_8$ heterocyclyl, optionally substituted C$_3$ to C$_8$ heteroaryl, —NR$^5$R$^{5'}$, —CH$_2$CCH, or —CH$_2$CN.

8. The compound of alternative 7, wherein R$^5$ and R$^{5'}$ are each independently selected from H or CH$_3$.

9. The compound of alternative 4, wherein L is —Z$_1$—Z$_2$—Z$_3$.

10. The compound of alternative 9, wherein Z$_1$ is —CH$_2$—, Z$_2$ is selected from the group consisting of —NR$^5$R$^{5'}$, —NHCH$_2$CO—, C$_3$ to C$_8$ cycloalkyl, optionally substituted C$_3$ to C$_8$ heterocyclyl, optionally substituted C$_3$ to C$_8$ heteroaryl and Z$_3$ is selected from the group consisting of H, deuterium, halo, optionally substituted C$_1$ to C$_6$ alkyl, optionally substituted C$_3$ to C$_8$ cycloalkyl, optionally substituted C$_6$ to C$_{10}$ aryl, or —CH$_2$-(optionally substituted aryl).

11. The compound of alternative 4, wherein Z$_1$ is —CH$_2$— and Z$_2$ is optionally substituted C$_3$ to C$_8$ heterocyclyl.

12. The compound of alternative 11, wherein the optionally substituted C$_3$ to C$_8$ heterocyclyl is

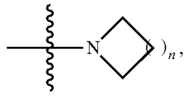

wherein n is 1, 2, 3 or 4.

13. The compound of alternative 11 or 12, wherein the optionally substituted C$_3$ to C$_8$ heterocyclyl is

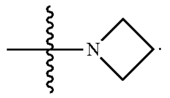

14. The compound of alternative 1, wherein R$^6$ is selected from the group consisting of H, deuterium, hydroxyl, halogen, and optionally substituted C$_1$ to C$_6$ alkyl.

15. The compound of alternative 1, having the structure depicted in Formula (Ia):

(Ia)

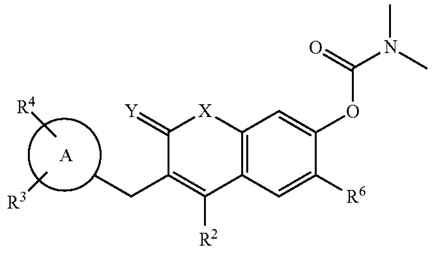

including pharmaceutically acceptable salts thereof, wherein:

Ring A is

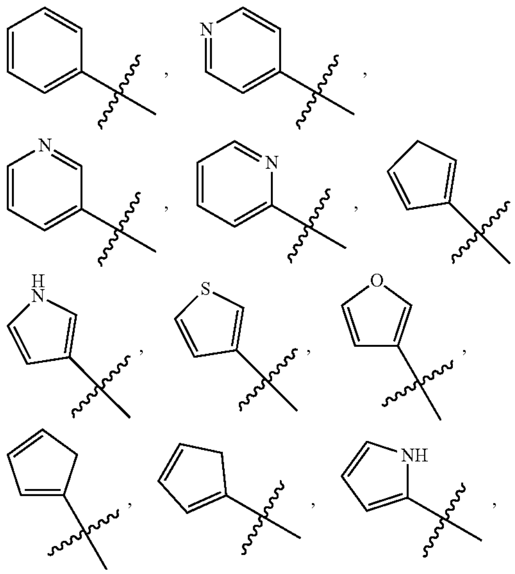

-continued

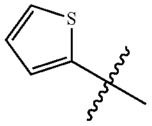, or 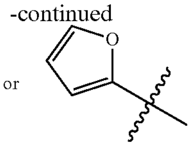;

$R^2$, $R^3$, and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

X is $C(R^5)_2$, $CH(R^5)$, $CH_2$, —O—,

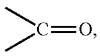, 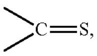, or 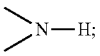;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$NHCH_2CO$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ are each independently selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

16. The compound of alternative 15, wherein the Ring A is

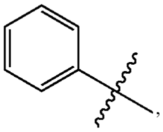, 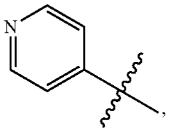,

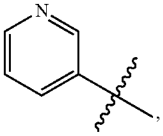, or 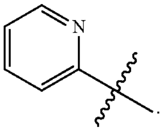.

17. The compound of alternative 15 or 16, wherein $R^2$ is —$CH_3$.

18. The compound of alternative 15 or 16, wherein $R^2$ is L.

19. The compound of alternative 18, wherein L is —$Z_1$—$Z_2$.

20. The compound of alternative 19, wherein $Z_1$ is —$CH_2$—.

21. The compound of alternative 19 or 20, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CH$, or —$CH_2CN$.

22. The compound of alternative 21, wherein $R^5$ is selected from H or $CH_3$.

23. The compound of alternative 18, wherein L is —$Z_1$—$Z_2$—$Z_3$.

24. The compound of alternative 23, wherein $Z_1$ is —$CH_2$—, $Z_2$ is selected from the group consisting of —$NR^5R^{5'}$, $C_3$ to $C_8$ cycloalkyl, optionally substituted $C_3$ to $C_8$ heterocyclyl, optionally substituted $C_3$ to $C_8$ heteroaryl and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or —$CH_2$-(optionally substituted aryl).

25. The compound of alternative 19, wherein $Z_1$ is —$CH_2$— and $Z_2$ is optionally substituted $C_3$ to $C_8$ heterocyclyl.

26. The compound of alternative 25, wherein the optionally substituted $C_3$ to $C_8$ heterocyclyl is

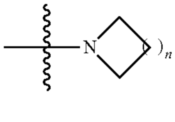, wherein n is 1, 2, 3 or 4.

27. The compound of alternative 25 or 26, wherein the optionally substituted $C_3$ to $C_8$ heterocyclyl is

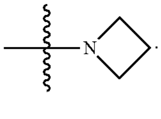.

28. The compound of alternative 1, having the structure depicted in Formula (Ib):

(Ib)

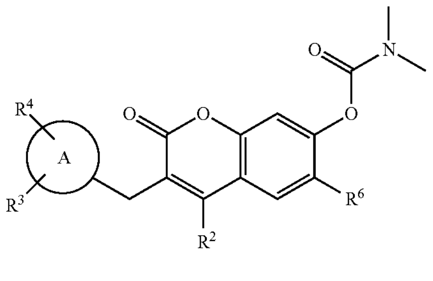

including pharmaceutically acceptable salts thereof, wherein:

Ring A is

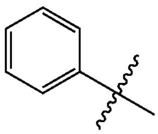, 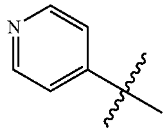,

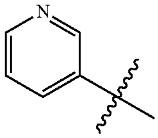, 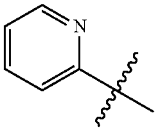, 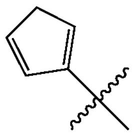,

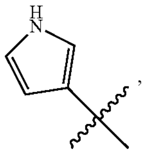, 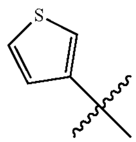, 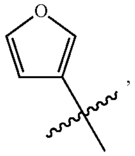,

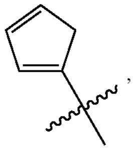, 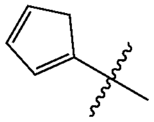, 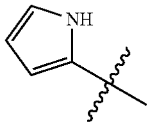,

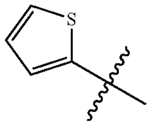, or 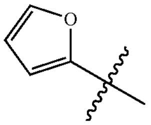;

$R^2$, $R^3$, and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl;

L is $—Z_1—Z_2$ or $—Z_1—Z_2—Z_3$;

$Z_1$, $Z_2$, and $Z_3$ are independently $—CH_2$, —O—, —S—, S═O, $—SO_2—$, C═O, $—CO_2—$, $—NO_2$, —NH—, $—CH_2CCH$, $—CH_2CN$, $—NR^5R^5$, —NH(CO)—, —(CO)NH—, $—(CO)NR^5R^5—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—NHCH_2CO—$, $—R^5NH(CO)—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and with the proviso that $R^1$ is not pyrimidyl.

29. The compound of alternative 28, wherein the Ring A is

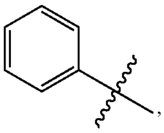, 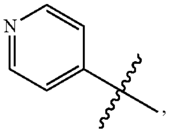,

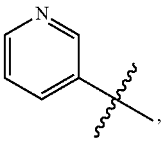, or 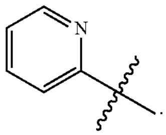.

30. The compound of alternative 28 or 29, wherein $R^2$ is $—CH_3$.

31. The compound of alternative 28 or 29, wherein $R^2$ is L.

32. The compound of alternative 31, wherein L is $—Z_1—Z_2$.

33. The compound of alternative 32, wherein $Z_1$ is $—CH_2—$.

34. The compound of alternative 32 or 33, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^{5'}$, $—CH_2CH$, or $—CH_2CN$.

35. The compound of alternative 34, wherein $R^5$ and $R^{5'}$ are each selected from H or $CH_3$.

36. The compound of alternative 31, wherein L is $—Z_1—Z_2—Z_3$.

37. The compound of alternative 36, wherein $Z_1$ is $—CH_2—$, $Z_2$ is selected from the group consisting of $—NR^5R^{5'}$, $—NHCH_2CO—$, $C_3$ to $C_8$ cycloalkyl, optionally substituted $C_3$ to $C_8$ heterocyclyl, optionally substituted $C_3$ to $C_8$ heteroaryl, and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or —$CH_2$-(optionally substituted aryl).

38. The compound of alternative 32, wherein $Z_1$ is —$CH_2$— and $Z_2$ is optionally substituted $C_3$ to $C_8$ heterocyclyl.

39. The compound of alternative 38, wherein the optionally substituted $C_3$ to $C_8$ heterocyclyl is

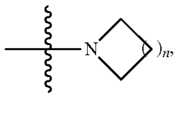

wherein n is 1, 2, 3 or 4.

40. The compound of alternative 38 or 39, wherein the optionally substituted $C_3$ to $C_8$ heterocyclyl is

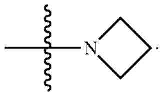 [SMILES: *N1CCC1]

41. The compound of alternative 1, having the structure depicted in Formula (Ic):

(Ic)

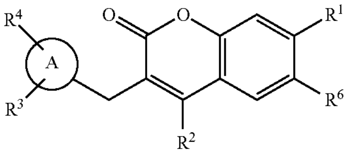

including pharmaceutically acceptable salts thereof, wherein:

Ring A is

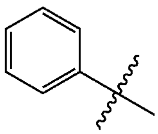, 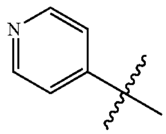, 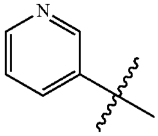, 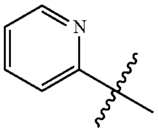, 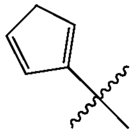, 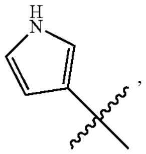, 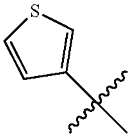, 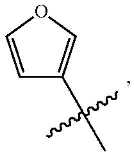, 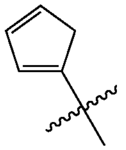, 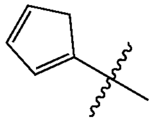, 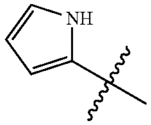, -continued

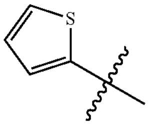, or 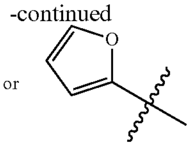;

$R^1$, $R^2$, $R^3$, and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl;

X is $C(R^5)_2$, $CH(R^5)$, $CH_2$, —O—,

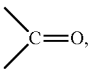, 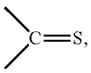, or 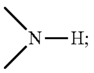;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^5$, —NH(CO)—, —(CO)NH—, —(CO)$NR^5R^5$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$NHCH_2CO$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

42. The compound of alternative 41, wherein the Ring A is

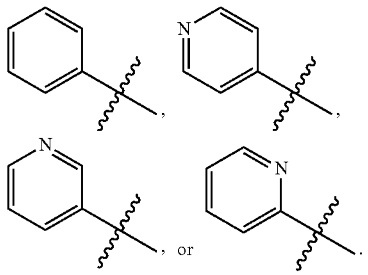

, , , or .

43. The compound of alternative 41 or 42, wherein $R^2$ is $—CH_3$.

44. The compound of alternative 41 or 42, wherein $R^2$ is L.

45. The compound of alternative 44, wherein L is $—Z_1—Z_2$.

46. The compound of alternative 45, wherein $Z_1$ is $—CH_2—$.

47. The compound of alternative 45 or 46, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CH$, or $—CH_2CN$.

48. The compound of alternative 47, wherein $R^5$ and $R^{5'}$ are each selected from H or $CH_3$.

49. The compound of alternative 44, wherein L is $—Z_1—Z_2—Z_3$.

50. The compound of alternative 45, wherein $Z_1$ is $—CH_2—$, $Z_2$ is selected from the group consisting of $—NR^5R^{5'}$, $—NHCH_2CO—$, $C_3$ to $C_8$ cycloalkyl, optionally substituted $C_3$ to $C_8$ heterocyclyl, optionally substituted $C_3$ to $C_8$ heteroaryl and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or $—CH_2$-(optionally substituted aryl).

51. The compound of alternative 45, wherein $Z_1$ is $—CH_2—$ and $Z_2$ is optionally substituted $C_3$ to $C_8$ heterocyclyl.

52. The compound of alternative 45, wherein the optionally substituted $C_3$ to $C_8$ heterocyclyl is

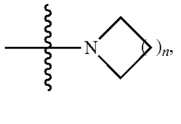

wherein n is 1, 2, 3 or 4.

53. The compound of alternative 45 or 46, wherein the optionally substituted $C_3$ to $C_8$ heterocyclyl is

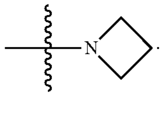 [SMILES: *N1CCC1]

54. The compound of alternative 1, having the structure depicted in Formula (Id):

(Id)

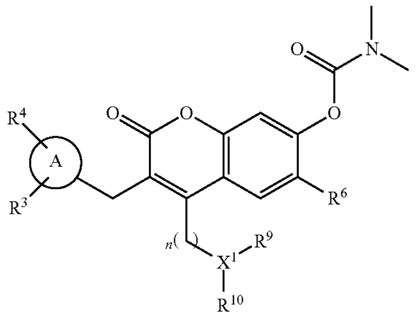

including pharmaceutically acceptable salts thereof, wherein:

Ring A is

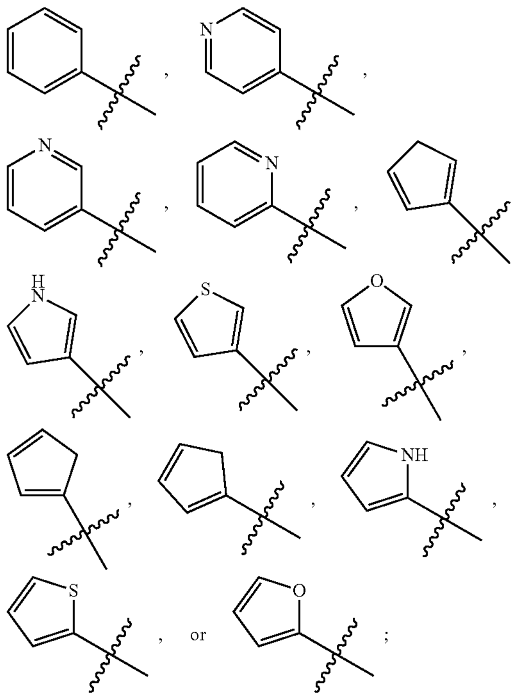

, , , , , , , , , , , or ;

$R^3$ and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, and L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

$R^9$ and $R^{10}$ are each independently selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

$X^1$ is selected from the group consisting of CH, B, N, or $PO_4$;

n is selected from 1, 2, 3, or 4;

each $R^5$ and $R^{5'}$ is independently selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, and optionally substituted $C_3$ to $C_{10}$ heteroaryl; and Y is $CH_2$, NH, or O, with the proviso that $R^1$ is not pyrimidyl.

55. The compound of alternative 54, wherein n is 1 or 2.

56. The compound of alternative 54 or 55, wherein $X^1$ is CH or N.

57. The compound of any one of alternatives 54 to 56, wherein $R^9$ is selected from optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

58. The compound of any one of alternatives 54 to 56, wherein $R^{10}$ is selected from optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

59. The compound of alternative 1, wherein the compound is selected from a compound of Table A.

60. A compound having the structure of Formula (II):

(II)

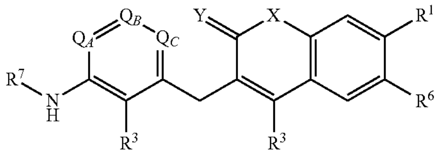

including pharmaceutically acceptable salts thereof, wherein:

$Q_A$, $Q_B$, $Q_C$ are independently C or N;

$R^1$, $R^2$, $R^3$, and $R^7$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl;

X is $C(R^5)_2$, $CH(R^5)$, $CH_2$, —O—,

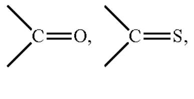

or

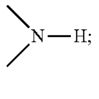

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5$NH(CO)—, —$R^5$(CO)NH—, —$NHCH_2CO$—, —$R^5$NH—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N, with the proviso that $R^1$ is not pyrimidyl.

61. The compound of alternative 60, wherein $R^2$ is —$CH_3$.

62. The compound of alternative 60, wherein $R^2$ is L.

63. The compound of alternative 62, wherein L is —$Z_1$—$Z_2$.

64. The compound of alternative 63, wherein $Z_1$ is —$CH_2$—.

65. The compound of alternative 63 or 64, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^5$, —$CH_2CH$, or —$CH_2CN$.

66. The compound of alternative 65, wherein $R^5$ and $R^{5'}$ are each selected from H or $CH_3$.

67. The compound of alternative 62, wherein L is —$Z_1$—$Z_2$—$Z_3$.

68. The compound of alternative 67, wherein $Z_1$ is —$CH_2$—, $Z_2$ is optionally substituted $C_3$ to $C_8$ heterocyclyl, and $Z_3$ is —$CH_2$-(optionally substituted aryl).

69. The compound of alternative 63, wherein $Z_1$ is $—CH_2—$ and $Z_2$ is optionally substituted $C_3$ to $C_8$ heterocyclyl.

70. The compound of alternative 69, wherein the optionally substituted $C_3$ to $C_8$ heterocyclyl is

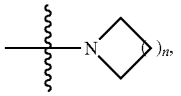

wherein n is 1, 2, 3 or 4.

71. The compound of alternative 69 or 70, wherein the optionally substituted $C_3$ to $C_8$ heterocyclyl is

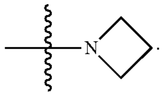

72. The compound of alternative 60, having the structure depicted in Formula (IIa):

(IIa)

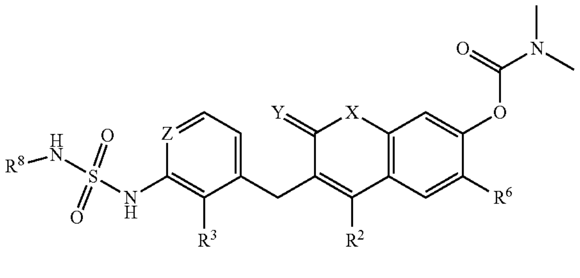

including pharmaceutically acceptable salts thereof, wherein:

$R^2$, $R^3$, $R^6$ and $R^8$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

X is $C(R^5)_2$, $CH(R^5)$, $CH_2$, —O—,

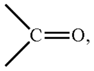 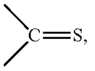 or 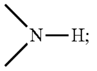

L is $—Z_1—Z_2$ or $—Z_1—Z_2—Z_3$;

$Z_1$, $Z_2$, and $Z_3$ are independently halo, $—CH_2$, —O—, —S—, S═O, $—SO_2—$, C═O, $—CO_2—$, $—NO_2$, —NH—, $—CH_2CCH$, $—CH_2CN$, $—NR^5R^{5'}$, —NH(CO)—, —(CO)NH—, $—(CO)NR^5R^{5'}—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—NHCH_2CO—$ $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N.

73. The compound of alternative 72, wherein $R^2$ is $—CH_3$.

74. The compound of alternative 72, wherein $R^2$ is L.

75. The compound of alternative 74, wherein L is $—Z_1—Z_2$.

76. The compound of alternative 75, wherein $Z_1$ is $—CH_2—$.

77. The compound of alternative 75 or 76, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^{5'}$, $—CH_2CCH$, or $—CH_2CN$.

78. The compound of alternative 77, wherein $R^5$ and $R^{5'}$ are each selected from H or $CH_3$.

79. The compound of alternative 74, wherein L is $—Z_1—Z_2—Z_3$.

80. The compound of alternative 75, wherein $Z_1$ is $—CH_2—$, $Z_2$ is selected from the group consisting of $—NR^5R^{5'}$, $—NHCH_2CO—$, $C_3$ to $C_8$ cycloalkyl, optionally substituted $C_3$ to $C_8$ heterocyclyl, optionally substituted $C_3$ to $C_8$ heteroaryl and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or $—CH_2$-(optionally substituted aryl).

81. The compound of alternative 75, wherein $Z_1$ is $—CH_2—$ and $Z_2$ is optionally substituted $C_3$ to $C_8$ heterocyclyl.

82. The compound of alternative 81, wherein the optionally substituted $C_3$ to $C_8$ heterocyclyl is

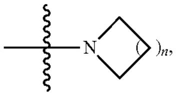

wherein n is 1, 2, 3 or 4.

83. The compound of alternative 81 to 82, wherein the optionally substituted $C_3$ to $C_8$ heterocyclyl is
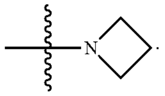 [SMILES: *N1CCC1]
84. The compound of alternative 51, wherein the compound is selected from a compound of Table A.
85. The compound of alternative 51, selected from the group consisting of:
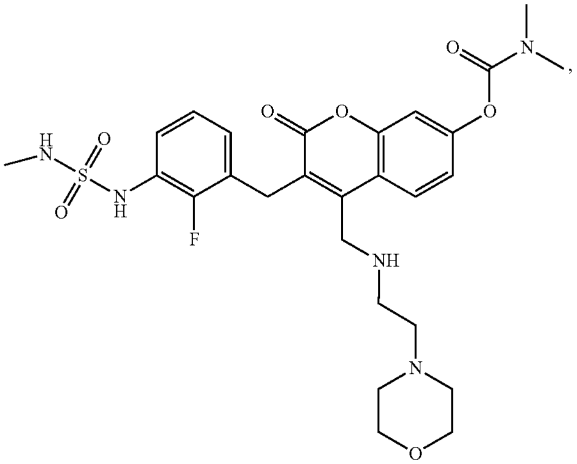
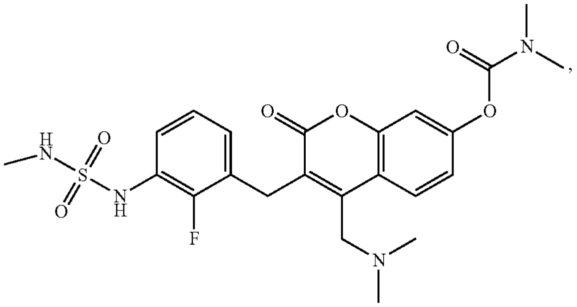
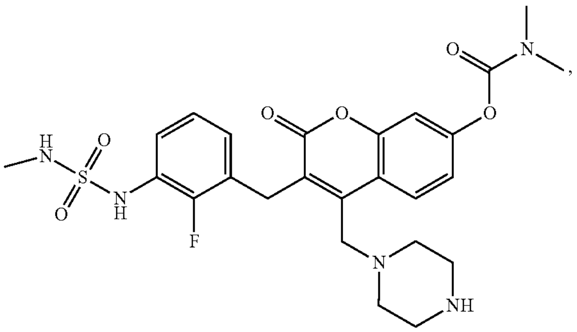
-continued
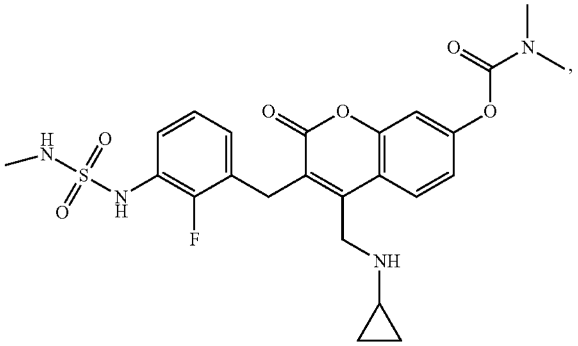
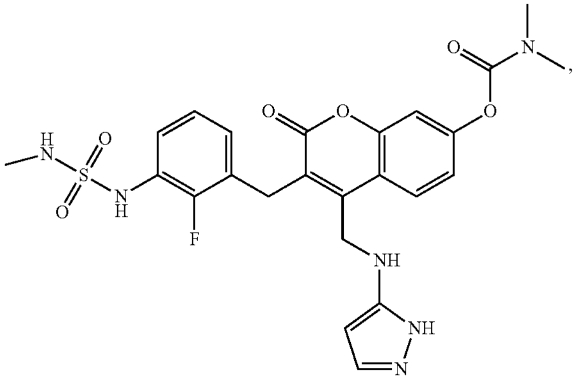
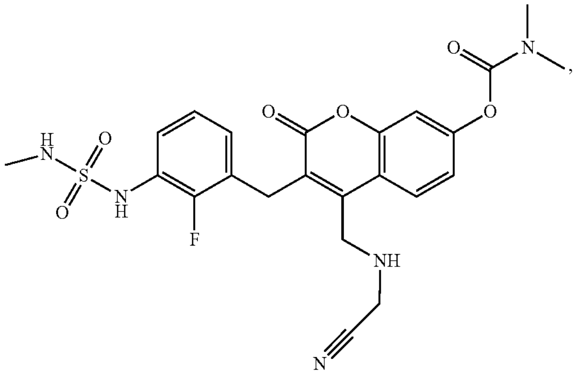
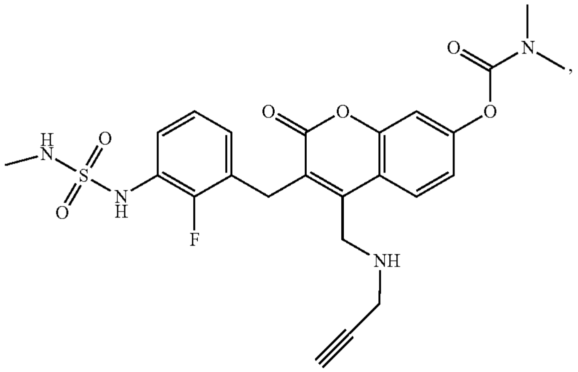

-continued
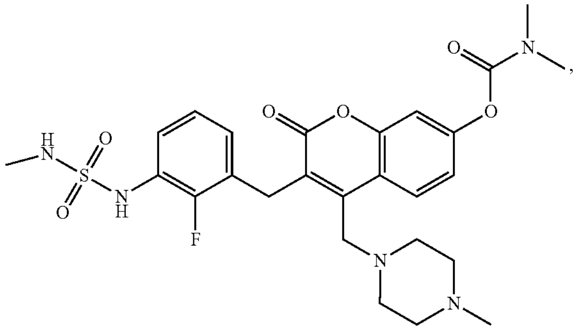
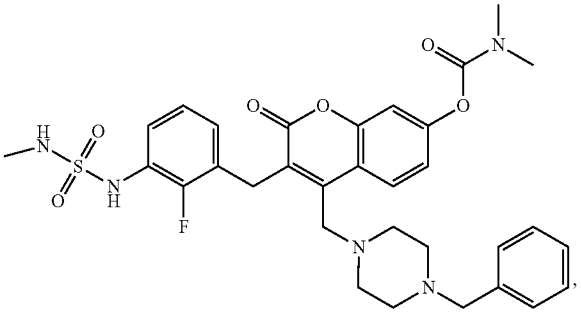
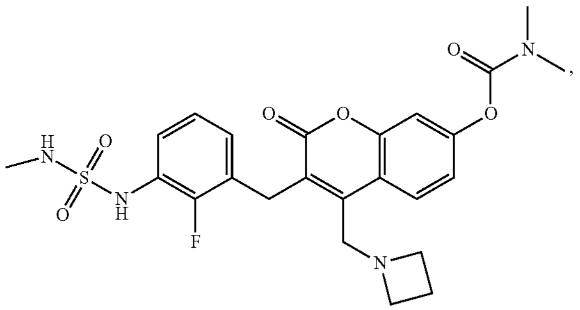
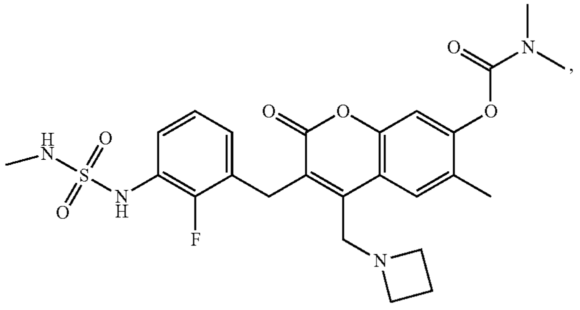
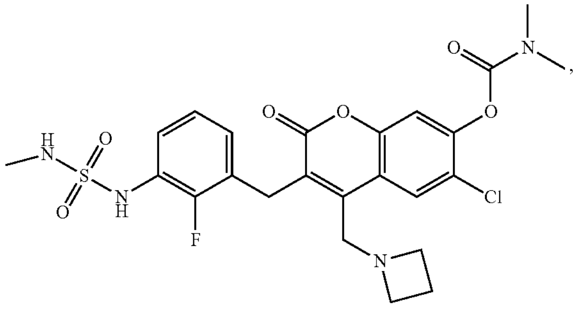
-continued
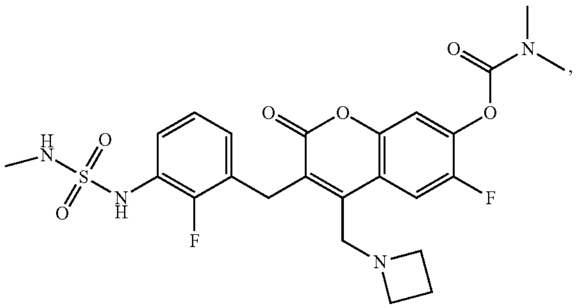
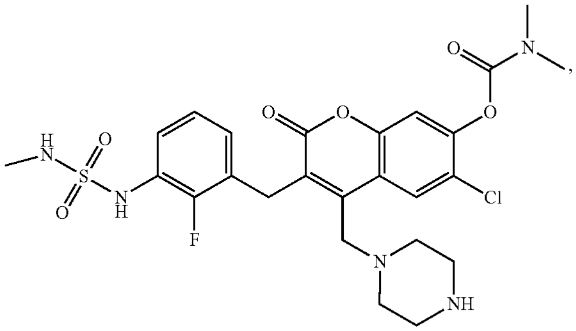
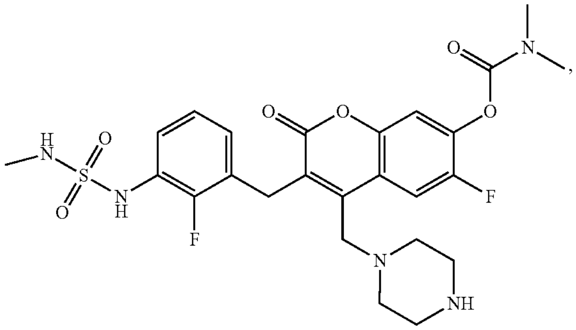
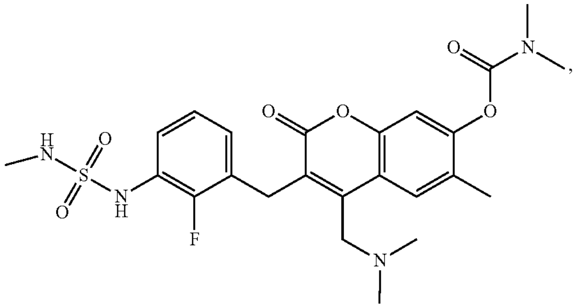
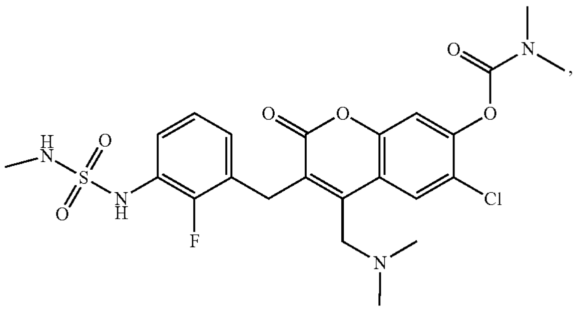

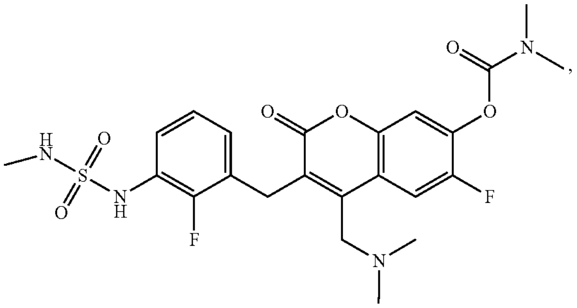
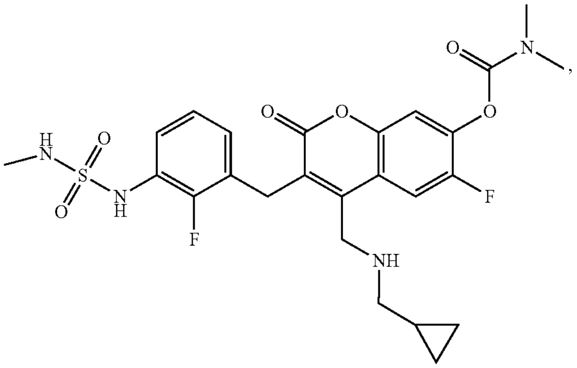
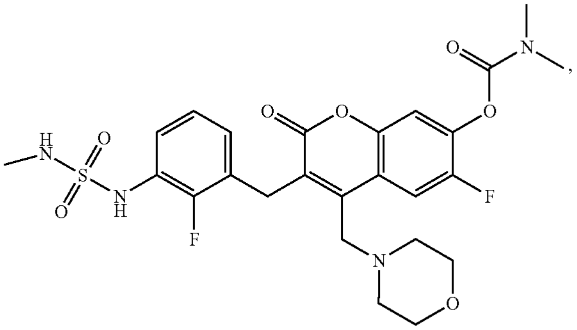
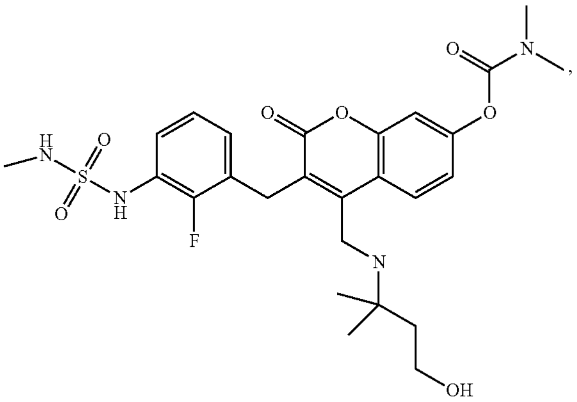
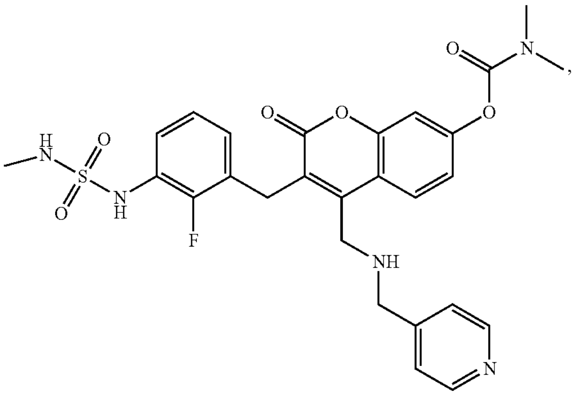
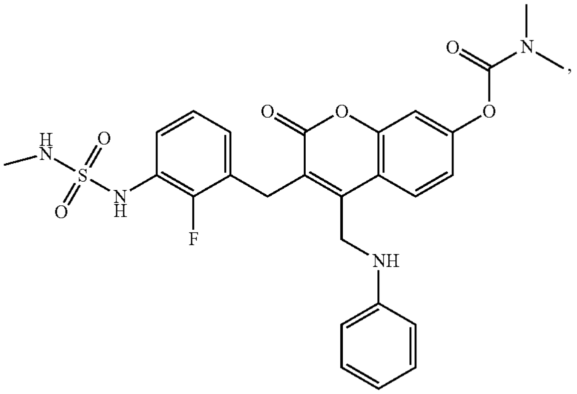
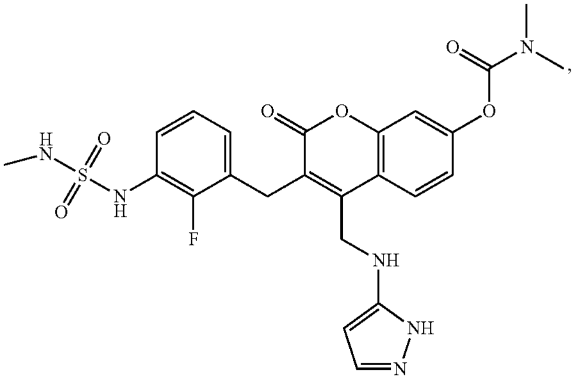
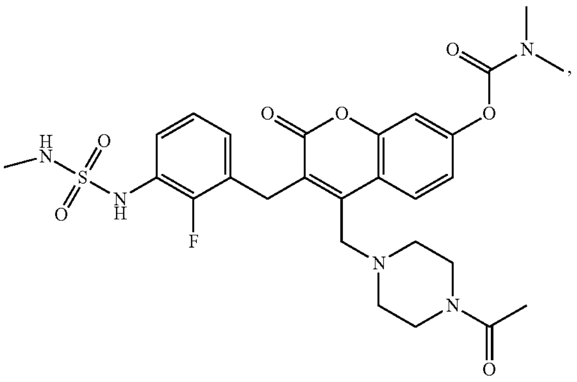

-continued

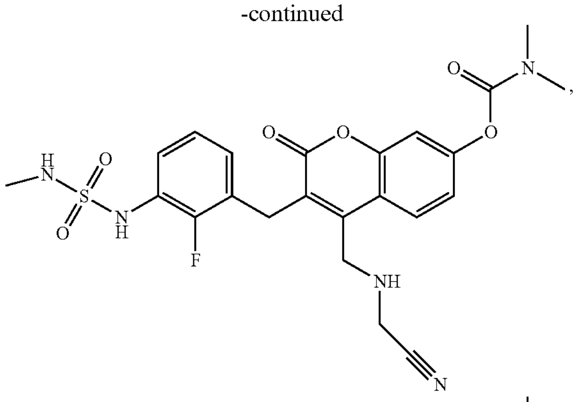

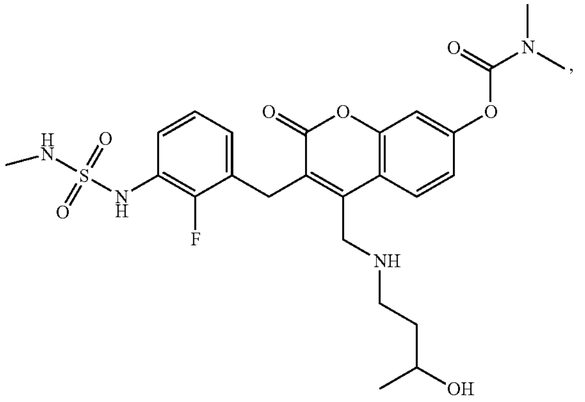

and pharmaceutically acceptable salts thereof.

86. The compound of alternative 60, having the structure depicted in Formula (IIb):

(IIb)

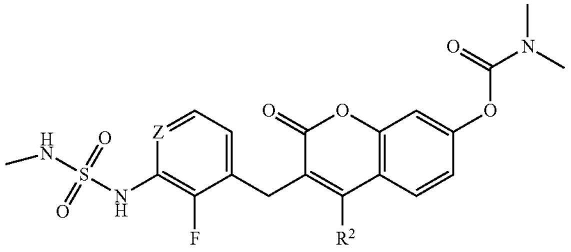

including pharmaceutically acceptable salts thereof, wherein:

$R^2$ is L;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, — $R^5NH$—, —$R^5NH(CO)$—, —$NHCH_2CO$—, —$R^5(CO)NH$—, —$R^5NH$—$SO_2$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Z is C or N.

87. The compound of alternative 86, wherein L is —$Z_1$—$Z_2$.

88. The compound of alternative 87, wherein $Z_1$ is —$CH_2$—.

89. The compound of alternative 86 or 87, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CCH$, or —$CH_2CN$.

90. The compound of alternative 89, wherein $R^5$ and $R^{5'}$ are each selected from H or $CH_3$.

91. The compound of alternative 86, wherein L is —$Z_1$—$Z_2$—$Z_3$.

92. The compound of alternative 87, wherein $Z_1$ is —$CH_2$—, $Z_2$ is optionally substituted $C_3$ to $C_8$ heterocyclyl, and $Z_3$ is —$CH_2$-(optionally substituted aryl).

93. The compound of alternative 87, wherein $Z_1$ is —$CH_2$— and $Z_2$ is optionally substituted $C_3$ to $C_8$ heterocyclyl.

94. The compound of alternative 93, wherein the optionally substituted $C_3$ to $C_8$ heterocyclyl is

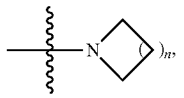

wherein n is 1, 2, 3 or 4.

95. The compound of alternative 93 or 94, wherein the optionally substituted $C_3$ to $C_8$ heterocyclyl is

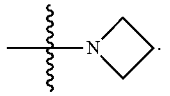 [SMILES: *N1CCC1]

96. The compound of alternative 86, selected from the group consisting of:

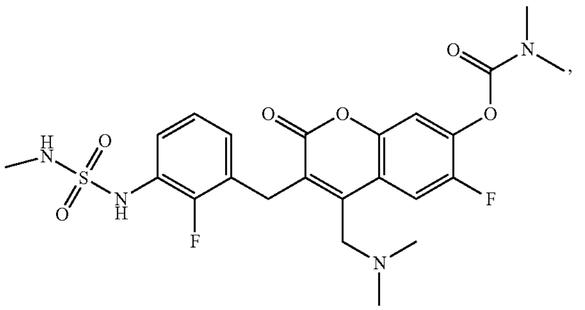

-continued
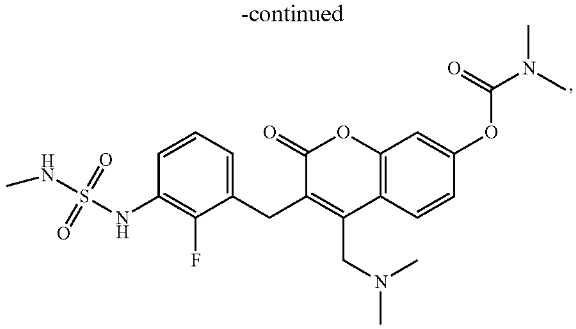
,
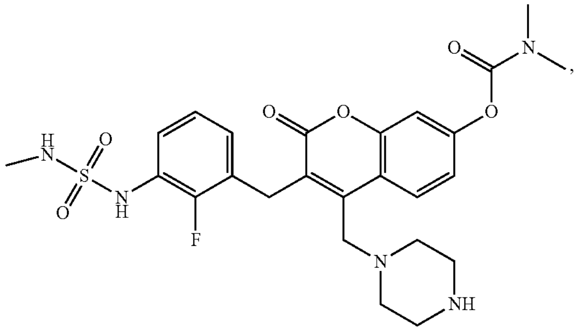
,
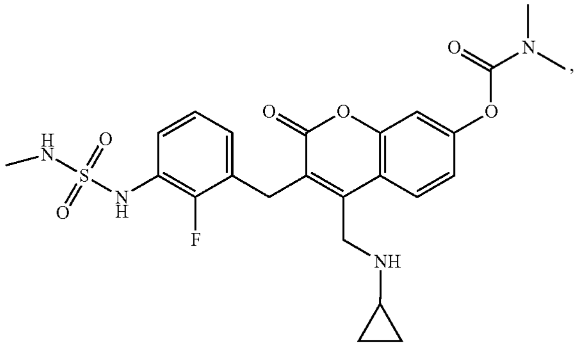
,
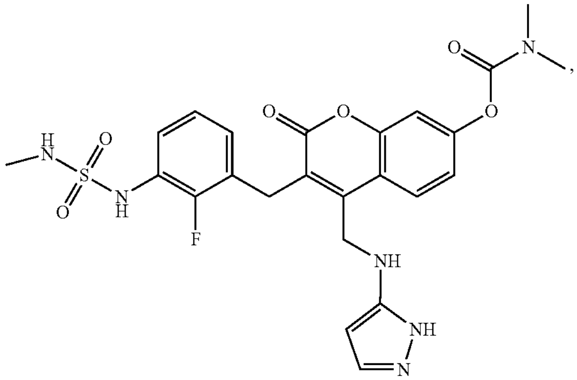
,
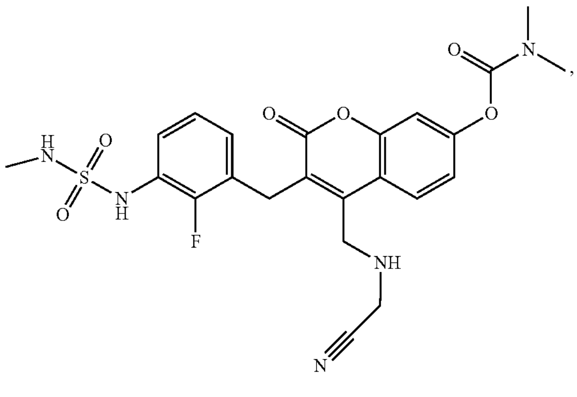
,
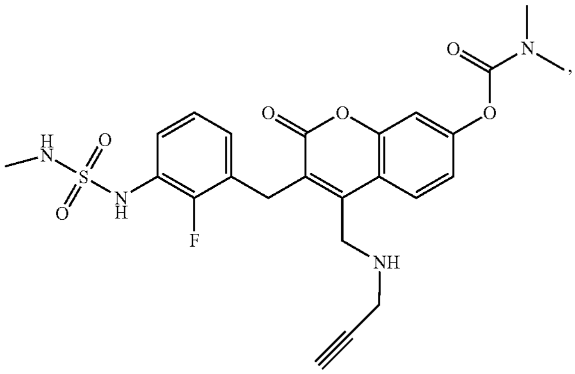
,
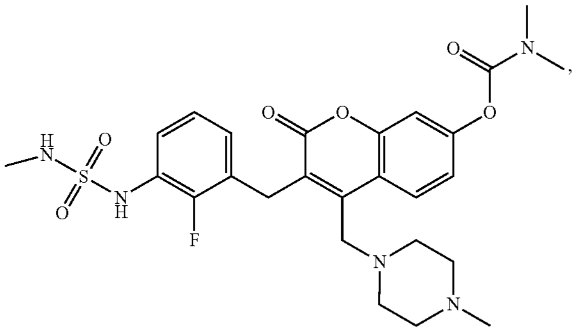
,
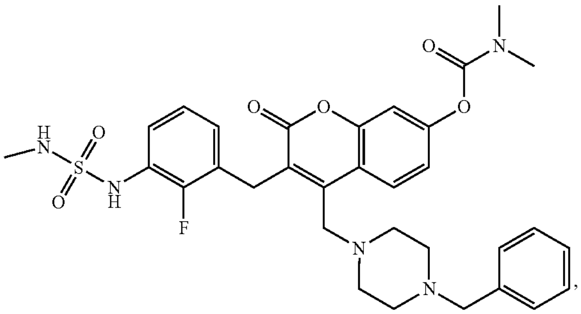
,
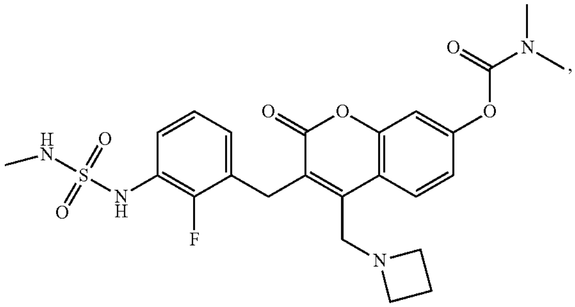
,
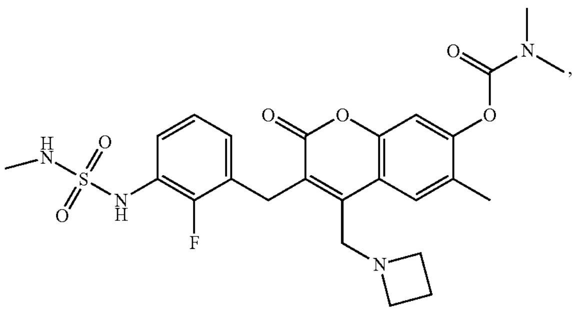
, -continued

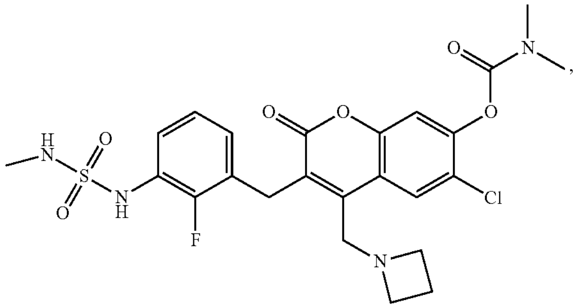

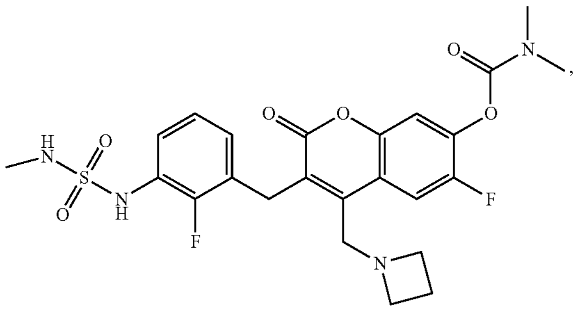

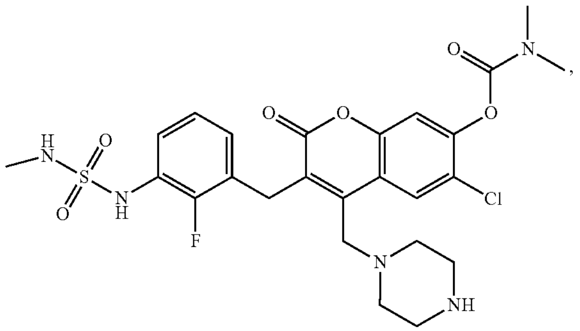

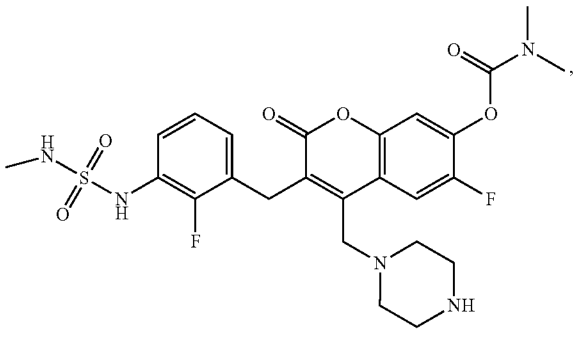

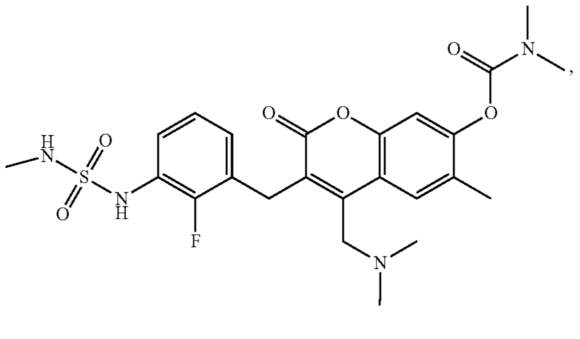

-continued

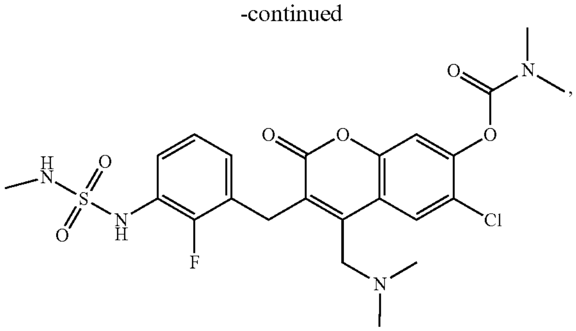

and pharmaceutically acceptable salts thereof.

97. The compound of alternative 60 having the structure of Formula (IIc):

(IIc)

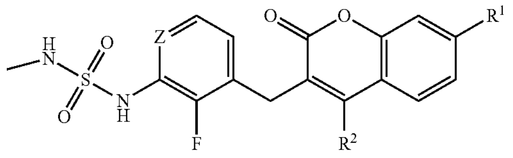

including pharmaceutically acceptable salts thereof, wherein:

$R^1$ and $R^2$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

L is $—Z_1—Z_2$ or $—Z_1—Z_2—Z_3$;

$Z_1$, $Z_2$, and $Z_3$ are independently $—CH_2$, —O—, —S—, S═O, $—SO_2—$, C═O, $—CO_2—$, $—NO_2$, —NH—, $—CH_2CCH$, $—CH_2CN$, $—NR^5R^{5'}$, —NH(CO)—, —(CO)NH—, $—(CO)NR^5R^{5'}—$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $—R^5NH—$, $—R^5NH(CO)—$, $—R^5(CO)NH—$, $—NHCH_2CO—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ and $R^{5'}$ is independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Z is C or N, with the proviso that $R^1$ is not pyrimidyl.

98. The compound of alternative 97, wherein $R^2$ is $—CH_3$.

99. The compound of alternative 97, wherein $R^2$ is L.

100. The compound of alternative 97 or 99, wherein L is $—Z_1—Z_2$.

101. The compound of alternative 101, wherein $Z_1$ is $—CH_2—$.

102. The compound of alternative 100 or 101, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^{5'}$, $—CH_2CCH$, or $—CH_2CN$.

103. The compound of alternative 102, wherein $R^5$ and $R^{5'}$ are each selected from H or $CH_3$.

104. The compound of alternative 99, wherein L is $—Z_1—Z_2—Z_3$.

105. The compound of alternative 104, wherein $Z_1$ is $—CH_2—$, $Z_2$ is selected from N or an optionally substituted $C_3$ to $C_8$ heterocyclyl, and $Z_3$ is selected optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

106. The compound of alternative 60 having the structure of Formula (IId):

(IId)

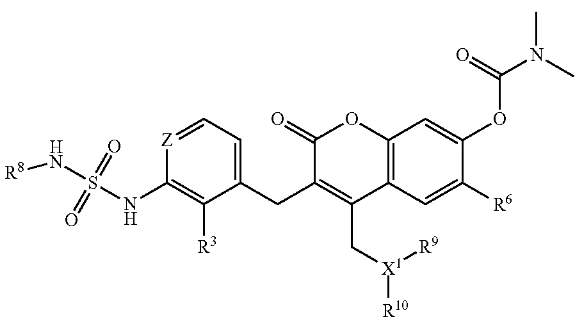

including pharmaceutically acceptable salts thereof, wherein:

$R^3$ is selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, and optionally substituted $C_2$ to $C_6$ alkynyl;

$R^8$ selected from H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, optionally substituted $C_3$ to $C_{10}$ heteroaryl;

$R^9$ and $R^{10}$ are each independently selected from hydrogen, deuterium, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl); and $X^1$ is selected from the group consisting of CH, B, N, or $PO_4$.

107. The compound of alternative 106, wherein $R^3$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

108. The compound of any one of alternatives 106 to 107, wherein $R^6$ is selected from H, deuterium, hydroxyl, halogen, cyano, nitro, optionally substituted amino, optionally optionally substituted $C_1$ to $C_6$ alkoxy, optionally substituted $C_1$ to $C_6$ alkyl.

109. The compound of any one of alternatives 106 to 18, wherein $R^8$ is selected from H, deuterium, hydroxyl, halogen, cyano, nitro, optionally substituted amino, optionally optionally substituted $C_1$ to $C_6$ alkoxy, optionally substituted $C_1$ to $C_6$ alkyl.

110. The compound of any one of alternatives 106 to 109, wherein $R^9$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

111. The compound of any one of alternatives 106 to 110, wherein $R^{10}$ is selected from H, deuterium, halogen, $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl.

112. The compound of any one of alternatives 1 to 111, wherein the pharmaceutically acceptable salt is an alkaline metal salt or an ammonium salt.

113. A pharmaceutical composition comprising a therapeutically effective amount of at least one compound having the structure of the Formula (I):

(I)

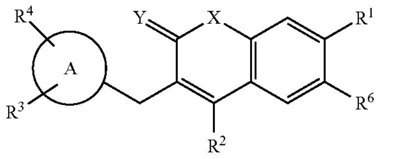

including pharmaceutically acceptable salts thereof, wherein:

Ring A is

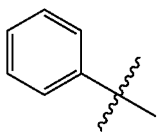, 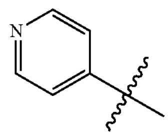, 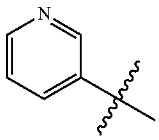, 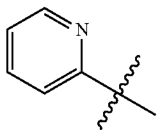, 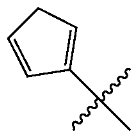, 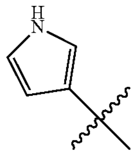, 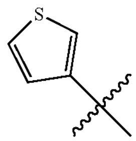, 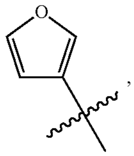, 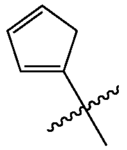, 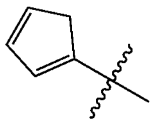, 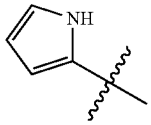, 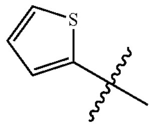, or 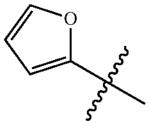;

$R^1$, $R^2$, $R^3$, and $R^4$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl;

X is $C(R^5)_2$, $CH(R^5)$, $CH_2$, —O—,

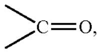, 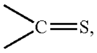, or 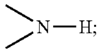;

L is —$Z_1$—$Z_2$ or —$Z_1$—$Z_2$—$Z_3$;

$Z_1$, $Z_2$, and $Z_3$ are independently —$CH_2$—, —O—, —S—, S═O, —$SO_2$—, C═O, —$CO_2$—, —$NO_2$, —NH—, —$CH_2CCH$, —$CH_2CN$, —$NR^5R^{5'}$, —NH(CO)—, —(CO)NH—, —(CO)$NR^5R^{5'}$—, —NH—$SO_2$—, —$SO_2$—NH—, —$R^5CH_2$—, —$R^5O$—, —$R^5S$—, $R^5$—S═O, —$R^5SO_2$—, $R^5$—C═O, —$R^5CO_2$—, —$R^5NH$—, —$R^5NH(CO)$—, —$R^5(CO)NH$—, —$R^5NH$—$SO_2$—, —$NHCH_2CO$—, —$R^5SO_2$—NH—, —$CH_2R^5$—, —$OR^5$—, —$SR^5$—, S═O—$R^5$, —$SO_2R^5$—, C═O—$R^5$, —$CO_2R^5$—, —$NHR^5$—, —NH(CO)$R^5$—, —(CO)$NHR^5$—, —NH—$SO_2R^5$—, —$SO_2$—$NHR^5$—, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, —$CH_2$-(optionally substituted aryl), —$CH_2$-(optionally substituted $C_3$ to $C_8$ cycloalkyl) or —$CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl; and Y is $CH_2$, NH or O, with the proviso that $R^1$ is not pyrimidyl.

114. The pharmaceutical composition of alternative 113, wherein $R^2$ is —$CH_3$.

115. The pharmaceutical composition of alternative 113, wherein $R^2$ is L.

116. The pharmaceutical composition of alternative 115, wherein L is —$Z_1$—$Z_2$.

117. The pharmaceutical composition of alternative 116, wherein $Z_1$ is —$CH_2$—.

118. The pharmaceutical composition of alternative 116 or 117, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, —$NR^5R^{5'}$, —$CH_2CCH$, or —$CH_2CN$.

119. The pharmaceutical composition of alternative 118, wherein $R^5$ and $R^{5'}$ are each selected from H or $CH_3$.

120. The pharmaceutical composition of alternative 113, wherein L is —$Z_1$—$Z_2$—$Z_3$.

121. The pharmaceutical composition of alternative 113, wherein $Z_1$ is —$CH_2$—, $Z_2$ is selected from the group consisting of —$NR^5R^{5'}$, $C_3$ to $C_8$ cycloalkyl, optionally substituted $C_3$ to $C_8$ heterocyclyl, optionally substituted $C_3$ to $C_8$ heteroaryl and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or —$CH_2$-(optionally substituted aryl).

122. The pharmaceutical composition of alternative 116, wherein $Z_1$ is —$CH_2$— and $Z_2$ is optionally substituted $C_3$ to $C_8$ heterocyclyl.

123. The pharmaceutical composition of alternative 122, wherein the optionally substituted $C_3$ to $C_8$ heterocyclyl is

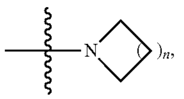

wherein n is 1, 2, 3 or 4.

124. The pharmaceutical composition of alternative 122 or 123, wherein the optionally substituted $C_3$ to $C_8$ heterocyclyl is

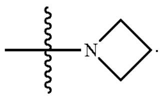 [SMILES: *N1CCC1]

125. The pharmaceutical composition of alternative 113, comprising a therapeutically effective amount of at least one compound selected from Table A.

126. The pharmaceutical composition of alternative 113, comprising a therapeutically effective amount of at least one compound selected from the group consisting of:

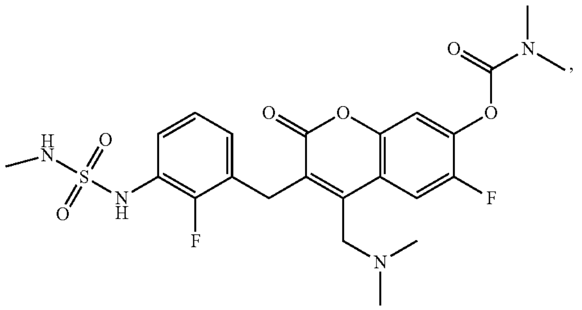

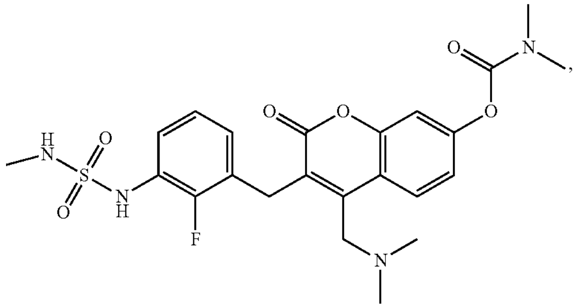

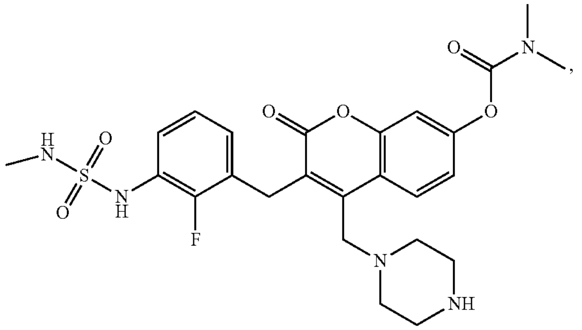

-continued

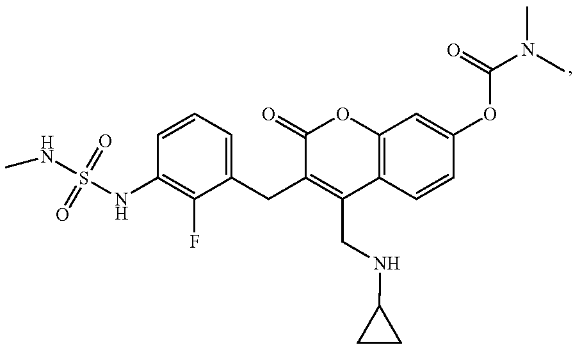

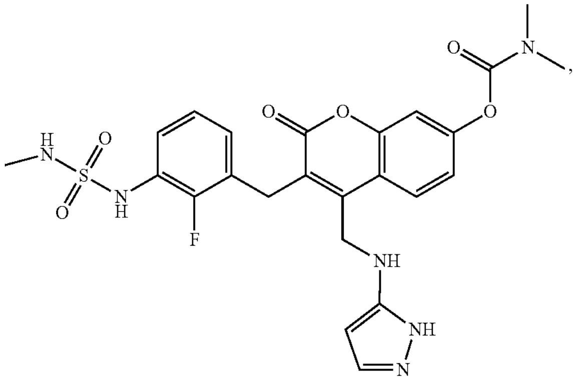

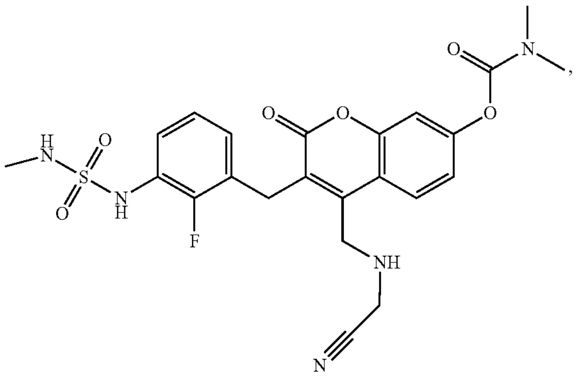

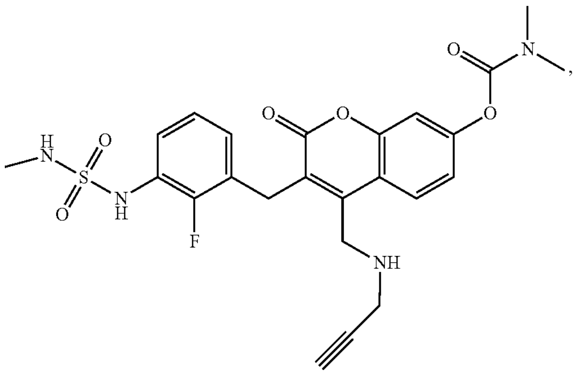

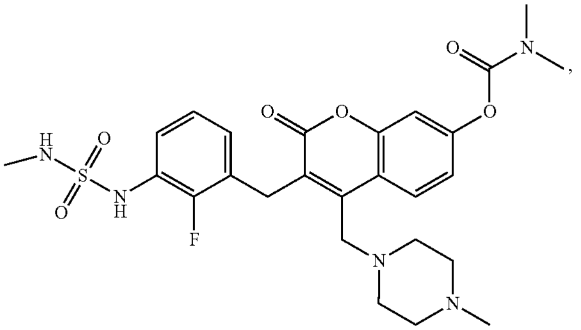,
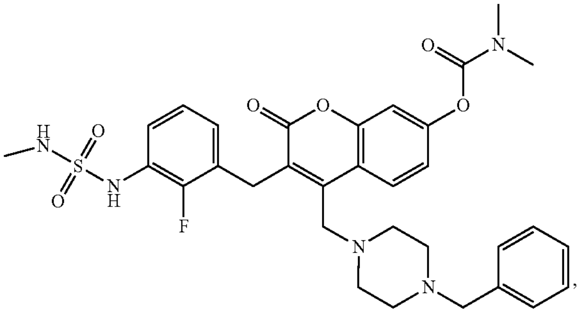,
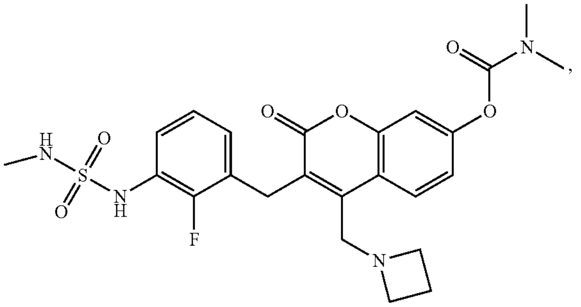,
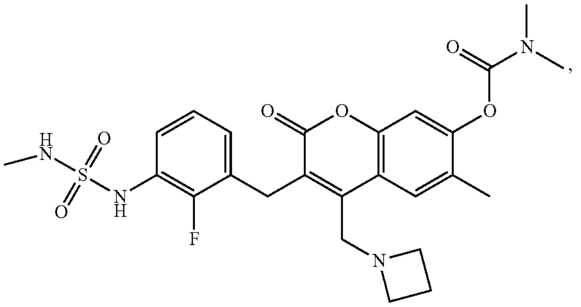,
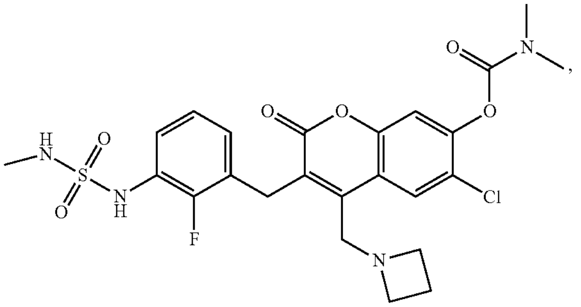,
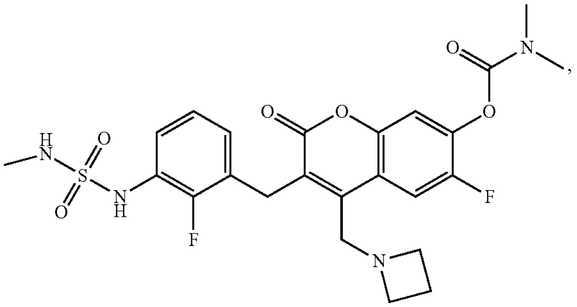,
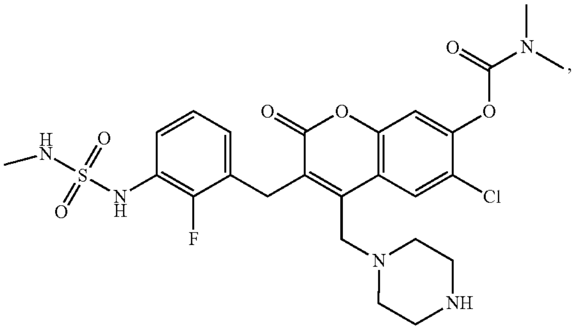,
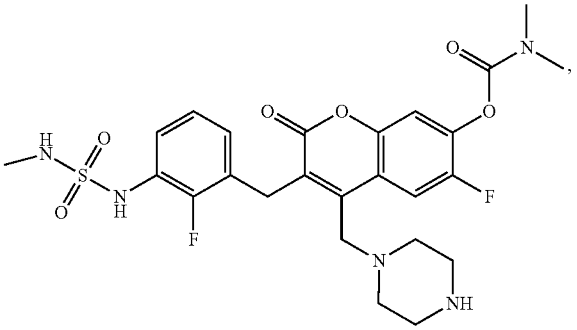,
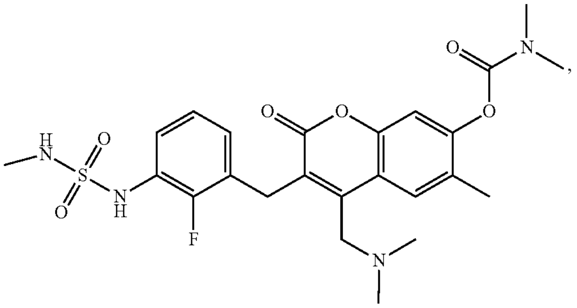,
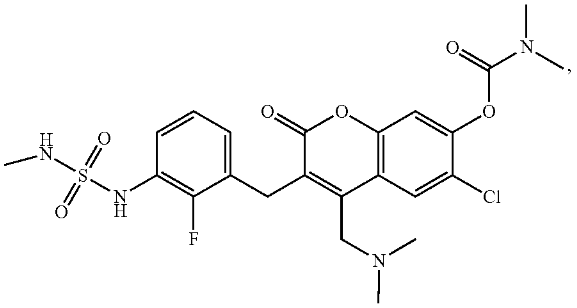, -continued

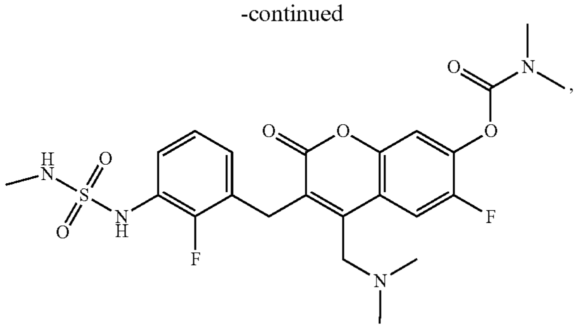

and pharmaceutically acceptable salts thereof, together with at least one pharmaceutically acceptable excipient.

127. A pharmaceutical composition comprising a therapeutically effective amount of at least one compound having the structure of the Formula (II):

(II)

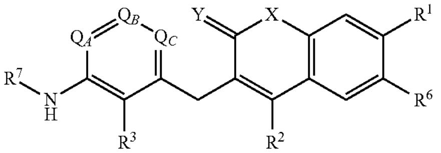

including pharmaceutically acceptable salts thereof, wherein:

$Q_A$, $Q_B$, $Q_C$ are independently C or N;

$R^1$, $R^2$, $R^3$, and $R^7$ are each independently selected from the group consisting of H, deuterium, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, or L;

$R^6$ is selected from the group consisting of H, deuterium, hydroxyl, halogen, cyano, nitro, optionally substituted amino, optionally optionally substituted $C_1$ to $C_6$ alkoxy, optionally substituted $C_1$ to $C_6$ alkyl, optionally substituted $C_2$ to $C_6$ alkenyl, optionally substituted $C_2$ to $C_6$ alkynyl;

X is $C(R^5)_2$, $CH(R^5)$, $CH_2$, —O—,

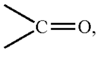, 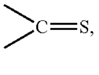, or 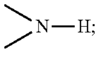;

L is $—Z_1—Z_2$ or $—Z_1—Z_2—Z_3$;

$Z_1$, $Z_2$, and $Z_3$ are independently $—CH_2—$, —O—, —S—, S═O, $—SO_2—$, C═O, $—CO_2—$, $—NO_2$, —NH—, $—CH_2CCH$, $—CH_2CN$, $—NR^5R^{5'}$, —NH(CO)—, —(CO)NH—, $—(CO)NR^5R^{5'}$, $—NH—SO_2—$, $—SO_2—NH—$, $—R^5CH_2—$, $—R^5O—$, $—R^5S—$, $R^5—S═O$, $—R^5SO_2—$, $R^5—C═O$, $—R^5CO_2—$, $— R^5NH—$, $—R^5NH(CO)—$, $—NHCH_2CO—$, $—R^5(CO)NH—$, $—R^5NH—SO_2—$, $—R^5SO_2—NH—$, $—CH_2R^5—$, $—OR^5—$, $—SR^5—$, $S═O—R^5$, $—SO_2R^5—$, $C═O—R^5$, $—CO_2R^5—$, $—NHR^5—$, $—NH(CO)R^5—$, $—(CO)NHR^5—$, $—NH—SO_2R^5—$, $—SO_2—NHR^5—$, optionally substituted $C_1$ to $C_6$ alkyl, optionally substituted $C_3$ to $C_8$ cycloalkyl, optionally substituted $C_6$ to $C_{10}$ aryl, optionally substituted $C_3$ to $C_8$ heterocyclyl, optionally substituted $C_3$ to $C_{10}$ heteroaryl, $—CH_2$-(optionally substituted aryl), $—CH_2$-(optionally substituted $C_3$ to $C_8$ cycloalkyl) or $—CH_2$-(optionally substituted $C_3$ to $C_{10}$ heteroaryl);

each $R^5$ and $R^{5'}$ are each independently H, deuterium, optionally substituted $C_1$ to $C_6$ alkyl, optionally substituted $C_2$ to $C_6$ alkenyl, optionally substituted $C_2$ to $C_6$ alkynyl, optionally substituted $C_3$ to $C_8$ carbocyclyl, optionally substituted $C_6$ to $C_{10}$ aryl, optionally substituted $C_3$ to $C_8$ heterocyclyl, or optionally substituted $C_3$ to $C_{10}$ heteroaryl;

Y is $CH_2$, NH or O; and

Z is C or N, with the proviso that $R^1$ is not pyrimidyl.

128. The pharmaceutical composition of alternative 127, wherein $R^2$ is $—CH_3$.

129. The pharmaceutical composition of alternative 127, wherein $R^2$ is L.

130. The pharmaceutical composition of alternative 129, wherein L is $—Z_1—Z_2$.

131. The pharmaceutical composition of alternative 129, wherein $Z_1$ is $—CH_2—$.

132. The pharmaceutical composition of alternative 129 or 130, wherein $Z_2$ is selected from optionally substituted $C_3$ to $C_8$ cycloalkyl, optionally substituted $C_3$ to $C_8$ heterocyclyl, optionally substituted $C_3$ to $C_8$ heteroaryl, $—NR^5R^5$, $—CH_2CCH$, or $—CH_2CN$.

133. The pharmaceutical composition of alternative 132, wherein $R^5$ and $R^{5'}$ are each selected from H or $CH_3$.

134. The pharmaceutical composition of alternative 129, wherein L is $—Z_1—Z_2—Z_3$.

135. The pharmaceutical composition of alternative 134, wherein $Z_1$ is $—CH_2—$, $Z_2$ selected from the group consisting of $—NR^5R^{5'}$, $C_3$ to $C_8$ cycloalkyl, optionally substituted $C_3$ to $C_8$ heterocyclyl, optionally substituted $C_3$ to $C_8$ heteroaryl and $Z_3$ is selected from the group consisting of H, deuterium, halo, optionally substituted $C_1$ to $C_6$ alkyl, optionally substituted $C_3$ to $C_8$ cycloalkyl, optionally substituted $C_6$ to $C_{10}$ aryl, or $—CH_2$-(optionally substituted aryl)

136. The pharmaceutical composition of alternative 130, wherein $Z_1$ is $—CH_2—$ and $Z_2$ is optionally substituted $C_3$ to $C_8$ heterocyclyl.

137. The pharmaceutical composition of alternative 136, wherein the optionally substituted $C_3$ to $C_8$ heterocyclyl is

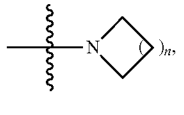

wherein n is 1, 2, 3 or 4.

138. The pharmaceutical composition of alternative 136 or 137, wherein the optionally substituted $C_3$ to $C_8$ heterocyclyl is

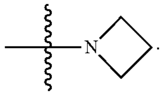 [SMILES: *N1CCC1]

139. The pharmaceutical composition of alternative 126, comprising a therapeutically effective amount of at least one compound selected from Table A.

140. The pharmaceutical composition of alternative 127, comprising a therapeutically effective amount of at least one compound selected from the group consisting of:

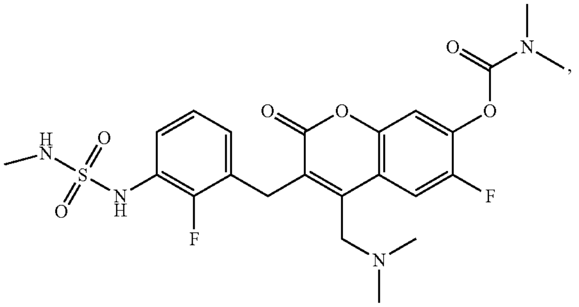

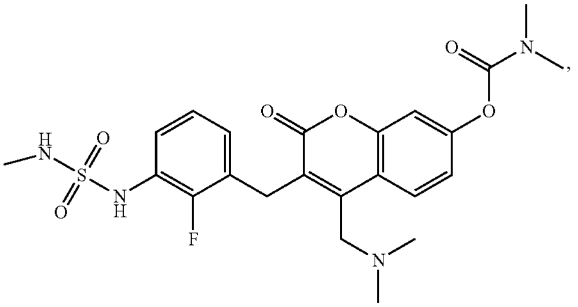

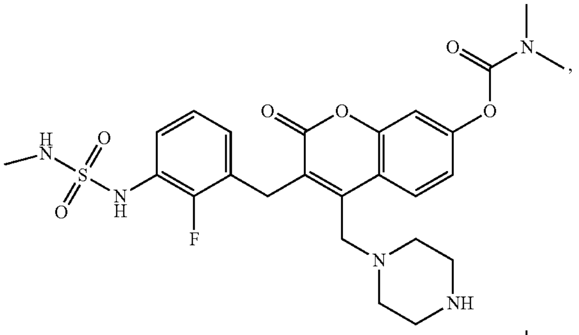

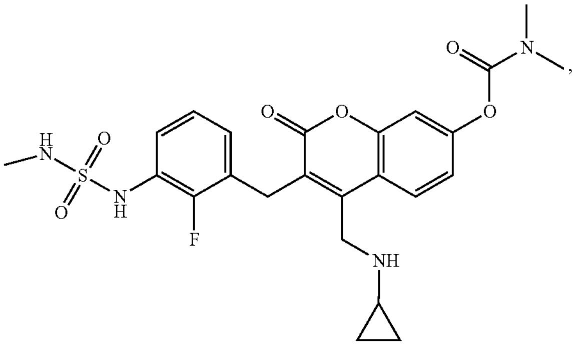

-continued

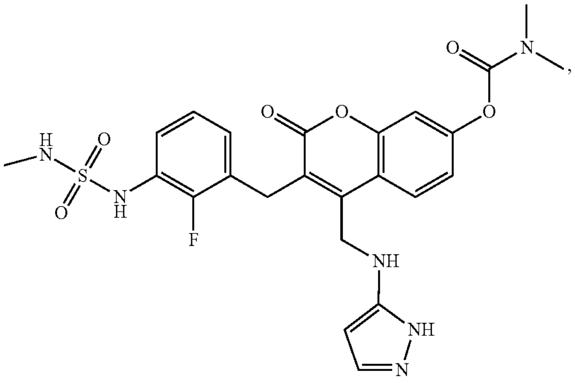

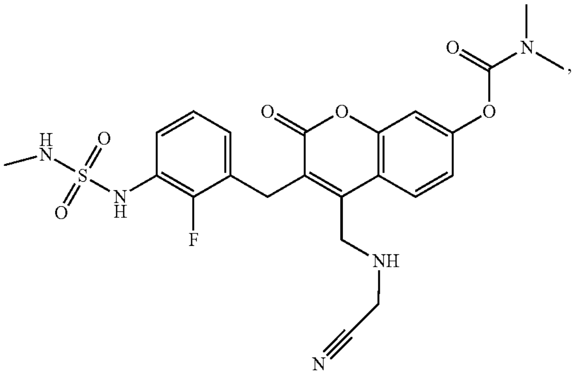

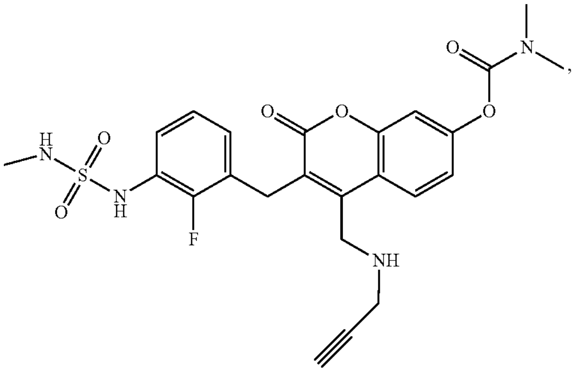

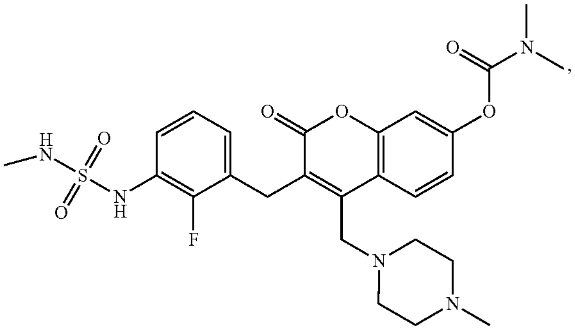

-continued
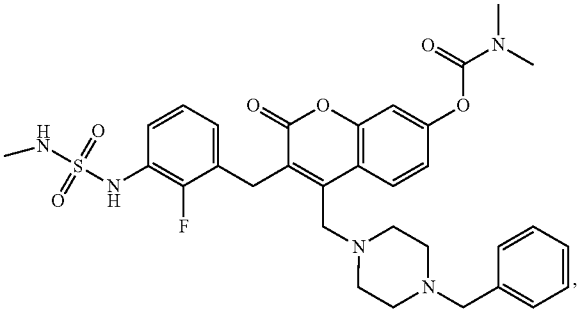,
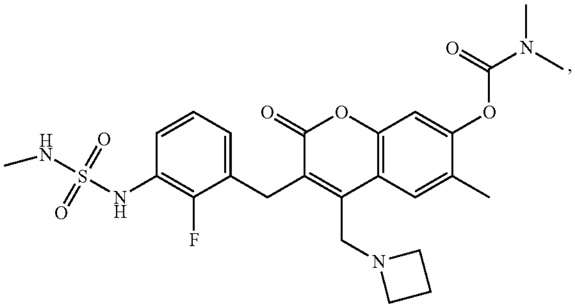,
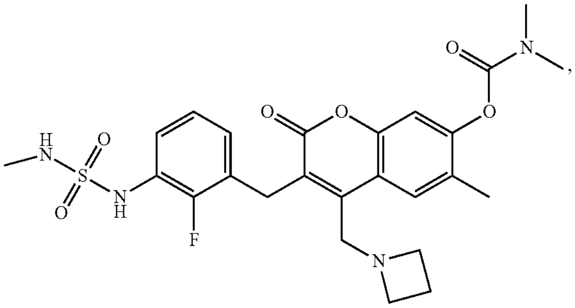,
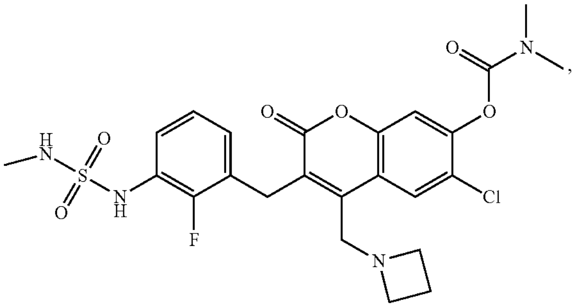,
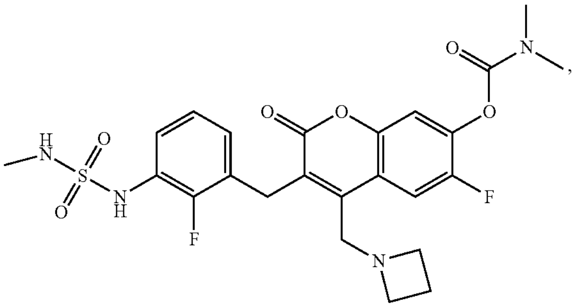,
-continued
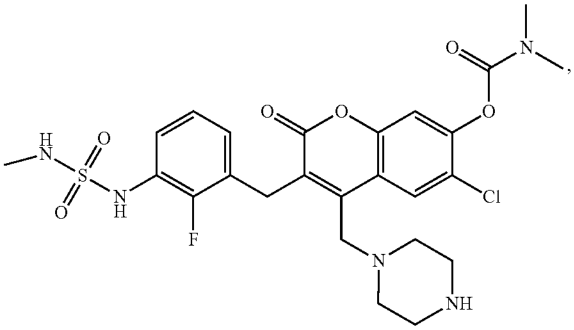,
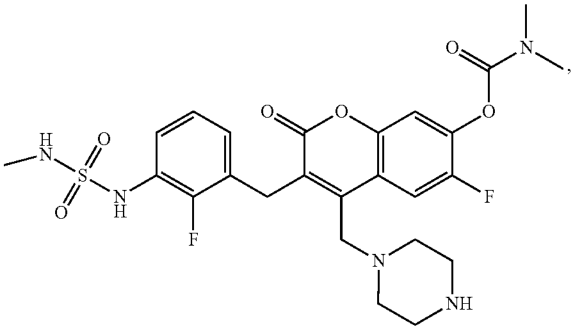,
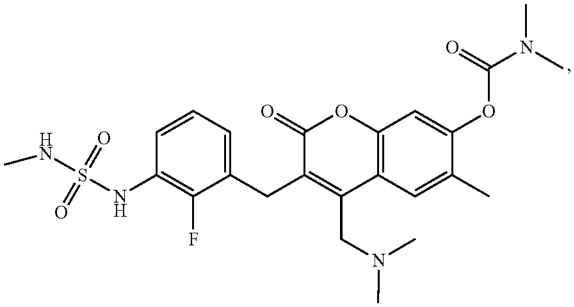,
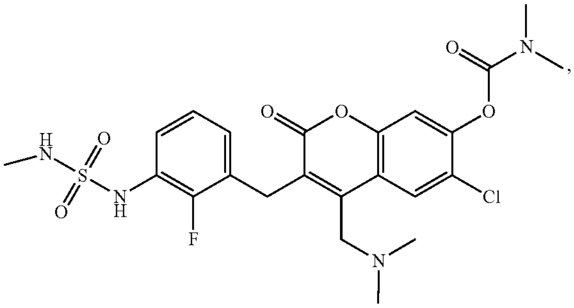,
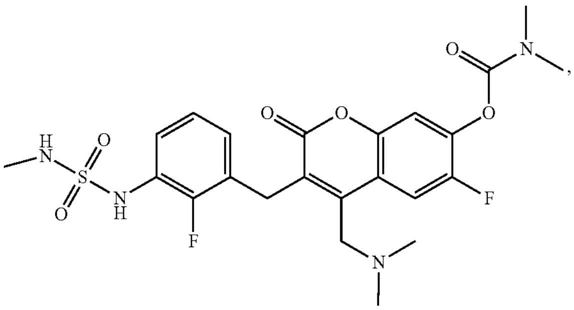,
and pharmaceutically acceptable salts thereof, together with at least one pharmaceutically acceptable excipient.

141. A method of treating a mammal having a disease or disorder, comprising administering to the mammal a therapeutically effective amount of a compound of any of alternative 1 to 140.

142. A method of treating a mammal having a disease or disorder, comprising administering to the mammal a therapeutically effective amount of a pharmaceutical composition of any one of alternative 113 to 140.

143. The method of alternative 141 or 142, wherein the mammal is a human.

144. The method of any one of alternative 141 or 142, further comprising administering to the subject an additional medicament.

145. A method of treating a disease or disorder, comprising administering to a subject suffering from said disease or disorder an effective amount of a compound of any one of alternatives 1 to 140, or a pharmaceutically acceptable salt thereof.

146. A method of treating a disease, comprising administering to a subject suffering from said disease an effective amount of a pharmaceutical composition of any one of alternatives 113 to 140.

147. The method of alternative 141 or 142, wherein the disease is cancer.

148. The method of alternative 147, wherein the cancer is selected from the group consisting of brain cancer, breast cancer, lung cancer, non-small cell lung cancer, ovarian cancer, pancreatic cancer, stomach cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis.

149. The method of alternative 147 or 148, wherein the cancer is associated with a RAS mutation.

150. The method of alternative 149, wherein the RAS mutation is a KRAS mutation selected from the group consisting of G12C, G12S, G12R, G12F, G12L, G12N, G12A, G12D, G12V, G13C, G13S, G13D, G13V, G13P, S17G, P34S, A59E, A59G, A59T, Q61K, Q61L, Q61R, and Q61H.

151. The method of alternative 141 or 142, wherein the disease is cancer cachexia.

152. A method of inhibiting proliferation of a cell, the method comprising contacting the cell with an effective amount of a compound of any one alternatives 1 to 112 or a pharmaceutical composition of any one of alternatives 113 to 140.

153. The method of alternative 152, wherein the cell has a RAS mutation.

154. A method of inducing apoptosis in a cell, the method comprising contacting the cell with an effective amount of a compound of any one alternatives 1 to 112 or a pharmaceutical composition of any one of alternatives 113 to 140.

155. A method of treating a subject with cancer resistant to treatment of a MEK protein kinase inhibitor, the method comprising contacting the cell with an effective amount of a compound of any one alternatives 1 to 112 or a pharmaceutical composition of any one of alternatives 113 to 140.

156. A method of treating a subject with cancer resistant to treatment of a RAF protein kinase inhibitor, the method comprising contacting the cell with an effective amount of a compound of any one alternatives 1 to 112 or a pharmaceutical composition of any one of alternatives 113 to 140.

157. A method of treating cancer cachexia in a mammal with cancer comprising administering an effective amount of a compound of any one alternatives 1 to 112 or a pharmaceutical composition of any one of alternatives 113 to 140.

158. The method according to any one of alternatives 141 to 157, wherein the compound of any one alternatives 1 to 112 or a pharmaceutical composition of any one of alternatives 113 to 140 is administered in a single dose.

159. The method according to any one of alternatives 43 to 47, wherein the compound of any one alternatives 1 to 112 or a pharmaceutical composition of any one of alternatives 113 to 140 is administered in a single dose.

160. The method according to any one of alternatives 141 to 157, wherein the compound of any one alternatives 1 to 112 or a pharmaceutical composition of any one of alternatives 113 to 140 is administered in a single dose, once daily.

161. The method according to any one of alternatives 141 to 157, wherein the compound of any one alternatives 1 to 112 or a pharmaceutical composition of any one of alternatives 113 to 140 is administered in multiple doses, more than once per day.

162. The method according to any one of alternatives 141 to 157, wherein the compound of any one alternatives 1 to 112 or a pharmaceutical composition of any one of alternatives 113 to 140 is administered twice a day.

163. The method according to any one of alternatives 141 to 157, wherein the compound of any one alternatives 1 to 112 or a pharmaceutical composition of any one of alternatives 113 to 140 is administered three times a day.

164. The method according to any one of alternatives 141 to 157, wherein the compound of any one alternatives 1 to 112 or a pharmaceutical composition of any one of alternatives 113 to 140 is administered as a dose between 0.1 mg and 2000 mg.

165. The method according to any one of alternatives 141 to 157, wherein the compound of any one alternatives 1 to 112 or a pharmaceutical composition of any one of alternatives 113 to 140 is administered as a dose between from about 0.001 to about 1000 mg/kg body weight/day.

166. The compound of any one alternatives 1 to 112 or a pharmaceutical composition of any one of alternatives 113 to 140, wherein the compound has a drug profile of RAF resistant, BID dosing, balance metabolism, and active between about 3 and about 6 hours.

167. The compound of any one alternatives 1 to 112 or a pharmaceutical composition of any one of alternatives 113 to 140, wherein the compound interacts with a first region comprising L115, L118, V127, and M143 of an MEK Kinase.

168. The compound of alternative 167, wherein the compound interacts with a second region comprising K97 of an MEK Kinase.

169. The compound of alternative 167 or 168, wherein the compound interacts with a third region comprising S212, 1215 and M219 of an MEK Kinase.

170. A method of developing molecules based on evaluation and balance of two downstream molecular targets, the method comprising:

administering a compound targeting pERK (T202/Y204) and pSTAT3(S727).

171. A method for preventing re-activation of MEK by CRAF-bypass, the method comprising:

administering an effective amount of any one alternatives 1 to 112 or a pharmaceutical composition of any one of alternatives 113 to 140.

172. A method for designing a drug therapeutic window for dual RAF/MEK inhibitors, the method comprising:

administering a therapeutic agent with a plasma half-life of less than 12 hours, QD or BID dosing, resistant to MEK reactivation by CRAF-bypass, and optimal metabolic balance between pERK and pSTAT3(S727) inhibition.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (IIb):

(IIb)

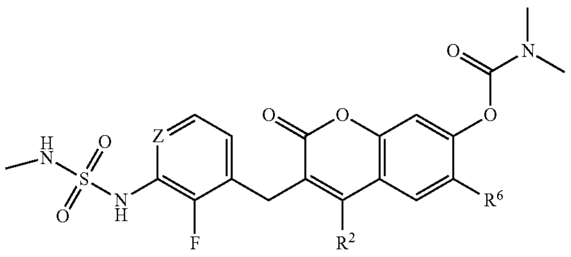

or a pharmaceutically acceptable salt thereof, wherein:

Z is C or N;

$R^2$ is L;

L is —$Z_1$—$Z_2$;

$Z_1$ is —$CH_2$—;

$Z_2$ is —$NR^5R^{5'}$;

each of $R^5$ and $R^{5'}$ are each independently $C_1$ to $C_6$ alkyl, and $R^6$ is H, deuterium, halogen, or $C_1$ to $C_6$ alkyl.

2. The compound of claim 1, wherein, $R^5$ and $R^{5'}$ are each independently methyl, ethyl, propyl, iso-propyl, n-butyl, iso-butyl, sec-butyl, or t-butyl; and $R_6$ is H.

3. The compound of claim 2, wherein Z is C.

4. The compound of claim 2, wherein Z is N.

5. The compound of claim 2, wherein the compound is:

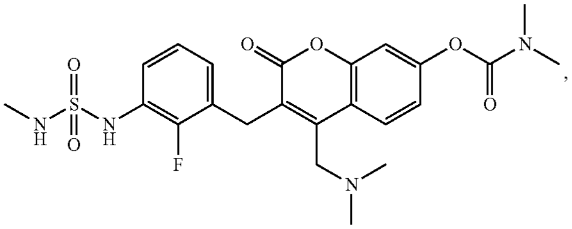

or a pharmaceutically acceptable salt thereof.

6. The compound of claim 2, wherein the compound is:

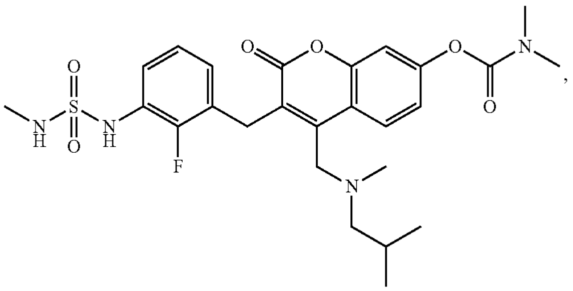

or a pharmaceutically acceptable salt thereof.

7. The compound of claim 2, wherein the compound is:

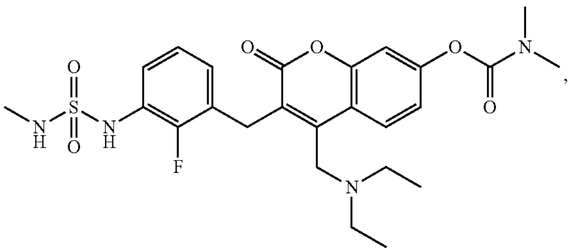

or a pharmaceutically acceptable salt thereof.

8. The compound of claim 2, wherein the compound is:

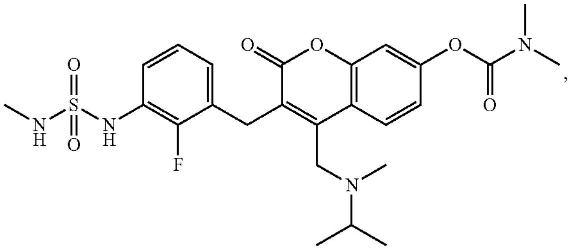

or a pharmaceutically acceptable salt thereof.

9. The compound of claim 2, wherein the compound is:

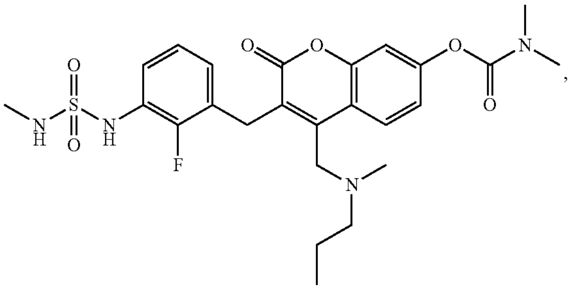

or a pharmaceutically acceptable salt thereof.

10. The compound of claim 2, wherein the compound is:

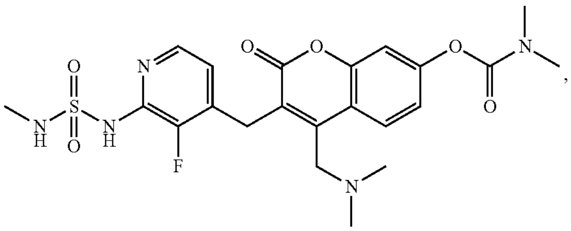, or a pharmaceutically acceptable salt thereof.

11. The compound of claim 2, wherein the compound is:

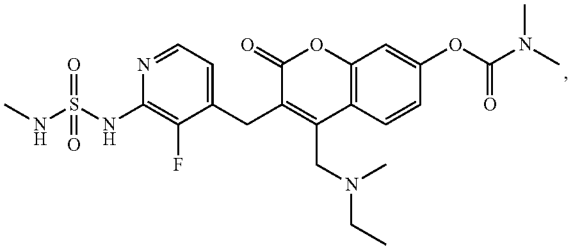, or a pharmaceutically acceptable salt thereof.

12. The compound claim 1, wherein $R_6$ is halogen, or a pharmaceutically acceptable salt thereof.

13. The compound of claim 12, selected from the group consisting of:

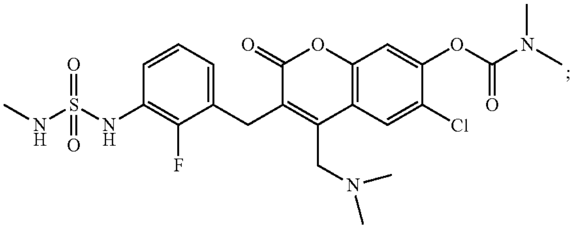;

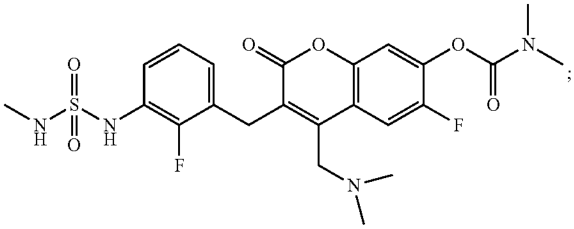;

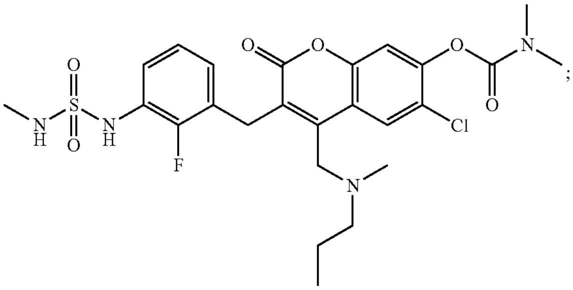;

-continued

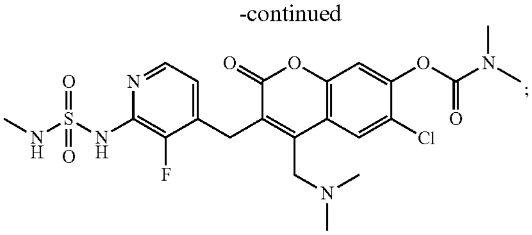; and

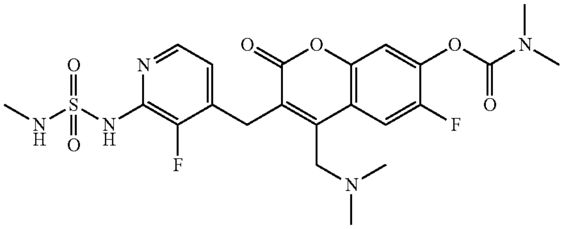, or a pharmaceutically acceptable salt thereof.

14. A compound of Formula (IIb):

(IIb)

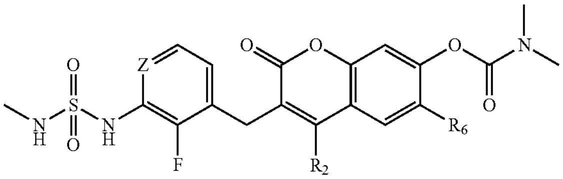

or a pharmaceutically acceptable salt thereof, wherein:

Z is C or N;

$R^2$ is L;

L is $-Z_1-Z_2$;

$Z_1$ is $-CH_2-$;

$Z_2$ is optionally substituted

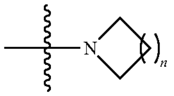

and n is 1, 2, 3 or 4; and $R^6$ is H, deuterium, halogen, or $C_1$ to $C_6$ alkyl.

15. The compound of claim 14, wherein $Z_2$ is

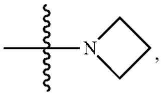, 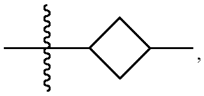,

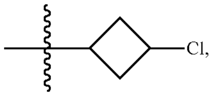, 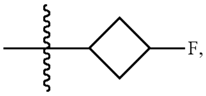,

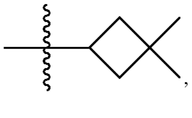, or 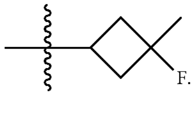.

16. The compound of claim 14, wherein $R^6$ is H.

17. The compound of claim 14, wherein $R^6$ is halogen.

18. The compound of claim 14, wherein the compound is selected from the group consisting of:
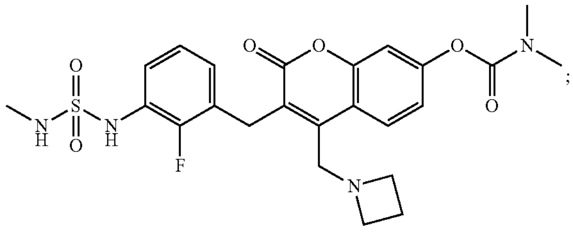
;
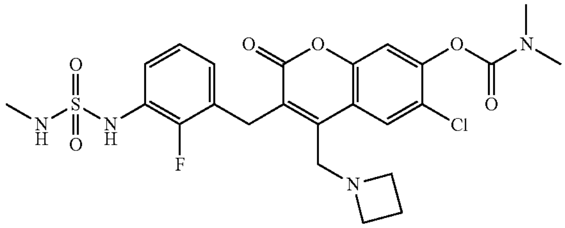
;
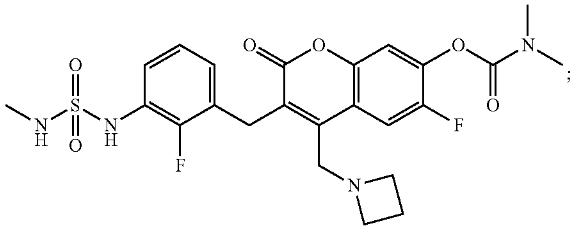
;
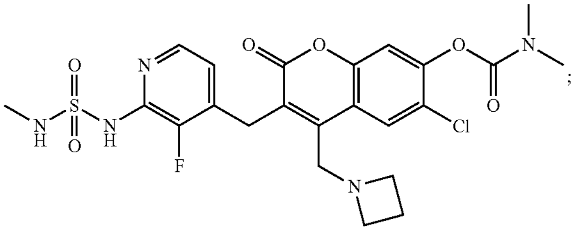
;
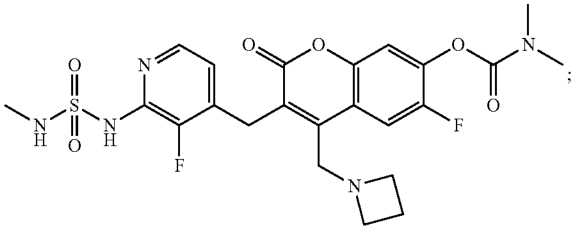
;
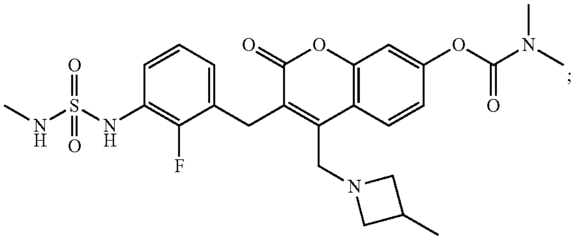
;
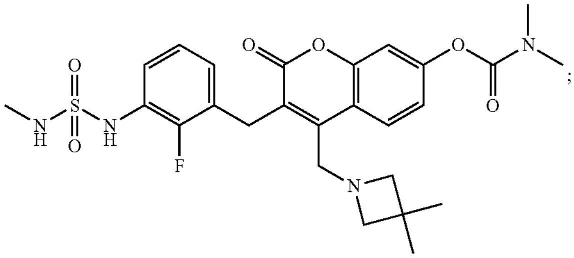
;
-continued
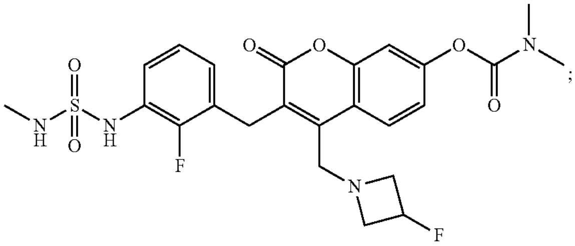
;
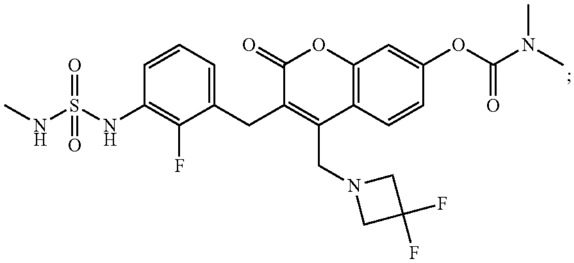
;
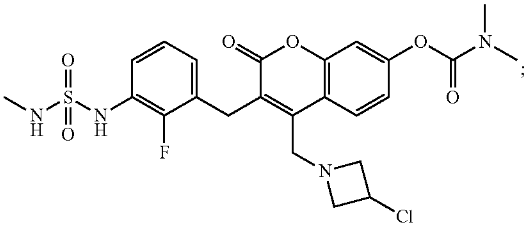
; and
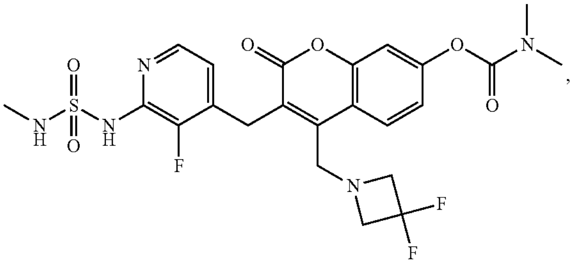
,
or a pharmaceutically acceptable salt thereof.
19. A compound of Formula (IIb):
(IIb)
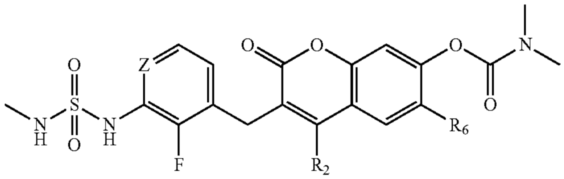
or a pharmaceutically acceptable salt thereof, wherein
Z is C or N;
$R^2$ is L;
L is $-Z_1-Z_2$;
$Z_1$ is $-CH_2-$;
$Z_2$ is optionally substituted
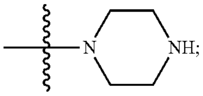

and $R^6$ is H, deuterium, halogen, or $C_1$ to $C_6$ alkyl.

20. The compound of claim 19, wherein the compound is selected from the group consisting of:

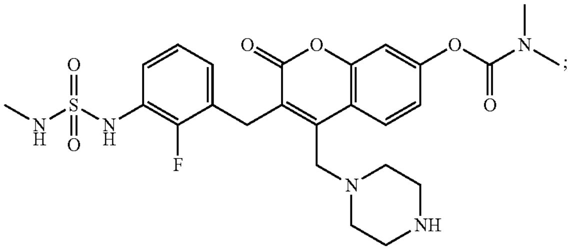

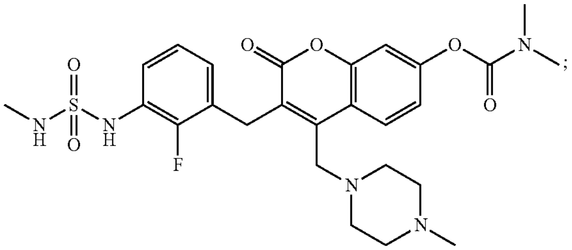

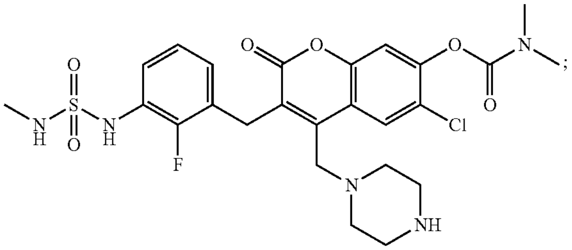

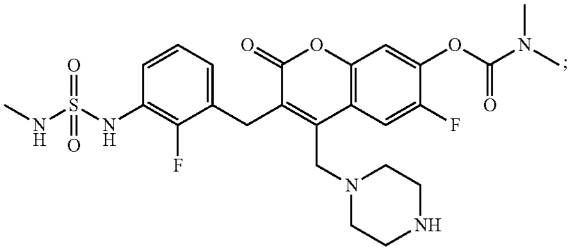

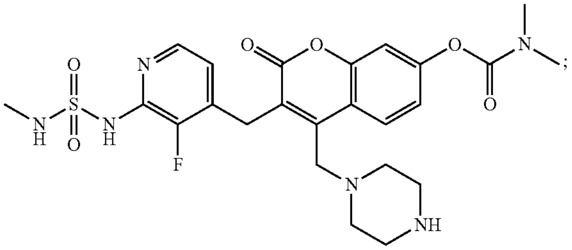

-continued and

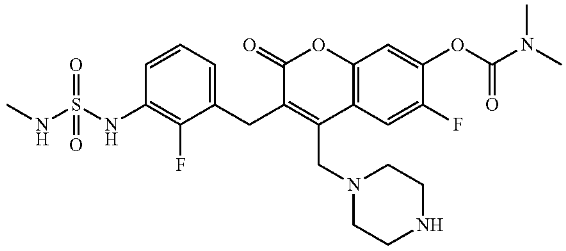

or a pharmaceutically acceptable salt thereof.

21. A compound having the structure depicted in Formula (IIa):

(IIa)

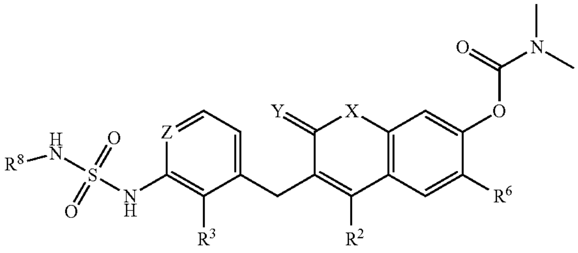

or a pharmaceutically acceptable salt thereof, wherein:

$R^2$ is L;

$R^3$ is the fluoro;

$R^6$ is H, deuterium, halogen, or $C_1$ to $C_6$ alkyl;

$R^8$ is $C_1$ to $C_6$ alkyl;

L is $—Z_1—Z_2$;

$Z_1$ is $—CH_2$;

$Z_2$ is selected from the group consisting of $—NR^5R^{5'}$, or $C_3$ to $C_8$ heterocyclyl;

each $R^5$ and $R^5$ are each independently H, deuterium, or $C_1$ to $C_6$ alkyl;

X is O;

Y is O; and

Z is C or N.

* * * * *

UNITED STATES PATENT AND TRADEMARK OFFICE

CERTIFICATE OF CORRECTION

PATENT NO. : 12,351,566 B2
APPLICATION NO. : 17/791755
DATED : July 8, 2025
INVENTOR(S) : Brett Matthew Hall et al.

It is certified that error appears in the above-identified patent and that said Letters Patent is hereby corrected as shown below:

On the Title Page

In Column 1, Page 3, Line 1, item (56) under Other Publications, delete "tumor modesl that" and insert --tumor models that--.

In Column 1, Page 3, Line 2, item (56) under Other Publications, delete "GENIE pateitns predict" and insert --GENIE patients predict--.

In Column 1, Page 3, Line 12, item (56) under Other Publications, delete "& Descovery, 8(9)" and insert --& Discovery, 8(9)--.

In Column 1, Page 3, Line 61, item (56) under Other Publications, delete "Koselugo (selumetiib)" and insert --Koselugo (selumetinib)--.

In Column 2, Page 3, Line 54, item (56) under Other Publications, delete "2016, Interkeukin-6 is" and insert --2016, Interleukin-6 is--.

In Column 1, Page 4, Line 63, item (56) delete "and inteleukin-11: same same but" and insert --and interleukin-11: same but--.

In Column 1, Page 5, Line 59, item (56) delete "inhibitor, Abtract #2515," and insert --inhibitor, Abstract #2515,--.

In Column 2, Page 7, Line 48, item (56) delete "fo metastatic" and insert --for metastatic--.

In the Specification

In Column 11, Line 55 (Approx.), delete "amino, optionally optionally substituted" and insert Signed and Sealed this
Thirtieth Day of September, 2025

John A. Squires
*Director of the United States Patent and Trademark Office*

--amino, optionally substituted--.

In Column 14, Line 60, delete “to C8 cycloalkyl” and insert --to $C_8$ cycloalkyl--.

In Column 18, Line 12 (Approx.), delete “amino, optionally optionally substituted” and insert --amino, optionally substituted--.

In Column 18, Line 42 (Approx.), delete “amino, optionally optionally substituted” and insert --amino, optionally substituted--.

In Column 18, Line 46 (Approx.), delete “amino, optionally optionally substituted” and insert --amino, optionally substituted--.

In Column 26, Line 49, delete “pSTAT3(5727).” and insert --pSTAT3(S727).--.

In Column 29, Line 56, delete “enantimoers. It” and insert --enantiomers. It--.

In Column 30, Line 11, delete “ethanesulfonic, p-toluensulfonic, salicylic” and insert --ethanesulfonic, p-toluenesulfonic, salicylic--.

In Column 33, Line 60, delete “and naphtylalkyl. In” and insert --and naphthylalkyl. In--.

In Columns 33-34, Lines 67 & 1, delete “pyridylalkyl, isoxazollylalkyl, and” and insert --pyridylalkyl, isoxazolylalkyl, and--.

In Column 44, Line 63, delete “amino, optionally optionally substituted” and insert --amino, optionally substituted--.

In Column 45, Line 4, delete “amino, optionally optionally substituted” and insert --amino, optionally substituted--.

In Column 45, Line 12, delete “amino, optionally optionally substituted” and insert --amino, optionally substituted--.

In Column 50, Lines 58-59, delete “amino, optionally optionally substituted” and insert --amino, optionally substituted--.

In Column 50, Lines 66-67, delete “amino, optionally optionally substituted” and insert --amino, optionally substituted--.

In Column 51, Lines 7-8, delete “amino, optionally optionally substituted” and insert --amino, optionally substituted--.

In Column 159, Line 45, delete “as croscaramellose sodium” and insert --as croscarmellose sodium--.

In Column 172, Line 13, delete “and croscarmelose; lubricants” and insert --and croscarmellose; lubricants--.

In Column 174, Line 58, delete “matrix-metalloprotienase 2” and insert --matrix-metalloproteinase 2--.

In Column 174, Line 59, delete “matrix-metalloprotienase 9” and insert --matrix-metalloproteinase 9--.

In Column 174, Line 63, delete “CELEBREX™ (alecoxib),” and insert --CELEBREX™ (celecoxib),--.

In Column 175, Line 24, delete “matrix-motalloproteinases (Le.,” and insert --matrix-metalloproteinases (Le.,--.

In Column 175, Line 25, delete “MMP-4, M7v1P-5,” and insert --MMP-4, MMP-5,--.

In Column 175, Line 26, delete “of M1v1P” and insert --of MMP--.

In Column 175, Line 41 (Approx.), delete “metabolites, epiclophyllotoxims; antineoplastic” and insert --metabolites, epipodophyllotoxins; antineoplastic--.

In Column 175, Line 45, delete “and baematopoietic growth” and insert --and hematopoietic growth--.

In Column 175, Line 65, delete “anti-neopiastic agents.” and insert --Anti-neoplastic agents.--.

In Column 176, Line 1, delete “metabolites, epidophyllotoxins; antineoplastic” and insert --metabolites, podophyllotoxins; antineoplastic--.

In Column 176, Line 33, delete “mytomycin; diaziquone” and insert --mitomycin; diaziquone--.

In Column 176, Line 53, delete “ytarabine; decitabine;” and insert --cytarabine; decitabine;--.

In Column 177, Line 8 (Approx.), delete “romidepsin; vorinosta; idelalisib;” and insert --romidepsin; vorinostat; idelalisib;--.

In Column 257, Lines 58-59, delete “and lyophillized to” and insert --and lyophilized to--.

In Column 258, Line 26 (Approx.), delete “propargylamone (3.1” and insert --propargylamine (3.1--.

In Column 258, Line 29, delete “were lyophillized to” and insert --were lyophilized to--.

In Column 258, Line 66, delete “lyophillized to” and insert --lyophilized to--.

In Column 260, Line 31 (Approx.), delete “lyophillized to” and insert --lyophilized to--.

In Column 261, Line 1, delete “were lyophillized to” and insert --were lyophilized to--.

In Column 261, Line 34, delete “propargylamone (3.1” and insert --propargylamine (3.1--.

In Column 261, Line 37, delete “were lyophillized to” and insert --were lyophilized to--.

In Column 277, Line 6 (Approx.) (TABLE 3), delete “Reamining” and insert --Remaining--.

In Column 277, Line 6 (Approx.) (TABLE 3), delete “Reamining” and insert --Remaining--.

In Column 277, Line 6 (Approx.) (TABLE 3), delete “Reamining” and insert --Remaining--.

In Column 278, Line 5 (Approx.) (TABLE 4), delete “Reamining” and insert --Remaining--.

In Column 278, Line 5 (Approx.) (TABLE 4), delete “Reamining” and insert --Remaining--.

In Column 278, Line 5 (Approx.) (TABLE 4), delete “Reamining” and insert --Remaining--.

In Column 278, Lines 65-66 (Approx.), delete “2D6 (dextromethophan), 3A4” and insert --2D6 (dextromethorphan), 3A4--.

In Column 294, Line 53 (Approx.), delete “amino, optionally optionally substituted” and insert --amino, optionally substituted--.

In Column 297, Line 28, delete “amino, optionally optionally substituted” and insert --amino, optionally substituted--.

In Column 300, Line 1, delete “amino, optionally optionally substituted” and insert --amino, optionally substituted--.

In Column 302, Line 28, delete “amino, optionally optionally substituted” and insert --amino, optionally substituted--.

In Column 305, Line 3, delete “amino, optionally optionally substituted” and insert --amino, optionally substituted--.

In Column 306, Line 8, delete "amino, optionally optionally substituted" and insert --amino, optionally substituted--.

In Column 322, Line 11, delete "amino, optionally optionally substituted" and insert --amino, optionally substituted--.

In Column 322, Lines 42-43, delete "amino, optionally optionally substituted" and insert --amino, optionally substituted--.

In Column 322, Lines 47-48, delete "amino, optionally optionally substituted" and insert --amino, optionally substituted--.

In Column 323, Line 67, delete "amino, optionally optionally substituted" and insert --amino, optionally substituted--.

In Column 329, Line 53, delete "amino, optionally optionally substituted" and insert --amino, optionally substituted--.

In the Claims

In Column 339, Claim 12, Line 32 (Approx.), delete "The compound claim" and insert --The compound of claim--.

In Column 340, Claim 15, Lines 61-63, delete " 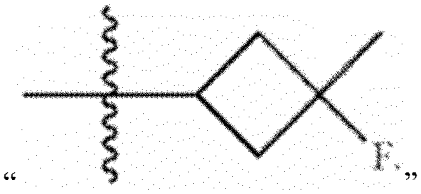 " and insert

-- 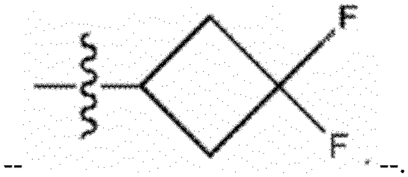 --.